US008404846B2

(12) United States Patent
Claridge et al.

(10) Patent No.: US 8,404,846 B2
(45) Date of Patent: *Mar. 26, 2013

(54) INHIBITORS OF PROTEIN TYROSINE KINASE ACTIVITY

(75) Inventors: Stephen William Claridge, Montreal (CA); Ljubomir Isakovic, Beaconsfield (CA); Michael Mannion, Montreal (CA); Stéphane Raeppel, St. Lazare (CA); Oscar Mario Saavedra, Montreal (CA); Frédéric Gaudette, Laval (CA); Lijie Zhan, Montreal (CA); Arkadii Vaisburg, Kirkland (CA)

(73) Assignee: MethylGene Inc., Montreal (CA)

( * ) Notice: Subject to any disclaimer, the term of this patent is extended or adjusted under 35 U.S.C. 154(b) by 389 days.

This patent is subject to a terminal disclaimer.

(21) Appl. No.: 12/200,939

(22) Filed: Aug. 29, 2008

(65) Prior Publication Data

US 2009/0264440 A1    Oct. 22, 2009

Related U.S. Application Data

(60) Provisional application No. 60/968,673, filed on Aug. 29, 2007.

(51) Int. Cl.
*C07D 513/02* (2006.01)
(52) U.S. Cl. ...................................... 546/114
(58) Field of Classification Search .............. 546/114
See application file for complete search history.

(56) References Cited

U.S. PATENT DOCUMENTS

| 8,003,662 | B2 * | 8/2011 | Blake et al. | 514/301 |
|---|---|---|---|---|
| 2004/0138251 | A1 | 7/2004 | Boschelli et al. | |
| 2007/0004675 | A1 | 1/2007 | Saavedra et al. | |
| 2007/0197537 | A1 * | 8/2007 | Blake et al. | 514/248 |
| 2009/0137580 | A1 | 5/2009 | Imamura et al. | |

FOREIGN PATENT DOCUMENTS

| CA | 2571680 | 1/2006 |
|---|---|---|
| CA | 2573538 | 2/2006 |
| CA | 2603125 | 10/2006 |
| CA | 2605680 | 11/2006 |
| CA | 2611370 | 11/2006 |
| CA | 2608726 | 5/2007 |
| CA | 2636242 | 5/2008 |
| WO | WO 97/17329 | 5/1997 |
| WO | WO 02/32872 | 4/2002 |
| WO | WO 02/088110 | 11/2002 |
| WO | WO 03/000660 | 1/2003 |
| WO | WO 2005/030140 | 4/2005 |
| WO | WO 2005/082855 | 9/2005 |
| WO | WO 2006104161 | * 5/2006 |
| WO | WO 2007/023768 | 3/2007 |
| WO | W02007/054831 | 5/2007 |
| WO | W02007/107005 | 9/2007 |
| WO | WO 2007/103308 | 9/2007 |
| WO | WO 2007/146824 | 12/2007 |
| WO | WO 2008/049855 | 5/2008 |

OTHER PUBLICATIONS

Wolff, Burger's medicinal Chemistry and Drug Discovery, vol. 1, Principles and Practice, John Wiley & sons, New York, 1997.*
West, Solid State Chemistry and Its Applications, John Wiley & Sons, 1984.*
Claridge et al.; "Discovery of a Novel and Potent Series of Thieno[3,2-b] Pyridine-Based Inhibitors of c-Met and VEGFR2 Tyrosine Kinases"; Bioorg. Med. Chem. Lett 18, 2793-2798, 2008.
Shafiee et al.; "Synthesis and Antihypertensive Activities of New 1, 4-Dihydropyridine Containing Nitroimidazolyl Substituent with a Nitrooxy Group at the 3-Ester Position"; Arch. Pharm. Pharm. Med. Chem, 2002, 2:69-76.
Klemm et al.; "Chemistry of Thienopyridines. XXXIII. Synthetic Routes to 5- and 7-Substituted Thieno[3,2-b] Pyridines from the N-Oxide"; J. Heterocyclic Chem., 1985, 22:1249-1252.
Wang et al.; "Selective Monolithiation of 2,5-Dibromopyridine with Butyllithium"; Tetrahedron Lett., 2000, 41:4335-4338.
Smolen et al.; "Amplification of MET May Identify a Subset of Cancers with Extreme Sensitivity to the Selective Tyrosine Kinase Inhibitor PHA-665752"; Proc. Natl. Acad. Sci., 2006, 2316-2321.
Miura et al.; "Effects of Hepatocyte Growth Factor on E-Cadherin-Mediated Cell-Cell Adhesion in DU145 Prostate Cancer Cells"; Urology, 2001, 58(6):1064-1069.
Nakamura et al.; "Induction of Hepatocyte Growth Factor in Fibroblasts by Tumor-Derived Factors Affects Invasive Growth of Tumor Cells: in Vitro Analysis of Tumor-Stromal Interactions"; Cancer Res., 1997, 57(15):3305-3313.

* cited by examiner

*Primary Examiner* — Nizal Chandrakumar
(74) *Attorney, Agent, or Firm* — Wood, Phillips, Katz, Clark & Mortimer

(57) ABSTRACT

This invention relates to compounds that inhibit protein tyrosine kinase activity. In particular the invention relates to compounds that inhibit the protein tyrosine kinase activity of growth factor receptors, resulting in the inhibition of receptor signaling, for example, the inhibition of VEGF receptor signaling and HGF receptor signaling. More particularly, the invention relates to compounds, compositions and methods for the inhibition of VEGF receptor signaling and HGF receptor signaling. The invention also provides compositions and methods for treating cell proliferative diseases and conditions.

49 Claims, No Drawings

INHIBITORS OF PROTEIN TYROSINE KINASE ACTIVITY

RELATED APPLICATIONS

This application claims the benefit of U.S. Provisional Application Ser. No. 60/968,673, filed Aug. 29, 2007. The entire teachings of the above-referenced application is incorporated herein by reference.

BACKGROUND OF THE INVENTION

1. Field of the Invention

This invention relates to compounds that inhibit protein tyrosine kinase activity. In particular the invention relates to compounds that inhibit the protein tyrosine kinase activity of growth factor receptors, resulting in the inhibition of receptor signaling, for example, the inhibition of VEGF receptor signaling and HGF receptor signaling. More particularly, the invention relates to compounds, compositions and methods for the inhibition of VEGF receptor signaling and HGF receptor signaling.

2. Summary of the Related Art

Tyrosine kinases may be classified as growth factor receptor (e.g. EGFR, PDGFR, FGFR and erbB2) or non-receptor (e.g. c-src and bcr-abl) kinases. The receptor type tyrosine kinases make up about 20 different subfamilies. The non-receptor type tyrosine kinases make up numerous subfamilies. These tyrosine kinases have diverse biological activity. Receptor tyrosine kinases are large enzymes that span the cell membrane and possess an extracellular binding domain for growth factors, a transmembrane domain, and an intracellular portion that functions as a kinase to phosphorylate a specific tyrosine residue in proteins and hence to influence cell proliferation. Aberrant or inappropriate protein kinase activity can contribute to the rise of disease states associated with such aberrant kinase activity.

Angiogenesis is an important component of certain normal physiological processes such as embryogenesis and wound healing, but aberrant angiogenesis contributes to some pathological disorders and in particular to tumor growth. VEGF-A (vascular endothelial growth factor A) is a key factor promoting neovascularization (angiogenesis) of tumors. VEGF induces endothelial cell proliferation and migration by signaling through two high affinity receptors, the fms-like tyrosine kinase receptor, Flt-1, and the kinase insert domain-containing receptor, KDR. These signaling responses are critically dependent upon receptor dimerization and activation of intrinsic receptor tyrosine kinase (RTK) activity. The binding of VEGF as a disulfide-linked homodimer stimulates receptor dimerization and activation of the RTK domain. The kinase activity autophosphorylates cytoplasmic receptor tyrosine residues, which then serve as binding sites for molecules involved in the propagation of a signaling cascade. Although multiple pathways are likely to be elucidated for both receptors, KDR signaling is most extensively studied, with a mitogenic response suggested to involve ERK-1 and ERK-2 mitogen-activated protein kinases.

Disruption of VEGF receptor signaling is a highly attractive therapeutic target in cancer, as angiogenesis is a prerequisite for all solid tumor growth, and that the mature endothelium remains relatively quiescent (with the exception of the female reproductive system and wound healing). A number of experimental approaches to inhibiting VEGF signaling have been examined, including use of neutralizing antibodies, receptor antagonists, soluble receptors, antisense constructs and dominant-negative strategies.

Despite the attractiveness of anti-angiogenic therapy by VEGF inhibition alone, several issues may limit this approach. VEGF expression levels can themselves be elevated by numerous diverse stimuli and perhaps most importantly, the hypoxic state of tumors resulting from VEGFr inhibition, can lead to the induction of factors that themselves promote tumor invasion and metastasis thus, potentially undermining the impact of VEGF inhibitors as cancer therapeutics.

The HGF (hepatocyte growth factor) and the HGF receptor, c-met, are implicated in the ability of tumor cells to undermine the activity of VEGF inhibition. HGF derived from either stromal fibroblasts surrounding tumor cells or expressed from the tumor itself has been suggested to play a critical role in tumor angiogenesis, invasion and metastasis. For example, invasive growth of certain cancer cells is drastically enhanced by tumor-stromal interactions involving the HGF/c-Met (HGF receptor) pathway. HGF, which was originally identified as a potent mitogen for hepatocytes is primarily secreted from stromal cells, and the secreted HGF can promote motility and invasion of various cancer cells that express c-Met in a paracrine manner. Binding of HGF to c-Met leads to receptor phosphorylation and activation of Ras/mitogen-activated protein kinase (MAPK) signaling pathway, thereby enhancing malignant behaviors of cancer cells. Moreover, stimulation of the HGF/c-met pathway itself can lead to the induction of VEGF expression, itself contributing directly to angiogenic activity.

Thus, anti-tumor anti-angiogenic strategies or approaches that target both VEGF/VEGFr signaling and HGF/c-met signaling may circumvent the ability of tumor cells to overcome VEGF inhibition alone and may represent improved cancer therapeutics.

Tyrosine kinases also contribute to the pathology of opthalmological diseases, disorders and conditions, such as age-related macular degeneration (AMD) and diabetic retinopathy (DR). Blindness from such diseases has been linked to anomalies in retinal neovascularization. The formation of new blood vessels is regulated by growth factors such as VEGF and HGF that activate receptor tyrosine kinases resulting in the initiation of signaling pathways leading to plasma leakage into the macula, causing vision loss. Recently, the Ax1 receptor tyrosine kinase has been implicated in the process of angiogenesis, by regulating cell survival, motility and invasions. These kinases are thus attractive targets for the treatment of eye diseases involving neovascularization.

Thus, there is a need to develop a strategy for controlling neovascularization of the eye and to develop a strategy for the treatment of ocular diseases.

Here we describe small molecules that are potent inhibitors of protein tyrosine kinase activity, such as that of, for example, both the VEGF receptor KDR and the HGF receptor c-met.

BRIEF SUMMARY OF THE INVENTION

The present invention provides new compounds and methods for treating a disease responsive to inhibition of kinase activity, for example a disease responsive to inhibition of protein tyrosine kinse activity, for example a disease responsive to inhibition of protein tyrosine kinase activity of growth factor receptors. The present invention also provides new compounds and methods for treating a disease responsive to inhibition of receptor type tyrosine kinase signaling, for example, a disease responsive to inhibition of VEGF receptor signaling and HGF receptor signaling. In one embodiment the disease is a cell proliferative disease. The compounds of the invention are inhibitors of protein tyrosine kinase activity. In one embodiment, the compounds of the invention are dual function inhibitors, capable of inhibiting both VEGF and HGF receptor signaling. Accordingly, the invention provides new inhibitors of protein tyrosine kinase receptor signaling, such as for example, VEGF receptor signaling and HGF receptor signaling, including the VEGF receptor KDR and the HGF receptor c-met.

In a first aspect, the invention provides compounds of Formula (I) that are useful as kinase inhibitors:

(I)

and N-oxides, hydrates, solvates, pharmaceutically acceptable salts, prodrugs and complexes thereof, and racemic and scalemic mixtures, diastereomers and enantiomers thereof, wherein D, M, Z, Ar and G are as defined herein. Because compounds of the present invention are useful as kinase inhibitors they are, therefore, useful research tools for the study of the role of kinases in both normal and disease states. In one embodiment, the invention provides compounds that are useful as inhibitors of VEGF receptor signaling and HGF receptor signaling and, therefore, are useful research tools for the study of the role of VEGF and HGF in both normal and disease states.

Reference to "a compound of the formula (I)", (or equivalently, "a compound according to the first aspect", or "a compound of the present invention", and the like), herein is understood to include reference to N-oxides, hydrates, solvates, pharmaceutically acceptable salts, prodrugs and complexes thereof, and racemic and scalemic mixtures, diastereomers, enantiomers and tautomers thereof, unless otherwise indicated.

In a second aspect, the invention provides compositions comprising a compound according to the present invention, or an N-oxide, hydrate, solvate, pharmaceutically acceptable salt, prodrug or complex thereof, or a racemic or scalemic mixture, diastereomers or enantiomer thereof, and a pharmaceutically acceptable carrier, excipient or diluent. For example, the invention provides compositions comprising a compound that is an inhibitor of VEGF receptor signaling and HGF receptor signaling, or a pharmaceutically acceptable salt thereof, and a pharmaceutically acceptable carrier, excipient, or diluent.

In a third aspect, the invention provides a method of inhibiting kinase activity, for example protein tyrosine kinase, for example tyrosine kinase activity of a growth factor receptor, the method comprising contacting the kinase with a compound according to the present invention, or with a composition according to the present invention. In another embodiment of this aspect, the invention provides a method of inhibiting receptor type tyrosine kinase signaling, for example inhibiting VEGF receptor signaling and HGF receptor signaling. Inhibition can be in a cell or a multicellular organism. If in a cell, the method according to this aspect of the invention comprises contacting the cell with a compound according to the present invention, or with a composition according to the present invention. If in a multicellular organism, the method according to this aspect of the invention comprises administering to the organism a compound according to the present invention, or a composition according to the present invention. In one embodiment the organism is a mammal, for example a primate, for example a human.

In a fourth aspect, the invention provides a method of inhibiting angiogenesis, the method comprising administering to a patient in need thereof a therapeutically effective amount of a compound according to the present invention, or a therapeutically effective amount of a composition according to the present invention. In one embodiment of this aspect, the angiogenesis to be inhibited is involved in tumor growth. In another embodiment the angiogenesis to be inhibited is retinal angiogenesis. In another embodiment of this aspect, the patient is a mammal, for example a primate, for example a human.

In a fifth aspect, the invention provides a method of treating a disease responsive to inhibition of kinase activity, for example a disease responsive to inhibition of protein tyrosine kinase activity, for example a disease responsive to inhibition of protein tyrosine kinase activity of growth factor receptors. In another embodiment of this aspect, the invention provides a method of treating a disease responsive to inhibition of receptor type tyrosine kinase signaling, for example a disease responsive to inhibition of VEGF receptor signaling and HGF receptor signaling, the method comprising administering to an organism in need thereof a therapeutically effective amount of a compound according to the present invention, or a composition according to the present invention. In one embodiment of this aspect, the organism is a mammal, for example a primate, for example a human.

In a sixth aspect, the invention provides a method of treating a cell proliferative disease, the method comprising administering to a patient in need thereof a therapeutically effective amount of a compound according to the present invention, or a therapeutically effective amount of a composition according to the present invention. In certain embodiments of this aspect, the cell proliferative disease is cancer. In an embodiment, the patient is a mammal, for example a primate, for example a human.

In a seventh aspect, the invention provides a method of treating an ophthalmic disease, disorder or condition, the method comprising administering to a patient in need thereof a therapeutically effective amount of a compound according to the present invention, or a therapeutically effective amount of a composition according to the present invention. In one embodiment of this aspect, the disease is caused by choroidal angiogenesis. In some embodiments of this aspect, the patient is a mammal, for example a primate, for example a human.

In an eighth aspect, the invention provides for the use of a compound according to the present invention for the manufacture of a medicament to inhibit kinase activity, for example to inhibit protein tyrosine kinase activity, for example to inhibit protein tyrosine kinase activity of growth factor receptors. In another embodiment of this aspect, the invention provides for the use of a compound according to the present invention for the manufacture of a medicament to inhibit receptor type tyrosine kinase signaling, for example to inhibit VEGF receptor signaling and HGF receptor signaling. In certain embodiments of this aspect, the invention provides for the use of a compound according to the present invention for the manufacture of a medicament to treat a disease responsive to inhibition of kinase activity. In certain embodiments of this aspect, the disease is responsive to inhibition of protein tyrosine kinase activity, for example inhibition of protein tyrosine kinase activity of growth factor receptors. In another embodiment of this aspect, the disease is responsive to inhibition of receptor type tyrosine kinase signaling, for example VEGF receptor signaling and HGF receptor signaling. In another embodiment embodiment, the disease is a cell proliferative disease, for example cancer. In another embodiment of this aspect, the disease is an ophthalmic disease, disorder or condition. In one embodiment of this aspect, the ophthalmic disease, disorder or condition is caused by choroidal angiogenesis. In another embodiment of this aspect, the disease is age-related macular degeneration, diabetic retinopathy or retinal edema.

In a nineth aspect, the invention provides for the use of a compound according to the present invention, or a composition thereof, to inhibit kinase activity, for example to inhibit receptor type tyrosine kinase activity, for example to inhibit protein tyrosine kinase activity of growth fractor receptors. In another embodiment of this aspect, the invention provides for the use of a compound according to the present invention, or a composition thereof, to inhibit receptor type tyrosine kinase signaling, for example to inhibit VEGF receptor signaling and HGF receptor signaling.

In a tenth aspect, the invention provides for the use of a compound according to the present invention, or a composition thereof, to treat a disease responsive to inhibition of kinase activity, for example a disease responsive to inhibition of protein tyrosine kinase activity, for example a disease responsive to inhibition or protein tyrosine kinase activity of growth factor receptors. In another embodiment of this aspect, the invention provides for the use of a compound according to the present invention, or a composition thereof, to treat a disease responsive to inhibition of receptor type tyrosine kinase signaling, for example a disease responsive to inhibition of VEGF receptor signaling and HGF receptor signaling. In an embodiment of this aspect, the disease is a cell proliferative disease, for example cancer. In another embodiment of this aspect, the disease is an ophthalmic disease, disorder or condition. In another embodiment of this aspect, the ophthalmic disease, disorder or condition is caused by choroidal angiogenesis.

The foregoing merely summarizes certain aspects of the invention and is not intended to be limiting in nature. These aspects and other aspects and embodiments are described more fully below.

DETAILED DESCRIPTION OF THE PREFERRED EMBODIMENTS

The invention provides compounds and methods for inhibiting kinase activity, for example protein tyrosine kinase activity, for example receptor protein kinase activity, for example the VEGF receptor KDR and the HGF receptor c-met. The invention also provides compositions and methods for inhibiting angiogenesis, treating a disease responsive to inhibition of kinase activity, treating cell proliferative diseases and conditions and treating ophthalmic diseases, disorders and conditions. The patent and scientific literature referred to herein reflects knowledge that is available to those with skill in the art. The issued patents, published patent applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which a divalent moiety is required and is stated as being "aryl," those skilled in the art will understand that the term "aryl" refers to the corresponding divalent moiety, arylene. All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—.

For simplicity, reference to a "$C_n$-$C_m$" heterocyclyl or "$C_n$-$C_m$" heteroaryl means a heterocyclyl or heteroaryl having from "n" to "m" annular atoms, where "n" and "m" are integers. Thus, for example, a $C_5$-$C_6$-heterocyclyl is a 5- or 6-membered ring having at least one heteroatom, and includes pyrrolidinyl ($C_5$) and piperazinyl and piperidinyl ($C_6$); $C_6$-heteroaryl includes, for example, pyridyl and pyrimidyl.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$ hydrocarbyl" includes a covalent bond, methyl, ethyl, ethenyl, ethynyl, propyl, propenyl, propynyl, and cyclopropyl.

The term "alkyl" is intended to mean a straight chain or branched aliphatic group having from 1 to 12 carbon atoms, alternatively 1-8 carbon atoms, and alternatively 1-6 carbon atoms. In some embodiments, the alkyl groups have from 2 to 12 carbon atoms, alternatively 2-8 carbon atoms and alternatively 2-6 carbon atoms. Examples of alkyl groups include, without limitation, methyl, ethyl, propyl, isopropyl, butyl, isobutyl, sec-butyl, tert-butyl, pentyl, hexyl and the like. A "$C_0$" alkyl (as in "$C_0$-$C_3$alkyl") is a covalent bond.

The term "alkenyl" is intended to mean an unsaturated straight chain or branched aliphatic group with one or more carbon-carbon double bonds, having from 2 to 12 carbon atoms, alternatively 2-8 carbon atoms, and alternatively 2-6 carbon atoms. Examples alkenyl groups include, without limitation, ethenyl, propenyl, butenyl, pentenyl, and hexenyl.

The term "alkynyl" is intended to mean an unsaturated straight chain or branched aliphatic group with one or more carbon-carbon triple bonds, having from 2 to 12 carbon atoms, alternatively 2-8 carbon atoms, and alternatively 2-6 carbon atoms. Examples of alkynyl groups include, without limitation, ethynyl, propynyl, butynyl, pentynyl, and hexynyl.

The terms "alkylene," "alkenylene," or "alkynylene" as used herein are intended to mean an alkyl, alkenyl, or alkynyl group, respectively, as defined hereinabove, that is positioned between and serves to connect two other chemical groups. Examples of alkylene groups include, without limitation, methylene, ethylene, propylene, and butylene. Examples of alkenylene groups include, without limitation, ethenylene, propenylene, and butenylene. Examples of alkynylene groups include, without limitation, ethynylene, propynylene, and butynylene.

The term "carbocycle" as employed herein is intended to mean a cycloalkyl or aryl moiety.

The term "cycloalkyl" is intended to mean a saturated, partially unsaturated or unsaturated mono-, bi-, tri- or polycyclic hydrocarbon group having about 3 to 15 carbons, alternatively having 3 to 12 carbons, alternatively 3 to 8 carbons, alternatively 3 to 6 carbons, and alternatively 5 or 6 carbons. In certain alternative embodiments, the cycloalkyl group is fused to an aryl, heteroaryl or heterocyclic group. Examples of cycloalkyl groups include, without limitation, cyclopenten-2-enone, cyclopenten-2-enol, cyclohex-2-enone, cyclohex-2-enol, cyclopropyl, cyclobutyl, cyclobutenyl, cyclopentyl, cyclopentenyl, cyclohexyl, cyclohexenyl, cycloheptyl, cyclooctyl, etc.

The term "heteroalkyl" is intended to mean a saturated, partially unsaturated or unsaturated, straight chain or branched aliphatic group, wherein one or more carbon atoms in the group are independently replaced by a heteroatom selected from the group consisting of O, S, and N.

The term "aryl" is intended to mean a mono-, bi-, tri- or polycyclic aromatic moiety, comprising one to three aromatic rings. In certain embodiments the aryl is a $C_6$-$C_{14}$ aromatic moiety, alternatively the aryl group is a $C_6$-$C_{10}$ aryl group, alternatively a $C_6$ aryl group. Examples of aryl groups include, without limitation, phenyl, naphthyl, anthracenyl, and fluorenyl.

The terms "aralkyl" or "arylalkyl" are intended to mean a group comprising an aryl group covalently linked to an alkyl group. If an aralkyl group is described as "optionally substituted", it is intended that either or both of the aryl and alkyl moieties may independently be optionally substituted or unsubstituted. In some embodiments, the aralkyl group is $(C_1$-$C_6)$alk$(C_6$-$C_{10})$aryl, including, without limitation, benzyl, phenethyl, and naphthylmethyl. For simplicity, when written as "arylalkyl" this term, and terms related thereto, is intended to indicate the order of groups in a compound as "aryl-alkyl". Similarly, "alkyl-aryl" is intended to indicate the order of the groups in a compound as "alkyl-aryl".

The terms "heterocyclyl", "heterocyclic" or "heterocycle" are intended to mean a group which is a mono-, bi-, or polycyclic structure having from about 3 to about 14 atoms, wherein one or more atoms are independently selected from the group consisting of N, O, and S. The ring structure may be saturated, unsaturated or partially unsaturated. In certain embodiments, the heterocyclic group is non-aromatic, in which case the group is also known as a heterocycloalkyl. In a bicyclic or polycyclic structure, one or more rings may be aromatic; for example, one ring of a bicyclic heterocycle or one or two rings of a tricyclic heterocycle may be aromatic, as in indan and 9,10-dihydro anthracene. Examples of heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In certain embodiments, the heterocyclic group is a heteroaryl group. As used herein, the term "heteroaryl" is intended to mean a mono-, bi-, tri- or polycyclic group having 5 to 14 ring atoms, alternatively 5, 6, 9, or 10 ring atoms; having 6, 10, or 14 pi electrons shared in a cyclic array; and having, in addition to carbon atoms, between one or more heteroatoms independently selected from the group consisting of N, O, and S. For example, a heteroaryl group include, without limitation, pyrimidinyl, pyridinyl, benzimidazolyl, thienyl, benzothiazolyl, benzofuranyl and indolinyl. Other examples of heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

The terms "arylene," "heteroarylene," or "heterocyclylene" are intended to mean an aryl, heteroaryl, or heterocyclyl group, respectively, as defined hereinabove, that is positioned between and serves to connect two other chemical groups.

Examples of heterocyclyls and heteroaryls include, but are not limited to, azepinyl, azetidinyl, acridinyl, azocinyl, benzidolyl, benzimidazolyl, benzofuranyl, benzofurazanyl, benzofuryl, benzothiofuranyl, benzothiophenyl, benzoxazolyl, benzothiazolyl, benzothienyl, benztriazolyl, benztetrazolyl, benzisoxazolyl, benzisothiazolyl, benzimidazolinyl, benzoxazolyl, benzoxadiazolyl, benzopyranyl, carbazolyl, 4aH-carbazolyl, carbolinyl, chromanyl, chromenyl, cinnolinyl, coumarinyl, decahydroquinolinyl, 1,3-dioxolane, 2H,6H-1,5,2-dithiazinyl, dihydrofuro[2,3-b]tetrahydrofuran, dihydroisoindolyl, dihydroquinazolinyl (such as 3,4-dihydro-4-oxo-quinazolinyl), furanyl, furopyridinyl (such as fuor[2,3-c]pyridinyl, furo[3,2-b]pyridinyl or furo[2,3-b]pyridinyl), furyl, furazanyl, hexahydrodiazepinyl, imidazolidinyl, imidazolinyl, imidazolyl, indazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolidinyl, isothiazolyl, isoxazolinyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxetanyl, 2-oxoazepinyl, 2-oxopiperazinyl, 2-oxopiperidinyl, 2-oxopyrrolodinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolopyridyl, 2H-pyrrolyl, pyrrolyl, quinazolinyl, quinolinyl, 4H-quinolizinyl, quinoxalinyl, quinuclidinyl, tetrahydro-1,1-dioxothienyl, tetrahydrofuranyl, tetrahydrofuryl, tetrahydroisoquinolinyl, tetrahydroquinolinyl, tetrahydropyranyl, tetrazolyl, thiazolidinyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thiamorpholinyl, thiamorpholinyl sulfoxide, thiamorpholuiyl sulfone, thianthrenyl, thiazolyl, thienyl, thienothiazolyl, thienooxazolyl, thienoimidazolyl, thiophenyl, triazinyl, triazinylazepinyl, triazolyl (e.g., 1,2,3-triazolyl, 1,2,4-triazolyl, 1,2,5-triazolyl, 1,3,4-triazolyl), and xanthenyl.

The term "azolyl" as employed herein is intended to mean a five-membered saturated or unsaturated heterocyclic group containing two or more hetero-atoms, as ring atoms, selected from the group consisting of nitrogen, sulfur and oxygen, wherein at least one of the hetero-atoms is a nitrogen atom. Examples of azolyl groups include, but are not limited to, optionally substituted imidazolyl, oxazolyl, thiazolyl, pyrazolyl, isoxazolyl, isothiazolyl, 1,3,4-thiadiazolyl, 1,2,4-thiadiazolyl, 1,2,4-oxadiazolyl, and 1,3,4-oxadiazolyl.

As employed herein, and unless stated otherwise, when a moiety (e.g., alkyl, heteroalkyl, cycloalkyl, aryl, heteroaryl, heterocyclyl, etc.) is described as "optionally substituted" it is meant that the group optionally has from one to four, alternatively from one to three, alternatively one or two, independently selected non-hydrogen substituents. Suitable substituents include, without limitation, halo, hydroxy, oxo (e.g., an annular —CH— substituted with oxo is —C(O)—) nitro, halohydrocarbyl, hydrocarbyl, alkyl, cycloalkyl, heterocyclyl, aryl, heteroaryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

Examples of substituents, which are themselves not further substituted (unless expressly stated otherwise) are:

(a) halo, cyano, oxo, carboxy, formyl, nitro, amino, amidino, guanidino, (b) $C_1$-$C_5$alkyl or alkenyl or arylalkyl imino, carbamoyl, azido, carboxamido, mercapto, hydroxy, hydroxyalkyl, alkylaryl, arylalkyl, $C_1$-$C_8$alkyl, $C_1$-$C_8$alkenyl, $C_1$-$C_8$alkoxy, $C_1$-$C_8$alkyamino, $C_1$-$C_8$alkoxycarbonyl, aryloxycarbonyl, $C_2$-$C_8$acyl, $C_2$-$C_8$acylamino, $C_1$-$C_8$alkylthio, arylalkylthio, arylthio, $C_1$-$C_8$alkylsulfinyl, arylalkylsulfinyl, arylsulfinyl, $C_1$-$C_8$alkylsulfonyl, arylalkylsulfonyl, arylsulfonyl, $C_0$-$C_6$N-alkyl carbamoyl, $C_2$-$C_{15}$N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$heterocycle, $C_5$-$C_{15}$heteroaryl or any of these rings fused or spiro-fused to a cycloalkyl, heterocyclyl, or aryl, wherein each of the foregoing is further optionally substituted with one more moieties listed in (a), above; and (c) —$(CR^{32}R^{33})_s$—$NR^{30}R^{31}$, wherein s is from 0 (in which case the nitrogen is directly bonded to the moiety that is substituted) to 6, $R^{32}$ and $R^{33}$ are each independently hydrogen, halo, hydroxyl or $C_1$-$C_4$alkyl, and $R^{30}$ and $R^{31}$ are each independently hydrogen, cyano, oxo, hydroxyl, $C_1$-$C_8$alkyl, $C_1$-$C_8$heteroalkyl, $C_1$-$C_8$alkenyl, carboxamido, $C_1$-$C_3$alkyl-carboxamido, carboxamido-$C_1$-$C_3$alkyl, amidino, $C_2$-$C_8$hydroxyalkyl, $C_1$-$C_3$alkylaryl, aryl-$C_1$-$C_3$alkyl, $C_1$-$C_3$alkylheteroaryl, heteroaryl-$C_1$-$C_3$alkyl, $C_1$-$C_3$alkylheterocyclyl, heterocyclyl-$C_1$-$C_3$alkyl $C_1$-$C_3$alkylcycloalkyl, cycloalkyl-$C_1$-$C_3$alkyl, $C_2$-$C_8$alkoxy, $C_2$-$C_8$alkoxy-$C_1$-$C_4$alkyl, $C_1$-$C_8$alkoxycarbonyl, aryloxycarbonyl, aryl-$C_1$-$C_3$alkoxycarbonyl, heteroaryloxycarbonyl, heteroaryl-$C_1$-$C_3$alkoxycarbonyl, $C_1$-$C_8$acyl, $C_0$-$C_8$alkyl-carbonyl, aryl-$C_0$-$C_8$alkyl-carbonyl, heteroaryl-$C_0$-$C_8$alkyl-carbonyl, cycloalkyl-$C_0$-$C_8$alkyl-carbonyl, $C_0$-$C_8$alkyl-NH-carbonyl, aryl-$C_0$-$C_8$alkyl-NH-carbonyl, heteroaryl-$C_0$-$C_8$alkyl-NH-carbonyl, cycloalkyl-$C_0$-$C_8$alkyl-NH-carbonyl, $C_0$-$C_8$alkyl-O-carbonyl, aryl-$C_0$-$C_8$alkyl-O-carbonyl, heteroaryl-$C_0$-$C_8$alkyl-O-carbonyl, cycloalkyl-$C_0$-$C_8$alkyl-O-carbonyl, $C_1$-$C_8$alkylsulfonyl, arylalkylsulfonyl, arylsulfonyl, heteroarylalkylsulfonyl, heteroarylsulfonyl, $C_1$-$C_8$alkyl-NH-sulfonyl, arylalkyl-NH-sulfonyl, aryl-NH-sulfonyl, heteroarylalkyl-NH-sulfonyl, heteroaryl-NH-sulfonyl aroyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, or protecting group, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$—$Y^{31}$—), wherein said heterocyclyl may also be bridged (forming a bicyclic moiety with a methylene, ethylene or propylene bridge); wherein $X^{30}$ is selected from the group consisting of $C_1$-$C_8$alkyl, $C_2$-$C_8$alkenyl-, $C_2$-$C_8$alkynyl-, —$C_0$-$C_3$alkyl-$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O—$C_0$-$C_3$alkyl-, HO—$C_0$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, (N($R^{30}$)($R^{31}$))$_2$—C═N—, $C_0$-$C_3$alkyl-S(O)$_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents from (a); and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C(N$R^{30}$)—N($R^{31}$)—, —N($R^{30}$)—C(N$R^{31}$)—, —C(N$R^{31}$)—N($R^{30}$)—, —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S(O)$_{0-2}$—, —SO$_2$N($R^{31}$)—, —N($R^{31}$)—SO$_2$— and —N($R^{30}$)—SO$_2$N($R^{31}$)—.

A moiety that is substituted is one in which one or more (for example one to four, alternatively from one to three and alternatively one or two), hydrogens have been independently replaced with another chemical substituent. As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted n-octyls include 2,4-dimethyl-5-ethyl-octyl and 3-cyclopentyl-octyl. Included within this definition are methylenes (—CH$_2$—) substituted with oxygen to form carbonyl —CO—.

When there are two optional substituents bonded to adjacent atoms of a ring structure, such as for example a phenyl, thiophenyl, or pyridinyl, the substituents, together with the atoms to which they are bonded, optionally form a 5- or 6-membered cycloalkyl or heterocycle having 1, 2, or 3 annular heteroatoms.

In certain embodiments, a hydrocarbyl, heteroalkyl, heterocyclic and/or aryl group is unsubstituted.

In other embodiments, a hydrocarbyl, heteroalkyl, heterocyclic and/or aryl group is substituted with from 1 to 3 independently selected substituents.

Examples of substituents on alkyl groups include, but are not limited to, hydroxyl, halogen (e.g., a single halogen substituent or multiple halo substituents; in the latter case, groups such as $CF_3$ or an alkyl group bearing $Cl_3$), oxo, cyano, nitro, alkyl, cycloalkyl, alkenyl, cycloalkenyl, alkynyl, heterocycle, aryl, —OR$^a$, —SR$^a$, —S(═O)R$^e$, —S(═O)$_2$R$^e$, —P(═O)$_2$R$^e$, —S(═O)$_2$OR$^e$, —P(═O)$_2$OR$^e$, —NR$^b$R$^c$, —NR$^b$S(═O)$_2$R$^e$, —NR$^b$P(═O)$_2$R$^e$, —S(═O)$_2$NR$^b$R$^c$, —P(═O)$_2$NR$^b$R$^c$, —C(═O)OR$^e$, —C(═O)R$^a$, —C(═O)NR$^b$R$^c$, —OC(═O)R$^a$, —OC(═O)NR$^b$R$^c$, —NR$^b$C(═O)OR$^e$, —NR$^d$C(═O)NR$^b$R$^c$, —NR$^d$S(═O)$_2$NR$^b$R$^c$, —NR$^d$P(═O)$_2$NR$^b$R$^c$, —NR$^b$C(═O)R$^a$ or —NR$^b$P(═O)$_2$R$^e$, wherein R$^a$ is hydrogen, alkyl, cycloalkyl, alkenyl, cycloalkenyl, alkynyl, heterocycle or aryl; R$^b$, R$^c$ and R$^d$ are independently hydrogen, alkyl, cycloalkyl, heterocycle or aryl, or said R$^b$ and R$^c$ together with the N to which they are bonded optionally form a heterocycle; and R$^e$ is alkyl, cycloalkyl, alkenyl, cycloalkenyl, alkynyl, heterocycle or aryl. In the aforementioned exemplary substituents, groups such as alkyl, cycloalkyl, alkenyl, alkynyl, cycloalkenyl, heterocycle and aryl can themselves be optionally substituted.

Examples of substituents on alkenyl and alkynyl groups include, but are not limited to, alkyl or substituted alkyl, as well as those groups recited as examples of alkyl substituents.

Examples of substituents on cycloalkyl groups include, but are not limited to, nitro, cyano, alkyl or substituted alkyl, as well as those groups recited above as examples of alkyl substituents. Other examples of substituents include, but are not limited to, spiro-attached or fused cyclic substituents, for example, spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Examples of substituents on cycloalkenyl groups include, but are not limited to, nitro, cyano, alkyl or substituted alkyl, as well as those groups recited as examples of alkyl substituents. Other examples of substituents include, but are not limited to, spiro-attached or fused cyclic substituents, for examples spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Examples of substituents on aryl groups include, but are not limited to, nitro, cycloalkyl or substituted cycloalkyl, cycloalkenyl or substituted cycloalkenyl, cyano, alkyl or substituted alkyl, as well as those groups recited above as examples of alkyl substituents. Other examples of substituents include, but are not limited to, fused cyclic groups, such as fused cycloalkyl, fused cycloalkenyl, fused heterocycle, or fused aryl, where the aforementioned cycloalkyl, cylcoalkenyl, heterocycle and aryl substituents can themselves be optionally substituted. Still other examples of substituents on aryl groups (phenyl, as a non-limiting example) include, but are not limited to, haloalkyl and those groups recited as examples of alkyl substituents.

Examples of substituents on heterocylic groups include, but are not limited to, cycloalkyl, substituted cycloalkyl, cycloalkenyl, substituted cycloalkenyl, nitro, oxo (i.e., =O), cyano, alkyl, substituted alkyl, as well as those groups recited as examples of alkyl substituents. Other examples substituents on heterocyclic groups include, but are not limited to, spiro-attached or fused cylic substituents at any available point or points of attachment, for example spiro-attached cycloalkyl, spiro-attached cycloalkenyl, spiro-attached heterocycle (excluding heteroaryl), fused cycloalkyl, fused cycloakenyl, fused heterocycle and fused aryl, where the aforementioned cycloalkyl, cycloalkenyl, heterocycle and aryl substituents can themselves be optionally substituted.

In certain embodiments, a heterocyclic group is substituted on carbon, nitrogen and/or sulfur at one or more positions. Examples of substituents on nitrogen include, but are not limited to alkyl, aryl, aralkyl, alkylcarbonyl, alkylsulfonyl, arylcarbonyl, arylsulfonyl, alkoxycarbonyl, or aralkoxycarbonyl. Examples of substituents on sulfur include, but are not limited to, oxo and $C_{1-6}$alkyl. In certain embodiments, nitrogen and sulfur heteroatoms may independently be optionally oxidized and nitrogen heteroatoms may independently be optionally quaternized.

Exemplary substituents on ring groups, such as aryl, heteroaryl, cycloalkyl and heterocyclyl, include halogen, alkoxy and alkyl.

Exemplary substituents on alkyl groups include halogen and hydroxy.

A "halohydrocarbyl" as employed herein is a hydrocarbyl moiety, in which from one to all hydrogens have been replaced with one or more halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include $NH_2$, alkylamino, dialkylamino (wherein each alkyl may be the same or different), arylamino, and cyclic amino groups. The term "ureido" as employed herein refers to a substituted or unsubstituted urea moiety.

The term "radical" as used herein means a chemical moiety comprising one or more unpaired electrons.

Where optional substituents are chosen from "one or more" groups it is to be understood that this definition includes all substituents being chosen from within one of the specified groups or from within the combination of all of the specified groups.

In addition, substituents on cyclic moieties (i.e., cycloalkyl, heterocyclyl, aryl, heteroaryl) include 5- to 6-membered mono- and 9- to 14-membered bi-cyclic moieties fused to the parent cyclic moiety to form a bi- or tri-cyclic fused ring system. Substituents on cyclic moieties also include 5- to 6-membered mono- and 9- to 14-membered bi-cyclic moieties attached to the parent cyclic moiety by a covalent bond to form a bi- or tri-cyclic bi-ring system. For example, an optionally substituted phenyl includes, but is not limited to, the following:

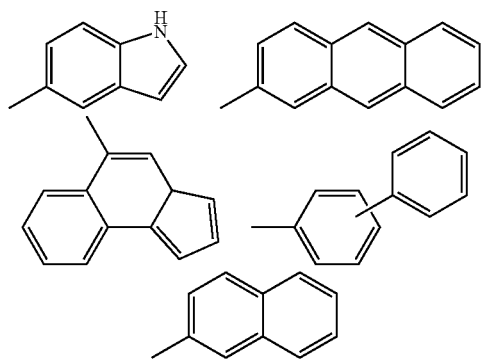

An "unsubstituted" moiety (e.g., unsubstituted cycloalkyl, unsubstituted heteroaryl, etc.) means a moiety as defined above that does not have any optional substituents.

A saturated, partially unsaturated or unsaturated three- to eight-membered carbocyclic ring is for example a four- to seven-membered, alternatively a five- or six-membered, saturated or unsaturated carbocyclic ring. Examples of saturated or unsaturated three- to eight-membered carbocyclic rings include phenyl, cyclopropyl, cyclobutyl, cyclopentyl, cyclohexyl, and cycloheptyl.

A saturated, partially unsaturated or unsaturated three- to eight-membered heterocyclic ring contains at least one heteroatom selected from oxygen, nitrogen, and sulfur atoms. The saturated or unsaturated three- to eight-membered heterocyclic ring for example contains one or two heteroatoms with the remaining ring-constituting atoms being carbon atoms. The saturated or unsaturated three- to eight-membered heterocyclic ring is alternatively a saturated or unsaturated four- to seven-membered heterocyclic ring, alternatively a saturated or unsaturated five- or six-membered heterocyclic ring. Examples of saturated or unsaturated three- to eight-membered heterocyclic groups include thienyl, pyridyl, 1,2,3-triazolyl, imidazolyl, isoxazolyl, pyrazolyl, piperazinyl, piperazino, piperidyl, piperidino, morpholinyl, morpholino, homopiperazinyl, homopiperazino, thiomorpholinyl, thiomorpholino, tetrahydropyrrolyl, and azepanyl.

A saturated or unsaturated carboxylic and heterocyclic group may condense with another saturated or heterocyclic group to form a bicyclic group, for example a saturated or unsaturated nine- to twelve-membered bicyclic carbocyclic or heterocyclic group. Bicyclic groups include naphthyl, quinolyl, 1,2,3,4-tetrahydroquinolyl, 1,4-benzoxanyl, indanyl, indolyl, and 1,2,3,4-tetrahydronaphthyl.

When a carbocyclic or heterocyclic group is substituted by two $C_{1-6}$ alkyl groups, the two alkyl groups may combine together to form an alkylene chain, for example a $C_{1-3}$ alkylene chain. Carbocyclic or heterocyclic groups having this crosslinked structure include bicyclo[2.2.2]octanyl and norbornanyl.

The terms "kinase inhibitor" and "inhibitor of kinase activity", and the like, are used to identify a compound which is capable of interacting with a kinase and inhibiting its enzymatic activity.

The term "inhibiting kinase enzymatic activity" is used to mean reducing the ability of a kinase to transfer a phosphate group from a donor molecule, such as ATP, to a specific target molecule (substrate). For example, the inhibition of kinase activity may be at least about 10%. In some embodiments of the invention, such reduction of kinase activity is at least about 25%, alternatively at least about 50%, alternatively at least about 75%, and alternatively at least about 90%. In other embodiments, kinase activity is reduced by at least 95% and alternatively by at least 99%. The $IC_{50}$ value is the concentration of kinase inhibitor which reduces the activity of a kinase to 50% of the uninhibited enzyme.

The terms "inhibitor of VEGF receptor signaling" and "inhibitor of HGF receptor signaling" are used to identify a compound having a structure as defined herein, which is capable, respectively, of interacting with a VEGF receptor and a HGF receptor and inhibiting the activity of the VEGF receptor and the HGF receptor. In some embodiments, such reduction of activity is at least about 50%, alternatively at least about 75%, and alternatively at least about 90%. In other embodiments, activity is reduced by at least 95% and alternatively by at least 99%.

The term "inhibiting effective amount" is meant to denote a dosage sufficient to cause inhibition of kinase activity. The kinase may be in a cell, which in turn may be in a multicellular organism. The multicellular organism may be, for example, a plant, a fungus or an animal, for example a mammal and for example a human. The fungus may be infecting a plant or a mammal, for example a human, and could therefore be located in and/or on the plant or mammal. If the kinase is in a multicellular organism, the method according to this aspect of the invention comprises the step of administering to the organism a compound or composition according to the present invention.

In an exemplary embodiment, such inhibition is specific, i.e., the kinase inhibitor reduces the ability of a kinase to transfer a phosphate group from a donor molecule, such as ATP, to a specific target molecule (substrate) at a concentration that is lower than the concentration of the inhibitor that is required to produce another, unrelated biological effect. For example, the concentration of the inhibitor required for kinase inhibitory activity is at least 2-fold lower, alternatively at least 5-fold lower, alternatively at least 10-fold lower, and alternatively at least 20-fold lower than the concentration required to produce an unrelated biological effect.

The term "therapeutically effective amount" as employed herein is an amount of a compound of the invention, that when administered to a patient, elicits the desired therapeutic effect. The therapeutic effect is dependent upon the disease being treated and the results desired. As such, the therapeutic effect can be treatment of a disease-state. Further, the therapeutic effect can be inhibition of kinase activity. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art.

In one embodiment, the therapeutic effect is inhibition of angiogenesis. The phrase "inhibition of angiogenesis" is used to denote an ability of a compound according to the present invention to retard the growth of blood vessels, preferably new blood vessels contacted with the inhibitor as compared to blood vessels not contacted. In one embodiment, angiogenesis is tumor angiogenesis. The phrase "tumor angiogenesis" is intended to mean the proliferation of blood vessels that penetrate into a cancerous growth, such as a tumor. In another embodiment, angiogenesis is abnormal blood vessel formation in the eye.

In an exemplary embodiment, angiogenesis is retarded by at least 25% as compared to angiogenesis of non-contacted blood vessels, alternatively at least 50%, alternatively at least 75%, alternatively at least 90%, alternatively at least 95%, and alternatively, at least 99%. Alternatively, angiogenesis is inhibited by 100% (i.e., the blood vessels do not increase in size or number). In certain embodiments, the phrase "inhibition of angiogenesis" includes regression in the number or size of blood vessels, as compared to non-contacted blood vessels. Thus, a compound according to the invention that inhibits angiogenesis may induce blood vessel growth retardation, blood vessel growth arrest, or induce regression of blood vessel growth.

In another embodiment, the therapeutic effect is treatment of an ophthalmic diseases, disorder or condition. The phrase "treatment of an ophthalmic disease or disorder" is intended to mean the ability of a compound according to the present invention to treat an exudative and/or inflammatory ophthalmic disease or disorder, a disorder related to impaired retinal vessel permeability and/or integrity, a disorder related to retinal microvessel rupture leading to focal hemorrhage, a disease of the back of the eye, a retinal disease, or a disease of the front of the eye, or other ophthalmic disease, disorder or condition.

In one embodiment, the ophthalmic disease, disorder or condition includes but is not limited to Age Related Macular Degeneration (ARMD), exudative macular degeneration (also known as "wet" or neovascular age-related macular degeneration (wet-AMD), macular oedema, aged disciform macular degeneration, cystoid macular oedema, palpebral oedema, retinal oedema, diabetic retinopathy, Acute Macular Neuroretinopathy, Central Serous Chorioretinopathy, chorioretinopathy, Choroidal Neovascularization, neovascular maculopathy, neovascular glaucoma, obstructive arterial and venous retinopathies (e.g. Retinal Venous Occlusion or Retinal Arterial Occlusion), Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angitis, Sickle Cell Retinopathy and other Hemoglobinopathies, Angioid Streaks, macular oedema occurring as a result of aetiologies such as disease (e.g. Diabetic Macular Oedema), eye injury or eye surgery, retinal ischemia or degeneration produced for example by injury, trauma or tumours, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, an ocular inflammatory disease caused by bacterial or viral infection or by an ophthalmic operation, an ocular inflammatory disease caused by a physical injury to the eye, and a symptom caused by an ocular inflammatory disease including itching, flare, oedema and ulcer, erythema, erythema exsudativum multiforme, erythema nodosum, erythema annulare, scleroedema, dermatitis, angioneurotic oedema, laryngeal oedema, glottic oedema, subglottic laryngitis, bronchitis, rhinitis, pharyngitis, sinusitis, laryngitis or otitis media.

In another embodiment, the ophthalmic disease, disorder or condition includes but is not limited to age-related macular degeneration, diabetic retinopathy, retinal edema, retinal vein occlusion, neovascular glaucoma, retinopathy of prematurity, pigmentary retinal degeneration, uveitis, corneal neovascularization or proliferative vitreoretinopathy.

In another embodiment, the ophthalmic disease, disorder or condition is age-related macular degeneration, diabetic retinopathy or retinal edema.

In another embodiment, the therapeutic effect is inhibition of retinal neovascularization. The phrase "inhibition of retinal neovascularization" is intended to mean the ability of a compound according to the present invention to retard the growth of blood vessels in the eye, for example new blood vessels originating from retinal veins, for example, to retard the growth of new blood vessels originating from retinal veins and extending along the inner (vitreal) surface of the retina.

In an exemplary embodiment, retinal neovascularization is retarded by at least 25% as compared to retinal neovascularization of non-contacted blood vessels, alternatively at least 50%, alternatively at least 75%, alternatively at least 90%, alternatively at least 95%, and alternatively, at least 99%. Alternatively, retinal neovascularization is inhibited by 100% (i.e., the blood vessels do not increase in size or number). In certain embodiments, the phrase "inhibition of retinal neovascularization" includes regression in the number or size of blood vessels, as compared to non-contacted blood vessels. Thus, a compound according to the invention that inhibits retinal neovascularization may induce blood vessel growth retardation, blood vessel growth arrest, or induce regression of blood vessel growth.

In another embodiment, the therapeutic effect is inhibition of cell proliferation. The phrase "inhibition of cell proliferation" is used to denote an ability of a compound according to the present invention to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers or comparing the size of the growth of contacted cells with non-contacted cells.

In an exemplary embodiment, growth of cells contacted with the inhibitor is retarded by at least 25% as compared to growth of non-contacted cells, alternatively at least 50%, alternatively at least 75%, alternatively at least 90%, alternatively at least 95%, and alternatively, at least 99%. Alternatively, cell proliferation is inhibited by 100% (i.e., the contacted cells do not increase in number). In certain embodiments, the phrase "inhibition cell proliferation" includes a reduction in the number or size of contacted cells, as compared to non-contacted cells. Thus, a compound according to the invention that inhibits cell proliferation in a contacted cell may induce the contacted cell to undergo growth retardation, to undergo growth arrest, to undergo programmed cell death (i.e., to apoptose), or to undergo necrotic cell death.

In some embodiments, the contacted cell is a neoplastic cell. The term "neoplastic cell" is used to denote a cell that shows aberrant cell growth. In certain embodiments, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth.

In some embodiments, the contacted cell is in an animal. Thus, the invention provides a method for treating a cell proliferative disease or condition in an animal, comprising administering to an animal in need of such treatment a therapeutically effective amount of a compound or composition of the invention. In certain exemplary embodiments, the animal is a mammal, for example a domesticated mammal. In some embodiments, the animal is a human.

The term "cell proliferative disease or condition" is meant to refer to any condition characterized by aberrant cell growth, preferably abnormally increased cellular proliferation. Examples of such cell proliferative diseases or conditions amenable to inhibition and treatment include, but are not limited to, cancer. Examples of particular types of cancer include, but are not limited to, breast cancer, lung cancer, colon cancer, rectal cancer, bladder cancer, prostate cancer leukemia and renal cancer. In particular embodiments, the invention provides a method for inhibiting neoplastic cell proliferation in an animal comprising administering to an animal having at least one neoplastic cell present in its body a therapeutically effective amount of a compound of the invention.

The term "patient" as employed herein for the purposes of the present invention includes humans and other animals, for example mammals, and other organisms. Thus the compounds, compositions and methods of the present invention are applicable to both human therapy and veterinary applications. In certain embodiments the patient is a mammal, for example a human.

The terms "treating", "treatment", or the like, as used herein covers the treatment of a disease-state in an organism, and includes at least one of: (i) preventing the disease-state from occurring, in particular, when such animal is predisposed to the disease-state but has not yet been diagnosed as having it; (ii) inhibiting the disease-state, i.e., partially or completely arresting its development; (iii) relieving the disease-state, i.e., causing regression of symptoms of the disease-state, or ameliorating a symptom of the disease; and (iv) reversal or regression of the disease-state, preferably eliminating or curing of the disease. In certain embodiments of the present invention the organism is an animal, for example a mammal, for example a primate, for example a human. As is known in the art, adjustments for systemic versus localized delivery, age, body weight, general health, sex, diet, time of administration, drug interaction, the severity of the condition, etc., may be necessary, and will be ascertainable with routine experimentation by one of ordinary skill in the art. In certain embodiments, the terms "treating", "treatment", or the like, as used herein covers the treatment of a disease-state in an organism and includes at least one of (ii), (iii) and (iv) above.

Administration may be by any route, including, without limitation, parenteral, oral, sublingual, transdermal, topical, intranasal, intratracheal, or intrarectal. In certain embodiments, compounds of the invention are administered intravenously in a hospital setting. In certain other embodiments, administration may be by the oral route.

Examples of routes of administration for ophthalmic diseases, disorders and conditions include but are not limited to, systemic, periocular, retrobulbar, intracanalicular, intravitral injection, topical (for example, eye drops), subconjunctival injection, subtenon, transcleral, intracameral, subretinal, electroporation, and sustained-release implant. Other routes of administration other injection sites or other forms of administration for ophthalmic situations will be known or contemplated by one skilled in the art and are intended to be within the scope of the present invention.

In certain embodiments of the present invention, routes of administration for ophthalmic diseases, disorders and conditions include topical, subconjunctival injection, intravitreal injection, or other ocular routes, systemically, or other methods known to one skilled in the art to a patient following ocular surgery.

In certain other embodiments of the present invention, routes of administration for ophthalmic diseases, disorders and conditions include topical, intravitreal, transcleral, periocular, conjunctival, subtenon, intracameral, subretinal, subconjunctival, retrobulbar, or intracanalicular.

In certain other embodiments of the present invention, routes of administration for ophthalmic diseases, disorders and conditions include topical administration (for example, eye drops), systemic administration (for example, oral or intravenous), subconjunctival injection, periocular injection, intravitreal injection, and surgical implant.

In certain other embodiments of the present invention, routes of administration for ophthalmic diseases, disorders and conditions include intravitreal injection, periocular injection, and sustained-release implant.

In certain other embodiments of the present invention, an intraocular injection may be into the vitreous (intravitreal), under the conjunctiva (subconjunctival), behind the eye (retrobulbar), into the sclera, under the Capsule of Tenon (sub-Tenon), or may be in a depot form.

The compounds of the present invention form salts which are also within the scope of this invention. Reference to a compound of the invention, for example a compound of Formula (I), herein is understood to include reference to salts thereof, unless otherwise indicated.

The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic (exhibiting minimal or no undesired toxicological effects), physiologically acceptable) salts are preferred, although other salts are also useful, e.g., in isolation or purification steps which may be employed during preparation. Salts of the compounds of the invention may be formed, for example, by reacting a compound of the present invention with an amount of acid or base, such as an equivalent amount, in a medium such as one in which the salts precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfanotes (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl and butyl chlorides, bromides and iodides), dialkyl sulfates (e.g. dimethyl, diethyl, dibuty and diamyl sulfates), long chain halides (e.g. decyl, lauryl, myristyl and stearyl chlorides, bromides and iodides), aralkyl halides (e.g. benzyl and phenethyl bromides), and others.

As used herein, the term "pharmaceutically acceptable salts" is intended to mean salts that retain the desired biological activity of the above-identified compounds and exhibit minimal or no undesired toxicological effects. Examples of such salts include, but are not limited to, salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. Other salts include pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Another aspect of the invention provides compositions including a compound, N-oxide, hydrate, solvate, pharmaceutically acceptable salt, complex or prodrug of a compound according to the present invention as described herein, or a racemic mixture, scalemic mixture, diastereomer, enantiomer or tautomer thereof. For example, in one embodiment of the invention, a composition comprises a compound, N-oxide, hydrate, solvate, pharmaceutically acceptable salt, complex or prodrug of a compound according to the present invention as described herein present in at least about 30% enantiomeric or diastereomeric excess. In certain embodiments of the invention, the compound, N-oxide, hydrates, solvate, pharmaceutically acceptable salt, complex or prodrug is present in at least about 50%, at least about 80%, or even at least about 90% enantiomeric or diastereomeric excess. In certain other embodiments of the invention, the compound, N-oxide, hydrate, solvate, pharmaceutically acceptable salt, complex or prodrug is present in at least about 95%, alternatively at least about 98% and alternatively at least about 99% enantiomeric or diastereomeric excess. In other embodiments of the invention, a compound, N-oxide, hydrate, solvate, pharmaceutically acceptable salt, complex or prodrug is present as a substantially racemic mixture.

Some compounds of the invention may have chiral centers and/or geometric isomeric centers (E- and Z-isomers), and it is to be understood that the invention encompasses all such optical, enantiomeric, diastereoisomeric and geometric isomers. The invention also comprises all tautomeric forms of the compounds disclosed herein. Where compounds of the invention include chiral centers, the invention encompasses the enantiomerically and/or diasteromerically pure isomers of such compounds, the enantiomerically and/or diastereomerically enriched mixtures of such compounds, and the racemic and scalemic mixtures of such compounds. For example, a composition may include a mixture of enantiomers or diastereomers of a compound of Formula (I) in at least about 30% diastereomeric or enantiomeric excess. In certain embodiments of the invention, the compound is present in at least about 50% enantiomeric or diastereomeric excess, in at least about 80% enantiomeric or diastereomeric excess, or even in at least about 90% enantiomeric or diastereomeric excess. In certain embodiments of the invention, the compound is present in at least about 95%, alternatively in at least about 98% enantiomeric or diastereomeric excess, and alternatively in at least about 99% enantiomeric or diastereomeric excess.

The chiral centers of the present invention may have the S or R configuration. The racemic forms can be resolved by physical methods, such as, for example, fractional crystallization, separation or crystallization of diastereomeric derivates or separation by chiral column chromatography. The individual optical isomers can be obtained either starting from chiral precursors/intermediates or from the racemates by any suitable method, including without limitation, conventional methods, such as, for example, salt formation with an optically active acid followed by crystallization.

The present invention also includes prodrugs of compounds of the invention. The term "prodrug" is intended to represent a compound covalently bonded to a carrier, which prodrug is capable of releasing the active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of the present invention), amides (e.g., trifluoroacetylamino, acetylamino, and the like), and the like.

The compounds of the invention may be administered as is or as a prodrug, for example in the form of an in vivo hydrolyzable ester or in vivo hydrolyzable amide. An in vivo hydrolyzable ester of a compound of the invention containing carboxy or hydroxy group is, for example, a pharmaceutically acceptable ester which is hydrolyzed in the human or animal body to produce the parent acid or alcohol. Suitable pharmaceutically acceptable esters for carboxy include $C_1$-$C_6$alkoxymethyl esters (e.g., methoxymethyl), $C_1$-$C_6$alkanoyloxymethyl esters (e.g., for example pivaloyloxymethyl), phthalidyl esters, $C_3$-$C_8$cycloalkoxycarbonyloxy-$C_1$-$C_6$alkyl esters (e.g., 1-cyclohexylcarbonyloxyethyl); 1,3-dioxolen-2-onylmethyl esters (e.g., 5-methyl-1,3-dioxolen-2-onylmethyl; and $C_1$-$C_6$alkoxycarbonyloxyethyl esters (e.g., 1-methoxycarbonyloxyethyl) and may be formed at any appropriate carboxy group in the compounds of this invention.

An in vivo hydrolyzable ester of a compound of the invention containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—$C_1$-$C_6$alkyl or N,N-di-$C_1$-$C_6$alkyl amide such as N-methyl, N-ethyl, N-propyl, N,N-dimethyl, N-ethyl-N-methyl or N,N-diethyl amide.

Upon administration to a subject, the prodrug undergoes chemical conversion by metabolic or chemical processes to yield a compound of the present invention, or, for example, a salt and/or solvate thereof. Solvates of the compounds of the present invention include, for example, hydrates.

Throughout the specification, embodiments of one or more chemical substituents are identified. Also encompassed are combinations of various embodiments. For example, the invention describes certain embodiments of D in the compounds and describes certain embodiments of group G. Thus, as an example, also contemplated as within the scope of the invention are compounds in which examples of D are as described and in which examples of group G are as described.

Compounds

According to one embodiment, the invention provides compounds of Formula (I):

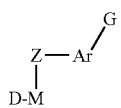
(I)

and N-oxides, hydrates, solvates, pharmaceutically acceptable salts, prodrugs and complexes thereof, and racemic and scalemic mixtures, diastereomers and enantiomers thereof, wherein, D is selected from the group consisting of an aromatic, heteroaromatic, cycloalkyl or heterocyclic ring system, each of which is optionally substituted with 1 to 5 independently selected $R^{38}$;

M is an optionally substituted fused heterocyclic moiety;

Z is selected from the group consisting of covalent bond, —O—, —O—CH$_2$—, —CH$_2$—O—, —S(O)$_{0-2}$—, —CH$_2$—, —N(R$^5$)—, —N(R$^5$)—CH$_2$— and —CH$_2$—N (R$^5$)—;

Ar is a 5 to 7 membered cycloalkyl, aromatic, heterocyclic or heteroaromatic ring system, any of which is optionally substituted with 0 to 4 $R^2$ groups; and G is a group B-L-T, wherein B is selected from the group consisting of absent, —N(R$^{13}$)—, —N(SO$_2$R$^{13}$)—, —O—, —S(O)$_{0-2}$ and —C(=O)—;

L is selected from the group consisting of absent, —C(=S)N(R$^{13}$)—, —C(=NR$^{14}$)N(R$^{13}$)—, —SO$_2$N(R$^{13}$)—, —SO$_2$—, —C(=O)N(R$^{13}$)—, —N(R$^{13}$)—, —C(=O)C$_{1-2}$ alkyl-N(R$^{13}$)—, —N(R$^{13}$)C$_{1-2}$alkyl-C(=O)—, —C(=O)C$_{0-1}$alkyl-C(=O)N(R$^{13}$)—, —C$_{0-4}$alkylene, —C(=O)C$_{0-1}$alkyl-C(=O)OR$^3$—, —C(=NR$^{14}$)—C$_{0-1}$ alkyl-C(=O)—, —C(=O)—, —C(=O)C$_{0-1}$alkyl-C(=O)— and an optionally substituted four to six-membered heterocyclyl containing between one and three annular heteroatoms including at least one nitrogen, wherein an alkyl group of the aforementioned L group is optionally substituted; and T is selected from the group consisting of —H, —R$^{13}$, —C$_{0-5}$ alkyl, —C$_{0-5}$alkyl-Q, —O—C$_{0-5}$alkyl-Q, —C$_{0-5}$alkyl-O-Q, —N(R$^{13}$)—C$_{0-5}$alkyl-Q, —C$_{0-5}$alkyl-SO$_2$—C$_{0-5}$alkyl-Q, —C(=O)—C$_{0-5}$alkyl-Q, —C(=S)—C$_{0-5}$-alkyl-Q, —C(=NR$^{14}$)—C$_{0-5}$-alkyl-Q, —C$_{0-5}$alkyl-N(R$^{13}$)-Q, —C(=O)—N(R$^{13}$)—C$_{0-5}$alkyl-Q, —C(=S)—N(R$^{13}$)—C$_{0-5}$alkyl-Q, —C(=NR$^4$)—N(R$^{13}$)—C$_{0-5}$alkyl-Q, —(C$_{0-5}$ alkyl-C(O))$_{0-1}$—C$_{0-5}$alkyl-Q wherein each C$_{0-5}$alkyl is optionally substituted;

or G is

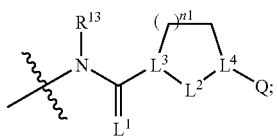

or G is selected from the group consisting of:

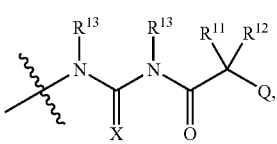

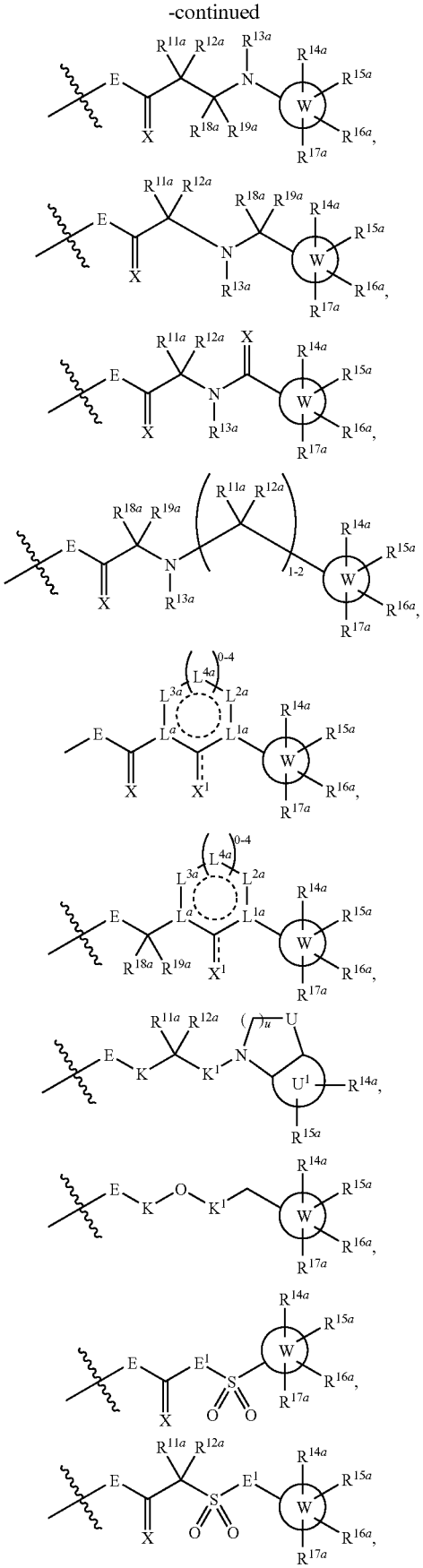

-continued

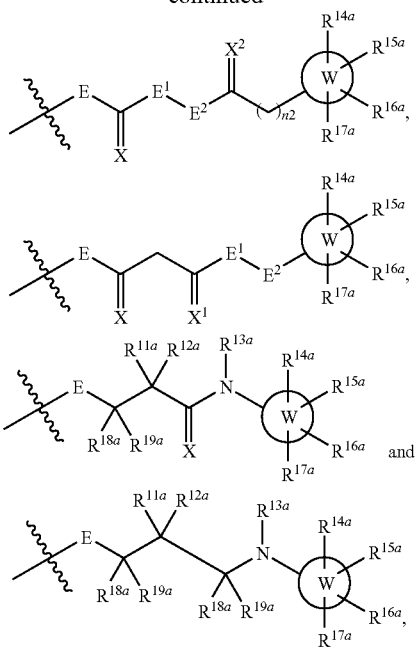

wherein
each $R^{38}$ is independently selected from the group consisting of halo, optionally substituted $C_1$-$C_6$ alkyl, —C(O)NR$^{36}$R$^{39}$, —C(O)O—(CH$_2$)$_n$NR$^{36}$R$^{39}$, —(CH$_2$)$_j$NR$^{39}$(CH$_2$)$_i$S(O)$_j$(C$_1$-$C_6$ alkyl), —(CH$_2$)$_j$NR$^{39}$(CH$_2$)$_n$R$^{36}$, —C(O)(CH$_2$)$_j$NR$^{39}$(CH$_2$)$_n$R$^{36}$, —(CH$_2$)$_n$P(=O)(C$_1$-C$_6$alkyl)$_2$, —(CH$_2$)$_j$NR$^{39}$CH$_2$(CH$_2$)$_n$P(=O)(C$_1$-C$_6$alkyl)$_2$, —NR$^{13}$C(X$^1$)NR$^{13}$-arylP(=O)(C$_1$-C$_6$alkyl)$_2$ and —NR$^{13}$C(X$^1$)NR$^{13}$-heteroarylP(=O)(C$_1$-C$_6$alkyl)$_2$, —(CH$_2$)$_j$NR$^{39}$(CH$_2$)$_i$[O(CH$_2$)$_i$]$_x$(CH$_2$)$_j$R$^{99}$, —(CH$_2$)$_j$NR$^{39}$(CH$_2$)$_i$SO$_{(0-2)}$(CH$_2$)$_i$[O(CH$_2$)$_i$]$_j$(CH$_2$)$_j$R$^{99}$, —(CH$_2$)$_j$NR$^{39}$(CH$_2$)$_j$R$^{100}$
wherein each j is an integer independently ranging from 0 to 4 and alternatively 1-2, n is an integer ranging from 0 to 6, x is an integer ranging from 1-6 and alternatively 2-3, each i is an integer independently ranging from 1 to 3, and the —(CH$_2$)$_i$— and —(CH$_2$)$_n$— moieties of the foregoing R$^{38}$ groups are optionally substituted, for example with C$_1$-C$_6$alkyl, and optionally include a carbon-carbon double or triple bond where n is an integer between 2 and 6;
$R^{36}$ is selected from the group consisting of H, —OH, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclyl) and —(CH$_2$)$_n$A$^4$R$^{37}$, wherein each n is an integer independently ranging from 0 to 6, A$^4$ is selected from the group consisting of O, S, SO, SO$_2$, and the alkyl, cycloalkyl, aryl and heterocyclyl moieties of the foregoing R$^{36}$ groups are optionally substituted, with the proviso that when R$^{36}$ and R$^{39}$ are both attached to the same nitrogen, then R$^{36}$ and R$^{39}$ are not both bonded to the nitrogen directly through an oxygen;
each $R^{37}$ and $R^{41}$ is independently selected from H, —O—C$_1$-C$_6$ alkyl, —O—C$_3$-C$_{10}$ cycloalkyl, —O—(CH$_2$)$_n$(C$_6$-C$_{10}$ aryl), —O—(CH$_2$)$_n$(5-10 membered heterocyclyl), optionally substituted C$_1$-C$_6$ alkyl, optionally substituted C$_2$-C$_6$ alkenyl, optionally substituted C$_2$-C$_6$ alkynyl, optionally substituted C$_3$-C$_{10}$ cycloalkyl, optionally substituted —O—(CH$_2$)$_n$A$^4$-C$_1$-C$_6$ alkyl, optionally substituted —O—(CH$_2$)$_n$A$^4$-C$_2$-C$_6$ alkenyl, optionally substituted —O—(CH$_2$)$_n$A$^4$-C$_2$-C$_6$ alkynyl and optionally substituted —O—(CH$_2$)$_n$A$^4$-C$_3$-C$_{10}$cycloalkyl;

$R^{39}$ is selected from the group consisting of H, —OH, C$_1$-C$_6$ alkyl, —C(O)—C$_1$-C$_6$alkyl, —SO$_2$—C$_1$-C$_6$alkyl, —C(O)—O—C$_1$-C$_6$alkyl-aryl and a protecting group used to protect secondary amino groups, with the proviso that when R$^{36}$ and R$^{39}$ are both attached to the same nitrogen, then R$^{36}$ and R$^{39}$ are not both bonded to the nitrogen directly through an oxygen;
each $R^{40}$ is independently selected from H, C$_1$-C$_{10}$ alkyl, —(CH$_2$)$_n$(C$_6$-C$_{10}$ aryl), C$_3$-C$_{10}$ cycloalkyl, and —(CH$_2$)$_n$(5-10 membered heterocyclyl), wherein n is an integer ranging from 0 to 6;
$R^{99}$ at each occurrence is independently selected from the group consisting of —H, halogen, trihalomethyl, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, P(=O)(OH)$_2$, —P(=O)(C$_1$-C$_6$alkyl)$_2$, —SO$_3$H—C(O)R$^3$, C$_1$-C$_4$ alkoxy, C$_1$-C$_4$ alkylthio, —O(CH$_2$)$_{0-6}$aryl, —O(CH$_2$)$_{0-6}$heteroaryl, —(CH$_2$)$_{0-5}$(aryl), —(CH$_2$)$_{0-5}$(heteroaryl), -, C$_1$-C$_6$ alkyl, C$_2$-C$_6$ alkenyl, C$_2$-C$_6$ alkynyl, —CH$_2$(CH$_2$)$_{0-4}$-T$^2$, wherein the aryl, heteroaryl, C$_1$-C$_6$ alkyl, C$_2$-C$_6$ alkenyl, and C$_2$-C$_6$ alkynyl are optionally substituted;
$R^{100}$ is a 12 to 24-membered optionally substituted heteroalicyclic macrocycle containing 4 to 8 oxygen atoms, for example 15-crown-5, 18-crown-6, or 21-crown-7;
$R^5$ is selected from the group consisting of H, an optionally substituted (C$_1$-C$_5$)acyl and C$_1$-C$_6$ alkyl-O—C(O), wherein C$_1$-C$_6$ alkyl is optionally substituted;
$R^2$ at each occurrence is independently selected from the group consisting of —H, halogen, trihalomethyl, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, C$_1$-C$_4$ alkoxy, C$_1$-C$_4$ alkylthio, —O(CH$_2$)$_{0-6}$aryl, —O(CH$_2$)$_{0-6}$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, wherein the aryl, heteroaryl, C$_1$-C$_6$ alkyl, C$_2$-C$_6$ alkenyl, and C$_2$-C$_6$ alkynyl are optionally substituted;
$T^2$ is selected from the group consisting of —OH, —OMe, —OEt, —NH$_2$, —NHMe, —NMe$_2$, —NHEt and —NEt$_2$;
each $R^3$ is independently selected from the group consisting of —H and R$^4$;
$R^4$ is selected from the group consisting of a (C$_1$-C$_6$)alkyl, an aryl, a lower arylalkyl, a heterocyclyl and a lower heterocyclylalkyl, each of which is optionally substituted, or
$R^3$ and $R^4$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;
each $R^{13}$ is independently selected from the group consisting of —H, halogen, trihalomethyl, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, —C(O)SR$^3$, C$_1$-C$_4$ alkoxy, C$_1$-C$_4$ alkylthio, —O(CH$_2$)$_{0-6}$aryl, —O(CH$_2$)$_{0-6}$heteroaryl, —(CH$_2$)$_{0-5}$(aryl), —(CH$_2$)$_{0-5}$(heteroaryl), —(CH$_2$)$_{0-5}$(cycloalkyl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$ alkylcarbonyl, and a saturated or unsaturated three- to seven-membered carboxylic or heterocyclic group, wherein the aryl, heteroaryl, C$_1$-C$_6$ alkyl, C$_2$-C$_6$ alkenyl, and C$_2$-C$_6$ alkynyl are optionally substituted;
two $R^{13}$, together with the atom or atoms to which they are attached, can combine to form a heteroalicyclic optionally substituted with between one and four of R$^{60}$, wherein the heteroalicyclic can have up to four annular heteroatoms, and the heteroalicyclic can have an aryl or heteroaryl fused thereto, in which case the aryl or heteroaryl is optionally substituted with an additional one to four of $R^{60}$;

$R^{14}$ is selected from the group —H, —$NO_2$, —$NH_2$, —$N(R^3)R^4$, —CN, —$OR^3$, an optionally substituted $(C_1$-$C_6)$alkyl, an optionally substituted heteroalicyclylalkyl, an optionally substituted aryl, an optionally substituted arylalkyl and an optionally substituted heteroalicyclic, $R^{60}$ is selected from the group consisting of —H, halogen, trihalomethyl, —CN, —$NO_2$, —$NH_2$, —$OR^3$, —$NR^3R^4$, —$S(O)_{0-2}R^3$, —$SO_2NR^3R^3$, —$CO_2R^3$, —$C(O)NR^3R^3$, —$N(R^3)SO_2R^3$, —$N(R^3)C(O)R^3$, —$N(R^3)CO_2R^3$, —$C(O)R^3$, an optionally substituted $(C_1$-$C_6)$alkyl, an optionally substituted aryl, an optionally substituted heteroarylalkyl and an optionally substituted arylalkyl; or two $R^{60}$, when attached to a non-aromatic carbon, can be oxo;

Q is $C_1$-$C_6$alkyl or a three- to ten-membered ring system, optionally substituted with between zero and four of $R^{20}$;

each $R^{20}$ is independently selected from the group consisting of —H, halogen, trihalomethyl, —O—trihalomethyl, oxo, —CN, —$NO_2$, —$NH_2$, —$OR^3$, —$OCF_3$, —$NR^3R^4$, —$S(O)_{0-2}R^3$, —$S(O)_2NR^3R^3$, —$C(O)OR^3$, —$C(O)NR^3R^3$, —$N(R^3)SO_2R^3$, —$N(R^3)C(O)R^3$, —$N(R^3)C(O)OR^3$, —$C(O)R^3$, —$C(O)SR^3$, $C_1$-$C_4$ alkoxy, $C_1$-$C_4$ alkylthio, —$O(CH_2)_{0-6}$aryl, —$O(CH_2)_{0-6}$heteroaryl, —$(CH_2)_{0-5}$(aryl), —$(CH_2)_{0-5}$(heteroaryl), $C_1$-$C_6$ alkyl, $C_2$-$C_6$ alkenyl, $C_2$-$C_6$ alkynyl, —$CH_2(CH_2)_{0-4}$-$T^2$, an optionally substituted $C_{1-4}$ alkylcarbonyl, $C_{1-4}$ alkoxy, an amino optionally substituted by $C_{1-4}$ alkyl optionally substituted by $C_{1-4}$ alkoxy and a saturated or unsaturated three- to seven-membered carboxyclic or heterocyclic group and wherein the aryl, heteroaryl, $C_1$-$C_6$ alkyl, $C_2$-$C_6$ alkenyl, and $C_2$-$C_6$ alkynyl are optionally substituted;

$L^1$ is selected from the group consisting of O, S and $N(R^{14})$;

$L^2$ is selected from the group consisting of —C(O)—, —C(S)—, —C(NH)—, >C=$N(C_1$-$C_6$ alkyl) and —$CH_2$—;

$L^3$ is selected from the group consisting of —CH—, —C($C_1$-$C_6$ alkyl)- and N;

$L^4$ is selected from the group consisting of —CH— and N;

n1 is an integer from 0 to 5;

each X is independently selected from the group consisting of O, S, NH, N-alkyl, N—OH, N—O-alkyl and NCN;

$R^{11}$ and $R^{12}$ are independently selected from the group consisting of H, $C_1$-$C_6$alkyl, halo, cyano and nitro, wherein the alkyl is optionally substituted; or $R^{11}$ and $R^{12}$, taken together with the atom to which they are attached, form a $C_3$-$C_7$cycloalkyl;

E is selected from the group consisting of O, S, —$CH_2$—, —CH($C_1$-$C_6$alkyl), —N(H)—, —N($C_1$-$C_6$alkyl)-, —$CH_2N(H)$— and —N(H)$CH_2$—;

$R^{11a}$ and $R^{12a}$ are independently selected from the group consisting of H, halogen, —OH, unsubstituted —O—($C_1$-$C_6$alkyl), substituted —O—($C_1$-$C_6$alkyl), unsubstituted —O-(cycloalkyl), substituted —O-(cycloalkyl), unsubstituted —NH($C_1$-$C_6$alkyl), substituted —NH($C_1$-$C_6$alkyl), —$NH_2$, —SH, unsubstituted —S—($C_1$-$C_6$alkyl), substituted —S—($C_1$-$C_6$alkyl), unsubstituted $C_1$-$C_6$alkyl and substituted $C_1$-$C_6$alkyl; or $R^{11a}$ and $R^{12a}$ taken together with the atom to which they are attached form a $C_3$-$C_7$ ring system, wherein said ring system is optionally substituted;

each $R^{13a}$ is independently selected from the group consisting of H, $C_1$-$C_6$alkyl, substituted $C_1$-$C_6$alkyl, cycloalkyl, substituted cycloalkyl, OH, unsubstituted —O—($C_1$-$C_6$alkyl), substituted —O—($C_1$-$C_6$alkyl); or $R^{12a}$ and $R^{13a}$ taken together with the atoms to which they are attached optionally form a 4 to 8 membered cycloalkyl or heterocyclic ring system, which ring system is optionally substituted;

$R^{14a}$, $R^{15a}$, $R^{16a}$ and $R^{17a}$ are independently selected from the group consisting of —H, halogen, trihalomethyl, —O-trihalomethyl, —CN, —$NO_2$, —$NH_2$, —$OR^3$, —$OCF_3$, —$NR^3R^4$, —$S(O)_{0-2}R^3$, —$S(O)_2NR^3R^3$, —$C(O)OR^3$, —$C(O)NR^3R^3$, —$N(R^3)SO_2R^3$, —$N(R^3)C(O)R^3$, —$N(R^3)C(O)OR^3$, —$C(O)R^3$, —$C(O)SR^3$, $C_1$-$C_4$ alkoxy, $C_1$-$C_4$ alkylthio, —$O(CH_2)_n$aryl, —$O(CH_2)_n$heteroaryl, $(CH_2)_{0-5}$(aryl), —$(CH_2)_{0-5}$(heteroaryl), $C_1$-$C_6$ alkyl, $C_2$-$C_6$ alkenyl, $C_2$-$C_6$ alkynyl, —$CH_2(CH_2)_{0-4}$-$T^2$, an optionally substituted $C_{1-4}$ alkylcarbonyl, $C_{1-4}$ alkoxy, an amino optionally substituted by $C_{1-4}$ alkyl optionally substituted by $C_{1-4}$ alkoxy and a saturated or unsaturated three- to seven-membered carboxyclic or heterocyclic group, wherein n is an integer ranging from 0 to 6, and the aryl, heteroaryl, $C_1$-$C_6$ alkyl, $C_2$-$C_6$ alkenyl, and $C_2$-$C_6$ alkynyl are optionally substituted; or $R^{13a}$ and $R^{14a}$ taken together with the atoms to which they are attached optionally form a 4 to 8 membered cycloalkyl or heterocyclic ring system, which ring system is optionally substituted;

$R^{18a}$ and $R^{19a}$ are independently selected from the group consisting of H, OH, halogen, $NO_2$, unsubstituted —O—($C_1$-$C_6$alkyl), substituted —O—($C_1$-$C_6$alkyl), $CH_3$, $CH_2F$, $CHF_2$, $CF_3$, CN, $C_1$-$C_6$alkyl, substituted $C_1$-$C_6$alkyl, partially fluorinated $C_1$-$C_6$alkyl, per-fluorinated $C_1$-$C_6$alkyl, heteroalkyl, substituted heteroalkyl and —$SO_2(C_1$-$C_6$alkyl); or $R^{18a}$ and $R^{19a}$ together with the atom to which they are attached form a 3 to 6 membered cycloalkyl or heterocycle, each of which is optionally substituted with 1 to 4 halo, for example F;

W is selected from the group consisting of H, alkyl, alkenyl, alkynyl, —$(CH_2)_{0-5}$(five- to ten-membered cycloalkyl), —$(CH_2)_{0-5}$(aryl), —$(CH_2)_{0-5}$(heterocyclic) and —$(CH_2)_{0-5}$(heteroaryl), each of which is optionally substituted; and ⫽ is a single or double bond;

$X^1$ is selected from the group consisting of O, S, $CH_2$, N—CN, N—O-alkyl, NH and N($C_1$-$C_6$alkyl) when ⫽ is a double bond, or $X^1$ is selected from the group consisting of H, halogen, trihaloalkyl, alkyl, alkenyl, alkynyl, CN, alkoxy, NH(alkyl) and alkyl-thio, when ⫽ is a single bond;

$L^a$ and $L^{1a}$ are independently selected from the group consisting of —CH—, N, —C(halogen)- and —C($C_1$-$C_6$alkyl)-;

$L^{2a}$ and $L^{3a}$ are independently selected from the group consisting of CH, $CH_2$, N, O and S;

$L^{4a}$ is selected from the group consisting of absent, CH, $CH_2$, N, O and S; and the group

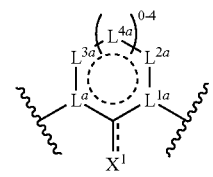

is aromatic or non-aromatic, provided that two 0 are not adjacent to each other;

K and K¹ are independently selected from the group consisting of —C(O)—, —C(S)—, —C(NH)—, —C(NCN)— and —C($R^{18a}R^{19a}$)—;

U is selected from the group consisting of O, S, $SO_2$, NH, and N($C_1$-$C_6$alkyl), wherein the $C_1$-$C_6$alkyl is optionally substituted with a substituent selected from the group consisting of —OH, -alkoxy, amino, NH($C_1$-$C_6$alkyl), N($C_1$-$C_6$alkyl)$_2$,

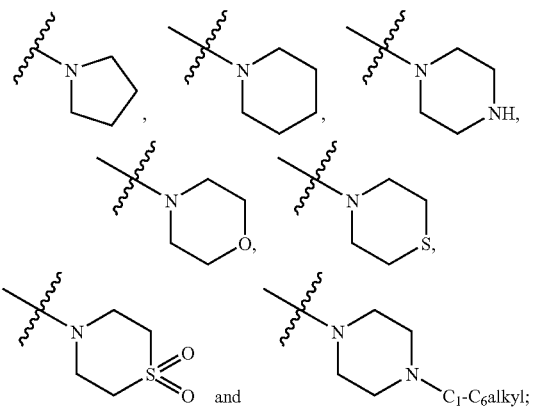

U¹ is a ring system selected from the group consisting of cycloalkyl, substituted cycloalkyl, heterocyclyl, substituted heterocyclyl, aryl, substituted aryl, heteroaryl and substituted heteroaryl;

E¹ is selected from the group consisting of —N(H)—, —N($C_1$-$C_6$alkyl)-, —$CH_2$N(H)— and —N(H)$CH_2$—;

E² is selected from the group consisting of —N(H)—, —N($C_1$-$C_6$alkyl)-, —$CH_2$N(H)— and —N(H)$CH_2$—;

X² is selected from the group consisting of O, S, NH, NOH, NOMe, NOEt and NCN; and $n_2$ is 0, 1, 2, 3 or 4.

In one embodiment of the compounds according to the present invention D is an aromatic or heteroaromatic ring system, each of which is optionally substituted with 1 to 5 independently selected $R^{38}$ groups, alternatively 1 to 3 independently selected $R^{38}$ groups, and alternatively 1 or 2 independently selected $R^{38}$ groups.

In another embodiment according to the present invention, D is substituted with one $R^{38}$ group.

In another embodiment according to the present invention, D is a 5- or 6-membered aromatic or 5- or 6-membered heteroaromatic ring system, each of which is optionally substituted with 1 to 5 independently selected $R^{38}$ groups, alternatively 1 to 3 independently selected $R^{38}$ groups, and alternatively 1 or 2 independently selected $R^{38}$ groups.

In another embodiment according to the present invention, D is a 6-membered aromatic or 6-membered heteroaromatic ring system, each of which is optionally substituted with 1 to 5 independently selected $R^{38}$ groups, alternatively 1 to 3 independently selected $R^{38}$ groups, and alternatively 1 or 2 independently selected $R^{38}$ groups.

In another embodiment according to the present invention, D is a 6-membered aromatic ring system, optionally substituted with 1 to 5 independently selected $R^{38}$ groups, alternatively 1 to 3 independently selected $R^{38}$ groups, and alternatively 1 or 2 independently selected $R^{38}$ groups.

In another embodiment according to the present invention, D is a 6-membered heteroaromatic ring system, optionally substituted with 1 to 5 independently selected $R^{38}$ groups, alternatively 1 to 3 independently selected $R^{38}$ groups, and alternatively 1 or 2 independently selected $R^{38}$ groups.

According to another embodiment of the present invention, D is selected from the group consisting of

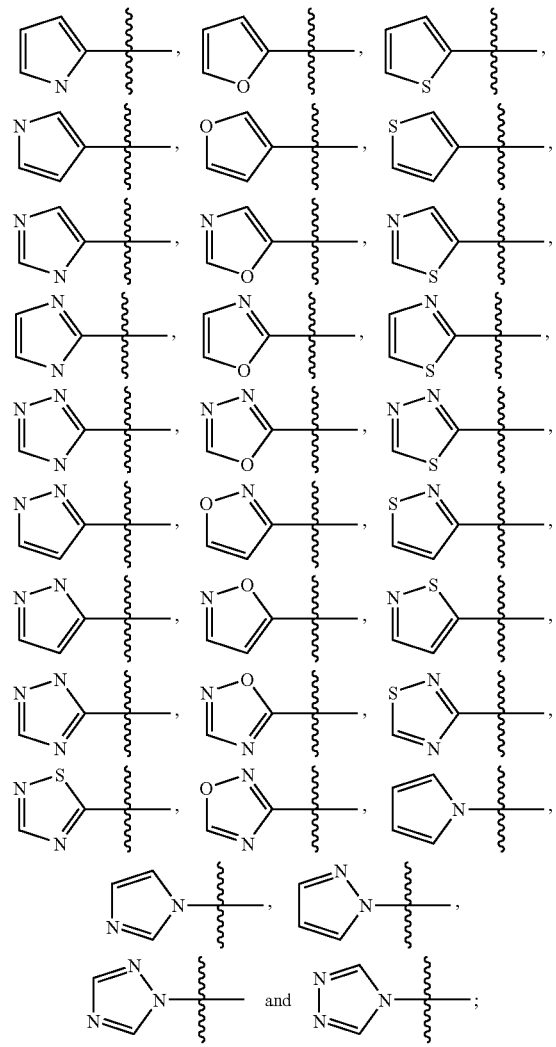

wherein the members of said group are optionally substituted with 1 to 5 independently selected $R^{38}$ groups, alternatively 1 to 3 independently selected $R^{38}$ groups, and alternatively 1 or 2 independently selected $R^{38}$ groups.

According to another embodiment of the present invention, D is selected from the group consisting of

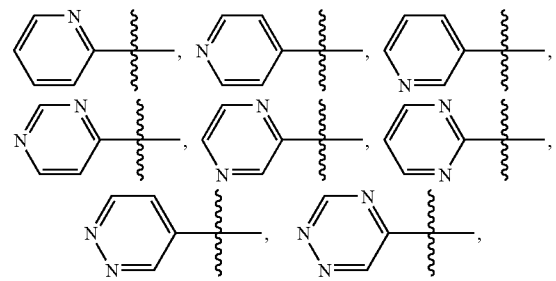

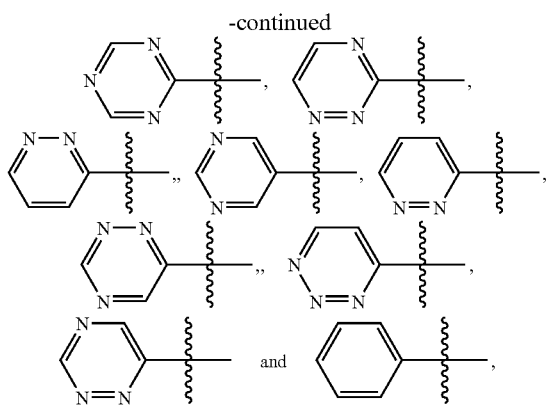

wherein the members of said group are optionally substituted with 1 to 5 independently selected $R^{38}$ groups, alternatively 1 to 3 independently selected $R^{38}$ groups, and alternatively 1 or 2 independently selected $R^{38}$ groups.

According to another embodiment of the present invention, D is phenyl, pyridyl, furanyl, imidazolyl, tetrahydropyridyl, thienyl, pyrazolyl, each of which is optionally substituted with 1 to 5 independently selected $R^{38}$ groups, alternatively 1 to 3 independently selected $R^{38}$ groups, and alternatively 1 or 2 independently selected $R^{38}$ groups.

In another embodiment according to the present invention, D is phenyl, optionally substituted with 1 to 5 independently selected $R^{38}$ groups, alternatively 1 to 3 independently selected $R^{38}$ groups, and alternatively 1 or 2 independently selected $R^{38}$ groups.

In another embodiment according to the present invention, D is pyridyl, optionally substituted with 1 to 5 independently selected $R^{38}$ groups, alternatively 1 to 3 independently selected $R^{38}$ groups, and alternatively 1 or 2 independently selected $R^{38}$ groups.

In another embodiment according to the present invention, D is phenyl, optionally substituted with one $R^{38}$.

In another embodiment according to the present invention, D is pyridyl, optionally substituted with one $R^{38}$.

In another embodiment according to the present invention, D is phenyl, substituted with one $R^{38}$.

In another embodiment according to the present invention, D is pyridyl, substituted with one $R^{38}$.

In another embodiment according to the present invention, D is imidazolyl, substituted with one $R^{38}$.

In another embodiment of the present invention, each $R^{38}$ is independently selected from the group consisting of —C(O)$NR^{36}R^{39}$, —C(O)O—(CH$_2$)$_n$$NR^{36}R^{39}$, —(CH$_2$)$_j$$NR^{39}$(CH$_2$)$_i$S(O)$_j$(C$_1$-C$_6$ alkyl), —(CH$_2$)$_j$$NR^{39}$(CH$_2$)$_i$[O(CH$_2$)$_i$]$_x$(CH$_2$)$_i$$R^{99}$, —(CH$_2$)$_j$$NR^{39}$(CH$_2$)$_n$$R^{36}$ and —C(O)(CH$_2$)$_j$$NR^{39}$(CH$_2$)$_n$$R^{16}$.

In another embodiment of the present invention each $R^{38}$ is independently selected from the group consisting of halo, optionally substituted C$_1$-C$_6$ alkyl, —(CH$_2$)$_j$$NR^{39}$(CH$_2$)$_i$[O(CH$_2$)$_i$]$_x$(CH$_2$)$_i$$R^{99}$, and —(CH$_2$)$_j$$NR^{39}$(CH$_2$)$_n$$R^{36}$.

In another embodiment of the present invention, $R^{36}$ is selected from the group consisting of H, —OH, C$_1$-C$_6$ alkyl and —(CH$_2$)$_n$$A^4R^{37}$, for example, —$R^{36}$ is (CH$_2$)$_n$$OR^{37}$, or —(CH$_2$)$_n$$SR^{37}$, wherein each n is an integer independently ranging from 0 to 6 (alternatively 0 to 4, alternatively 0 to 2, alternatively 1 or 0, alternatively 0), wherein the $R^{37}$ is selected from the group consisting of H, optionally substituted C$_1$-C$_6$ alkyl, optionally substituted C$_2$-C$_6$ alkenyl, optionally substituted C$_2$-C$_6$ alkynyl and optionally substituted C$_3$-C$_{10}$ cycloalkyl.

In another embodiment of the present invention, each $R^{38}$ is independently halo, C$_1$-C$_6$alkyl or —(CH$_2$)$_j$$NR^{39}$(CH$_2$)$_n$$R^{36}$.

In another embodiment of the present invention, each $R^{38}$ is independently —(CH$_2$)$_j$$NR^{39}$(CH$_2$)$_n$$R^{36}$, wherein j is 1 and n is 2.

In another embodiment of the present invention each $R^{38}$ is independently —(CH$_2$)$_j$NH(CH$_2$)A$^4$$R^{37}$.

In another embodiment of the present invention each $R^{38}$ is independently —(CH$_2$)$_j$NH(CH$_2$)$_n$$OR^{37}$, wherein j is 1 or 2 and n is 2.

In another embodiment of the present invention each $R^{38}$ is independently —(CH$_2$)NH(CH$_2$)$_2$$OR^{37}$, wherein $R^{37}$ is optionally substituted C$_1$-C$_6$ alkyl, for example —CH$_3$.

In another embodiment of the present invention each $R^{38}$ is independently —(CH$_2$)NH(CH$_2$)$_3$$OR^{37}$, wherein $R^{37}$ is optionally substituted C$_1$-C$_6$ alkyl, for example —CH$_3$.

In another embodiment of the present invention each $R^{38}$ is independently —(CH$_2$)$_2$NH(CH$_2$)$_2$$OR^{37}$ wherein $R^{37}$ is optionally substituted C$_1$-C$_6$ alkyl, for example —CH$_3$.

In another embodiment of the present invention each $R^{38}$ is independently —(CH$_2$)$_2$NH(CH$_2$)$_3$$OR^{37}$, wherein $R^{37}$ is optionally substituted C$_1$-C$_6$ alkyl, for example —CH$_3$.

In another embodiment of the present invention, each $R^{38}$ is independently —(CH$_2$)$_j$$NR^{39}$(CH$_2$)$_i$S(O)$_j$(C$_1$-C$_6$ alkyl), for example —(CH$_2$)NH(CH$_2$)$_2$S(O)$_2$CH$_3$.

In another embodiment of the present invention, each $R^{38}$ is independently —C(O)(CH$_2$)$_j$$NR^{39}$(CH$_2$)$_n$$R^{36}$.

In another embodiment of the present invention, each $R^{38}$ is independently —C(O)$NR^{39}$(CH$_2$)$_2$$OR^{37}$.

In another embodiment of the present invention, each $R^{38}$ is independently —C(O)NH(CH$_2$)$_2$$OR^{37}$, wherein $R^{37}$ is optionally substituted C$_1$-C$_6$ alkyl, for example —CH$_3$.

In another embodiment of the present invention, each $R^{38}$ is independently —C(O)O—(CH$_2$)$_n$$NR^{36}R^{39}$.

In another embodiment of the present invention, each $R^{38}$ is independently —C(O)O—(CH$_2$)$_n$$NR^{36}R^{39}$, wherein $R^{36}$ and $R^{39}$ are each independently C$_1$-C$_6$ alkyl, for example —CH$_3$.

In another embodiment of the present invention, each $R^{38}$ is independently —C(O)O—(CH$_2$)$_n$$NHR^{36}R^{39}$, wherein $R^{36}$ and $R^{39}$ are each independently C$_1$-C$_6$ alkyl, for example —CH$_3$, and n is for example 2.

In another embodiment of the present invention each $R^{38}$ is independently —(CH$_2$)$_j$$NR^{39}$(CH$_2$)$_n$C$_3$-C$_7$cycloalkyl, for example —(CH$_2$)NHC$_3$cycloalkyl.

In another embodiment of the present invention each $R^{38}$ is independently selected from the group consisting of —(CH$_2$)$_n$ P(=O)(C$_1$-C$_6$alkyl)$_2$, —(CH$_2$)$_j$$NR^{39}$CH$_2$(CH$_2$)$_n$ P(=O)(C$_1$-C$_6$alkyl)$_2$, —$NR^{13}$C(X$^1$)$NR^{13}$-arylP(=O)(C$_1$-C$_6$alkyl)$_2$ and —$NR^{13}$C(X$^1$)$NR^{13}$-heteroarylP(=O)(C$_1$-C$_6$alkyl)$_2$, wherein X$^1$ is for example O or S.

In another embodiment of the present invention each $R^{38}$ is independently —(CH$_2$)$_n$P(=O)(C$_1$-C$_6$alkyl)$_2$.

In another embodiment of the present invention each $R^{38}$ is independently —(CH$_2$)$_{1-3}$P(=O)(C$_1$-C$_6$alkyl)$_2$.

In another embodiment of the present invention each $R^{38}$ is independently —(CH$_2$)$_n$P(=O)(C$_1$-C$_3$alkyl)$_2$.

In another embodiment of the present invention each $R^{38}$ is independently —(CH$_2$)$_{1-3}$P(=O)(C$_1$-C$_3$alkyl)$_2$.

In another embodiment of the present invention each $R^{38}$ is independently —(CH$_2$)$_n$P(=O)(CH$_3$)$_2$.

In another embodiment of the present invention each $R^{38}$ is independently —(CH$_2$)$_{1-3}$P(=O)(CH$_3$)$_2$.

In another embodiment of the present invention each $R^{38}$ is independently —(CH$_2$)$_j$$NR^{39}$CH$_2$(CH$_2$)$_n$P(=O)(C$_1$-C$_6$alkyl)$_2$.

In another embodiment of the present invention each $R^{38}$ is independently —$(CH_2)_j NHCH_2(CH_2)_n P(=O)(C_1-C_6 alkyl)_2$.

In another embodiment of the present invention each $R^{38}$ is independently —$(CH_2)_{1-2} NR^{39}(CH_2)_{1-3} P(=O)(C_1-C_6 alkyl)_2$.

In another embodiment of the present invention each $R^{38}$ is independently —$(CH_2)_{1-2} NH(CH_2)_{1-3} P(=O)(C_1-C_6 alkyl)_2$.

In another embodiment of the present invention each $R^{38}$ is independently —$(CH_2)_{1-2} NR^{39}(CH_2)_{1-3} P(=O)(C_1-C_3 alkyl)_2$.

In another embodiment of the present invention each $R^{38}$ is independently —$(CH_2)_{1-2} NH(CH_2)_{1-3} P(=O)(C_1-C_3 alkyl)_2$.

In another embodiment of the present invention each $R^{38}$ is independently —$(CH_2)_{1-2} NH(CH_2)_{1-3} P(=O)(CH_3)_2$.

In another embodiment of the present invention each $R^{38}$ is independently —$(CH_2)_1 NR^{39}(CH_2)_2 P(=O)(C_1-C_6 alkyl)_2$.

In another embodiment of the present invention each $R^{38}$ is independently —$(CH_2)_1 NH(CH_2)_2 P(=O)(C_1-C_6 alkyl)_2$.

In another embodiment of the present invention each $R^{38}$ is independently —$(CH_2)_1 NH(CH_2)_2 P(=O)(C_1-C_3 alkyl)_2$.

In another embodiment of the present invention each $R^{38}$ is independently —$(CH_2)_1 NH(CH_2)_2 P(=O)(CH_3)_2$.

In another embodiment of the present invention each $R^{38}$ is independently selected from the group consisting of —$NR^{13}C(O)NR^{13}$-arylP$(=O)(C_1-C_6 alkyl)_2$, —$NR^{13}C(S)NR^{13}$-arylP$(=O)(C_1-C_6 alkyl)_2$, —$NR^{13}C(O)NR^{13}$-heteroarylP$(=O)(C_1-C_6 alkyl)_2$ and —$NR^{13}C(S)NR^{13}$-heteroarylP$(=O)(C_1-C_6 alkyl)_2$.

In another embodiment of the present invention each $R^{38}$ is independently selected from the group consisting of —$NR^{13}C(O)NR^{13}$-arylP$(=O)(C_1-C_3 alkyl)_2$, —$NR^{13}C(S)NR^{13}$-arylP$(=O)(C_1-C_3 alkyl)_2$, —$NR^{13}C(O)NR^{13}$-heteroarylP$(=O)(C_1-C_3 alkyl)_2$ and —$NR^{13}C(S)NR^{13}$-heteroarylP$(=O)(C_1-C_3 alkyl)_2$.

In another embodiment of the present invention, each $R^{38}$ is independently selected from —$(CH_2)_j NR^{39}(CH_2)_i[O(CH_2)_i]_x(CH_2)_j R^{99}$, wherein $R^{99}$ is selected from $NH_2$ and —$NR^3R^4$.

In another embodiment of the present invention, each $R^{38}$ is independently selected from —$(CH_2)_j NR^{39}(CH_2)_i[O(CH_2)_i]_x(CH_2)_j R^{99}$, wherein $R^{99}$ is $NH_2$.

In another embodiment of the present invention, each $R^{38}$ is independently selected from —$(CH_2)_j NH(CH_2)_i[O(CH_2)_i]_x(CH_2)_j R^{99}$, wherein $R^{99}$ is $NH_2$.

In another embodiment of the present invention, each $R^{38}$ is independently selected from —$(CH_2)_1 NH(CH_2)_{2-3}[O(CH_2)_2]_{2-3}(CH_2)_{0-1} R^{99}$, wherein $R^{99}$ is $NH_2$.

In another embodiment of the present invention, each $R^{38}$ is independently selected from —$(CH_2)_1 NH(CH_2)_3[O(CH_2)_2]_3(CH_2)_1 R^{99}$ and —$(CH_2)_1 NH(CH_2)_2[O(CH_2)_2]_2 R^{99}$, wherein $R^{99}$ is $NH_2$.

In another embodiment of the present invention, $R^{38}$ is —$(CH_2)_j NR^{39}(CH_2)_n R^{36}$, wherein the —$(CH_2)_n$— group is optionally substituted with $C_1-C_6 alkyl$, for example Me, $R^{36}$ is —$(CH_2)_{n3} A^4 R^{37}$, for example —$(CH_2)_{n3} OR^{37}$ wherein each n3 is an integer independently ranging from 0 to 6 (alternatively 0 to 4, alternatively 0 to 2, alternatively 1 or 0, alternatively 0), wherein the $R^{37}$ is optionally substituted $C_1-C_6$ alkyl, and $R^{39}$ is —$C(O)$—$C_1-C_3 alkyl$, for example —$C(O)$—$CH_3$.

In another embodiment of the present invention, D is substituted with an $R^{38}$ as described an embodiment herein, and further substituted with halo or $C_1-C_6 alkyl$.

In another embodiment of the present invention, D is phenyl or pyridinyl, and $R^{38}$ is $C_1-C_6 alkyl$, —$(CH_2)_j NR^{39}(CH_2)_n R^{36}$—$(CH_2)_j NR^{39} CH_2(CH_2)_n P(=O)(C_1-C_6 alkyl)_2$, —$NR^{13}C(X^1)NR^{13}$-arylP$(=O)(C_1-C_6 alkyl)_2$ or —$NR^{13}C(X^1)NR^{13}$-heteroarylP$(=O)(C_1-C_6 alkyl)_2$, wherein $X^1$ is for example O or S.

In another embodiment of the present invention, $R^{39}$ is H or $C_1-C_6 alkyl$.

In another embodiment of the present invention, $R^{39}$ is H.

In another embodiment of the present invention, D is a 5- or 6-membered aryl or a 5- or 6-membered heteroaryl, optionally substituted with one or two (alternatively one) $R^{38}$, wherein each said $R^{38}$ is independently selected from the group consisting of halo, $C_1-C_6$ alkyl, —$C(O)NR^{36}R^{39}$, —$C(O)O$—$(CH_2)_n NR^{36}R^{39}$, —$(CH_2)_j NR^{39}(CH_2)_i S(O)_j(C_1-C_6 alkyl)$, —$(CH_2)_j NR^{39}(CH_2)_n R^{36}$ and —$C(O)(CH_2)_j NR^{39}(CH_2)_n R^{36}$, wherein each j is an integer independently selected from 0 to 4 (alternatively 1 to 4, alternatively 1 or 2, alternatively 1), n is an integer from 0 to 6 (alternatively 2 to 6, alternatively 2 to 4, alternatively, 1 or 2), i is 2 or 3, $R^{39}$ is H or $C_1-C_6 alkyl$, and $R^{36}$ is selected from the group consisting of H, —OH, $C_1-C_6$ alkyl, $C_3-C_{10}$ cycloalkyl, —$(CH_2)_{n3}$ $(C_6-C_{10}$ aryl), —$(CH_2)_{n3}$(5-10 membered heterocyclyl) and —$(CH_2)_{n3} A^4 R^{37}$, for example —$(CH_2)_{n3} OR^{37}$ or —$(CH_2)_{n3} SR^{37}$, wherein each n3 is an independently selected integer ranging from 0 to 6 (alternatively 0 to 4, alternatively 0 to 2, alternatively 1 or 0, alternatively 0), and $R^{37}$ is H or $C_1-C_6 alkyl$, for example, $C_1-C_6 alkyl$, alternatively $C_1-C_2 alkyl$.

According to another embodiment of the present invention, D is phenyl or pryidinyl (alternatively pyridinyl), optionally substituted with one or two (alternatively one) $R^{38}$, wherein each said $R^{38}$ is independently selected from the group consisting of halo, $C_1-C_6$ alkyl, —$C(O)NR^{36}R^{39}$, —$C(O)O$—$(CH_2)_n NR^{36}R^{39}$, —$(CH_2)_j NR^{39}(CH_2)_i S(O)_j(C_1-C_6$ alkyl), —$(CH_2)_j NR^{39}(CH_2)_n R^{36}$ and —$C(O)(CH_2)_j NR^{39}(CH_2)_n R^{36}$, wherein each j is an integer independently selected from 0 to 4 (alternatively 1 to 4, alternatively 1 or 2, alternatively 1), n is an integer from 0 to 6 (alternatively 2 to 6, alternatively 2 to 4, alternatively, 1 or 2), i is 2 or 3, $R^{39}$ is H or $C_1-C_6 alkyl$, and $R^{36}$ is selected from the group consisting of H, —OH, $C_1-C_6$ alkyl, $C_3-C_{10}$ cycloalkyl, —$(CH_2)_{n3}(C_6-C_{10}$ aryl), —$(CH_2)_{n3}$(5-10 membered heterocyclyl) and —$(CH_2)_{n3} A^4 R^{37}$, for example —$(CH_2)_{n3} OR^{37}$ or —$(CH_2)_{n3} SR^{37}$, wherein n3 is an integer ranging from 0 to 6 (alternatively 0 to 4, alternatively 0 to 2, alternatively 1 or 0, alternatively 0), and $R^{37}$ is H or $C_1-C_6 alkyl$, for example, $C_1-C_6 alkyl$, alternatively $C_1-C_2 alkyl$.

In another embodiment of the present invention, D is a 5- or 6-membered aryl or a 5- or 6-membered heteroaryl, optionally substituted with one or two (alternatively one) $R^{38}$, wherein each said $R^{38}$ is independently selected from the group consisting of halo, $C_1-C_6$ alkyl, —$(CH_2)_n P(=O)(C_1-C_6 alkyl)_2$, —$(CH_2)_j NR^{39} CH_2(CH_2)_n P(=O)(C_1-C_6 alkyl)_2$, —$NR^{13}C(X^1)NR^{13}$-arylP$(=O)(C_1-C_6 alkyl)_2$ and —$NR^{13}C(X^1)NR^{13}$-heteroarylP$(=O)(C_1-C_6 alkyl)_2$, wherein $X^1$ is for example O or S, j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is H or $C_1-C_6 alkyl$, and $R^{36}$ is selected from the group consisting of H, —OH, $C_1-C_6$ alkyl, $C_3-C_{10}$ cycloalkyl, —$(CH_2)_{n3}(C_6-C_{10}$ aryl), —$(CH_2)_{n3}$(5-10 membered heterocyclyl) and —$(CH_2)_{n3} A^4 R^{37}$, for example —$(CH_2)_{n3} OR^{37}$ or —$(CH_2)_{n3} SR^{37}$, wherein n3 is an integer ranging from 0 to 6 (alternatively 0 to 4, alternatively 0 to 2, alternatively 1 or 0, alternatively 0), and $R^{37}$ is H or $C_1-C_6 alkyl$, for example, $C_1-C_6 alkyl$, alternatively $C_1-C_2 alkyl$.

According to another embodiment of the present invention, D is phenyl or pryidinyl (for example, pyridinyl), optionally substituted with one or two (for example, one) $R^{38}$, wherein each said $R^{38}$ is independently selected from group consisting of halo, $C_1$-$C_6$ alkyl, —$(CH_2)_nP(=O)(C_1$-$C_6alkyl)_2$, —$(CH_2)_jNR^{39}CH_2(CH_2)_nP(=O)(C_1$-$C_6alkyl)_2$, —$NR^{13}C(X^1)NR^{13}$-arylP$(=O)(C_1$-$C_6alkyl)_2$ and —$NR^{13}C(X^1)NR^{13}$-heleroarylP$(=O)(C_1$-$C_6alkyl)_2$, wherein $X^1$ is for example O or S, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —$(CH_2)_n(C_6$-$C_{10}$ aryl), —$(CH_2)_n$(5-10 membered heterocyclyl) and —$(CH_2)_nA^4R^{37}$, for example, —$(CH_2)_nOR^{37}$ or —$(CH_2)_nSR^{37}$, wherein each n is an independently selected integer ranging from 0 to 6 (alternatively 0 to 4, alternatively 0 to 2, alternatively 1 or 0, alternatively 0), and $R^{37}$ is H or $C_1$-$C_6$alkyl, for example, $C_1$-$C_6$alkyl, alternatively $C_1$-$C_2$alkyl.

According to another embodiment of the present invention, $A^4$ is O.

In another embodiment of the present invention, M is a structure selected from the group consisting of

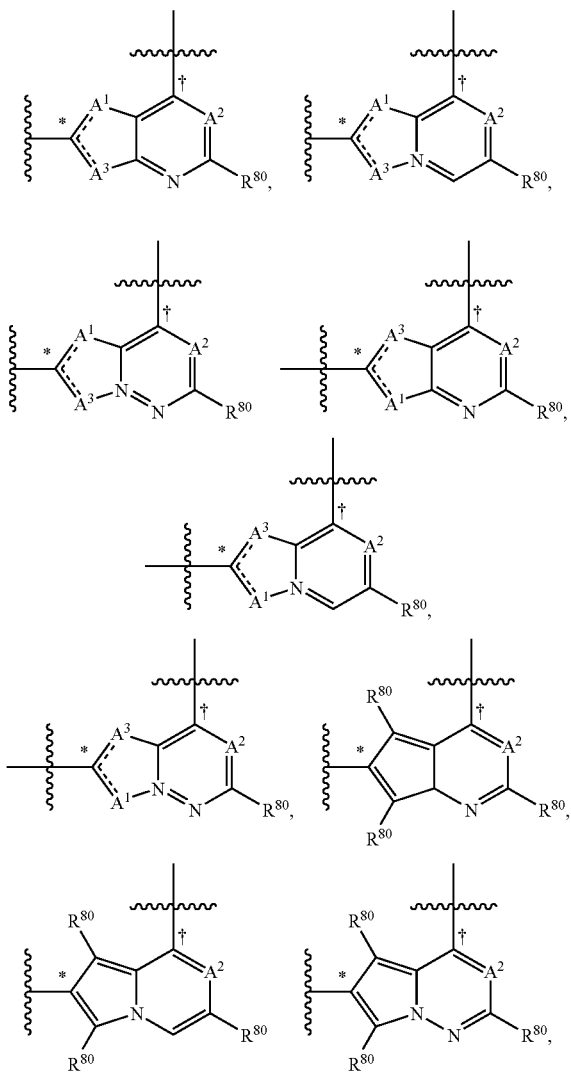

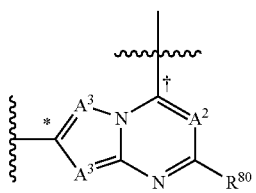

wherein

* represents the point of attachment to D;

† represents the point of attachment to Z;

$A^1$ is selected from the group consisting of —$CH_2$—, —O—, —S—, —N(H)—, —N($C_1$-$C_6$ alkyl)-, —N—(Y-aryl)-, —N-OMe, —$NCH_2$OMe and N-Bn;

Y is a bond or —$(C(R^x)(H))_t$—, wherein t is an integer from 1 to 6; and $R^x$ at each occurrence is independently selected from the group consisting of H and $C_1$-$C_6$ alkyl, wherein the $C_1$-$C_6$ alkyl is optionally substituted;

$A^2$ is selected from the group consisting of N and CR, wherein R is selected from the group consisting of —H, halogen, —CN, $C_1$-$C_6$ alkyl, $C_2$-$C_6$ alkenyl, $C_2$-$C_6$ alkynyl, —COOH and —C(O)Oalkyl, wherein the $C_1$-$C_6$ alkyl, $C_2$-$C_6$ alkenyl, $C_2$-$C_6$ alkynyl and —C(O)Oalkyl are optionally substituted;

each $A^3$ is independently selected from the group consisting of CH, C-D and N, for example, CH or N;

each $R^{80}$ is independently selected from the group consisting of H, halogen, $NO_2$, cyano, $OR^{83}$, $N(R^{83})_2$, $CO_2R^{83}$, $C(O)N(R^{83})_2$, $SO_2R^{83}$, $SO_2N(R^{83})_2$, $NR^{83}SO_2R^{83}$, $NR^{83}C(O)R^{83}$, $NR^{83}CO_2R^{83}$, —$CO(CH_2)_lR^{83}$, —$CONH(CH_2)_lR^{83}$, alkylaminoalkyl, alkylaminoalkynyl, $C_1$-$C_6$alkyl, substituted $C_1$-$C_6$alkyl, $C_3$-$C_7$cycloalkyl, substituted $C_3$-$C_7$cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl, and substituted heterocycloalkyl; and each $R^{83}$ is independently selected from the group consisting of H, alkyl, substituted alkyl, cycloalkyl, substituted cycloalkyl, aryl, substituted aryl, arylalkyl, substituted arylalkyl, heteroaryl, substituted heteroaryl, heterocycloalkyl, and substituted heterocycloalkyl; or two $R^{83}$ taken together with the N atom to which they are attached form a heterocyclic ring.

In another embodiment of the present invention, M is a structure selected from the group consisting of

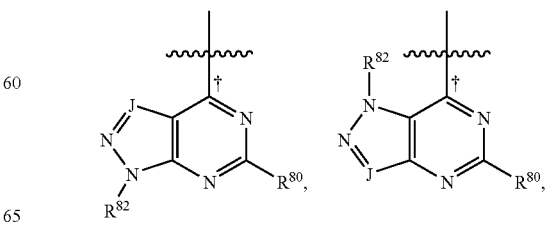

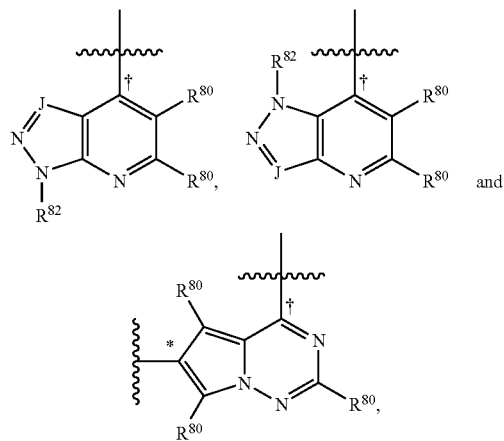
wherein
J is $CR^{80}$ or N;
$R^{82}$ is selected from the group consisting of H, $C_1$-$C_6$alkyl or substituted $C_1$-$C_6$alkyl, —Y-(aryl), —Y-(heteroaryl), -alkoxy and —$CH_2OMe$;
wherein *, †, $R^{80}$ and Y are as defined above.
In another embodiment of the present invention, M is a structure selected from the group consisting of
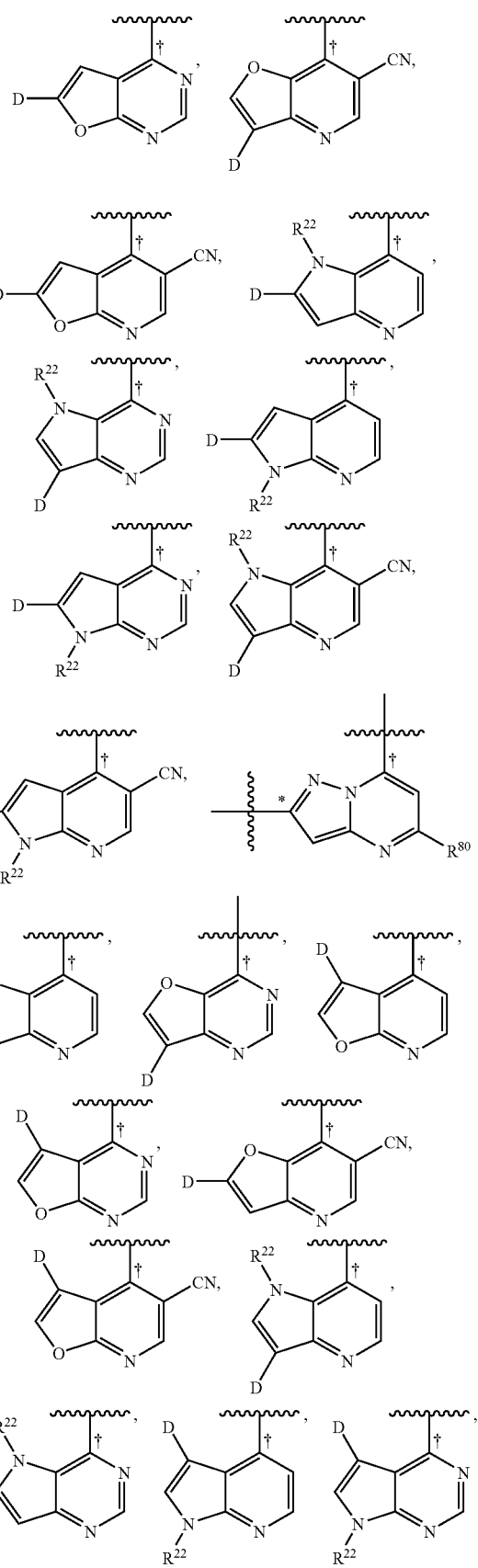

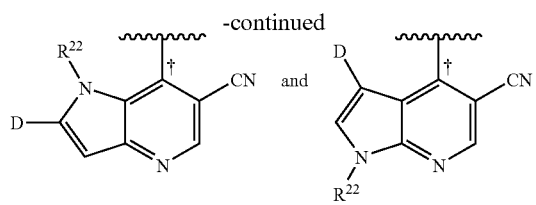

wherein
† is as defined above; and
R[22] is selected from the group consisting of —H, —C$_1$-C$_6$alkyl, —Y-aryl, alkoxy, —CH$_2$—O-Me and —Bn.

According to another embodiment of the present invention, M is

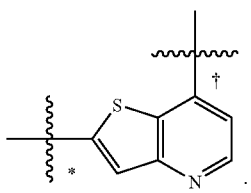 [SMILES: *c1cc2nccc(*)c2s1]

In another embodiment of the present invention, A$^1$ is S.

In another embodiment of the present invention, A$^2$ is —CH— or —C(CN)—.

In another embodiment of the present invention, A$^3$ is —C(R$^q$)— or N, wherein R$^q$ is selected from the group consisting of H, halogen, NO$_2$, cyano, OR″, NR′R″, CO$_2$R″, C(O)NR′R″, SO$_2$R″, SO$_2$NR′R″, NR″SO$_2$R″, NR″C(O)R″, NR″CO$_2$R″, —CO(CH$_2$)$_{0-4}$R″, —CONH(CH$_2$)$_{0-4}$R″, alkylaminoalkyl, alkylaminoalkynyl, C$_1$-C$_6$alkyl, substituted C$_1$-C$_6$alkyl, C$_3$-C$_7$cycloalkyl, substituted C$_3$-C$_7$cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl and substituted heterocycloalkyl; wherein each R″ is independently selected from the group consisting of H, alkyl, substituted alkyl, cycloalkyl, substituted cycloalkyl, aryl, substituted aryl, arylalkyl, substituted arylalkyl, heteroaryl, substituted heteroaryl, heterocycloalkyl and substituted heterocycloalkyl.

According to another embodiment of the present invention, Z is selected from the group consisting of —O—, —S— and —NR$^5$—, wherein R$^5$ is selected from the group consisting of H, an optionally substituted (C$_1$-C$_5$)acyl and C$_1$-C$_6$ alkyl-O—C(O), wherein C$_1$-C$_6$ alkyl is optionally substituted.

According to another embodiment of the present invention, Z is —O—.

According to another embodiment of the present invention, Ar is a 6-membered aromatic or heteroaromatic ring system.

According to another embodiment of the present invention, Ar is a 6-membered aromatic ring system.

According to another embodiment of the present invention, Ar is selected from the group consisting of phenyl, pyrazine, pyridazine, pryimidine and pyridine, wherein each of said phenyl, pyrazine, pyridazine, pryimidine and pyridine is optionally substituted with 0 to 4 R$^2$ groups.

According to another embodiment of the present invention, Ar is phenyl, optionally substituted with 0 to 4 R$^2$ groups, for example, with between zero and four halo.

In another embodiment of the present invention, G is B-L-T.

In another embodiment of the present invention G is

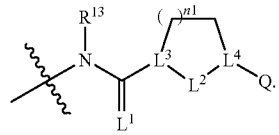

In another embodiment of the present invention G is selected from the group consisting of

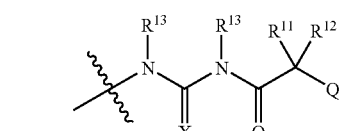

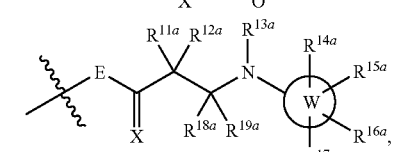

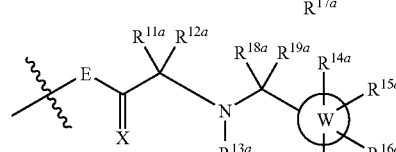

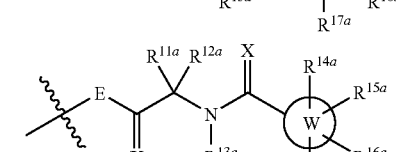

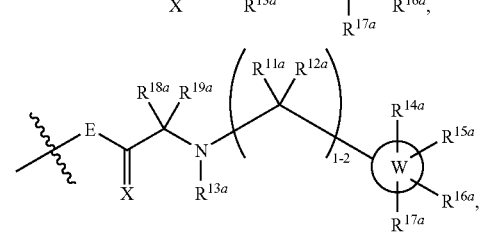

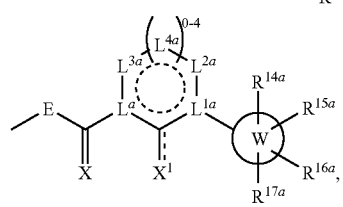

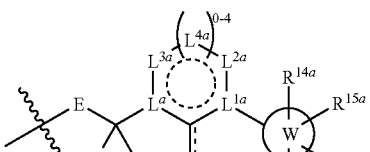

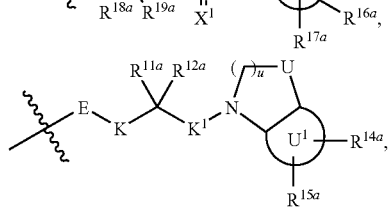

-continued
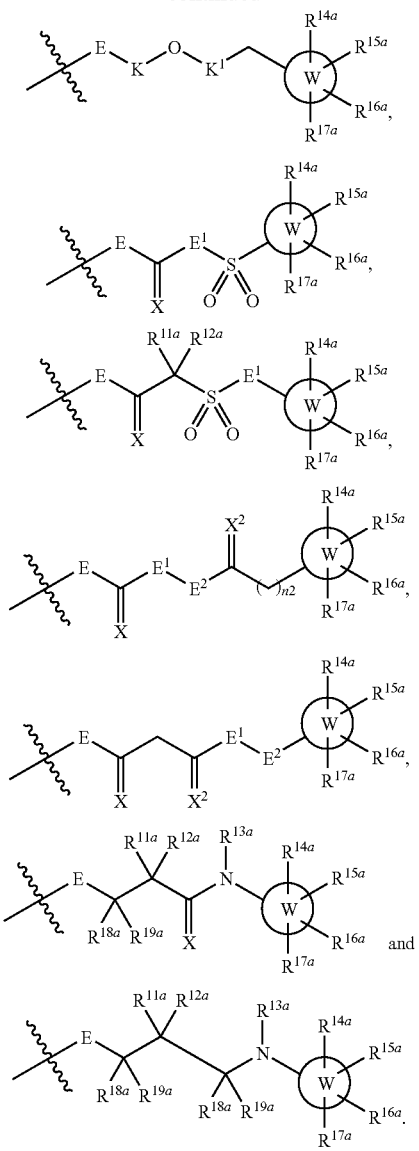
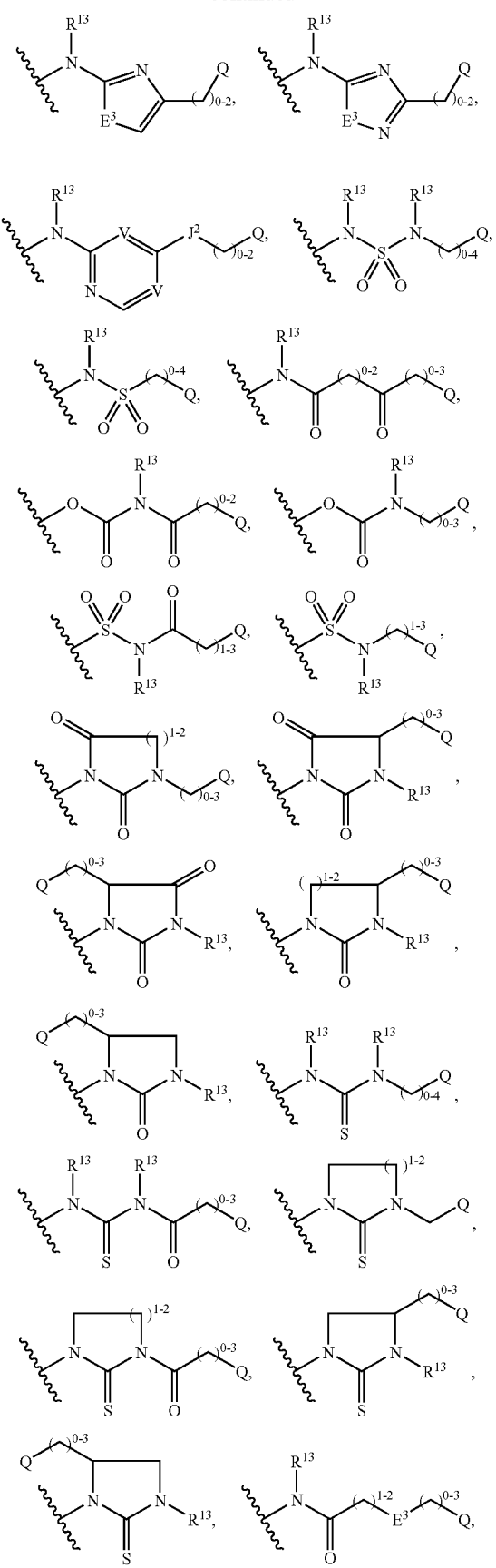
In another embodiment of the compounds according to the present invention, G is selected from the group consisting of
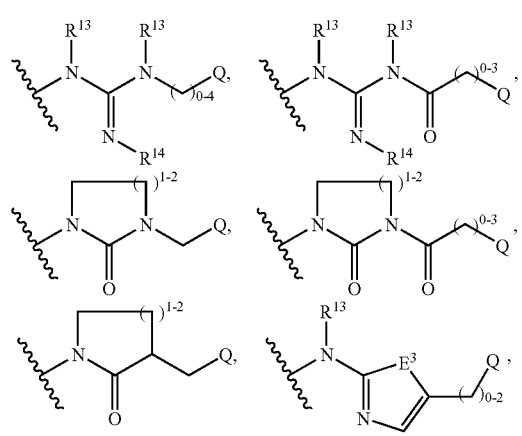

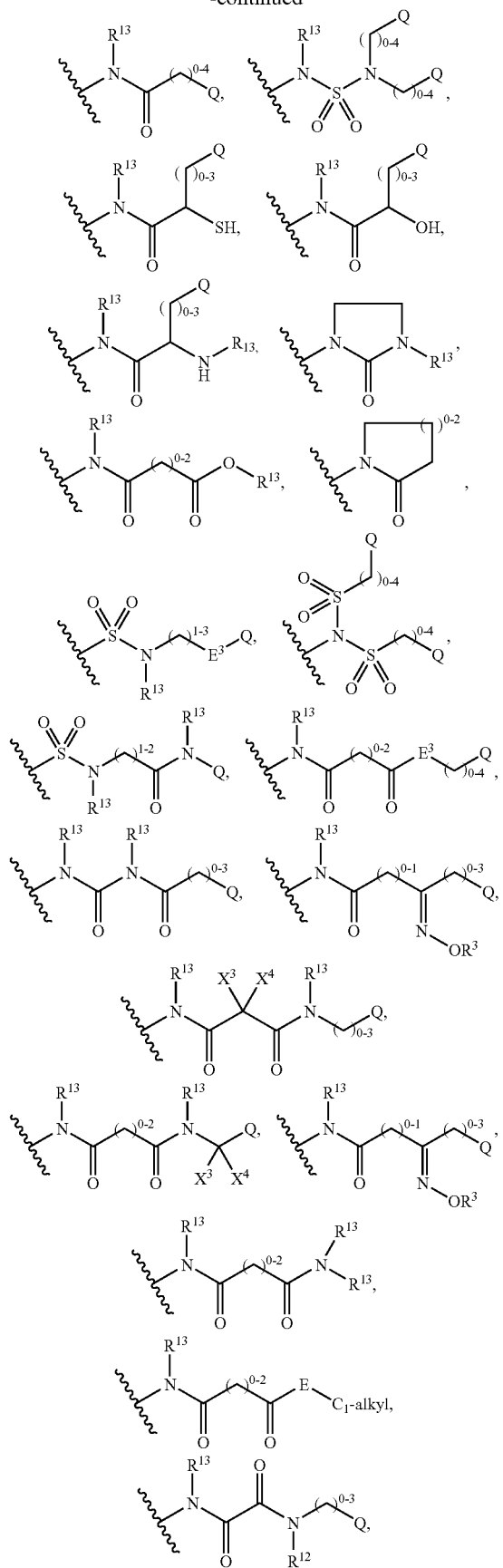
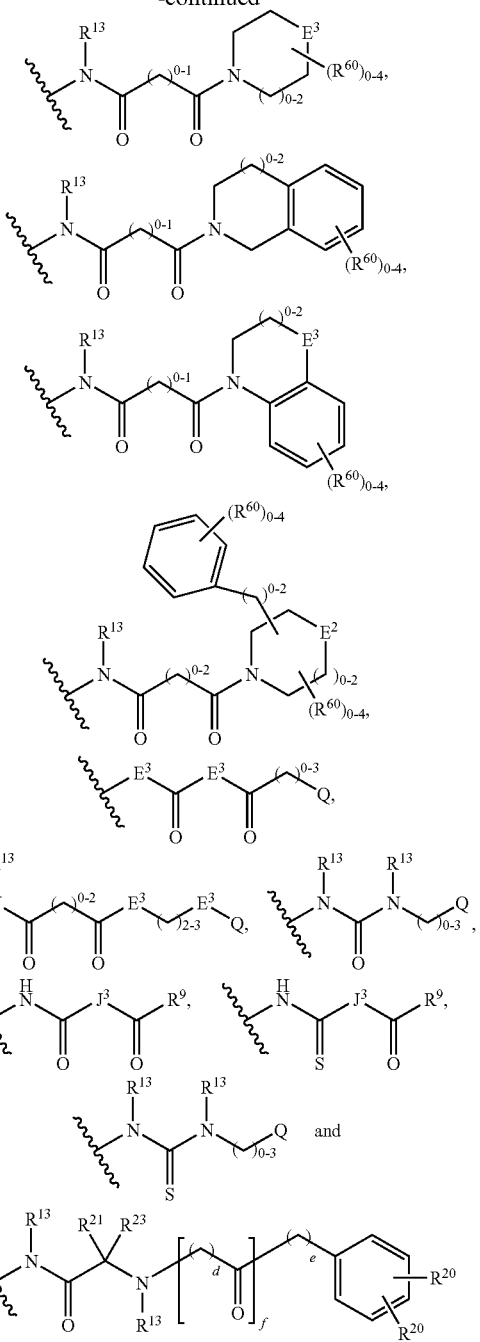

wherein $R^{13}$, $R^{14}$, Q, $R^{60}$ and $R^3$ are as defined above;
any methylene group is independently optionally substituted with $R^{25}$, wherein
$R^{25}$ is selected from the group consisting of halogen, trihalomethyl, —CN, —$NO_2$, —$NH_2$, —$OR^3$, —$NR^3$, $R^4$, —$S(O)_{0-2}R^3$, —$SO_2NR^3R^3$, —$CO_2R^3$, —$C(O)NR^3R^3$, —$N(R^3)SO_2R^3$, —$N(R^3)C(O)R^3$, —$N(R^3)CO_2R^3$, —$C(O)R^3$, an optionally substituted aryl, an optionally substituted arylalkyl, an optionally substituted heteroarylalkyl, and an optionally substituted ($C_1$-$C_6$)alkyl, or
two $R^{25}$, together with the carbon or carbons to which they are attached, can combine to form a three- to seven-membered alicyclic or heteroalicyclic, or
two $R^{25}$, on a single carbon can be oxo;

$R^9$ is selected from the group consisting of a $C_{1-6}$ alkyl on which one or more hydrogen atoms are optionally substituted by —$R^{24}$, -$T^1$-$R^{15}$, or —$NR^{16}R^{17}$, a —$N(R^{18})(R^{19})$ moiety and a saturated or unsaturated three- to eight-membered carbocyclic or heterocyclic group which is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_{1-6}$ alkylthio, a phenoxy, an acetyl, or a saturated or unsaturated five- or six-membered heterocyclyl ring wherein, when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, wherein $T^1$ is selected from the group consisting of —O—, —S— and —NH—;

$R^{24}$ represents a saturated or unsaturated three- to eight-membered carbocyclic or heterocyclic group;

$R^{15}$, $R^{16}$, and $R^{17}$, which may be the same or different, represent a $C_{1-6}$ alkyl or a saturated or unsaturated three- to eight-membered carbocyclic or heterocyclic group; wherein the three- to eight-membered carbocyclic or heterocyclic group represented by $R^{24}$, $R^{15}$, $R^{16}$, and $R^{17}$ is optionally substituted by a $C_{1-6}$ alkyl, a $C_{1-6}$ alkoxy, a halogen atom, nitro, a trifluoromethyl, a $C_{1-6}$ alkoxy carbonyl, a cyano, a cyano $C_{1-6}$ alkyl, a $C_{1-6}$ alkylthio, a phenoxy, an acetyl, or a saturated or unsaturated five- or six-membered heterocyclyl ring; and wherein when the three- to eight-membered carbocyclic or heterocyclic group is substituted by two $C_{1-6}$ alkyl groups, the two alkyl groups may combine together to form an alkylene chain; and wherein the three- to eight-membered carbocyclic or heterocyclic group may be a bicyclic group condensed with another saturated or unsaturated three- to eight-membered carbocyclic or heterocyclic group; and $R^{18}$ and $R^{19}$, which may be the same or different, represent (1) a hydrogen atom, (2) a $C_{1-6}$ alkyl which is optionally substituted by a $C_{1-6}$ alkoxy, a $C_{1-6}$ alkylthio, or a saturated or unsaturated three- to eight-membered carbocyclic or heterocyclic group in which the three- to eight-membered carbocyclic or heterocyclic group is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_{1-6}$ alkylthio, a phenoxy, an acetyl, or a saturated or unsaturated five- or six-membered heterocyclyl ring and wherein when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, or (3) a saturated or unsaturated three- to eight-membered carbocyclic or heterocyclic group which is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_{1-6}$ alkylthio, a phenoxy, an acetyl, or a saturated or unsaturated five- or six-membered heterocyclyl ring and in which, when the three to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group;

$X^3$ and $X^4$ are each independently selected from the group consisting of —H, halogen, cyano, nitro, $C_1$-$C_6$ alkyl, or $X^3$ and $X^4$ together with the atom to which they are attached form a $C_3$-$C_4$ cycloalkyl;

each $E^3$ is independently selected from the group consisting of —O—, —$N(R^{13})$—, —$CH_2$— and —$S(O)_{0-2}$;

$J^2$ is selected from the group consisting of —O—, —$N(R^{13})$—, —$CH_2$— and —$C(=O)N(R^{13})$;

$J^3$ represents —$C(R^{26})(R^{27})$—, wherein $R^{26}$ and $R^{27}$ are independently selected from the group consisting of a hydrogen atom, a $C_{1-4}$ alkyl, a $C_{1-4}$ alkoxy and —$N(R^{12b})$, wherein $R^{12b}$ is a hydrogen atom or a $C_{1-4}$ alkyl;

each V is independently selected from the group consisting of =N— and =C(H)—;

$R^{21}$ and $R^{23}$ are independently selected from the group consisting of H, halogen, —OH, unsubstituted —O—($C_1$-$C_6$alkyl), substituted —O—($C_1$-$C_6$alkyl), unsubstituted —O-(cycloalkyl), substituted —O-(cycloalkyl), unsubstituted —NH($C_1$-$C_6$alkyl), substituted —NH($C_1$-$C_6$alkyl), —$NH_2$, —SH, unsubstituted —S—($C_1$-$C_6$alkyl), substituted —S—($C_1$-$C_6$alkyl), unsubstituted $C_1$-$C_6$alkyl and substituted $C_1$-$C_6$alkyl; or $R^{21}$ and $R^{23}$ taken together with the atom to which they are attached form a $C_3$-$C_7$ ring system, wherein said ring system is optionally substituted;

d is 0, 1, 2 or 3;

e is 0, 1, 2 or 3; and f is 0 or 1.

According to another embodiment of the present invention, G is selected from the group consisting of

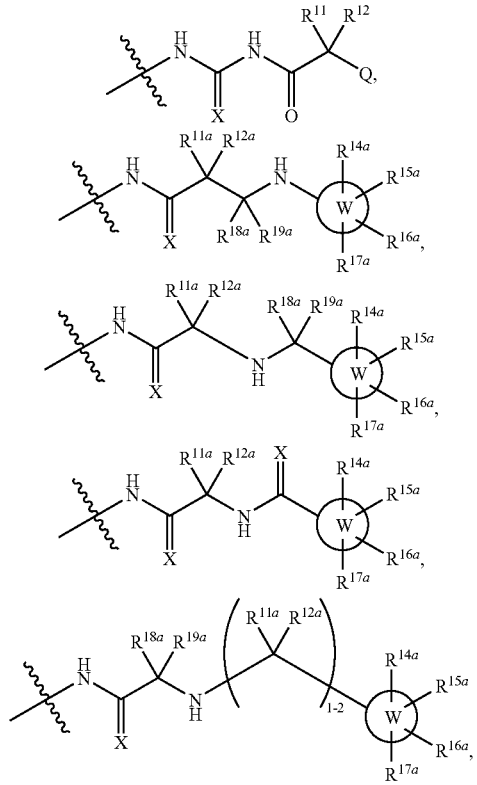

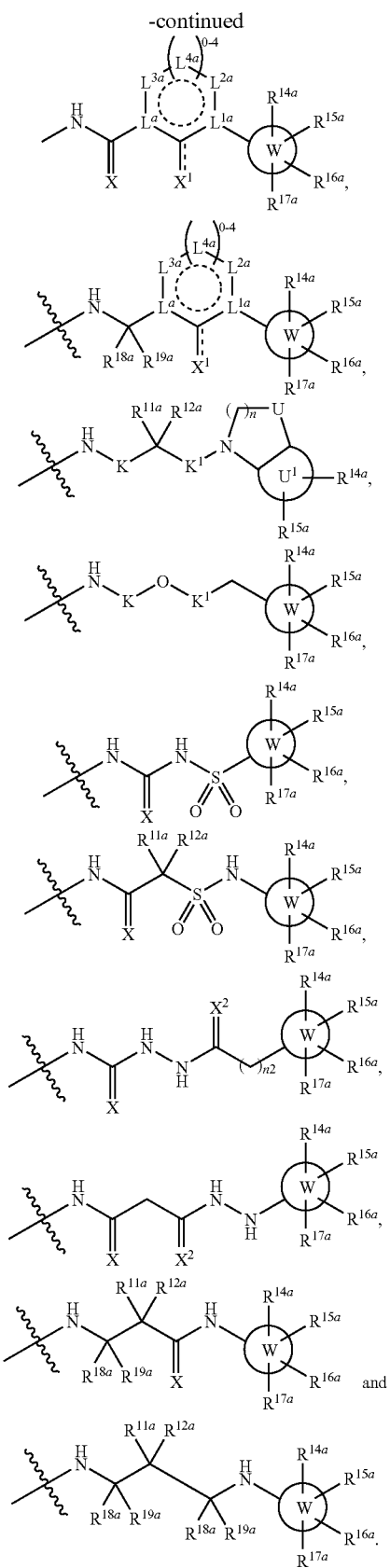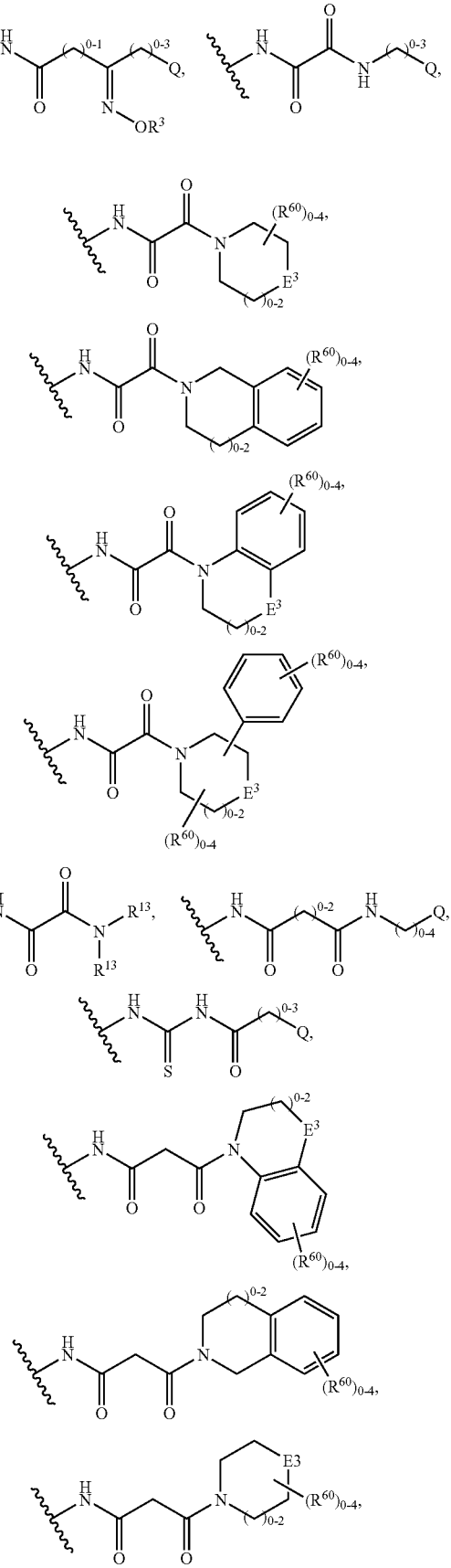
In another embodiment of the present invention, G is selected from the group consisting of

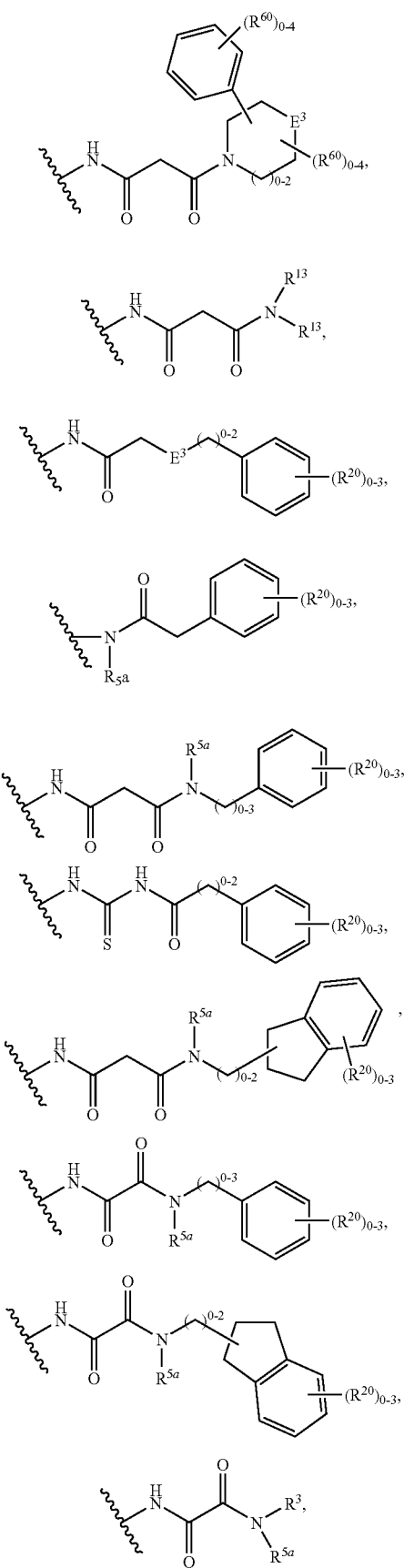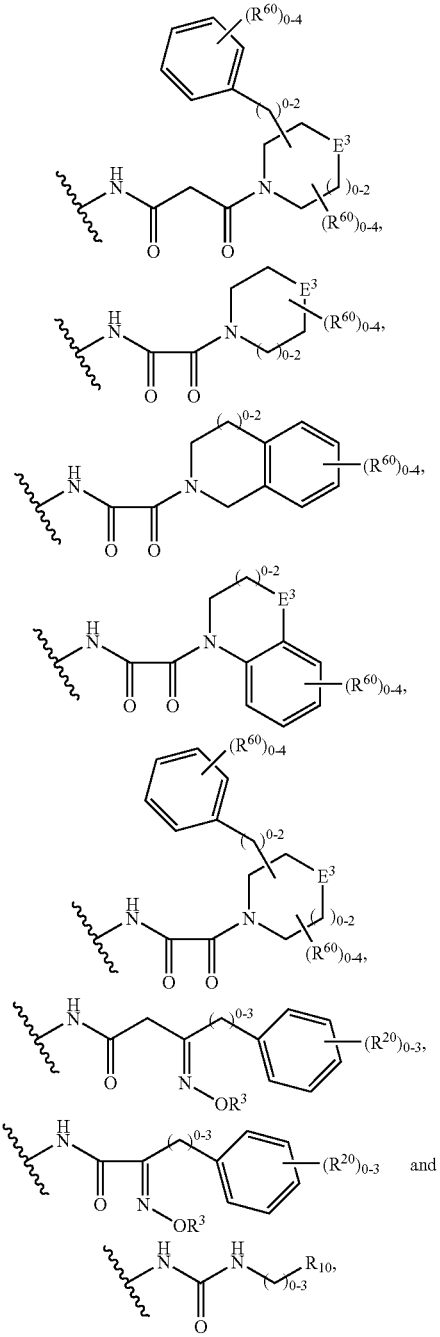

wherein each methylene in any of the above formulae, other than those in a depicted ring, is independently optionally substituted with $R^{25}$;

$R^{5a}$ is —H or an optionally substituted $(C_1-C_6)$alkyl;

$R^{10}$ is an azolyl, wherein one or more hydrogen atoms are optionally substituted by a moiety selected from the group consisting of a halogen, $C_{1-4}$ alkyl, $C_{1-4}$ alkoxy, $C_{1-4}$ alkylthio, trihalomethyl, nitro, amino optionally independently substituted by one or two of $C_{1-4}$ alkyl, a $C_{1-4}$ alkoxycarbonyl $C_{1-4}$ alkyl, a $C_{1-4}$ alkylcarbonyl and a $C_{3-5}$ cyclic alkyl.

In another embodiment of the compounds according to the present invention, a methylene group between two carbonyl groups is mono- or di-substituted with either an optionally substituted (C$_1$-C$_6$)alkyl or an optionally substituted spirocycle.

In another embodiment of the compounds according to the present invention, R$^{10}$ is selected from the group consisting of

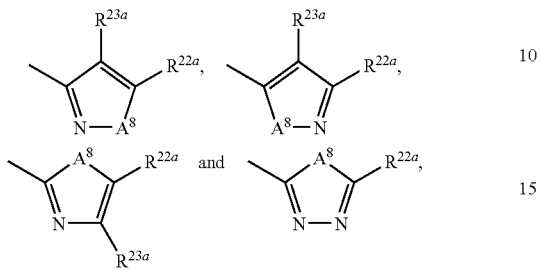

wherein A$^8$ is selected from the group consisting of —O—, —S— and —NH—; and

R$^{22a}$ and R$^{23a}$ are independently selected from the group consisting of —H, halogen, C$_{1-4}$ alkyl, C$_{1-4}$ alkoxy, C$_{1-4}$ alkylthio, trihalomethyl, nitro, amino optionally independently substituted by one or two of C$_{1-4}$ alkyl, a C$_{1-4}$ alkoxycarbonyl C$_{1-4}$ alkyl, a C$_{1-4}$ alkylcarbonyl and a C$_{3-5}$ cyclic alkyl.

According to another embodiment of the present invention, G is selected from the group consisting of

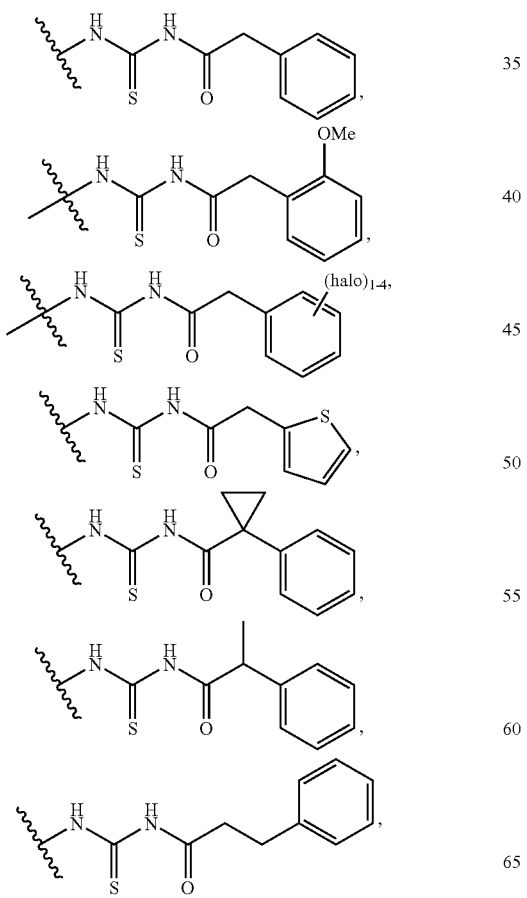

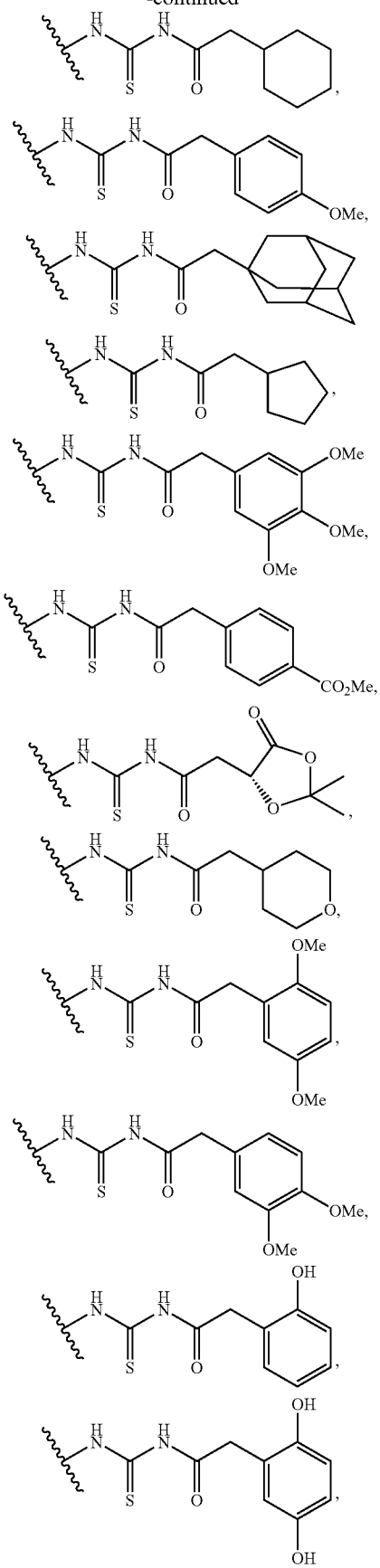

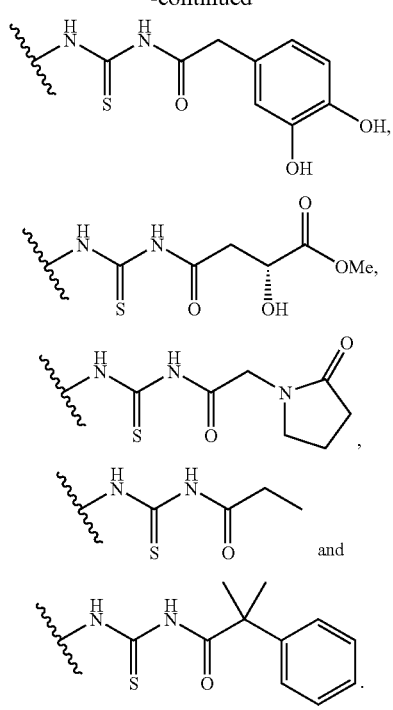
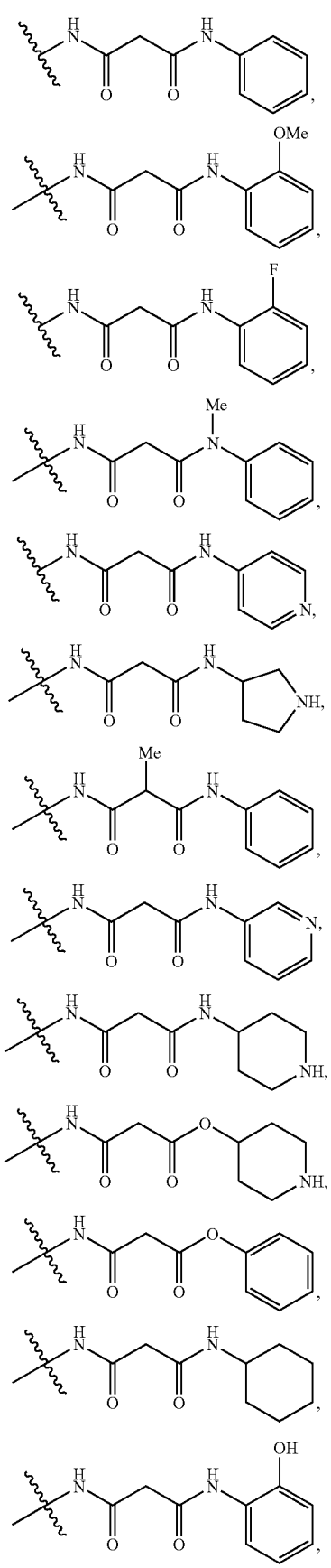
According to another embodiment of the present invention, G is selected from the group consisting of
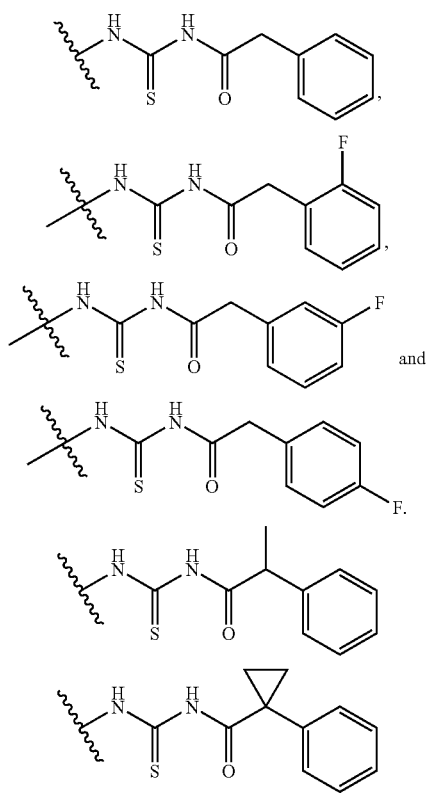
According to another embodiment of the present invention, G is selected from the group consisting of

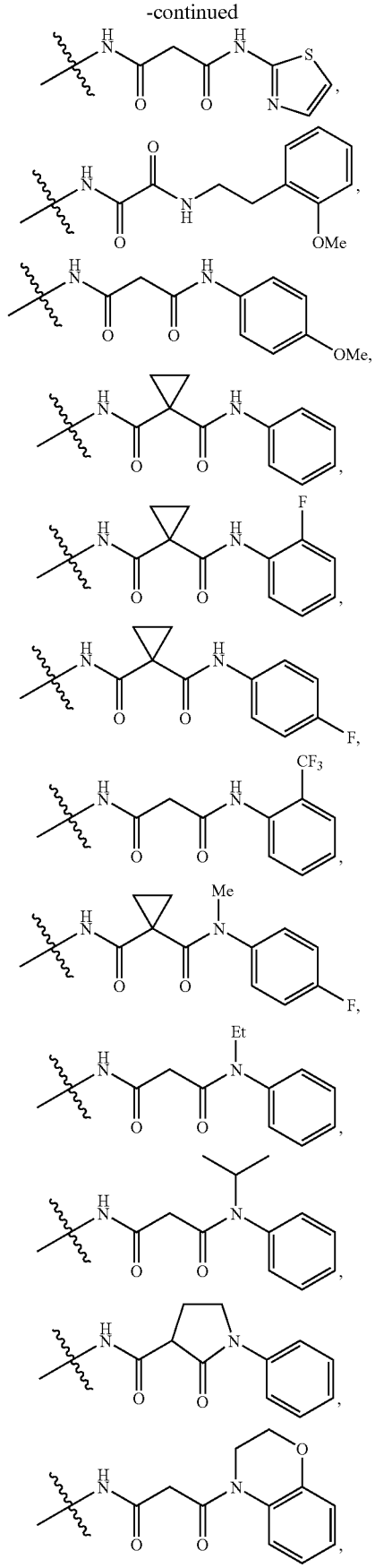
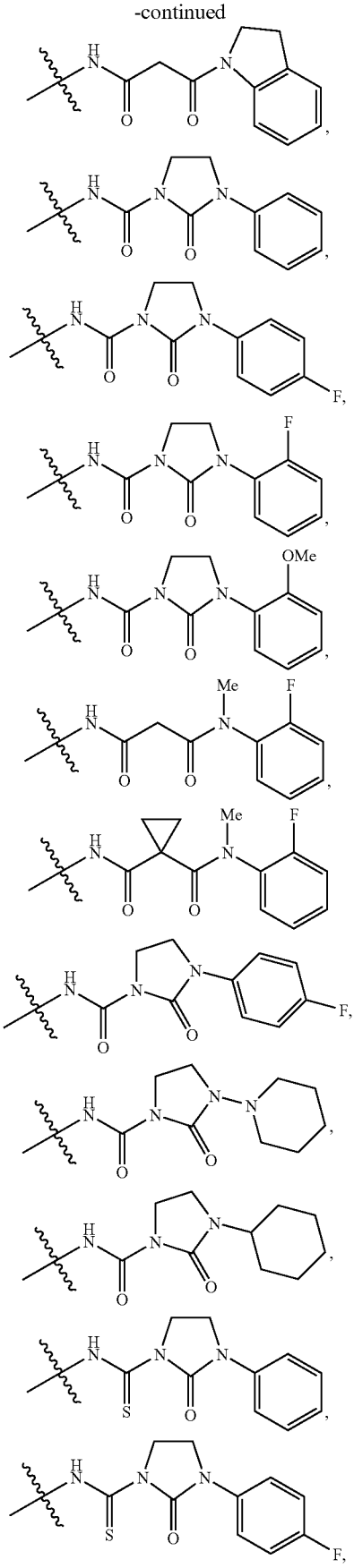

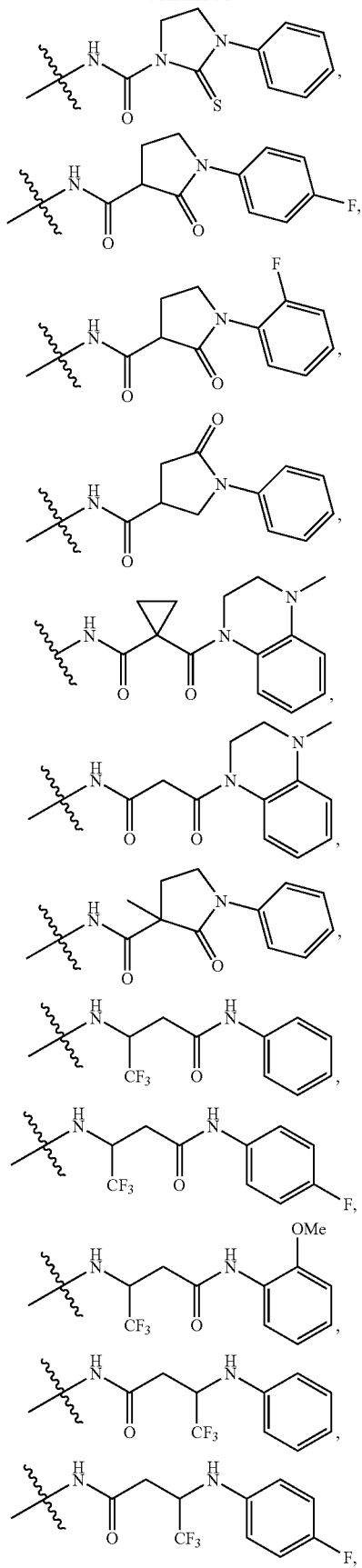
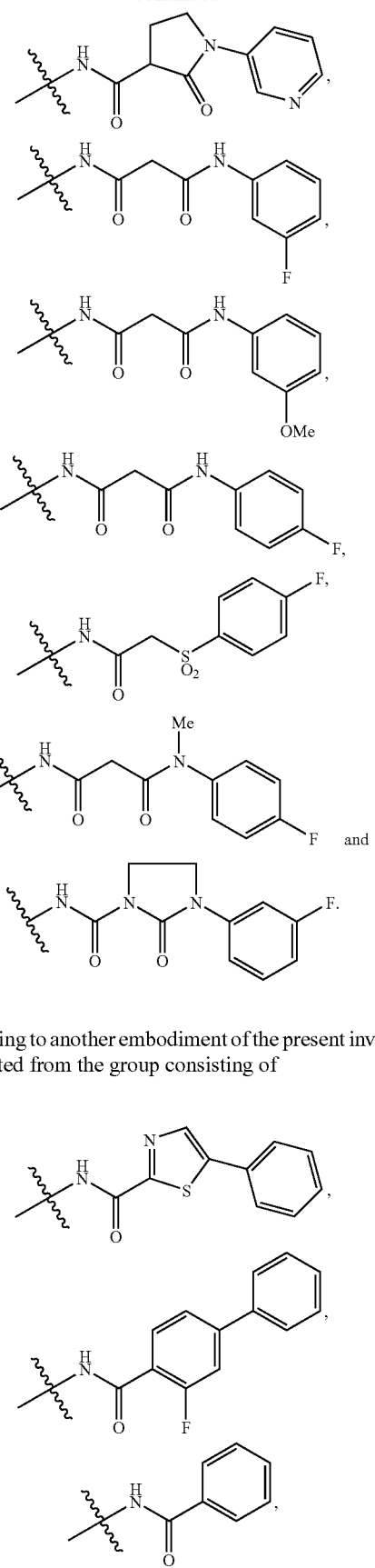
According to another embodiment of the present invention, G is selected from the group consisting of
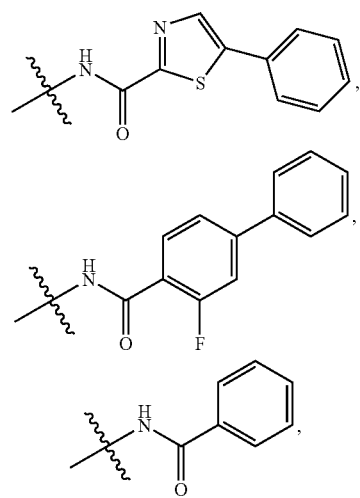

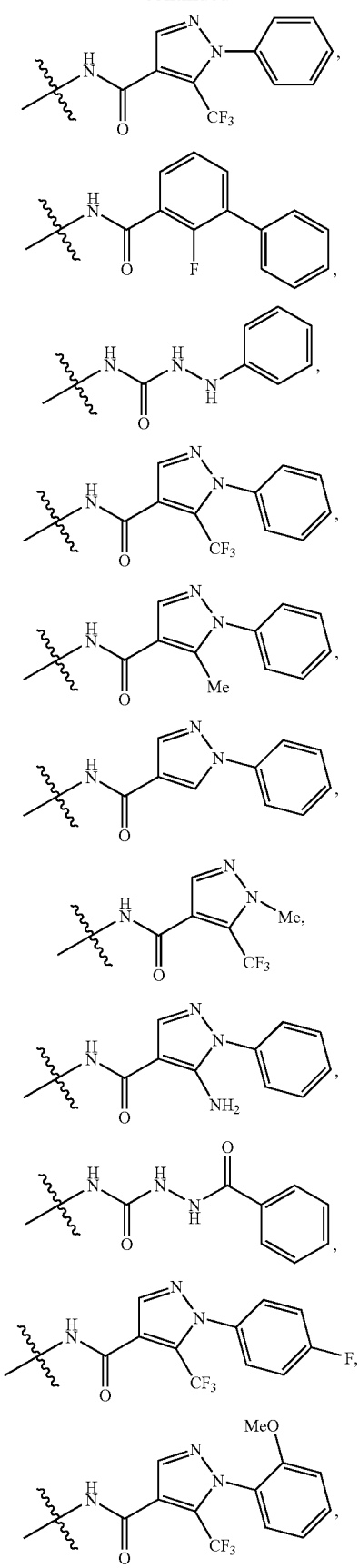
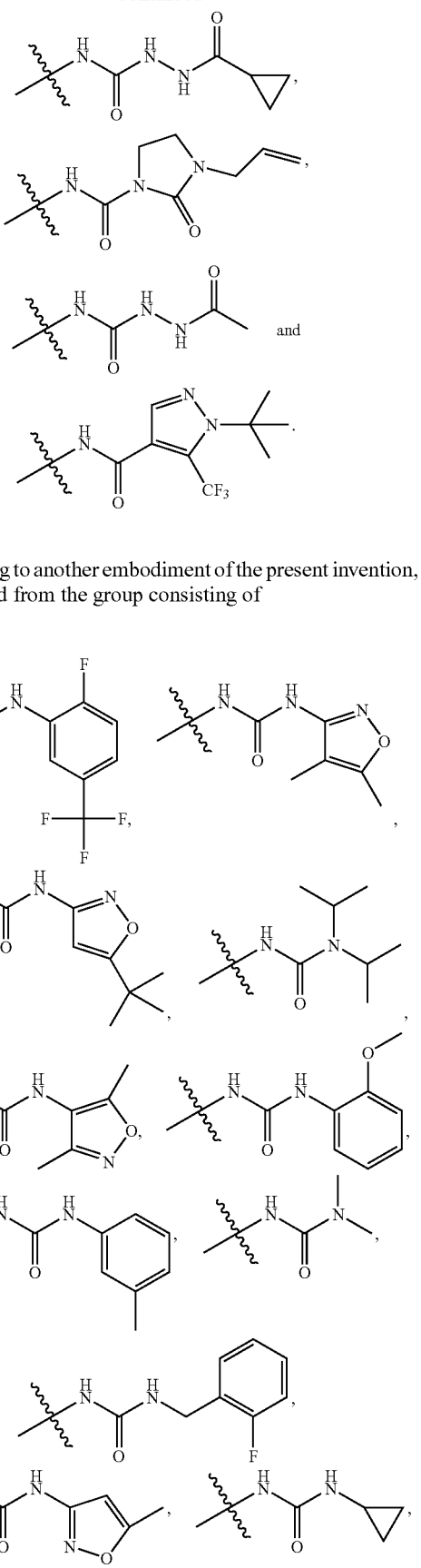
According to another embodiment of the present invention, G is selected from the group consisting of

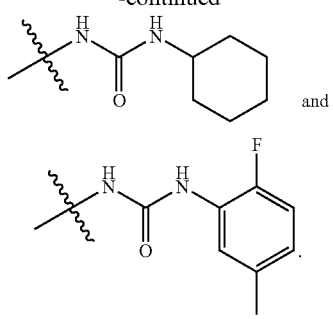

According to another embodiment of the present invention, G is selected from the group consisting of

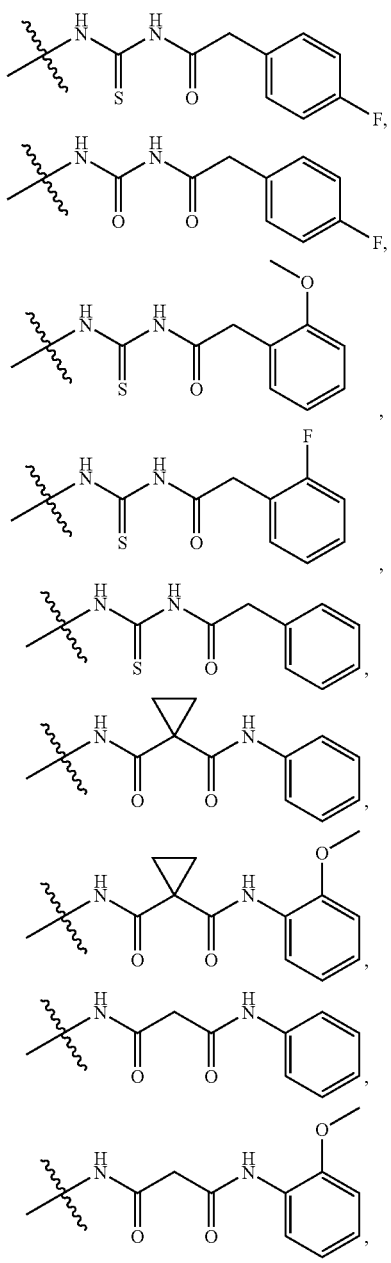

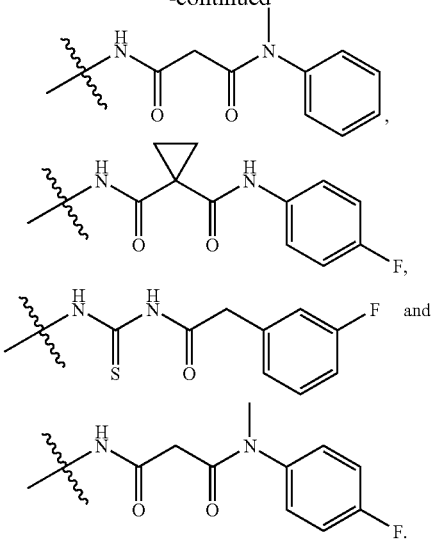

According to another embodiment of the present invention, any of E, $E^1$, $E^2$ or $E^3$ are independently —NH—.

According to another embodiment of the present invention, one of $R^{18a}$ and $R^{19a}$ is —CF$_3$ and the other is —H.

According to another embodiment of the present invention, $R^{11}$ and $R^{12}$ are each —H.

According to another embodiment of the present invention, X is S or O, for example, S.

According to another embodiment of the present invention, $R^{13}$ is H.

According to another embodiment of the present invention, $R^{11}$, $R^{12}$ and $R^{13}$ are each —H.

According to another embodiment of the present invention, X is O, one of $R^{18a}$ and $R^{19a}$ is —CF$_3$ and the other is —H, and $R^{11}$, $R^{12}$ and $R^{13}$ are each —H.

According to another embodiment of the present invention, W is selected from the group consisting of

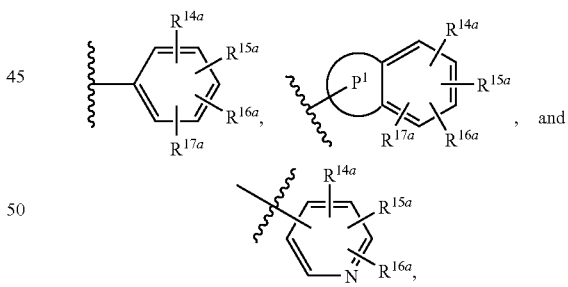

wherein $P^1$ is a five- to seven-membered ring, including the two shared carbon atoms of the aromatic ring to which $P^1$ is fused, and wherein $P^1$ optionally contains between one and three heteroatoms.

According to another embodiment of the present invention, W is selected from the group consisting of phenyl, napthyl, 1,2,3,4-tetrahydronaphthyl, indanyl, benzodioxanyl, benzofuranyl, phenazinyl, phenothiazinyl, phenoxazinyl, tetrahydroisoquinolyl, pyrrolyl, pyrazolyl, pyrazolidinyl, imidazolyl, imidazolinyl, imidazolidinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, thiazolyl, thiazolinyl, thiazolidinyl, isothiazolyl, isothiazolidinyl, indolyl, isoindolyl, indolinyl, isoindolinyl, octahydroindolyl, octahydroisoindolyl, quinolyl, isoquinolyl, benzimidazolyl, thiadiazolyl, benzopyranyl, benzothiazolyl, benzoxazolyl, furyl, thienyl, benzothieliyl, and oxadiazolyl; each optionally substituted.

According to another embodiment of the present invention, W is selected from the group consisting of phenyl, napthyl, 1,2,3,4-tetrahydronaphthyl, indanyl, benzodioxanyl, benzofuranyl, phenazinyl, phenothiazinyl, phenoxazinyl, tetrahydroisoquinolyl, pyrrolyl, pyrazolyl, pyrazolidinyl, imidazolyl, imidazolinyl, imidazolidinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, thiazolyl, thiazolinyl, thiazolidinyl, isothiazolyl, isothiazolidinyl, indolyl, isoindolyl, indolinyl, isoindolinyl, octahydroindolyl, octahydroisoindolyl, quinolyl, isoquinolyl, benzimidazolyl, thiadiazolyl, benzopyranyl, benzothiazolyl, benzoxazolyl, furyl, thienyl, benzothieliyl, and oxadiazolyl; each optionally substituted with one or more of R14a, R15a, R16a and R17a.

According to another embodiment of the present invention, W is phenyl, optionally substituted.

According to another embodiment of the present invention, W is phenyl, optionally substituted with one or more of $R^{14a}$, $R^{15a}$, $R^{16a}$ and $R^{17a}$.

According to another embodiment of the present invention, W is substituted by a halogen and either an alkenyl or alkynyl.

According to another embodiment of the present invention W is phenyl substituted by a halogen and either an alkenyl or alkynyl.

In another embodiment of the compounds according to the present invention, Q is selected from the group consisting of

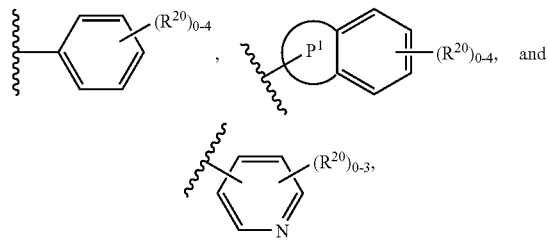

wherein $P^1$ is a five- to seven-membered ring, including the two shared carbon atoms of the aromatic ring to which $P^1$ is fused, and wherein $P^1$ optionally contains between one and three heteroatoms.

In another embodiment of the compounds according to the present invention, Q is selected from the group consisting of phenyl, napthyl, 1,2,3,4-tetrahydronaphthyl, indanyl, benzodioxanyl, benzofuranyl, phenazinyl, phenothiazinyl, phenoxazinyl, tetrahydroisoquinolyl, pyrrolyl, pyrazolyl, pyrazolidinyl, imidazolyl, imidazolinyl, imidazolidinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, thiazolyl, thiazolinyl, thiazolidinyl, isothiazolyl, isothiazolidinyl, indolyl, isoindolyl, indolinyl, isoindolinyl, octahydroindolyl, octahydroisoindolyl, quinolyl, isoquinolyl, benzimidazolyl, thiadiazolyl, benzopyranyl, benzothiazolyl, benzoxazolyl, furyl, thienyl, benzothieliyl, and oxadiazolyl; each optionally substituted with between one and four of $R^{20}$, wherein According to another embodiment of the present invention, Q is phenyl, optionally substituted.

According to another embodiment of the present invention, Q is phenyl, optionally substituted with one or more of $R^{20}$.

According to another embodiment of the presention invention, Q is substituted by a halogen and either an alkenyl or alkynyl.

According to another embodiment of the presention invention Q is phenyl substituted by a halogen and either an alkenyl or alkynyl.

According to another embodiment of the present invention, $R^{14a}$ and $R^{15a}$ are both H, $R^{16a}$ is $C_2$-$C_7$ alkenyl or $C_2$-$C_6$ alkynyl and $R^{17a}$ is halogen, for example fluorine.

In another embodiment, $L^3$ and $L^4$ are independently —CH— or N.

In another embodiment of the present invention, $R^{39}$ is selected from the group consisting of H, $C_1$-$C_6$alkyl and $C_1$-$C_6$cycloalkyl In another embodiment of the present invention,
D is a 5- or 6-membered aryl or a 5- or 6-membered heteroaryl, each of which is optionally substituted with 1 to 5 independently selected $R^{38}$ groups, alternatively 1 to 3 independently selected $R^{38}$ groups, and alternatively 1 or 2 independently selected $R^{38}$ group;
M is

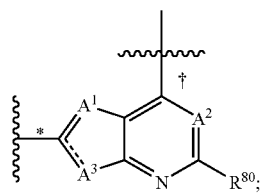

Z is —O—, —S—, —SO—, —SO_2—, —CH_2O—, —OCH_2—, —CH_2— or —N(R^5)—, for example, —O—;
Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and
G is

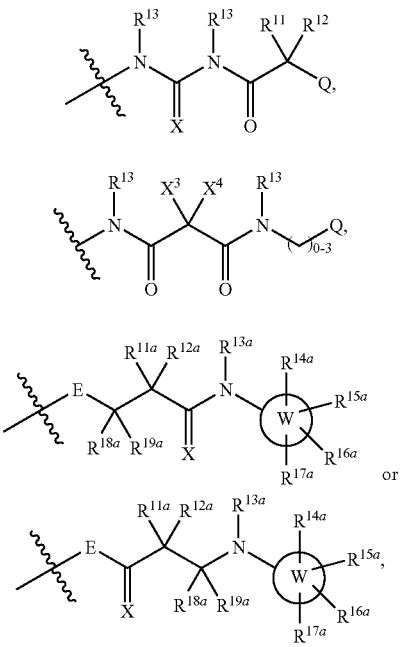

wherein Q is optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo In another embodiment of the present invention, D is a 5- or 6-membered aryl or a 5- or 6-membered heteroaryl, each of which is optionally substituted with 1 to 5 independently selected $R^{38}$ groups, alternatively 1 to 3 independently selected $R^{38}$ groups, and alternatively 1 or 2 independently selected $R^{38}$ group, wherein each said $R^{38}$ is independently selected from the group consisting of halo, $C_1$-$C_6$ alkyl, —C(O)NR$^{36}$R$^{39}$, —C(O)O—(CH$_2$)$_n$NR$^{36}$R$^{39}$, —(CH$_2$)$_j$NR$^{39}$(CH$_2$)$_i$S(O)$_j$(C$_1$-C$_6$ alkyl), —(CH$_2$)$_j$NR$^{39}$(CH$_2$)$_n$R$^{36}$ and —C(O)(CH$_2$)$_j$NR$^{39}$(CH$_2$)$_n$R$^{36}$ (for example —(CH$_2$)$_j$NR$^{39}$(CH$_2$)$_n$R$^{36}$) wherein each j is an integer independently selected from 0 to 4 (alternatively 1 to 4, alternatively 1 or 2, alternatively 1), n is an integer from 0 to 6 (alternatively 2 to 6, alternatively 2 to 4, alternatively, 1 or 2), i is 2 or 3, $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —(CH$_2$)$_n$($C_6$-$C_{10}$ aryl), —(CH$_2$)$_n$(5-10 membered heterocyclyl) and —(CH$_2$)$_n$A$^4$R$^{37}$, for example —(CH$_2$)$_n$OR$^{37}$ or —(CH$_2$)$_n$SR$^{37}$, wherein each n is an independently selected integer ranging from 0 to 6 (alternatively 0 to 4, alternatively 0 to 2, alternatively 1 or 0, alternatively 0), and $R^{37}$ is H or $C_1$-$C_6$alkyl, for example, $C_1$-$C_6$alkyl, alternatively $C_1$-$C_2$alkyl;

M is

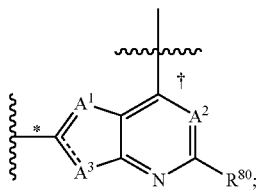

Z is —O—, —S—, —SO—, —SO$_2$—, —CH$_2$O—, —OCH$_2$—, —CH$_2$— or —N(R$^5$)—, for example —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and G is

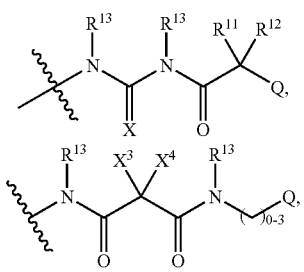

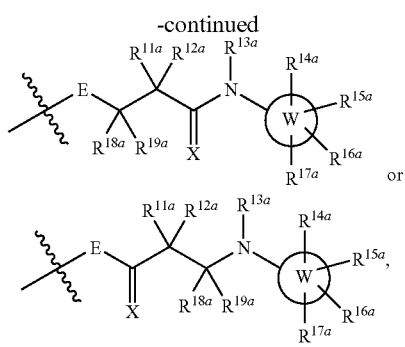

wherein Q is optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,

D is phenyl or pyridinyl (for example pyridinyl), each of which is optionally substituted with 1 to 5 independently selected $R^{38}$ groups, alternatively 1 to 3 independently selected $R^{38}$ groups, and alternatively 1 or 2 independently selected $R^{38}$ group;

M is

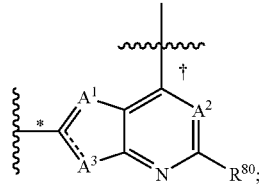

Z is —O—, —S—, —SO—, —SO$_2$—, —CH$_2$O—, —OCH$_2$—, —CH$_2$— or —N(R$^5$)—, for example —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and G is

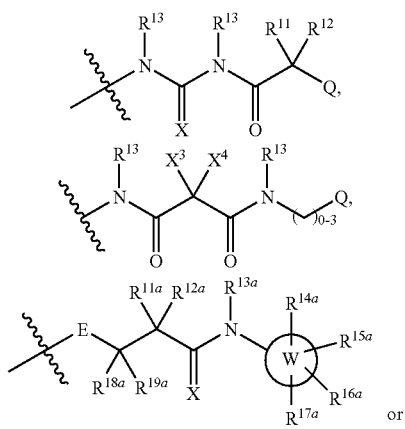

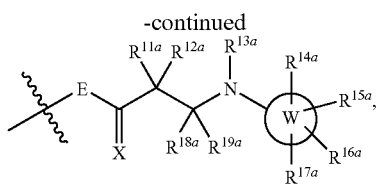

wherein Q is optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments each $R^{20}$ is halogen. In some embodiments, Ar is phenyl optionally substituted with 0 to 4 $R^2$ groups, for example with between zero and four halo.

In another embodiment of the present invention,
D is phenyl or pyridinyl (for example pyridinyl), each of which is optionally substituted with 1 to 5 independently selected $R^{38}$ groups, alternatively 1 to 3 independently selected $R^{38}$ groups, and alternatively 1 or 2 independently selected $R^{38}$ group, wherein each said $R^{38}$ is independently selected from the group consisting of halo, $C_1$-$C_6$ alkyl, —C(O)NR$^{36}$R$^{39}$, —C(O)O—(CH$_2$)$_n$NR$^{36}$R$^{39}$, —(CH$_2$)$_j$NR$^{39}$(CH$_2$)$_i$S(O)$_j$(C$_1$-$C_6$alkyl), —(CH$_2$)$_j$NR$^{39}$ (CH$_2$)$_n$R$^{36}$ and —C(O)(CH$_2$)$_j$NR$^{39}$(CH$_2$)$_n$R$^{36}$, (for example —(CH$_2$)$_j$NR$^{39}$(CH$_2$)$_n$R$^{36}$) wherein each j is an integer independently selected from 0 to 4 (alternatively 1 to 4, alternatively 1 or 2, alternatively 1), n is an integer from 0 to 6 (alternatively 2 to 6, alternatively 2 to 4, alternatively, 1 or 2), i is 2 or 3, $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —(CH$_2$)$_{n3}$ (C$_6$-$C_{10}$ aryl), —(CH$_2$)$_{n3}$(5-10 membered heterocyclyl) and —(CH$_2$)$_{n3}$A$^4$R$^{37}$, for example, —(CH$_2$)$_{n3}$OR$^{37}$ or —(CH$_2$)$_{n3}$SR$^{37}$, wherein n3 is an integer ranging from 0 to 6 (alternatively 0 to 4, alternatively 0 to 2, alternatively 1 or 0, alternatively 0), and $R^{37}$ is H or $C_1$-$C_6$alkyl, for example, $C_1$-$C_6$alkyl, alternatively $C_1$-$C_2$alkyl;
M is

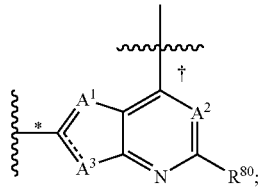

Z is —O—, —S—, —SO—, —SO$_2$—, —CH$_2$O—, —OCH$_2$—, —CH$_2$— or —N(R$^5$)—, for example —O—;
Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and
G is

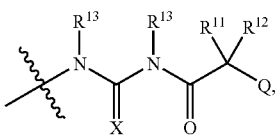

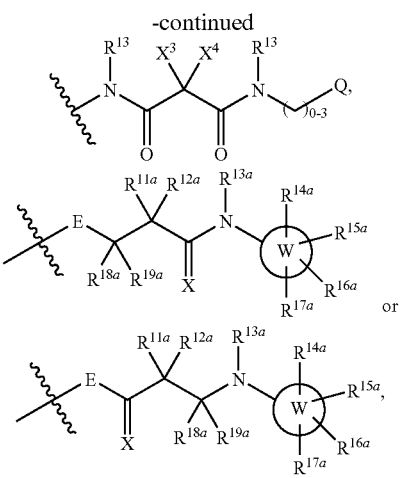

wherein Q is optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,
D is a 5- or 6-membered aryl or a 5- or 6-membered heteroaryl, each of which is optionally substituted with 1 to 5 independently selected $R^{38}$ groups, alternatively 1 to 3 independently selected $R^{38}$ groups, and alternatively 1 or 2 independently selected $R^{38}$ group;
M is

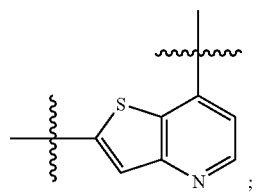 [SMILES: *c1cc2nccc(*)c2s1 ; ";"]

Z is —O—, —S—, —SO—, —SO$_2$—, —CH$_2$O—, —OCH$_2$—, —CH$_2$— or —N(R$^5$)—, for example —O—;
Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and
G is

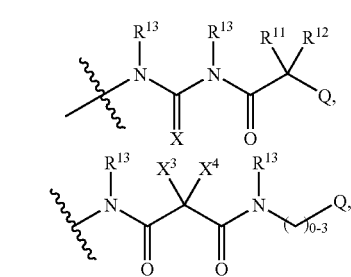

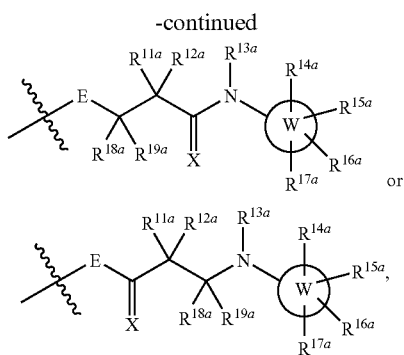

wherein Q is optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,

D is a 5- or 6-membered aryl or a 5- or 6-membered heteroaryl, each of which is optionally substituted with 1 to 5 independently selected $R^{38}$ groups, alternatively 1 to 3 independently selected $R^{38}$ groups, and alternatively 1 or 2 independently selected $R^{38}$ group, wherein each said $R^{38}$ is independently selected from the group consisting of halo, $C_1$-$C_6$ alkyl, —C(O)$NR^{36}R^{39}$, —C(O)O—(CH$_2$)$_n$$NR^{36}R^{39}$, —(CH$_2$)$_j$$NR^{39}$ (CH$_2$)$_i$S(O)$_i$(C$_1$-C$_6$ alkyl), —(CH$_2$)$_j$$NR^{39}$(CH$_2$)$_n$$R^{36}$ and —C(O)(CH$_2$)$_j$$NR^{39}$(CH$_2$)$_n$$R^{36}$, (for example —(CH$_2$)$_j$$NR^{39}$(CH$_2$)$_n$$R^{36}$) wherein each j is an integer independently selected from 0 to 4 (alternatively 1 to 4, alternatively 1 or 2, alternatively 1), n is an integer from 0 to 6 (alternatively 2 to 6, alternatively 2 to 4, alternatively, 1 or 2), i is 2 or 3, $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —(CH$_2$)$_{n3}$(C$_6$-C$_{10}$ aryl), —(CH$_2$)$_{n3}$(5-10 membered heterocyclyl) and —(CH$_2$)$_{n3}$A$^4$R$^{37}$, for example —(CH$_2$)$_{n3}$OR$^{37}$ or —(CH$_2$)$_{n3}$SR$^{37}$, wherein n3 is an integer ranging from 0 to 6 (alternatively 0 to 4, alternatively 0 to 2, alternatively 1 or 0, alternatively 0), and $R^{37}$ is H or $C_1$-$C_6$alkyl, for example $C_1$-$C_6$alkyl, alternatively $C_1$-$C_2$alkyl;

M is

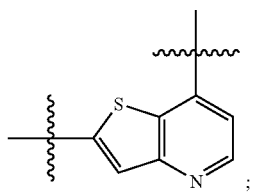 [SMILES: *c1cc2nccc(*)c2s1 ; ";"]

Z is —O—, —S—, —SO—, —SO$_2$—, —CH$_2$O—, —OCH$_2$—, —CH$_2$— or —N(R$^5$)—, for example, —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and G is

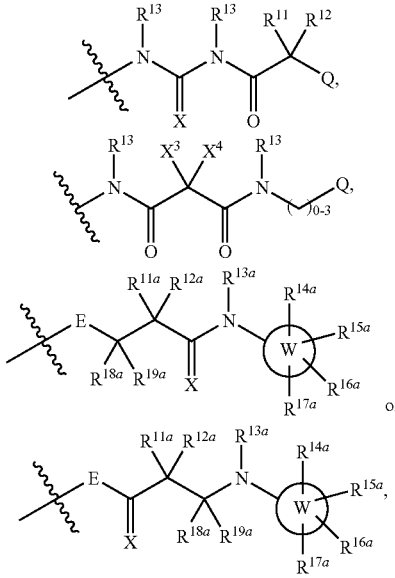

wherein Q is optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,

D is phenyl or pyridinyl (for example pyridinyl), each of which is optionally substituted with 1 to 5 independently selected $R^{38}$ groups, alternatively 1 to 3 independently selected $R^{38}$ groups, and alternatively 1 or 2 independently selected $R^{38}$ group;

M is

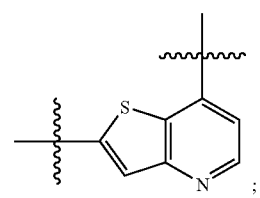 [SMILES: *c1cc2nccc(*)c2s1 ; ";"]

Z is —O—, —S—, —SO—, —SO$_2$—, —CH$_2$O—, —OCH$_2$—, —CH$_2$— or —N(R$^5$)—, for example, —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and G is

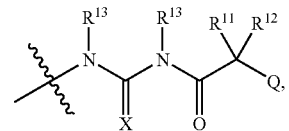

-continued

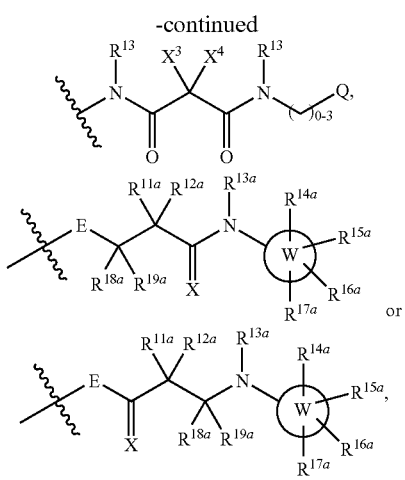

or wherein Q is optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,

D is phenyl or pyridinyl (for example pyridinyl), each of which is optionally substituted with 1 to 5 independently selected $R^{38}$ groups, alternatively 1 to 3 independently selected $R^{38}$ groups, and alternatively 1 or 2 independently selected $R^{38}$ group, wherein each said $R^{38}$ is independently selected from the group consisting of halo, $C_1$-$C_6$ alkyl, —C(O)NR$^{36}$R$^{39}$, —C(O)O—(CH$_2$)$_n$NR$^{36}$R$^{39}$, —(CH$_2$)$_j$NR$^{39}$ (CH$_2$)$_i$S(O)$_j$(C$_1$-$C_6$ alkyl), —(CH$_2$)$_j$NR$^{39}$ (CH$_2$)$_n$R$^{36}$ and —C(O)(CH$_2$)$_j$NR$^{39}$(CH$_2$)$_n$R$^{36}$, (for example, —(CH$_2$)$_j$NR$^{39}$(CH$_2$)$_n$R$^{36}$) wherein each j is an integer independently selected from 0 to 4 (alternatively 1 to 4, alternatively 1 or 2, alternatively 1), n is an integer from 0 to 6 (alternatively 2 to 6, alternatively 2 to 4, alternatively, 1 or 2), i is 2 or 3, $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —(CH$_2$)$_{n3}$($C_6$-$C_{10}$ aryl), —(CH$_2$)$_{n3}$(5-10 membered heterocyclyl) and —(CH$_2$)$_{n3}$A$^4$R$^{37}$, for example, —(CH$_2$)$_{n3}$OR$^{37}$ or —(CH$_2$)$_{n3}$SR$^{37}$, wherein n3 is an integer ranging from 0 to 6 (alternatively 0 to 4, alternatively 0 to 2, alternatively 1 or 0, alternatively 0), and $R^{37}$ is H or $C_1$-$C_6$alkyl, for example, $C_1$-$C_6$alkyl, alternatively $C_1$-$C_2$alkyl;

M is

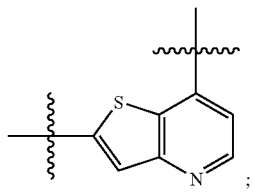

Z is —O—, —S—, —SO—, —SO$_2$—, —CH$_2$O—, —OCH$_2$—, —CH$_2$— or —N(R$^5$)—, for example, —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and G is

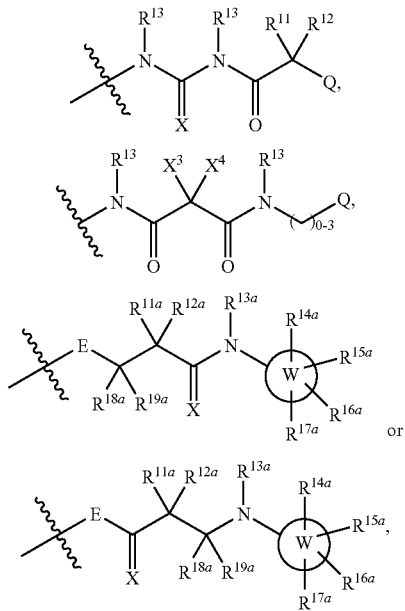

or wherein Q is optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,

D is a 5- or 6-membered aryl or a 5- or 6-membered heteroaryl, each of which is optionally substituted with 1 to 5 independently selected $R^{38}$ groups, alternatively 1 to 3 independently selected $R^{38}$ groups, and alternatively 1 or 2 independently selected $R^{38}$ group;

M is

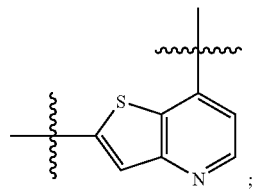 [SMILES: *c1cc2nccc(*)c2s1 ; ";"]

Z is —O—, —S—, —SO—, —SO$_2$—, —CH$_2$O—, —OCH$_2$—, —CH$_2$— or —N(R$^5$)—, for example, —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and G is

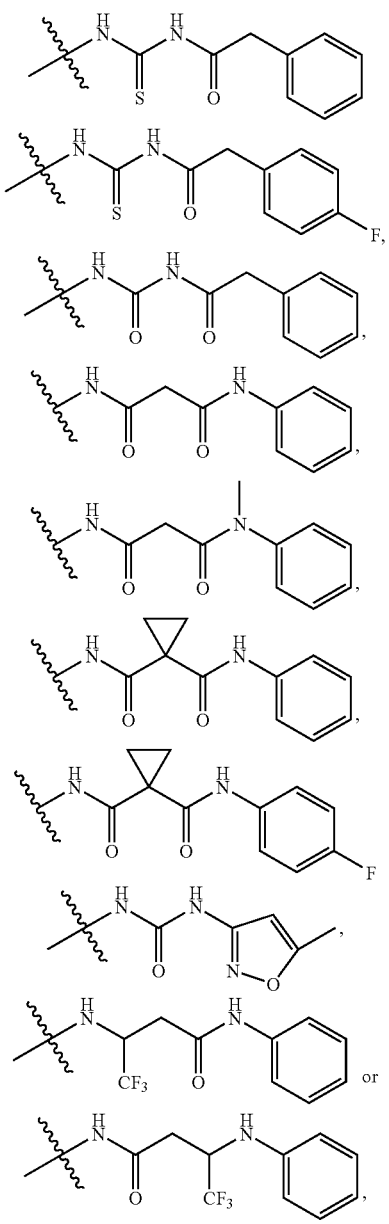

wherein said phenyl groups of G are optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,
D is a 5- or 6-membered aryl or a 5- or 6-membered heteroaryl, each of which is optionally substituted with 1 to 5 independently selected $R^{38}$ groups, alternatively 1 to 3 independently selected $R^{38}$ groups, and alternatively 1 or 2 independently selected $R^{38}$ group, wherein each said $R^{38}$ is independently selected from the group consisting of halo, $C_1$-$C_6$ alkyl, —C(O)NR$^{36}$R$^{39}$, —C(O)O—(CH$_2$)$_n$NR$^{36}$R$^{39}$, —(CH$_2$)$_j$NR$^{39}$(CH$_2$)$_i$S(O)$_j$(C$_1$-C$_6$alkyl), —(CH$_2$)$_j$NR$^{39}$(CH$_2$)$_n$R$^{36}$ and —C(O)(CH$_2$)$_j$NR$^{39}$(CH$_2$)$_n$R$^{36}$, (for example, —(CH$_2$)$_j$NR$^{39}$(CH$_2$)$_n$R$^{36}$) wherein each j is an integer independently selected from 0 to 4 (alternatively 1 to 4, alternatively 1 or 2, alternatively 1), n is an integer from 0 to 6 (alternatively 2 to 6, alternatively 2 to 4, alternatively, 1 or 2), i is 2 or 3, $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —(CH$_2$)$_{n3}$(C$_6$-C$_{10}$ aryl), —(CH$_2$)$_{n3}$(5-10 membered heterocyclyl) and —(CH$_2$)$_{n3}$A$^4$R$^{37}$, for example, —(CH$_2$)$_{n3}$OR$^{37}$ or —(CH$_2$)$_{n3}$SR$^{37}$, wherein n3 is an integer ranging from 0 to 6 (alternatively 0 to 4, alternatively 0 to 2, alternatively 1 or 0, alternatively 0), and $R^{37}$ is H or $C_1$-$C_6$alkyl, for example $C_1$-$C_6$alkyl, alternatively $C_1$-$C_2$alkyl;

M is

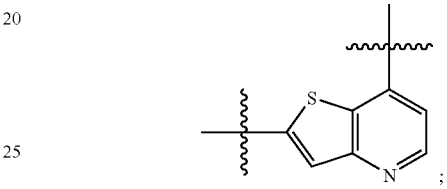

Z is —O—, —S—, —SO—, —SO$_2$—, —CH$_2$O—, —OCH$_2$—, —CH$_2$— or —N(R$^5$)—, for example, —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and G is

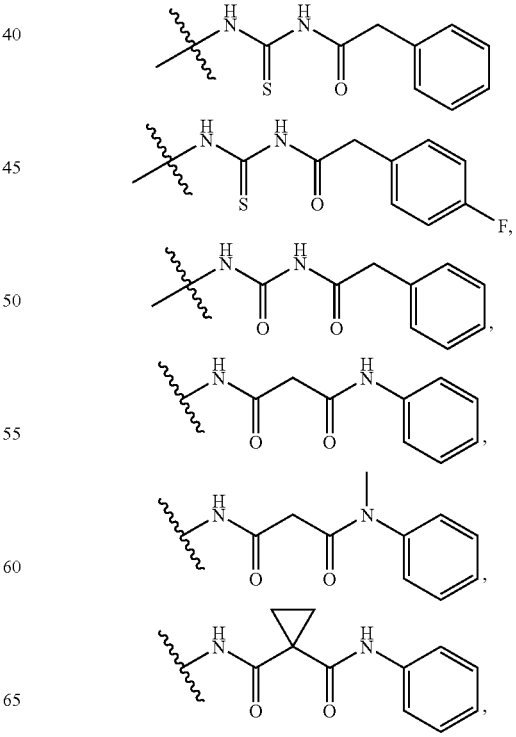

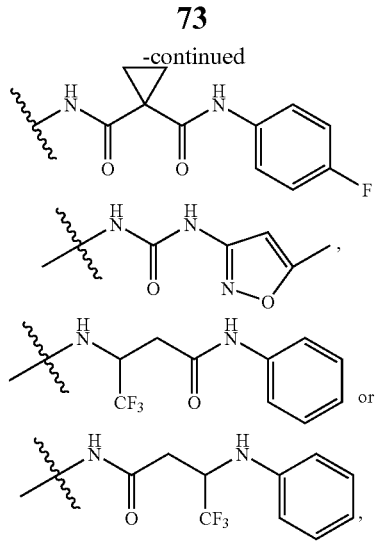

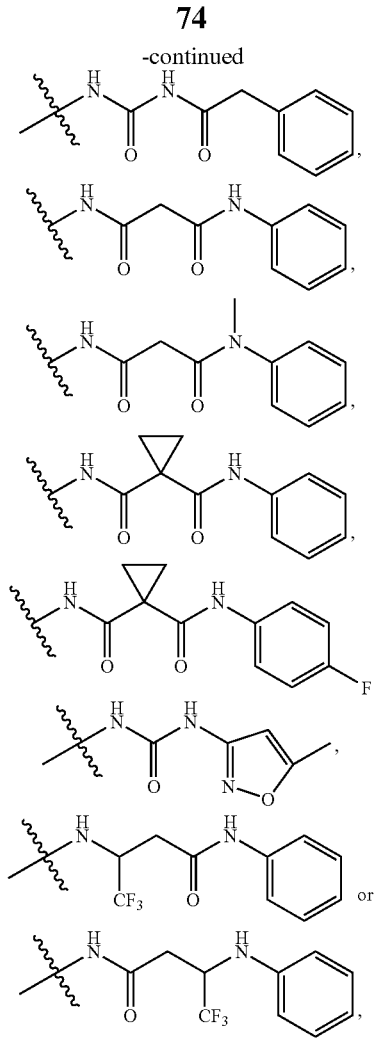

wherein said phenyl groups of G are optionally substituted with from 0 to 4 (alternatively 0 to 2, alternatively 1) independently selected $R^{20}$, wherein each $R^{20}$ is selected from, for example, for example halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,
D is phenyl or pyridyl (for example, pyridyl), each of which is optionally substituted with 1 to 5 independently selected $R^{38}$ groups, alternatively 1 to 3 independently selected $R^{38}$ groups, and alternatively 1 or 2 independently selected $R^{38}$ group;
M is

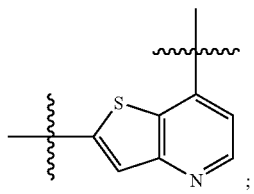 [SMILES: *c1cc2nccc(*)c2s1 ; ";"]

Z is —O—, —S—, —SO—, —SO$_2$—, —CH$_2$O—, —OCH$_2$—, —CH$_2$— or —N(R$^5$)—, for example, —O—;
Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and
G is

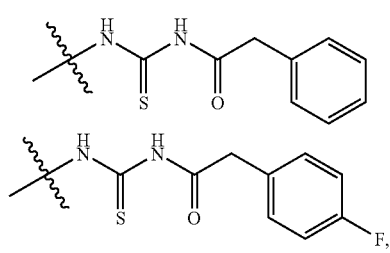

wherein said phenyl groups of G are optionally substituted with from 0 to 4 (alternatively 0 to 2, alternatively 1) independently selected $R^{20}$, wherein each $R^{20}$ is selected from, for example, for example halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,
D is phenyl or pyridyl (for example, pyridyl), each of which is optionally substituted with 1 to 5 independently selected $R^{38}$ groups, alternatively 1 to 3 independently selected $R^{38}$ groups, and alternatively 1 or 2 independently selected $R^{38}$ group, wherein each said $R^{38}$ is independently selected from the group consisting of halo, $C_1$-$C_6$ alkyl, —C(O)NR$^{36}$R$^{39}$, —C(O)O—(CH$_2$)$_n$NR$^{36}$R$^{39}$, —(CH$_2$)$_j$NR$^{39}$ (CH$_2$)$_i$S(O)$_j$ ($C_1$-$C_6$alkyl), —(CH$_2$)$_j$NR$^{39}$(CH$_2$)$_n$R$^{36}$ and —C(O)(CH$_2$)$_j$ NR$^{39}$(CH$_2$)$_n$R$^{36}$, (for example, —(CH$_2$)$_j$NR$^{39}$(CH$_2$)$_n$R$^{36}$) wherein each j is an integer independently selected from 0 to 4 (alternatively 1 to 4, alternatively 1 or 2, alternatively 1), n is an integer from 0 to 6 (alternatively 2 to 6, alternatively 2 to 4, alternatively, 1 or 2), i is 2 or 3, $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —(CH$_2$)$_{n3}$($C_6$-$C_{10}$ aryl), —(CH$_2$)$_{n3}$ (5-10 membered heterocyclyl) and —(CH$_2$)$_{n3}$A$^4$R$^{37}$, for example, —(CH$_2$)$_{n3}$OR$^{37}$ or —(CH$_2$)$_{n3}$SR$^{37}$, wherein n3 is an integer ranging from 0 to 6 (preferably 0 to 4, alternatively 0 to 2, alternatively 1 or 0, alternatively 0), and $R^{37}$ is H or $C_1$-$C_6$alkyl, for example, $C_1$-$C_6$alkyl, alternatively $C_1$-$C_2$alkyl;

M is

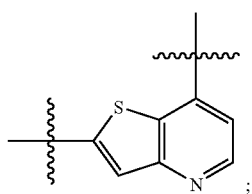 [SMILES: *c1cc2nccc(*)c2s1 ; ";"]

Z is —O—, —S—, —SO—, —SO$_2$—, —CH$_2$O—, —OCH$_2$—, —CH$_2$— or —N(R$^5$)—, for example, —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and G is

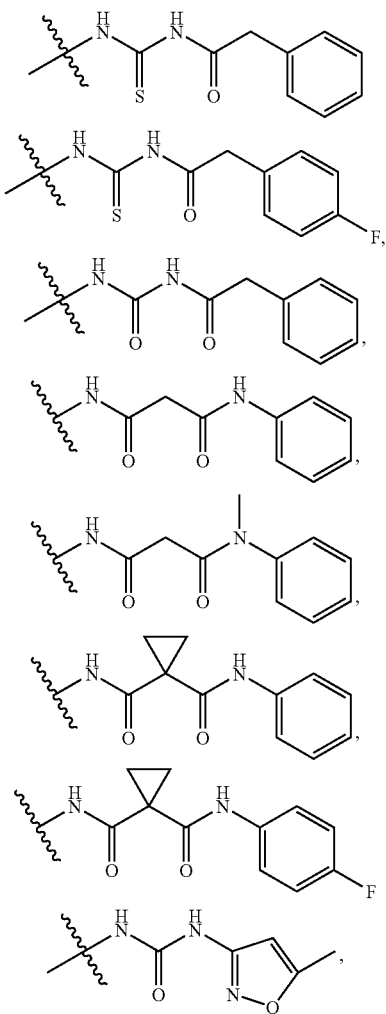

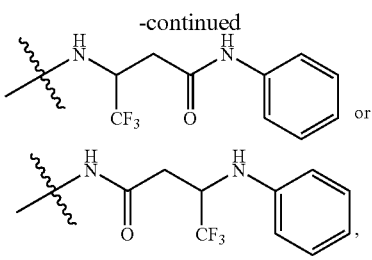

wherein said phenyl groups of G are optionally substituted with from 0 to 4 (alternatively 0 to 2, alternatively 1) independently selected $R^{20}$ wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,

D is a 5- or 6-membered aryl or a 5- or 6-membered heteroaryl, each of which is optionally substituted with 1 to 5 independently selected $R^{38}$ groups, alternatively 1 to 3 independently selected $R^{38}$ groups, and alternatively 1 or 2 independently selected $R^{38}$ group, wherein each said $R^{38}$ is independently selected from the group consisting of halo, $C_1$-$C_6$ alkyl, —(CH$_2$)$_n$P(=O)(C$_1$-C$_6$alkyl)$_2$, —(CH$_2$)$_j$NR$^{39}$CH$_2$(CH$_2$)$_n$P(=O)(C$_1$-C$_6$alkyl)$_2$, —NR$^{13}$C(X$^1$)NR$^{13}$-arylP(=O)(C$_1$-C$_6$alkyl)$_2$ and —NR$^{13}$C(X$^1$)NR$^{13}$-heteroarylP(=O)(C$_1$-C$_6$alkyl)$_2$ (for example —(CH$_2$)$_j$NR$^{39}$CH$_2$(CH$_2$)$_n$P(=O)(C$_1$-C$_6$alkyl)$_2$), wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —(CH$_2$)$_{n3}$(C$_6$-C$_{10}$ aryl), —(CH$_2$)$_{n3}$(5-10 membered heterocyclyl) and —(CH$_2$)$_{n3}$A$^4$R$^{37}$, for example, —(CH$_2$)$_{n3}$OR$^{37}$ or —(CH$_2$)$_{n3}$SR$^{37}$, wherein n3 is an integer ranging from 0 to 6 (alternatively 0 to 4, alternatively 0 to 2, alternatively 1 or 0, alternatively 0), and $R^{37}$ is H or $C_1$-$C_6$alkyl, for example, $C_1$-$C_6$alkyl, alternatively $C_1$-$C_2$alkyl;

M is

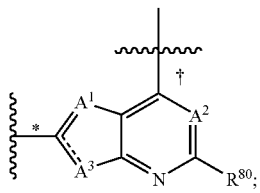

Z is —O—, —S—, —SO—, —SO$_2$—, —CH$_2$O—, —OCH$_2$—, —CH$_2$— or —N(R$^5$)—, for example, —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and G is

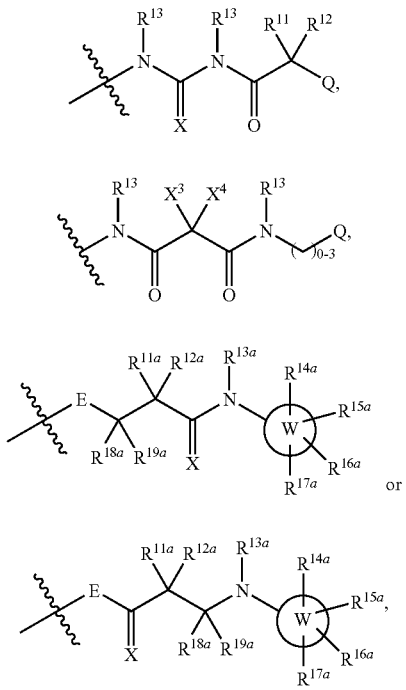

wherein Q is optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,

D is phenyl or pyridinyl (for example, pyridinyl), each of which is optionally substituted with 1 to 5 independently selected $R^{38}$ groups, alternatively 1 to 3 independently selected $R^{38}$ groups, and alternatively 1 or 2 independently selected $R^{38}$ group, wherein each said $R^{38}$ is independently selected from the group consisting of halo, $C_1$-$C_6$ alkyl, —$(CH_2)_n$P(=O)($C_1$-$C_6$alkyl)$_2$, —$(CH_2)_j$NR$^{39}$CH$_2$(CH$_2$)$_n$P(=O)($C_1$-$C_6$alkyl)$_2$, —NR$^{13}$C(X$^1$)NR$^{13}$-arylP(=O)($C_1$-$C_6$alkyl)$_2$ and —NR$^{13}$C(X$^1$)NR$^{13}$-heteroarylP(=O)($C_1$-$C_6$alkyl)$_2$ (for example, —$(CH_2)_j$NR$^{39}$CH$_2$(CH$_2$)$_n$P(=O)($C_1$-$C_6$alkyl)$_2$), wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —$(CH_2)_{n3}$($C_6$-$C_{10}$ aryl), —$(CH_2)_{n3}$(5-10 membered heterocyclyl) and —$(CH_2)_{n3}$A$^4$R$^{37}$, for example, —$(CH_2)_{n3}$OR$^{37}$ or —$(CH_2)_{n3}$SR$^{37}$, wherein n3 is an integer ranging from 0 to 6 (alternatively 0 to 4, alternatively 0 to 2, alternatively 1 or 0, alternatively 0), and $R^{37}$ is H or $C_1$-$C_6$alkyl, for example, $C_1$-$C_6$alkyl, alternatively $C_1$-$C_2$alkyl;

M is

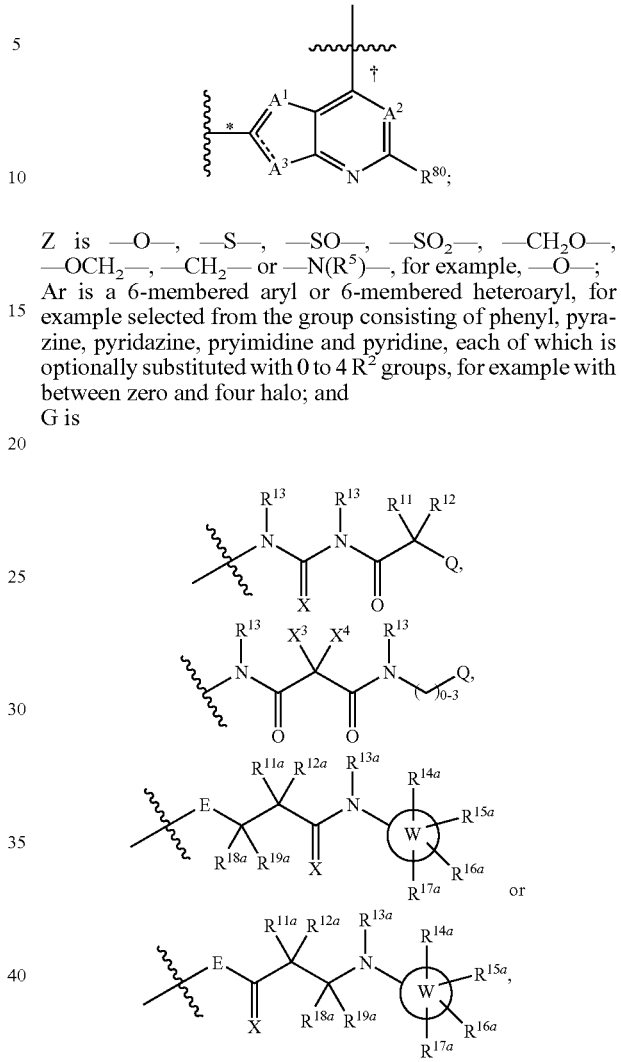

Z is —O—, —S—, —SO—, —SO$_2$—, —CH$_2$O—, —OCH$_2$—, —CH$_2$— or —N(R$^5$)—, for example, —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and G is wherein Q is optionally substituted with from 0 to 4 (alternatively 0 to 2, alternatively 1) independently selected $R^{20}$, wherein each $R^{20}$ is selected from, for example halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,

D is a 5- or 6-membered aryl or a 5- or 6-membered heteroaryl, each of which is optionally substituted with 1 to 5 independently selected $R^{38}$ groups, alternatively 1 to 3 independently selected $R^{38}$ groups, and alternatively 1 or 2 independently selected $R^{38}$ group, wherein each said $R^{38}$ is independently selected from the group consisting of halo, $C_1$-$C_6$ alkyl, —$(CH_2)_n$P(=O)($C_1$-$C_6$alkyl)$_2$, —$(CH_2)_j$NR$^{39}$CH$_2$(CH$_2$)$_n$P(=O)($C_1$-$C_6$alkyl)$_2$, —NR$^{13}$C(X$^1$)NR$^{13}$-arylP(=O)($C_1$-$C_6$alkyl)$_2$ and —NR$^{13}$C(X$^1$)NR$^{13}$-heteroarylP(=O)($C_1$-$C_6$alkyl)$_2$ (for example, —$(CH_2)_j$NR$^{39}$CH$_2$(CH$_2$)$_n$P(=O)($C_1$-$C_6$alkyl)$_2$), wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —$(CH_2)_{n3}(C_6$-$C_{10}$ aryl), —$(CH_2)_{n3}$(5-10 membered heterocyclyl) and —$(CH_2)_{n3}A^4R^{37}$, for example, —$(CH_2)_{n3}OR^{37}$ or —$(CH_2)_{n3}SR^{37}$, wherein n3 is an integer ranging from 0 to 6 (alternatively 0 to 4, alternatively 0 to 2, alternatively 1 or 0, alternatively 0), and $R^{37}$ is H or $C_1$-$C_6$alkyl, for example, $C_1$-$C_6$alkyl, alternatively $C_1$-$C_2$alkyl;

M is

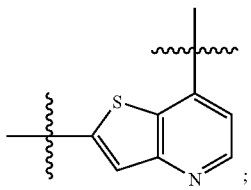 [SMILES: *c1cc2nccc(*)c2s1]

Z is —O—, —S—, —SO—, —$SO_2$—, —$CH_2O$—, —$OCH_2$—, —$CH_2$— or —$N(R^5)$—, for example, —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and

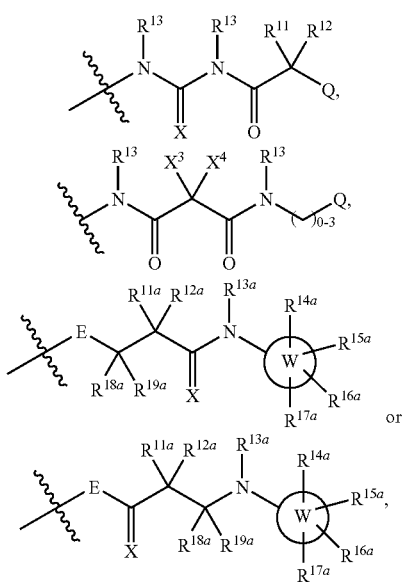

wherein Q is optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,

D is phenyl or pyridinyl (for example, pyridinyl), each of which is optionally substituted with 1 to 5 independently selected $R^{38}$ groups, alternatively 1 to 3 independently selected $R^{38}$ groups, and alternatively 1 or 2 independently selected $R^{38}$ group, wherein each said $R^{38}$ is independently selected from the group consisting of halo, $C_1$-$C_6$ alkyl, —$(CH_2)_nP(=O)(C_1$-$C_6$alkyl)$_2$, —$(CH_2)_jNR^{39}CH_2(CH_2)_n$ $P(=O)(C_1$-$C_6$alkyl)$_2$, —$NR^{13}C(X^1)NR^{13}$-arylP(=O)($C_1$-$C_6$alkyl)$_2$ and —$NR^{13}C(X^1)NR^{13}$-heteroarylP(=O)($C_1$-$C_6$alkyl)$_2$ (for example, —$(CH_2)_jNR^{39}CH_2(CH_2)_nP(=O)$ $(C_1$-$C_6$alkyl)$_2$), wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —$(CH_2)_{n3}(C_6$-$C_{10}$ aryl), —$(CH_2)_{n3}$(5-10 membered heterocyclyl) and —$(CH_2)_{n3}A^4R^{37}$, for example, —$(CH_2)_{n3}OR^{37}$ or —$(CH_2)_{n3}SR^{37}$, wherein n3 is an integer ranging from 0 to 6 (alternatively 0 to 4, alternatively 0 to 2, alternatively 1 or 0, alternatively 0), and $R^{37}$ is H or $C_1$-$C_6$alkyl, for example. $C_1$-$C_6$alkyl, alternatively $C_1$-$C_2$alkyl;

M is

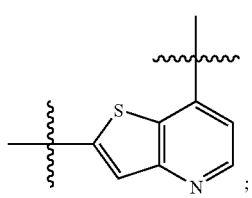 [SMILES: *c1cc2nccc(*)c2s1]

Z is —O—, —S—, —SO—, —$SO_2$—, —$CH_2O$—, —$OCH_2$—, —$CH_2$— or —$N(R^5)$—, for example, —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and G is

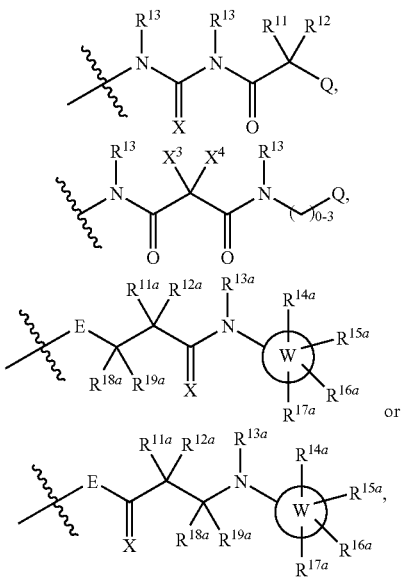

wherein Q is optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,

D is a 5- or 6-membered aryl or a 5- or 6-membered heteroaryl, each of which is optionally substituted with 1 to 5 independently selected $R^{38}$ groups, alternatively 1 to 3 independently selected $R^{38}$ groups, and alternatively 1 or 2 independently selected $R^{38}$ group, wherein each said $R^{38}$ is independently selected from the group consisting of halo, $C_1$-$C_6$ alkyl, —$(CH_2)_nP(=O)(C_1$-$C_6$alkyl$)_2$, —$(CH_2)_jNR^{39}CH_2(CH_2)_nP(=O)(C_1$-$C_6$alkyl$)_2$, —$NR^{13}C(X^1)NR^{13}$-arylP$(=O)(C_1$-$C_6$alkyl$)_2$ and —$NR^{13}C(X^1)NR^{13}$-heteroarylP$(=O)(C_1$-$C_6$alkyl$)_2$ (for example, —$(CH_2)_jNR^{39}CH_2(CH_2)_nP(=O)(C_1$-$C_6$alkyl$)_2$), wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —$(CH_2)_{n3}(C_6$-$C_{10}$ aryl), —$(CH_2)_{n3}$(5-10 membered heterocyclyl) and —$(CH_2)_{n3}A^4R^{37}$, for example, —$(CH_2)_{n3}OR^{37}$ or —$(CH_2)_{n3}SR^{37}$, wherein n3 is an integer ranging from 0 to 6 (alternatively 0 to 4, alternatively 0 to 2, alternatively 1 or 0, alternatively 0), and $R^{37}$ is H or $C_1$-$C_6$alkyl, for example, $C_1$-$C_6$alkyl, alternatively $C_1$-$C_2$alkyl;

M is

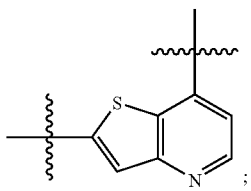 [SMILES: *c1cc2nccc(*)c2s1]

Z is —O—, —S—, —SO—, —$SO_2$—, —$CH_2O$—, —$OCH_2$—, —$CH_2$— or —$N(R^5)$—, for example, —O—;

Ar is a 6-membered aryl or 6-membered heteroaryl, for example selected from the group consisting of phenyl, pyrazine, pyridazine, pryimidine and pyridine, each of which is optionally substituted with 0 to 4 $R^2$ groups, for example with between zero and four halo; and G is

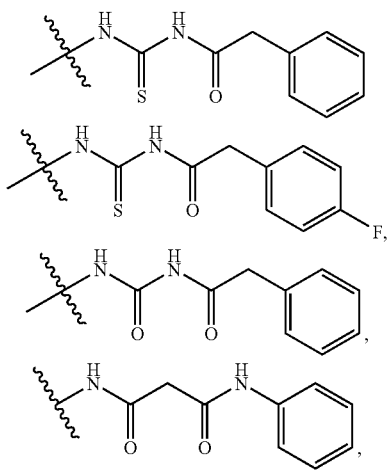

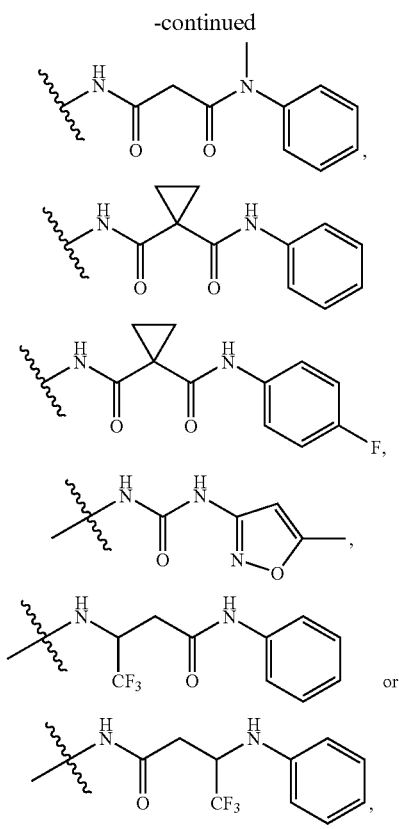

wherein said phenyl groups of G are optionally substituted with from 0 to 4 (alternatively 0 to 2, alternatively 1) independently selected $R^{20}$, wherein each $R^{20}$ is selected from, for example, halogen, trihalomethyl, alkoxy, optionally substituted $C_1$-$C_6$alkyl, optionally substituted $C_2$-$C_6$alkenyl or optionally substituted $C_2$-$C_6$alkynyl. In some embodiments, $R^{20}$ is halogen. In some embodiments, Ar is phenyl optionally substituted with 0 to 4 $R^2$ groups, for example with between zero and four halo.

In another embodiment of the present invention,

D is phenyl or pyridinyl (for example, pyridinyl), each of which is optionally substituted with 1 to 5 independently selected $R^{38}$ groups, alternatively 1 to 3 independently selected $R^{38}$ groups, and alternatively 1 or 2 independently selected $R^{38}$ group, wherein each said $R^{38}$ is independently selected from the group consisting of halo, $C_1$-$C_6$ alkyl, —$(CH_2)_nP(=O)(C_1$-$C_6$alkyl$)_2$, —$(CH_2)_jNR^{39}CH_2(CH_2)_nP(=O)(C_1$-$C_6$alkyl$)_2$, —$NR^{13}C(X^1)NR^{13}$-arylP$(=O)(C_1$-$C_6$alkyl$)_2$ and —$NR^{13}C(X^1)NR^{13}$-heteroarylP$(=O)(C_1$-$C_6$alkyl$)_2$ (for example, —$(CH_2)_jNR^{39}CH_2(CH_2)_nP(=O)(C_1$-$C_6$alkyl$)_2$), wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —$(CH_2)_{n3}(C_6$-$C_{10}$ aryl), —$(CH_2)_{n3}$(5-10 membered heterocyclyl) and —$(CH_2)_{n3}A^4R^{37}$, for example, —$(CH_2)_{n3}OR^{37}$ or —$(CH_2)_{n3}SR^{37}$, wherein n3 is an integer ranging from 0 to 6 (alternatively 0 to 4, alternatively 0 to 2, alternatively 1 or 0, alternatively 0), and $R^{37}$ is H or $C_1$-$C_6$alkyl, for example, $C_1$-$C_6$alkyl, alternatively $C_1$-$C_2$alkyl;

M is

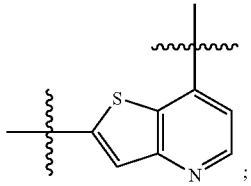 [SMILES: *c1cc2nccc(*)c2s1]

Z is —O—, —S—, —SO—, —SO$_2$—, —CH$_2$O—, —OCH$_2$—, —CH$_2$— or —N(R$^5$)—, for example, —O—;

Ar is a 6-membered aryl or 6-membered heteroaryl, for example selected from the group consisting of phenyl, pyrazine, pyridazine, pryimidine and pyridine, each of which is optionally substituted with 0 to 4 R$^2$ groups, for example with between zero and four halo; and G is

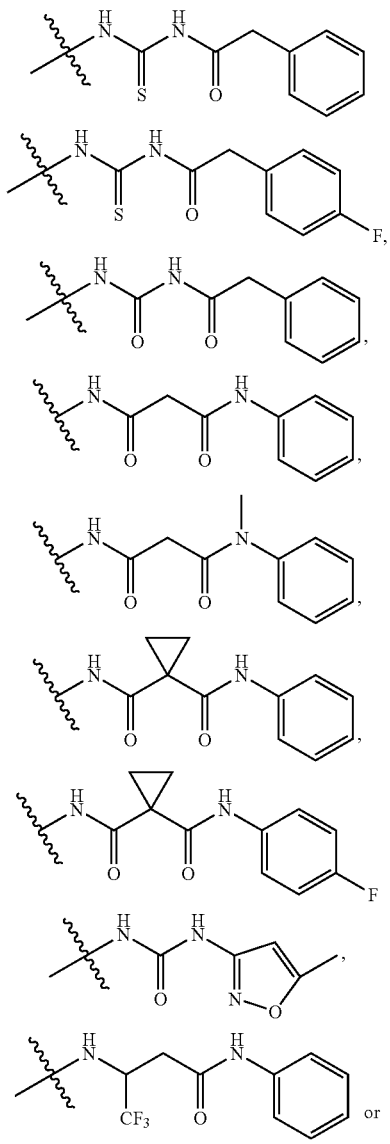

-continued

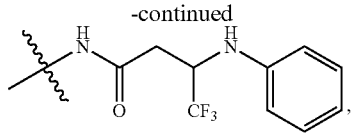

wherein said phenyl groups of G are optionally substituted with from 0 to 4 (alternatively 0 to 2, alternatively 1) independently selected R$^{20}$, wherein each R$^{20}$ is selected from, for example, halogen, trihalomethyl, alkoxy, optionally substituted C$_1$-C$_6$alkyl, optionally substituted C$_2$-C$_6$alkenyl or optionally substituted C$_2$-C$_6$alkynyl. In some embodiments, R$^{20}$ is halogen. In some embodiments, Ar is phenyl optionally substituted with 0 to 4 R$^2$ groups, for example with between zero and four halo.

In another embodiment of the present invention,

D is a 5- or 6-membered aryl or a 5- or 6-membered heteroaryl, each of which is optionally substituted with 1 or 2 independently selected R$^{38}$ groups;

M is

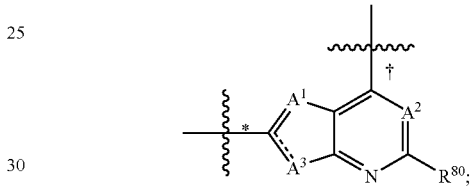

Z is —O—, —S—, —SO—, —SO$_2$—, —CH$_2$O—, —OCH$_2$—, —CH$_2$— or —N(R$^5$)—;

Ar is a 6-membered aryl or 6-membered heteroaryl, each of which is optionally substituted with 0 to 4 R$^2$ groups; and G is

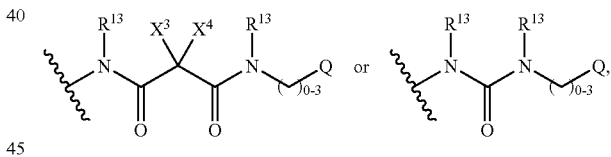

wherein Q is optionally substituted with from 0 to 4 independently selected R$^{20}$.

In another embodiment of the present invention,

D is a 5- or 6-membered aryl or a 5- or 6-membered heteroaryl, each of which is optionally substituted with 1 or 2 independently selected R$^{38}$ groups;

M is

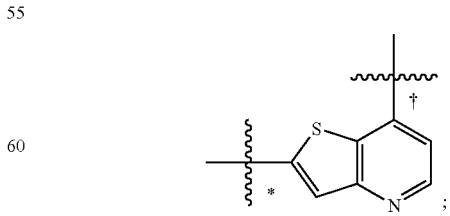

Z is —O—;

Ar is a 6-membered aryl or 6-membered heteroaryl, each of which is optionally substituted with 0 to 4 R$^2$ groups; and G is

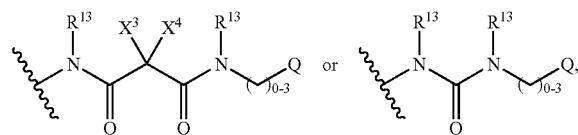

wherein Q is optionally substituted with from 0 to 4 independently selected $R^{20}$.

In another embodiment of the present invention,
D is a 5- or 6-membered aryl or a 5- or 6-membered heteroaryl, each of which is optionally substituted with 1 or 2 independently selected $R^{38}$ groups, wherein $R^{38}$ is $C_1$-$C_6$alkyl or —$(CH_2)_j NR^{39}(CH_2)_n R^{36}$, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and the —$(CH_2)_n$— group is optionally substituted with $C_1$-$C_6$alkyl (for example Me), $R^{36}$ is —$(CH_2)_{n3} A^4 R^{37}$, for example —$(CH_2)_{n3} OR^{37}$, wherein each n3 is an integer independently ranging from 0 to 6 (alternatively 0 to 4, alternatively 0 to 2, alternatively 1 or 0, alternatively 0), wherein the $R^{37}$ is optionally substituted $C_1$-$C_6$ alkyl, and $R^{39}$ is H or —C(O)—$C_1$-$C_3$alkyl (for example, —C(O)—$CH_3$);
M is

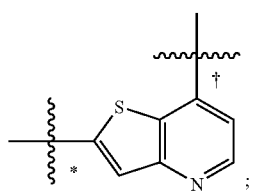 [SMILES: *c1cc2nccc(*)c2s1]

Z is —O—;
Ar is a 6-membered aryl or 6-membered heteroaryl, each of which is optionally substituted with 0 to 4 $R^2$ groups; and
G is

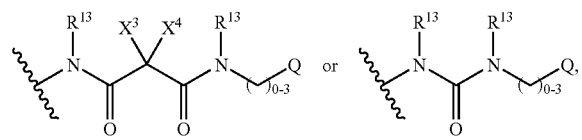

wherein Q is optionally substituted with from 0 to 4 independently selected $R^{20}$.

In another embodiment of the present invention,
D is imidazolyl, pyridinyl or phenyl, each of which is optionally substituted with 1 or 2 independently selected $R^{38}$ groups, wherein $R^{38}$ is $C_1$-$C_6$alkyl or —$(CH_2)_j NR^{39}(CH_2)_n R^{36}$, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and the —$(CH_2)_n$— group is optionally substituted with $C_1$-$C_6$alkyl, for example Me, $R^{36}$ is —$(CH_2)_{n3} A^4 R^{37}$, for example —$(CH_2)_{n3} OR^{37}$ wherein each n3 is an integer independently ranging from 0 to 6 (alternatively 0 to 4, alternatively 0 to 2, alternatively 1 or 0, alternatively 0), wherein the $R^{37}$ is optionally substituted $C_1$-$C_6$ alkyl, and $R^{39}$ is H or —C(O)—$C_1$-$C_3$alkyl (for example, —C(O)—$CH_3$);
M is

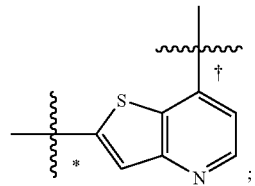 [SMILES: *c1cc2nccc(*)c2s1]

Z is —O—;
Ar is a 6-membered aryl or 6-membered heteroaryl, each of which is optionally substituted with 0 to 4 $R^2$ groups; and
G is

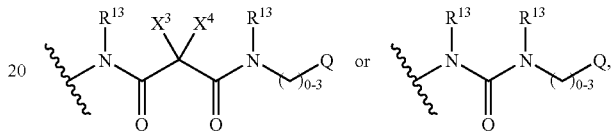

wherein Q is optionally substituted with from 0 to 4 independently selected $R^{20}$.

In another embodiment of the present invention,
D is imidazolyl substituted with $C_1$-$C_6$alkyl (for example Me) and —$(CH_2)_j NR^{39}(CH_2)_n R^{36}$, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and $R^{36}$ is —$(CH_2)_{n3} OR^{37}$ wherein each n3 is an integer independently ranging from 0 to 6 (alternatively 0 to 4, alternatively 0 to 2, alternatively 1 or 0, alternatively 0), wherein the $R^{37}$ is optionally substituted $C_1$-$C_6$ alkyl, and $R^{39}$ is H;
M is

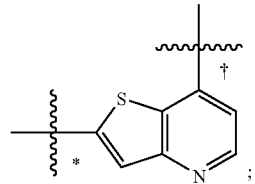 [SMILES: *c1cc2nccc(*)c2s1]

Z is —O—;
Ar is a 6-membered aryl or 6-membered heteroaryl, each of which is optionally substituted with 0 to 4 $R^2$ groups; and
G is

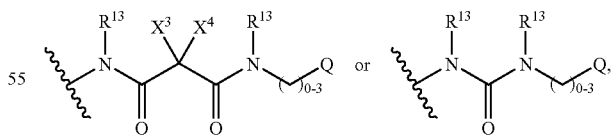

wherein Q is optionally substituted with from 0 to 4 independently selected $R^{20}$.

In another embodiment of the present invention,
D is imidazolyl substituted on a nitrogen atom with $C_1$-$C_6$alkyl (for example Me) and on a carbon atom with —$(CH_2)_j NR^{39}(CH_2)_n R^{36}$, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and $R^{36}$ is —$(CH_2)_{n3} OR^{37}$ wherein each n3 is an integer independently ranging from 0 to 6 (alternatively 0 to 4, alternatively 0 to 2, alternatively 1 or 0, alternatively 0), wherein the $R^{37}$ is optionally substituted $C_1$-$C_6$ alkyl, and $R^{39}$ is H;

M is

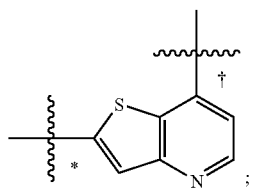 [SMILES: *c1cc2nccc(*)c2s1]

Z is —O—;

Ar is a 6-membered aryl or 6-membered heteroaryl, each of which is optionally substituted with 0 to 4 $R^2$ groups; and G is

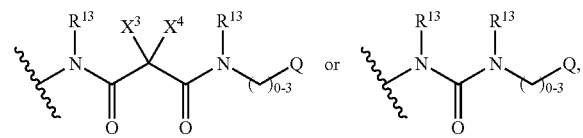

wherein Q is optionally substituted with from 0 to 4 independently selected $R^{20}$.

In another embodiment of the present invention,

D is imidazolyl substituted with $C_1$-$C_6$ alkyl (for example Me) and —$(CH_2)_j NR^{39}(CH_2)_n R^{36}$, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and $R^{36}$ is —$(CH_2)_{n3} OR^{37}$ wherein each n3 is an integer independently ranging from 0 to 6 (alternatively 0 to 4, alternatively 0 to 2, alternatively 1 or 0, alternatively 0), wherein the $R^{37}$ is optionally substituted $C_1$-$C_6$ alkyl, and $R^{39}$ is H;

M is

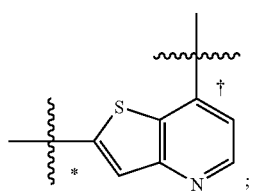

Z is —O—;

Ar is phenyl substituted with at least one halogen, for example, one F; and

G is

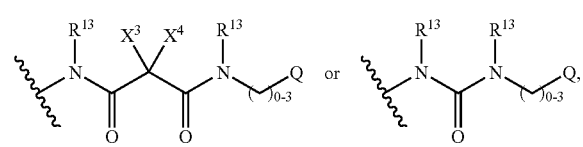

wherein Q is optionally substituted with from 0 to 4 independently selected $R^{20}$.

In another embodiment of the present invention,

D is imidazolyl substituted with $C_1$-$C_6$ alkyl (for example Me) and —$(CH_2)_j NR^{39}(CH_2)_n R^{36}$, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and $R^{36}$ is —$(CH_2)_{n3} OR^{37}$ wherein each n3 is an integer independently ranging from 0 to 6 (alternatively 0 to 4, alternatively 0 to 2, alternatively 1 or 0, alternatively 0), wherein the $R^{37}$ is optionally substituted $C_1$-$C_6$ alkyl, and $R^{39}$ is H;

M is

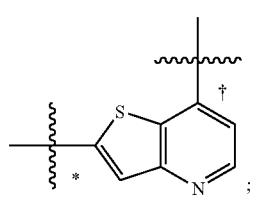 [SMILES: *c1cc2nccc(*)c2s1]

Z is —O—;

Ar is phenyl substituted with at least one halogen, for example, one F;

G is

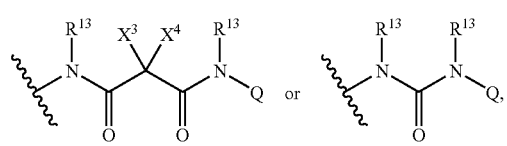

wherein $R^{13}$ is H; and

Q is optionally substituted with from 0 to 4 independently selected $R^{20}$.

In another embodiment of the present invention,

D is imidazolyl substituted with $C_1$-$C_6$ alkyl (for example Me) and —$(CH_2)_j NR^{39}(CH_2)_n R^{36}$, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and $R^{36}$ is —$(CH_2)_{n3} OR^{37}$ wherein each n3 is an integer independently ranging from 0 to 6 (alternatively 0 to 4, alternatively 0 to 2, alternatively 1 or 0, alternatively 0), wherein the $R^{37}$ is optionally substituted $C_1$-$C_6$ alkyl, and $R^{39}$ is H;

M is

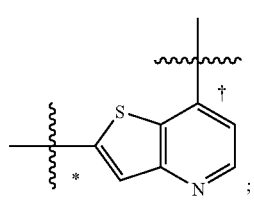 [SMILES: *c1cc2nccc(*)c2s1]

Z is —O—;

Ar is phenyl substituted with at least one halogen, for example, one F;

G is

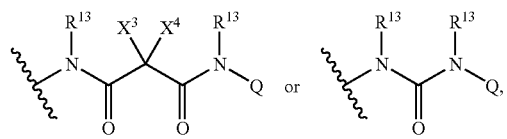

wherein
R$^{13}$ is H;
X$^3$ and X$^4$ are each H or taken together with the carbon to which they are attach are cyclopropyl; and
Q is cycloalkyl, heteroaryl or phenyl, optionally substituted with from 0 to 4 independently selected R$^{20}$.

In another embodiment of the present invention,
D is imidazolyl substituted with C$_1$-C$_6$alkyl (for example Me) and —(CH$_2$)$_j$NR$^{39}$(CH$_2$)$_n$R$^{36}$, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and R$^{36}$ is —(CH$_2$)$_{n3}$OR$^{37}$ wherein each n3 is an integer independently ranging from 0 to 6 (alternatively 0 to 4, alternatively 0 to 2, alternatively 1 or 0, alternatively 0), wherein the R$^{37}$ is optionally substituted C$_1$-C$_6$ alkyl (for example Me), and R$^{39}$ is H;
M is

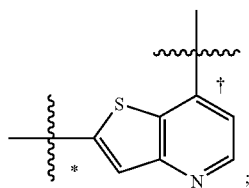

Z is —O—;
Ar is phenyl substituted with at least one halogen, for example, one F;
G is

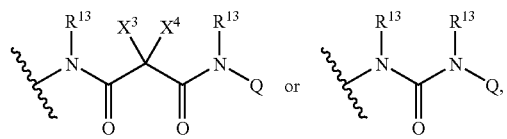

wherein
R$^{13}$ is H;
X$^3$ and X$^4$ are each H or taken together with the carbon to which they are attach are cyclopropyl; and
Q is cyclopropyl, isoxazole or phenyl, optionally substituted with from 0 to 2 independently selected R$^{20}$, for example halogen (for example F), C$_1$-C$_6$alkyl or —CF$_3$.

In another embodiment of the present invention,
D is pyridinyl substituted with —(CH$_2$)$_j$NR$^{39}$(CH$_2$)$_n$R$^{36}$, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and R$^{36}$ is —(CH$_2$)$_{n3}$OR$^{37}$ wherein each n3 is an integer independently ranging from 0 to 6 (alternatively 0 to 4, alternatively 0 to 2, alternatively 1 or 0, alternatively 0), wherein the R$^{37}$ is optionally substituted C$_1$-C$_6$ alkyl, and R$^{39}$ is H;

M is

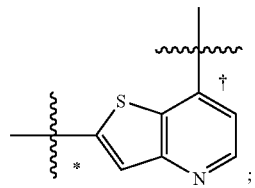 [SMILES: *c1cc2nccc(*)c2s1]

Z is —O—;
Ar is a 6-membered aryl or 6-membered heteroaryl, each of which is optionally substituted with 0 to 4 R$^2$ groups; and
G is

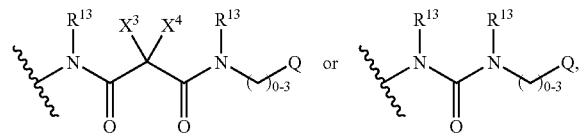

wherein Q is optionally substituted with from 0 to 4 independently selected R$^{20}$.

In another embodiment of the present invention,
D is pyridinyl substituted with —(CH$_2$)$_j$NR$^{39}$(CH$_2$)$_n$R$^{36}$ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and R$^{36}$ is —(CH$_2$)$_{n3}$OR$^{37}$ wherein each n3 is an integer independently ranging from 0 to 6 (alternatively 0 to 4, alternatively 0 to 2, alternatively 1 or 0, alternatively 0), wherein the R$^{37}$ is optionally substituted C$_1$-C$_6$ alkyl, and R$^{39}$ is H;
M is

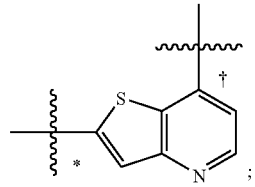 [SMILES: *c1cc2nccc(*)c2s1]

Z is —O—;
Ar is phenyl substituted with at least one halogen, for example, one F; and
G is

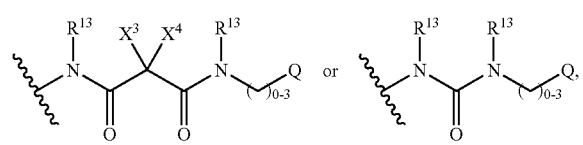

wherein Q is optionally substituted with from 0 to 4 independently selected R$^{20}$.

In another embodiment of the present invention,
D is pyridinyl substituted with —(CH$_2$)$_j$NR$^{39}$(CH$_2$)$_n$R$^{36}$, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and R$^{36}$ is —(CH$_2$)$_{n3}$OR$^{37}$ wherein each n3 is an integer independently ranging from 0 to 6 (alternatively 0 to 4, alternatively 0 to 2, alternatively 1 or 0, alternatively 0), wherein the R$^{37}$ is optionally substituted C$_1$-C$_6$ alkyl, and R$^{39}$ is H;

M is

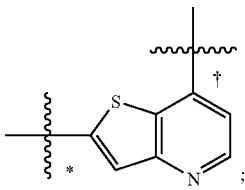

Z is —O—;
Ar is phenyl substituted with at least one halogen, for example, one F;
G is

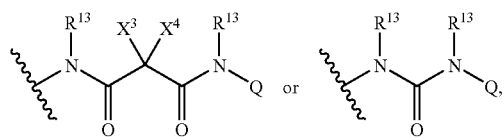

for example,

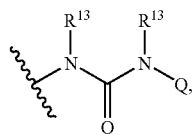

wherein
R¹³ is H; and
Q is optionally substituted with from 0 to 4 independently selected R²⁰.

In another embodiment of the present invention,
D is pyridinyl substituted with —(CH₂)ⱼNR³⁹(CH₂)ₙR³⁶, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and R³⁶ is —(CH₂)ₙ₃OR³⁷ wherein each n3 is an integer independently ranging from 0 to 6 (alternatively 0 to 4, alternatively 0 to 2, alternatively 1 or 0, alternatively 0), wherein the R³⁷ is optionally substituted C₁-C₆ alkyl, and R³⁹ is H;
M is

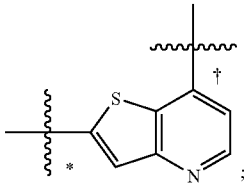

Z is —O—;
Ar is phenyl substituted with at least one halogen, for example, one F;
G is

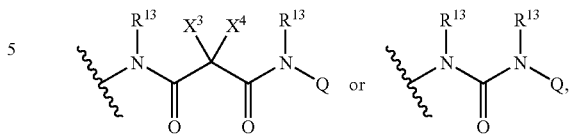

for example,

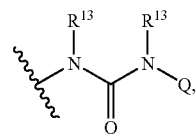

wherein
R¹³ is H;
X³ and X⁴ are each H or taken together with the carbon to which they are attach are cyclopropyl; and
Q is cycloalkyl, heteroaryl or phenyl, optionally substituted with from 0 to 4 independently selected R²⁰.

In another embodiment of the present invention,
D is pyridinyl substituted with —(CH₂)ⱼNR³⁹(CH₂)ₙR³⁶, wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), and R³⁶ is —(CH₂)ₙ₃OR³⁷ wherein each n3 is an integer independently ranging from 0 to 6 (alternatively 0 to 4, alternatively 0 to 2, alternatively 1 or 0, alternatively 0), wherein the R³⁷ is optionally substituted C₁-C₆ alkyl (preferably Me), and R³⁹ is H;
M is

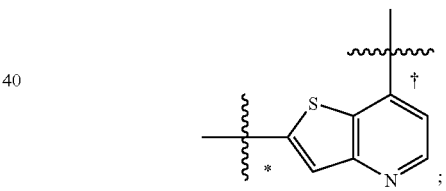

Z is —O—;
Ar is phenyl substituted with at least one halogen, for example, one F;
G is

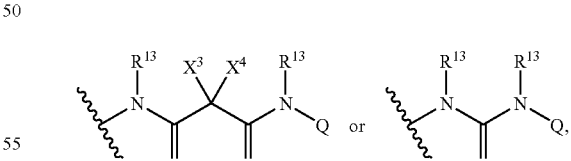

for example,

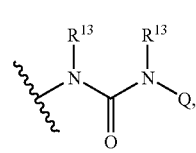

wherein
R$^{13}$ is H or C$_1$-C$_6$ alkyl;
X$^3$ and X$^4$ are each H or taken together with the carbon to which they are attach are cyclopropyl; and
Q is cyclopropyl, cyclopentyl, cyclohexyl, pyridine or phenyl, optionally substituted with from 0 to 2 independently selected R$^{20}$, for example halogen (for example F), C$_1$-C$_6$alkyl, —S(O)$_2$(C$_1$-C$_6$)alkyl, —C(O)NH$_2$, —C(O)(C$_1$-C$_6$)alkyl or —CF$_3$.

In another embodiment of the present invention,

D is tetrahydropyridine substituted with —C(O)(CH$_2$)$_j$NR$^{39}$(CH$_2$)$_n$R$^{36}$, wherein j is an integer from 0 to 4, n is an integer from 0 to 6, and R$^{36}$ is —(CH$_2$)$_{n3}$OR$^{37}$ wherein n3 is an integer ranging from 0 to 6, wherein the R$^{37}$ is optionally substituted C$_1$-C$_6$ alkyl, and R$^{39}$ is H;
M is

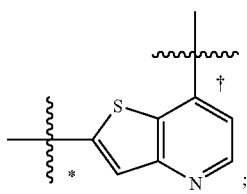 [SMILES: *c1cc2nccc(*)c2s1]

Z is —O—;
Ar is phenyl substituted with at least one halogen; and
G is

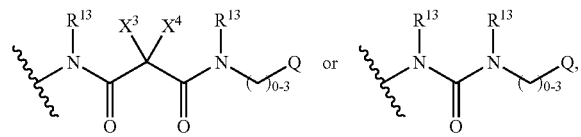

Q is cycloalkyl, heteroaryl or phenyl (for example cyclopropyl, phenyl or isoxazole), optionally substituted with from 0 to 4 independently selected R$^{20}$ (for example halogen, —CF$_3$ or —C$_1$-C$_6$alkyl).

In another embodiment of the present invention

D is tetrahydropyridine substituted on nitrogen with —C(O)(CH$_2$)$_j$NR$^{39}$(CH$_2$)$_n$R$^{36}$, wherein j is an integer from 0 to 4, n is an integer from 0 to 6, and R$^{36}$ is —(CH$_2$)$_{n3}$OR$^{37}$ wherein n3 is an integer ranging from 0 to 6, wherein the R$^{37}$ is optionally substituted C$_1$-C$_6$ alkyl, and R$^{39}$ is H;
M is

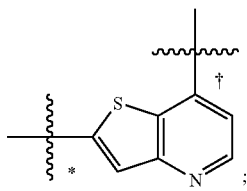 [SMILES: *c1cc2nccc(*)c2s1]

Z is —O—;
Ar is phenyl substituted with at least one halogen; and
G is

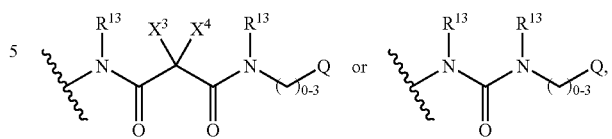

Q is cycloalkyl, heteroaryl or phenyl (for example cyclopropyl, phenyl or isoxazole), optionally substituted with from 0 to 4 independently selected R$^{20}$ (for example halogen, —CF$_3$ or —C$_1$-C$_6$alkyl).

In another embodiment of the present invention,

D is phenyl substituted with —(CH$_2$)$_j$NR$^{39}$(CH$_2$)$_n$R$^{36}$, wherein j is an integer from 0 to 4, n is an integer from 0 to 6, and the —(CH$_2$)$_n$— group is optionally substituted with C$_1$-C$_6$alkyl, R$^{36}$ is —(CH$_2$)$_{n3}$OR$^{37}$, wherein n3 is an integer ranging from 0 to 6, the R$^{37}$ is optionally substituted C$_1$-C$_6$ alkyl, and R$^{39}$ is H or —C(O)—C$_1$-C$_3$alkyl;
M is

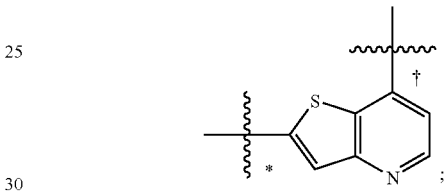

Z is —O—;
Ar is phenyl substituted with at least one halogen; and
G is

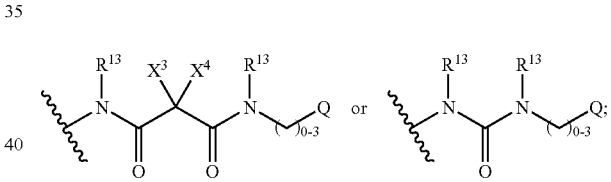

wherein
Q is phenyl or isoxazole optionally substituted with from 0 to 4 independently selected halogen or C$_1$-C$_6$alkyl;
R13 is H; and
X$^3$ and X$^4$ are each H or taken together with the carbon to which they are attached are cyclopropyl.

Certain compounds of above formulas may generally be prepared according to the following Schemes. Tautomers and solvates (e.g., hydrates) of the compounds of above formulas are also within the scope of the present invention. Methods of solvation are generally known in the art. Accordingly, the compounds of the present invention may be in the free, hydrate or salt form, and may be obtained by methods exemplified by the following schemes below.

The following examples and preparations describe the manner and process of making and using the invention and are illustrative rather than limiting. It should be understood that there may be other embodiments which fall within the spirit and scope of the invention as defined by the claims appended hereto.

Examples of compounds according to the invention include those described in the examples below. Compounds were named using Chemdraw Ultra version 10.0 or version 8.0.3, which are available through Cambridgesoft.com, 100 Cambridge Park Drive, Cambridge, Mass. 02140, or were derived therefrom.

The data presented herein demonstrate the inhibitory effects of the kinase inhibitors of the invention. These data lead one to reasonably expect that the compounds of the invention are useful not only for inhibition of kinase activity, protein tyrosine kinase activity, or other embodiments thereof, such as, VEGF receptor signaling and HGF receptor signaling, but also as therapeutic agents for the treatment of proliferative diseases, including cancer and tumor growth.

Synthetic Schemes and Experimental Procedures

The compounds of the invention can be prepared according to the reaction schemes or the examples illustrated below utilizing methods known to one of ordinary skill in the art. These schemes serve to exemplify some procedures that can be used to make the compounds of the invention. One skilled in the art will recognize that other general synthetic procedures may be used. The compounds of the invention can be prepared from starting components that are commercially available. Any kind of substitutions can be made to the starting components to obtain the compounds of the invention according to procedures that are well known to those skilled in the art.

PARTICULAR EXAMPLES

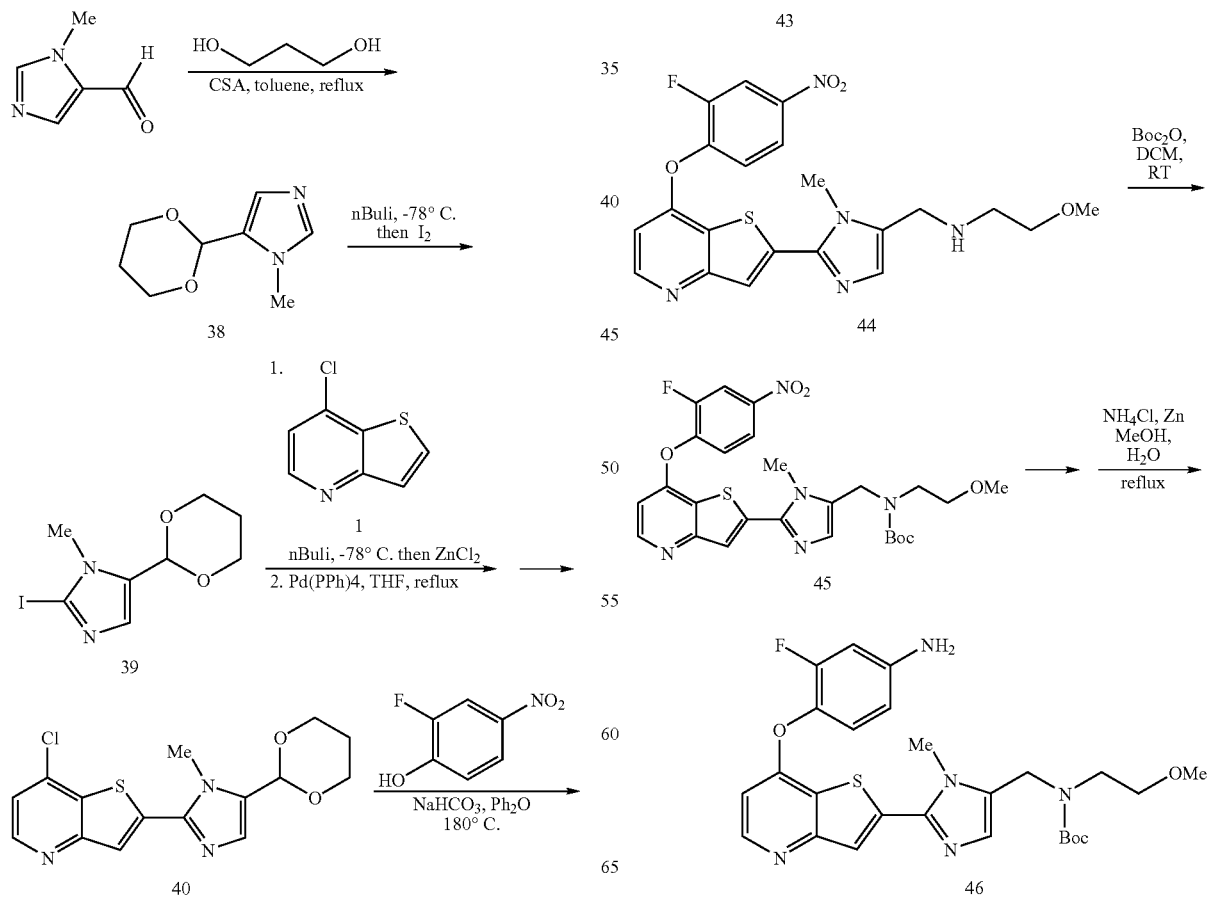

tert-Butyl (2-(7-(4-amino-2-fluorophenoxy)thieno[3,2-b]pyridin-2-yl)-1-methyl-1H-imidazol-5-yl)methyl (2-methoxyethyl)carbamate (46)

Step 1. 5-(1,3-Dioxan-2-yl)-1-methyl-1H-imidazole (38) [Shaflee A., Rastkary N., Jorjani M., Shafaghi B., Arch. Pharm. Pharm. Med. Chem. 2002, 2, 69-76]

To a solution of 1-methyl-1H-imidazole-5-carbaldehyde (2.9 g, 26.3 mmol) in toluene (20 mL) was added propane-1,3-diol (4.01 g, 52.7 mmol) and CSA (0.306 g, 1.317 mmol) and the reaction mixture was heated to reflux with azeotropic removal of the evolved water for 24 hours. The reaction mixture was cooled to RT, diluted with DCM and washed with NaHCO$_3$ solution. It was then dried over Na$_2$SO$_4$, filtered and concentrated. Purification by column chromatography (80% EtOAc in Hexane to EtOAc) afforded 38 (2.53 g, 57% yield) as a yellow oil which solidified on standing to a yellow solid. MS (m/z): 169.2 (M+H).

Step 2. 5-(1,3-Dioxan-2-yl)-2-iodo-1-methyl-1H-imidazole (39)

To a solution of 38 (295 g, 1.754 mmol) in dry THF (10 mL) at −78° C. was added n-BuLi (0.772 mL, 1.929 mmol, 2.5 M solution in hexanes) and the reaction mixture was stirred for 20 min. Iodine (445 mg, 1.754 mmol) in THF (2 mL) was slowly added dropwise while maintaining the temperature at −78° C. and the reaction mixture was stirred for a further 30 min, and was quenched by the addition of water and then extracted with EtOAc. The organic phase was washed with sodium thiosulfate solution, separated, dried over Na$_2$SO$_4$, filtered and concentrated. Purification by column chromatography (20% EtOAc/Hexane) afforded 39 (305 mg, 59% yield) as a white solid. MS (m/z): 294.1 (M+H).

Step 3. 2-(5-(1,3-Dioxan-2-yl)-1-methyl-1H-imidazol-2-yl)-7-chlorothieno[3,2-b]pyridine (40)

To a solution of 7-chlorothieno[3,2-b]pyridine (1) [Klemm, L. H.; Louris, J. N.; Boisvert, W.; Higgins, C.; Muchiri, D. R.; J. Heterocyclic Chem., 22, 1985, 1249-1252] (11.7 g, 69.0 mmol) in THF (300 mL) was added, at −78° C., a solution of n-BuLi (30.46 mL, 76 mmol, 2.5 M in hexanes) and the reaction mixture was stirred for 10 min. A solution of ZnCl$_2$ (76.15 mL, 76 mmol, 1.0 M in Et$_2$O) was added and the mixture was stirred at RT for 10 min. Pd(PPh$_3$)$_4$ (2.287 mg, 0.104 mmol) was added along with a solution of 39 (5.82 g, 19.79 mmol) in THF (20 mL) and the reaction mixture was heated to reflux under an atmosphere of N$_2$ gas for 4 hours. The reaction was then cooled to RT, and diluted with ammonium hydroxide and EtOAc. The organic phase was collected, dried over Na$_2$SO$_4$, filtered and concentrated. The resultant material was triturated with Et$_2$O to afford the title compound 40 (5.79 g, 87% yield) as a white solid. MS (m/z): 336.1 (M+H).

Step 4. 2-(5-(1,3-Dioxan-2-yl)-1-methyl-1H-imidazol-2-yl)-7-(2-fluoro-4-nitrophenoxy)thieno[3,2-b]pyridine, (41)

A mixture of 40 (5.9 g, 17.57 mmol), 2-fluoro-4-nitrophenol (5.52 g, 35.1 mmol) and NaHCO$_3$ (1.346 g, 16.02 mmol) in Ph$_2$O (7 mL) was heated to 180° C. for 4 hours. The reaction mixture was cooled to RT and diluted with DCM, filtered and concentrated. Purification of the residue by column chromatography (eluent EtOAc) afforded 41 (2.5 g, 31% yield) as a yellow solid. MS (m/z): 457.1 (M+H).

Step 5. 2-(5-(Dimethoxymethyl)-1-methyl-1H-imidazol-2-yl)-7-(2-fluoro-4-nitrophenoxy)thieno[3,2-b]pyridine (42)

To a solution of 41 (2.5 g, 5.48 mmol) in MeOH (200 mL) was added CSA (127 mg, 0.548 mmol) and the reaction mixture was heated to reflux for 5 hours. It was then cooled to RT and solid NaHCO$_3$ was added. The mixture was filtered and the filtrate was concentrated to dryness. The residual solid was dissolved in DCM, washed with water, dried over Na$_2$SO$_4$, filtered and concentrated. The resultant solid was triturated with Et$_2$O to afford 42 (1.8 g, 74% yield) which was used without any further purification. MS (m/z): 445.1 (M+H).

Step 6. 2-(7-(2-Fluoro-4-nitrophenoxy)thieno[3,2-b]pyridin-2-yl)-1-methyl-1H-imidazole-5-carbaldehyde (43)

To a solution 42 (1.8 g, 4.05 mmol) in acetone (100 mL) and water (100 mL) was added diluted HCl (20 mL, 2M, 40.0 mmol) and the reaction mixture was stirred at RT overnight. It was then concentrated to dryness. The residual solid was dissolved in DCM, washed with water, dried over Na$_2$SO$_4$, filtered and concentrated. The resultant solid was triturated with Et$_2$O to afford 43 (1.3 g, 81% yield), which used without additional purification. MS (m/z): 399.2 (M+H).

Step 7. N-((2-(7-(2-Fluoro-4-nitrophenoxy)thieno[3,2-b]pyridin-2-yl)-1-methyl-1H-imidazol-5-yl)methyl)-2-methoxyethanamine (44)

To a suspension of 43 (1.3 g, 3.26 mmol) in dry DCM (50 mL) at RT was added 2-methoxyethanamine (1.226 g, 16.32 mmol), acetic acid (0.98 g, 16.32 mmol) and sodium triacetoxyborohydride (3.46 g, 16.32 mmol), and the reaction mixture was stirred at RT for 24 hours. It was then diluted with additional DCM and washed with saturated NaHCO$_3$ solution, dried over Na$_2$SO$_4$, filtered and concentrated to dryness to afford 44 (1.5 g, 100% yield) as an yellow oil which was used crude in the next step with no additional purification. MS (m/z): 458.2 (M+H).

Step 8. tert-Butyl (2-(7-(2-fluoro-4-nitrophenoxy)thieno[3,2-b]pyridin-2-yl)-1-methyl-1H-imidazol-5-yl)methyl(2-methoxyethyl)carbamate (45)

To a solution of 44 (1.5 g, 3.28 mmol) in DCM (50 mL) at RT was added Boc$_2$O (1.073 mg, 4.92 mmol) and the reaction mixture was stirred at RT overnight. The mixture was concentrated to dryness and the residue was purified by column chromatography (eluent EtOAc) to afford 45 (1.3 g, 71% yield) as a yellow solid. MS (m/z): 558.2 (M+H).

Step 9. tert-Butyl (2-(7-(4-amino-2-fluorophenoxy)thieno[3,2-b]pyridin-2-yl)-1-methyl-1H-imidazol-5-yl)methyl(2-methoxyethyl)carbamate (46)

To a solution of 45 (1.1 g, 0.717 mmol) in MeOH (30 mL) and water (10 mL) was added ammonium chloride (211 mg, 3.95 mmol) and zinc (1.61 g, 17.76 mmol) and the reaction mixture was heated to reflux for 24 hours. The reaction mixture was cooled to RT then concentrated to dryness. The residue was partitioned between DCM and water and the organic phase was collected, dried over Na$_2$SO$_4$, filtered and concentrated to afford the title compound 46 (1.04 g, 100% yield), which was used crude in the next step with no additional purification. MS (m/z): 528.1 (M+H).

Scheme 2

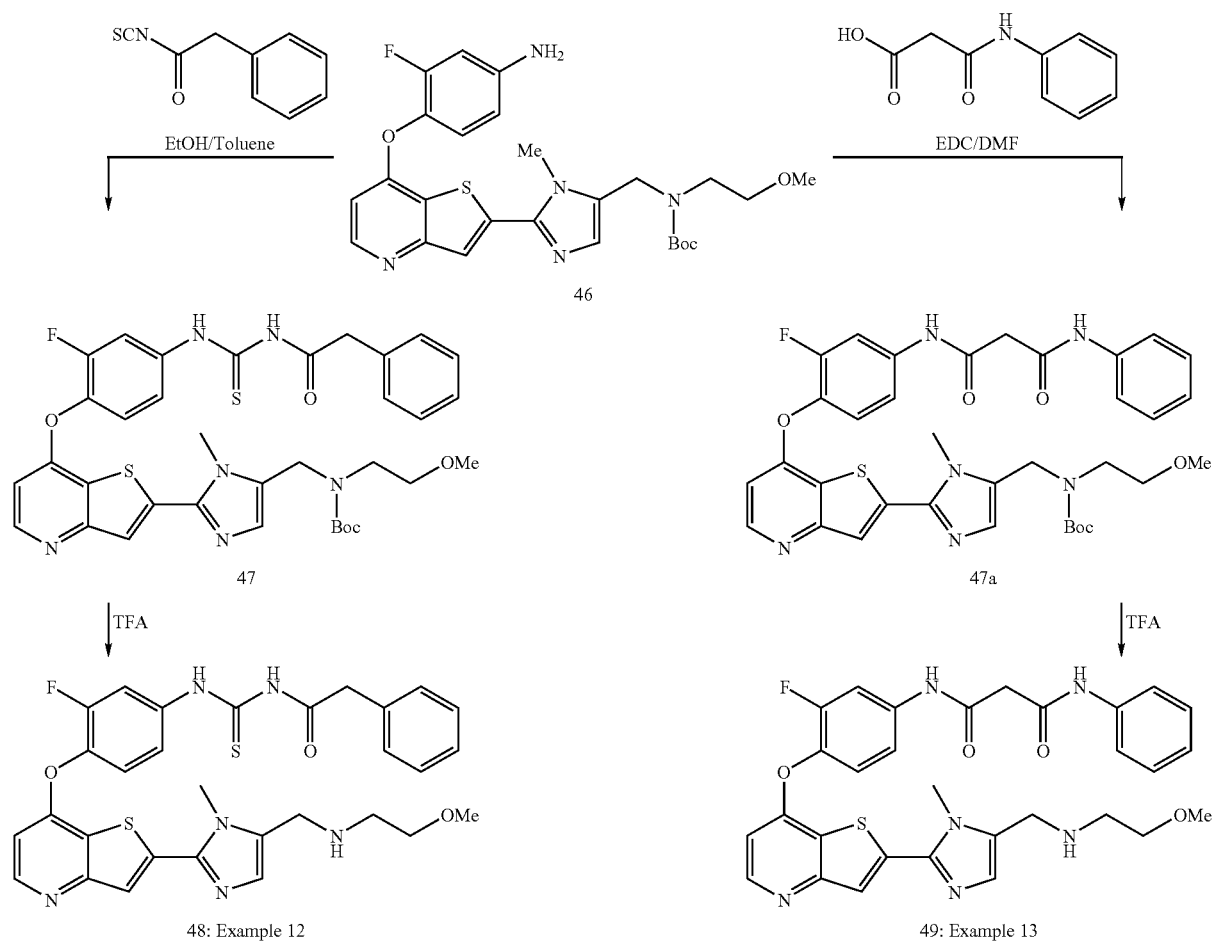

Example 12

N-(3-Fluoro-4-(2-(5-((2-methoxyethylamino)methyl)-1-methyl-1H-imidazol-2-yl)thieno[3,2-b]pyridin-7-yloxy)phenylcarbamothioyl)-2-phenylacetamide (48)

Step 10. tert-Butyl (2-(7-(2-fluoro-4-(3-(2-phenylacetyl)thioureido)phenoxy)thieno[3,2-b]pyridin-2-yl)-1-methyl-1H-imidazol-5-yl)methyl(2-methoxyethyl)carbamate (47)

To a solution of 46 (375 mg, 0.711 mmol) in a mixture of EtOH (5 mL) and toluene (5 mL) at RT was added phenylacetyl isothiocyanate (189 mg, 1.066 mmol) and the reaction mixture was stirred at RT for 3 hours. The mixture was concentrated to dryness then purified by column chromatography (eluent a gradient of 80% EtOAc in hexane to EtOAc), to afford 47 (400 mg, 80%) as a red solid. MS (m/z): 705.2 (M+H).

Step 11. N-(3-Fluoro-4-(2-(5-((2-methoxyethylamino)methyl)-1-methyl-1H-imidazol-2-yl)thieno[3,2-b]pyridin-7-yloxy)phenylcarbamothioyl)-2-phenylacetamide (48)

To a solution of 47 (400 mg, 0.568 mmol) in toluene (10 mL) was added TFA (0.874 mL, 11.35 mmol) and the reaction mixture was stirred at RT overnight. The mixture was concentrated to dryness and the residue was purified by Gilson Reverse Phase HPLC (Aquasil $C_{18}$, elient a linear gradient of 35% MeOH in water to 95% MeOH in water with 0.05% of formic acid, 60 min run) to afford 48 as a white solid, (305 mg, 65% yield) as the TFA salt. MS (m/z): 605.3 (M+H).

Example 13

$N^1$-(3-Fluoro-4-(2-(5-((2-methoxyethylamino)methyl)-1-methyl-1H-imidazol-2-yl)thieno[3,2-b]pyridin-7-yloxy)phenyl)-$N^3$-phenylmalonamide (49)

Step 1. tert-Butyl (2-(7-(2-fluoro-4-(3-oxo-3-(phenylamino)propanamido)phenoxy)thieno[3,2-b]pyridin-2-yl)-1-methyl-1H-imidazol-5-yl)methyl(2-methoxyethyl)carbamate (47a)

To a solution of 46 (333 mg, 0.631 mmol) in DMF (8 mL) at RT was added 3-oxo-3-(phenylamino)propanoic acid (226 mg, 2 eq, 1.262 mmol) and EDC (242 mg, 2 eq, 1.262 mmol), and the reaction mixture was stirred at RT for 24 hours. It was then concentrated to dryness then purified by column chromatography (eluent a gradient of 80% EtOAc in hexane to EtOAc), to afford 47a (357 mg, 82% yield) as a white solid. MS (m/z): 689.4 (M+H).

Step 2. N¹-(3-Fluoro-4-(2-(5-((2-methoxyethylamino)methyl)-1-methyl-1H-imidazol-2-yl)thieno[3,2-b]pyridin-7-yloxy)phenyl)-N³-phenylmalonamide (49)

To a solution of 47 (357 mg, 0.518 mmol) in toluene (20 mL) was added TFA (0.799 mL, 20 eq, 10.36 mmol) and the reaction mixture was stirred at RT for 5 hours. The mixture was concentrated to dryness and the residue was purified by Gilson Reverse Phase HPLC (Aquasil $C_{18}$, elient a linear gradient of 35% MeOH in water to 95% MeOH in water with 0.05% of formic acid, 60 min run) to afford 49 as a yellow solid (270 mg, 88% yield) as the TFA salt. Characterization of compound 49 is provided in the Table 1.

Example 14

N¹-(3-Fluoro-4-(2-(5-((2-methoxyethylamino)methyl)-1-methyl-1H-imidazol-2-yl)thieno[3,2-b]pyridin-7-yloxy)phenyl)-N3-methyl-N3-phenylmalonamide (50)

Title compound 50 was obtained similarly to the compound 49 starting from the compound 46 (scheme 2) and using 3-(methyl(phenyl)amino)-3-oxopropanoic acid [US 2007/0004675 A-1] instead of 3-oxo-3-(phenylamino)propanoic) acid. Characterization of 50 is provided in the Table 1.

Example 15

N-(3-Fluoro-4-(2-(5-((2-methoxyethylamino)methyl)-1-methyl-1H-imidazol-2-yl)thieno[3,2-b]pyridin-7-yloxy)phenyl)-N-phenylcyclopropane-1,1-dicarboxamide (51)

Title compound 51 was obtained similarly to the compound 49 starting from the compound 46 (scheme 2) and using 1-(phenylcarbamoyl)cyclopropanecarboxylic acid [US 2007/0004675 A-1] instead of 3-oxo-3-(phenylamino)propanoic) acid. Characterization of 51 is provided in the Table 1.

Example 16

N-(3-Fluoro-4-(2-(5-((2-methoxyethylamino)methyl)-1-methyl-1H-imidazol-2-yl)thieno[3,2-b]pyridin-7-yloxy)phenyl)-2-oxo-3-phenylimidazolidine-1-carboxamide (52)

Title compound 52 was obtained similarly to the compound 49 starting from the compound 46 (scheme 2) and using 2-oxo-3-phenylimidazolidine-1-carbonyl chloride [US 2007/0004675 A-1] in the presence of Hunig's base in DCM instead of 3-oxo-3-(phenylamino)propanoic) acid. Characterization of 52 is provided in the Table 1.

TABLE 1

| Cpd. # | Ex. # | Structure | Characterization |
|---|---|---|---|
| 49 | 13 | 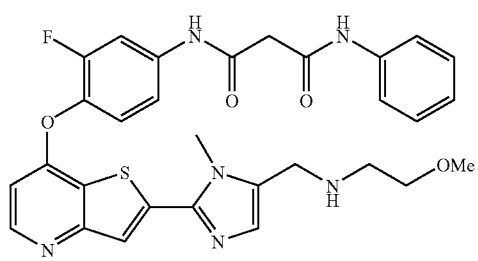 [SMILES: COCCNCc1cnc(-c2cc3nccc(Oc4ccc(NC(=O)CC(=O)Nc5ccccc5)cc4F)c3s2)n1C] | ¹H NMR (400 MHz, DMSO-$d_6$) δ (ppm) 10.60 (s, 1 H), 10.22 (s, 1 H), 8.95 (s, 2 H), 8.56 (d, J = 5.28 Hz, 1 H), 8.12 (s, 1 H), 7.90 (m, 1 H), 7.60 (m, 2 H), 7.49 (m, 3 H), 7.31 (m, 3 H), 7.05 (m, 1 H), 6.74 (m, 1 H), 4.35 (m, 1 H), 3.93 (s, 3 H), 3.60 (m, 2 H), 3.51 (s, 2 H), 3.31 (s, 3 H), 3.21 (m, 2 H). LCMS: 589.3 (M + H). (mono-formate salt) MS (m/z): 589.3 (M + H). |
| 50 | 14 | 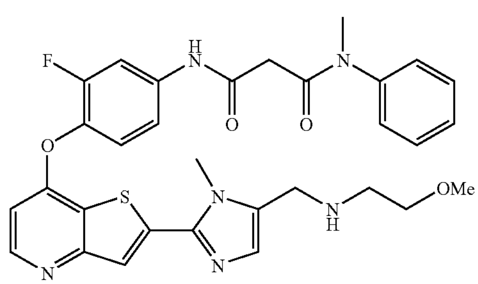 [SMILES: COCCNCc1cnc(-c2cc3nccc(Oc4ccc(NC(=O)CC(=O)N(C)c5ccccc5)cc4F)c3s2)n1C] | ¹H NMR (400 MHz, DMSO-$d_6$) δ (ppm) 10.29 (s, 1 H), 8.50 (m, 1 H), 8.49 (m, 1 H), 8.17 (s, 2 H), 7.90 (m, 2 H), 7.76 (m, 1 H), 7.46 (m, 10 H), 3.91 (s, 1 H), 3.90 (s, 3 H), 3.77 (m, 2 H), 3.38 (m, 4 H), 2.71 (m, 4 H), (mono-formate salt). MS (m/z): 603.3 (M + H). |
| 51 | 15 | 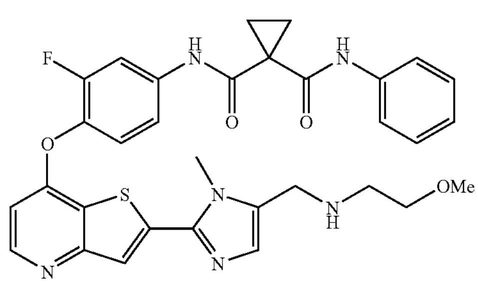 [SMILES: COCCNCc1cnc(-c2cc3nccc(Oc4ccc(NC(=O)C5(C(=O)Nc6ccccc6)CC5)cc4F)c3s2)n1C] | ¹H NMR (400 MHz, DMSO-$d_6$) δ (ppm) 10.46 (s, 1 H), 10.01 (s, 1 H), 9.5 (s, 2 H), 8.70 (m, 1 H), 8.15 (m, 1 H), 7.92 (m, 1 H), 7.62 (m, 2 H), 7.51 (m, 3 H), 7.31 (m, 3 H), 7.05 (m, 1 H), 6.98 (m, 1 H), 3.98 (s, 3 H), 3.36 (m, 2 H), 3.66 (m, 2 H), 3.31 (s, 3 H), 3.18 (m, 2 H), 1.47 (s, 4 H) (tris-trifluoroacetate salt). MS (m/z): 615.3 (M + H). |

TABLE 1-continued
| Cpd. # | Ex. # | Structure | Characterization |
|---|---|---|---|
| 52 | 16 | 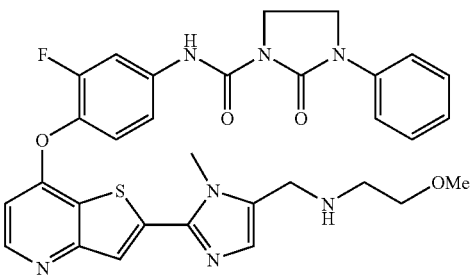 [SMILES: COCCNCc1cnc(-c2cc3nccc(Oc4ccc(NC(=O)N5CCN(c6ccccc6)C5=O)cc4F)c3s2)n1C] | ¹H NMR (400 MHz, DMSO-$d_6$) δ (ppm) 10.51 (s, 1 H), 8.51 (m, 1 H), 8.21 (s, 1 H), 7.89 (s, 1 H), 7.86 (m, 1 H), 7.61 (m, 2 H), 7.47 (m, 5 H), 7.16 (t, J = 7.04, 1 H), 6.95 (s, 1 H), 6.67 (m, 1 H), 3.95 (s, 4 H), 3.90 (s, 3 H), 3.75 (s, 2 H), 3.39 (m, 2 H), 3.23 (s, 3 H), 2.68 (m, 3 H). (tris-trifluoroacetate salt) MS (m/z): 616.3 (M + H). |
Scheme 3
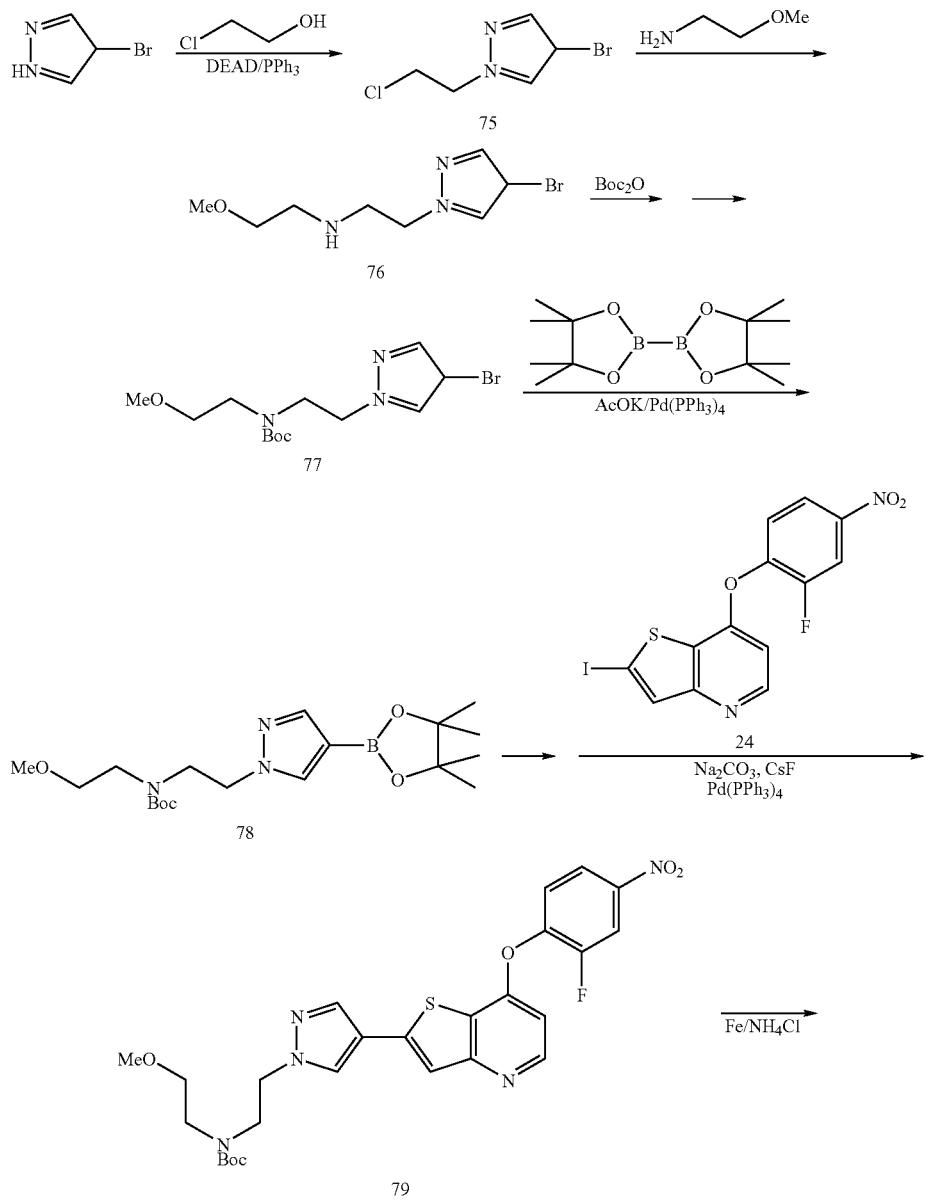

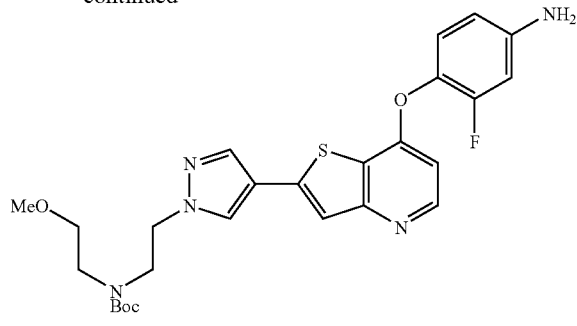

80 tert-Butyl 2-(4-(7-(4-amino-2-fluorophenoxy)thieno[3,2-b]pyridin-2-yl)-1H-pyrazol-1-yl)ethyl (2-methoxyethyl)carbamate (80)

Step 1. 4-Bromo-1-(2-chloroethyl)-1H-pyrazole (75)

To a solution of 4-bromo-1H-pyrazole (5 g, 34.02 mmol), 2-chloroethanol (2.7 mL, 40.82 mmol) and PPh$_3$ (10.71 g, 40.82 mmol) and in THF (68 mL) at 0° C. was added DEAD (6.4 mL, 40.8 mmol). The mixture was allowed to warm-up to room temperature and stirred overnight. It was then concentrated under reduced pressure, the residue was treated with ether and the resultant suspension was filtered. The filtrate was collected and concentrated under reduced pressure to afford the title compound 75 which was used in the next step without further purification. MS (m/z). 209.0 (M+H).

Step 2. 2-(4-Bromo-1H-pyrazol-1-yl)-N-(2-methoxyethyl)ethanamine (76)

A solution of 2-methoxyethanamine (8.9 mL, 102.06 mmol) and chloride 75 (7.13 g, 34.02 mmol) in DMSO (20 mL) was heated at 60° C. 5 h. The mixture was then cooled to room temperature, diluted with EtOAc, washed with aqueous sodium bicarbonate, water and brine. The organic phase was further extracted with 1N HCl and the acid extract was collected and basified with 2N NaOH (pH~11). The basic aqueous solution was extracted with DCM, the DCM extract was dried over anhydrous sodium sulphate, and concentrated under reduced pressure to afford title compound 76 (8.44 g, 99%) as brown foam. MS (m/z): 248.04 (M+H).

Step 3. tert-Butyl 2-(4-bromo-1H-pyrazol-1-yl)ethyl (2-methoxyethyl)carbamate (77)

A solution of 76 (8.44 g, 34.02 mmol) and Boc$_2$O (8.91 g, 40.82 mmol) in THF (68 mL) was stirred overnight at room temperature. The reaction mixture was transferred onto a flash chromatography column and eluted with EtOAc/Hexane 1:3, to afford title compound 77 (4.2 g, 35%) as transparent syrup. MS (m/z): 349.08 (M+1).

Step 4. tert-Butyl 2-methoxyethyl(2-(4-(4,4,5,5-tetramethyl-1,3,2-dioxaborolan-2-yl)-1H-pyrazol-1-yl)ethyl)carbamate (78)

A mixture of 77 (369.3 mg, 1.06 mmol), bis(pinacolato)diboron (323.2 mg, 1.27 mmol), Pd(PPh$_3$)$_4$ (61.3 mg, 0.05 mmol) and AcOK (312.3 mg, 3.18 mmol) in THF (2.1 mL) was heated to reflux overnight under nitrogen. It was then diluted with DCM, washed with water, dried over anhydrous sodium sulphate and concentrated under reduced pressure affording crude 78 (11.06 mmol, 100% yield) that was used in the next step without further purification. MS (m/z): 396.2 (M+H).

Step 5: tert-Butyl 2-(4-(7-(2-fluoro-4-nitrophenoxy)thieno[3,2-b]pyridin-2-yl)-1H-pyrazol-1-yl)ethyl(2-methoxyethyl)carbamate (79)

A mixture of 78 (369.3 mg, 0.93 mmol), 7-(2-fluoro-4-nitrophenoxy)-2-iodothieno[3,2-b]pyridine (24) [US 2006/0287343 A1] (466.6 mg, 1.12 mmol), Pd(PPh$_3$)$_4$ (54 mg, 0.05 mmol) and Na$_2$CO$_3$ (305 mg, 2.8 mmol) in DME (1.9 mL) was heated to reflux overnight under nitrogen. It was then diluted with DCM, washed with water, dried over anhydrous sodium sulphate and concentrated under reduced pressure. The residue was purified by flash chromatography, eluents EOAc/Hex 1:1, EtOAc, 5% MeOH in DCM affording title compound 79 (203 mg, 39%) as brown syrup. MS (m/z): 558.2 (100%) (M+H).

Step 6. tert-Butyl 2-(4-(7-(4-amino-2-fluorophenoxy)thieno[3,2-b]pyridin-2-yl)-1H-pyrazol-1-yl)ethyl (2-methoxyethyl)carbamate (80)

Starting from the nitro compound 79 and following the procedure described below for the synthesis of compound 126 (Scheme 6, step 4, example 49), title compound 80 was obtained in 100% yield. MS (m/z): 528.3 (100%) (M+H).

Example 24

N-(3-Fluoro-4-(2-(1-(2-(2-methoxyethylamino)ethyl)-1H-pyrazol-4-yl)thieno[3,2-b]pyridin-7-yloxy)phenylcarbamothioyl)-2-phenylacetamide (81)

Title compound 81 was obtained similarly to the compound 48 (example 12) but starting from the amine 80 (scheme 3). Characterization of 81 is provided in the Table 2.

Example 25

N-(3-Fluoro-4-(2-(1-(2-(2-methoxyethylamino)ethyl)-1H-pyrazol-4-yl)thieno[3,2-b]pyridin-7-yloxy)phenyl)-N-(4-fluorophenyl)cyclopropane-1,1-dicarboxamide (82)

Title compound 82 was obtained similarly to the compound 51 (example 15) but starting from the amine 80

(scheme 3) and using 1-(4-fluorophenylcarbamoyl)cyclopropane-carboxylic acid instead of 1-(phenylcarbamoyl)cyclopropanecarboxylic acid. Characterization of 82 is provided in the Table 2.

Example 26

N-(3-Fluoro-4-(2-(1-(2-(2-methoxyethylamino)ethyl)-1H-pyrazol-4-yl)thieno[3,2-b]pyridin-7-yloxy)phenyl)-N-phenylcyclopropane-1,1-dicarboxamide (83)

Title compound 83 was obtained similarly to the compound 51 (example 15) but starting from the amine 80 (scheme 3) and using 1-(phenylcarbamoyl)cyclopropanecarboxylic acid. Characterization of 83 is provided in the Table 2.

Example 27

$N^1$-(3-Fluoro-4-(2-(1-(2-(2-methoxyethylamino)ethyl)-1H-pyrazol-4-yl)thieno[3,2-b]pyridin-7-yloxy)phenyl)-$N^3$-methyl-$N^3$-phenylmalonamide (84)

Title compound 84 was obtained similarly to the compound 50 (example 14) but starting from the amine 80 (scheme 3) and using 3-(methyl(phenyl)amino)-3-oxopropanoic acid. Characterization of 84 is provided in the Table 2.

TABLE 2

| Cpd. No. | Ex. No. | Structure | Characterization |
|---|---|---|---|
| 81 | 24 | (structure) | $^1$H-NMR (DMSO-D$_6$, 400 MHz) 12.5 (br, 1 H), 11.85 (br, 1 H), 8.48 (d, J = 5.5 Hz, 1 H), 8.41 (s, 1 H), 8.11 (dd, J = 0.6 Hz, 1 H), 8.07 (d, J = 12.13 Hz, 1 H), 7.75 (s, 1 H), 7.74-7.50 (m, 2 H), 7.37-7.24 (m, 5 H), 6.62 (dd, J = 5.5 Hz, J = 0.8 Hz, 1 H), 4.45 (t, J = 6.26 Hz, 2 H), 3.83 (s, 2 H), 3.59-3.53 (m, 3 H), 3.36-3.33 (m, 3 H), 3.29 (s, 3 H), 3.04 (t, J = 5.1 Hz, 2 H) (presumably a dihydrochloride salt). MS (m/z): 605.2 (M + 1). |
| 82 | 25 | (structure) | $^1$H NMR (400 MHz, MeCN-d$_3$) δ (ppm): 10.11 (s, 1 H), 8.85 (s, 1 H), 8.56 (d, J = 6.5 Hz, 1 H), 8.32 (s, 1 H), 8.06 (s, 1 H), 7.88 (dd, J = 12.7, 2.2 Hz, 1 H), 7.83 (s, 1 H), 7.56-7.53 (m, 2 H), 7.53-7.43 (m, 1 H), 7.38 (m, 1 H), 7.13-7.08 (m, 2 H), 6.88 (dd, J = 6.5, 0.8 Hz, 1 H), 4.54 (dd, J = 6.3, 6.0 Hz, 2 H), 3.63 (t, J = 5 Hz, 2 H), 3.55 (m, 2 H), 3.35 (s, 3 H), 3.24 (m, 2 H), 1.65-1.62 (m, 4 H) (presumably bis-trifluoroacetate salt). MS (m/z): 633.2 (M + 1). |
| 83 | 26 | (structure) | $^1$H NMR (400 MHz, CD$_3$CN) δ (ppm): 10.06 (s, 1 H), 8.86 (s, 1 H), 8.56 (d, J = 6.4 Hz, 1 H), 8.22 (s, 1 H), 8.05 (s, 1 H), 7.88 (dd, J = 12.9, 2.3 Hz, 1 H), 7.82 (s, 1 H), 7.56-7.54 (m, 2 H), 7.46-7.34 (m, 4 H), 7.17-7.13 (m, 1 H), 6.87 (d, J = 6.4 Hz, 1 H), 4.54 (dd, J = 5.5, 5.1 Hz, 2 H), 3.63 (dd, J = 5.3, 4.9 Hz, 2 H), 3.55 (dd, J = 5.3, 4.9 Hz, 2 H), 3.35 (s, 3 H), 3.24 (dd, J = 5.3, 4.7 Hz, 2 H), 1.65-1.62 (m, 4 H) di TFA salt. MS (m/z): 615.2 (M + 1). |

TABLE 2-continued
| Cpd. No. | Ex. No. | Structure | Characterization |
|---|---|---|---|
| 84 | 27 | 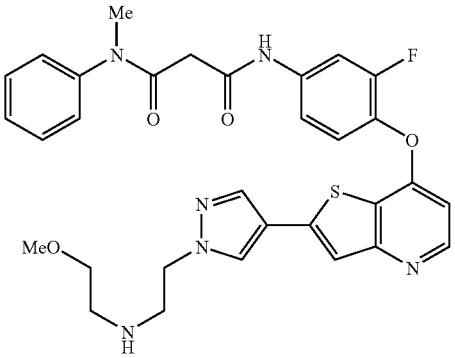 [SMILES: COCCNCCn1cc(-c2cc3nccc(Oc4ccc(NC(=O)CC(=O)N(C)c5ccccc5)cc4F)c3s2)cn1] | ¹H NMR (400 MHz, DMSO-d₆) δ (ppm): 10.37 (s, 1 H), 8.79 (br, 1 H), 8.51 (d, J = 5.7 Hz, 1 H), 8.44 (s, 1 H), 8.18 (d, J = 0.4 Hz, 1 H), 7.82 (d, J = 11.3 Hz, 1 H), 7.78 (s, 1 H), 7.50-7.33 (m, 7 H), 6.68 (d, J = 5.7 Hz, 1 H), 4.51 (dd, J = 6.3, 6.1 Hz, 2 H), 3.58 (dd, J = 5.3, 4.9 Hz, 2 H), 3.48 (m, 2 H), 3.31 (s, 3 H), 3.23 (s, 2 H), 3.21 (s, 3 H), 3.18 (m, 2 H) (presumably dihydrochloride salt) MS (m/z): 603.3 (M + 1). |
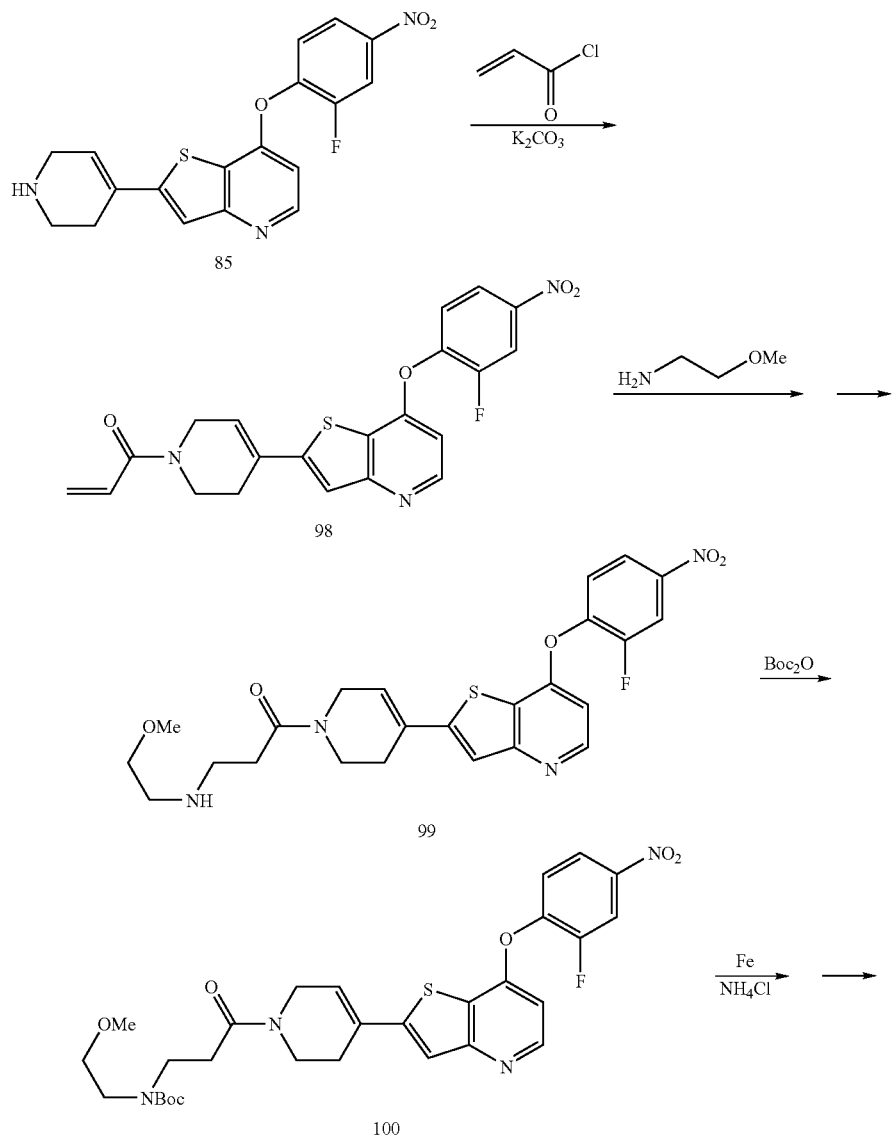

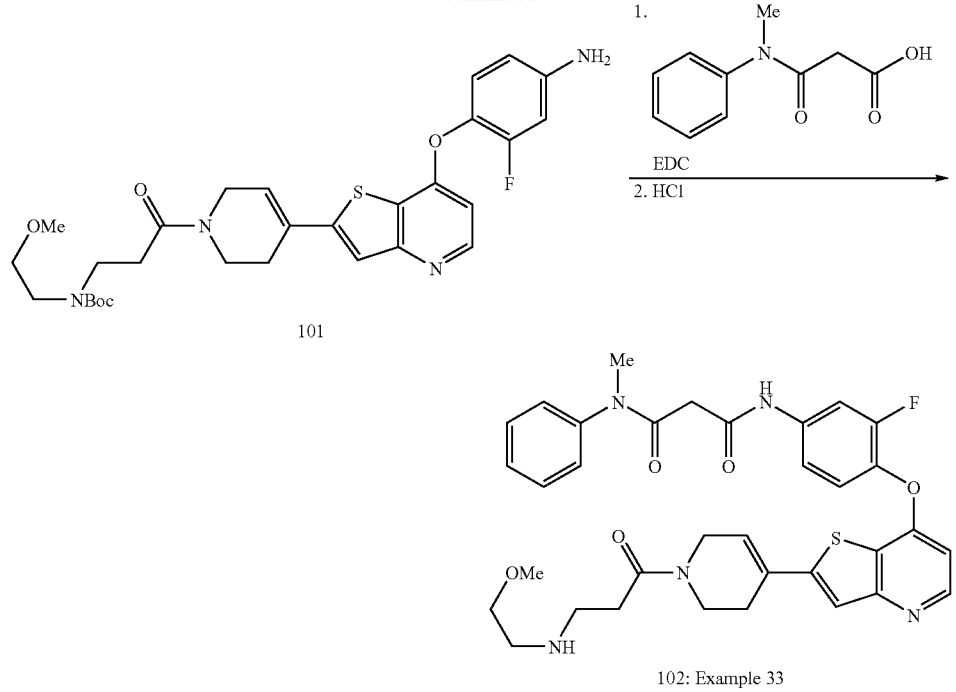

102: Example 33

Example 33

$N^1$-(3-Fluoro-4-(2-(1-(3-(2-methoxyethylamino)propanoyl)-1,2,3,6-tetrahydropyridin-4-yl)thieno[3,2-b]pyridin-7-yloxy)phenyl)-$N^3$-methyl-$N^3$-phenyl-malonamide (102)

Step 1. 1-(4-(7-(2-Fluoro-4-nitrophenoxy)thieno[3,2-b]pyridin-2-yl)-5,6-dihydropyridin-1(2H)-yl)prop-2-en-1-one (98)

Acryloyl chloride (131.3 mL, 1.62 mmol) was added to a suspension of 7-(2-fluoro-4-nitrophenoxy)-2-(1,2,3,6-tetrahydropyridin-4-yl)thieno[3,2-b]pyridine (85) [US 2007/0004675 A1] (150 mg, 0.40 mmol) and K$_2$CO$_3$ (223.4 1.62 mmol) and the mixture was stirred overnight at room temperature. It was then filtered and concentrated under reduced pressure affording title compound 98 (172 mg, 100% yield) that was used in the next step without further purification. MS (m/z): 426.1 (M+1)

Step 2. 1-(4-(7-(2-Fluoro-4-nitrophenoxy)thieno[3,2-b]pyridin-2-yl)-5,6-dihydropyridin-1(2H)-yl)-3-(2-methoxyethylamino)propan-1-one (99)

A solution of the compound 98 (171.0 mg, 0.4 mmol) and 2-methoxyethanamine (0.14 mL, 1.62 mmol) in THF (98.1 mL) was stirred overnight at room temperature. It was then diluted with DCM, washed with aqueous sodium bicarbonate and water. The organic phase was extracted with 1N HCl, the aqueous acidic phase was basified by addition of 1N NaOH (pH 11) and extracted with DCM. The DCM extract was dried over anhydrous sodium sulphate and concentrated under reduced pressure affording title compound 99 (89.0 mg, 45% yield) as cream foam. MS (m/z): 501.2 (M+1).

Step 3: tert-Butyl 3-(4-(7-(2-fluoro-4-nitrophenoxy)thieno[3,2-b]pyridin-2-yl)-5,6-dihydropyridin-1(2H)-yl)-3-oxopropyl(2-methoxyethyl)carbamate (100)

To a solution of compound 99 (89 mg, 0.178 mmol) in THF (1.778 mL) di-tert-butyl dicarbonate (46.6 mg, 0.213 mmol) was added. The reaction mixture was stirred at room temperature overnight, poured onto a silica gel column and eluted with 5% MeOH in CH$_2$Cl$_2$, affording title compound 100 (106 mg, 99% yield) as a red syrup. MS (m/z): 601.3 (M+1).

Step 4: tert-Butyl 3-(4-(7-(4-amino-2-fluorophenoxy)thieno[3,2-b]pyridin-2-yl)-5,6-dihydropyridin-1(2H)-yl)-3-oxopropyl(2-methoxyethyl)carbamate (101)

Starting from the nitro compound 100, title compound 101 was obtained by following the same procedures as described below for the synthesis of compound 126 (Scheme 6, step 4). MS (m/z): 571.3 (M+1).

Steps 5 and 6. $N^1$-(3-Fluoro-4-(2-(1-(3-(2-methoxyethylamino)propanoyl)-1,2,3,6-tetrahydropyridin-4-yl)thieno[3,2-b]pyridin-7-yloxy)phenyl)-$N^3$-methyl-N-phenylmalonamide (102)

Title compound 102 was obtained similarly to the compound 84 (example 27, Table 2)

$^1$H NMR (400 MHz, CD$_3$OD) δ (ppm): 8.72 (dd, J=6.6, 1.6 Hz, 1H), 7.87 (dd, J=12.5, 1.6 Hz, 1H), 7.68 (s, 1H), 7.52-7.36 (m, 7H), 7.12 (dd, J=6.8, 1.6 Hz, 1H), 6.77-6.73 (m, 1H), 4.95-4.34 (m, 2H), 3.91 (t, J=5.7 Hz, 0.9H), 3.82 (t, J=5.7 Hz, 1.1H), 3.69-3.66 (m, 2H), 3.43 (s, 3H), 3.38-3.35 (m, 2H), 3.34 (s, 2H), 3.33 (s, 3H), 3.28 (m, 2H), 2.98 (t, J=6.0 Hz, 1.1H), 2.91 (t, J=6.0 Hz, 0.9H), 2.84 (m, 1.1H), 2.74 (m, 0.9H) (presumably di-hydrochloride salt). MS (m/z): 646.3 (M+1).

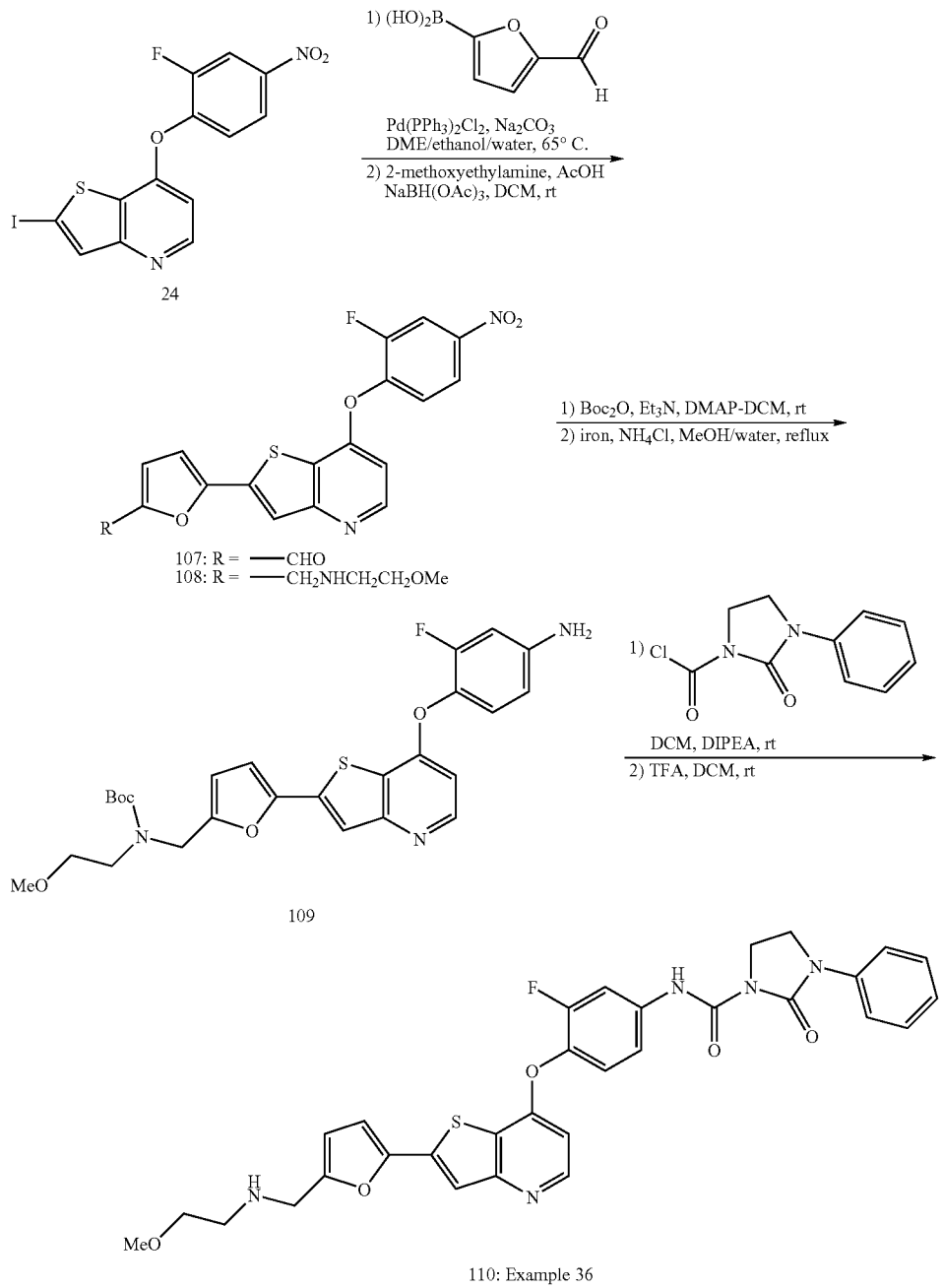

Example 36

N-(3-Fluoro-4-(2-(5-((2-methoxyethylamino)methyl)furan-2-yl)thieno[3,2-b]pyridin-7-yloxy)phenyl)-2-oxo-3-phenylimidazolidine-1-carboxamide (110)

Step 1. 5-(7-(2-Fluoro-4-nitrophenoxy)thieno[3,2-b]pyridin-2-yl)furan-2-carbaldehyde (107)

A stirred suspension of 7-(2-fluoro-4-nitrophenoxy)-2-iodothieno[3,2-b]pyridine (24) [US 2006/0287343 A1] (5.00 g, 12.01 mmol, scheme 4)], 5-formyl-2-furanboronic acid (2.19 g, 15.19 mmol), Pd(PPh₃)₂Cl₂ (422 mg, 0.6 mmol), Na₂CO₃ (8.53 g, 80.50 mmol) in a mixture of DME/ethanol/water (60 mL/40 mL/40 mL) was degassed with nitrogen for 15 min, and heated at 65° C. for five hours under nitrogen. The reaction mixture was allowed to cool to room temperature, and filtered. The cake was successively washed with water and AcOEt. The filtrate and washings were combined, extracted with AcOEt. The extract was successively washed with water, saturated solution of ammonium chloride, water and brine, and concentrated. The residue was combined with the cake, absorbed on silica gel and subjected to flash column chromatography on silica gel (eluents AcOEt/DCM: 10/90 to 20/90, then MeOH/DCM: 5/95) followed by trituration with AcOEt, to afford aldehyde 107 (3.886 g, 84% yield) as a pale clay solid. MS (m/z): 385.0 (M+H).

Step 2. N-((5-(7-(2-fluoro-4-nitrophenoxy)thieno[3,2-b]pyridin-2-yl)furan-2-yl)methyl)-2-methoxyethanamine (108)

A suspension of 107 (2.00 g, 5.20 mmol), 2-methoxyethylamine (1.954 g, 26.02 mmol), NaBH(OAc)$_3$ (5.52 g, 26.02 mmol) and acetic acid (1.49 ml, 26.02 mmol) in anhydrous dichloromethane was stirred at room temperature under nitrogen for five days. The reaction mixture was then carefully quenched with a saturated solution of NaHCO$_3$ (pH 8-9), and extracted with DCM. The extract was dried over anhydrous magnesium sulfate, filtered, and concentrated to afford the title compound 108 as a yellow-orange sticky oil. The material was used in the next step without further purification. MS (m/z): 444.2 (M+H).

Steps 3 and 4. tert-Butyl (5-(7-(4-amino-2-fluorophenoxy)thieno[3,2-b]pyridin-2-yl)furan-2-yl)methyl(2-methoxyethyl)carbamate (109)

Title compound 109 was obtained in 2 steps from 108 as a yellow sticky foam, following similar procedures as for the compound 45 (Scheme 1) and compound 126 (Scheme 6). MS (m/z): 514.3 (M+H).

Steps 5 and 6. N-(3-fluoro-4-(2-(5-((2-methoxyethylamino)methyl)furan-2-yl)thieno[3,2-b]pyridin-7-yloxy)phenyl)-2-oxo-3-phenylimidazolidine-1-carboxamide (110)

Title compound 110 was obtained in two steps according to procedures similar to ones used for the synthesis of compound 52 (example 16, Table 1) as an off-white solid $^1$H NMR (400 MHz, DMSO-d$_6$) δ (ppm): 10.59 (s, 1H), 8.50 (d, J=5.5 Hz, 1H), 7.86 dd, J=12.9, 2.3 Hz, 1H), 7.77 (s, 1H), 7.67-7.61 (m, 2H), 7.50 (t, J=8.7 Hz, 1H), 7.48-7.40 (m, 3H), 7.18 (ti, J=7.4, 1.1 Hz, 1H), 7.09 (d, J=3.1 Hz, 1H), 6.64 (dd, J=5.5, 1.0 Hz, 1H), 6.47 (d, J=3.5 Hz, 1H), 4.02-3.91 (m, 4H), 3.78 (s, 2H), 3.40 (t, S=5.7 Hz, 2H), 3.24 (s, 3H), 2.71 (t, J=5.7 Hz, 2H), 2.26-2.06 (m, 1H). MS (m/z): 602.3 (M+H).

Compounds 111-113 (examples 37-39) were prepared in two steps from the amine 109 similarly to compounds 48 (scheme 2, example 12,) and 51 (Table 2). Characterization of compounds 111-113 (examples 37-39) is provided in the Table 3.

TABLE 3

111-113: Examples 37-39

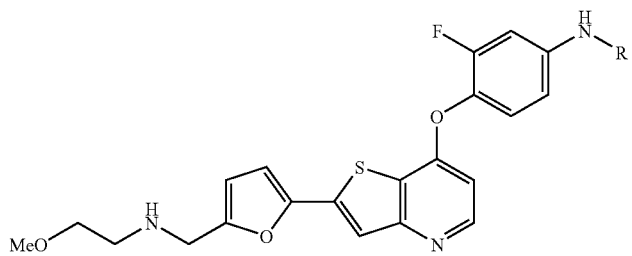

| Cpd. | Ex. | R | Name | Characterization |
|---|---|---|---|---|
| 111 | 37 | (phenylacetyl thioamide group) | N-(3-fluoro-4-(2-(5-((2-methoxyethylamino)-methyl)furan-2-yl)thieno[3,2-b]pyridin-7-yloxy)phenylcarbamothioyl)-2-phenylacetamide | $^1$H NMR (400 MHz, DMSO-d$_6$) δ (ppm): 12.55-12.30 (m, 1 H), 12.05-11.60 (m, 1 H), 8.51 (d, J = 5.5 Hz, 1 H), 8.02 (dd, J = 12.3, 1.3 Hz, 1 H), 7.77 (s, 1 H), 7.58-7.50 (m, 2 H), 7.39-7.25 (m, 5 H), 7.09 (d, J = 3.1 Hz, 1 H), 6.65 (dd, J = 5.5, 0.8 Hz, 1 H), 6.47 (d, J = 3.3 Hz, 1 H), 3.83 (s, 2 H), 3.78 (s, 2 H), 3.40 (t, J = 5.7 Hz, 2 H), 3.24 (s, 3 H), 2.71 (t, J = 5.7 Hz, 2 H), one N$\underline{H}$ is missing. MS (m/z): 591.2 (M + H). |
| 112 | 38 | (4-fluorophenylacetyl thioamide group) | N-(3-fluoro-4-(2-(5-((2-methoxyethylamino)-methyl)furan-2-yl)thieno[3,2-b]pyridin-7-yloxy)phenylcarbamothioyl)-2-(4-fluorophenyl)acetamide | $^1$H NMR (400 MHz, DMSO-d$_6$) δ (ppm): 12.56-12.38 (m, 1 H), 11.94-11.74 (m, 1 H), 8.52 (d, J = 5.5 Hz, 1 H), 8.02 (dd, J = 12.3, 1.2 Hz, 1 H), 7.77 (s, 1 H), 7.58-7.50 (m, 2 H), 7.42-7.35 (m, 2 H), 7.22-7.15 (m, 2 H), 7.09 (d, J = 3.3 Hz, 1 H), 6.65 (dd, J = 5.5, 0.8 Hz, 1 H), 6.47 (d, J = 3.3 Hz, 1 H), 3.83 (s, 2 H), 3.78 (s, 2 H), 3.40 (t, J = 5.7 Hz, 2 H), 3.24 (s, 3 H), 2.71 (t, J = 5.7 Hz, 2 H), one N$\underline{H}$ is missing. MS (m/z): 609.2 (M + H). |

TABLE 3-continued

111-113: Examples 37-39

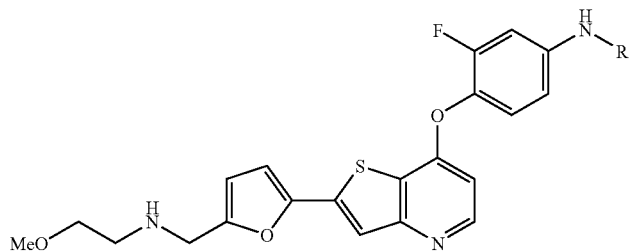

| Cpd. | Ex. | R | Name | Characterization |
|---|---|---|---|---|
| 113 | 39 | (cyclopropane-1,1-dicarboxamide, N-phenyl) | N-(3-fluoro-4-(2-(5-((2-methoxyethylamino)-methyl)furan-2-yl)thieno[3,2-b]pyridin-7-yloxy)phenyl)-N-phenylcyclopropane-1,1-dicarboxamide | $^1$H NMR (400 MHz, DMSO-$d_6$) δ (ppm): 10.38 (s, 1 H), 9.99 (s, 1 H), 8.49 (d, J = 5.4 Hz, 1 H), 8.17 (s, 1 H), 7.90 (dd, J = 13.2, 2.2 Hz, 1 H), 7.77 (s, 1 H), 7.63 (dd, J = 8.6, 1.2 Hz, 2 H), 7.52 (dd, J = 9.1, 1.9 Hz, 1 H), 7.46 (t, J = 8.8 Hz, 1 H), 7.34-7.27 (m, 2 H), 7.12-7.04 (m, 2 H), 6.60 (d, J = 5.5 Hz, 1 H), 6.48 (d, J = 3.3 Hz, 1 H), 3.79 (s, 2 H), 3.41 (t, J = 5.7 Hz, 2 H), 3.24 (s, 3 H), 2.72 (t, J = 5.6 Hz, 2 H), 2.08 (s, 1 H), 1.52-1.44 (m, 4 H). MS (m/z): 601.3 (M + H). |

Compounds 114-115 (examples 40-41) were prepared starting from 5-bromopicolinaldehyde (Wang X., Rabbat P., O'Shea P., Tillyer R., Grabovski E. J. J., Reider P. S., *Tetrahedron Lett.* 2000, 41, 4335) and 7-(2-fluoro-4-nitrophenoxy)-2-iodothieno[3,2-b]pyridine (24) [US 2006/0287343 A1] according to the synthetic procedures similar to ones shown in the Scheme 5. Characterization of compounds 114-115 (examples 40-41) is provided in the Table 4.

TABLE 4

114-115: Examples 40-41

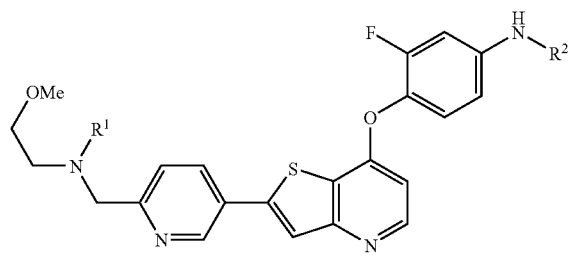

| Cpd | Ex. | R$^1$ | R$^2$ | Name | Characterization |
|---|---|---|---|---|---|
| 114 | 40 | H | (N-H-C(=S)-C(=O)-CH$_2$-phenyl) | N-(3-fluoro-4-(2-(6-((2-methoxyethylamino)methyl)pyridin-3-yl)thieno[3,2-b]pyridin-7-yloxy)phenylcarbamothioyl)-2-phenylacetamide | $^1$H NMR (400 MHz, DMSO-$d_6$): 12.50 (bs, 1 H), 11.84 (bs, 1 H), 9.09 (d, J = 2.2 Hz, 1 H), 8.55 (d, J = 5.3 Hz, 1 H), 8.31 (dd, J = 8.1, 2.5 Hz, 1 H), 8.23 (s, 1 H), 8.13 (s, 1 H), 8.02 (m, 1 H), 7.59 (d, J = 8.4 Hz, 1 H), 7.55 (m, 2 H), 7.32-7.35 (m, 4 H), 7.28 (m, 2 H), 6.68 (bd, J = 5.5 Hz, 1 H), 4.09 (s, 2 H), 3.82 (s, 2 H), 3.50 (m, 2 H), 3.27 (s, 3 H), 2.91 (m, 2 H). MS (m/z): 602.3 (M + H). |

TABLE 4-continued
114-115: Examples 40-41
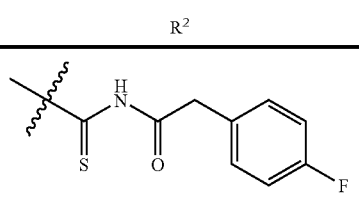
| Cpd | Ex. | R¹ | R² | Name | Characterization |
|---|---|---|---|---|---|
| 115 | 41 | H | 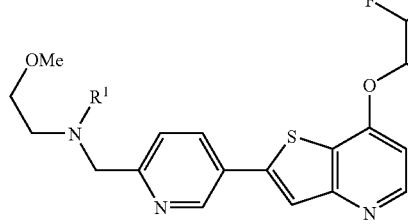 | N-(3-fluoro-4-(2-(6-((2-methoxyethylamino)methyl)pyridin-3-yl)thieno[3,2-b]pyridin-7-yloxy)phenylcarbamothioyl)-2-(4-fluorophenyl)acetamide | ¹H NMR (400 MHz, DMSO-d₆): 12.47 (bs, 1 H), 11.83 (bs, 1 H), 9.13 (d, J = 2.2 Hz, 1 H), 8.56 (d, J = 5.5 Hz, 1 H), 8.34 (dd, J = 8.2, 2.5 Hz, 1 H), 8.26 (s, 1 H), 8.12 (s, 1 H), 7.61 (d, J = 8.4 Hz, 1 H), 7.55 (m, 2 H), 7.55 (m, 2 H), 7.35-7.39 (m, 2 H), 7.15-7.20 (m, 2 H), 6.69 (bd, J = 5.5 Hz, 1 H), 4.21 (s, 2 H), 3.82 (s, 2 H), 3.55 (m, 2 H), 3.29 (s, 3 H), 3.03 (m, 2 H). MS (m/z): 620.3 (M + H). |
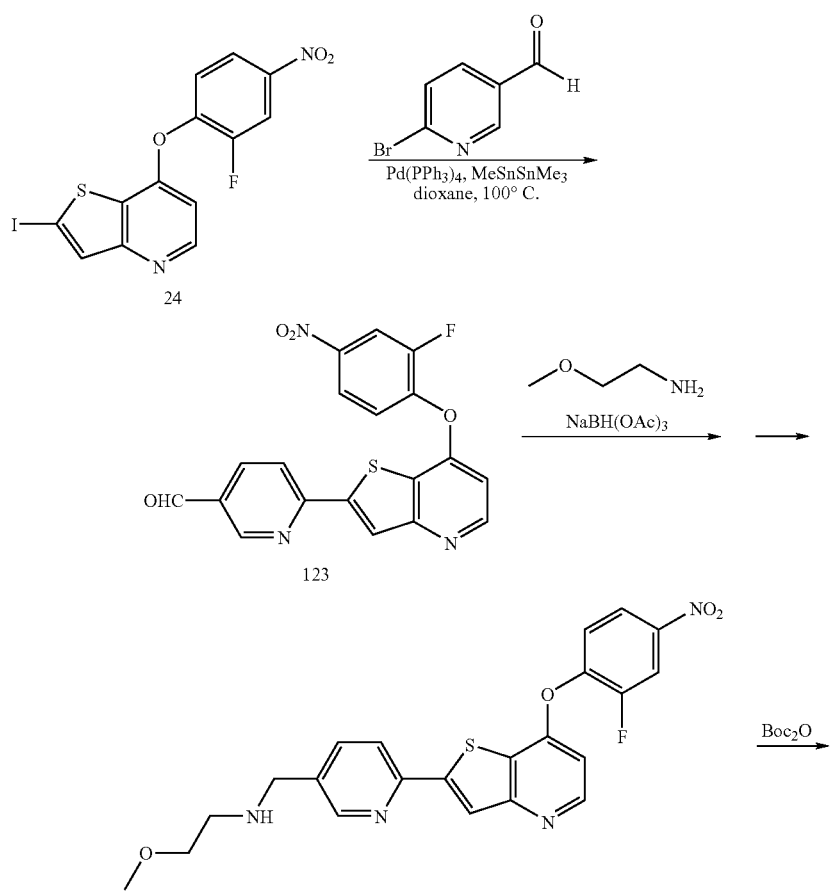

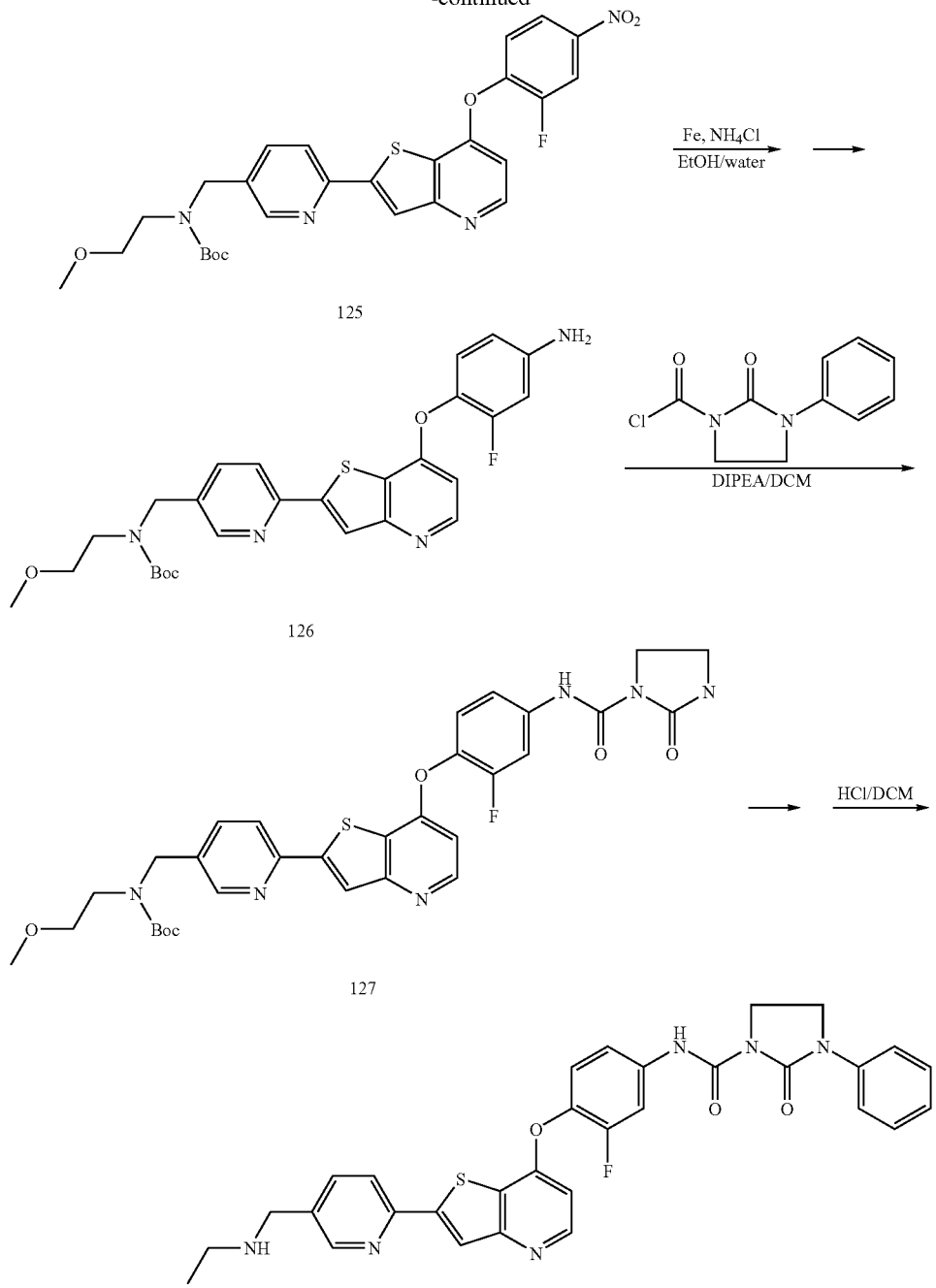

Example 49

N-(3-Fluoro-4-(2-(5-(((2-methoxyethylamino)methyl)pyridin-2-yl)thieno[3,2-b]pyridin-7-yloxy)phenyl)-2-oxo-3-phenylimidazolidine-1-carboxamide (128)

Step 1. 6-(7-(2-Fluoro-4-nitrophenoxy)thieno[3,2-b]pyridin-2-yl)nicotinaldehyde (123)

To a solution of 7-(2-fluoro-4-nitrophenoxy)-2-iodothieno[3,2-b]pyridine (24) [US 2006/0287343 A1] (6 g, 14.42 mmol) in dioxane (40 mL) were added 6-bromopyridine-3-carbaldehyde (3.22 g, 17.30 mmol), palladium tetrakistriphenylphosphine (0.500 g, 0.433 mmol) and hexamethyldistannane (3.29 mL, 15.86 mmol). The mixture was heated at 100° C. for 20 h. It was then concentrated and adsorbed on silica gel, transferred onto a silica gel column and eluted with DCM/MeOH (100/0, 99/1, 98/2, 97/3) to afford title compound 123 (2.864 g, 50% yield). MS (m/z): 396.1 (M+H).

Step 2: N-((6-(7-(2-Fluoro-4-nitrophenoxy)thieno[3,2-b]pyridin-2-yl)pyridin-3-yl)methyl)-2-methoxyethanamine (124)

A mixture of 123 (700 mg, 1.77 mmol) and 2-methoxyethanamine (185 □L, 160 mg, 2.12 mmol) in DCM (7 mL) was stirred at room temperature for 10 min. It was then treated with NaBH(OAc)₃ (526 mg, 2.48 mmol) and stirred at room temperature overnight. The reaction mixture was diluted with DCM (20 mL) and washed with saturated NaHCO₃ solution (20 mL). The organic phase was collected, dried over anhydrous Na₂SO₄, filtered and concentrated. The residue was purified by flash chromatography using the gradient 4-8% MeOH/DCM to afford 124 (675 mg, 65% yield). MS (m/z): 455.2 (M+H).

Step 3: tert-Butyl (6-(7-(2-fluoro-4-nitrophenoxy) thieno[3,2-b]pyridin-2-yl)pyridin-3-yl)methyl(2-methoxyethyl)carbamate (125)

A solution of 124 (470 mg, 1.03 mmol) and Boc anhydride (338 mg, 1.55 mmol) in THF (10 mL) was stirred at room temperature overnight. The reaction mixture was then concentrated and the residue was purified by flash chromatography using EtOAc as the eluent, to afford 125 (443 mg, 77% yield). MS (m/z): 555.2 (M+H).

Step 4: tert-Butyl (6-(7-(4-amino-2-fluorophenoxy) thieno[3,2-b]pyridin-2-yl)pyridin-3-yl)methyl(2-methoxyethyl)carbamate (126)

A solution of 125 (443 mg, 0.80 mmol) and NH₄Cl (37 mg, 0.68 mmol) in 2:1 mixture of EtOH/water (10.5 mL) was treated with iron powder (380 mg, 6.79 mmol) and stirred at reflux for 1 hour. The reaction mixture was then filtered through a celite pad and concentrated to afford title compound 126 that was used without further purification (440 mg, 100% yield). MS (m/z): 525.2 (M+H).

Step 5. tert-Butyl (6-(7-(2-fluoro-4-(2-oxo-3-phenylimidazolidine-1-carboxamido) phenoxy)thieno[3,2-b]pyridin-2-yl)pyridin-3-yl)methyl(2-methoxyethyl)carbamate (127)

A solution of 126 (100 mg, 0.19 mmol) and iso-Pr₂NEt (133 □L, 99 mg, 0.76 mmol) in DCM (2 mL) was treated with 3-oxo-3-phenylimidazoline-1-carbonyl chloride (51 mg, 0.23 mmol) at 0° C. and stirred at room temperature for 2 hrs. The reaction mixture was then concentrated and partitioned between EtOAc (5 mL) and NaHCO₃ saturated solution (5 mL). The organic phase was collected, dried over anhydrous Na₂SO₄, filtered and concentrated. The residue was purified by flash chromatography using a gradient 0-5% MeOH in EtOAc as an eluent, to afford 127 (61 mg, 44%). MS (m/z): 713.3 (M+H).

Step 6. N-(3-Fluoro-4-(2-(5-((2-methoxyethylamino) methyl)pyridin-2-yl)thieno[3,2-b]pyridin-7-yloxy) phenyl)-2-oxo-3-phenylimidazolidine-1-carboxamide (128)

HCl gas was bubbled into a solution of 127 (61 mg, 0.08 mmol) in DCM. The flask was capped and the mixture was stirred at room temperature for 30 min. Formed precipitate was collected by filtration and washed with DCM to afford 128 (52 mg, 84% yield), presumably as a trihydrochloride salt. ¹H NMR (400 MHz, DMSO-d₆) δ (ppm): 10.59 (s, 1H), 9.34 (br.s, 2H), 8.75 (s, 1H), 8.62 (d, J=5.7 Hz, 1H), 8.43 (s, 1H), 8.38 (d, J=8.5 Hz, 1H), 8.15 (dd, J=8.2, 2.1 Hz, 1H), 7.86 (dd, J=12.9, 2.4 Hz, 1H), 7.62 (d, J=7.6 Hz, 2H), 7.4-7.6 (m, 4H), 7.17 (t, J=7.3 Hz, 1H), 6.81 (d, J=5.5 Hz, 1H), 4.25 (m, 2H), 3.95 (m, 4H), 3.62 (m, 2H), 3.29 (s, 3H), 3.13 (br.s, 2H). MS (m/z): 613.3 (M+H).

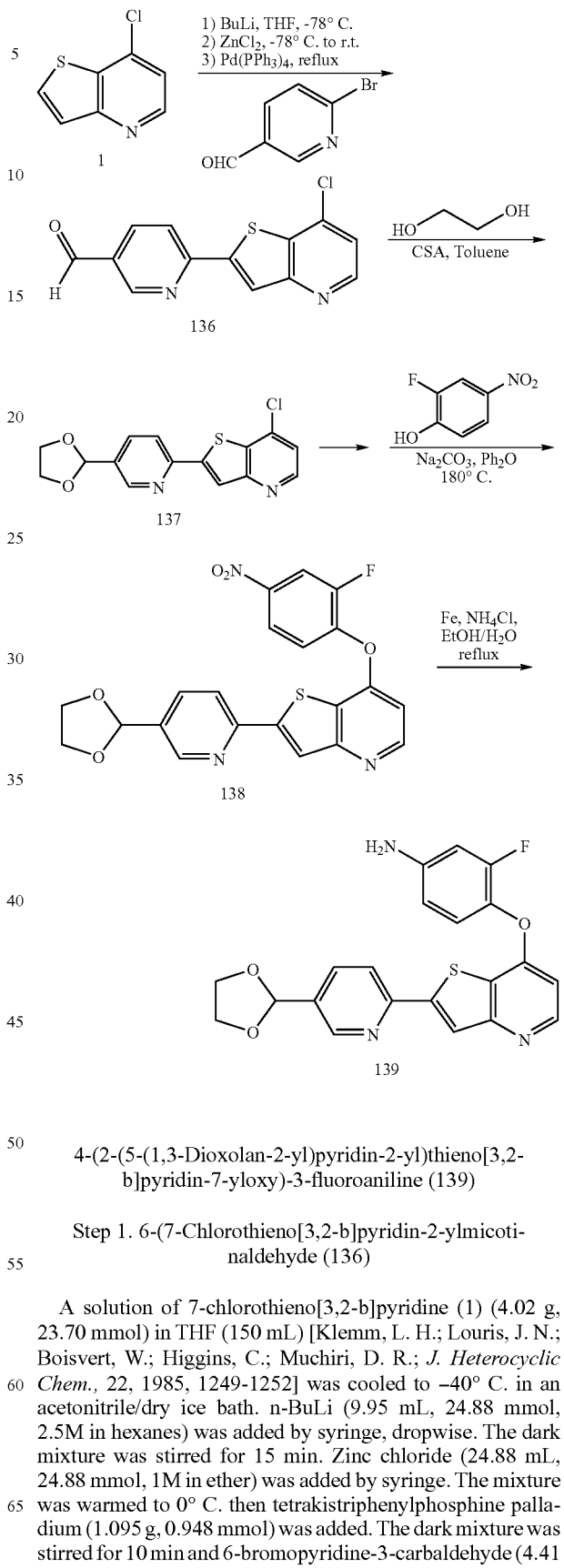

4-(2-(5-(1,3-Dioxolan-2-yl)pyridin-2-yl)thieno[3,2-b]pyridin-7-yloxy)-3-fluoroaniline (139)

Step 1. 6-(7-Chlorothieno[3,2-b]pyridin-2-yl)nicotinaldehyde (136)

A solution of 7-chlorothieno[3,2-b]pyridine (1) (4.02 g, 23.70 mmol) in THF (150 mL) [Klemm, L. H.; Louris, J. N.; Boisvert, W.; Higgins, C.; Muchiri, D. R.; *J. Heterocyclic Chem.*, 22, 1985, 1249-1252] was cooled to −40° C. in an acetonitrile/dry ice bath. n-BuLi (9.95 mL, 24.88 mmol, 2.5M in hexanes) was added by syringe, dropwise. The dark mixture was stirred for 15 min. Zinc chloride (24.88 mL, 24.88 mmol, 1M in ether) was added by syringe. The mixture was warmed to 0° C. then tetrakistriphenylphosphine palladium (1.095 g, 0.948 mmol) was added. The dark mixture was stirred for 10 min and 6-bromopyridine-3-carbaldehyde (4.41 g, 23.70 mmol) was added. The mixture was heated to reflux and a precipitate formed rapidly. After 3 h, the reaction mixture was cooled down to r.t., quenched with 2 mL NH$_4$Cl and left overnight. The solid was isolated by suction filtration, rinsed with small amount of THF and suspended in a mixture of water (200 mL) and EtOAc (100 mL), isolated by suction filtration and finally triturated with acetic acid (100 mL) and dried in vacuum to afford title compound 136 (4.95 g, 76% yield). $^1$H NMR (400 MHz, DMSO-d$_6$) δ (ppm): 10.13 (s, 1H), 9.14 (d, J=1.4 Hz, 1H), 8.70 (d, J=5.1 Hz, 1H), 8.65 (s, 1H), 8.53 (d, J=8.4 Hz, 1H), 8.39 (dd, J=8.4, 2.1 Hz, 1H), 7.65 (d, J=4.9 Hz, 1H). MS (m/z): 275.1 (M+H).

Step 1. 2-(5-(1,3-Dioxolan-2-yl)pyridin-2-yl)-7-chlorothieno[3,2-b]pyridine (137)

A suspension of 136 (2.69 g, 9.79 mmol), ethylene glycol (2.184 mL, 39.2 mmol), and (1R)-(−)-10-camphorsulfonic acid (0.227 g, 0.979 mmol) in toluene (150 mL) was heated to reflux with a Dean-Stark trap. After 3 h, the mixture was cooled down and filtered through celite (while still warm). The filtrate was washed with water, NaHCO$_3$ (aq., sat.), NaOH (aq) and brine. The solution was then dried over MgSO$_4$ and concentrated to afford compound 137 (2.77 g, 89% yield) as an off-white solid. MS (m/z): 319.1 (M+H).

Step 3: 2-(5-(1,3-dioxolan-2-yl)pyridin-2-yl)-7-(2-fluoro-4-nitrophenoxy)thieno[3,2-b]pyridine (138)

Following the procedure described above for the synthesis of compound 41 (scheme 1) but substituting compound 40 for compound 137, title compound 138 was obtained in 72% yield. $^1$H NMR (400 MHz, DMSO-d$_6$) δ (ppm): 8.68 (d, J=1.8 Hz, 1H), 8.64 (d, J=5.5 Hz, 1H), 8.49 (dd, J=10.4, 2.5 Hz, 1H), 8.47 (s, 1H), 8.35 (d, J=8.4 Hz, 1H), 8.23-8.21 (m, 1H), 8.00 (dd, J=8.2, 2.0 Hz, 1H), 7.73 (t, J=8.5 Hz, 1H), 6.99 (d, J=5.5 Hz, 1H), 5.89 (s, 1H), 4.12-4.06 (m, 2H), 4.04-3.98 (m, 2H). MS (m/z): 440.1 (M+H).

Step 4: 4-(2-(5-(1,3-Dioxolan-2-yl)pyridin-2-yl)thieno[3,2-b]pyridin-7-yloxy)-3-fluoroaniline (139)

Following the procedure described above for the synthesis of compound 126 (Scheme 6) but substituting compound 125 for compound 138, title compound 139 was obtained in 95% yield. $^1$H NMR (400 MHz, DMSO-d$_6$) δ (ppm): 8.68 (d, J=1.8 Hz, 1H), 8.50 (d, J=5.5 Hz, 1H), 8.36 (s, 1H), 8.29 (d, J=8.2 Hz, 1H), 7.96 (dd, J=8.2, 2.0 Hz, 1H), 7.11 (t, J=9.0 Hz, 1H), 6.60 (d, J=5.3 Hz, 1H), 6.53 (dd, J=13.1, 2.5 Hz, 1H), 6.44 (dd, J=8.7, 1.9 Hz, 1H), 5.87 (s, 1H), 5.55 (s, 2H), 4.11-4.07 (m, 2H), 4.00-3.97 (m, 2H). MS (m/z): 410.2 (M+H).

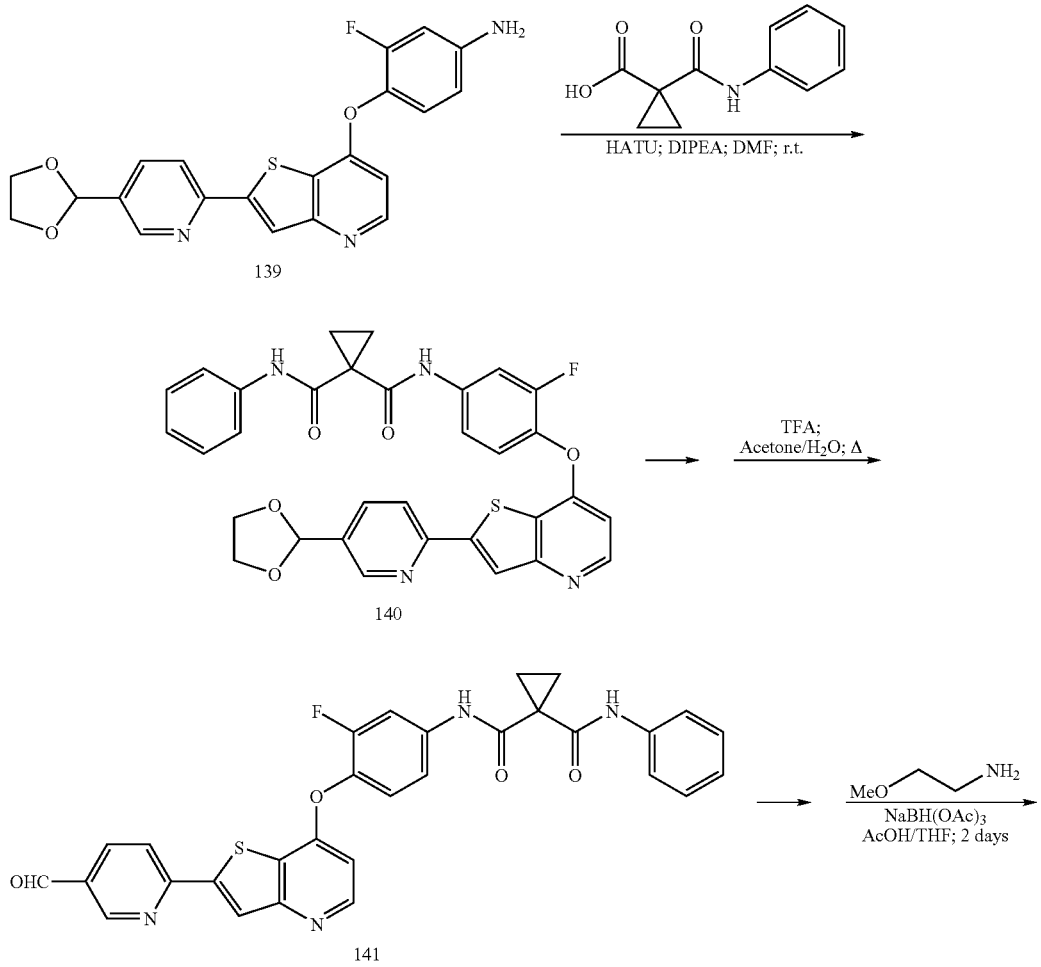

Scheme 8

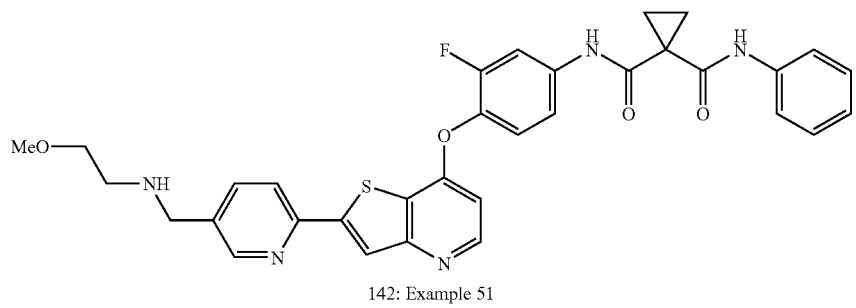

142: Example 51

Example 51

N-(3-Fluoro-4-(2-(5-((2-methoxyethylamino)methyl)pyridin-2-yl)thieno[3,2-b]pyridin-7-yloxy)phenyl)-N-phenylcyclopropane-1,1-dicarboxamide (142)

Step 1. N-(4-(2-(5-(1,3-Dioxolan-2-yl)pyridin-2-yl)thieno[3,2-b]pyridin-7-yloxy)-3-fluorophenyl)-N-phenylcyclopropane-1,1-dicarboxamide (140)

To aniline 139 (Scheme 7) (0.46 g, 1.1 mmol) in dry DMF (20 mL) was added acid 1-(phenylcarbamoyl)cyclopropanecarbpxylic acid (0.46 g, 2.2 mmol), DIPEA (0.98 mL, 5.6 mmol) and HATU (1.07 g, 2.81 mmol) and the mixture was stirred at r.t. for 18 h. It was then partitioned between ethyl acetate and water; the organic phase was collected, washed with water, 1M NaOH, saturated $NH_4Cl$, and brine, dried ($MgSO_4$), filtered and concentrated. Silica gel chromatography of the residue (eluent 2% methanol/ethyl acetate) afforded 140 (0.23 g, 34% yield). $^1$H NMR (400 MHz, DMSO-$d_6$) δ (ppm): 10.37 (s, 1H), 9.98 (s, 1H), 8.68 (s, 1H), 8.53 (d, J=5.3 Hz, 1H), 8.40 (s, 1H), 8.31 (d, J=8.2 Hz, 1H), 7.97 (dd, J=8.2, 2.0 Hz, 1H), 7.90 (dd, J=13.1, 2.0 Hz, 1H), 7.62 (d, J=7.6, 2H), 7.53-7.46 (m, 2H), 7.30 (t, J=7.4 Hz, 2H), 7.06 (t, J=7.4 Hz, 1H), 6.66 (d, J=5.3 Hz, 1H), 5.88 (s, 1H), 4.11-3.97 (m, 4H), 1.47 (br s, 4H). MS (m/z): 597.2 (M+H).

Step 2. N-(3-Fluoro-4-(2-(5-formylpyridin-2-yl)thieno[3,2-b]pyridin-7-yloxy)phenyl)-N-phenylcyclopropane-1,1-dicarboxamide (141)

Compound 140 (0.22 g, 0.37 mmol) was dissolved in acetone (50 mL) to give a colorless solution. The reaction mixture was diluted with water (20 mL) and TFA (2 mL), and heated to reflux for 2 h. It was then cooled and concentrated. The precipitated product was isolated by suction filtration. A small amount of toluene (5 mL) was added to the wet solid, and the mixture was concentrated to remove water azeotropically. The residue was dried in vacuum to provide aldehyde 141 (0.21 g, 103% yield). MS (m/z): 553.2 (M+H).

Step 3: N-(3-Fluoro-4-(2-(5-((2-methoxyethylamino)methyl)pyridin-2-yl)thieno[3,2-b]pyridin-7-yloxy)phenyl)-N-phenylcyclopropane-1,1-dicarboxamide (142)

Aldehyde 141 (0.20 g, 0.362 mmol) and 2-methoxyethylamine (0.158 mL, 1.810 mmol) were dissolved in THF (50 mL) to give a colorless solution. Sodium trisacetoxyborohydride (0.384 g, 1.810 mmol) was added and the mixture was stirred at r.t. for 20 h. Additional 2-methoxyethylamine (0.158 mL, 1.810 mmol) and sodium trisacetoxyborohydride (0.384 g, 1.810 mmol) were added, and the mixture was stirred for a further 20 h. It was then concentrated, partitioned between water and dichloromethane. Organic phase was collected, washed with $H_2O$, 1M NaOH, and brine, dried ($MgSO_4$), filtered and concentrated. The residue was purified by Gilson Reverse Phase HPLC (Aquasil $C_{18}$, 40-90% MeOH/water, 30 min, elutes 20 min) and lyophilized, to afford title compound 142. Starting material (50 mg) was also isolated.

The recovered starting material was re-subjected to the reaction conditions except in acetic acid (5 mL), with 1 mL methoxyethylamine and 0.030 g sodium trisacetoxyborohydride. After stirring for 5 min the mixture was concentrated. The residue was purified by Gilson Reverse Phase HPLC as before. The isolated product—title compound 142 was combined with that above (0.13 g, 59% yield) as a colorless solid. $^1$H NMR (400 MHz, DMSO-$d_6$) δ (ppm): 10.38 (s, 1H), 9.99 (s, 1H), 8.55 (s, 1H), 8.51 (d, J=5.5 Hz, 1H), 8.31 (s, 1H), 8.22 (d, J=9.4 Hz, 1H), 7.92-7.87 (m, 2H), 7.62 (d, J=7.5 Hz, 2H), 7.52-7.43 (m, 2H), 7.34-7.27 (m, 2H), 7.08-7.04 (m, 1H), 6.64 (d, J=5.5, 2H), 3.77 (s, 2H), 3.40 (t, J=5.7 Hz, 2H), 3.23 (s, 3H), 2.64 (t, J=5.7 Hz, 2H), 1.47 (s, 4H). MS (m/z): 612.3 (M+H).

Scheme 9

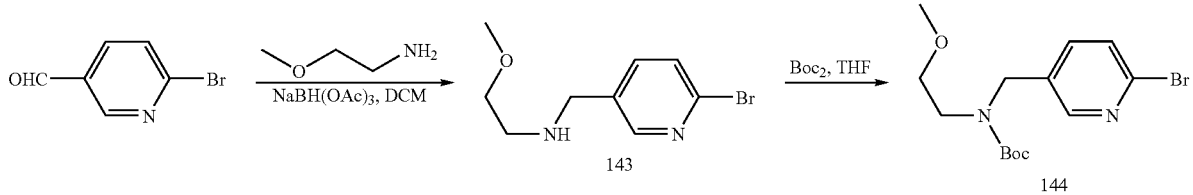

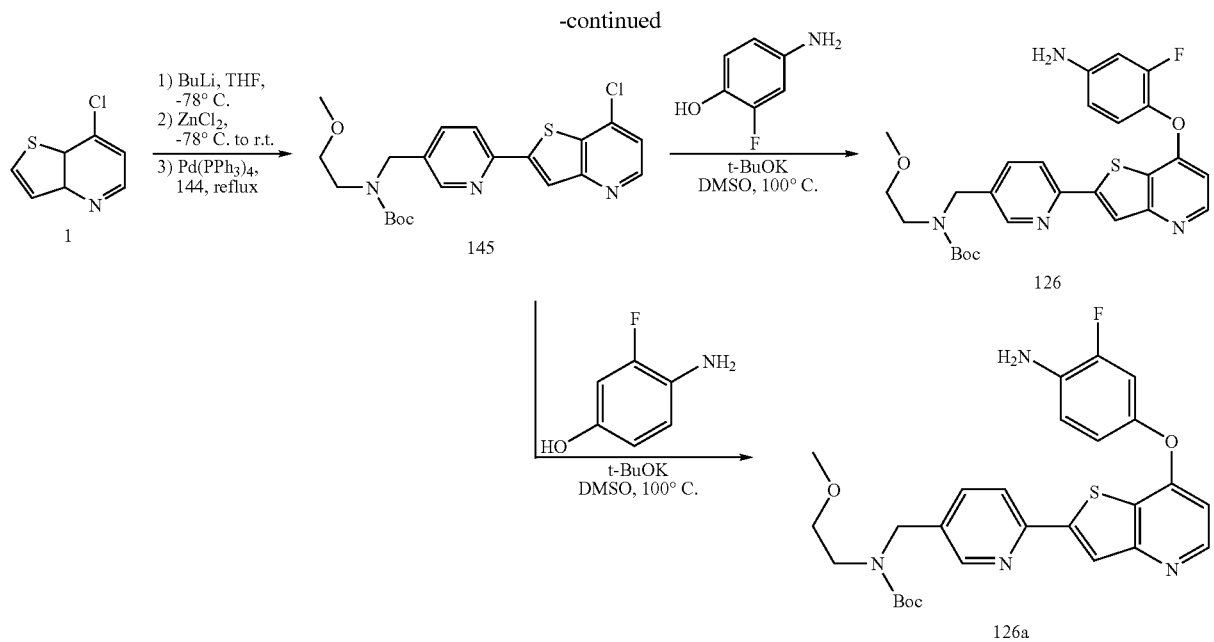

Step 1. N-((6-Bromopyridin-3-yl)methyl)-2-methoxyethanamine (143)

To a solution of 6-bromopyridine-3-carbaldehyde (5 g, 26.9 mmol) in DCM (40 mL). was added 2-methoxyethylamine (2.80 mL, 32.3 mmol). After 10 min, sodium triacetoxyborohydride (7.98 g, 37.6 mmol) was added to the mixture and it was stirred at r.t for 17 h. DCM (100 mL water (50 mL and NH$_4$Cl (50 mL) were added to the reaction mixture. The organic phase was collected and the aqueous layer was extracted with DCM (3×100 mL). The combined organic solutions were washed with brine and concentrated under reduce pressure. The residue was purified by flash column chromatography, eluent 98/2 to 95/5 DCM/MeOH, to afford title 143 (2.958 g, 45% yield) as a brown oil. $^1$H NMR (400 MHz, DMSO-d$_6$) δ (ppm): 8.31 (dd, J=2.6, 0.6 Hz, 1H), 7.70 (dd, J=8.2, 2.6 Hz, 1H), 7.58 (d, J=8.4 Hz, 1H), 3.69 (s, 2H), 3.37 (t, J=5.8 Hz, 2H), 3.22 (s, 3H), 2.60 (t, J=5.8 Hz, 2H). MS (m/z): 245.1 (M+H).

Step 2. tert-Butyl(6-bromopyridin-3-yl)methyl(2-methoxyethyl)carbamate (144)

To a solution of 143 (13.072 g, 53.3 mmol) in THF (40 mL) was added di-tert-butyl dicarbonate (14.86 mL, 64.0 mmol). The mixture was stirred at r.t. for 16 h and concentrated under reduce pressure. The residue was purified by flash column chromatography, eluent Hexane/EtOAc:7/3, 6/4, 5/5, to afford title compound 144 (16.196 g, 88% yield) as a yellow oil. $^1$H NMR (400 MHz, DMSO-d$_6$) δ (ppm): 8.26 (dd, J=2.4, 0.8 Hz, 1H), 7.64-7.58 (m, 2H), 4.39 (s, 2H), 3.40-3.33 (m, 4H), 3.20 (s, 3H), 1.41-1.31 (m, 9H). MS (m/z): 345.2 (M+H).

Step 3. tert-Butyl (6-(7-chlorothieno[3,2-b]pyridin-2-yl)pyridin-3-yl)methyl(2-methoxyethyl)carbamate (145)

To a solution of 7-chlorothieno[3,2-b]pyridine (1) (8.84 g, 52.1 mmol) in THF (100 mL) at −78° C. was added n-butyllithium (20.86 mL, 52.1 mmol). After 30 min, zinc chloride (52.1 mL, 52.1 mmol) (1M in ether) was added at −78° C. and the reaction mixture was warmed to r.t. After 1 h, palladium tetrakistriphenylphosphine (1.004 g, 0.869 mmol) and 144 (6 g, 17.38 mmol) in THF (25 mL) were added and the mixture was heated to reflux for 1 h. It was then partitioned between saturated aqueous NaHCO$_3$ solution and EtOAc. The organic layer was collected and the aqueous layer was extracted with EtOAc (3×100 mL). The combined organic layers were washed with brine and evaporated under reduce pressure. The residue was purified by flash column chromatography, eluents Hexane/EtOAc:5/5, 3/7, 0/10, to afford compound 145 (5.41 g, 72% yield). $^1$H NMR (400 MHz, DMSO-d$_6$) δ (ppm): 8.65 (d, J=5.1 Hz, 1H), 8.52 (d, J=1.6 Hz, 1H), 8.39 (s, 1H), 8.27 (d, J=8.0 Hz, 1H), 7.80 (dd, J=8.1, 2.1 Hz, 1H), 7.58 (d, J=5.1 Hz, 1H), 4.48 (s, 2H), 3.43-3.35 (m, 4H), 3.22 (s, 3H), 1.43-1.33 (m, 9H). MS (m/z): 434.2 (M+H).

Step 4. tert-Butyl (6-(7-(4-amino-2-fluorophenoxy)thieno[3,2-b]pyridin-2-yl)pyridin-3-yl)methyl(2-methoxyethyl)carbamate (126)

To a solution of 4-amino-2-fluorophenol (1.933 g, 15.21 mmol) in DMSO (30 mL) was added potassium tert-butoxide (2.017 g, 17.97 mmol). After 30 min, chloride 145 (6 g, 13.83 mmol) was added and the reaction mixture was heated at 100° C. for 45 min. The mixture was cooled down then poured in water (250 mL) at 40-45° C. and stirred for 30 min. The precipitate was collected by filtration, washed with water (2×30 mL) and dried overnight. The crude solid was triturated with Et$_2$O (50 mL) for 1 h, to afford title compound 126 (4.18 g, 58% yield) as a brown solid. MS (m/z): 525.2 (M+H).

Step 5. tert-Butyl (6-(7-(4-amino-3-fluorophenoxy)thieno[3,2-b]pyridin-2-yl)pyridin-3-yl)methyl(2-methoxyethyl)carbamate (126a)

To a solution of 4-amino-3-fluorophenol in DMSO (12 mL) was added potassium tert-butoxide (0.824 g, 7.34 mmol). After 30 min, intermediate 145 (2.451 g, 5.65 mmol)

was added and the reaction mixture was heated at 100° C. for 1.5 h. It was then cooled down, poured in water (50 mL) at 40-45° C. and stirred for 30 min. EtOAc (40 mL), DCM (40 mL) and water (40 ml) were added and pH was adjusted to 7 by addition of HCl. Solids were removed by filtration through a paper filter and the two phases were separated. The organic layer was collected, dried over anhydrous $Na_2SO_4$, filtered and concentrated. The residue was purified by flash column chromatography, eluent DCM/MeOH:99/1, 98/2, 95/5, to afford intermediate 126a (0.952 g, 32% yield). MS (m/z): 525.2 (M+H).

was stirred at r.t. for 18 h. It was then partitioned between ethyl acetate and water, the organic phase was washed with water, 1M NaOH, brine, dried ($MgSO_4$), filtered, and concentrated. Silica gel chromatography (ethyl acetate) afforded title compound 146 (0.60 g, 74% yield). $^1$H NMR (400 MHz, DMSO-$d_6$) δ (ppm): 10.40 (s, 1H), 10.01 (s, 1H), 8.52-8.49 (m, 2H), 8.33 (s, 1H), 8.27-8.24 (m, 1H), 7.92-7.88 (m, 1H), 7.78 (dd, J=8.2, 2.1 Hz, 1H) 7.65-7.60 (m, 2H), 7.52-7.42 (m, 2H), 7.14 (t, J=8.8 Hz, 2H), 6.65 (d, J=5.1 Hz 1H), 4.47 (s, 2H), 3.42-3.30 (m, 4H), 3.22 (s, 3H), 1.46-1.30 (m, 13H). MS (m/z): 730.1 (M+H).

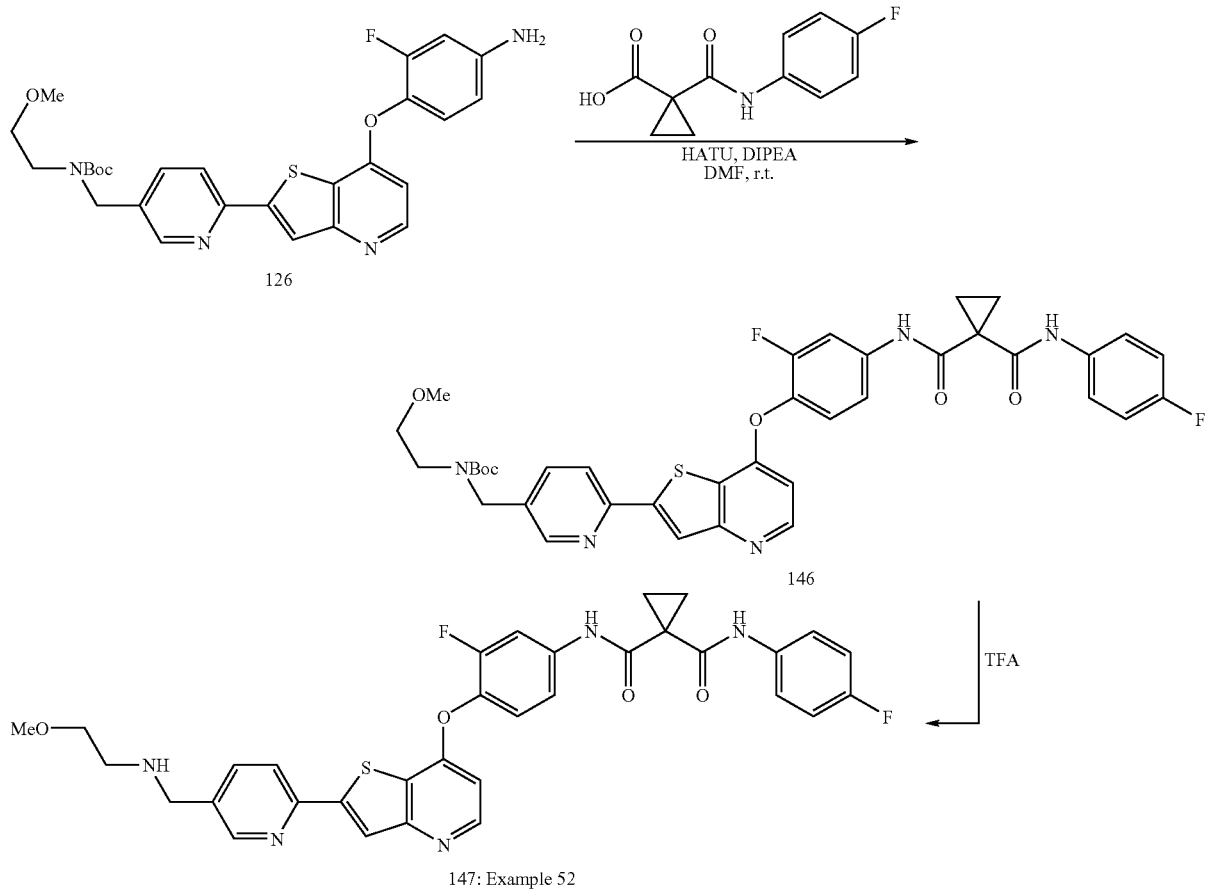

Example 52

N-(3-Fluoro-4-(2-(5-((2-methoxyethylamino)methyl) pyridin-2-yl)thieno[3,2-b]pyridin-7-yloxy)phenyl)-N-(4-fluorophenyl)cyclopropane-1,1-dicarboxamide Step 1: tert-Butyl (6-(7-(2-Fluoro-4-(1-(4-fluorophenylcarbamoyl)-cyclopropanecarboxamido)phenoxy) thieno[3,2-b]pyridin-2-yl)pyridin-3-yl)methyl(2-methoxyethyl)carbamate (146)

To aniline 126 (0.58 g, 1.1 mmol) and DIPEA (0.58 mL, 0.43 g, 3.3 mmol) in dry DMF (20 mL) was added 1-(4-fluorophenylcarbamoyl)cyclopropanecarbpxylic acid (0.35 g, 1.5 mmol) and HATU (0.72 g, 1.9 mmol) and the mixture Step 2. N-(3-Fluoro-4-(2-(5-((2-methoxyethylamino) methyl)pyridin-2-yl)thieno[3,2-b]pyridin-7-yloxy) phenyl)-N-(4-fluorophenyl)cyclopropane-1,1-dicarboxamide (147)

To the compound 146 (0.59 g, 0.81 mmol) in dichloromethane (50 mL) was added TFA (3 mL). The solution was stirred for 18 h then concentrated. The residue was partitioned between dichloromethane and 1M NaOH, and filtered to remove insolubles. The organic phase was collected, washed with 1M NaOH, brine, dried ($MgSO_4$), filtered, and concentrated to afford title compound 147 (0.35 g, 69% yield). $^1$H NMR (400 MHz, DMSO-$d_6$) δ (ppm): 10.40 (s, 1H), 10.01 (s, 1H), 8.55 (d, J=1.6 Hz, 1H), 8.51 (d, J=5.3 Hz, 1H), 8.31 (s, 1H), 8.22 (d, J=8.0 Hz, 1H), 7.92-7.87 (m, 2H), 7.65-7.61 (m, 2H), 7.52-7.43 (m, 2H), 7.17-7.12 (m, 2H), 6.64 (d, J=5.5 Hz, 1H), 3.77 (s, 2H), 3.40 (t, J=5.7 Hz, 2H), 3.23 (s, 3H), 2.64 (t, J=5.7 Hz, 2H), 1.46 (br s, 4H). MS (m/z): 630.1 (M+H).

Scheme 11

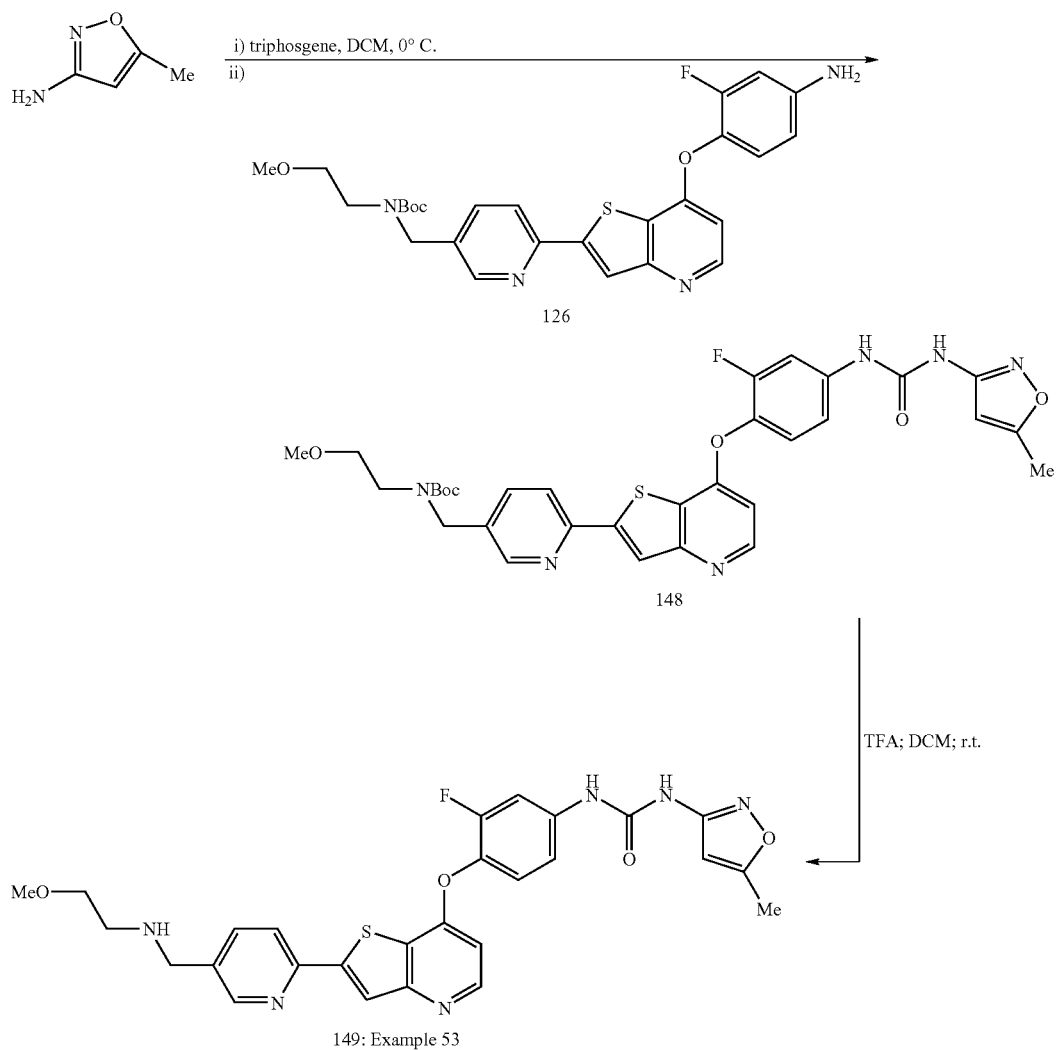

149: Example 53

Example 53

1-(3-Fluoro-4-(2-(5-((2-methoxyethylamino)methyl)pyridin-2-yl)thieno[3,2-b]pyridin-7-yloxy)phenyl)-3-(5-methylisoxazol-3-yl)urea Step 1. tert-Butyl (6-(7-(2-fluoro-4-(3-(5-methylisoxazol-3-yl)ureido)phenoxy)-thieno[3,2-b]pyridin-2-yl)pyridin-3-yl)methyl(2-methoxyethyl)carbamate (148)

To a solution of triphosgene (1.00 g, 3.4 mmol) in dichloromethane (50 mL) at 0° C. was added 3-methyl-5-aminoisoxazole (1.0 g, 10.2 mmol). The mixture was warmed to r.t. and stirred for 1 h. DIPEA (3.6 mL, 20.4 mmol) was added to afford a carbamyl chloride suspension. Half of this suspension was added to a solution of aniline 126 (0.26 g, 0.50 mmol) in small portions. The mixture was heated to reflux for 2 h, then cooled. It was then washed with water, 1M NaOH, and brine, dried (MgSO$_4$), filtered and concentrated. Silica gel chromatography (5% methanol/ethyl acetate) of the residue provided 148 (0.28 g, 87% yield). MS (m/z): 649.2 (M+H).

Step 2: 1-(3-Fluoro-4-(2-(5-((2-methoxyethylamino)methyl)pyridin-2-yl)thieno[3,2-b]pyridin-7-yloxy)phenyl)-3-(5-methylisoxazol-3-yl)urea (149)

To compound 148 (0.27 g, 0.42 mmol) in dichloromethane (75 mL) was added TFA (3 mL). The solution was stirred for 18 h then concentrated. The residue was partitioned between dichloromethane and 1M NaOH, and filtered to remove insolubles. The organic phase was collected, washed with 1M NaOH, brine, dried (anhydrous MgSO$_4$), Filtered, and concentrated. The residue was triturated with ether to afford title compound 149 (0.10 g, 45% yield). $^1$H NMR (400 MHz, DMSO-d$_6$) δ (ppm): 9.67 (s, 1H), 9.23 (s, 1H), 8.56 (d, J=1.4 Hz, 1H), 8.51 (d, J=5.3 Hz, 1H), 8.31 (s, 1H), 8.22 (d, J=8.0 Hz, 1H), 7.88 (dd, J=8.0, 2.0 Hz, 1H), 7.73 (dd, J=12.9, 2.3 Hz, 1H), 7.46 (t, J=9.0 Hz, 1H), 7.29-7.26 (m, 1H), 6.65 (d, J=5.5 Hz, 1H), 6.55 (s, 1H), 3.77 (s, 2H), 3.40 (t, J=5.7 Hz, 2H), 3.23 (s, 3H), 2.64 (t, J=5.7 Hz, 2H), 2.36 (s, 3H). MS (m/z): 549.1 (M+H).

Scheme 12
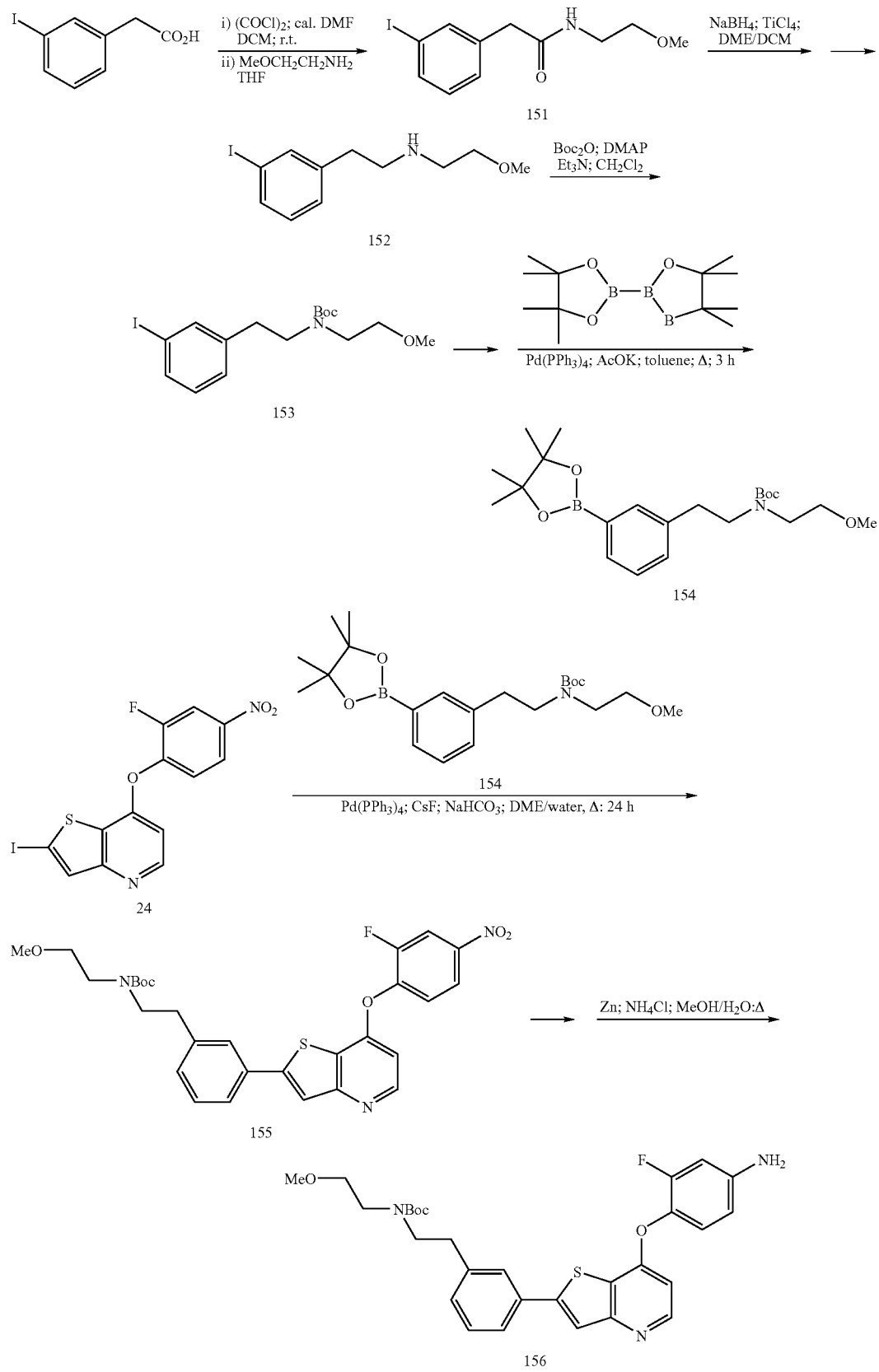

tert-Butyl 3-(7-(4-Amino-2-fluorophenoxy)thieno[3,2-b]pyridin-2-yl)phenethyl(2-methoxyethyl)carbamate (156)

Step 1: 2-(3-Iodophenyl)-N-(2-methoxyethyl)acetamide (151)

To a solution of 3 iodophenylacetic acid (1.12 g, 4.3 mmol) in dichloromethane (50 mL) was added oxalyl chloride (0.75 mL, 8.6 mmol) and DMF (0.05 mL). The mixture was stirred for 1 h at room temperature and concentrated. The residue was dissolved in dry THF (40 mL) and 2-methoxyethylamine (2.0 mL, 23 mmol) was added. The mixture was stirred for 2 h and concentrated. The residue was partitioned between water and ethyl acetate, the organic phase was collected, washed with 1M HCl, water, saturated $NaHCO_3$, brine, dried ($MgSO_4$), filtered and concentrated to afford pure 151 (1.23 g, 89%). $^1$H NMR (400 MHz, $CDCl_3$) δ (ppm): 7.64-7.61 (m, 2H), 7.26-7.24 (m, 1H), 7.10-7.06 (m, 1H), 5.81 (br s, 1H), 3.49 (s, 2H), 3.44-3.40 (m, 4H), 3.32 (s, 1H). MS (m/z): 320.1 (M+H).

Steps 2 and 3. tert-Butyl 3-iodophenethyl(2-methoxyethyl)carbamate, (153)

To $TiCl_4$ (1M in dichloromethane, 7.5 mL, 7.5 mmol) at r.t. was added sodium borohydride (0.60 g, 15 mmol) resulting in a dark blue solution. This was added to a solution of amide 151 (1.22 g, 3.8 mmol) in DME (70 mL) and the resulting dark mixture was stirred for 20 h. The mixture was concentrated, the residue partitioned between dichloromethane and $NH_4OH$(aq), and filtered. The filtrate was separated, the organic phase was washed with brine, dried ($MgSO_4$), filtered and concentrated to afford crude amine 152. This material was dissolved in dichloromethane (100 mL), and $Boc_2O$ (1.06 g, 4.8 mmol), DMAP (0.055 g, 0.63 mmol) and triethylamine (0.80 mL, 5.6 mmol) were added, and the mixture was stirred at r.t. for 3 h. It was then washed with water, saturated $NaHCO_3$, brine, dried ($MgSO_4$), filtered and concentrated. Silica gel chromatography (15% ethyl acetate/hexanes) provided title compound 153 (0.95 g, 79% yield). MS (m/z): 305.9 (M−Boc+H).

Step 4. tert-Butyl 2-methoxyethyl(3-(4,4,5,5-tetramethyl-1,3,2-dioxaborolan-2-yl)phenethyl)carbamate (154)

Compound 153 (0.95 g, 2.3 mmol), bis(pinacolato)diboron (0.65 g, 2.6 mmol), potassium acetate (0.80 g, 8.2 mmol) and tetrakis(triphenylphosphine)palladium (0.20 g, 0.17 mmol) were suspended in toluene (75 mL). The mixture was degassed with an $N_2$ flow and heated under reflux for 3 h. The mixture was then cooled and the toluene was removed under reduced pressure. The residue was partitioned between water and ethyl acetate, the organic phase was collected, washed with brine and dried ($MgSO_4$), filtered, and concentrated to afford title compound 154, which was used in the next step with no additional purification.

Step 5. tert-Butyl 3-(7-(2-fluoro-4-nitrophenoxy)thieno[3,2-b]pyridin-2-yl)phenethyl(2-methoxyethyl)carbamate (155)

Iodothienopyridine 24 (scheme 4) (0.89 g, 2.1 mmol) and boronate 154 (2.3 mmol) were dissolved in dry DME (100 mL). Cesium fluoride (0.96 g, 6.3 mmol) and sodium bicarbonate (0.60 g, 7.1 mmol) were dissolved in water (5 ml each) and added to the reaction mixture. Tetrakis(triphenylphosphine)palladium (0.10 g, 0.086 mmol) was added, and the mixture was then heated to reflux for 18 h, and cooled. The mixture was partitioned between ethyl acetate and water, washed with brine, dried ($MgSO_4$), filtered, and concentrated. Silica gel chromatography (25-75% ethyl acetate/hexanes) provided title compound 155 (0.44 g, 37% yield). $^1$H NMR (400 MHz, DMSO-$d_6$) δ (ppm): 8.60 (d, J=5.3 Hz, 1H), 8.47 (dd, J=10.6, 2.7 Hz, 1H), 8.22-8.18 (m, 1H), 8.10-8.06 (m, 1H), 7.75-7.67 (m, 3H), 7.43 (t, J=7.8 Hz, 1H), 7.29-7.25 (m, 1H), 6.94 (d, J=5.3 Hz, 1H), 3.45-3.25 (m, 6H), 3.23 (s, 3H), 2.83 (t, J=7.2 Hz, 2H), 1.35-1.25 (m, 9H). MS (m/z): 568.3 (M+H).

Step 6. tert-Butyl 3-(7-(4-Amino-2-fluorophenoxy)thieno[3,2-b]pyridin-2-yl)phenethyl(2-methoxyethyl)carbamate (156)

To nitro compound 155 (0.44 g, 0.78 mmol) and zinc dust (0.65 g, 10 mmol) in methanol (50 mL) was added ammonium chloride (0.075 g, 1.4 mmol) in water (6 mL). The resulting mixture was heated to reflux for 2 h, then cooled, filtered through celite and concentrated. Silica gel chromatography (70% ethyl acetate/hexanes) afforded title compound 156 (0.36 g, 88% yield). MS (m/z): 538.3 (M+H).

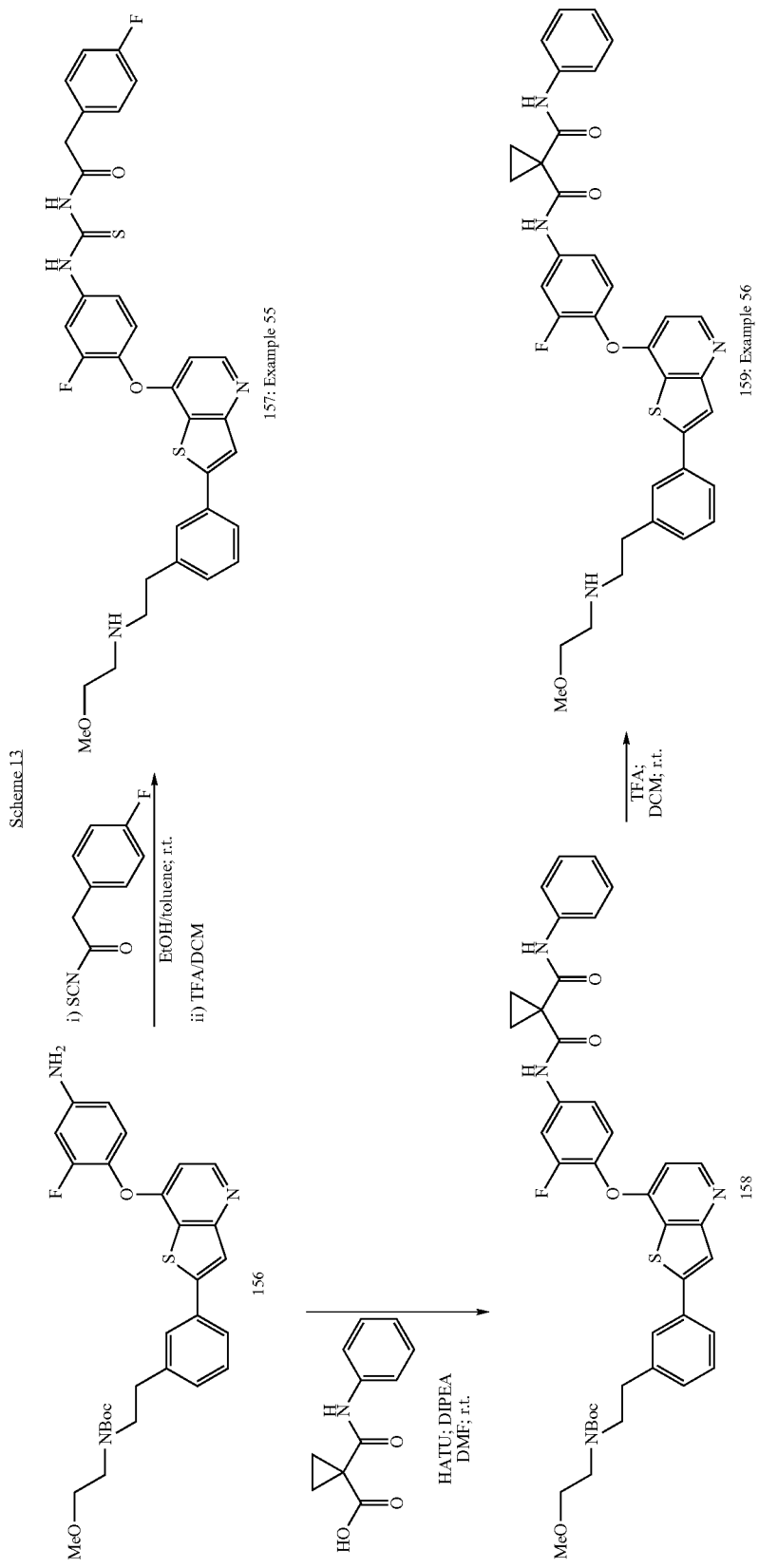

Example 55

N-(3-Fluoro-4-(2-(3-(2-(2-methoxyethylamino)ethyl)phenyl)thieno[3,2-b]pyridin-7-yloxy)phenylcarbamothioyl)-2-(4-fluorophenyl)acetamide (157)

Steps 1 and 2. N-(3-Fluoro-4-(2-(3-(2-(2-methoxyethylamino)ethyl)phenyl)thieno[3,2-b]pyridin-7-yloxy)phenylcarbamothioyl)-2-(4-fluorophenyl)acetamide (157)

To a solution of 156 (0.17 g, 0.32 mmol) in 1:1 absolute ethanol/toluene (20 mL), p-fluorophenylacetyl isothiocyanate (0.11 g, 0.56 mmol) in 1:1 absolute ethanol/toluene (5 mL) was added and the reaction was allowed to stir for 2 h at r.t. The solvents were removed under reduced pressure and the residue was purified by chromatography on silica gel (75% EtOAc/hexane) to give the intermediate Boc-protected product [not shown in the scheme] as a white solid. This material was dissolved in dichloromethane (20 mL) and trifluoroacetic acid (3 mL) and stirred for 6 h at r.t. The mixture was then concentrated and the residue was purified by Gilson reverse phase HPLC (Aquasil C-18 column, 35-85% MeOH/$H_2O$+$HCO_2H$, 30 min. linear gradient elution) and lyophilized to afford title compound 157 (0.100 g, 50% yield). $^1$H NMR (400 MHz, DMSO-$d_6$) δ (ppm): 8.55 (d, J=5.3 Hz, 1H), 8.24 (s, 1H), 8.06 (s, 1H), 8.03-8.00 (m, 1H), 7.76 (s, 1H), 7.73 (d, J=7.8 Hz, 1H), 7.57-7.53 (m, 2H), 7.43 (t, J=7.6 Hz, 1H), 7.40-7.35 (m, 2H), 7.32 (d, J=7.6 Hz, 1H), 7.21-7.16 (m, 2H), 6.67 (d, J=5.5 Hz, 1H), 3.84 (s, 2H), 3.43 (t, J=5.5 Hz, 2H), 3.24 (s, 3H), 2.92-2.82 (m, 4H), 2.79 (t, J=5.5 Hz, 2H) (presumably as a formate salt). MS (m/z): 633.2 (M+H).

Example 56

N-(3-Fluoro-4-(2-(3-(2-(2-methoxyethylamino)ethyl)phenyl)thieno[3,2-b]pyridin-7-yloxy)phenyl)-N-phenylcyclopropane-1,1-dicarboxamidem (159)

Step 1. tert-Butyl 3-(7-(2-Fluoro-4-(1-(phenylcarbamoyl)cyclopropanecarboxamido)phenoxy)-thieno[3,2-b]pyridin-2-yl)phenethyl(2-methoxyethyl)carbamate (158)

To aniline 156 (0.17 g, 0.32 mmol) in dry DMF (6 mL) was added 1-(phenylcarbamoyl)cyclopropanecarbpxylic acid (0.22 g, 1.1 mmol), DIPEA (0.3 mL, 0.2 g, 1.5 mmol), and HATU (0.50 g, 1.3 mmol) and the mixture was stirred at r.t. for 18 h. It was then partitioned between ethyl acetate and water, the organic phase was collected, washed with water, $NaHCO_3$ (aq), brine, dried ($MgSO_4$), filtered, and concentrated. Silica gel chromatography (75% ethyl acetate/hexanes) provided title compound 158 (0.14 g, 62% yield). MS (m/z): 725.3 (M+H).

Step 2. N-(3-Fluoro-4-(2-(3-(2-(2-methoxyethylamino)ethyl)phenyl)thieno[3,2-b]pyridin-7-yloxy)phenyl)-N-phenylcyclopropane-1,1-dicarboxamide (159)

Compound 158 (0.14 g, 0.20 mmol) was dissolved in dichloromethane (20 mL) and trifluoroacetic acid (2 mL) and stirred for 6 h at r.t. The mixture was concentrated, purified by reverse phase HPLC (Aquasil C-18 column, 35-85% MeOH/$H_2O$+$HCO_2H$, 30 min. linear gradient elution) and lyophilized to afford title compound 159 (0.080 g, 65% yield). $^1$H NMR (400 MHz, DMSO-$d_6$) δ (ppm): 10.37 (s, 1H), 9.98 (s, 1H), 8.50 (d, J=5.3 Hz, 1H), 8.26 (s, 1H), 8.04 (s, 1H), 7.90 (d, J=12.9 Hz, 1H), 7.76-7.74 (m, 1H), 7.72-7.68 (m, 1H), 7.63-7.60 (m, 2H), 7.53-7.39 (m, 3H), 7.32-7.27 (m, 3H), 7.08-7.03 (m, 1H), 6.59 (d, J=5.5 Hz, 1H), 3.38 (t, J=5.7 Hz, 2H), 3.22 (s, 3H); 2.84-2.78 (m, 4H); 2.72 (t, J=5.7 Hz, 2H); 1.48-1.46 (m, 4H) (presumably as a formate salt). MS (m/z): 625.3 (M+H).

| Cpd. # | Ex. # | Structure | Characterization |
|---|---|---|---|
| 166 | 59 | 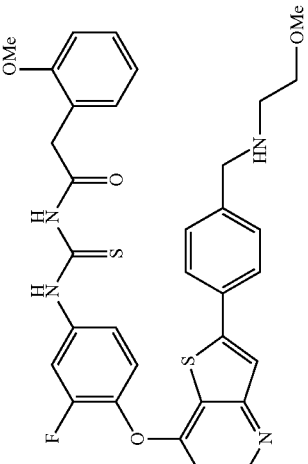<br>N-(3-fluoro-4-(2-(4-((2-methoxyethylamino)methyl)phenyl)thieno[3,2-b]pyridin-7-yloxy)phenylcarbamothioyl)-2-(2-methoxyphenyl)acetamide | $^1$H NMR (400 MHz, DMSO-d$_6$) δ (ppm) 12.56 (s, 1 H), 11.75 (s, 1 H), 8.97 (s, 2 H), 8.54 (d, J = 5.5, 1 H), 8.14 (s, 1 H), 8.04 (m, 1 H), 7.99 (d, J = 8.4 Hz, 1 H), 7.62 (d, J = 8.4 Hz, 2 H), 7.55 (m, 2 H), 7.22 (m, 2 H), 6.98 (d, J = 8.0 Hz, 1 H), 6.90 (m, 1 H), 6.69 (d, J = 5.5 Hz, 1 H), 4.2 (m, 2 H), 3.70-3.60 (m, 4 H), 3.59 (m, 2 H), 3.30 (s, 3 H), 3.11 (m, 2 H) (presumably bis-trifluoroacetate salt). MS (m/z): 631.2 (M + H). |
| 167 | 60 | 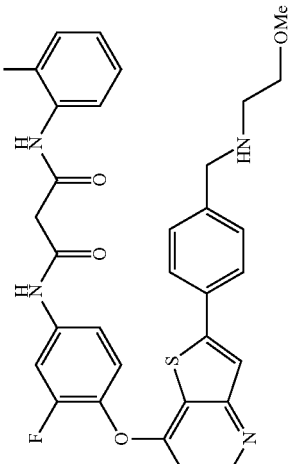<br>N1-(3-fluoro-4-(2-(4-((2-methoxyethylamino)methyl)phenyl)thieno[3,2-b]pyridin-7-yloxy)phenyl)-N3-(2-methoxyphenyl)malonamide | $^1$H NMR (400 MHz, DMSO-d$_6$) δ (ppm) 10.6 (s, 1 H), 9.61 (s, 1 H), 8.90 (s, 2 H), 8.52 (m, 1 H), 8.06 (m, 1 H), 7.99 (m, 1 H), 7.89 (m, 2 H), 7.62 (d, J = 8.0 Hz, 2 H), 7.47 (m, 2 H), 7.06 (m, 2 H), 6.90 (m, 1 H), 6.68 (d, J = 5.5 Hz, 1 H), 4.22 (m, 2 H), 3.84 (s, 3 H), 3.63 (s, 2 H), 3.57 (m, 2 H), 3.30 (m, 3 H), 3.12 (m, 2 H) (presumably bis-trifluoroacetate salt). MS (m/z): 615.3 (M + H). |

| Cpd. # | Ex. # | Structure | Characterization |
|---|---|---|---|
| 168 | 61 | N1-(3-fluoro-4-(2-(2-fluoro-4-((2-methoxyethylamino)methyl)phenyl)thieno[3,2-b]pyridin-7-yloxy)phenyl)-N3-phenylmalonamide | ¹H NMR (400 MHz, DMSO-d₆) δ (ppm) 10.59 (s, 1 H), 10.21 (s, 1 H), 8.51 (d, J = 5.3 Hz, 1 H), 8.21 (s, 1 H), 8.12 (s, 1 H), 7.87 (m, 2 H), 7.77 (m, 1 H), 7.75 (m, 1 H), 6.61 (d, J = 8.6 Hz, 3 H), 7.45 (m, 2 H), 7.33 (m, 2 H), 7.05 (m, 1 H), 6.65 (m, 1 H), 4.0 (m, 2 H), 3.6 (m, 3 H), 3.33 (s, 3 H), 2.80 (m, 2 H), (presumably monoformate salt). MS (m/z): 603.3 (M + H). |
| 170 | 63 | (S)-N-(3-fluoro-4-(2-(4-((1-methoxypropan-2-ylamino)methyl)phenyl)thieno[3,2-b]pyridin-7-yloxy)phenylcarbamothioyl)-2-phenylacetamide | ¹H NMR (400 MHz, DMSO-d₆) δ (ppm): 12.00-11.70 (m, 1 H), 8.53 (d, J = 5.3 Hz, 1 H), 8.04 (s, 1 H), 8.02 (bd, J = 12.7 Hz, 1 H), 7.84 (d, J = 8.2 Hz, 2 H), 7.58-7.51 (m, 2 H), 7.46 (d, J = 8.4 Hz, 2 H), 7.39-7.26 (m, 5 H), 6.65 (dd, J = 5.5, 0.8 Hz, 1 H), 3.84 (s, 2 H), 3.83 (d, J = 14.1 Hz, 1 H), 3.75 (d, J = 14.1 Hz, 1 H), 3.27 (dd, J = 9.3, 6.4 Hz, 1 H), 3.24 (s, 3 H), 3.19 (dd, J = 9.4, 5.5 Hz, 1 H), 2.83-2.73 (m, 1 H), 0.98 (d, J = 6.3 Hz, 3 H), two NH are missing. MS (m/z): 615.3 (M + H). |

| Cpd. # | Ex. # | Structure | Characterization |
|---|---|---|---|
| 171 | 64 | (S)-N-(3-fluoro-4-(2-(4-((1-methoxypropan-2-ylamino)methyl)phenyl)thieno[3,2-b]pyridin-7-yloxy)phenylcarbamothioyl)-2-(4-fluorophenyl)acetamide | $^1$H NMR (400 MHz, DMSO-d$_6$) δ (ppm): 8.53 (d, J = 5.5 Hz, 1 H), 8.04 (s, 1 H), 8.02 (bd, J = 12.0 Hz, 1 H), 7.84 (d, J = 8.2 Hz, 2 H), 7.59-7.51 (m, 2 H), 7.47 (d, J = 8.4 Hz, 2 H), 7.42-7.35 (m, 2 H), 7.23-7.15 (m, 2 H), 6.66 (dd, J = 5.4, 0.7 Hz, 1 H), 3.84 (s, 2 H), AB system (δ$_A$ = 3.83, δ$_B$ = 3.75, J$_{AB}$ = 14.2 Hz, 2 H), 3.27 (dd, J = 9.3, 6.4 Hz, 1 H), 3.24 (s, 3 H), 3.19 (dd, J = 9.2, 5.5 Hz, 1 H), 2.82-2.73 (m, 1 H), 0.98 (d, J = 6.3 Hz, 3 H), three NH are missing. MS (m/z): 633.2 (M + H). |
| 172 | 65 | (S)-N-(3-fluoro-4-(2-(4-((1-methoxypropan-2-ylamino)methyl)phenyl)thieno[3,2-b]pyridin-7-yloxy)phenyl)-N-phenylcyclopropane-1,1-dicarboxamide | $^1$H NMR (400 MHz, DMSO-d$_6$) δ (ppm): 10.39 (s, 1 H), 9.99 (s, 1 H), 8.51 (d, J = 5.5 Hz, 1 H), 8.15 (s, 1 H), 8.05 (s, 1 H), 7.91 (dd, J = 13.1, 2.3 Hz, 1 H), 7.86 (d, J = 8.2 Hz, 2 H), 7.65-7.60 (m, 2 H), 7.55-7.44 (m, 4 H), 7.34-7.28 (m, 2 H), 7.07 (tt, J = 7.4, 1.2 Hz, 1 H), 6.61 (dd, J = 5.4, 0.9 Hz, 1 H), AB system (δ$_A$ = 3.90, δ$_B$ = 3.83, J = 14.0 Hz, 2 H), one CH$_2$ is overlapped with peak of residual water, 3.26 (s, 3 H), 2.92-2.82 (m, 1 H), 1.52-1.43 (m, 4 H), 1.03 (d, J = 6.5 Hz, 3 H), one NH is missing. MS (m/z): 625.3 (M + H). (presumably mono-formate salt). |

| Cpd. # | Ex. # | Structure | Characterization |
|---|---|---|---|
| 174 | 67 | (S)-N-(3-fluoro-4-(2-(3-((1-methoxypropan-2-yl)amino)methyl)phenyl)thieno[3,2-b]pyridin-7-yloxy)phenylcarbamothioyl)-2-(4-fluorophenyl)acetamide 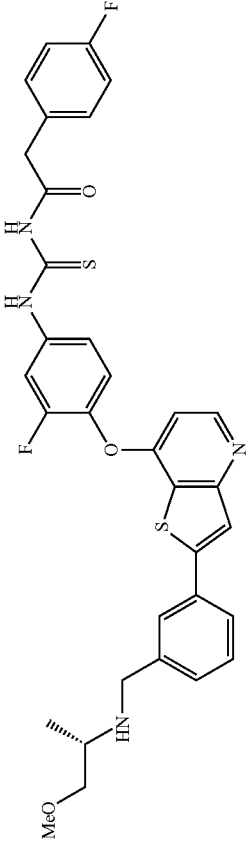 | $^1$H NMR (400 MHz, DMSO-d$_6$) δ (ppm): 8.54 (d, J = 5.3 Hz, 1 H), 8.05 (s, 1 H), 8.02 (d, J = 11.9 Hz, 1 H), 7.86 (s, 1 H), 7.76 (d, J = 7.4 Hz, 1 H), 7.54 (bs, 2 H), 7.49-7.34 (m, 4 H), 7.19 (t, J = 8.9 Hz, 2 H), 6.67 (d, J = 5.3 Hz, 1 H), 3.90-3.74 (m, 4 H), 3.32-3.16 (m, 5 H), 2.79 (hex, J = 6.0 Hz, 1 H), 0.99 (d, J = 6.5 Hz, 3 H), three NH are missing. MS (m/z): 633.2 (M + H). |
| 175 | 68 | N-(3-fluoro-4-(2-(3-((N-(2-methoxyethyl)acetamido)methyl)phenyl)thieno[3,2-b]pyridin-7-yloxy)phenylcarbamothioyl)-2-(4-fluorophenyl)acetamide 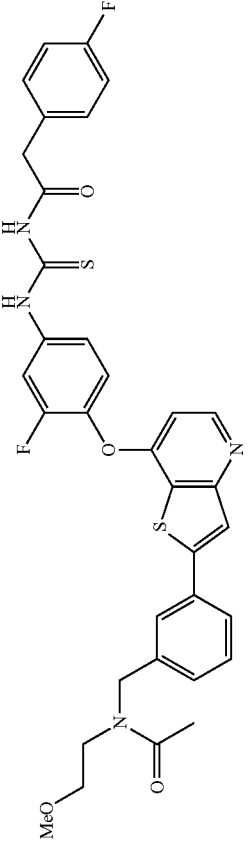 | $^1$H NMR (400 MHz, MeOH-d$_4$) δ (ppm): Mixture of rotamers, 12.46 (s, 1 H), 11.83 (s, 1 H), 8.53 (dd, J = 5.5, 2.0 Hz, 1 H), 8.03 (s, 1 H), 8.01 (dd, J = 12.3, 2.0 Hz, 1 H), 7.79 (dd, J = 17.6, 8.4 Hz, 1 H), 7.70 (d, J = 1.6 Hz, 1 H), 7.57-7.49 (m, 2 H), 7.45 (t, J = 7.6 Hz, 1 H), 7.37 (dd, J = 8.8, 5.7 Hz, 2 H), 7.28 (d, J = 7.6 Hz, 1 H), 7.17 (t, J = 9.0 Hz, 2 H), 6.66 (d, J = 5.5 Hz, 1 H), 4.69 and 4.60 (2 s, 2 H), 3.82 (s, 2 H), 3.48-3.41 (m, 4 H), 3.21 and 3.19 (2 s, 3 H), 2.12 and 2.02 (2s, 3 H). MS (m/z): 661.2 (M + H). |

| Cpd. # | Ex. # | Structure | Characterization |
|---|---|---|---|
| 178 | 71 | 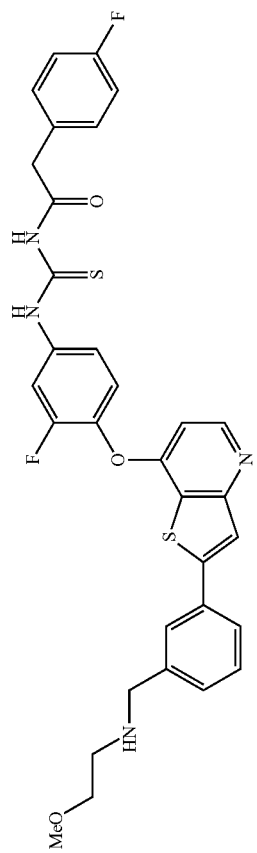<br>N-(3-fluoro-4-(2-(3-((2-methoxyethylamino)methyl)phenyl)thieno[3,2-b]pyridin-7-yloxy)phenylcarbamothioyl)-2-(4-fluorophenyl)acetamide | $^1$H NMR (400 MHz, d$_6$ DMSO) δ (ppm): 8.54 (d, J = 5.2 Hz, 1 H), 8.05 (s, 1 H), 8.02 (d, J = 12.0 Hz, 1 H), 7.85 (s, 1 H), 7.77 (d, J = 7.2 Hz, 1 H), 7.59-7.51 (m, 2 H), 7.48-7.35 (m, 4 H), 7.19 (t, J = 8.8 Hz, 2 H), 6.67 (d, J = 5.2 Hz, 1 H), 3.84 (s, 2 H), 3.80 (s, 2 H), 3.42 (t, J = 5.6 Hz, 2 H), 3.24 (s, 3 H), 2.68 (t, J = 5.6 Hz, 2 H). MS (m/z): 619.2 (M + H) |
| 179 | 72 | 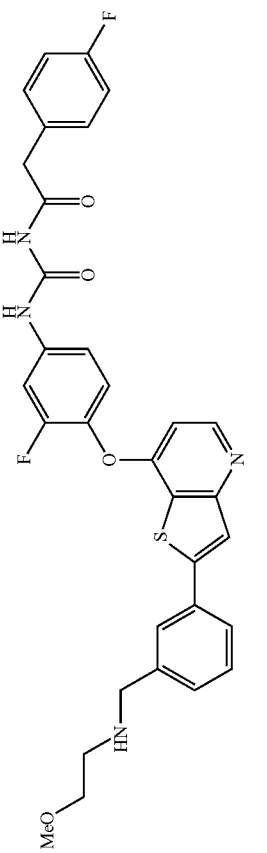<br>N-(3-fluoro-4-(2-(3-((2-methoxyethylamino)methyl)phenyl)thieno[3,2-b]pyridin-7-yloxy)phenylcarbamoyl)-2-(4-fluorophenyl)acetamide | $^1$H NMR (400 MHz, d$_6$ DMSO) δ (ppm): 11.07 (s, 1 H), 10.63 s, 1 H), 8.51 (d, J = 5.6 Hz, 1 H), 8.05 (s, 1 H), 7.87 (bs, 1 H), 7.83 (dd, J = 12.8, 2.4 Hz, 1 H), 7.77 (d, J = 8.0 Hz, 1 H), 7.52-7.40 (m, 4 H), 7.39-7.34 (dd, J = 8.8, 5.6 Hz, 2 H), 7.18 (t, J = 8.8 Hz, 2 H), 6.63 (d, J = 5.6 Hz, 1 H), 3.82 (s, 2 H), 3.75 (s, 2 H), 3.43 (t, J = 5.6 Hz, 2 H), 3.25 (s, 3 H), 2.70 (t, J = 5.6 Hz, 2 H). MS (m/z): 603.2 (M + H). |

| Cpd. # | Ex. # | Structure | Characterization |
|---|---|---|---|
| 180 | 73 | N-(3-fluoro-4-(3-((2-methoxyethylamino)methyl)phenyl)thieno[3,2-b]pyridin-7-yloxy)phenylcarbamothioyl)-2-(2-methoxyphenyl)acetamide | $^1$H NMR (400 MHz, d$_6$ DMSO) δ (ppm): 12.56 (bs, 1 H), 11.76 (bs, 1 H), 8.54 (d, J = 5.2 Hz, 1 H), 8.09-8.03 (m, 2 H), 7.91 (s, 1 H), 7.82 (d, J = 7.6 Hz, 1 H), 7.59-7.43 (m, 4 H), 7.28 (td, J = 7.8, 1.6 Hz, 1 H), 7.23 (dd, J = 7.6, 1.6 Hz, 1 H), 7.00 (d, J = 7.6 Hz, 1 H), 6.94 (td, J = 7.6, 1.2 Hz, 1 H), 6.69 (d, J = 5.2 Hz, 1 H), 3.92 (s, 2 H), 3.82 (s, 2 H), 3.79 (s, 3 H), 3.47 (t, J = 5.6 Hz, 2 H), 3.26 (s, 3 H), 2.81 (t, J = 5.6 Hz, 2 H). MS (m/z): 631.4 (M + H). |
| 181 | 74 | N-(3-fluoro-4-(3-((2-methylsulfonyl)ethylamino)methyl)phenyl)thieno[3,2-b]pyridin-7-yloxy)phenylcarbamothioyl)-2-phenylacetamide | $^1$H NMR (400 MHz, DMSO-d$_6$) δ (ppm): 12.50 (s, 1 H), 11.85 (s, 1 H), 8.55 (d, J = 5.6 Hz, 1 H), 8.07 (s, 1 H), 8.03 (d, J = 13.6 Hz, 1 H), 7.92 (s, 1 H), 7.87-7.82 (m, 1 H), 7.59-7.44 (m, 4 H), 7.39-7.26 (m, 4 H), 6.68 (d, J = 5.6 Hz, 1 H), 3.95 (bs, 2 H), 3.83 (s, 2 H), 3.45-3.25 (m, 2 H, hidden under water signal), 3.15-3.00 (m, 5 H). MS (m/z): 649.4 (M + H). |

| Cpd. # | Ex. # | Structure | Characterization |
|---|---|---|---|
| 182 | 75 | 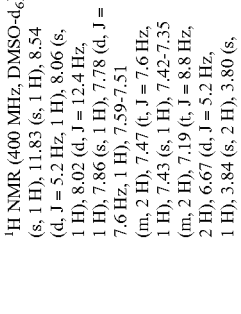<br>N-(3-fluoro-4-(2-(3-((2-(methylsulfonyl)ethylamino)methyl)phenyl)thieno[3,2-b]pyridin-7-yloxy)phenylcarbamothioyl)-2-(4-fluorophenyl)acetamide | $^1$H NMR (400 MHz, DMSO-$d_6$) δ (ppm): 12.47 (s, 1 H), 11.83 (s, 1 H), 8.54 (d, J = 5.2 Hz, 1 H), 8.06 (s, 1 H), 8.02 (d, J = 12.4 Hz, 1 H), 7.86 (s, 1 H), 7.78 (d, J = 7.6 Hz, 1 H), 7.59-7.51 (m, 2 H), 7.47 (t, J = 7.6 Hz, 1 H), 7.43 (s, 1 H), 7.42-7.35 (m, 2 H), 7.19 (t, J = 8.8 Hz, 2 H), 6.67 (d, J = 5.2 Hz, 1 H), 3.84 (s, 2 H), 3.80 (s, 2 H), 3.28 (t, J = 6.8 Hz, 2 H), 3.04 (s, 3 H), 2.93 (t, J = 6.8 Hz, 2 H). MS (m/z): 667.2 (M + H). |
| 183 | 76 | 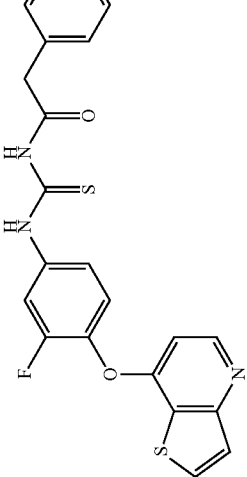<br>N-(3-fluoro-4-(2-(4-((2-(methylsulfonyl)ethylamino)methyl)phenyl)thieno[3,2-b]pyridin-7-yloxy)phenylcarbamothioyl)-2-(4-fluorophenyl)acetamide | $^1$H NMR (400 MHz, DMSO-$d_6$) δ (ppm): 12.47 (s, 1 H), 11.84 (s, 1 H), 8.53 (d, J = 5.2 Hz, 1 H), 8.05 (s, 1 H), 8.02 (d, J = 12.4 Hz, 1 H), 7.86 (d, J = 8.0 Hz, 2 H), 7.58-7.51 (m, 2 H), 7.47 (d, J = 8.0 Hz, 2 H), 7.41-7.35 (m, 2 H), 7.22-7.15 (m, 2 H), 6.66 (d, J = 5.2 Hz, 1 H), 3.84 (s, 2 H), 3.77 (s, 2 H), 2.27 (t, J = 6.8 Hz, 2 H), 3.03 (s, 3 H), 2.92 (t, J = 6.8 Hz, 2 H). MS (m/z): 667.2 (M + H). |

| Cpd. # | Ex. # | Structure | Characterization |
|---|---|---|---|
| 184 | 77 | 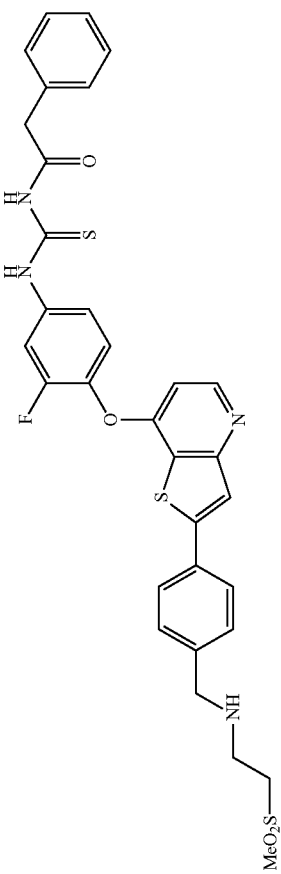  N-(3-fluoro-4-(2-(4-((2-(methylsulfonyl)ethylamino)methyl)phenyl)thieno[3,2-b]pyridin-7-yloxy)phenylcarbamothioyl)-2-phenylacetamide | $^1$H NMR (400 MHz, DMSO-d$_6$) δ (ppm): 12.50 (s, 1 H), 11.85 (s, 1 H), 8.53 (d, J = 5.4 Hz, 1 H), 8.05 (s, 1 H), 8.03 (d, J = 12.4 Hz, 1 H), 7.86 (d, J = 8.4 Hz, 2 H), 7.58-7.51 (m, 2 H), 7.46 (d, J = 8.4 Hz, 2 H), 7.39-7.26 (m, 5 H), 6.66 (d, J = 5.4 Hz, 1 H), 3.83 (s, 2 H), 3.77 (s, 2 H), 3.27 (t, J = 6.8 Hz, 2 H), 3.03 (s, 3 H), 2.92 (t, J = 6.8 Hz, 2 H). MS (m/z): 649.2 (M + H). |
| 186 | 79 | 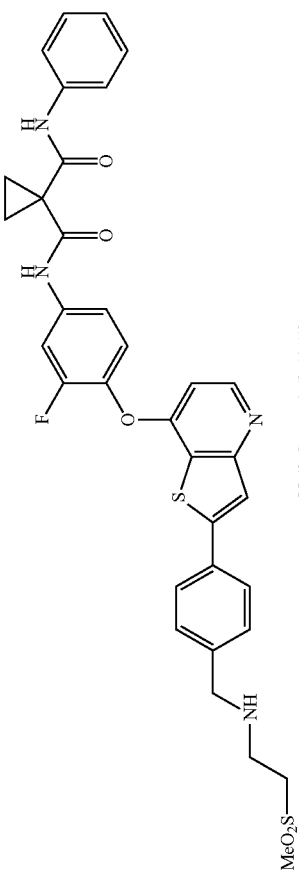  N-(3-fluoro-4-(2-(4-((2-(methylsulfonyl)ethylamino)methyl)phenyl)thieno[3,2-b]pyridin-7-yloxy)phenyl)-N-phenylcyclopropane-1,1-dicarboxamide | $^1$H NMR (400 MHz, DMSO-d$_6$) δ (ppm): 10.45 (s, 1 H), 10.00 (s, 1 H), 9.65 (bs, 2 H), 8.61 (d, J = 5.6 Hz, 1 H), 8.18 (s, 1 H), 8.03 (d, J = 8.4 Hz, 2 H), 7.94 (dd, J = 13.2, 2.0 Hz, 1 H), 7.72 (d, J = 8.4 Hz, 2 H), 7.63 (dd, J = 8.8, 2.0 Hz, 1 H), 7.55 (dd, J = 8.8 Hz, 1 H), 7.51 (t, J = 8.8 Hz, 1 H), 7.31 (t, J = 7.2 Hz, 2 H), 7.07 (t, J = 7.2 Hz, 1 H), 6.76 (d, J = 5.6 Hz, 1 H), 4.29 (t, J = 5.2 Hz, 2 H), 3.67-3.60 (m, 2 H), 3.44-3.34 (m, 2 H), 3.15 (s, 3 H), 1.53-1.45 (m, 4 H) (presumably hydrochloride salt). MS (m/z): 659.2 (M + H). |

| Cpd. # | Ex. # | Structure | Characterization |
|---|---|---|---|
| 187 | 80 | N-(3-fluoro-4-(2-(4-((2-(methylsulfonyl)ethyl)amino)methyl)phenyl)thieno[3,2-b]pyridin-7-yloxy)phenyl)-N3-methyl-N3-phenylmalonamide | $^1$H NMR (400 MHz, DMSO-d$_6$) δ (ppm): 10.31 (s, 1 H), 8.50 (d, J = 5.6 Hz, 1 H), 8.19 (s, 1 H), 8.04 (s, 1 H), 7.85 (d, J = 8.4 Hz, 2 H), 7.80 (d, J = 12.8 Hz, 1 H), 7.55-7.28 (m, 10 H), 6.62 (d, J = 5.6 Hz, 1 H), 3.77 (s, 2 H), 3.27 (t, J = 6.8 Hz, 2 H), 3.24-3.19 (m, 5 H), 3.03 (s, 3 H), 2.92 (t, J = 6.8 Hz, 2 H) (presumably formate salt). MS (m/z): 647.2 (M + H). |
| 192 | 85 | N-(3-fluoro-4-(2-(3-((2-methoxyethylamino)methyl)phenyl)thieno[3,2-b]pyridin-7-yloxy)phenyl)-N-phenylcyclopropane-1,1-dicarboxamide | $^1$H NMR (400 MHz, DMSO-d$_6$) δ (ppm): 10.41 (s, 1 H), 9.97 (s, 1 H), 8.54 (d, J = 5.6 Hz, 1 H), 8.14 (s, 0.5 H, formate), 8.08 (s, 1 H), 8.06 (s, 1 H), 7.96 (d, J = 7.2, 1.6 Hz, 1 H), 7.92 (dd, J = 13.2, 2.0 Hz, 1 H), 7.66-7.44 (m, 6 H), 7.31 (t, J = 8.0 Hz, 2 H), 7.08 (t, J = 8.0 Hz, 1 H), 6.65 (d, J = 5.6 Hz, 1 H), 4.24 (s, 2 H), 3.60 (t, J = 5.2 Hz, 2 H), 3.32 (s, 3 H), 3.13 (t, J = 5.2 Hz, 2 H), 1.53-1.44 (m, 4 H) (semiformate salt). MS (m/z): 611.3 (M + H). |

| Cpd. # | Ex. # | Structure | Characterization |
|---|---|---|---|
| 193 | 86 | 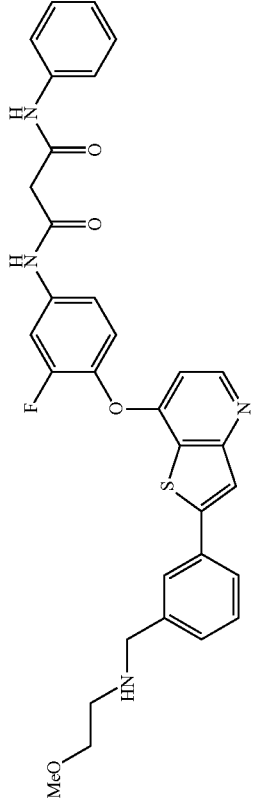<br>N1-(3-fluoro-4-(2-(3-((2-methoxyethylamino)methyl)phenyl)thieno[3,2-b]pyridin-7-yloxy)phenyl)-N3-phenylmalonamide | ¹H NMR (400 MHz, DMSO-d₆) δ (ppm): 10.59 (s, 1 H), 10.23 (s, 1 H), 9.01 (bs, 2 H), 8.54 (d, J = 5.6 Hz, 1 H), 8.09 (s, 1 H), 8.07 (s, 1 H), 7.98 (dt, J = 7.2, 1.6 Hz, 1 H), 7.90 (dd, J = 12.8, 2.4 Hz, 1 H), 7.64-7.54 (m, 4 H), 7.51 (t, J = 8.8 Hz, 1 H), 7.45 (dd, J = 8.8, 2.4 Hz, 1 H), 7.33 (t, J = 8.0 Hz, 2 H), 7.07 (t, J = 7.2 Hz, 1 H), 6.69 (d, J = 5.6 Hz, 1 H), 4.30-4.24 (m, 2 H), 3.61 (t, J = 5.6 Hz, 2 H), 3.52 (s, 2 H), 3.32 (s, 3 H), 3.21-3.13 (m, 2 H) (probably formate salt). MS (m/z): 585.3 (M + H). |
| 194 | 87 | 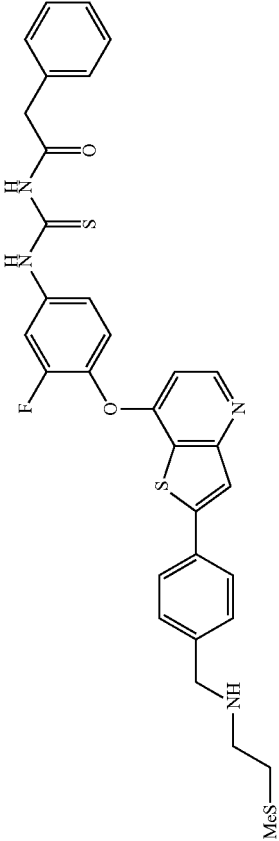<br>N-(3-fluoro-4-(2-(4-((2-(methylthio)ethylamino)methyl)phenyl)thieno[3,2-b]pyridin-7-yloxy)phenylcarbamothioyl)-2-phenylacetamide | ¹H NMR (400 MHz, DMSO-d₆) δ (ppm): 12.51 (s, 1 H), 11.86 (s, 1 H), 8.90 (bs, 2 H), 8.56 (d, J = 5.6 Hz, 1 H), 8.16 (s, 1 H), 8.06-7.99 (m, 3 H), 7.63 (d, J = 8.4 Hz, 2 H), 7.60-7.52 (m, 2 H), 7.40-7.26 (m, 5 H), 6.69 (dd, J = 5.2, 0.8 Hz, 1 H), 4.28-4.23 (m, 2 H), 3.84 (s, 2 H), 3.22-3.14 (m, 2 H), 2.76 (t, J = 7.2 Hz, 2 H), 2.11 (s, 3 H) (presumably formate salt). MS (m/z): 617.2 (M + H). |

| Cpd. # | Ex. # | Structure | Characterization |
|---|---|---|---|
| 195 | 88 | 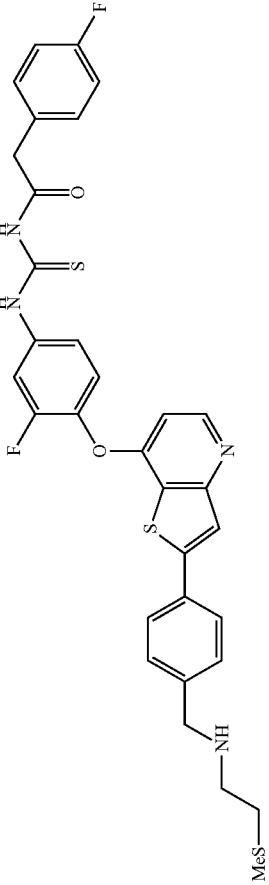 N-(3-fluoro-4-(2-(4-((2-(methylthio)ethylamino)methyl)phenyl)thieno[3,2-b]pyridin-7-yloxy)phenylcarbamothioyl)-2-(4-fluorophenyl)acetamide | ¹H NMR (400 MHz, DMSO-d₆) δ (ppm): 12.47 (s, 1 H), 11.84 (s, 1 H), 8.54 (d, J = 5.6 Hz, 1 H), 8.14 (s, 1 H), 8.10 (s, 1 H), 8.02 (d, J = 14.0 Hz, 1 H), 7.93 (d, J = 8.4 Hz, 2 H), 7.58-7.52 (m, 4 H), 7.41-7.35 (m, 2 H), 7.22-7.15 (m, 2 H), 6.67 (dd, J = 5.6, 0.8 Hz, 1 H), 4.02 (s, 2 H), 3.84 (s, 28), 2.95 (t, J = 7.2 Hz, 2 H), 2.68 (t, J = 7.2 Hz, 2 H), 2.08 (s, 3 H) (presumably formate salt). MS (m/z): 635.2 (M + H). |
| 205 | 98 | 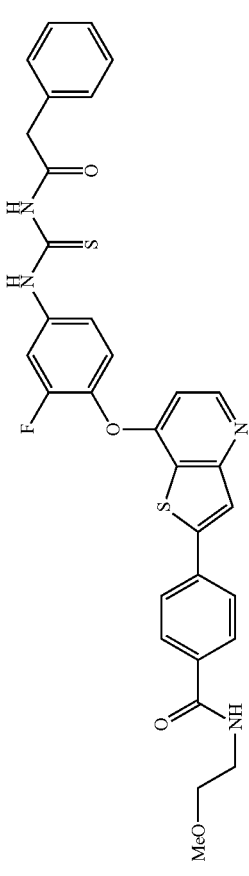 4-(7-(2-fluoro-4-(3-(2-phenylacetyl)thioureido)phenoxy)thieno[3,2-b]pyridin-2-yl)-N-(2-methoxyethyl)benzamide | ¹H NMR (400 MHz, DMSO-d₆) δ (ppm): 12.50 (s, 1 H), 11.85 (s, H), 8.67 (t, J = 5.2 Hz, 1 H), 8.56 (d, J = 5.6 Hz, 1 H), 8.20 (s, 1 H), 8.06-7.94 (m, 5 H), 7.59-7.52 (m, 2 H), 7.39-7.33 (m, 4 H), 7.33-7.26 (m, 1 H), 6.70 (d, J = 5.6 Hz, 1 H), 3.84 (s, 2 H), 3.51-3.42 (m, 4 H), 3.28 (s, 3 H). MS (m/z): 615.2 (M + H). |

| Cpd. # | Ex. # | Structure | Characterization |
|---|---|---|---|
| 207 | 100 | 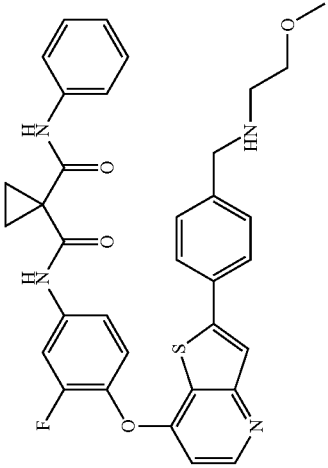

N-(3-fluoro-4-(2-(4-((2-methoxyethyl)amino)methyl)phenyl)thieno[3,2-b]pyridin-7-yloxy)phenyl)-N-phenylcyclopropane-1,1-dicarboxamide | $^1$H NMR (400 MHz, DMSO-d$_6$) δ (ppm): 10.42 (s, 1 H), 9.97 (s, 1 H), 9.22 (s, 2 H), 8.58 (d, J = 5.8 Hz, 1 H), 8.14 (s, 1 H), 7.99 (d, J = 8.4 Hz, 2 H), 7.92 (dd, , J = 13.1, 2.1 Hz, 1 H), 7.67 (d, J = 8.6 Hz, 2 H), 7.61 (dd, J = 8.6, 1.0 Hz, 2 H), 7.53 (dd, J = 9.2, 2.3 Hz, 1 H), 7.48 (t, J = 8.7 Hz, 1 H), 7.29 (m, 2 H), 7.05 (m, 1 H), 6.72 (d, J = 5.6 Hz, 1 H), 4.21 (t, J = 5.6 Hz, 2 H), 3.61 (t, J = 5.1 Hz, 2 H), 3.38 (s, 3 H), 3.09 (m, 2 H), 1.48 (m, 4 H) (presumably hydro chloride salt). MS (m/z): 611.3 (M + H). |
| 208 | 101 | 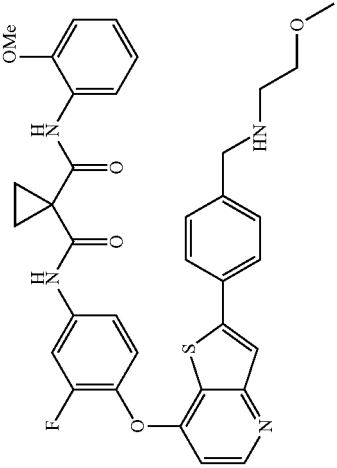

N-(3-fluoro-4-(2-(4-((2-methoxyethyl)amino)methyl)phenyl)thieno[3,2-b]pyridin-7-yloxy)phenyl)-N-(2-methoxyphenyl)cyclopropane-1,1-dicarboxamide | $^1$H NMR (400 MHz, DMSO-d$_6$) δ (ppm): 10.28 (s, 1 H), 10.12 (s, 1 H), 9.22 (s, broad, 2 H), 8.56 (d, J = 5.6 Hz, 1 H), 8.15 (s, 1 H), 8.04-7.97 (m, 3 H) 7.86 (d, J = 13.5 Hz, 1 H), 7.67 (d, J = 8.3 Hz, 2 H), 7.56 (m, 2 H), 7.05 (m, 2 H), 6.91 (m, 1 H), 6.69 (d, J = 5.6 Hz, 1 H), 4.21 (t, 2 H), 3.81 (s, 3 H), 3.61 (t, 2 H), 3.29 (s, 3 H), 3.09 (m, 2 H), 1.58 (m, 4 H) (presumably hydro chloride salt). MS (m/z): 641.3 (M + H). |

| Cpd. # | Ex. # | Structure | Characterization |
|---|---|---|---|
| 209 | 102 | N-(3-fluoro-4-(2-(4-((2-methoxyethylamino)methyl)phenyl)thieno[3,2-b]pyridin-7-yloxy)phenyl)carbamothioyl-2-(2-fluorophenyl)acetamide | $^1$H NMR (400 MHz, DMSO-d$_6$) δ (ppm): 12.41 (s, 1 H), 11.89 (s, 1 H), 9.12 (s, broad, 2 H), 8.59 (d, J = 5.6 Hz, 1 H), 8.14 (s, 1 H), 8.04-7.96 (m, 3 H), 7.65 (d, J = 8.4 Hz, 2 H), 7.54 (m, 2 H), 7.38 (dt, J = 7.5, 1.6 Hz, 1 H), 7.35-7.31 (m, 1 H), 7.21-7.15 (m, 2 H), 6.76 (d, J = 5.1 Hz, 1 H), 4.20 (t, J = 5.3 Hz, 2 H), 3.91 (S, 2 H), 3.60-3.53 (m, 2 H), 3.29 (s, 3), 3.10 (m, 4 H) (presumably hydrochloride salt). MS (m/z): 619.1 (M + H). |
| 211 | 104 | N1-(3-fluoro-4-(2-(4-(2-(2-methoxyethylamino)ethyl)phenyl)thieno[3,2-b]pyridin-7-yloxy)phenyl)-N3-phenylmalonamide | $^1$H NMR (400 MHz, DMSO-d$_6$) δ (ppm): 10.60 (s, 1 H), 10.20 (s, 1 H), 8.48 (d, J = 5.3 Hz, 1 H), 8.00 (s, 1 H), 7.88-7.10 (m, 3 H), 7.58 (d, J = 7.6 Hz, 2 H), 7.48 (t, J = 8.7 Hz, 1 H), 7.42 (dd, J = 9.0, 1.8 Hz, 1 H), 7.37 (d, J = 8.2 Hz, 2 H), 7.31 (t, J = 7.6 Hz, 2 H), 7.05 (t, J = 7.3 Hz, 1 H), 6.61 (d, J = 5.3 Hz, 1 H), 3.26 (s, 3 H), 3.00-2.86 (m, 6 H) (presumably formate salt). MS (m/z): 599.3 (M + H) |

| Cpd. # | Ex. # | Structure | Characterization |
|---|---|---|---|
| 212 | 105 | 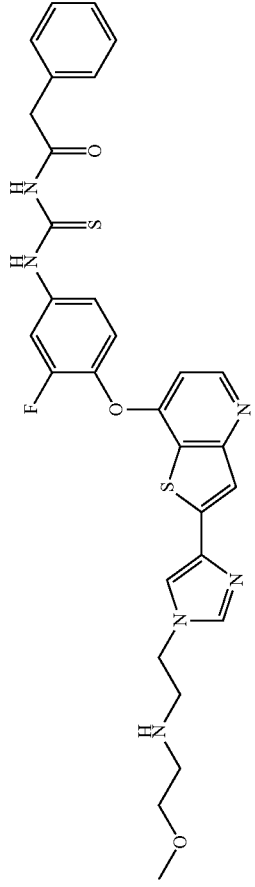<br>N-(3-fluoro-4-(2-(1-(2-(2-methoxyethylamino)ethyl)-1H-imidazol-4-yl)thieno[3,2-b]pyridin-7-yloxy)phenyl)carbamothioyl)-2-phenylacetamide | $^1$H NMR (400 MHz, DMSO-d$_6$) δ (ppm): 12.50 (s, 1 H), 11.84 (s, 1 H), 8.68 (s, br, 2 H), 8.45 (d, J = 5.5 Hz, 1 H), 8.02 (dd, J = 12.5, 2.4 Hz, 1 H), 7.94 (d, J = 1.2 Hz, 1 H), 7.81 (d, J = 1.2 Hz, 1 H), 7.70 (s, 1 H), 7.55-7.48 (m, 2 H), 7.34-7.32 (m, 4 H), 7.30-7.22 (m, 1 H), 6.58 (dd, J = 5.5, 0.8 Hz, 1 H), 4.34 (t, J = 6.0 Hz, 2 H), 3.81 (s, 2 H), 3.55 (t, J = 5.0 Hz, 1 H), 3.34-3.30 (m, 1 H), 3.15 (m, 4 H) (presumably formate salt). MS (m/z): 605.3 (M + H). |
| 213 | 106 | 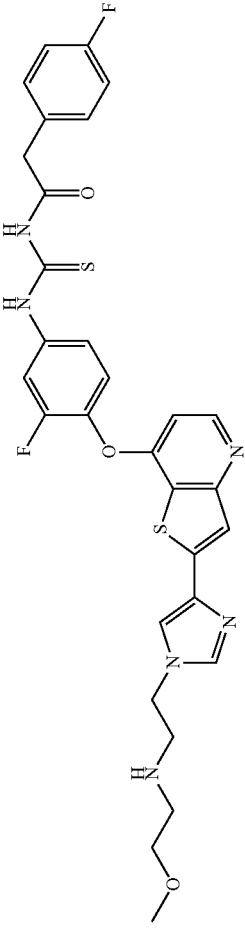<br>N-(3-fluoro-4-(2-(1-(2-(2-methoxyethylamino)ethyl)-1H-imidazol-4-yl)thieno[3,2-b]pyridin-7-yloxy)phenyl)carbamothioyl)-2-(4-fluorophenyl)acetamide | $^1$H NMR (400 MHz, DMSO-d$_6$) δ (ppm): 12.47 (s, 1 H), 11.83 (s, 1 H), 8.70 (s, br, 2 H), 8.48 (d, J = 5.5 Hz, 1 H), 8.02 (dd, J = 2.9, 2.2 Hz, 1 H), 7.97 (d, J = 1.2 Hz, 1 H), 7.84 (d, J = 1.2 Hz, 1 H), 7.71 (s, 1 H), 7.56-7.38 (m, 2 H), 7.38-7.34 (m, H), 7.20-7.15 (m, 2 H), 6.63 (dd, J = 5.7, 0.6 Hz, 1 H), 4.35 (t, J = 6.0 Hz, 2 H), 3.82 (s, 2 H), 3.56 (t, J = 5.0 Hz, 2 H), 3.44-3.41 (m, 2 H), 3.31 (s, 3 H), 3.15-3.12 (m, 2 H) (presumably trifluoroacetic acid salt). MS (m/z): 623.2 (M + H). |

-continued

| Cpd. # | Ex. # | Structure | Characterization |
|---|---|---|---|
| 215 | 108 | N-(3-fluoro-4-(2-(5-((2-methoxyethylamino)methyl)thiophen-2-yl)thieno[3,2-b]pyridin-7-yloxy)phenylcarbamothioyl)-2-phenylacetamide | $^1$H NMR (400 MHz, DMSO-d$_6$) δ (ppm): 12.49 (s, 1 H), 11.84 (s, 1 H), 9.03 (s br, 2 H), 8.53 (d, J = 5.5 Hz, 1 H), 8.02 (dd, J = 13.3, 2.0 Hz, 1 H), 7.87 (s, 1 H), 7.61 (d, J = 3.5 Hz, 1 H), 7.54-53 (m, 2 H), 7.35-7.32 (m, 5 H), 7.29-7.26 (m, 1 H), 6.68 (dd, J = 5.5, 0.8 Hz, 1 H), 4.43 (t, J = 5.0 Hz, 2 H), 3.81 (s, 2 H), 3.57 (t, J = 5.1 Hz, 2 H), 3.14-3.12 (m, 2 H) (presumably trifluoroacetic acid salt). MS (m/z): 607.1 (M + H). |
| 218 | 111 | N-(3-fluoro-4-(2-(5-((2-methoxyethylamino)methyl)pyridin-2-yl)thieno[3,2-b]pyridin-7-yloxy)phenyl carbamothioyl)-2-phenylacetamide | $^1$H NMR (400 MHz, CH3CN-d$_3$) δ (ppm): 12.51 (s, 1 H), 11.85 (s, 1 H), 9.3 (br.s, 1 H), 8.74 (d, J = 1.5 Hz, 1 H), 8.61 (d, J = 5.7 Hz, 1 H), 8.44 (s, 1 H), 8.38 (d, J = 8.0 Hz, 1 H), 8.14 (dd, J = 8.2, 1.9 Hz, 1 H), 8.04 (d, J = 13.1 Hz, 1 H), 7.56 (m, 2 H), 7.25-7.35 (m, 5 H), 6.77 (d, J = 5.2 Hz, 1 H), 4.25 (m, 2 H), 3.82 (s, 2 H), 3.61 (m, 2 H), 3.30 (s, 3 H), 3.13 (m, 2 H) (presumably HCl trisalt). MS (m/z): 602.2 (M + H). |

| Cpd. # | Ex. # | Structure | Characterization |
|---|---|---|---|
| 219 | 112 | 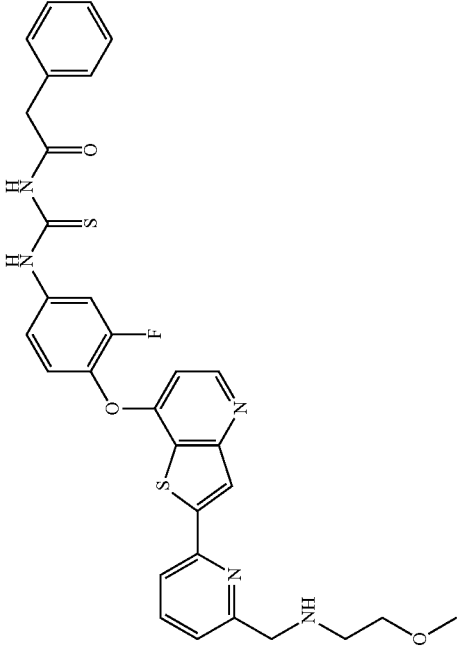 N-(3-fluoro-4-(2-(6-((2-methoxyethylamino)methyl)pyridin-2-yl)thieno[3,2-b]pyridin-7-yloxy)phenyl carbamothioyl)-2-phenylacetamide | $^1$H NMR (400 MHz, DMSO-d$_6$) δ (ppm): 12.53 (s, 1 H), 11.87 (s, 1 H), 9.48 (brs, 2 H), 8.69 (d, J = 5.9 Hz, 1 H), 8.51 (s, 1 H), 8.33 (d, J = 7.8 Hz, 1 H), 8.06 (m, 2 H), 7.60 (m, 3 H), 7.2-7.4 (m, 7 H), 6.87 (d, J = 5.7 Hz, 1 H), 4.43 (s, 2 H), 3.83 (s, 3 H), 3.70 (m, 2 H), 3.55 (s, 2 H) (presumably HCl trisalt). MS (m/z): 602.2 (M + H). |
| 220 | 113 | 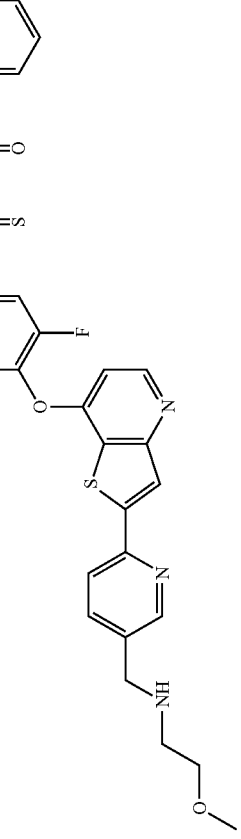 N-(3-fluoro-4-(2-(5-((2-methoxyethylamino)methyl)pyridin-2-yl)thieno[3,2-b]pyridin-7-yloxy)phenyl carbamothioyl)-2-(2-methoxyphenyl)acetamide | $^1$H NMR (400 MHz, DMSO-d$_6$) δ (ppm): 12.59 (s, 1 H), 11.77 (s, 1 H), 9.61 (brs, 1 H), 8.81 (s, 1 H), 8.78 (d, J = 6.1 Hz, 1 H), 8.49 (s, 1 H), 8.45 (d, J = 8.6 Hz, 1 H), 8.24 (d, J = 7.2 Hz, 1 H), 8.13 (d, J = 12.1 Hz, 1 H), 7.62 (s, 2 H), 7.2-7.3 (m., 2 H), 7.03 (d, J = 6.3 Hz, 1 H), 6.98 (t, J = 8.0 Hz, 1 H), 6.90 (t, J = 7.2 Hz, 1 H), 4.26 (s, 2 H), 3.6-4.0 (m, 4 H), 3.77 (s, 3 H), 3.29 (s, 3 H), 3.12 (s, 2 H) (presumably HCl trisalt). MS (m/z): 632.3 (M + H). |

| Cpd. # | Ex. # | Structure | Characterization |
|---|---|---|---|
| 223 | 116 | N1-(3-fluoro-4-(2-(5-((2-methoxyethylamino)methyl)pyridin-2-yl)thieno[3,2-b]pyridin-7-yloxy)phenyl)-N3-methyl-N3-phenylmalonamide | $^1$H NMR (400 MHz, MeOH-d$_4$) δ (ppm): 8.58 (d, J = 1.5 Hz, 1 H), 8.46 (d, J = 5.4 Hz, 1 H), 8.09 (s, 1 H), 8.06 (s, 1 H), 7.92 (dd, J = 8.2, 2.2 Hz, 1 H), 7.75 (dd, J = 12.7, 2.2 Hz, 1 H), 7.25-7.5 (m, 7 H), 3.88 (s, 2 H), 3.53 (t, J = 5.1 Hz, 2 H), 3.35 (s, 3 H), 3.34 (s, 2 H), 2.81 (t, J = 5.1 Hz, 2 H) (presumably HCl salt). MS (m/z): 600.3 (M + H). |
| 224 | 117 | N-(3-fluoro-4-(2-(6-((2-methoxyethylamino)methyl)pyridin-2-yl)thieno[3,2-b]pyridin-7-yloxy)phenyl)-N-phenylcyclopropane-1,1-dicarboxamide | $^1$H NMR (400 MHz, DMSO-d$_6$) δ (ppm): 10.38 (s, 1 H), 9.99 (s, 1 H), 8.51 (d, J = 5.5 Hz, 1 H), 8.35 (s, 1 H), 8.21 (br.s, 0.6 H), 8.12 (d, J = 7.9 Hz, 1 H), 7.92 (m, 2 H), 7.62 (d, J = 7.6 Hz, 2 H), 7.46 (m, 3 H), 7.30 (t, J = 7.7 Hz, 2 H), 7.06 (t, J = 7.2 Hz, 1 H), 6.61 (d, J = 5.3 Hz, 2 H), 3.89 (s, 2 H), 3.24 (s, 3 H), 2.75 (t, J = 5.2 Hz, 2 H), 1.47 (s, 4 H) (presumably as formate salt). MS (m/z): 612.2 (M + H). |

| Cpd. # | Ex. # | Structure | Characterization |
|---|---|---|---|
| 225 | 118 | 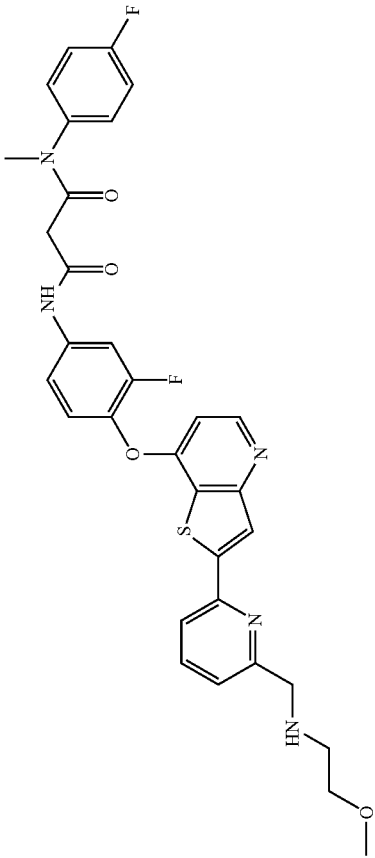 N1-(3-fluoro-4-(2-(6-((2-methoxyethylamino)methyl)pyridin-2-yl)thieno[3,2-b]pyridin-7-yloxy)phenyl)-N3-(4-fluorophenyl)-N3-methylmalonamide | $^1$H NMR (400 MHz, DMSO-d$_6$) δ (ppm): 10.37 (s, 1 H), 8.59 (d, J = 5.5 Hz, 1 H), 8.43 (s, 1 H), 8.21 (d, J = 7.8 Hz, 1 H), 8.00 (t, J = 7.9 Hz, 1 H), 7.88 (d, J = 13.7 Hz, 1 H), 7.56 (m, 4 H), 7.39 (m, 3 H), 6.72 (d, J = 4.9 Hz, 1 H), 3.95 (s, 2 H), 3.52 (t, J = 5.7 Hz, 2 H), 3.33 (s, 3 H), 3.31 (s, 2 H), 3.27 (s, 3 H), 2.82 (t, J = 5.5 Hz, 3 H). MS (m/z): 618.2 (M + H). |
| 229 | 122 | 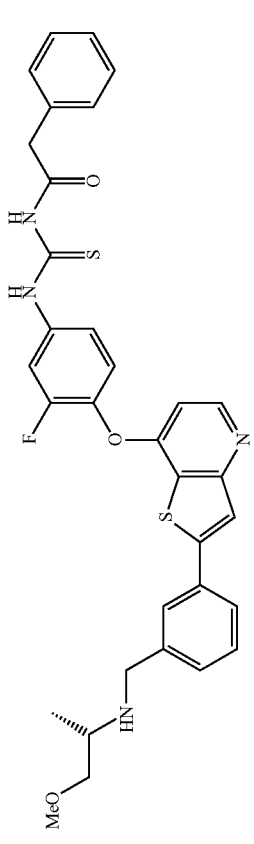 (S)-N-(3-fluoro-4-(2-(3-(((1-methoxypropan-2-yl)amino)methyl)phenyl)thieno[3,2-b]pyridin-7-yloxy)phenylcarbamothioyl)-2-phenylacetamide | $^1$H NMR (400 MHz, DMSO-d$_6$) δ (ppm): 8.54 (d, J = 5.5 Hz, 1 H), 8.06 (s, 1 H), 8.03-8.00 (m, 1 H), 7.97 (s, 1 H), 7.88-7.84 (m, 1 H), 7.54-7.50 (m, 4 H), 7.35-7.32 (m, 4 H), 7.29-7.26 (m, 1 H), 6.67 (d, J = 5.3 Hz, 1 H), 4.11-4.02 (m, 2 H), 3.82 (s, 2 H), 3.40 (s, 3 H), 5.5 Hz, 2 H), 3.28 (s, 3 H), 3.16-3.11 (m, 1 H), 1.15 (d, J = 6.5 Hz, 3 H). MS (m/z): 615.2 (M + H). |

| Cpd. # | Ex. # | Structure | Characterization |
|---|---|---|---|
| 230 | 123 | 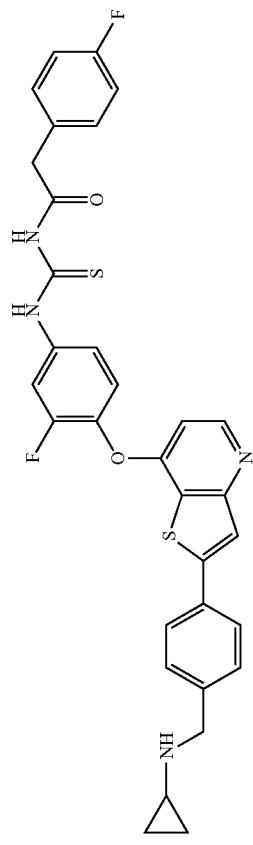<br>N-(4-(2-(4-((cyclopropylamino)methyl)phenyl)thieno[3,2-b]pyridin-7-yloxy)-3-fluorophenylcarbamothioyl)-2-(4-fluorophenyl)acetamide | ¹H NMR (400 MHz, DMSO-d₆) δ (ppm): 12.48 (br s, 1 H), 11.85 (br s, 1 H), 8.53 (d, J = 5.5 Hz, 1 H), 8.18 (s, 1 H), 8.06 (s, 1 H), 8.02 (d, J = 11.9 Hz, 1 H), 7.86 (d, J = 8.4 Hz, 2 H), 7.55-7.53 (m, 2 H), 7.49 (d, J = 8.4 Hz, 2 H), 7.40-7.36 (m, 2 H), 7.21-7.16 (m, 2 H), 6.65 (d, J = 5.3 Hz, 1 H), 3.88 (s, 2 H), 3.84 (s, 2 H), 2.19 (septet, J = 3.7 Hz, 1 H), 0.45-0.38 (m, 4 H) (presumably formate salt). MS (m/z): 601.2 (M + H). |
| 231 | 124 | 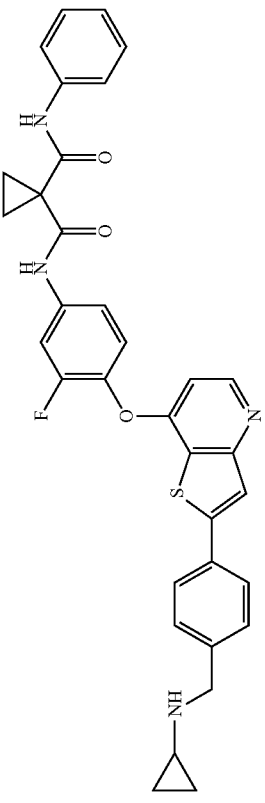<br>N-(4-(2-(4-((cyclopropylamino)methyl)phenyl)thieno[3,2-b]pyridin-7-yloxy)-3-fluorophenyl)-N-phenylcyclopropane-1,1-dicarboxamide | ¹H NMR (400 MHz, DMSO-d₆) δ (ppm): 10.39 (s, 1 H), 10.00 (s, 1 H), 8.50 (d, J = 5.5 Hz, 1 H), 8.12 (s, 1 H), 7.99 (s, 1 H), 7.91 (d, J = 12.9 Hz, 1 H), 7.85-7.82 (m, 2 H), 7.65-7.62 (m, 2 H), 7.54-7.45 (m, 4 H), 7.33-7.29 (m, 2 H), 7.09-7.04 (m, 1 H), 6.60 (d, J = 5.5, 1 H), 3.78 (s, 2 H), 2.06 (sept, J = 3.5, 1 H), 0.39-0.27 (m, 4 H) (presumably formate salt). MS (m/z): 593.2 (M + H). |

| Cpd. # | Ex. # | Structure | Characterization |
|---|---|---|---|
| 233 | 126 | N-(3-fluoro-4-(2-(4-((2,2,2-trifluoroethylamino)methyl)phenyl)thieno[3,2-b]pyridin-7-yloxy)phenyl)-N-phenylcyclopropane-1,1-dicarboxamide | $^1$H NMR (400 MHz, DMSO-d$_6$) δ (ppm): 10.37 (s, 1 H), 9.97 (s, 1 H), 8.49 (d, J = 5.5 Hz, 1 H), 8.03 (s, 1 H), 7.90 (d, J = 13.3 Hz, 1 H), 7.86-7.83 (m, 2 H), 7.63-7.60 (m, 2 H), 7.52-7.43 (m, 4 H), 7.32-7.27 (m, 2 H), 7.07-7.03 (m, 1 H), 6.59 (d, J = 5.5 Hz, 1 H), 3.84-3.82 (m, 2 H), 3.27-3.15 (m, 2 H), 3.02 (quint, J = 6.7, 1 H), 1.46 (br s, 4 H). MS (m/z): 635.2 (M + H). |
| 235 | 128 | N1-(3-fluoro-4-(2-(5-((2-methoxyethylamino)methyl)pyridin-2-yl)thieno[3,2-b]pyridin-7-yloxy)phenyl)-N3-phenylmalonamide | $^1$H NMR (400 MHz, DMSO-d$_6$) δ (ppm): 10.64 (s, 1 H), 10.26 (s, 1 H), 8.57 (d, J = 1.4 Hz, 1 H), 8.52 (d, J = 5.3 Hz, 1 H), 8.32 (s, 1 H), 8.23 (d, J = 8.0 Hz, 1 H), 7.91 (s, 1 H), 7.89-7.87 (m, 1 H), 7.63-7.60 (m, 2 H), 7.50 (t, J = 9.0 Hz, 1 H), 7.45 (dd, J = 6.9, 0.8 Hz, 1 H), 7.34-7.30 (m, 2 H), 7.09-7.04 (m, 1 H), 6.68 (dd, J = 5.3, 0.8 Hz, 1 H), 3.78 (s, 2 H), 3.52 (s, 2 H), 3.41 (t, J = 5.7 Hz, 2 H), 3.24 (s, 3 H), 2.65 (t, J = 5.5 Hz, 2 H). MS (m/z): 586.3 (M + H). |

| Cpd. # | Ex. # | Structure | Characterization |
|---|---|---|---|
| 236 | 129 | 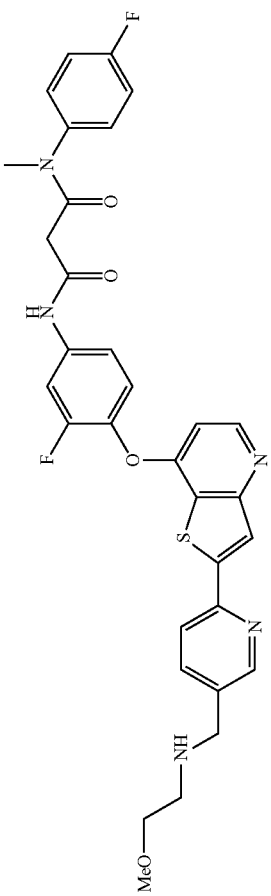<br>N1-(3-fluoro-4-(2-(5-((2-methoxyethylamino)methyl)pyridin-2-yl)thieno[3,2-b]pyridin-7-yloxy)phenyl)-N3-(4-fluorophenyl)-N3-methylmalonamide | $^1$H NMR (400 MHz, DMSO-d$_6$) δ (ppm): 10.28 (s, 1 H), 8.58 (s, 1 H), 8.52 (d, J = 5.3 Hz, 1 H), 8.33 (s, 1 H), 8.24 (d, J = 8.0 Hz, 1 H), 8.15 (s, 1 H), 7.91 (dd, J = 8.0, 2.0 Hz, 1 H), 7.79 (dd, J = 12.9, 2.0 Hz, 1 H), 7.49-7.43 (m, 3 H), 7.33-7.27 (m, 3 H), 6.66 (d, J = 5.3 Hz, 1 H), 3.92 (s, 2 H), 3.42 (t, J = 5.7 Hz, 2 H), 3.25 (s, 3 H), 3.23 (s, 2 H), 3.19 (s, 3 H), 2.69 (t, J = 5.5 Hz, 2 H). MS (m/z): 618.3 (M + H). |
| 237 | 130 | 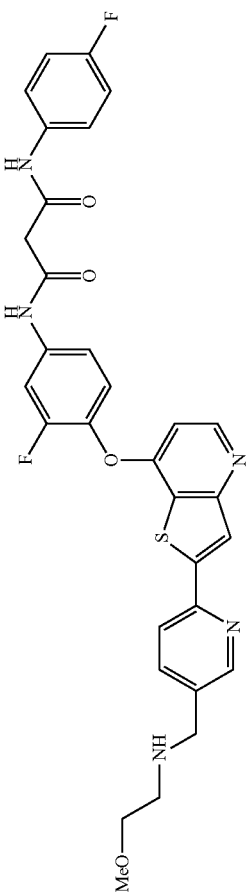<br>N1-(3-fluoro-4-(2-(5-((2-methoxyethylamino)methyl)pyridin-2-yl)thieno[3,2-b]pyridin-7-yloxy)phenyl)-N3-(4-fluorophenyl)malonamide | $^1$H NMR (400 MHz, DMSO-d$_6$) δ (ppm): 10.61 (s, 1 H), 10.32 (s, 1 H); 8.57 (s, 1 H); 8.52 (d, J = 1.4, 1 H); 8.33 (s, 1 H); 8.23 (d, J = 8.0, 1 H); 7.91 (d, J = 2.2, 1 H); 7.89-7.86 (m, 1 H); 7.66-7.60 (m, 2 H); 7.51 (t, J = 8.8, 1 H); 7.44 (dd, J = 9.0, 2.0, 1 H); 7.20-7.14 (m, 2 H); 6.68 (d, J = 5.5, 1 H); 3.78 (s, 2 H); 3.51 (s, 2 H); 3.41 (t, J = 5.7, 2 H); 3.24 (s, 3 H); 2.65 (t, J = 5.7, 2 H). MS (m/z): 604.2 (M + H). |

| Cpd. # | Ex. # | Structure | Characterization |
|---|---|---|---|
| 244 | 137 | N-(2-fluoro-4-(2-(5-((2-methoxyethylamino)methyl)pyridin-2-yl)thieno[3,2-b]pyridin-7-yloxy)phenylcarbamothioyl)-2-(4-fluorophenyl)acetamide | $^1$H NMR (400 MHz, DMSO-d$_6$) δ (ppm): 12.27 (s, 1 H), 11.94 (s, 1 H), 9.50 (s, 2 H), 8.77 (s, 1 H), 8.72 (m, 1 H), 8.41 (m, 2 H), 8.21 (m, 1 H), 8.10 (m, 1 H), 7.55 (m, 1 H), 7.36 (m, 2 H), 7.25 (m, 1 H), 7.15 (m, 3 H), 6.95 (m, 1 H), 4.21 (m, 2 H), 3.83 (s, 3 H), 3.63 (m, 2 H), 3.13 (m, 2 H) (presumably trihydrochloride salt). MS (m/z): 620.1 (M + H). |
| 252 | 145 | 1-(5-tert-butylisoxazol-3-yl)-3-(3-fluoro-4-(2-(5-((2-methoxyethylamino)methyl)pyridin-2-yl)thieno[3,2-b]pyridin-7-yloxy)phenyl)urea | $^1$H NMR (DMSO-d$_6$) d (ppm) 1 H: 9.89 (s, 1 H); 9.41 (s, 1 H); 8.56 (s, 1 H); 8.51 (d, J = 5.5, 1 H); 8.32 (s, 1 H); 8.23 (d, J = 8.0, 1 H); 7.89 (dd, J = 10.0, 1.8, 1 H); 7.55 (dd, J = 13.1, 2.3, 1 H); 7.46 (t, J = 9.0, 1 H); 7.30-7.27 (m, 1 H); 6.66 (d, J = 5.3, 1 H); 6.51 (s, 1 H); 3.77 (s, 2 H); 3.40 (t, J = 5.7, 2 H); 3.23 (s, 3 H); 2.65 (t, J = 5.5, 2 H); 1.29 (s, 9 H). LRMS (ESI): (calc.) 591.2 (found) 591.2 (MH)$^+$ |

| Cpd. # | Ex. # | Structure | Characterization |
|---|---|---|---|
| 253 | 146 | 1-(3-fluoro-4-(2-(5-(((2-methoxyethyl)amino)methyl)pyridin-2-yl)thieno[3,2-b]pyridin-7-yloxy)phenyl)-3-(2-fluoro-5-(trifluoromethyl)phenyl)urea | $^1$H NMR (400 MHz, DMSO-d$_6$) δ (ppm): 9.60 (s, 1 H), 9.07 (d, J = 2.7 Hz, 1 H), 8.68 (d, J = 1.6 Hz, 1 H), 8.59 (dd, J = 7.1, 2.3 Hz, 1 H), 8.55 (d, J = 5.5 Hz, 1 H), 8.41 (s, 1 H), 8.34 (d, J = 8.2 Hz, 1 H), 8.03 (dd, J = 8.1, 2.1 Hz, 1 H), 7.79 (dd, J = 13.1, 2.5 Hz, 1 H), 7.58-7.40 (m, 3 H), 7.28 (bd, J = 8.6 Hz, 1 H), 6.70 (d, J = 5.3 Hz, 1 H), 4.13 (bs, 2 H), 3.54 (t, J = 5.2 Hz, 2 H), 3.30 (s, 3 H), 3.08-12.96 (m, 2 H), one NH is not observed (presumably trifluoroacetate salt). MS (m/z): 630.2 (M + H). |
| 254 | 147 | N-(3-fluoro-4-(2-(5-(((2-methoxyethyl)amino)methyl)furan-2-yl)thieno[3,2-b]pyridin-7-yloxy)phenyl)-N-(4-fluorophenyl)cyclopropane-1,1-dicarboxamide | $^1$H NMR (400 MHz, DMSO-d$_6$) □ (ppm): 10.42 (s, 1 H), 10.01 (s, 1 H), 8.49 (d, J = 5.3 Hz, 1 H), 8.15 (s, 1 H, formate salt), 7.90 (dd, J = 13.3, 2.0 Hz, 1 H), 7.77 (s, 1 H), 7.68-7.60 (m, 2 H), 7.54-7.43 (m, 2 H), 7.20-7.11 (m, 2 H), 7.10 (d, J = 3.3 Hz, 1 H), 6.60 (d, J = 5.5 Hz, 1 H), 6.50 (d, J = 3.3 Hz, 1 H), 3.82 (s, 2 H), one CH$_2$ is masked by water peak, 3.24 (s, 3 H), 2.74 (t, J = 5.7 Hz, 2 H), 1.51-1.43 (m, 4 H), one NH is missing. MS (m/z): 619.2 (M + H). |

| Cpd. # | Ex. # | Structure | Characterization |
|---|---|---|---|
| 255 | 148 | 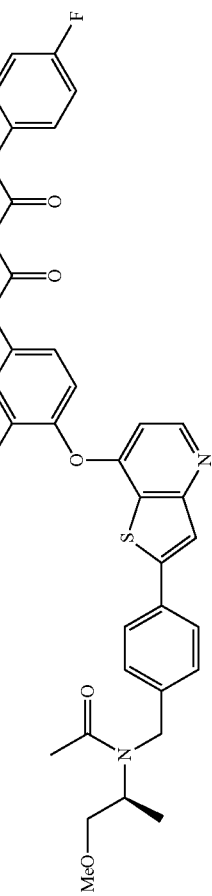<br>(S)-N-(3-fluoro-4-(2-(4-((N-(1-methoxypropan-2-yl)acetamido)methyl)phenyl)thieno[3,2-b]pyridin-7-yloxy)phenyl)-N-(4-fluorophenyl)cyclopropane-1,1-dicarboxamide | $^1$H NMR (400 MHz, DMSO-d$_6$) (ppm) (ppm): mixture of rotamers, 10.42 (s, 1 H), 10.02 (s, 1 H), 8.53-8.47 (m, 1 H), 8.06 and 8.02 (2 s, 1 H), 7.95-7.77 (m, 3 H), 7.68-7.60 (m, 2 H), 7.55-7.43 (m, 2 H), 7.41 and 7.35 (2 d, J = 8.2 Hz, 2 H), 7.15 (t, J = 8.8 Hz, 2 H), 6.60 (t, J = 5.3 Hz, 1 H), 4.73-4.17 (m, 3 H), 3.42-3.23 (m, 2 H), 3.16 (s, 3 H), 2.16 and 1.93 (2 s, 3 H), 1.53-1.42 (m, 4 H), 1.09-1.00 (m, 3 H). MS (m/z): 685.3 (M + H) |
| 256 | 149 | 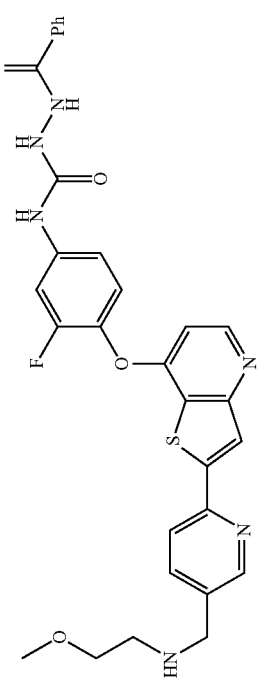<br>2-benzoyl-N-(3-fluoro-4-(2-(5-((2-methoxyethylamino)methyl)pyridin-2-yl)thieno[3,2-b]pyridin-7-yloxy)phenyl)hydrazinecarboxamide | $^1$H NMR (400 MHz, DMSO-d$_6$) δ (ppm): 10.36 (br, 1 H), 9.37 (br, 1 H), 8.57-8.49 (m, 3 H), 8.38 (s, 1 H), 8.23 (dd, J = 8.2 Hz, 1 H), 7.95-7.88 (m, 3 H), 7.78 (d, J = 12.9 Hz, 1 H), 7.59-7.56 (m, 1 H), 7.52-7.49 (m, 2 H), 7.45-7.41 (m, 2 H), 6.66 (d, J = 5.5 Hz, 1 H), 3.78 (s, 2 H), 3.41 (t, J = 5.7 Hz, 2 H), 3.24 (s, 3 H), 2.65 (t, J = 5.7 Hz, 2 H), 2.28 (br, 1 H). MS (m/z): 587.3 (M + H). |

| Cpd. # | Ex. # | Structure | Characterization |
|---|---|---|---|
| 257 | 150 | N-(3-fluoro-4-(2-(6-((2-methoxyethyl)amino)methyl)pyridin-2-yl)thieno[3,2-b]pyridin-7-yloxy)phenyl)-N-(4-fluorophenyl)cyclopropane-1,1-dicarboxamide | ¹H NMR (400 MHz, DMSO-d₆) δ (ppm): 8.51 (d, J = 5.5 Hz, 1 H), 8.32 (s, 1 H), 8.11 (d, J = 7.7 Hz, 2 H), 7.90 (m, 2 H), 7.62 (m, 2 H), 7.45 (m, 3 H), 7.13 (t, J = 8.8 Hz, 2 H), 6.61 (d, J = 5.1 Hz, 1 H), 3.86 (s, 2 H), 2.72 (m, 2 H), 1.41 (brs, 4 H). MS (m/z): 630.3 (M + H). |
| 258 | 151 | (S)-N-(3-fluoro-4-(2-(4-((N-(1-methoxypropan-2-yl)acetamido)methyl)phenyl)thieno[3,2-b]pyridin-7-yloxy)phenyl)-1-phenyl-5-(trifluoromethyl)-1H-pyrazole-4-carboxamide | ¹H NMR (400 MHz, DMSO-d₆) δ (ppm): mixture of rotamers, 10.92 (s, 1 H), 8.52 (dd, J = 5.5, 3.5 Hz, 1 H), 8.36 (s, 1 H), 8.07 and 8.03 (2 s, 1 H), 7.96 (dd, J = 13.7, 2.0 Hz, 1 H), 7.91 (d, J = 8.2 Hz, 1 H), 7.82 (d, J = 8.2 Hz, 1 H), 7.67-7.51 (m, 7 H), 7.41 (d, J = 8.2 Hz, 1 H), 7.36 (d, J = 8.2 Hz, 1 H), 6.67 (t, J = 5.5 Hz, 1 H), 4.74-4.16 (m, 3 H), 3.42-3.24 (m, 2 H), 3.16 (s, 3 H), 2.16 and 1.93 (2 s, 3 H), 1.09-1.01 (m, 3 H). MS (m/z): 718.3 (M + H). |

| Cpd. # | Ex. # | Structure | Characterization |
|---|---|---|---|
| 259 | 152 | 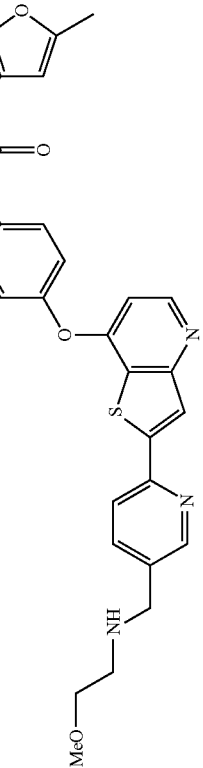 1-(2-fluoro-4-(2-(5-((2-methoxyethylamino)methyl)pyridin-2-yl)thieno[3,2-b]pyridin-7-yloxy)phenyl)-3-(5-methylisoxazol-3-yl)urea | $^1$H NMR (400 MHz, DMSO-$d_6$) δ (ppm): 9.92 (s, 1 H), 9.02 (s, 1 H), 8.57 (d, J = 1.4 Hz, 1 H), 8.54 (d, J = 5.3 Hz, 1 H), 8.32 (s, 1 H), 8.26 (s, 1 H), 8.24-8.17 (m, 2 H), 7.89 (dd, J = 8.0 Hz, 1 H), 7.44 (dd, J = 11.6, 2.7, 1 H), 7.17-7.14 (m, 1 H), 6.74 (d, J = 5.5 Hz, 1 H), 6.54 (d, J = 1.0 Hz, 1 H), 3.78 (s, 2 H), 3.41 (t, J = 5.7 Hz, 2 H), 3.24 (s, 3 H), 2.65 (t, J = 5.7 Hz, 2 H), 2.37 (s, 3 H). MS (m/z): 549.1 (M + H). |
| 260 | 153 | 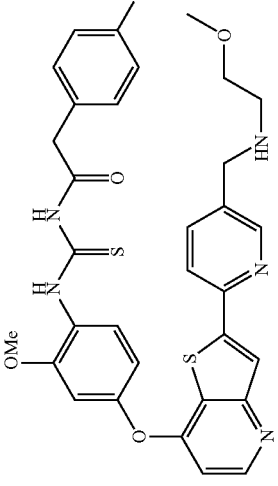 2-(4-fluorophenyl)-N-(2-methoxy-4-(2-(5-((2-methoxyethylamino)methyl)pyridin-2-yl)thieno[3,2-b]pyridin-7-yloxy)phenyl)carbamothioyl)acetamide | $^1$H NMR (400 MHz, DMSO-$d_6$) δ (ppm): 12.70 (s, 1 H), 11.73 (s, 1 H), 9.04 (s, 2 H), 8.7 (s, 1 H), 8.64 (d, J = 8.8 Hz, 1 H), 8.56 (m, 1 H), 8.41 (s, 1 H), 8.36 (d, J = 8.2 Hz, 1 H), 8.08 (m, 1 H), 7.36 (m, 2 H), 7.15 (m, 3 H), 6.92 (m, 1 H), 6.75 (m, 1 H), 4.2 (m, 2 H), 3.82 (m, 5 H), 3.58 (m, 2 H), 3.31 (s, 3 H), 3.15 (m, 2 H). MS (m/z): 632.1 (M + H). |

| Cpd. # | Ex. # | Structure | Characterization |
|---|---|---|---|
| 261 | 154 | 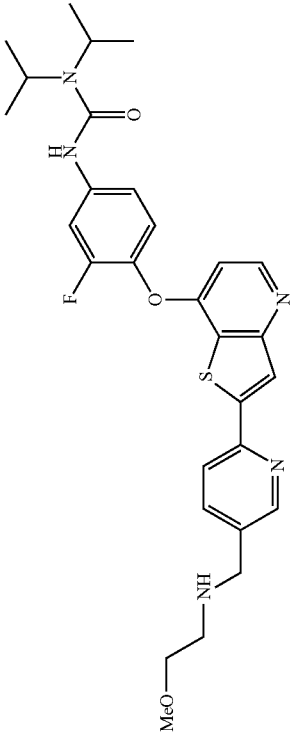<br>3-(3-fluoro-4-(2-(5-((2-methoxyethylamino)methyl)pyridin-2-yl)thieno[3,2-b]pyridin-7-yloxy)phenyl)-1,1-diisopropylurea | ¹H NMR (400 MHz, DMSO-d₆) δ (ppm): 8.55 (s, 1 H), 8.50 (d, J = 5.3 Hz, 1 H), 8.41 (s, 1 H), 8.30 (s, 1 H), 8.21 (d, J = 8.8 Hz, 1 H), 7.88 (dd, J 8.0, 2.2 Hz, 1 H), 7.70 (dd, J = 13.0, 2.3 Hz, 1 H), 7.37-7.33 (m, 2 H), 6.62 (dd, J = 5.3, 0.8 Hz, 1 H), 3.83 (sept, J = 6.7 Hz, 2 H), 3.76 (s, 2 H), 3.39 (t, J = 5.7 Hz, 2 H), 3.23 (s, 3 H), 2.64 (t, J = 5.7 Hz, 2 H), 1.25 (d, J = 6.7 Hz, 12 H). MS (m/z): 552.2 (M + H). |
| 262 | 155 | 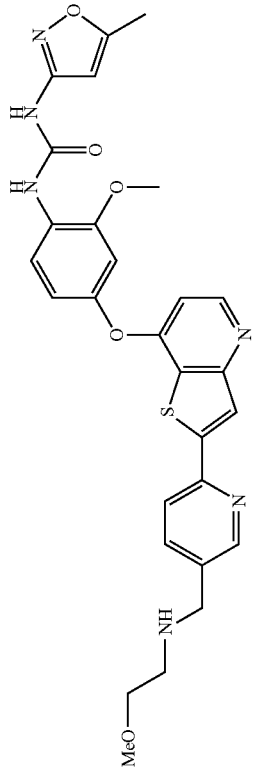<br>1-(2-methoxy-4-(2-(5-((2-methoxyethylamino)methyl)pyridin-2-yl)thieno[3,2-b]pyridin-7-yloxy)phenyl)-3-(5-methylisoxazol-3-yl)urea | ¹H NMR (400 MHz, DMSO-d₆) δ (ppm): 10.01 (s, 1 H), 8.76 (bs, 1 H), 8.57 (d, J = 1.2 Hz, 1 H), 8.51 (d, J = 5.6 Hz, 1 H), 8.31 (s, 1 H), 8.23 (d, J = 8.4 Hz, 1 H), 8.20 (d, J = 8.8 Hz, 1 H), 7.89 (dd, J = 8.4, 1.6 Hz, 1 H), 7.10 (d, J = 2.8 Hz, 1 H), 6.87 (dd, J = 8.8, 2.8 Hz, 1 H), 6.67 (d, J = 5.6 Hz, 1 H), 6.52 (s, 1 H), 3.89 (s, 3 H), 3.78 (s, 2 H), 3.41 (t, J = 5.6 Hz, 2 H), 3.24 (s, 3 H), 2.65 (t, J = 5.6 Hz, 2 H), 2.37 (s, 3 H). MS (m/z): 561.1 (M + H). |

-continued

| Cpd. # | Ex. # | Structure | Characterization |
|---|---|---|---|
| 263 | 156 | 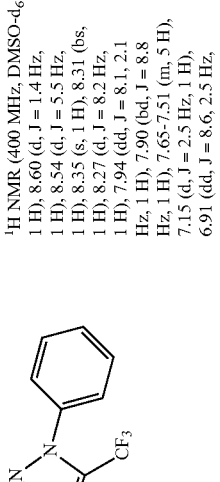<br>N-(2-methoxy-4-(2-(5-(((2-methoxyethylamino)methyl)pyridin-2-yl)thieno[3,2-b]pyridin-7-yloxy)phenyl)-1-phenyl-5-(trifluoromethyl)-1H-pyrazole-4-carboxamide | ¹H NMR (400 MHz, DMSO-d₆) δ (ppm): 9.86 (s, 1 H), 8.60 (d, J = 1.4 Hz, 1 H), 8.54 (d, J = 5.5 Hz, 1 H), 8.35 (s, 1 H), 8.31 (bs, 1 H), 8.27 (d, J = 8.2 Hz, 1 H), 7.94 (dd, J = 8.1, 2.1 Hz, 1 H), 7.90 (bd, J = 8.8 Hz, 1 H), 7.65-7.51 (m, 5 H), 7.15 (d, J = 2.5 Hz, 1 H), 6.91 (dd, J = 8.6, 2.5 Hz, 1 H), 6.74 (d, J = 5.3 Hz, 1 H), 3.93-3.81 (m, 5 H), 3.45 (t, J = 5.6 Hz, 2 H), 3.26 (s, 3 H), 2.76 (bt, J = 5.1 Hz, 2 H). MS (m/z): 675.2 (M + H). |
| 264 | 157 | 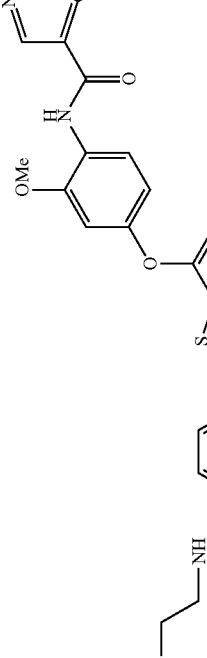<br>N-(4-fluorophenyl)-N-(2-methoxy-4-(2-(5-((2-methoxyethylamino)methyl)pyridin-2-yl)thieno[3,2-b]pyridin-7-yloxy)phenyl)cyclopropane-1,1-dicarboxamide | ¹H NMR (400 MHz, DMSO-d₆) δ (ppm): 10.67 (s, 1 H), 9.78 (s, 1 H), 8.54 (d, J = 1.1 Hz, 1 H), 8.50 (d, J = 5.5 Hz, 1 H), 8.29 (s, 1 H), 8.26-8.17 (m, 2 H), 7.87 (dd, J = 8.0, 2.0 Hz, 1 H), 7.59-7.56 (m, 2 H), 7.21-7.16 (m, 2 H), 7.12-7.09 (m, 1 H), 6.84 (dd, J = 8.8, 2.5 Hz, 1 H), 6.65 (d, J = 5.5 Hz, 1 H), 3.82 (s, 3 H), 3.76 (s, 2 H), 3.29 (m, 2 H), 3.22 (s, 3 H), 2.64-2.62 158 (m, 2 H), 1.61-1.56 (m, 4 H). MS (m/z): 642.2 (M + H). |

| Cpd. # | Ex. # | Structure | Characterization |
|---|---|---|---|
| 265 | 158 | 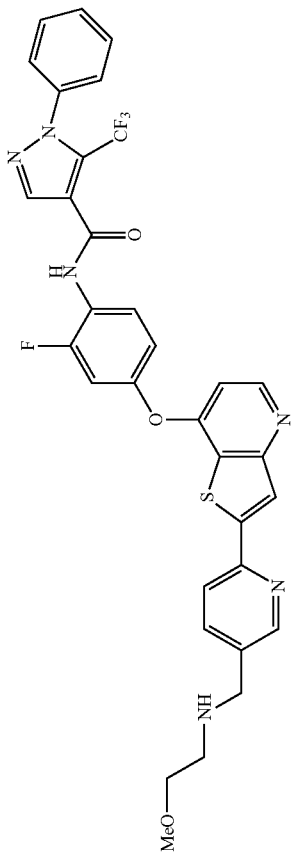 N-(2-fluoro-4-(2-(5-((2-methoxyethylamino)methyl)pyridin-2-yl)thieno[3,2-b]pyridin-7-yloxy)phenyl)-1-phenyl-5-(trifluoromethyl)-1H-pyrazole-4-carboxamide | $^1$H NMR (400 MHz, DMSO-d$_6$) δ (ppm): 10.50 (s, 1 H), 8.60-8.55 (m, 2 H), 8.34 (s, 2 H), 8.25 (d, J = 8.2 Hz, 1 H), 7.90 (dd, J = 8.2, 2.2 Hz, 1 H), 7.84 (t, J = 8.8 Hz, 1 H), 7.65-7.52 (m, 5 H), 7.47 (dd, J = 11.1, 2.6 Hz, 1 H), 7.24-7.19 (m, 1 H), 6.82 (d, J = 5.5 Hz, 1 H), 3.79 (s, 2 H), 3.41 (t, J = 5.7 Hz, 2 H), 3.24 (s, 3 H), 2.66 (t, J = 5.7 Hz, 2 H). MS (m/z): 663.2 (M + H). |
| 266 | 159 | 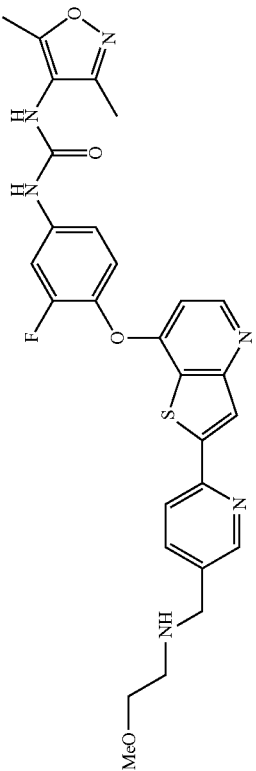 1-(3,5-dimethylisoxazol-4-yl)-3-(3-fluoro-4-(2-(5-((2-methoxyethylamino)methyl)pyridin-2-yl)thieno[3,2-b]pyridin-7-yloxy)phenyl)urea | $^1$H NMR (400 MHz, DMSO-d$_6$) δ (ppm): 9.26 (s, 1 H), 8.57 (d, J = 1.2 Hz, 1 H), 8.52 (s, 1 H), 8.23 (d, J = 5.6 Hz, 1 H), 8.32 (s, 1 H), 7.91 (s, 1 H), 8.0 Hz, 1 H), 7.89 (d, J = 2.0 Hz, 1 H), 7.73 (dd, J = 13.2, 2.4 Hz, 1 H), 7.43 (t, J = 8.8 Hz, 1 H), 7.29 (d, J = 8.8 Hz, 1 H), 6.65 (dd, J = 5.6, 0.8 Hz, 1 H), 3.78 (s, 2 H), 3.41 (t, J = 5.6 Hz, 2 H), 3.24 (s, 3 H), 2.65 (t, J = 5.6 Hz, 2 H), 2.30 (s, 3 H), 2.13 (s, 3 H). MS (m/z): 563.2 (M + H). |

| Cpd. # | Ex. # | Structure | Characterization |
|---|---|---|---|
| 267 | 160 | 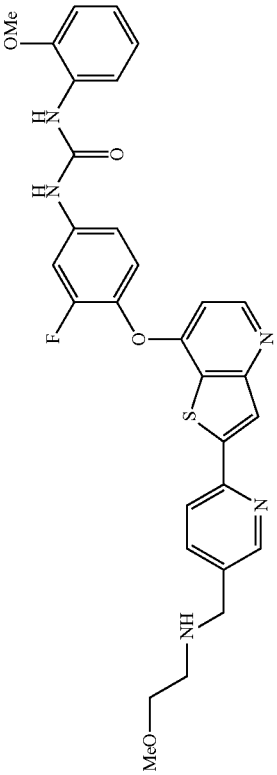<br>1-(3-fluoro-4-(2-(5-((2-methoxyethylamino)methyl)pyridin-2-yl)thieno[3,2-b]pyridin-7-yloxy)phenyl)-3-(2-methoxyphenyl)urea | $^1$H NMR (400 MHz, DMSO-$d_6$) (ppm) (ppm): 9.69 (s, 1 H), 8.57 (d, J = 1.2 Hz, 1 H), 8.53 (d, J = 5.6 Hz, 1 H), 8.33 (s, 1 H), 8.33 (s, 1 H), 8.24 (d, J = 8.0 Hz, 1 H), 8.33 J = 8.0, 1.6 Hz, 1 H), 7.90 (dd, J = 8.0, 2.0 Hz, 1 H), 7.78 (dd, J = 13.2, 2.4 Hz, 1 H), 7.45 (t, J = 9.2 Hz, 1 H), 7.21 (d, J = 9.0 Hz, 1 H), 7.40 (dd, J = 8.4, 1.6 Hz, 1 H), 6.98 (td, J = 8.0, 1.6 Hz, 1 H), 6.91 (td, J = 8.0, 1.6 Hz, 1 H), 6.67 (d, J = 5.6 Hz, 1 H), 3.90 (s, 3 H), 3.78 (s, 2 H), 3.41 (t, J = 5.6 Hz, 2 H), 3.24 (s, 3 H), 2.65 (t, J = 5.6 Hz, 2 H). MS (m/z): 574.2 (M + H). |
| 268 | 161 | 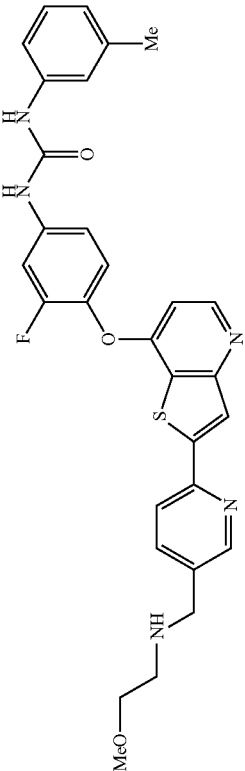<br>1-(3-fluoro-4-(2-(5-((2-methoxyethylamino)methyl)pyridin-2-yl)thieno[3,2-b]pyridin-7-yloxy)phenyl)-3-m-tolylurea | $^1$H NMR (400 MHz, DMSO-$d_6$) δ (ppm): 9.68 (s, 1 H), 9.31 (s, 1 H), 8.64 (d, J = 1.6 Hz, 1 H), 8.53 (d, J = 5.5 Hz, 1 H), 8.36 (s, 1 H), 8.28 (d, J = 8.2 Hz, 1 H), 7.97 (dd, J = 8.2, 2.2 Hz, 1 H), 7.79 (dd, J = 13.5, 2.5 Hz, 1 H), 7.44 (t, J = 9.1 Hz, 1 H), 7.34 (bs, 1 H), 7.31-7.25 (m, 2 H), 7.16 (t, J = 7.7 Hz, 1 H), 6.80 (d, J = 7.4 Hz, 1 H), 6.68 (dd, J = 5.5, 0.8 Hz, 1 H), 3.99 (s, 2 H), 3.49 (t, J = 5.4 Hz, 2 H), 3.27 (s, 3 H), 2.87 (t, J = 5.4 Hz, 2 H), 2.28 (s, 3 H). MS (m/z): 558.1 (M + H). |

| Cpd. # | Ex. # | Structure | Characterization |
|---|---|---|---|
| 269 | 162 | 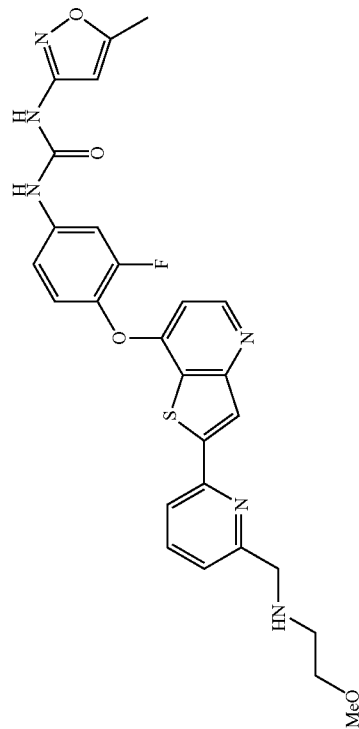1-(3-fluoro-4-(2-(6-((2-methoxyethylamino)methyl)pyridin-2-yl)thieno[3,2-b]pyridin-7-yloxy)phenyl)-3-(5-methylisoxazol-3-yl)urea | 1H NMR (400 MHz, DMSO-d6) δ (ppm): 9.63 (s, 1 H), 9.22 (s, 1 H), 8.52 (d, J = 5.5 Hz, 1 H), 8.36 (s, 1 H), 8.15 (d, J = 7.4 Hz, 1 H), 7.93 (t, J = 7.8 Hz, 1 H), 7.74 (dd, J = 12.9, 2.5 Hz, 1 H), 7.46 (t, J = 8.0 Hz, 2 H), 7.27 (m, 1 H), 6.64 (dd, J = 5.2, 0.8 Hz, 1 H), 6.55 (s, 1 H), 3.94 (s, 2 H), 3.46 (t, J = 5.4 Hz, 2 H), 3.25 (s, 3 H), 2.81 (m, 2 H), 2.37 (s, 3 H). MS (m/z): 549.1 (M + H). |
| 270 | 163 | 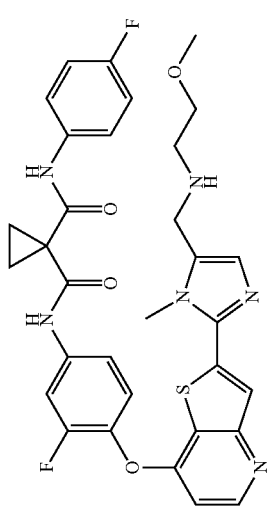N-(3-fluoro-4-(2-(5-((2-methoxyethylamino)methyl)-1-methyl-1H-imidazol-2-yl)thieno[3,2-b]pyridin-7-yloxy)phenyl)-N-(4-fluorophenyl)cyclopropane-1,1-dicarboxamide | 1H NMR (400 MHz, DMSO-d6) □ (ppm): 10.40 (s, 1 H), 10.02 (s, 1 H), 8.51 (d, J = 5.28 Hz, 1 H), 7.89 (m, 2 H), 7.63 (m, 2 H), 7.48 (m, 2 H), 7.15 (t, J = 8.80, 2 H), 6.95 (s, 1 H), 6.67 (d, J = 5.28 Hz, 1 H) k, 3.91 (s, 3 H), 3.76 (s, 2 H), 3.40 (t, J = 5.68 Hz, 2 H), 3.24 (s, 3 H), 2.68 (t, J = 5.68 Hz, 2 H), 1.46 (s, 4 H). MS (m/z): 633.7 (M + H). |

| Cpd. # | Ex. # | Structure | Characterization |
|---|---|---|---|
| 271 | 164 | 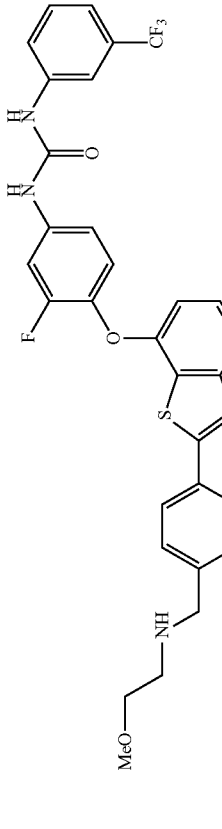 1-(3-fluoro-4-(2-(5-((2-methoxyethylamino)methyl)pyridin-2-yl)thieno[3,2-b]pyridin-7-yloxy)phenyl)-3-(3-(trifluoromethyl)phenyl)urea | $^1$H NMR (400 MHz, DMSO-d$_6$) δ (ppm): 9.24 (bs, 2 H), 8.58 (d, J = 1.6 Hz, 1 H), 8.53 (d, J = 5.5 Hz, 1 H), 8.33 (s, 1 H), 8.25 (d, J = 8.2 Hz, 1 H), 8.02 (bs, 1 H), 7.91 (dd, J = 8.2, 2.2 Hz, 1 H), 7.77 (dd, J = 13.2, 2.4 Hz, 1 H), 7.62 (bd, J = 8.6 Hz, 1 H), 7.54 (t, J = 7.9 Hz, 1 H), 7.47 (t, J = 9.1 Hz, 1 H), 7.37-7.27 (m, 2 H), 6.67 (dd, J = 5.4, 0.7 Hz, 1 H), 3.81 (s, 2 H), 3.25 (s, 3 H), 5.6 Hz, 2 H), 3.42 (t, J = 2.69 (t, J = 5.7 Hz, 2 H). MS (m/z): 612.3 (M + H). |
| 272 | 165 | 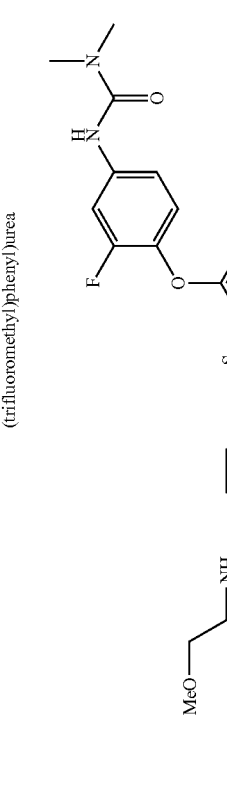 3-(3-Fluoro-4-(2-(5-((2-methoxyethylamino)methyl)pyridin-2-yl)thieno[3,2-b]pyridin-7-yloxyphenyl)-1,1-dimethylurea | $^1$H NMR (400 MHz, DMSO-d$_6$) δ (ppm): 8.65 (s, 1 H); 8.57 (d, J = 1.6, 1 H); 8.51 (d, J = 5.5, 1 H); 8.32 (s, 1 H); 8.23 (d, J = 8.6, 1 H); 7.90 (dd, J = 8.2, 2.4, 1 H); 7.74-7.71 (m, 1 H); 7.40-7.37 (m, 2 H); 6.64 (d, J = 5.5, 1 H); 3.79 (s, 2 H); 3.41 (t, J = 5.7, 2 H); 3.24 (s, 3 H); 2.95 (s, 6 H); 2.67 (t, J = 5.7, 2 H). MS (m/z): 496.3 (M + H). |

| Cpd. # | Ex. # | Structure | Characterization |
|---|---|---|---|
| 273 | 166 | 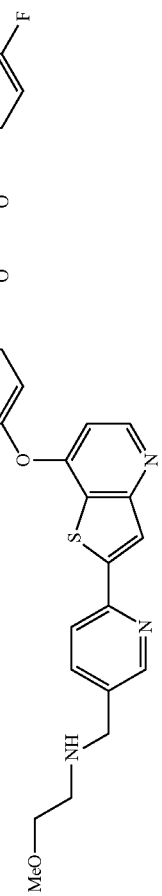<br>N-(2-Fluoro-4-(2-(5-((2-methoxyethylamino)methyl)pyridin-2-yl)thieno[3,2-b]pyridin-7-yloxy)phenyl)-N-(4-fluorophenyl)cyclopropane-1,1-dicarboxamide | $^1$H NMR (400 MHz, DMSO-d$_6$) δ (ppm): 10.66 (s, 1 H); 9.95 (s, 1 H); 8.55-8.53 (m, 2 H); 8.32 (s, 1 H); 8.23-8.21 (m, 1 H); 7.99 (t, J = 8.8, 1 H); 7.88 (dd, J = 8.0, 2.2, 1 H); 7.61-7.58 (m, 2 H); 7.43-7.40 (m, 1 H); 7.19-7.13 (m, 3 H); 6.75 (d, J = 5.3, 1 H); 3.77 (s, 2 H); 3.40 (t, J = 5.7, 2 H); 3.23 (s, 3 H); 2.64 (t, J = 5.3, 2 H); 1.60-1.55 (m, 4 H). MS (m/z): 630.3 (M + H) |
| 274 | 167 | 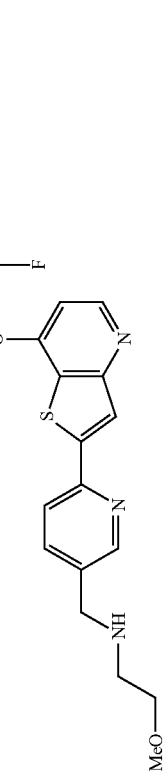<br>1-allyl-3-(3-fluoro-4-(2-(5-((2-methoxyethylamino)methyl)pyridin-2-yl)thieno[3,2-b]pyridin-7-yloxy)phenyl)urea | $^1$H NMR (400 MHz, DMSO-d$_6$) δ (ppm): 8.93 (s, 1 H), 8.56 (d, 1 H, J = 1.3 Hz), 8.51 (d, 1 H, J = 5.5 Hz), 8.30 (s, 1 H), 8.22 (d, 1 H, J = 8.0 Hz), 7.89 (dd, 1 H, J = 2.2 Hz, J = 8.0 Hz), 7.72 (dd, 1 H, J = 2.6 Hz, J = 13.5 Hz), 7.37 (t, 1 H, J = 9.2 Hz), 7.16 (m, 1 H), 6.63 (d, 1 H, J = 5.9 Hz), 6.43 (m, 1 H), 5.86 (m, 1 H), 5.17 (dd, 1 H, J = 1.8 Hz, J = 17.2 Hz), 5.08 (dd, 1 H, J = 1.6 Hz, J = 10.2 Hz), 3.77 (s, 2 H), 7.74 (t, 2 H, J = 5.5 Hz), 3.40 (t, 2 H, J = 5.7 Hz), 3.23 (s, 2 H), 2.64 (t, 2 H, J = 5.6 Hz). MS (m/z): 508.3 (M + H). |

| Cpd. # | Ex. # | Structure | Characterization |
|---|---|---|---|
| 275 | 168 | 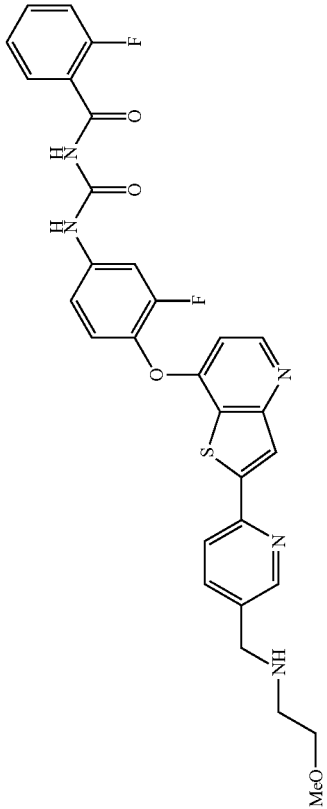 1-(3-fluoro-4-(2-(5-((2-methoxyethylamino)methyl)pyridin-2-yl)thieno[3,2-b]pyridin-7-yloxy)phenyl)-3-(2-fluorobenzyl)urea | $^1$H NMR (400 MHz, DMSO-$d_6$) δ (ppm): 9.03 (s, 1 H), 8.56 (m, 1 H), 8.50 (d, 1 H, J = 5.5 Hz), 8.31 (s, 1 H), 8.22 (d, 1 H, J = 8.0 Hz), 7.89 (dd, 1 H, J = 2.2 Hz, J = 8.0 Hz), 7.71 (dd, 1 H, J = 2.4 Hz, J = 13.5 Hz), 7.1–7.4 (m, 6 H), 6.81 (t, 1 H, J = 6.0 Hz), 6.63 (dd, 1 H, J = 1.0 Hz, J = 5.5 Hz), 4.36 (d, 2 H, J = 6.0 Hz), 3.77 (s, 2 H), 3.40 (t, 2 H, J = 5.5 Hz), 3.23 (s, 3 H), 2.64 (t, 2 H, J = 5.6 Hz). MS (m/z): 576.3 (M + H). |
| 276 | 169 | 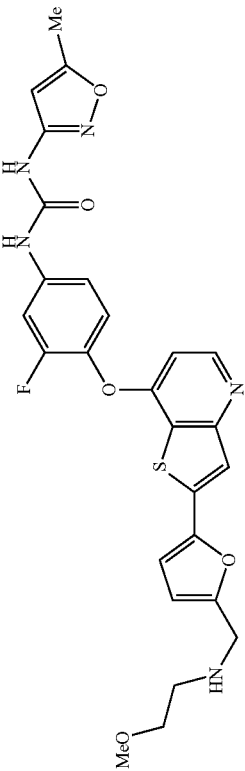 1-(3-fluoro-4-(2-(5-((2-methoxyethylamino)methyl)furan-2-yl)thieno[3,2-b]pyridin-7-yloxy)phenyl)-3-(5-methylisoxazol-3-yl)urea | $^1$H NMR (400 MHz, DMSO-$d_6$) δ (ppm): 9.66 (s, 1 H), 9.21 (s, 1 H), 8.49 (d, J = 5.5 Hz, 1 H), 7.77 (s, 1 H), 7.74 (dd, J = 13.0, 2.4 Hz, 1 H), 7.46 (t, J = 9.0 Hz, 1 H), 7.31–7.25 (m, 1 H), 7.09 (d, J = 3.3 Hz, 1 H), 6.62 (d, J = 5.5 Hz, 1 H), 6.56 (d, J = 1.0 Hz, 1 H), 6.47 (d, J = 3.3 Hz, 1 H), 3.78 (s, 2 H), 3.40 (t, J = 5.7 Hz, 2 H), 3.24 (s, 3 H), 2.71 (t, J = 5.7 Hz, 2 H), 2.37 (d, J = 0.8 Hz, 3 H), one NH is missing. MS (m/z): 538.3 (M + H). |

| Cpd. # | Ex. # | Structure | Characterization |
|---|---|---|---|
| 277 | 170 | 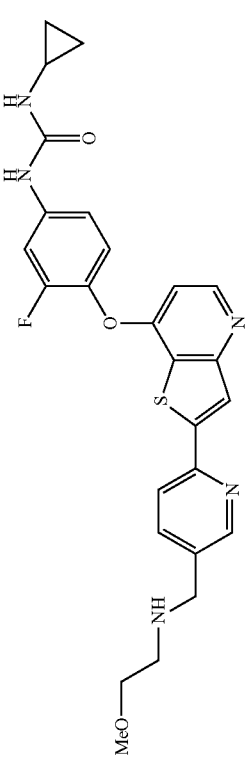<br>1-Cyclopropyl-3-(3-fluoro-4-(2-(5-((2-methoxyethylamino)methyl)pyridin-2-yl)thieno[3,2-b]pyridin-7-yloxy)phenyl)urea | $^1$H NMR (400 MHz, DMSO-d$_6$) δ (ppm): 8.80 (s, 1 H); 8.57 (s, 1 H); 8.51 (d, J = 5.5, 1 H); 8.31 (s, 1 H); 8.23 (d, J = 8.0, 1 H); 7.89 (dd, J = 8.0, 1.5, 1 H); 7.73 (dd, J = -13.5, 2.2, 1 H); 7.38 (t, J = 9.0, 1 H); 7.20 (d, J = 8.2, 1 H); 6.66-6.62 (m, 2 H); 3.78 (s, 2 H); 3.41 (t, J = 5.7, 2 H); 3.24 (s, 3 H); 2.65 (d, J = 5.7, 2 H); 2.57-2.51 (m, 1 H); 0.66-0.62 (m, 2 H); 0.44-0.41 (m, 2 H). MS (m/z): 508.3 (M + H). |
| 278 | 171 | 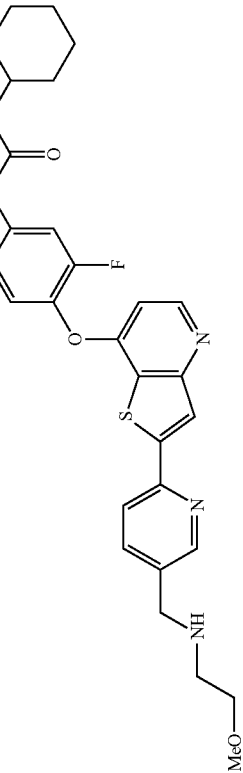<br>1-cyclohexyl-3-(3-fluoro-4-(2-(5-((2-methoxyethylamino)methyl)pyridin-2-yl)thieno[3,2-b]pyridin-7-yloxy)phenyl)urea | $^1$H NMR (400 MHz, DMSO-d$_6$) δ (ppm): 8.74 (s, 1 H), 8.56 (d, 1 H, J = 0.6 Hz), 8.51 (d, 1 H, J = 5.2 Hz), 8.30 (s, 1 H), 8.22 (d, 1 H, J = 7.8 Hz), 7.89 (dd, 1 H, J = 1.9 Hz, J = 6.1 Hz), 7.36 (t, 1 H, J = 9.0 Hz), 7.12 (m, 1 H), 6.63 (d, 1 H, J = 5.5 Hz), 6.26 (d, 1 H, J = 8.0 Hz), 3.79 (s, 2 H), [3.44 (2 H)], 3.23 (s, 3 H), 2.66 (t, 2 H, 5.5 Hz), 1.80 (m, 2 H), 1.66 (m, 2 H), 1.52 (m, 1 H), 2.1-2.4 (m, 6 H). MS (m/z): 550.4 (M + H). |

| Cpd. # | Ex. # | Structure | Characterization |
|---|---|---|---|
| 279 | 172 | 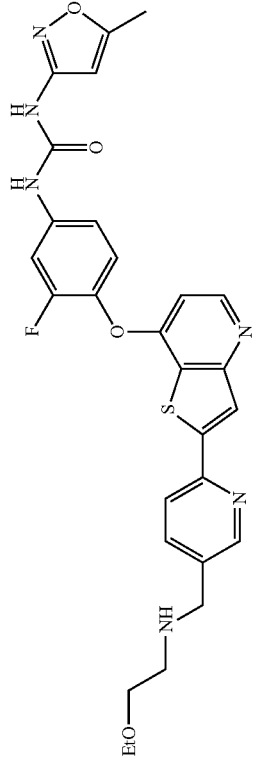<br>1-(4-(2-(5-((2-ethoxyethylamino)methyl)pyridin-2-yl)thieno[3,2-b]pyridin-7-yloxy)-3-fluorophenyl)-3-(5-methylisoxazol-3-yl)urea | ¹H NMR (400 MHz, DMSO-d₆) δ (ppm): 9.77 (s, 1 H); 9.35 (s, 1 H); 9.00 (s, 2 H); 8.73 (d, J = 1.4, 1 H); 8.55 (d, J = 5.5, 1 H); 8.43 (s, 1 H); 8.38 (d, J = 8.0, 1 H); 8.08 (dd, J = 8.2, 2.2, 1 H); 7.75 (dd, J = 13.1, 2.5, 1 H); 7.47 (t, J = 9.0, 1 H); 7.31-7.28 (m, 1 H); 6.70 (dd, J = 5.5, 0.7, 1 H); 6.56 (d, J = 1.0, 1 H); 4.28 (s, 2 H); 3.63 (t, J = 5.0, 2 H); 3.50 (q, 7.0, 2 H); 3.16 (brs, 2 H); 2.38 (d, J = 0.7, 3 H); 1.16 (t, J = 7.1, 3 H). MS (m/z): 563.3 (M + H). |
| 280 | 173 | 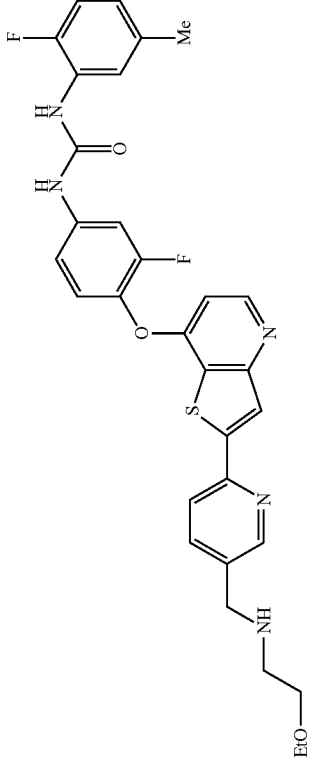<br>1-(4-(2-(5-((2-ethoxyethylamino)methyl)pyridin-2-yl)thieno[3,2-b]pyridin-7-yloxy)-3-fluorophenyl)-3-(2-fluoro-5-methylphenyl)urea | ¹H NMR (400 MHz, DMSO-d₆) δ (ppm): 9.45 (s, 1 H), 8.97 (br, s, 2 H), 8.72 (d, 1 H, (dd, 1 H, J = J = 1.4 Hz), 8.62 (d, 1 H, J = 2.3 Hz), 8.57 (d, 1 H, J = 5.5 Hz), 8.42 (s, H) 8.38 (d, 1 H, J = 8. Hz), 8.08 (dd, 1 H, J = 2.2 Hz, J = 8.2 Hz), 7.93 (dd, 1 H, J = 2.0 Hz, J = 7.8 Hz) 7.78 (dd, 1 H, J = 2.6 Hz, J = 13.3 Hz), 7.46 (t, 1 H, J = 9.0 Hz), 7.24 (m, 1 H), 7.12 (dd, 1 H, J = 8.4 Hz, J = 11.1 Hz), 6.84 (m, 1 H), 6.74 (d, 1 H, J = 5.5 Hz), 4.27 (m, 2 H), [3.2-3.6 (9 H)], 2.27 (s, 3 H), 1.15 (t, 3 H, J = 7.0 Hz). MS (m/z): 590.4 (M + H). |

| Cpd. # | Ex. # | Structure | Characterization |
|---|---|---|---|
| 281 | 173 | 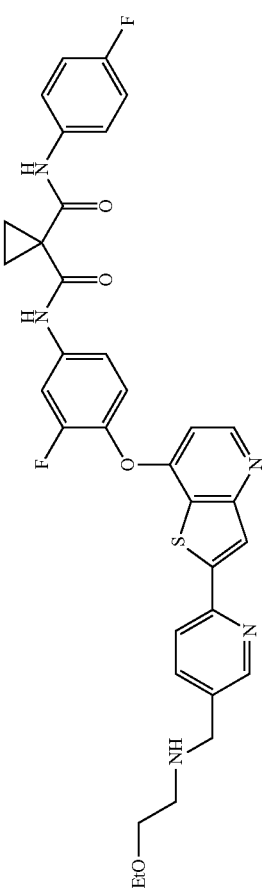<br>N-(4-(2-(5-((2-Ethoxyethylamino)methyl)pyridin-2-yl)thieno[3,2-b]pyridin-7-yloxy)-3-fluorophenyl)-N-(4-fluorophenyl)cyclopropane-1,1-dicarboxamide | ¹H NMR (400 MHz, DMSO-d₆) δ (ppm): 10.41 (s, 1 H); 10.02 (s, 1 H); 8.57 (d, J = 1.4, 1 H); 8.52 (d, J = 5.5, 1 H); 8.32 (s, 1 H); 8.21 (d, J = 9.8, 1 H); 7.94-7.88 (m, 2 H); 7.67-7.62 (m, 2 H); 7.54-7.44 (m, 2 H); 7.17-7.12 (m, 2 H); 6.65 (d, J = 5.5, 1 H); 3.79 (s, 2 H); 3.44 (t, J = 5.9, 2 H); 3.41 (q, J = 7.7, 2 H); 2.66 (t, J = 5.7, 2 H); 1.10 (t, J = 7.0, 3 H). MS (m/z): 644.4 (M + H). |
| 282 | 175 | 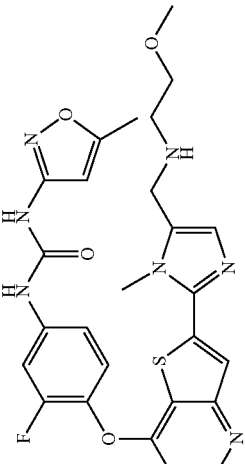<br>1-(3-fluoro-4-(2-(5-((2-methoxyethylamino)methyl)-1-methyl-1H-imidazol-2-yl)thieno[3,2-b]pyridin-7-yloxy)phenyl)-3-(5-methylisoxazol-3-yl)urea | ¹H NMR (400 MHz, DMSO-d₆) δ (ppm): 9.67 (s, 1 H), 9.23 (s, 1 H), 8.52 (d, J = 5.48 Hz, 1 H), 7.89 (s, 1 H), 7.73 (m, 1 H), 7.46 (t, J = 8.99 Hz, 1 H), 7.28 (m, 1 H), 6.97 (s, 1 H), 6.68 (m, 1 H), 6.55 (s, 1 H), 3.91 (s, 3 H), 3.7 (s, 2 H), 3.4– (m, 2 H), 3.29 (s, 3 H), 2.68 (t, J = 5.67 Hz, 2 H), 2.37 (s, 3 H). MS (m/z): 552.3 (M + H). |

| Cpd. # | Ex. # | Structure | Characterization |
|---|---|---|---|
| 283 | 176 | 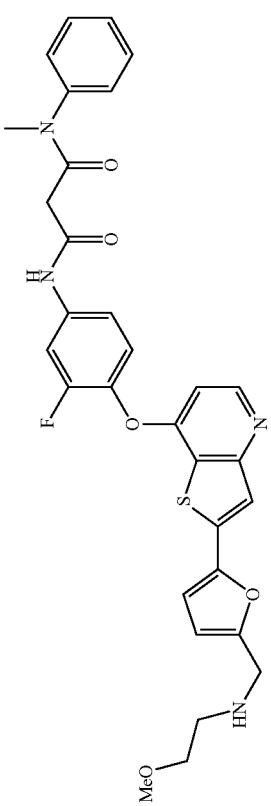 N1-(3-fluoro-4-(2-(5-((2-methoxyethylamino)methyl)furan-2-yl)thieno[3,2-b]pyridin-7-yloxy)phenyl)-N3-methyl-N3-phenylmalonamide | 1H NMR (400 MHz, DMSO-d6) δ (ppm): 10.30 (s, 1 H), 8.48 (d, J = 5.5 Hz, 1 H), 8.23 (s, 1 H, formate salt), 7.80 (bd, J = 13.5 Hz, 1 H), 7.76 (s, 1 H), 7.52-7.28 (m, 7 H), 7.09 (d, J = 3.3 Hz, 1 H), 6.62 (d, J = 5.5 Hz, 1 H), 6.47 (d, J = 3.3 Hz, 1 H), 3.78 (s, 2 H), one CH2 is masked by water, 3.24 (s, 3 H), 3.25-3.20 (m, 5 H), 2.71 (t, J = 5.7 Hz, 2 H), one NH is missing (as formate salt). MS (m/z): 589.3 (M + H). |
| 284 | 177 | 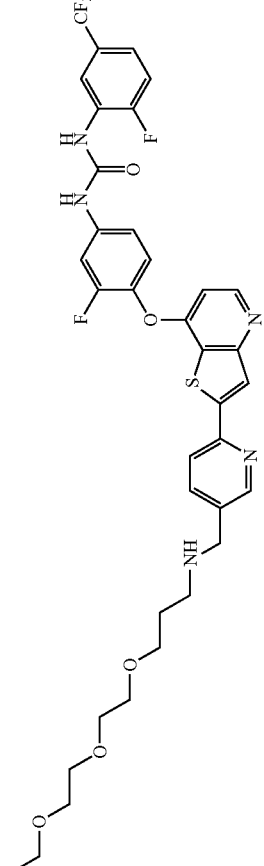 1-(4-(2-(5-((15-Amino-6,9,12-trioxa-2-azapentadecyl)pyridin-2-yl)thieno[3,2-b]pyridin-7-yloxy)-3-fluorophenyl)-3-(2-fluoro-5-(trifluoromethyl)phenyl)urea | 1H NMR (400 MHz, DMSO-d6) δ (ppm): 10.52 (s, 1 H); 8.58 (d, J = 1.6, 1 H); 8.53 (d, J = 5.5, 1 H); 8.52-8.48 (m, 1 H); 8.35 (s, 2 H); 8.32 (s, 1 H); 8.23 (d, J = 8.0, 1 H); 7.88 (dd, J = 8.0, 1.8, 1 H); 7.81 (dd, J = 13.1, 2.4, 1 H); 7.52-7.40 (m, 3 H); 7.36-7.33 (m, 1 H); 6.68 (d, J = 5.3, 1 H); 3.76 (s, 2 H); 3.50-3.40 (m, ~12 H, on top of water peak); 2.80 (t, J = 7.4, 2 H); 2.54 (t, J = 7.1, 2 H); 1.73 (quint, J = 7.4, 2 H); 1.68 (quint, J = 7.4, 2 H) (formate salt). MS (m/z): 775.5 (M + H). |

| Cpd. # | Ex. # | Structure | Characterization |
|---|---|---|---|
| 285 | 178 | 1-(4-(2-(5-((2-(2-(2-Aminoethoxy)ethylamino)methyl)pyridin-2-yl)thieno[3,2-b]pyridin-7-yloxy)-3-fluorophenyl)-3-(2-fluoro-5-(trifluoromethyl)phenyl)urea | $^1$H NMR (400 MHz, DMSO-d$_6$) δ (ppm): 10.39 (s, 1 H); 8.58 (d, J = 1.6, 1 H); 8.53 (d, J = 5.5, 1 H); 8.52-8.50 (m, 1 H); 8.33 (s, 3 H); 8.23 (d, J = 8.0, 1 H); 7.89 (dd, J = 8.0, 1.8, 1 H); 7.80 (dd, J = 13.1, 2.4, 1 H); 7.52-7.40 (m, 3 H); 7.35-7.32 (m, 1 H); 6.68 (d, J = 5.5, 1 H); 3.79 (s, 2 H); 3.56-3.48 (m, ~8 H, on top of water peak); 2.91 (t, J = 5.3, 2 H); 2.66 (t, J = 5.6, 2 H) (as formate salt). MS (m/z): 703.4 (M + H). |

Scheme 14

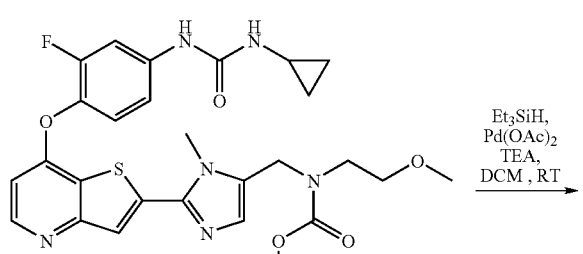

286

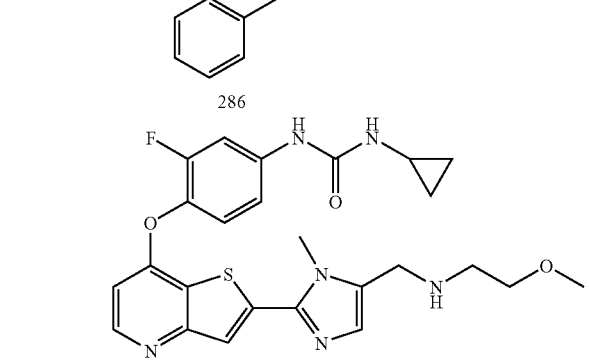

287: Example 179

Example 179

1-cyclopropyl-3-(3-fluoro-4-(2-(5-((2-methoxyethy-lamino)methyl)-1-methyl-1H-imidazol-2-yl)thieno[3,2-b]pyridin-7-yloxy)phenyl)urea (287)

To a solution of the 286 (150 mg, 0.233 mmol, obtained similarly to compounds 47 or 47a, scheme 2) in DCM (1 ml) was added triethylsilane (37.9 mg, 0.326 mmol, 1.4 eq.), TEA (3.3 mg, 0.0033 mmol, 0.14 eq,) and Pd(OAc)$_2$ (2.089 mg, 0.04 eq, 9.31 μM) and the reaction mixture was heated to reflux for 3 days. The reaction was stopped after 3 days (not complete) and the reaction mixture was extracted with EtOAc and water. The organic phase was collected, dried over Na$_2$SO$_4$, filtered and concentrated. Purification by column chromatography (30% MeOH in EtOAc) afforded the title compound 287 (21 mg, 18% yield) as a yellow solid. Characterization of compound 287 is provided in the Table 6.

Scheme 15

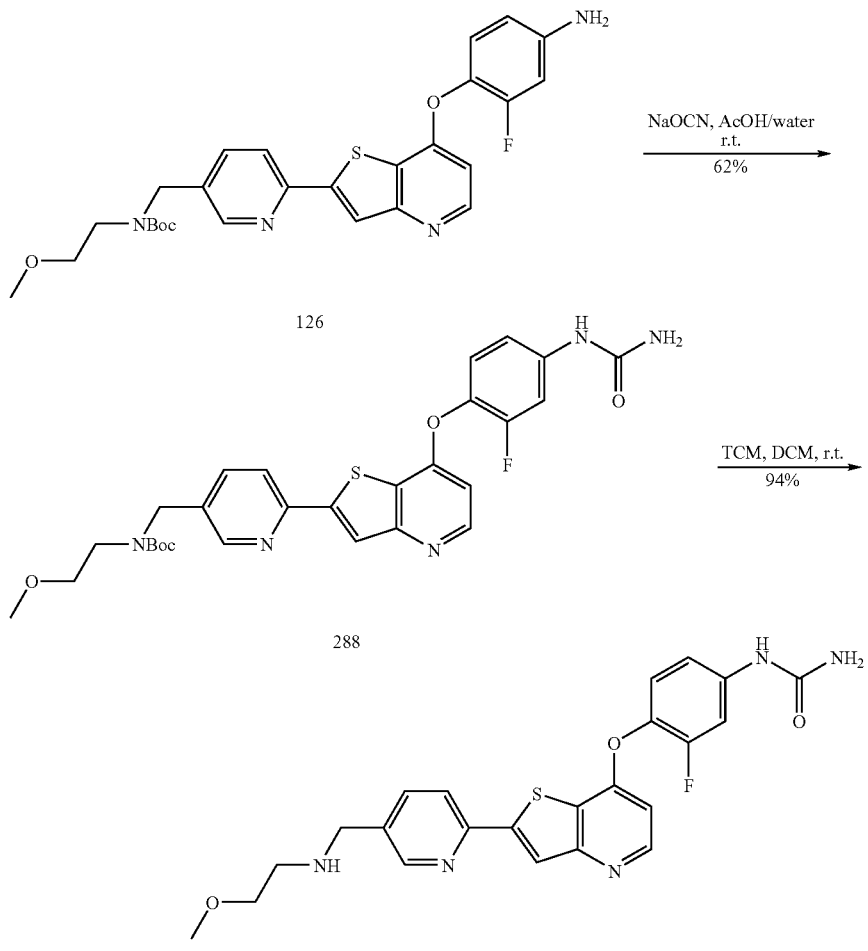

Example 180

1-(3-fluoro-4-(2-(5-((2-methoxyethylamino)methyl) pyridin-2-yl)thieno[3,2-b]pyridin-7-yloxy)phenyl) urea (289)

Step 1: tert-butyl (6-(7-(2-fluoro-4-ureidophenoxy) thieno[3,2-b]pyridin-2-yl)pyridin-3-yl)methyl(2-methoxyethyl)carbamate (288)

To a solution of compound 126 (3.0 g, 5.72 mmol) in AcOH (13.6 mL) at 0° C. was added a solution of sodium cyanate (0.743 g, 11.44 mmol, 2 eq.) in water (5.2 mL). The mixture was stirred at r.t. for 20 h. Water (100 mL) was added and the reaction mixture turned into a suspension. After 30 min, the solid was collected by filtration and the product cake was washed with water (2×20 mL), dried in vacuum and purified by Biotage SP1 Flash Purification System (eluent a gradient EA/MeOH, 100/0 to 90/10) to afford 288 as a white solid (2.0 g, 3.52 mmol, 62% yield). MS (m/z): 568.4 (M+H).

Step 2: 1-(3-fluoro-4-(2-(5-((2-methoxyethylamino) methyl)pyridin-2-yl)thieno[3,2-b]pyridine-7-yloxy) phenyl)urea (289)

To a solution of compound 288 (0.33 g, 0.581 mmol) in DCM (11.6 mL) was added TFA (0.53 mL, 6.98 mmol, 12 eq.). The reaction mixture was stirred at r.t. for 24 h, concentrated and the residue was purified by Biotage SP1 Flash Purification System (eluent a gradient DCM/MeOH/NH$_4$OH, 95/5/0.1 to 9/1/0.2) to afford 289 as a white solid (0.256 g, 0.548 mmol, 94% yield). Characterization of compound 289 is provided in the Table 6.

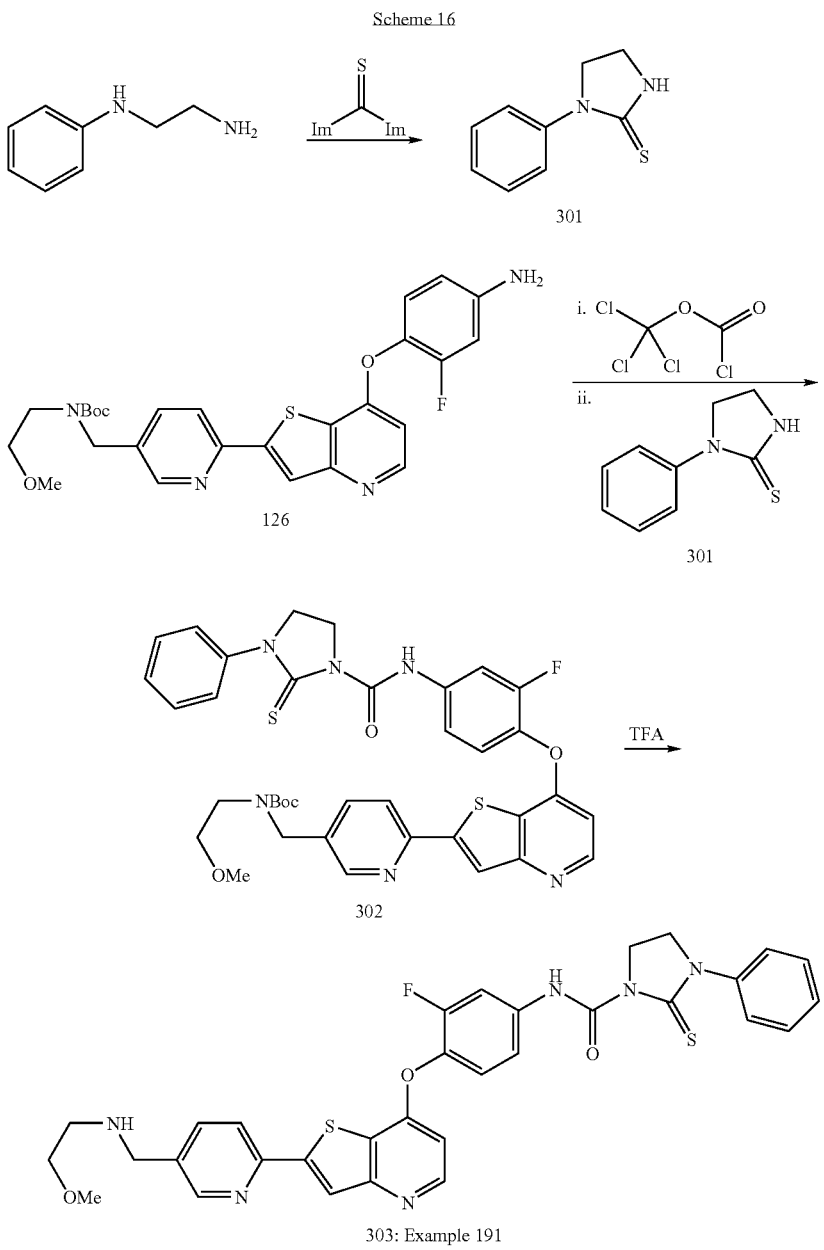

Scheme 16

Example 191

N-(3-fluoro-4-(2-(5-((2-methoxyethylamino)methyl) pyridin-2-yl)thieno[3,2-b]pyridin-7-yloxy)phenyl)-3-phenyl-2-thioxoimidazolidine-1-carboxamide (303)

Step 1. 1-phenylimidazolidine-2-thione (301)

1,1'-Thiocarbonyldiimidazole (4.51 g, 25.3 mmol) was added to a solution of N-phenylethylenediamine (3 mL, 23.02 mmol) in THF (230 mL) and the mixture was stirred for 2 h at room temperature. DCM was added and the solution was washed with 1N HCl, dried over anhydrous sodium sulfate and concentrated under reduced pressure affording title compound 301 (1.45 g, 8.13 mmol, 35.3% yield). m/z: 179.1 (M+H)+

Step 2. tert-butyl (6-(7-(2-fluoro-4-(3-phenyl-2-thioxoimidazolidine-1-carboxamido)phenoxy)thieno [3,2-b]pyridin-2-yl)pyridin-3-yl)methyl(2-methoxyethyl)carbamate (302)

Diphosgene (0.023 ml, 0.191 mmol) was added in one portion to a solution of 126 (schemes 6 or 9) (0.200 g, 0.381 mmol) in THF (3.81 ml) and the reaction mixture stirred vigorously for 2 h. 1-Phenylimidazolidine-2-thione (301, 0.102 g, 0.572 mmol) and sodium hydride (60% in mineral oil) (0.046 g, 1.143 mmol) were added sequentially and the mixture was stirred at room temperature for an additional 1 h. The crude mixture was then suspended in EtOAc, washed with water, dried over anhydrous sodium sulfate and concentrated under reduced pressure. The residue was purified by preparative HPLC (column: Luna C18 (2), 5.0 cm ID; gradient: 80% MeOH to 95% MeOH in water, 60 min) affording title compound 302 (0.068 g, 0.093 mmol, 24.5% yield) as creamy solid. m/z: (M+1)+ 729.4 (100%).

Step 2. N-(3-fluoro-4-(2-(5-((2-methoxyethylamino) methyl)pyridin-2-yl)thieno[3,2-b]pyridin-7-yloxy) phenyl)-3-phenyl-2-thioxoimidazolidine-1-carboxamide (303)

TFA (1 ml, 12.98 mmol) was added to a suspension of 302 (0.093 g, 0.128 mmol) in DCM (1.000 ml) and the mixture was stirred at room temperature for 2 h. The reaction mixture was then concentrated under reduced pressure, the residue was dissolved in DCM, washed with 1N NaOH solution, water, dried over anhydrous sodium sulfate and concentrated affording title compound 303 (0.0714 g, 0.109 mmol, 85% yield) as white solid.

TABLE 6

| Cpd. No. | Ex. No. | Structure | Characterization |
|---|---|---|---|
| 287 | 179 | 1-cyclopropyl-3-(3-fluoro-4-(2-(5-((2-methoxyethylamino)methyl)-1-methyl-1H-imidazol-2-yl)thieno[3,2-b]pyridin-7-yloxy)phenyl)urea | 1H NMR (400 MHz, DMSO-d6) δ (ppm): 8.75 (bs, 1H), 8.69 (bs, 1H), 8.13 (d, J = 5.48 Hz, 1H), 7.59 (s, 1H), 7.32 (m, 1H), 6.96 (t, J = 9.19 Hz, 1H), 6.89 (s, 1H), 6.28 (m, 1H), 6.28 (m, 2H), 3.92 (bs, 2H), 3.54 (s, 3H), 3.23 (t, J = 5.09 Hz, 2H), 2.91 (s, 3H), 2.80 (m, 2H), 2.09 (m, 1H), 0.24 (m, 2H), 0.05 (m, 2H). LRMS(ESI): (calc.) 510.58 (found) 511.4 (MH)+ |
| 289 | 180 | 1-(3-fluoro-4-(2-(5-((2-methoxyethylamino)methyl)pyridin-2-yl)thieno[3,2-b]pyridin-7-yloxy)phenyl)urea | 1H NMR (400 MHz, DMSO-d6) δ (ppm): 8.97 (s, 1H); 8.68 (d, J = 1.6, 1H); 8.52 (d, J = 5.5, 1H); 8.39 (s, 1H); 8.33 (d, J = 7.8, 1H); 8.02 (dd, J = 8.2, 2.2, 1H); 7.73 (dd, J = 14.2, 2.3, 1H); 7.37 (t, J = 9.0, 1H); 7.17-7.15 (m, 1H); 6.65 (d, J = 4.5, 1H); 6.05 (s, 2H); 4.14 (s, 2H); 3.54 (t, J = 5.1, 2H); 3.29 (s, 3H); 3.03 (t, J = 5.1, 2H). LRMS(ESI): (calc.) 467.5 (found) 468.3 (MH)+ |

Other compounds according to the present invention are shown in Table 7.

TABLE 7

| Cpd No. | Ex. No. | Structure | Characterization |
|---|---|---|---|
| 293 | 183 | N1-(4-(2-(5-((2-(2-(2-Aminoethoxy)ethoxy)ethylamino)methyl)pyridin-2-yl)thieno[3,2-b]pyridin-7-yloxy)-3-fluorophenyl)-N3-methyl-N3-phenylmalonamide | $^1$H NMR (400 MHz, DMSO-$d_6$) δ (ppm): 1H: 10.38 (s, 1H); 8.57 (d, J = 1.6, 1H); 8.51 (d, J = 5.5, 1H); 8.37 (s, 1H); 8.32 (s, 1H); 8.23 (d, J = 8.0, 1H); 7.89 (dd, J = 8.1, 2.1, 1H); 7.80 (d, J = 13.2, 1H); 7.50-7.42 (m, 3H); 7.41-7.32 (m, 4H); 6.67 (d, J = 5.3, 1H); 3.79 (s, 2H); 3.55-3.47 (m, 8H); 3.23-3.21 (m, 5H); 2.83 (t, J = 5.5, 2H); 2.66 (t, J = 5.7, 2H). MS (M/Z): (calc.) 673.3 (found) 673.4 |
| 294 | 184 | 1-(4-(2-(5-((2-(2-(2-Aminoethoxy)ethoxy)ethylamino)methyl)pyridin-2-yl)thieno[3,2-b]pyridin-7-yloxy)-3-fluorophenyl)-3-(5-methylisoxazol-3-yl)urea | $^1$H NMR (400 MHz, DMSO-$d_6$) δ (ppm): 1H: 10.66 (1H), 8.60 (s, 1H); 8.55-8.53 (m, 1H); 8.40-8.34 (m, 2H); 8.28-8.24 (m, 1H); 7.93-7.90 (m, 1H); 7.82-7.78 (m, 1H); 7.45-7.35 (m, 2H); 6.70-6.68 (m, 1H); 6.60-6.57 (m, 1H); 3.81 (s, 2H); 3.60-3.50 (m, 8H); 2.93-2.90 (m, 2H); 2.70-2.65 (m, 2H); 2.37 (s, 3H). MS (M/Z): (calc.) 622.2 (found) 622.4 |
| 298 | 188 | 1-(3-Fluoro-4-(2-(5-((2-methoxyethylamino)methyl)pyridin-2-yl)thieno[3,2-b]pyridin-7-yloxy)phenyl)-3-methylurea | $^1$H NMR (400 MHz, DMSO-$d_6$) δ (ppm): 1H: 8.96 (s, 1H); 8.69 (d, J = 1.4, 1H); 8.53 (d, J = 5.3, 1H); 8.40 (s, 1H); 8.34 (d, J = 8.2, 1H); 8.04 (dd, J = 8.2, 2.0, 1H); 7.72 (dd, J = 13.7, 2.5, 1H); 7.37 (t, J = 9.2, 1H); 7.19-7.16 (m, 1H); 6.65 (d, J = 5.4, 1H); 6.20 (q, J = 4.6, 1H); 4.18 (s, 1H); 3.56 (t, J = 5.3, 1H); 3.30 (s, 3H); 3.10-3.06 (m, 2H); 2.66 (d, J = 4.5, 3H). MS: (calc.) 482.2 (found) 482.3 (MH)+ |
| 298a | 188a | 1-(2-chloro-4-(2-(5-((2-methoxyethylamino)methyl)pyridin-2-yl)thieno[3,2-b]pyridin-7-yloxy)phenyl)-3-(5-methylisoxazol-3-yl)urea | $^1$H NMR (400 MHz, DMSO-$d_6$) δ (ppm): 8.88 (s, 1H), 8.56 (s, 1H), 8.54 (d, 1H, J = 5.3 Hz), 8.32 (s, 1H), 8.23 (m, 2H), 7.89 (d, 1H, J = 8.2 Hz), 7.59 (d, 1H, J = 2.9 Hz), 7.31 (dd, 1H, J = 2.7 Hz, J = 8.8 Hz), 6.74 (d, 1H, J = 5.3 Hz), 5.97 (s, 1H), 3.78 (s, 2H), 3.42 (s, 2H), 3.24 (s, 3H), 2.65 (t, 2H, J = 5.7 Hz), 2.17 (s, 3H) MS: (calc.) 564.1 (found) 565.3 (MH)+ |

TABLE 7-continued

| Cpd No. | Ex. No. | Structure | Characterization |
|---|---|---|---|
| 299 | 189 | 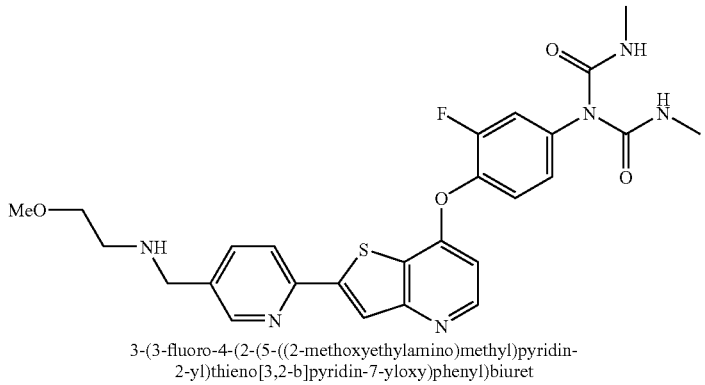<br>3-(3-fluoro-4-(2-(5-((2-methoxyethylamino)methyl)pyridin-2-yl)thieno[3,2-b]pyridin-7-yloxy)phenyl)biuret | $^1$H NMR (400 MHz, DMSO-d$_6$) δ (ppm): 1H: 8.58-8.56 (m, 2H); 8.36 (s, 1H); 8.25 (d, J = 8.0, 1H); 7.90 (dd, J = 8.2, 1.8); 7.68 (q, J = 4.5, 2H); 7.59-7.50 (m, 2H); 7.22-7.18 (m, 1H); 6.84 (d, J = 5.3, 1H); 3.78 (s, 2H); 3.41 (t, J = 5.7, 2H); 3.24 (s, 3H); 2.67 (d, J = 4.5, 6H); 2.65 (t, J = 5.7, 2H). MS: (calc.) 539.3 (found) 539.3 (MH)+ |

Other compounds according to the present invention are shown in Table 8.

TABLE 8

| Cmpd. # | Ex. # | STRUCTURE | CHARACTERIZATION |
|---|---|---|---|
| 303 | 191 | 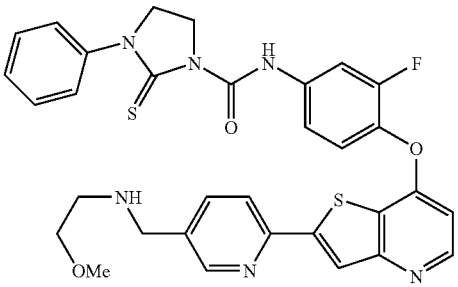<br>N-(3-fluoro-4-(2-(5-((2-methoxyethylamino)methyl)pyridin-2-yl)thieno[3,2-b]pyridin-7-yloxy)phenyl)-3-phenyl-2-thioxoimidazolidine-1-carboxamide | $^1$H NMR (400 MHz, DMSO-d$_6$) δ (ppm): 12.572 (s, 1H), 9.22 br, 2H), 8.75 (d, J = 2.0 Hz, 1H), 8.57 (d, J = 5.5 Hz, 1H), 8.45 (s, 1H), 8.38 (d, J = 8.4 Hz, 1H), 8.13 (dd, J = 2.1 Hz, J = 8.2 Hz, 1H), 7.84 (dd, J = 2.3 Hz, J = 11.7 Hz, 1H), 7.55-7.50 (m, 4H), 7.42-7.38 (m, 2H), 6.75 (dd, J = 0.8 Hz, J = 4.7 Hz, 1H), 4.28-4.22 (m, 4H), 4.14-4.09 (m, 2H), 3.62 (t, J = 4.9 Hz, 2H), 3.32 (s, 3H), 3.17 (m, 2H). MS (m/z): (M + 2)+ 2/2 315.2 (73%), (M + 1)+ 629.4 (100%). |
| 304 | 192 | 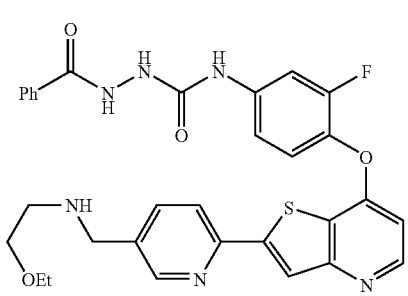 [SMILES: CCOCCNCc1ccc(-c2cc3nccc(Oc4ccc(NC(=O)NNC(=O)c5ccccc5)cc4F)c3s2)nc1]<br>2-benzoyl-N-(4-(2-(5-((2-ethoxyethylamino)methyl)pyridin-2-yl)thieno[3,2-b]pyridin-7-yloxy)-3-fluorophenyl)hydrazinecarboxamide | $^1$H NMR (400 MHz, DMSO-d$_6$) δ (ppm): 10.36 (s, 1H), 9.42 (br, 1H), 8.63 (s, 1H), 8.53-8.48 (m, 2H), 8.35 (s, 1H), 8.27 (d, J = 8.2 Hz, 1H), 7.99-7.93 (m, 3H), 7.77 (d, J = 13.7 Hz, 1H), 7.61-7.36 (m, 5H), 6.67 (d, J = 5.3 Hz, 1H), 3.94 (s, 2H), 3.52-3.42 (m, 4H), 2.81 (m, 2H), 1.12 (t, J = 7.0 Hz, 3H). MS (m/z): (M + 2)+ 2/2 301.2 (100%), (M + 1)+ 601.4 (64%). |

TABLE 8-continued

| Cmpd. # | Ex. # | STRUCTURE | CHARACTERIZATION |
|---|---|---|---|
| 305 | 193 | 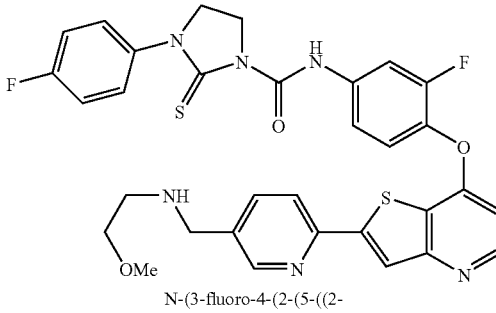<br>N-(3-fluoro-4-(2-(5-((2-methoxyethylamino)methyl)pyridin-2-yl)thieno[3,2-b]pyridin-7-yloxy)phenyl)-3-(4-fluorophenyl)-2-thioxoimidazolidine-1-carboxamide | $^1$H NMR (400 MHz, DMSO-d$_6$) δ (ppm): 12.52 (s, 1H), 8.57 (br, 1H), 8.53 (d, J = 5.4 Hz, 1H), 8.33 (s, 1H), 8.24 (d, J = 8.0 Hz, 1H), 7.9 (d, J = 8.0 Hz, 1H), 7.8 (dd, J = 12.7 Hz, J = 1.7 Hz, 1H), 7.57-7.50 (m, 3H), 7.38-7.34 (m, 3H), 6.7 (d, J = 5.4 Hz, 1H), 4.23 (dd, J = 8.7 Hz, J = 7.1 Hz, 1H), 4.09 (dd, J = 8.7 Hz, J = 7.1 Hz, 1H), 3.41 (t, J = 3.41 Hz, 2H), 3.17 (s, 1H), 4.09 (t, J = 3.41 Hz, 2H). MS (m/z): (M + 2)+ 2/2 324.2 (73%), (M + 1)+ 647.4 (100%) |
| 306 | 194 | 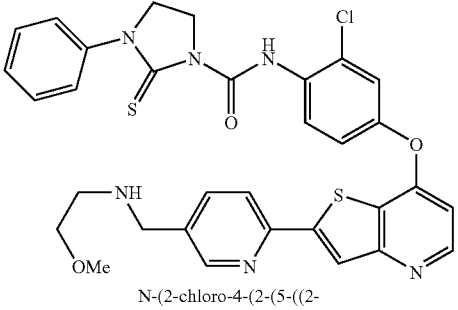<br>N-(2-chloro-4-(2-(5-((2-methoxyethylamino)methyl)pyridin-2-yl)thieno[3,2-b]pyridin-7-yloxy)phenyl)-3-phenyl-2-thioxoimidazolidine-1-carboxamide | $^1$H NMR (400 MHz, DMSO-d$_6$) δ (ppm): 12.40 (s, 1H), 8.56-8.54 (m, 2H), 8.32-8.28 (m, 2H), 8.23 (d, J = 8.3 Hz, 1H), 1.89 (dd, J = 8.2 Hz, J = 2.2 Hz, 1H), 7.62 (d, J = 2.5 Hz, 1H), 7.53-7.48 (m, 4H), 7.41-7.35 (m, 2H), 6.77 (d, J = 2.5 Hz, 1H), 4.25 (m, 2H), 4.12 (m, 2H), 3.78 (s, 2H), 5.49 (t, J = 5.49 Hz, 2H), 3.24 (s, 3H), 2.65 (t, J = 5.49 Hz, 2H). MS (m/z): (M + 2)+ 2/2 323.1 (58%), 324 (39%); (M + 1)+ 645.4 (100%), 647.4 (48%). |
| 307 | 195 | 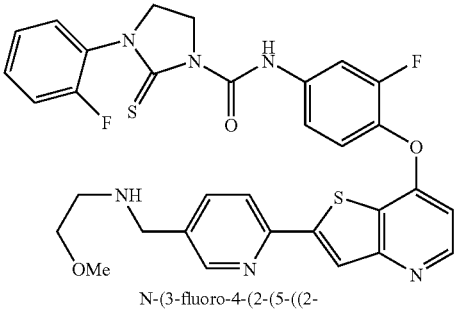<br>N-(3-fluoro-4-(2-(5-((2-methoxyethylamino)methyl)pyridin-2-yl)thieno[3,2-b]pyridin-7-yloxy)phenyl)-3-(2-fluorophenyl)-2-thioxoimidazolidine-1-carboxamide | $^1$H NMR (400 MHz, DMSO-d$_6$) δ (ppm): 12.39 (s, 1H), 8.78 (m, 1H), 8.53 (d, J = 5.2 Hz, 1H), 8.33 (s, 1H), 8.23 (dd, J = 0.6 Hz, J = 8.2 Hz, 1H), 7.90 (dd, J = 2.1 Hz, J = 8.1 Hz, 1H), 7.83 (dd, J = 2.6 Hz, J = 12.7 Hz, 1H), 7.60-7.49 (m, 3H), 7.46-7.34 (m, 3H), 6.7 (dd, J = 0.9 Hz, J = 5.4 Hz, 1H), 4.31 (m, 2H), 4.04 (m, 2H) 3.80 (s, 2H), 3.80 (s, 2H), 3.42 (t, J = 5.6 Hz, 2H), 3.25 (s, 3H), 2.68 (t, J = 5.6 Hz, 2H). MS (m/z): (M + 2)+ 2/2 324.2 (89%), (M + 1)+ 647.4 (100%). |
| 308 | 196 | 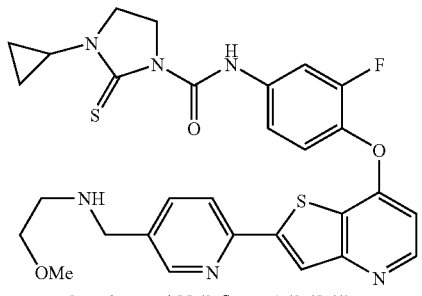<br>3-cyclopropyl-N-(3-fluoro-4-(2-(5-((2-methoxyethylamino)methyl)pyridin-2-yl)thieno[3,2-b]pyridin-7-yloxy)phenyl)-2-thioxoimidazolidine-1-carboxamide | $^1$H NMR (400 MHz, DMSO-d$_6$) δ (ppm): 12.60 (s, 1H), 8.56 (m, 1H), 8.52 (d, J = 5.6 Hz, 1H), 8.32 (s, 1H), 8.23 (dd, J = 8.2 Hz, J = 0.8 Hz, 1H), 7.89 (dd, J = 7.7 Hz, J = 1.9 Hz, 1H), 7.80 (dd J = 12.8 Hz, 2.3 Hz, 1H), 7.51 (t, J = 8.9 Hz, 1H), 7.36-7.33 (m, 1H), 6.99 (dd, J = 5.4 Hz, J =0.8 Hz, 1H), 4.02 (m, 2H), 3.77 (s, 2H), 3.61 (m, 2H), 3.41 (t, J = 5.7 Hz, 2H), 3.24 (s, 3H), 3.06-3.02 (m, 1H), 2.64 (t, J = 5.7 Hz, 2H), 0.87-0.84 (m 4H). MS (m/z): (M + 2)+ 2/2 297.2 (100%), (M + 1)+ 593.3 (32%) |

TABLE 8-continued

| Cmpd. # | Ex. # | STRUCTURE | CHARACTERIZATION |
|---|---|---|---|
| 309 | 197 | N-(4-(2-(5-((2-ethoxyethylamino)methyl)pyridin-2-yl)thieno[3,2-b]pyridin-7-yloxy)-3-fluorophenyl)-3-phenyl-2-thioxoimidazolidine-1-carboxamide | $^1$H NMR (400 MHz, DMSO-d$_6$) δ (ppm): 12.57 (s, 1H), 8.57 (s, 1H), 8.53 (d, J = 5.3 Hz, 1H), 8.32 (s, 1H), 8.24 (d, J = 7.5 Hz, 1H), 7.91-7.82 (m, 2H), 7.54-7.51 (m, 5H), 7.41-7.37 (m, 2H), 6.7 (d, J = 5.3 Hz, 1H), 4.24 (m, 2H), 4.11 (m, 2H), 3.78 (s, 2H), 3.43 (q, J = 5.8 Hz, 2H), 3.39 (m, 2H), 2.65 (m, 2H), 1.11 (t, J = 5.8 Hz, 3H). MS (m/z): (M + 2)+ 2/2 322.3 (89%), (M + 1)+ 643.4 (100%). |
| 310 | 198 | 3-benzyl-N-(3-fluoro-4-(2-(5-((2-methoxyethylamino)methyl)pyridin-2-yl)thieno[3,2-b]pyridin-7-yloxy)phenyl)-2-thioxoimidazolidine-1-carboxamide | $^1$H NMR (400 MHz, DMSO-d$_6$) δ (ppm): 12.5 (s, 1H), 8.57 (dd, J = 0.7 Hz, J = 2.1 Hz, 1H), 8.53 (d, J = 5.5 Hz, 1H), 8.32 (s, 1H), 8.23 (dd, J = 0.7 Hz, J = 8.2 Hz, 1H), 7.89 (dd, J = 2.2 Hz, J = 8.2 Hz, 1H), 7.82 (dd, J = 2.5 Hz, J = 12.7 Hz, 1H), 7.52 (t, J = 9.1 Hz, 1H), 7.42-7.32 (m, 6H), 6.70 (dd, J = 0.7 Hz J =5.5 Hz, 1H), 4.89 (s, 2H), 4.09 (m, 2H), 3.78 (s, 2H), 3.64 (m, 2H), 3.41 (t, H = 5.7 Hz, 2H), 3.24 (s, 3H), 2.65 (t, J = 5.7 Hz, 2H). MS (m/z): (M + 2)+ 2/2 322.3 (100%), (M + 1)+ 643.4 (51%). |
| 311 | 199 | N-(3-fluoro-4-(2-(5-((2-methoxyethylamino)methyl)pyridin-2-yl)thieno[3,2-b]pyridin-7-yloxy)phenyl)-3-propyl-2-thioxoimidazolidine-1-carboxamide | $^1$H NMR (400 MHz, DMSO-d$_6$) δ (ppm): 12.52 (s, 1H), 8.57 (dd, J = 0.7 Hz, J = 2.0 Hz, 1H), 8.53 (d, J = 5.4 Hz, 1H), 8.33 (s, 1H), 8.23 (dd, J = 0.7 Hz, J = 8.1 Hz, 1H), 7.90 (dd, 2.1 Hz, 8.2 Hz, 1H), 7.81 (dd, J = 2.6 Hz, J = 12.7 Hz, 1H), 7.51 (t, J = 9.2 Hz, 1H), 7.37-7.34 (m, 1H), 6.69 (dd, J = 0.8 Hz, J = 5.4 Hz, 1H), 4.07 (m, 2H), 3.78 (s, 2H), 3.73 (m, 2H), 3.58 (m, 2H), 3.41 (t, J = 5.7 Hz, 2H), 3.24 (s, 3H), 2.65 (t, J = 5.7 Hz, 2H), 1.66-1.61 (m, 2H), 0.94 (t, J = 7.5 Hz, 3H). MS (m/z): (M + 2)+ 2/2 298.2 (100%), (M + 1)+ 595.4 (51%). |
| 312 | 200 | N-(3-fluoro-4-(2-(5-((2-methoxyethylamino)methyl)pyridin-2-yl)thieno[3,2-b]pyridin-7-yloxy)phenyl)-3-(3-fluorophenyl)-2-thioxoimidazolidine-1-carboxamide | $^1$H NMR (400 MHz, DMSO-d$_6$) δ (ppm): 12.48 (s, 1H), 8.57 (dd, J = 0.7 Hz, J = 2.2 Hz, 1H), 8.53 (d, J = 8.53 Hz, 1H), 8.33 (s, 1H), 8.24 (dd, J = 0.7 Hz, J = 8.2 Hz, 1H), 7.90 (dd, J = 2.1 Hz, J = 8.2 Hz, 1H), 7.83 (dd, J = 2.5 Hz, J = 12.6 Hz, 1H), 7.59-7.46 (m, 3H), 7.41-7.37 (m, 2H), 7.29-7.24 (m, 1H), 6.70 (dd, J = 0.9 Hz, J = 5.5 Hz, 1H), 4.24 (m, 2H), 4.12 (m, 2H), 3.78 (s, 2H), 3.41 (t, J = 5.7 Hz, 2H), 3.24 (s, 3H), 2.65 (t, J = 5.7 Hz, 2H). MS (m/z): (M + 2)+ 2/2 324.2 (100%), (M + 1)+ 647.3 (46%). |

TABLE 8-continued

| Cmpd. # | Ex. # | STRUCTURE | CHARACTERIZATION |
|---|---|---|---|
| 313 | 201 | N-(2,3-difluoro-4-(2-(5-((2-methoxyethylamino)methyl)pyridin-2-yl)thieno[3,2-b]pyridin-7-yloxy)phenyl)-3-phenyl-2-thioxoimidazolidine-1-carboxamide | $^1$H NMR (400 MHz, DMSO-d$_6$) δ (ppm): 12.62 (s, 1H), 8.57 (dd, J = 0.6 Hz, J = 2.0 Hz, 1H), 8.54 (d, J = 5.5 Hz, 1H), 8.35 (s, 1H), 8.24 (d, J = 8.2 Hz, 1H), 8.10-8.05 (m, 1H), 7.90 (dd, J = 2.2 Hz, J = 8.2 Hz, 1H), 7.54-7.51 (m, 4H), 7.44-7.38 (m, 2H), 6.83 (dd, J = 0.8 Hz, J = 5.5 Hz, 1H), 4.28-4.24 (m, 2H), 4.15-4.01 (m, 2H), 3.79 (s, 2H), 3.41 (t, J = 5.8 Hz, 2H), 3.24 (s, 3H), 2.66 (t, J = 5.8 Hz, 2H). MS (m/z): (M + 2)+ 2/2 324.2 (100%), (M + 1)+ 647.3 (55%) |

Other compounds according to the present invention are shown in Table 9.

TABLE 9

| Cpd. No. | Ex. No. | Structure | Characterization |
|---|---|---|---|
| 318 | 204 | 1-(3-fluoro-4-(2-(6-((2-methoxyethylamino)methyl)pyridin-2-yl)thieno[3,2-b]pyridin-7-yloxy)phenyl)urea | $^1$H NMR (400 MHz, DMSO-d6) δ (ppm): 9.44 (s, 1H), 8.49 (d, 1H, J = 5.5 Hz), 8.32 (s, 1H), 8.27 (br.s, 2H), 8.11 (d, 1H, J = 6.2 Hz), 7.90 (t, 2H, J = 7.6 Hz), 7.73 (dd, 1H, J = 2.2 Hz, J = 13.7 Hz), 7.45 (d, 1H, J = 8.0 Hz), 7.33 (t, 1H, J = 9.0 Hz), 7.17 (d, 1H, J = 9.0 Hz), 6.58 (d, 1H, J = 5.1 Hz), 6.17 (s, 2H), 3.89 (s, 2H), 3.43 (s, 2H), 3.23 (s, 3H), 2.76 (br.s, 2H) LRMS(ESI): (calc.) 467.1 (found) 468.3 (MH)+ |
| 319 | 205 | 1-(3-fluoro-4-(2-(5-((2-methoxyethylamino)methyl)pyridin-2-yl)thieno[3,2-b]pyridin-7-yloxy)phenyl)thiourea | $^1$H NMR (400 MHz, DMSO-d6) δ (ppm): 9.96 (s, 1H); 8.56 (d, J = 1.6, 1H); 8.52 (d, J = 5.5, 1H); 8.32 (s, 1H); 8.23 (d, J = 7.8, 1H); 7.89 (dd, J = 8.0, 2.0, 1H); 7.81 (dd, J = 12.5, 2.0, 1H); 7.47 (t, J = 9.0, 1H); 7.29-7.26 (m, 1H); 6.67 (d, J = 4.7, 1H); 3.77 (s, 2H); 3.40 (t, J = 5.7, 2H); 3.23 (s, 3H); 2.65 (t, J = 5.5, 2H). LRMS(ESI): (calc.) 483.1 (found) 484.3 (MH)+ |

TABLE 9-continued

| Cpd. No. | Ex. No. | Structure | Characterization |
|---|---|---|---|
| 320 | 206 | 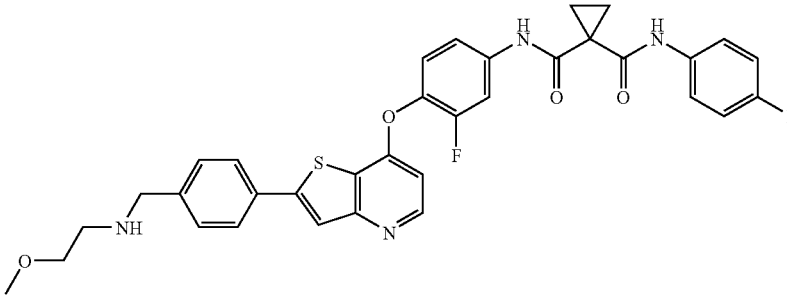<br>N-(3-fluoro-4-(2-(4-((2-methoxyethylamino)methyl)phenyl)thieno[3,2-b]pyridin-7-yloxy)phenyl)-N-(4-fluorophenyl)cyclopropane-1,1-dicarboxamide | $^1$H NMR (400 MHz, DMSO-d6) δ (ppm): 10.42 (s, 1H), 10.01 (s, 1H), 8.51 (d, J = 5.6 Hz, 1H), 8.04 (s, 1H), 7.91 (dd, J = 2.4 and 13.6 Hz, 1H), 7.87-7.83 (m, 2H), 7.65-7.61 (m, 2H), 7.54-7.44 (m, 4H), 7.19-7.12 (m, 2H), 6.60 (dd, J = 0.8 and 5.6 Hz, 1H), 3.81 (s, 2H), 3.42 (t, J = 5.6 Hz, 2H), 3.25 (s, 3H), 2.70 (t, J = 5.6 Hz, 2H), 1.50-1.43 (m, 4H).<br>LRMS(ESI): (calc.) 628.2 (found) 629.5 (MH)+ |
| 322 | 208 | 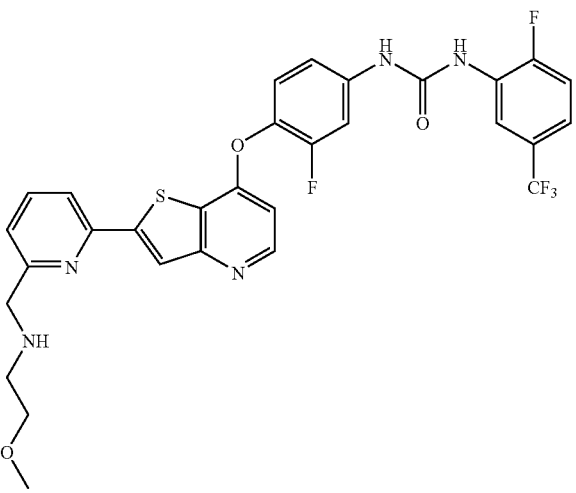 [SMILES: COCCNCc1cccc(-c2cc3nccc(Oc4ccc(NC(=O)Nc5cc(C(F)(F)F)ccc5F)cc4F)c3s2)n1]<br>1-(3-fluoro-4-(2-(6-((2-methoxyethylamino)methyl)pyridin-2-yl)thieno[3,2-b]pyridin-7-yloxy)phenyl)-3-(2-fluoro-5-(trifluoromethyl)phenyl)urea | $^1$H NMR (400 MHz, DMSO-d6) δ (ppm): 9.50 (s, 1H), 9.00 (d, 1H, J = 2.7 Hz), 8.57 (dd, 1H, J = 2.2 Hz, J = 7.3 Hz), 8.51 (d, 1H, J =5.5 Hz), 8.34 (s, 1H), 8.11 (d, 1H, J = 7.6 Hz), 7.89 (t, 1H, J = 7.8 Hz), 7.76 (dd, 1H, J = 2.6 Hz, J = 12.9 Hz), 7.4-7.6 (4H), 7.24 (m, 1H), 6.63 (d, 1H, J = 5.5 Hz), 3.85 (s, 2H), 3.41 (t, 2H, J = 5.5 Hz), 3.22 (s, 3H), 2.71 (t, 2H, J = 5.5 Hz)<br>LRMS(ESI): (calc.) 629.1 (found) 630.5 (MH)+ |
| 329 | 215 | 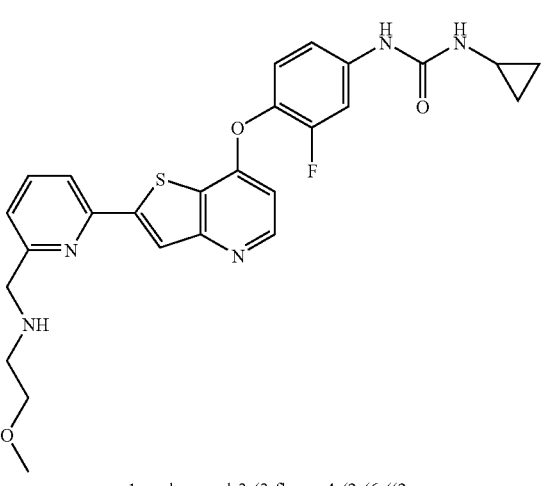<br>1-cyclopropyl-3-(3-fluoro-4-(2-(6-((2-methoxyethylamino)methyl)pyridin-2-yl)thieno[3,2-b]pyridin-7-yloxy)phenyl)urea | $^1$H NMR (400 MHz, DMSO-d6) δ (ppm): 8.18 (d, 1H, J = 5.3 Hz0, 7.99 (s, 1H), 7.79 (d, 1H, J = 7.6 Hz), 7.59 (t, 1H, J = 7.6 Hz), 7.37 (d, 1H, J = 15.3 Hz), 7.14 (d, 1H, J = 7.4 Hz), 6.70 (t, 1H, J = 9.0 Hz), 6.61 (d, 1H, J = 8.8 Hz), 6.25 (d, 1H, J = 4.9 Hz), 3.57 (d, 2H, J = 6.5 Hz), 2.94 (s, 3H), 2.43 (m, 2H), 2.03 (m, 1H), 0.20 (d, 2H, J = 5.1 Hz), 0.00 (s, 2H).<br>LRMS(ESI): (calc.) 507.2 (found) 508.4 (MH)+ |

| Cpd. No. | Ex. No. | Structure | Characterization |
|---|---|---|---|
| 332 | 218 | 1-(3-fluoro-4-(2-(5-((2-methoxyethylamino)methyl)pyridin-2-yl)thieno[3,2-b]pyridin-7-yloxy)phenyl)-3-(2-fluorophenyl)urea | $^1$H NMR (400 MHz, DMSO-d6) δ (ppm): 8.49 (s, 1H), 8.68 (s, 1H), 8.54 (s, 1H), 8.50 (d, 1H, J = 5.4 Hz), 8.29 (s, 1H), 8.20 (d, 1H, J = 8.3 Hz), 8.09 (t, 1H, J = 8.2 Hz), 7.87 (dd, 1H, J = 1.7 Hz, J = 8.0 Hz), 7.75 (dd, 1H, J = 2.6 Hz, J = 13.1 Hz), 7.44 (t, 1H, J = 9.0 Hz), 7.24 (m, 2H), 7.14 (t, 1H, J = 7.8 Hz), 6.65 (d, 1H, J = 5.5 Hz), 3.75 (s, 2H), 3.38 (t, 2H, J = 5.7 Hz), 3.21 (s, 3H), 2.62 (t, 2H, J = 5.7 Hz) LRMS(ESI): (calc.) 561.2 (found) 562.5 (MH)+ |
| 333 | 219 | 3-(3-(3-fluoro-4-(2-(5-((2-methoxyethylamino)methyl)pyridin-2-yl)thieno[3,2-b]pyridin-7-yloxy)phenyl)ureido)benzamide | $^1$H NMR (400 MHz, DMSO-d6) δ (ppm): 9.20 (s, 1H), 9.03 (s, 1H), 8.64 (d, J = 1.6 Hz, 1H), 8.54 (d, J = 5.3 Hz, 1H), 8.37 (s, 1H), 8.29 (d, J = 8.0 Hz, 1H), 8.03-7.89 (m, 3H), 7.78 (dd, J = 13.2, 2.4 Hz, 1H), 7.67-7.61 (m, 1H), 7.49 (d, J = 8.8 Hz, 1H), 7.45 (d, J = 9.2 Hz, 1H), 7.37 (t, J = 7.9 Hz, 1H), 7.36 (bs, 1H), 7.32-7.26 (m, 1H), 6.69 (d, J = 5.3 Hz, 1H), 3.98 (bs, 2H), 3.49 (t, J = 5.3 Hz, 2H), 3.27 (s, 3H), 2.92-2.83 (m, 2H), one NH is missing (probably due to signal overlap with the solvent signals) LRMS(ESI): (calc.) 586.64 (found) 587.5 (MH)+ |
| 336 | 222 | 1-(3-fluoro-4-(2-(5-((2-methoxyethylamino)methyl)pyridin-2-yl)thieno[3,2-b]pyridin-7-yloxy)phenyl)-3-(3-(methylsulfonyl)phenyl)urea | $^1$H NMR (400 MHz, DMSO-d6) δ (ppm): 9.29 (s, 1H), 9.21 (s, 1H), 8.57 (d, J = 1.8 Hz, 1H), 8.53 (d, J = 5.5 Hz, 1H), 8.33 (s, 1H), 8.24 (d, J = 8.2 Hz, 1H), 8.18 (t, J = 1.8 Hz, 1H), 7.90 (dd, J = 8.2, 2.0 Hz, 1H), 7.77 (dd, J = 13.2, 2.4 Hz, 1H), 7.70 (dt, J = 7.8, 1.7 Hz, 1H), 7.62-7.52 (m, 2H), 7.47 (t, J = 9.0 Hz, 1H), 7.31 (dd, J = 8.8, 1.6 Hz, 1H), 6.68 (d, J = 5.5 Hz, 1H), 3.79 (s, 2H), 3.41 (t, J = 5.6 Hz, 2H), 3.24 (s, 3H), 3.21 (s, 3H), 2.66 (t, J = 5.7 Hz, 2H), one NH is missing (probably due to signal overlap with the solvent signals) LRMS(ESI): (calc.) 621.7 (found) 622.4 (MH)+ |

| Cpd. No. | Ex. No. | Structure | Characterization |
|---|---|---|---|
| 337 | 223 | 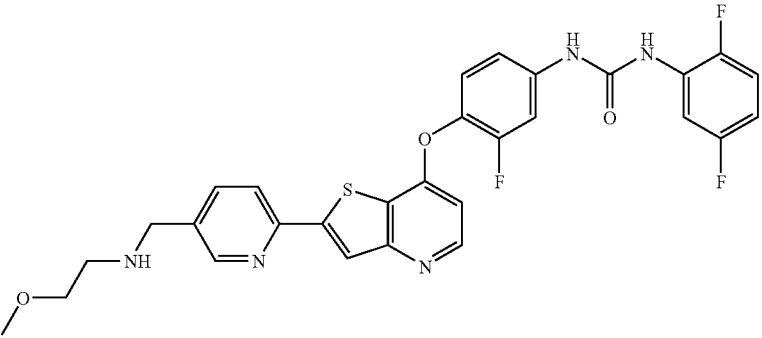 [SMILES: COCCNCc1ccc(-c2cc3nccc(Oc4ccc(NC(=O)Nc5cc(F)ccc5F)cc4F)c3s2)nc1]<br>1-(2,5-difluorophenyl)-3-(3-fluoro-4-(2-(5-((2-methoxyethylamino)methyl)pyridin-2-yl)thieno[3,2-b]pyridin-7-yloxy)phenyl)urea | $^1$H NMR (400 MHz, DMSO-d6) δ (ppm): 8.54 (s, 1H), 8.50 (d, 1H, J = 5.3 Hz), 8.29 (s, 1H), 8.20 (d, 1H, J = 8.0 Hz), 7.98 (m, 1H), 7.86 (d, 1H, J = 8.0 Hz), 7.74 (d, 1H, J = 13.1 Hz), 7.43 (t, 1H, J = 9.0 Hz0, 7.25 (m, 2H), 6.82 (m, 1H), 6.64 (d, 1H, J = 5.3 Hz), 3.75 (s, 2H), [3.34 (2H)], 3.21 (s, 3H), 2.62 (br.s, 2H), 2.22 (br.s, 1H)<br>LRMS(ESI): (calc.) 579.2 (found) 580.4 (MH)+ |
| 338 | 224 | 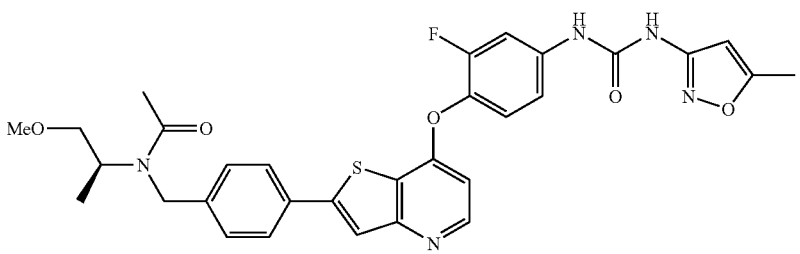 [SMILES: COC[C@H](C)N(Cc1ccc(-c2cc3nccc(Oc4ccc(NC(=O)Nc5cc(C)on5)cc4F)c3s2)cc1)C(C)=O]<br>(S)-N-(4-(7-(2-fluoro-4-(3-(5-methylisoxazol-3-yl)ureido)phenoxy)thieno[3,2-b]pyridin-2-yl)benzyl)-N-(1-methoxypropan-2-yl)acetamide | $^1$H NMR (400 MHz, DMSO-d6) δ (ppm): mixture of rotamers, 9.64 (s, 1H), 9.18 (s, 1H), 8.54-8.48 (m, 1H), 8.06 and 8.02 (2s, 1H), 7.90 (d, J = 8.2 Hz, 1H), 7.81 (d, J = 8.2 Hz, 1H), 7.74 (dd, J = 13.0, 2.4 Hz, 1H), 7.47 (t, J = 8.9 Hz, 1H), 7.41 (d, J = 8.4 Hz, 1H), 7.35 (d, J = 8.2 Hz, 1H), 7.28 (bd, J = 8.8 Hz, 1H), 6.62 (t, J = 5.9 Hz, 1H), 6.58-6.52 (m, 1H), 4.74-4.16 (m, 3H), 3.42-3.23 (m, 2H), 3.16 (s, 3H), 2.54-2.47 (m, 3H), 2.16 and 1.93 (2s, 3H), 1.09-1.00 (m, 3H).<br>LRMS(ESI): (calc.) 603.66 (found) 604.5 (MH)+ |
| 339 | 225 | 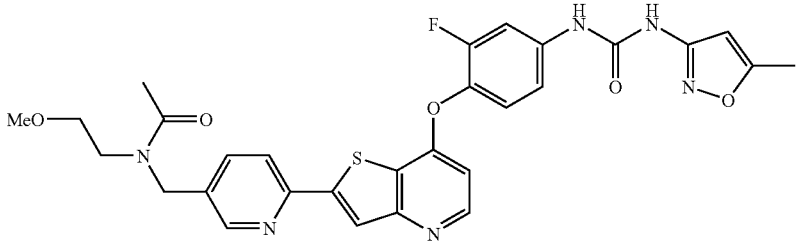 [SMILES: COCCN(Cc1ccc(-c2cc3nccc(Oc4ccc(NC(=O)Nc5cc(C)on5)cc4F)c3s2)nc1)C(C)=O]<br>N-((6-(7-(2-fluoro-4-(3-(5-methylisoxazol-3-yl)ureido)phenoxy)thieno[3,2-b]pyridin-2-yl)pyridin-3-yl)methyl)-N-(2-methoxyethyl)acetamide | $^1$H NMR (400 MHz, DMSO-d6) δ (ppm): 9.66 (s, 1H); 9.23 (s, 1H); 8.50-8.45 (m, 2H); 8.32 (s, 0.3H); 8.28 (s, 0.7H); 8.24 (d, J = 8.0, 0.3H); 8.18 (d, J = 8.0, 0.7H); 7.78-7.68 (m, 2H); 7.42 (t, J = 9.0, 1H); 7.25-7.21 (m, 1H); 6.64-6.61 (m, 1H); 6.51 (s, 1H); 4.67 (s, 0.6H); 4.54 (s, 1.4H); 3.50-3.40 (m, 4H); 3.19 (s, 1.9H); 3.16 (s, 1.1H); 2.33 (s, 3H); 2.08 (s, 2.2H); 2.00 (s, 0.8H) (2.3:1 mixture of rotamers)<br>LRMS(ESI): (calc.) 591.2 (found) 591.3 (MH)+ |
| 340 | 226 | 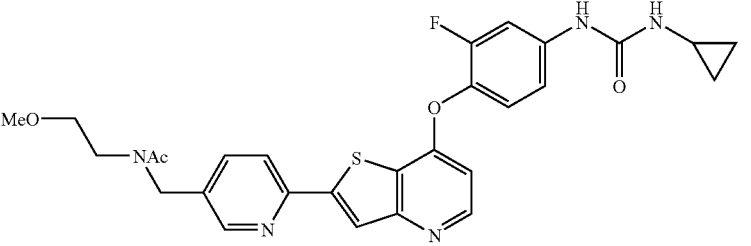<br>N-((6-(7-(4-(3-cyclopropylureido)-2-fluorophenoxy)thieno[3,2-b]pyridin-2-yl)pyridin-3-yl)methyl)-N-(2-methoxyethyl)acetamide | $^1$H NMR (400 MHz, DMSO-d6) δ (ppm): 8.74 (s, 1H); 8.55-8.49 (m, 2H); 8.35 (s, 0.3H); 8.32 (s, 0.7H); 8.28 (d, J = 8.6, 0.3H); 8.22 (d, J = 0.7H, 0.7H); 7.80-7.68 (m, 2H); 7.38 (t, J = 9.0, 1H); 7.24-7.19 (m, 1H); 6.66-6.56 (m, 2H); 4.71 (s, 0.6H); 4.59 (s, 1.4H); 3.53-3.41 (m, 4H); 3.24 (m, 2.2H); 3.20 (m, 0.8H); 2.57-2.50 (m, 1H); 2.13 (s, 2.2H); 2.05 (s, 0.8H); 0.67-0.63 (m, 2H); 0.41-0.40 (m, 2H). (3:1 mixture of rotamers)<br>LRMS(ESI): (calc.) 550.2 (found) 550.5 (MH)+ |

Other compounds according to the present invention are shown in Table 10.

TABLE 10

| Cpd. No. | Ex. No. | Structure | Characterization |
|---|---|---|---|
| 341 | 227 | 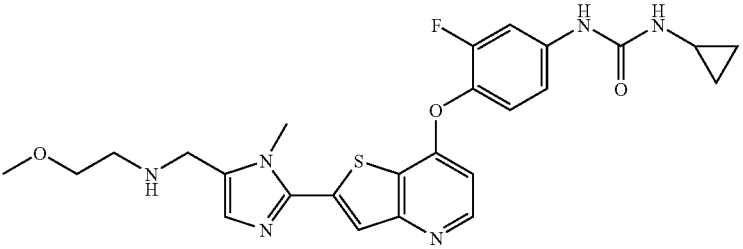 [SMILES: COCCNCc1cnc(-c2cc3nccc(Oc4ccc(NC(=O)NC5CC5)cc4F)c3s2)n1C]<br>1-cyclopropyl-3-(3-fluoro-4-(2-(5-((2-methoxyethylamino)methyl)-1-methyl-1H-imidazol-2-yl)thieno[3,2-b]pyridin-7-yloxy)phenyl)urea | |
| 342 | 228 | 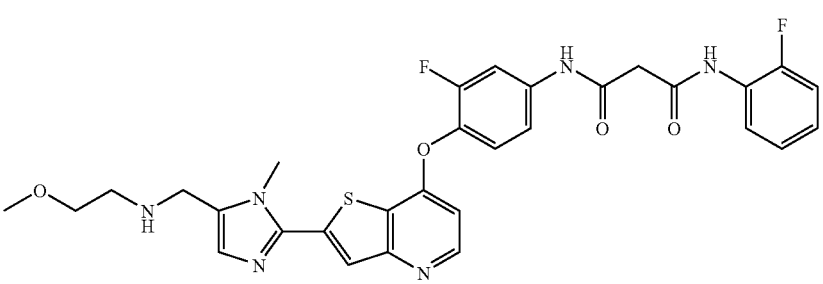 [SMILES: COCCNCc1cnc(-c2cc3nccc(Oc4ccc(NC(=O)CC(=O)Nc5ccccc5F)cc4F)c3s2)n1C]<br>N1-(3-fluoro-4-(2-(5-((2-methoxyethylamino)methyl)-1-methyl-1H-imidazol-2-yl)thieno[3,2-b]pyridin-7-yloxy)phenyl)-N3-(2-fluorophenyl)malonamide | |
| 343 | 229 | 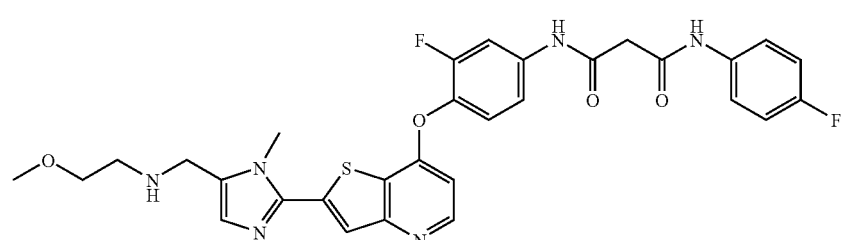<br>N$^1$-(3-fluoro-4-(2-(5-((2-methoxyethylamino)methyl)-1-methyl-1H-imidazol-2-yl)thieno[3,2-b]pyridin-7-yloxy)phenyl)-N3-(4-fluorophenyl)malonamide | $^1$H NMR (400 MHz, DMSO-d6) δ (ppm): LRMS(ESI): (calc.) 606.2 (found) 607.5 (MH)+ |
| 344 | 230 | 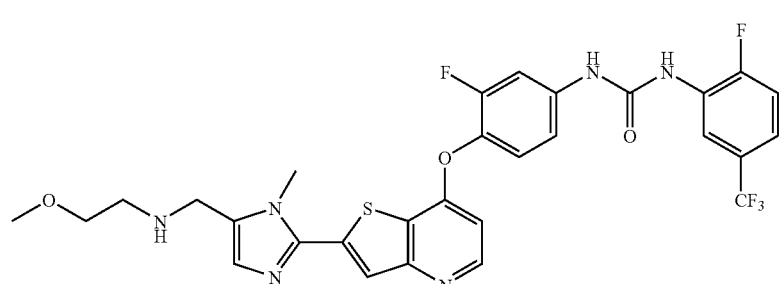<br>1-(3-fluoro-4-(2-(5-((2-methoxyethylamino)methyl)-1-methyl-1H-imidazol-2-yl)thieno[3,2-b]pyridin-7-yloxy)phenyl)-3-(2-fluoro-5-(trifluoromethyl)phenyl)urea | |

TABLE 10-continued

| Cpd. No. | Ex. No. | Structure | Characterization |
|---|---|---|---|
| 345 | 231 | 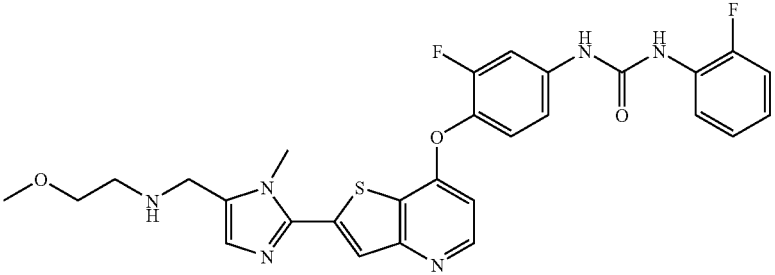 [SMILES: COCCNCc1cnc(-c2cc3nccc(Oc4ccc(NC(=O)Nc5ccccc5F)cc4F)c3s2)n1C] 1-(3-fluoro-4-(2-(5-(((2-methoxyethylamino)methyl)-1-methyl-1H-imidazol-2-yl)thieno[3,2-b]pyridin-7-yloxy)phenyl)-3-(2-fluorophenyl)urea | |
| 346 | 232 | 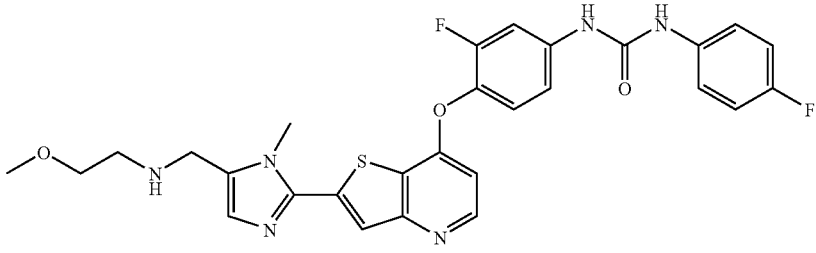 [SMILES: COCCNCc1cnc(-c2cc3nccc(Oc4ccc(NC(=O)Nc5ccc(F)cc5)cc4F)c3s2)n1C] 1-(3-fluoro-4-(2-(5-(((2-methoxyethylamino)methyl)-1-methyl-1H-imidazol-2-yl)thieno[3,2-b]pyridin-7-yloxy)phenyl)-3-(4-fluorophenyl)urea | |
| 347 | 233 | 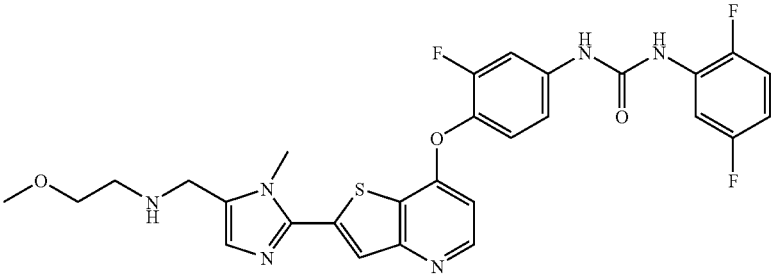 [SMILES: COCCNCc1cnc(-c2cc3nccc(Oc4ccc(NC(=O)Nc5cc(F)ccc5F)cc4F)c3s2)n1C] 1-(2,5-difluorophenyl)-3-(3-fluoro-4-(2-(5-(((2-methoxyethylamino)methyl)-1-methyl-1H-imidazol-2-yl)thieno[3,2-b]pyridin-7-yloxy)phenyl)urea | |
| 348 | 234 | 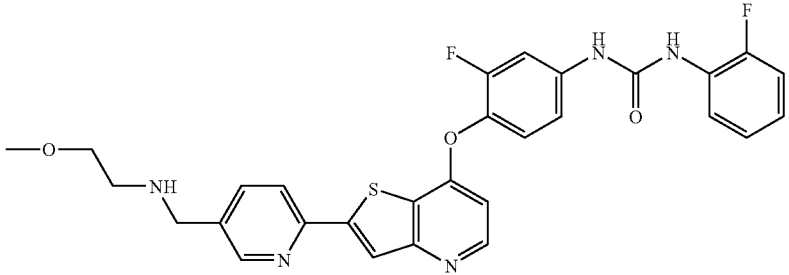 [SMILES: COCCNCc1ccc(-c2cc3nccc(Oc4ccc(NC(=O)Nc5ccccc5F)cc4F)c3s2)nc1] 1-(3-fluoro-4-(2-(5-(((2-methoxyethylamino)methyl)pyridin-2-yl)thieno[3,2-b]pyridin-7-yloxy)phenyl)-3-(2-fluorophenyl)urea | |

246

TABLE 10-continued

| Cpd. No. | Ex. No. | Structure | Characterization |
|---|---|---|---|
| 349 | 235 | 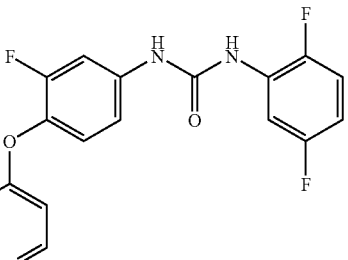<br>1-(2,5-difluorophenyl)-3-(3-fluoro-4-(2-(5-((2-methoxyethylamino)methyl)pyridin-2-yl)thieno[3,2-b]pyridin-7-yloxy)phenyl)urea | |

Other compounds according to the present invention are shown in Table 11.

TABLE 11

| Cpd. No. | Ex. No. | Structure | Characterization |
|---|---|---|---|
| 350 | 236 | 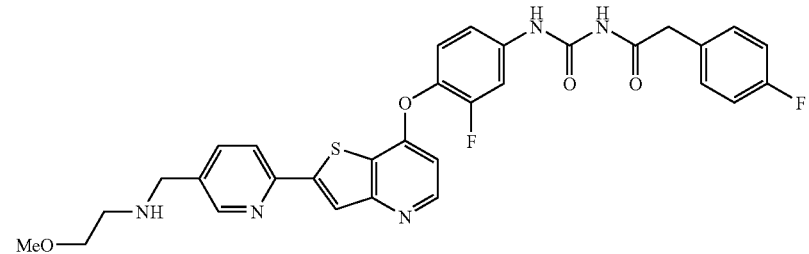 [SMILES: COCCNCc1ccc(-c2cc3nccc(Oc4ccc(NC(=O)NC(=O)Cc5ccc(F)cc5)cc4F)c3s2)nc1]<br>N-(3-fluoro-4-(2-(5-((2-methoxyethylamino)methyl)pyridin-2-yl)thieno[3,2-b]pyridin-7-yloxy)phenylcarbamoyl)-2-(4-fluorophenyl)acetamide | $^1$H NMR (400 MHz, DMSO-d6) δ (ppm): 11.09 (s, 1H), 10.64 (s, 1H), 9.16 (s, 1H), 8.72 (s, 1H), 8.58 (s, 1H), 8.43 (s, 1H), 8.38 (d, J = 8.0 Hz, 2H), 8.09 (d, J = 7.6 Hz, 1H), 7.84 (d, J = 12.4 Hz, 1H), 7.51-7.42 (m, 2H), 7.41-7.32 (m, 2H), 7.20-7.15 (m, 2H), 6.72 (d, J = 4.8 Hz, 1H), 4.28 (s, 2H), 3.75 (s, 2H), 3.62-3.58 (m, 2H), 3.31 (s, 3H), 3.22-3.12 (m, 2H).<br>LRMS(ESI): (calc.) 603.6 (found) 604.4 (MH)+ |
| 351 | 237 | 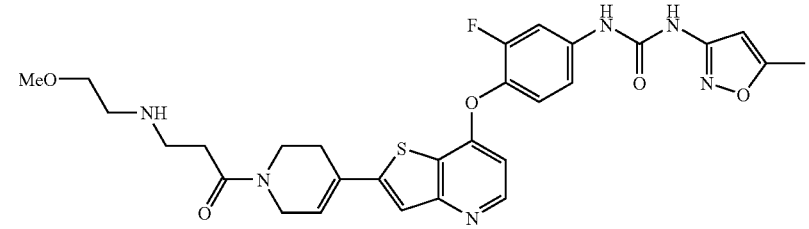 [SMILES: COCCNCCC(=O)N1CC=C(c2cc3nccc(Oc4ccc(NC(=O)Nc5cc(C)on5)cc4F)c3s2)CC1]<br>1-(3-fluoro-4-(2-(1-(3-(2-methoxyethylamino)propanoyl)-1,2,3,6-tetrahydropyridin-4-yl)thieno[3,2-b]pyridin-7-yloxy)phenyl)-3-(5-methylisoxazol-3-yl)urea | $^1$H NMR (400 MHz, DMSO-d6) δ (ppm): 9.72 (br, 1H), 9.41 (s, 1H), 8.47 (d, J = 5.4 Hz, 1H), 7.73 (dd, J = 2.0 Hz, J = 12.9 Hz, 1H), 7.57 (d, H = 6.2 Hz, 1H), 7.44 (t, J = 8.9 Hz, 1H), 7.27 (m, 1H), 6.62 (t, J = 4.5 Hz, 1H), 6.55 (d, J = 1 Hz, 1H), 6.42 (m, 1H), 4.22-4.18 (m, 2H), 3.73-3.68 (m, 2H), 3.43-3.41 (m, 2H), 3.25 (s, 3H), 2.85-2.78 (m, 2H), 2.70 (m, 1H), 2.67-2.56 (m, 3H), 2.37 (d, J = 0.8 Hz, 3H)<br>LRMS(ESI): (calc.) 594.7 (found) 595.5 (MH)+ |

TABLE 11-continued

| Cpd. No. | Ex. No. | Structure | Characterization |
|---|---|---|---|
| 352 | 238 | 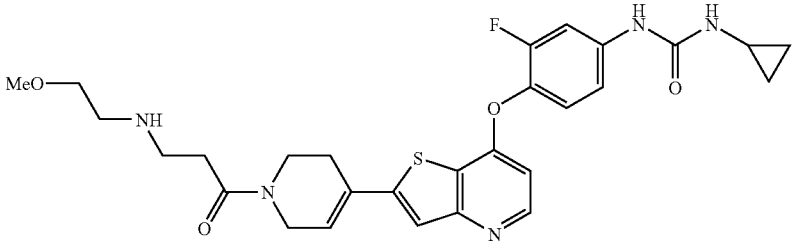 [SMILES: COCCNCCC(=O)N1CC=C(c2cc3nccc(Oc4ccc(NC(=O)NC5CC5)cc4F)c3s2)CC1]<br>1-cyclopropyl-3-(3-fluoro-4-(2-(1-(3-(2-methoxyethylamino)propanoyl)-1,2,3,6-tetrahydropyridin-4-yl)thieno[3,2-b]pyridin-7-yloxy)phenyl)urea | $^1$H NMR (400 MHz, DMSO-d6) δ (ppm): 1H: 8.79 (br, 1H), 8.45 (d, J = 6.0 Hz, 1H), 7.71 (dd, J = 2.3 Hz, J = 13.4 Hz, 1H), 7.56 (d, J = 7.1 Hz, 1H), 7.35 (t, J = 9.0 Hz, 1H), 7.19 (d, J = 9.0 Hz, 1H), 6.63 (br, 1H), 6.58 (t, J = 4.5 Hz, 1H), 6.41 (m, 1H), 4.22-4.18 (m, 2H), 3.73-3.67 (m, 2H), 3.42-3.39 (m, 2H), 3.24 (s, 3H), 2.84-2.81 (m, 2H), 2.76-2.74 (m, 2H), 2.69 (m, 1H), 2.63-2.52 (m, 4H), 0.67-0.62 (m, 2H), 0.44-0.40 (m, 2H) LRMS(ESI): (calc.) 553.7 (found) 554.5 (MH)+ |
| 353 | 239 | 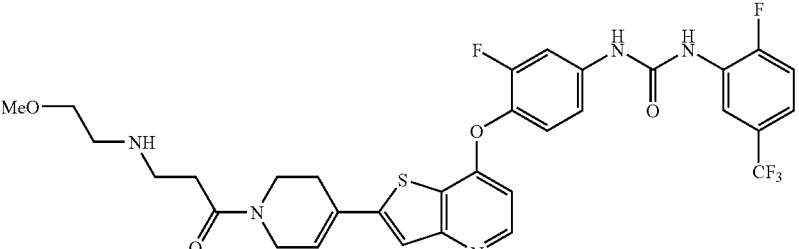<br>1-(3-fluoro-4-(2-(1-(3-(2-methoxyethylamino)propanoyl)-1,2,3,6-tetrahydropyridin-4-yl)thieno[3,2-b]pyridin-7-yloxy)phenyl)-3-(2-fluoro-5-(trifluoromethyl)phenyl)urea | $^1$H NMR (400 MHz, DMSO-d6) δ (ppm): 10.08 (br, 1H), 9.24 (br, 1H), 8.59 (dd, J = 2.3 Hz, J = 7.3 Hz, 1H), 8.47 (d, J = 5.6 Hz, 1H), 8.47 (d, J = 5.6 Hz, 1H), 7.77 (dd, J = 2.2 Hz, J = 13.0 Hz, 1H), 7.58 (d, J = 3.4 Hz, 1H), 7.54-7.41 (m, 3H), 7.27 (d, J = 10.1 Hz, 1H), 6.64 (t, J = 5.0 Hz, 1H), 6.43 (m, 1H), 4.20 (m, 2H), 3.75-3.67 (m, 2H), 3.55-3.52 (m, 2H), 3.28 (s, 3H), 3.07-3.01 (m, 4H), 2.81-2.72 (m, 3H), 2.62 (m, 1H) LRMS(ESI): (calc.) 675.7 (found) 676.5 (MH)+ |
| 354 | 240 | 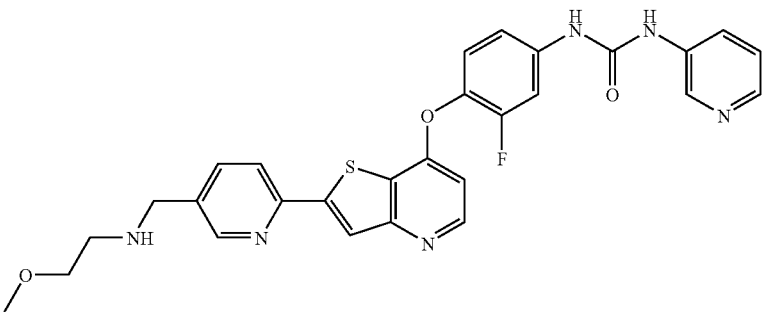 [SMILES: COCCNCc1ccc(-c2cc3nccc(Oc4ccc(NC(=O)Nc5cccnc5)cc4F)c3s2)nc1]<br>1-(3-fluoro-4-(2-(5-((2-methoxyethylamino)methyl)pyridin-2-yl)thieno[3,2-b]pyridin-7-yloxy)phenyl)-3-(pyridin-3-yl)urea | $^1$H NMR (400 MHz, DMSO-d6) δ (ppm): 9.24 (s, 1H), 9.03 (s, 1H), 8.58 (d, 1H, J = 2.0 Hz), 8.53 (d, 1H, J = 1.6 Hz), 8.48 (d, 1H, J = 5.5 Hz), 8.27 (s, 1H), 8.18 (d, 1H, J = 8.2 Hz), 8.10 (m, 1H), 7.91 (m, 1H), 7.85 (dd, 1H, J = 2.2 Hz, J = 8.0), 7.71 (dd, 1H, J = 2.5 Hz, J = 13.3 Hz), 7.41 (t, 1H, J = 9.0 Hz), 7.30 (dd, J = 5.1 Hz, J = 8.2 Hz), 7.25 (m, 1H), 6.63 (d, 1H, J = 5.1 Hz), 3.73 (s, 2H), [3.3 2H], 3.19 (s, 3H), 2.60 (t, 2H, J = 5.7 Hz) LRMS(ESI): (calc.) 544.2 (found) 545.5 (MH)+ |

TABLE 11-continued

| Cpd. No. | Ex. No. | Structure | Characterization |
|---|---|---|---|
| 355 | 241 | 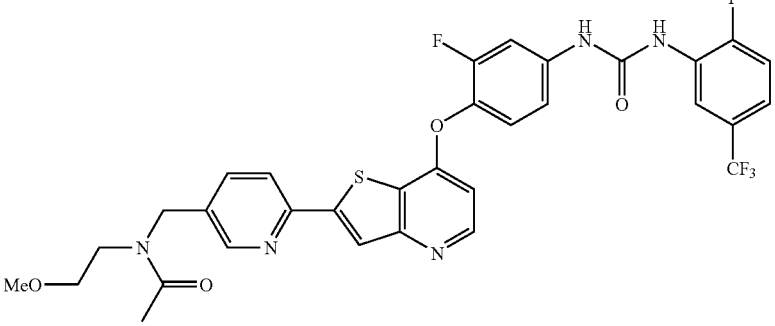<br>N-((6-(7-(2-fluoro-4-(3-(2-fluoro-5-(trifluoromethyl)phenyl)ureido)phenoxy)thieno[3,2-b]pyridin-2-yl)pyridin-3-yl)methyl)-N-(2-methoxyethyl)acetamide | $^1$H NMR (400 MHz, DMSO-d6) δ (ppm): mixture of rotamers; 9.52 (s, 1H), 9.02 and 9.01 (2s, 1H), 8.59 (dd, J = 7.2, 2.0 Hz, 1H), 8.56-8.49 (m, 2H), 8.37 and 8.34 (2s, 1H), 8.29 and 8.23 (2d, J = 8.0 Hz, 1H), 7.82-7.74 (m, 2H), 7.56-7.40 (m, 3H), 7.30-7.24 (m, 1H), 6.71-6.66 (m, 1H), 4.71 and 4.59 (2s, 2H), 3.53-3.38 (m, 4H), 3.24 and 3.21 (2s, 3H), 2.13 and 2.05 (2s, 3H).<br>LRMS(ESI): (calc.) 671.16 (found) 672.5 (MH)+ |
| 356 | 242 | 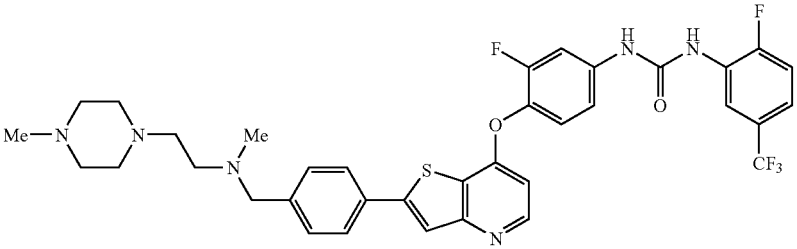 [SMILES: CN1CCN(CCN(C)Cc2ccc(-c3cc4nccc(Oc5ccc(NC(=O)Nc6cc(C(F)(F)F)ccc6F)cc5F)c4s3)cc2)CC1]<br>1-(3-fluoro-4-(2-(4-((methyl(2-(4-methylpiperazin-1-yl)ethyl)amino)methyl)phenyl)thieno[3,2-b]pyridin-7-yloxy)phenyl)-3-fluoro-5-(trifluoromethyl)phenyl)urea | $^1$H NMR (400 MHz, DMSO-d6) δ (ppm): 9.49 (s, 1H), 8.98 (s, d, 1H, J = 2.4 Hz), 8.56 (dd, 1H, J1 = 7.0 Hz, J2 = 2.0 Hz), 8.48 (d, 1H, 7.81 (d, 2H, J = 8.2 Hz), J = 5.5 Hz), 8.00 (s, 1H), 7.81 (d, 2H, J = 8.2 Hz), 7.74 (dd, J1 = 2.4 Hz, J2 = 12.9 Hz), 7.49-7.39 (m, 5H), 7.23 (d, 1H, J = 9.0 Hz), 6.59 (d, 1H, J = 5.5 Hz), 3.50 (s, 2H), 2.50-2.28 (m, 12H), 2.13 (s, 3H), 2.11 (s, 3H).<br>LRMS(ESI): (calc.) 710.2 (found) 711.5 (MH)+ |
| 357 | 243 | 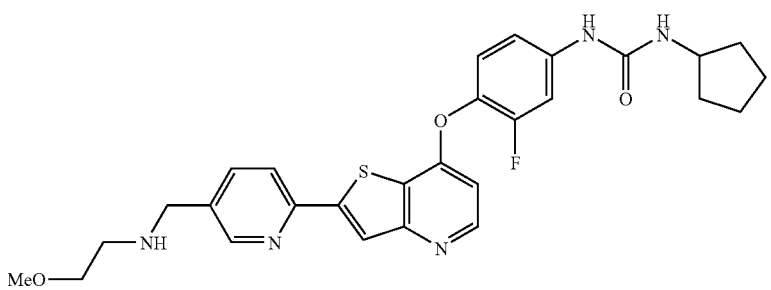 [SMILES: COCCNCc1ccc(-c2cc3nccc(Oc4ccc(NC(=O)NC5CCCC5)cc4F)c3s2)nc1]<br>1-cyclopentyl-3-(3-fluoro-4-(2-(5-((2-methoxyethylamino)methyl)pyridin-2-yl)thieno[3,2-b]pyridin-7-yloxy)phenyl)urea | $^1$H NMR (400 MHz, DMSO-d6) δ (ppm): 8.61 (s, 1H), 8.53 (d, 1H, J = 1.6 Hz), 8.47 (d, 1H, J = 5.3 Hz), 8.27 (s, 1H), 8.18 (d, 1H, J = 8.2 Hz), 7.85 (dd, 1H, J = 2.1 Hz, J = 8.2 Hz), 7.67 (dd, 1H, J = 2.6 Hz, J = 13.5 Hz), 7.32 (t, 1H, J = 9.0 Hz), 7.09 (m, 1H), 6.59 (d, 1H, J = 5.4 Hz), 6.28 (d, 1H, J = 7.1 Hz)<br>LRMS(ESI): (calc.) 535.2 (found) 536.4 (MH)+ |
| 358 | 244 | 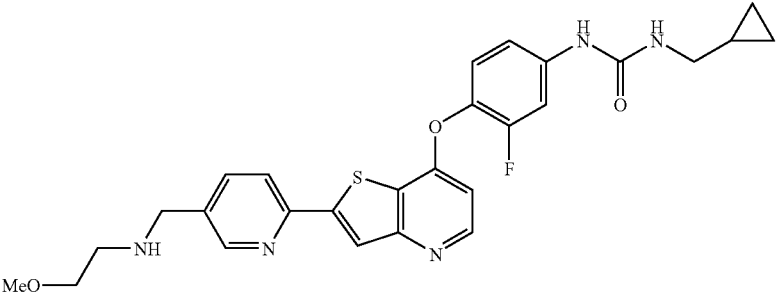 [SMILES: COCCNCc1ccc(-c2cc3nccc(Oc4ccc(NC(=O)NCC5CC5)cc4F)c3s2)nc1]<br>1-(cyclopropylmethyl)-3-(3-fluoro-4-(2-(5-((2-methoxyethylamino)methyl)pyridin-2-yl)thieno[3,2-b]pyridin-7-yloxy)phenyl)urea | $^1$H NMR (400 MHz, DMSO-d6) δ (ppm): DMSO-d69.20 (s, 1H), 8.39 (s, 1H), 8.33 (d, 1H, J = 5.3 Hz), 8.12 (s, 1H), 8.04 (d, 1H, J = 8.2 Hz), 7.71 (dd, 1H, J = 1.7 Hz, J = 8.2 Hz), 7.55 (dd, 1H, J = 2.2 Hz, J = 13.7 Hz), 7.17 (t, 1H, J = 9.2 Hz), 7.00 (d, 1H, J = 8.6 Hz), 6.70 (m, 1H), 6.45 (d, 1H, J = 5.4 Hz), 3.59 (s, 2H), 3.22 (t, 2H, 5.7 Hz), 3.05 (s, 3H), 2.79 (t, 2H, J = 6.2 Hz), 1.54 (s, 1H), 0.76 (m, 1H), 0.23 (m, 2H), 0.01 (m, 2H)<br>LRMS(ESI): (calc.) 521.2 (found) 522.4 (MH)+ |

TABLE 11-continued

| Cpd. No. | Ex. No. | Structure | Characterization |
|---|---|---|---|
| 359 | 245 | 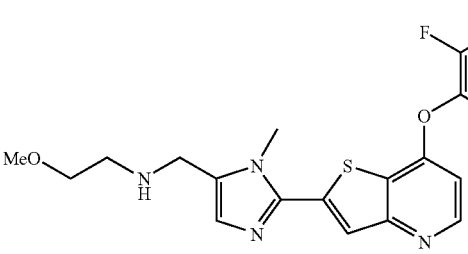
1-(2,4-difluorophenyl)-3-(3-fluoro-4-(2-(5-((2-methoxyethylamino)methyl)-1-methyl-1H-imidazol-2-yl)thieno[3,2-b]pyridin-7-yloxy)phenyl)urea | $^1$H NMR (400 MHz, DMSO-d6) δ (ppm): 10.90 (s, 1H), 8.89 (s, 1H), 8.50 (d, J = 5.48 Hz, 1H), 7.98 (m, 1H), 7.95 (s, 1H), 7.72 (m, 1H), 7.41 (m, 1H), 7.28-7.20 (m, 3H), 7.04 (m, 1H), 4.28 (s, 2H), 3.92 (s, 3H), 3.61 (m, 2H), 3.27 (s, 3H), 3.13 (m, 2H) LRMS(ESI): (calc.) 582.60 (found) 583.5 (MH)+ |
| 360 | 246 | 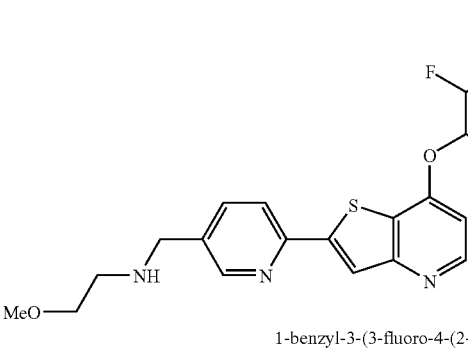
1-benzyl-3-(3-fluoro-4-(2-(5-((2-methoxyethylamino)methyl)pyridin-2-yl)thieno[3,2-b]pyridin-7-yloxy)phenyl)urea | $^1$H NMR (400 MHz, DMSO-d6) δ (ppm): 9.0 (s, 1H), 8.57 (d, J = 1.4 Hz, 1H), 8.51 (d, J = 5.6 Hz, 1H), 8.31 (s, 1H), 8.23 (d, J = 8.5 Hz, 1H), 7.89 (dd, J = 1.8 Hz, J = 8.1 Hz, 1H), 7.73 (dd, J = 2.6 Hz, J = 13.5 Hz, 1H), 7.41-7.24 (m, 5H), 7.24-7.18 (m, 2H), 6.82-6.79 (m, 1H), 5.28 (d, J = 5.28 Hz, 1H), 4.32 (d, J = 6.4 Hz, 2H), 3.78 (s, 2H), 3.41 (t, J = 5.8 Hz, 2H), 3.26 (s, 3H), 2.65 (t, J = 5.8 Hz, 2H) LRMS(ESI): (calc.) 557.6 (found) 558.5 (MH)+ |
| 361 | 247 | 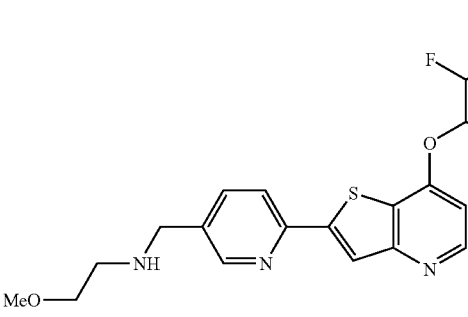
benzyl 3-fluoro-4-(2-(5-((2-methoxyethylamino)methyl)pyridin-2-yl)thieno[3,2-b]pyridin-7-yloxy)phenylcarbamate | $^1$H NMR (400 MHz, DMSO-d6) δ (ppm): 10.2 (s, 1H), 8.57 (d, J = 1.9 Hz, 1H), 8.51 (d, J = 5.5 Hz, 1H), 8.32 (s, 1H), 8.23 (d, J = 7.9 Hz, 1H), 7.90 (dd, J = 1.9 Hz, J = 8.1 Hz, 1H), 7.66 (dd, J = 8.3 Hz, J = 8.1 Hz, 1H), 7.49-7.33 (m, 7H), 6.65 (dd, J = 0.6 Hz, J = 5.5 Hz, 1H), 5.19 (s, 2H), 3.79 (s, 2H), 3.41 (t, J = 5.7 Hz, 2H), 3.24 (s, 3H), 2.66 (t, J = 5.7 Hz, 2H) LRMS(ESI): (calc.) 558.6 (found) 559.4 (MH)+ |
| 362 | 248 | 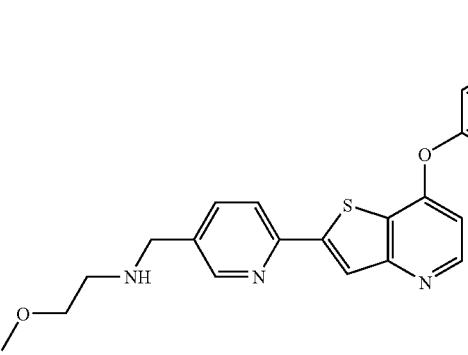
1-(cyclohexylmethyl)-3-(3-fluoro-4-(2-(5-((2-methoxyethylamino)methyl)pyridin-2-yl)thieno[3,2-b]pyridin-7-yloxy)phenyl)urea | $^1$H NMR (400 MHz, DMSO-d6) δ (ppm): DMSO-d6 8.80 (s, 1H), 8.51 (s, 1H), 8.46 (d, 1H, J = 5.3 Hz), 8.26 (s, 1H), 8.17 (d, 1H, J = 8.0 Hz), 7.83 (d, 1H, J = 7.9 Hz), 7.67 (d, 1H, J = 13.5 Hz), 7.31 (t, 1H, J = 9.0 Hz), 7.09 (d, 1H, J = 8.4 Hz), 6.58 (d, 1H, J = 5.0 Hz), 6.33 (m, 1H), 3.72 (s, 2H), 3.35 (t, Hz), 2.59 (t, 2H, J = 5.3 Hz0, 1.62 (m, 5H), 1.34 (m, 1H), 1.11 (m, 3H), 0.86 (m, 2H) LRMS(ESI): (calc.) 563.2 (found) 564.5 (MH)+ |

Other compounds according to the present invention are shown in Table 12.

TABLE 12

| Cpd. No. | Ex. No. | Structure |
|---|---|---|
| 363 | 249 | 3-(3-fluoro-4-(2-(5-((2-methoxyethylamino)methyl)pyridin-2-yl)thieno[3,2-b]pyridin-7-yloxy)phenyl)-1-(2-fluoro-5-(trifluoromethyl)phenyl)-1-methylurea |
| 364 | 250 | 1-cyclopentyl-3-(3-fluoro-4-(2-(5-((2-methoxyethylamino)methyl)pyridin-2-yl)thieno[3,2-b]pyridin-7-yloxy)phenyl)urea |
| 365 | 251 | 1-(3-acetylphenyl)-3-(3-fluoro-4-(2-(5-((2-methoxyethylamino)methyl)pyridin-2-yl)thieno[3,2-b]pyridin-7-yloxy)phenyl)urea |
| 366 | 252 | 1-cyclopropyl-3-(3-fluoro-4-(2-(4-((methyl(2-(4-methylpiperazin-1-yl)ethyl)amino)methyl)phenyl)thieno[3,2-b]pyridin-7-yloxy)phenyl)urea |

TABLE 12-continued

| Cpd. No. | Ex. No. | Structure |
|---|---|---|
| 367 | 253 | 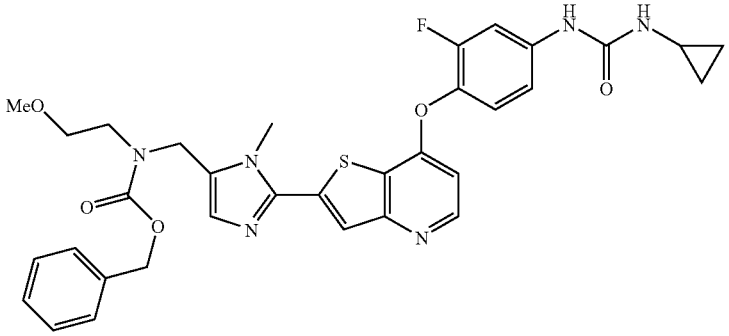 [SMILES: COCCN(Cc1cnc(-c2cc3nccc(Oc4ccc(NC(=O)NC5CC5)cc4F)c3s2)n1C)C(=O)OCc1ccccc1] benzyl (2-(7-(4-(3-cyclopropylureido)-2-fluorophenoxy)thieno[3,2-b]pyridin-2-yl)-1-methyl-1H-imidazol-5-yl)methyl(2-methoxyethyl)carbamate |

Other compounds according to the present invention are shown in Table 13.

TABLE 13

| Cpd. No. | Ex. No. | Structure | Characterization |
|---|---|---|---|
| 368 | 254 | 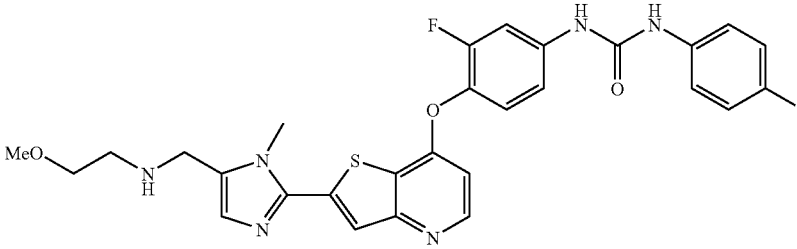 1-(4-chlorophenyl)-3-(3-fluoro-4-(2-(5-((2-methoxyethylamino)methyl)-1-methyl-1H-imidazol-2-yl)thieno[3,2-b]pyridin-7-yloxyl)phenyl)urea | $^1$H NMR (400 MHz, DMSO-d6) δ (ppm): 9.27 (s, 1 H), 9.11 (s, 1 H), 8.48 (d, J = 5.48 Hz, 1 H), 7.87 (s, 1 H), 7.70 (m, 1 H), 7.46 (d, J = 9 Hz, 2 H), 7.41 (t, J = 7.82 Hz, 1 H), 7.30 (d, J = 8.80 Hz, 2 H), 7.21 (m, 1 H), 6.95 (s, 1 H), 6.65 (d, J = 5.28 H, 1 H), 3.88 (s, 3 H), 3.79 (s, 2 H), 3.39 (m, 2 H), 3.21 (s, 3 H), 2.71 (m, 2 H) LRMS (ESI): (calc.) 581.06 (found) 581.4 (MH)+ |
| 369 | 255 | 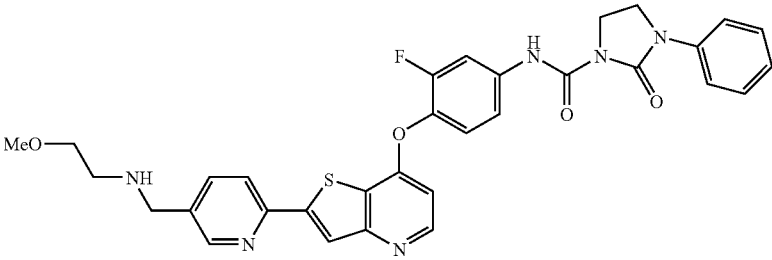 N-(3-fluoro-4-(2-(5-((2-methoxyethylamino)methyl)pyridin-2-yl)thieno[3,2-b]pyridin-7-yloxy)phenyl)-3-(4-fluorophenyl)-2-oxoimidazolidine-1-carboxamide | $^1$H NMR (400 MHz, DMSO-d6) δ (ppm): 10.56 (s, 1 H), 8.56 (d, J = 2.2 Hz, 1 H), 8.53 (d, J = 5.5 Hz, 1 H), 8.32 (s, 1 H), 8.23 (d, J = 8.2 Hz, 1 H), 7.90 (dd, J = 8.0, 2.0 Hz, 1 H), 7.85 (dd, J = 12.9, 2.3 Hz, 1 H), 7.69-7.61 (m, 2 H), 7.50 (t, J = 8.7 Hz, 1 H), 7.44 (dd, J = 9.0, 2.3 Hz, 1 H), 7.33-7.24 (m, 2 H), 6.68 (d, J = 5.3 Hz, 1 H), 3.96 (bs, 4 H), 3.78 (s, 2 H), one CH2 is masked by water, 3.33 (s, 3 H), 2.65 (t, J = 5.7 Hz, 2 H), one NH is missing. LRMS (ESI): (calc.) 630.66 (found) 631.5 (MH)+ |

TABLE 13-continued

| Cpd. No. | Ex. No. | Structure | Characterization |
|---|---|---|---|
| 370 | 256 | 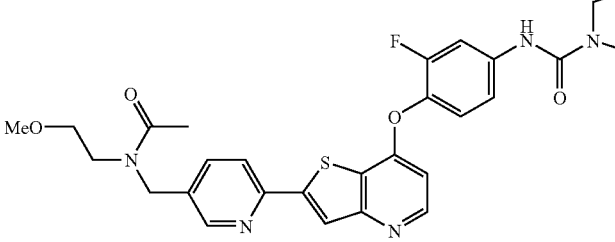<br>N-(3-fluoro-4-(2-(5-((N-(2-methoxyethyl)acetamido)methyl)pyridin-2-yl)thieno[3,2-b]pyridin-7-yloxy)phenyl)-3-(4-fluorophenyl)-2-oxoimidazolidine-1-carboxamide | $^1$H NMR (400 MHz, DMSO-d6) δ (ppm): mixture of rotamers, 10.56 (s, 1 H), 8.58-8.46 (m, 2 H), 8.40-8.20 (m, 2 H), 7.90-7.74 (m, 2 H), 7.70-7.60 (m, 2 H), 7.55-7.42 (m, 2 H), 7.29 (t, J = 8.9 Hz, 2 H), 6.73-6.66 (m, 1 H), 4.71 and 4.59 (2 s, 2 H), 3.96 (bs, 4 H), 3.54-3.40 (m, 4 H), 3.24 and 3.20 (2 s, 3 H), 2.13 and 2.05 (2 s, 3 H).<br>LRMS (ESI): (calc.) 672.7 (found) 673.3 (MH)+ |
| 371 | 257 | 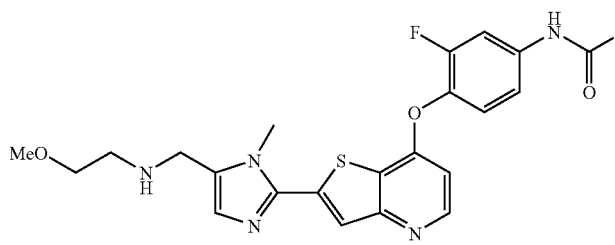<br>1-(3-fluoro-4-(2-(5-((2-methoxyethylamino)methyl)-1-methyl-1H-imidazol-2-yl)thieno[3,2-b]pyridin-7-yloxy)phenyl)-3-(4-(trifluoromethoxy)phenyl)urea | $^1$H NMR (400 MHz, DMSO-d6) δ (ppm): 9.12 (s, 1 H), 0.02 (s, 1 H), 8.48 (d, J = 5.48 Hz, 1 H), 7.85 (s, 1 H), 7.70 (m, 1 H), 7.53 (d, J = 9.19 Hz, 2 H), 7.41 (t, J = 8.99 Hz, 1 H), 7.27 (m, 3 H), 6.92 (s, 1 H), 6.65 (d, J = 5.28 Hz, 1 H), 3.87 (s, 3 H) (, 3.73 (s, 2 H), 3.34 (m, 2 H), 3.20 (s, 3 H), 2.62 (t, J = 5.67 Hz, 2 H).<br>LRMS (ESI): (calc.) 630.6 (found) 632.5 (MH)+ |

Pharmaceutical Compositions

In one embodiment, the invention provides pharmaceutical compositions comprising a compound according to the invention and a pharmaceutically acceptable carrier, excipient, or diluent. Compositions of the invention may be formulated by any method well known in the art and may be prepared for administration by any route, including, without limitation, parenteral, oral, sublingual, transdermal, topical, intranasal, intratracheal, or intrarectal. In certain embodiments, compositions of the invention are administered intravenously in a hospital setting. In certain other embodiments, administration may be by, for example, the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term "pharmaceutically acceptable salt (s)" refers to salts that retain the desired biological activity of the above-identified compounds and exhibit minimal or no undesired toxicological effects. Examples of such salts include, but are not limited to, salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

Inhibition of VEGF Receptor Signaling and HGF Receptor Signaling

In another embodiment the invention provides a method of inhibiting VEGF receptor signaling and HGF receptor signaling in a cell, comprising contacting a cell in which inhibition of VEGF receptor signaling and HGF receptor signaling is desired with an inhibitor of VEGF receptor signaling and HGF receptor signaling according to the invention. Because compounds of the invention inhibit VEGF receptor signaling and HGF receptor signaling, they are useful research tools for in vitro study of the role of VEGF receptor signaling and HGF receptor signaling in biological processes. In one example of this embodiment, the method causes an inhibition of cell proliferation of the contacted cells.

ASSAY EXAMPLES

Inhibition of c-Met and VEGF Activity

The following protocols were used to assay the compounds of the invention.

Assay Example 1

In Vitro Receptor Tyrosine Kinase Assays (c-Met/HGF Receptor and VEGF Receptor KDR)

These tests measure the ability of compounds to inhibit the enzymatic activity of recombinant human c-Met/HGF receptor and VEGF receptor enzymatic activity.

A 1.3-kb cDNA corresponding to the intracellular domain of c-Met or c-Met IC (Genbank accession number NP000236-1 amino acid 1078 to 1337) is cloned into the BamHI/XhoI sites of the pBlueBacHis2A vector (Invitrogen) for the production of a histidine-tagged version of that enzyme. This construct is used to generate recombinant baculovirus using the Bac-N-Blue™ system according to the manufacturer's instructions (Invitrogen).

The c-Met IC protein is expressed in Hi-5 cells (*Trichoplusia Ni*) upon infection with recombinant baculovirus construct. Briefly, Hi-5 cells grown in suspension and maintained in serum-free medium (Sf900 II supplemented with gentamycin) at a cell density of about $2 \times 10^6$ cells/ml are infected with the above-mentioned viruses at a multiplicity of infection (MOI) of 0.2 during 72 hours at 27° C. with agitation at 120 rpm on a rotary shaker. Infected cells are harvested by centrifugation at 398 g for 15 min. Cell pellets are frozen at −80° C. until purification is performed.

All steps described in cell extraction and purification are performed at 4° C. Frozen Hi-5 cell pellets infected with the C-Met IC recombinant baculovirus are thawed and gently resuspended in Buffer A (20 mM Tris pH 8.0, 10% glycerol, 1 g/ml pepstatin, 2 μg/ml Aprotinin and leupeptin, 50 μg/ml PMSF, 50 μg/ml TLCK and 10 μM E64, 0.5 mM DTT and 1 mM Levamisole) using 3 ml of buffer per gram of cells. The suspension is Dounce homogenized after which it is centrifuged at 22500 g, 30 min., 4° C. The supernatant (cell extract) is used as starting material for purification of c-Met IC.

The supernatant is loaded onto a QsepharoseFF column (Amersham Biosciences) equilibrated with Buffer B (20 mM Tris pH 8.0, 10% glycerol) supplemented with 0.05M NaCl. Following a ten column volume (CV) wash with equilibration buffer, bound proteins are eluted with a 5 CV salt linear gradient spanning from 0.05 to 1M NaCl in Buffer B. Typically, the conductivity of selected fractions rank between 6.5 and 37 mS/cm. This Qsepharose eluate has an estimated NaCl concentration of 0.33M and is supplemented with a 5M NaCl solution in order to increase NaCl concentration at 0.5M and also with a 5M Imidazole (pH 8.0) solution to achieve a final imidazole concentration of 15 mM. This material is loaded onto a HisTrap affinity column (GE Healthcare) equilibrated with Buffer C (50 mM NaPO4 pH 8.0, 0.5M NaCl, 10% glycerol) supplemented with 15 mM imidazole. After a 10 CV wash with equilibration buffer and an 8 CV wash with buffer C+40 mM imidazole, bound proteins are eluted with an 8 CV linear gradient (15 to 500 mM) of imidazole in buffer C. C-Met IC enriched fractions from this chromatography step are pooled based on SDS-PAGE analysis. This pool of enzyme undergoes buffer exchange using PD-10 column (GE Healthcare) against buffer D (25 mM HEPES pH 7.5, 0.1M NaCl, 10% glycerol and 2 mM β-mercaptoethanol). Final C-Met IC protein preparations concentrations are about 0.5 mg/ml with purity approximating 80%. Purified c-Met IC protein stocks are supplemented with BSA at 1 mg/ml, aliquoted and frozen at −80° C. prior to use in enzymatic assay.

In the case of VEGF receptor KDR a 1.6-kb cDNA corresponding to the catalytic domain of VEGFR2 or KDR (Genbank accession number AF035121 amino acid 806 to 1356) is cloned into the Pst I site of the pDEST20 Gateway vector (Invitrogen) for the production of a GST-tagged version of that enzyme. This construct is used to generate recombinant baculovirus using the Bac-to-Bac™ system according to the manufacturer's instructions (Invitrogen).

The GST-VEGFR2806-1356 protein is expressed in Sf9 cells (*Spodoptera frugiperda*) upon infection with recombinant baculovirus construct. Briefly, Sf9 cells grown in suspension and maintained in serum-free medium (Sf900 II supplemented with gentamycin) at a cell density of about $2 \times 10^6$ cells/ml are infected with the above-mentioned viruses at a multiplicity of infection (MOI) of 0.1 during 72 hours at 27° C. with agitation at 120 rpm on a rotary shaker. Infected cells are harvested by centrifugation at 398 g for 15 min. Cell pellets are frozen at −80° C. until purification is performed.

All steps described in cell extraction and purification are performed at 4° C. Frozen Sf9 cell pellets infected with the GST-VEGFR2806-1356 recombinant baculovirus are thawed and gently resuspended in Buffer A (PBS pH 7.3 supplemented with 1 μg/ml pepstatin, 2 μg/ml Aprotinin and leupeptin, 50 μg/ml PMSF, 50 μg/ml TLCK and 10 μM E64 and 0.5 mM DTT) using 3 ml of buffer per gram of cells. Suspension is Dounce homogenized and 1% Triton X-100 is added to the homogenate after which it is centrifuged at 22500 g, 30 min., 4° C. The supernatant (cell extract) is used as starting material for purification of GST-VEGFR2806-1356.

The supernatant is loaded onto a GST-agarose column (Sigma) equilibrated with PBS pH 7.3. Following a four column volume (CV) wash with PBS pH 7.3+1% Triton X-100 and 4 CV wash with buffer B (50 mM Tris pH 8.0, 20% glycerol and 100 mM NaCl), bound proteins are step eluted with 5 CV of buffer B supplemented with 5 mM DTT and 15 mM glutathion. GST-VEGFR2806-1356 enriched fractions from this chromatography step are pooled based on U.V. trace i.e. fractions with high O.D.280. Final GST-VEGFR2806-1356 protein preparations concentrations are about 0.7 mg/ml with purity approximating 70%. Purified GST-VEGFR2806-1356 protein stocks are aliquoted and frozen at −80° C. prior to use in enzymatic assay.

Inhibition of c-Met/HGF receptor and VEGFR/KDR is measured in a DELFIA™ assay (Perkin Elmer). The substrate poly(Glu4,Tyr) is immobilized onto black high-binding polystyrene 96-well plates. The coated plates are washed and stored at 4° C. During the assay, enzymes are pre-incubated with inhibitor and Mg-ATP on ice in polypropylene 96-well plates for 4 minutes, and then transferred to the coated plates. The subsequent kinase reaction takes place at 30° C. for 10-30 minutes. ATP concentrations in the assay are 10 uM for C-Met (5× the Km) and 0.6 uM for VEGFR/KDR (2× the Km). Enzyme concentration is 25 nM (C-Met) or 5 nM (VEGFR/KDR). After incubation, the kinase reactions are quenched with EDTA and the plates are washed. Phosphorylated product is detected by incubation with Europium-labeled anti-phosphotyrosine MoAb. After washing the plates, bound MoAb is detected by time-resolved fluorescence in a Gemini SpectraMax reader (Molecular Devices). Compounds are evaluated over a range of concentrations and $IC_{50}$'s (concentration of compounds giving 50% inhibition of enzymatic activity) are determined. The results are shown in Table 2, columns B and C Assay Example 2

Inhibition of c-Met Phosphorylation in MKN45 Cells

The following assay is used to determine inhibition of c-Met phosphorylation.

The c-Met receptor is expressed in numerous cancer cell lines derived from tumors of epithelial origin. In MKN45 gastric carcinoma cells the c-Met gene is amplified, resulting in several-fold overexpression of the receptor and its constitutive activation. For this reason constitutively high levels of ERK1/2 are also detected in these cells, independently of HGF-added stimulation (Smolen G A, Sordella R, Muir B, Mohapatra G, Barmettler A, Archibald H, et al. Amplification of MET may identify a subset of cancers with extreme sensitivity to the selective tyrosine kinase inhibitor PHA-665752. *Proc Natl Acad Sci USA* 2006). We have developed a sensitive method to follow c-Met phosphorylation in these cells. In previous studies with earlier generation c-Met inhibitors, we established that the $IC_{50}$s for the inhibition of c-Met phosphorylation were identical using this novel ELISA approach and standard western blot procedure, with antibodies directed against the activating autocatalysis tyrosine residues of c-MET (Tyr Y1230-34-35).

Cell treatments: MKN45 cells are seeded into wells of 96-well plates at a density of $3 \times 10^4$ cells/well in RPMI medium supplemented with 10% FBS. HA-TPR-RON expressing 293T (clone 18) cells are seeded into wells of 96-well plates at a density of $3 \times 10^4$ cells/well in DMEM medium supplemented with 10% FBS. Cells are grown for 48 h prior to treatments with compounds of interest. Inhibitors are added to the medium in triplicate wells at the indicated doses. After 3 h of treatment, media is aspirated and cells are lysed by one freeze-thaw cycle in 50 µL/well hypotonic lysis buffer (25 mM HEPES pH 7.5, 10 mM NaCl with 1 mM 4-(2-aminoethyl)benzenesulfonyl fluoride hydrochloride, 200 µM sodium orthovanadate, 1 mM sodium fluoride, 10 µg/mL of leupeptin, 10 µg/mL of aprotinin/mL, 1 µg/mL of pepstatin and 50 µg/mL Na-p-tosyl-L-lysine chloromethyl ketone hydrochloride.

Detection of phosphorylated c-Met by direct ELISA: Lysate samples (5 µL) from wells of treatment plates are transferred to 80 µL of binding buffer (25 mM HEPES pH 7.5, 200 mM NaCl) in wells of high binding white polysterene 96-well plates (Corning). After an overnight protein binding incubation at 4° C., lysates are aspirated and wells are blocked for 1 h at 37° C. in TBST supplemented with 5% BSA. Plates are incubated with the primary antibodies anti-phospho-Tyrosine (Millipore, 4G10) diluted 1/15000 in TBST supplemented with 5% BSA for 1 h at room temperature. Plates are washed 3 times on a plate washer (SkanWasher, Molecular Devises), and incubated with the reporter antibody anti-rabbit-horseradish peroxidase (Sigma) diluted 1/15000 in TBST supplemented with 5% BSA, for 1 h at room temperature. Plates are washed 3 times with TBST using on a plate washer and subsequently incubated with chemiluminescent substrate solution (ECL, Roche). Luminescence signal is captured on a Polar Star Optima apparatus (BMG LabTech).

Average values of the triplicate samples are used to prepare $IC_{50}$ curves using a 4-parameter fit model. These curves are calculated using, for example, GraFit 5.0 software. For assay standardization purpose, an internal control is included on each experimental test plate. The results are shown in Table 2, column F.

Assay Example 3

Inhibition of c-MET Dependent Motiliy

Activation of the c-Met receptor by its ligand HGF induces signal transduction pathways implicated in the regulation of cell migration The prostate carcinoma cells DU145 have been shown to express high levels of the c-Met receptor and respond to HGF in cell based assays by cell scattering (Miura H, Nishimura K, Tsujimura A, Matsumiya K, Matsumoto K, Nakamura T, et al. Effects of hepatocyte growth factor on E-cadherin-mediated cell-cell adhesion in DU145 prostate cancer cells. *Urology* 2001; 58(6):1064-9). The A549 cells are lung carcinoma cells that have also been shown to express high levels of c-Met, and exhibit motility upon stimulation with HGF in the context of wound healing cell based assays (Nakamura T, Matsumoto K, Kiritoshi A, Tano Y, Nakamura T. Induction of hepatocyte growth factor in fibroblasts by tumor-derived factors affects invasive growth of tumor cells: in vitro analysis of tumor-stromal interactions. *Cancer Res* 1997; 57(15):3305-13).

Scatter assays in DU145. The scatter assay is performed as described previously (Miura H, Nishimura K, Tsujimura A, Matsumiya K, Matsumoto K, Nakamura T, et al. Effects of hepatocyte growth factor on E-cadherin-mediated cell-cell adhesion in DU145 prostate cancer cells. *Urology* 2001; 58(6):1064-9) for DU145 prostate carcinoma cells with the indicated modifications. In brief, DU145 cells (ATCC) are seeded in 24-well plates at a density of $7 \times 10^3$ cells/well in MEM medium complemented with 10% FBS and cultured for 48 h, to allow the formation of small compact colonies of cells. Inhibitors are subsequently added at a range of doses (0.00032-10 uM) for 3 h. Cells are then stimulated to migrate by the addition of HGF (in the form of conditioned medium from 293T cells over-expressing the human HGF gene) and the culture is continued for another 24 h. The $IC_{50}$ values is defined as the last dose that created an inhibitory effect on scattering. For the purpose of standardization a control is carried on every test plates for the DU145 scattering assays. The results are shown in Table 2, column E.

Wound healing assay in A549 cells. A549 cells (ATCC) are seeded in DMEM low glucose medium complemented with 10% FBS into 24-well plates at a density of $7.5 \times 10^4$ cells/well and grown to confluence (48 h). Inhibitors were added to the medium at a range of doses (0.00032-10 uM) for 3 h at which point a gap is introduced by scraping cells with a P1000 pipette tip. Cells are then stimulated to migrate by the addition of HGF (in the form of conditioned medium from 293T cells over-expressing the human HGF gene) and the culture is continued for 24 h. The $IC_{50}$ values are defined as the last dose that inhibited gap closing by more than 25%. For the purpose of standardization, a control is carried on every assay plates. The results are shown in Table 2, column D.

Biological Assay Results

The activities of some of the compounds according to the invention measured by the above assays are displayed in Table 2. In the table, "a" indicates inhibitory activity at a concentration of less than 250 nanomolar; "b" indicates inhibitory activity at a concentration $\geq 250$ but <500 nanomolar, "c" indicates inhibitory activity at $\geq 500$ but <1000 nanomolar; and "d" indicates inhibitory activity $\geq 1000$ nanomolar.

TABLE 2
| A Structure | B CMET IC50 (µM) | C VEGFR IC50 (µM) | D A549 WOUND_ HEALING IC50 (µM) |
|---|---|---|---|
| 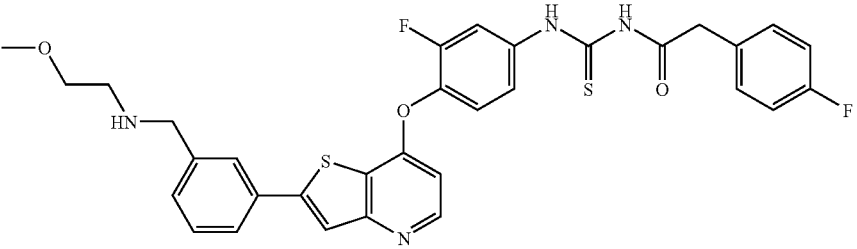 | a | a | b |
| 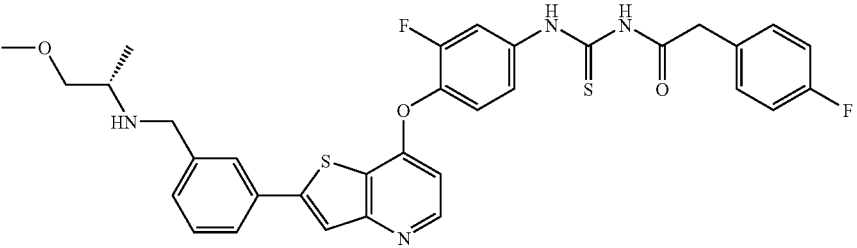 [SMILES: COC[C@H](C)NCc1cccc(-c2cc3nccc(Oc4ccc(NC(=S)NC(=O)Cc5ccc(F)cc5)cc4F)c3s2)c1] | a | a | b |
| 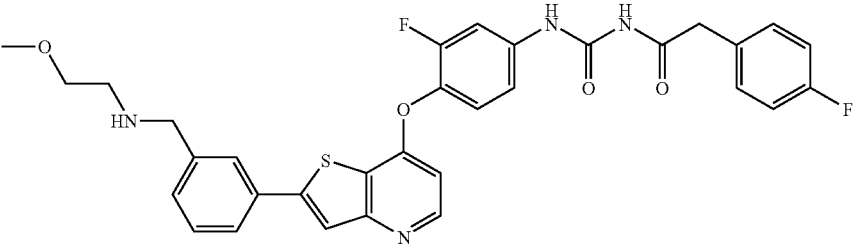 [SMILES: COCCNCc1cccc(-c2cc3nccc(Oc4ccc(NC(=O)NC(=O)Cc5ccc(F)cc5)cc4F)c3s2)c1] | a | b | d |
| 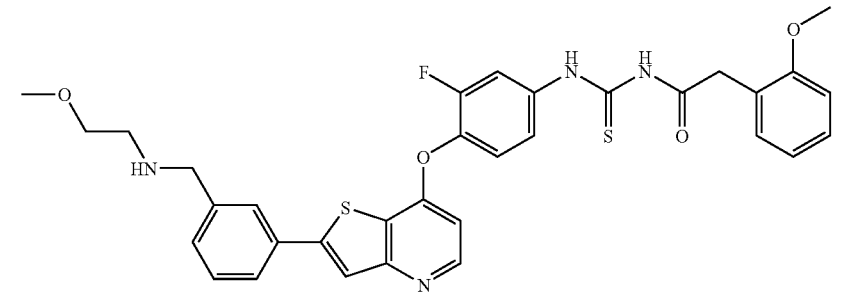 | a | a | b |
| 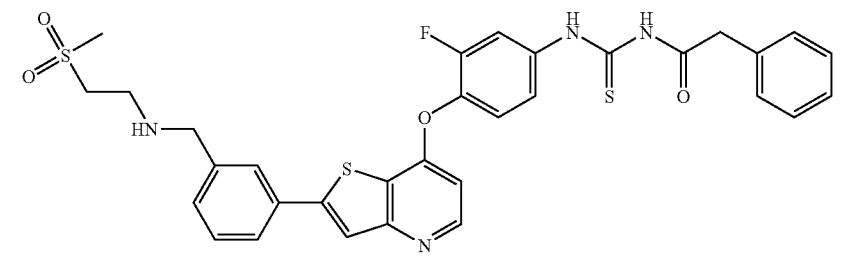 [SMILES: CS(=O)(=O)CCNCc1cccc(-c2cc3nccc(Oc4ccc(NC(=S)NC(=O)Cc5ccccc5)cc4F)c3s2)c1] | a | a | d |

TABLE 2-continued
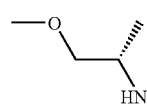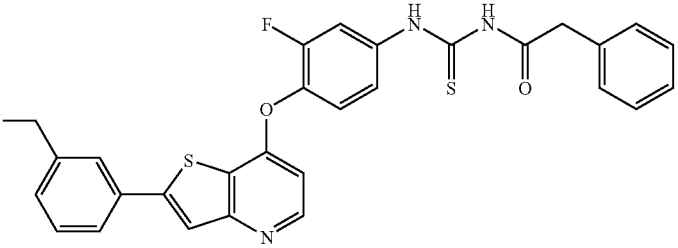  a  a  b
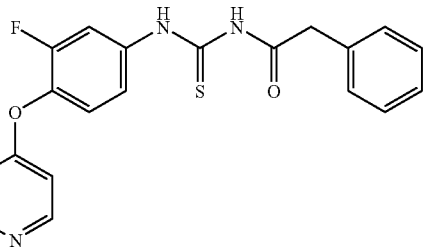  a  a  b
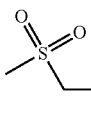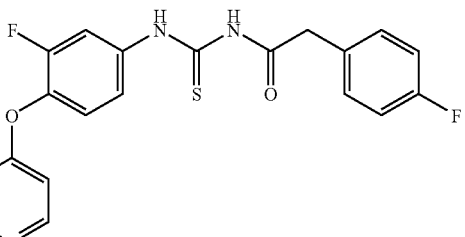  a  a  d
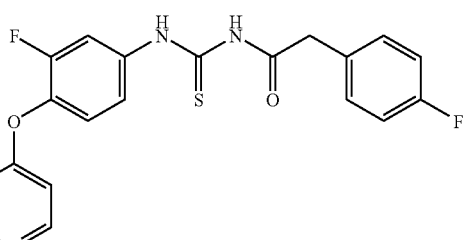  a  a  b
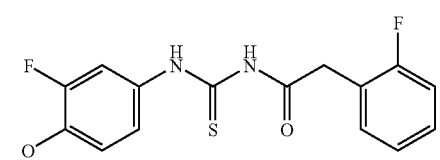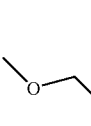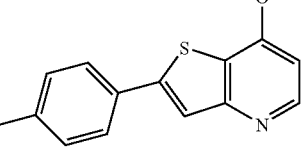  a  a  b TABLE 2-continued

| | | | | a | a | b |
| | | | | a | a | b |
| | | | | a | b | b |
| | | | | a | a | b |
| | | | | a | a | a |

TABLE 2-continued
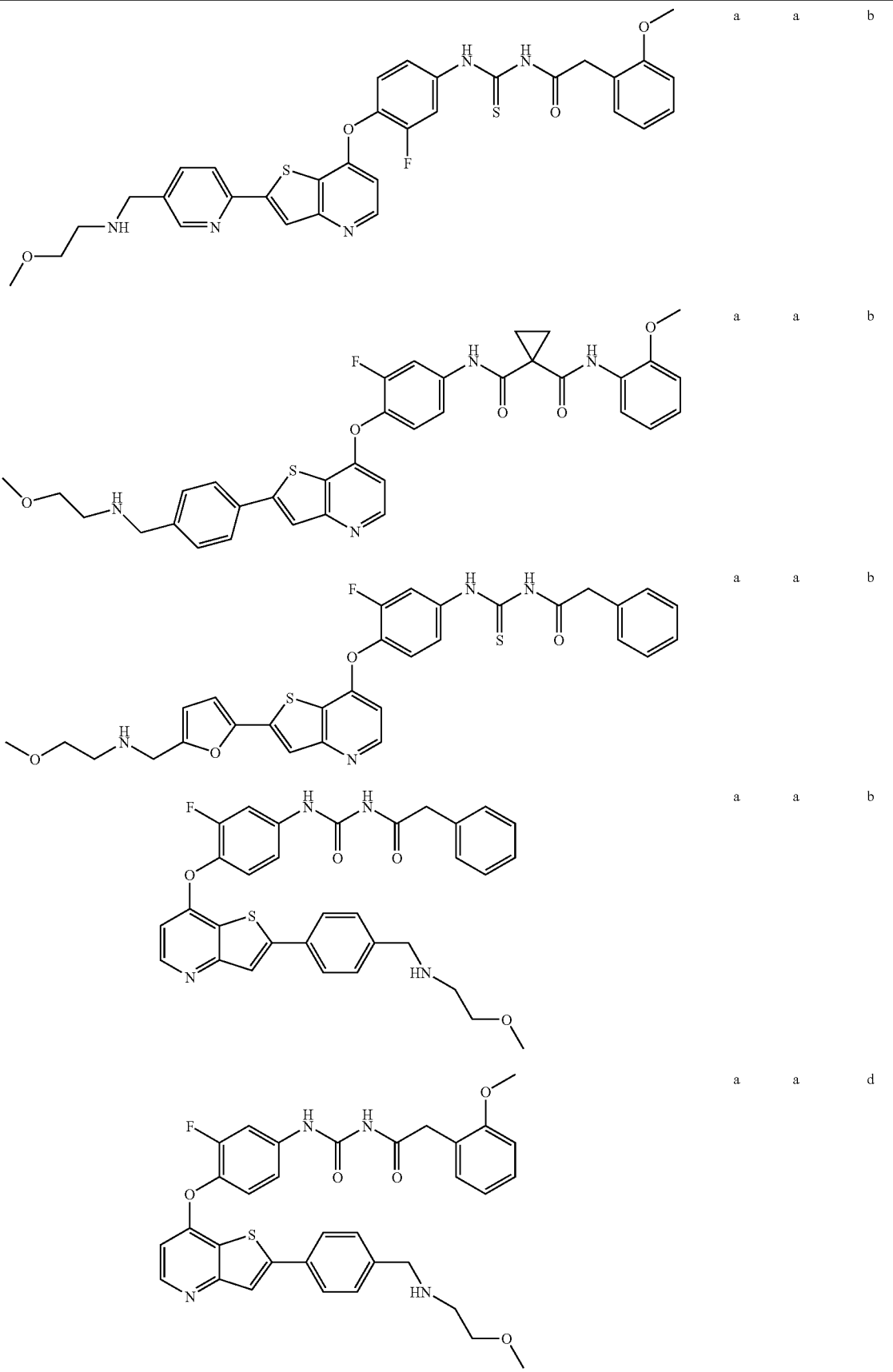
| | | |
|---|---|---|
| a | a | b |
| a | a | b |
| a | a | b |
| a | a | b |
| a | a | d |

TABLE 2-continued
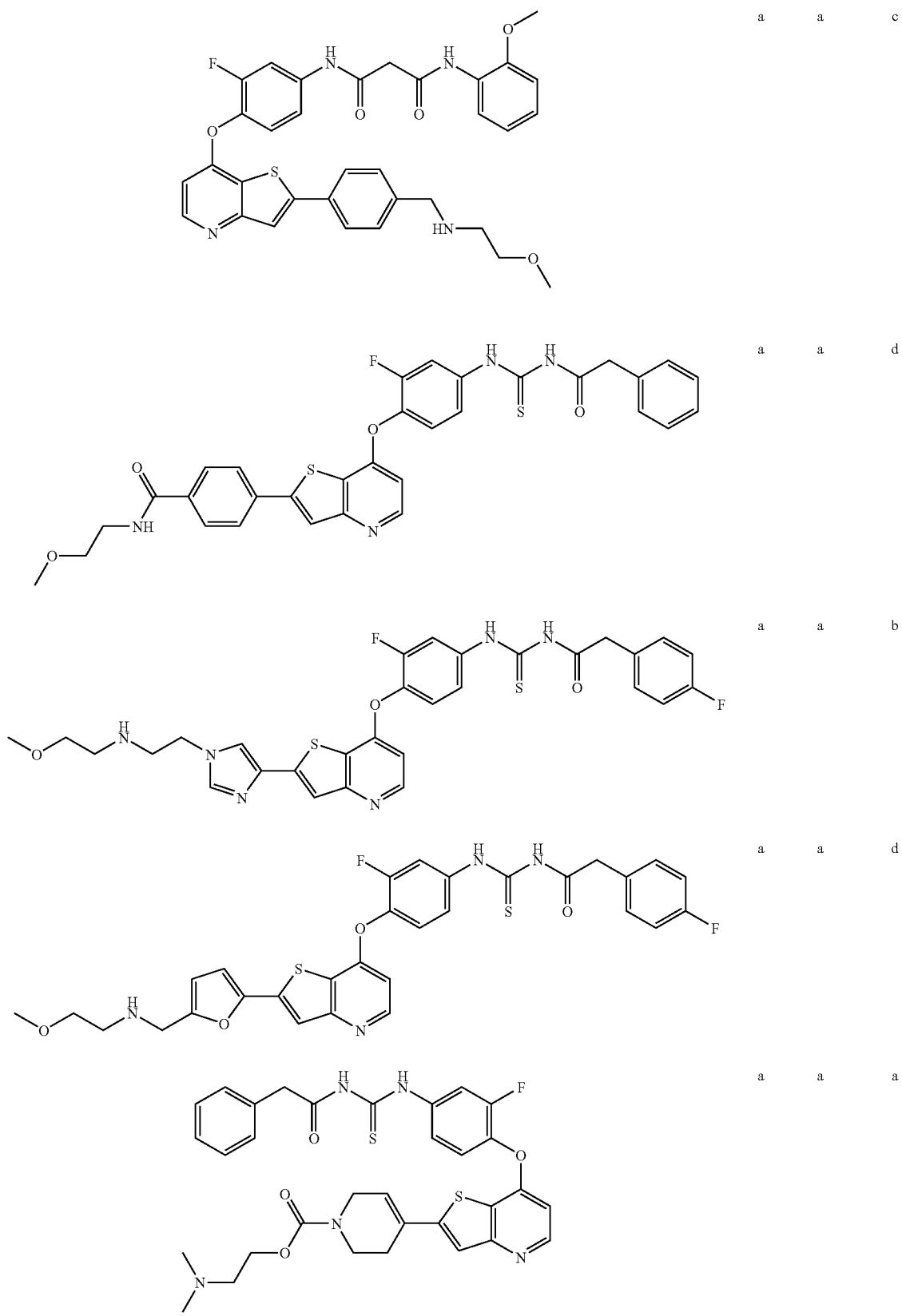
| | | |
|---|---|---|
| a | a | c |
| a | a | d |
| a | a | b |
| a | a | d |
| a | a | a |

TABLE 2-continued

| | | |
|---|---|---|
| a | a | b |
| a | a | d |
| a | a | b |
| a | a | d |
| a | a | d |

TABLE 2-continued
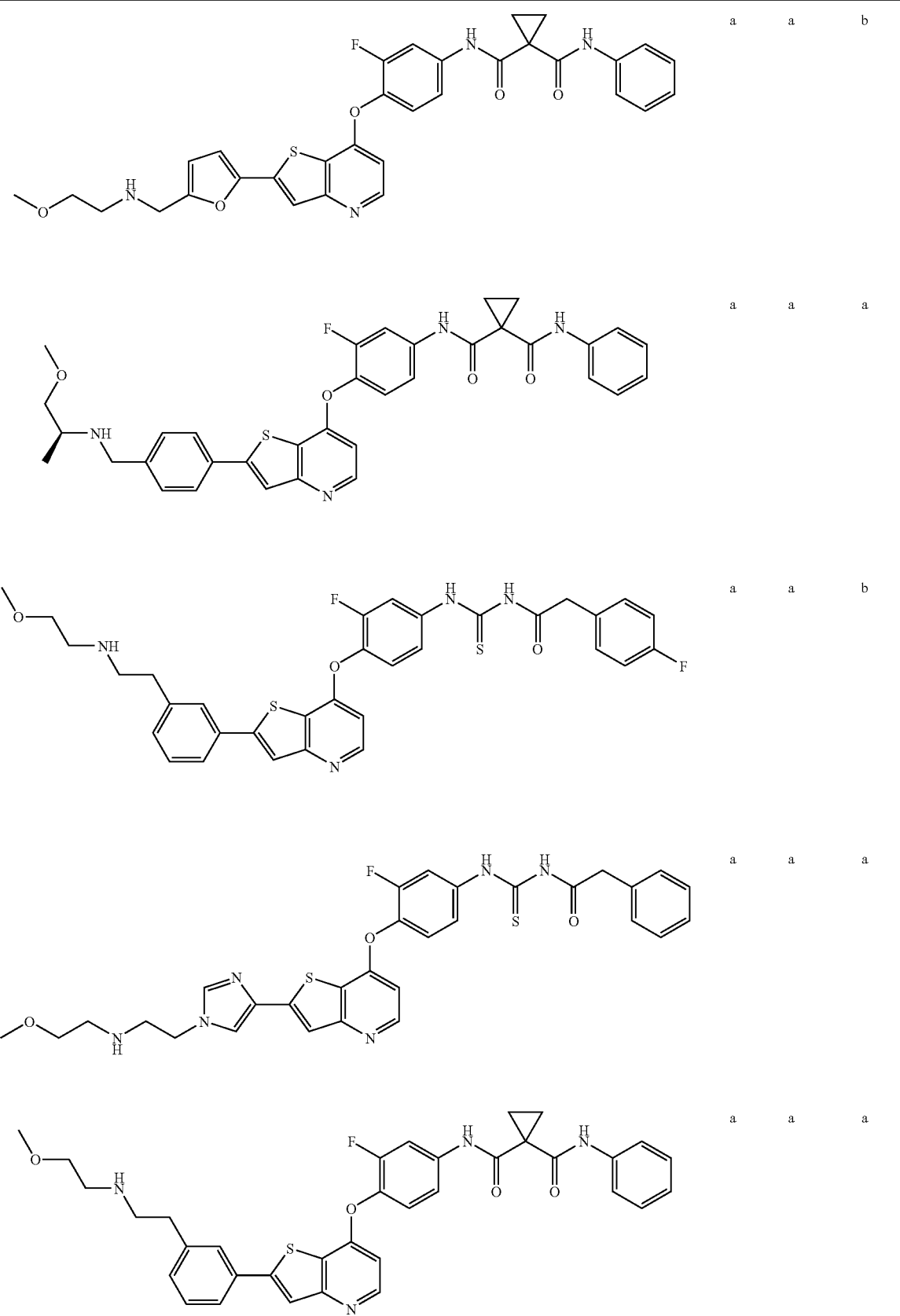

TABLE 2-continued
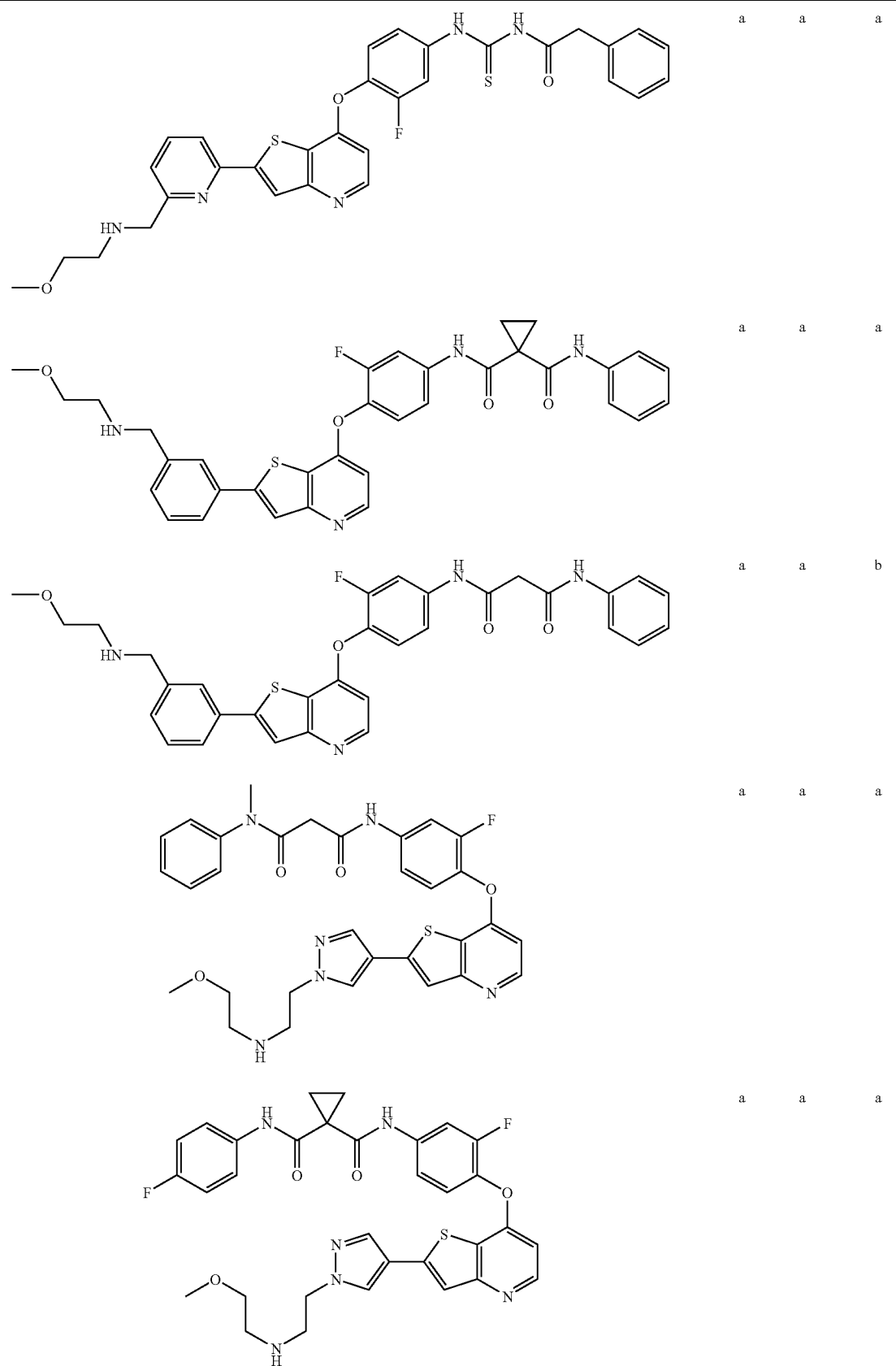
| | | |
|---|---|---|
| a | a | a |
| a | a | a |
| a | a | b |
| a | a | a |
| a | a | a |

TABLE 2-continued

| | | |
|---|---|---|
| a | a | d |
| a | a | b |
| a | a | b |
| a | a | a |
| a | a | a |

TABLE 2-continued
| | | |
|---|---|---|
| 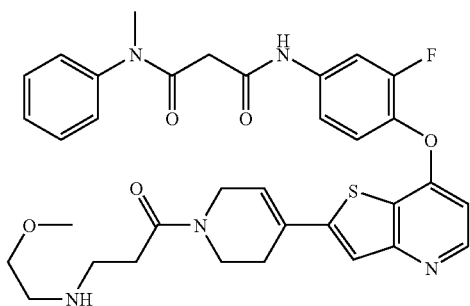 [SMILES: COCCNCCC(=O)N1CC=C(c2cc3nccc(Oc4ccc(NC(=O)CC(=O)N(C)c5ccccc5)cc4F)c3s2)CC1] | a a | b |
| 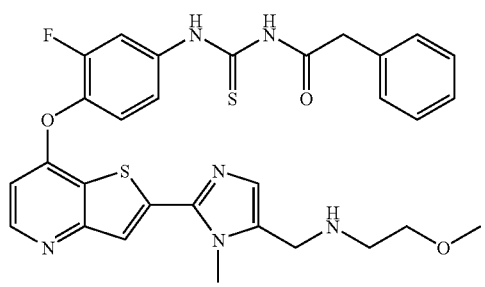 [SMILES: COCCNCc1cnc(-c2cc3nccc(Oc4ccc(NC(=S)NC(=O)Cc5ccccc5)cc4F)c3s2)n1C] | a a | a |
| 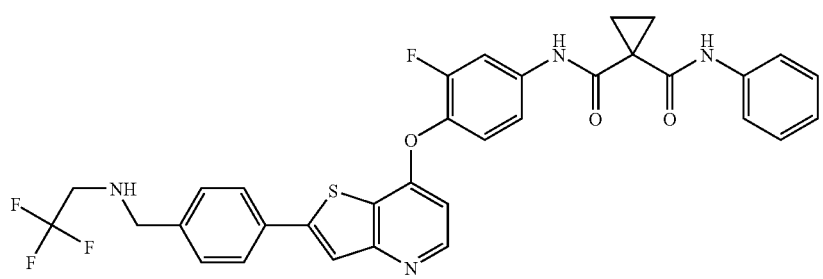 [SMILES: O=C(Nc1ccccc1)C1(C(=O)Nc2ccc(Oc3ccnc4cc(-c5ccc(CNCC(F)(F)F)cc5)sc34)c(F)c2)CC1] | a a | a |
| 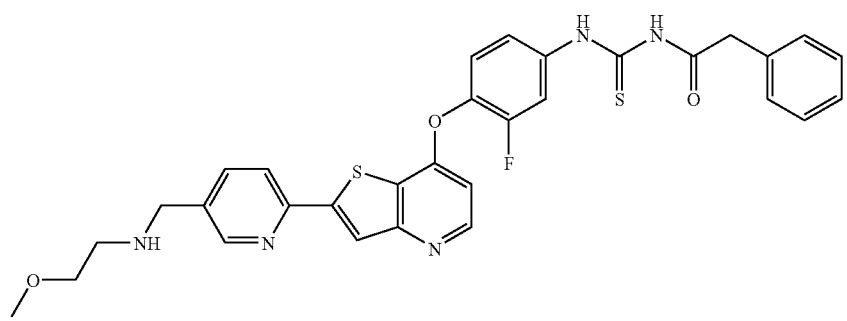 [SMILES: COCCNCc1ccc(-c2cc3nccc(Oc4ccc(NC(=S)NC(=O)Cc5ccccc5)cc4F)c3s2)nc1] | a a | a |
| 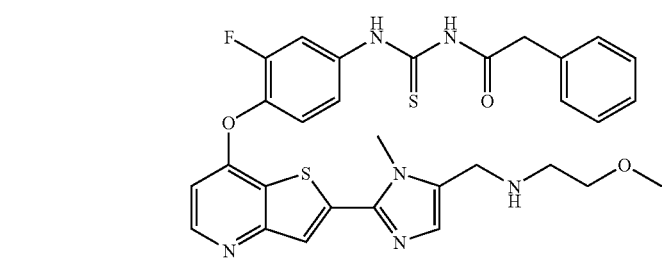 [SMILES: COCCNCc1cnc(-c2cc3nccc(Oc4ccc(NC(=S)NC(=O)Cc5ccccc5)cc4F)c3s2)n1C] | a a | b |

TABLE 2-continued
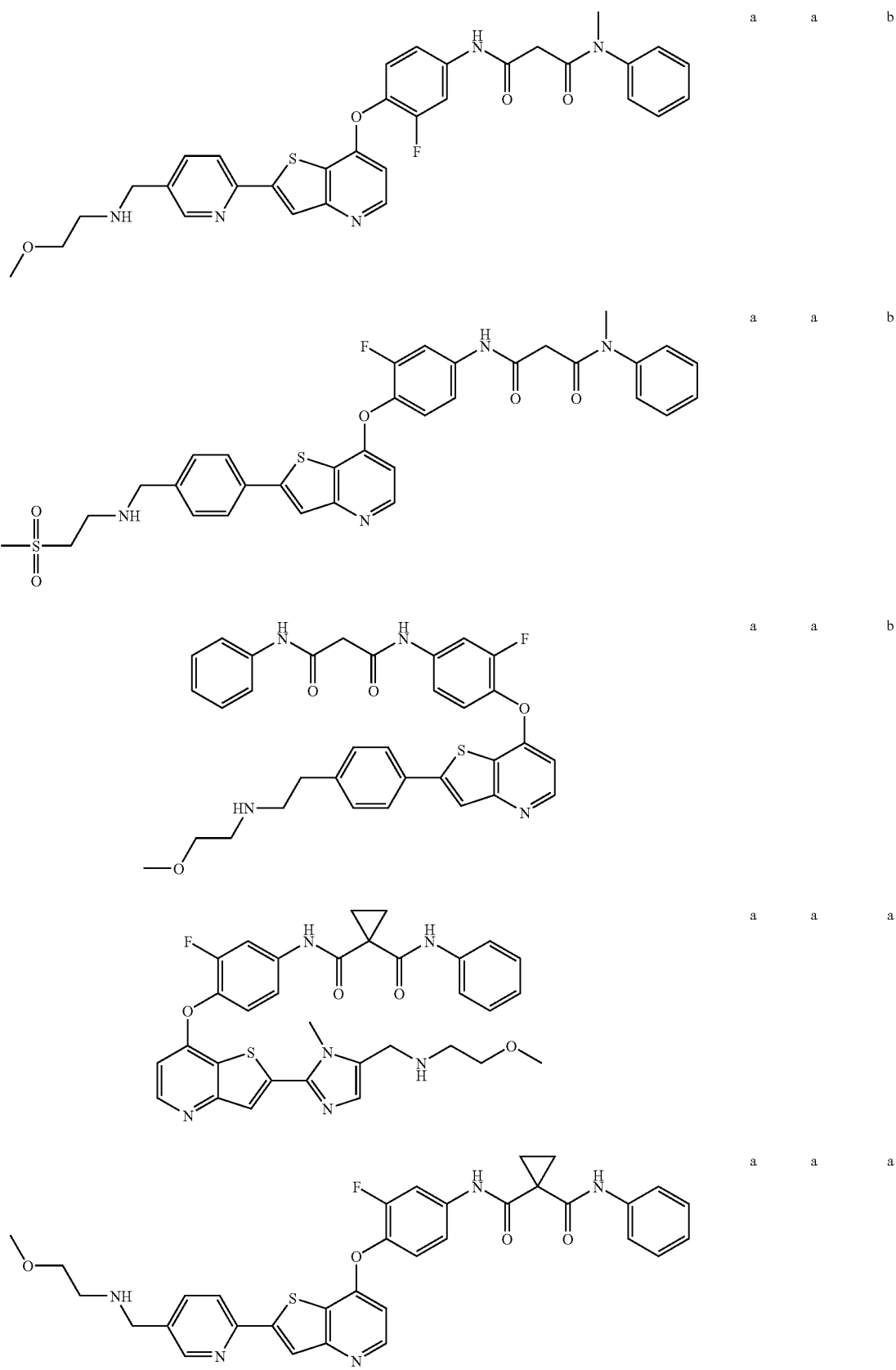

TABLE 2-continued
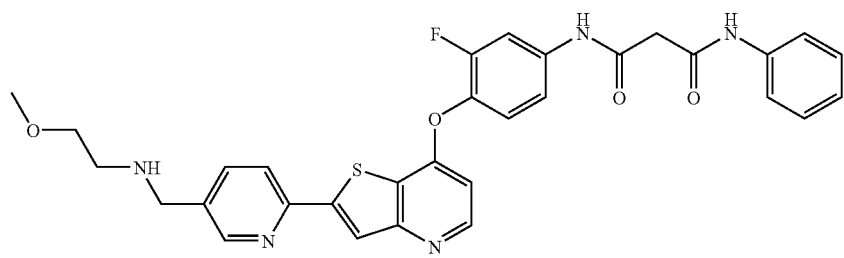 [SMILES: COCCNCc1ccc(-c2cc3nccc(Oc4ccc(NC(=O)CC(=O)Nc5ccccc5)cc4F)c3s2)nc1]
a a a
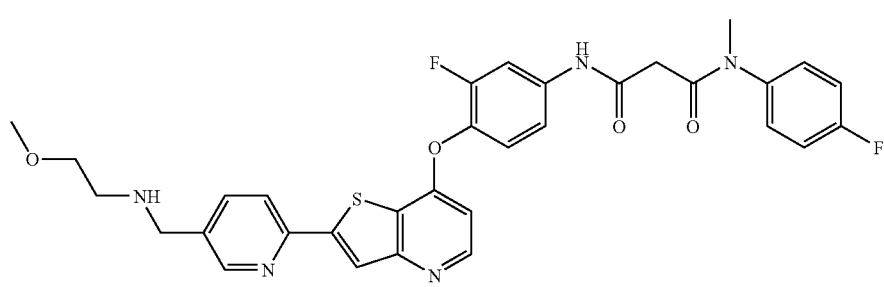 [SMILES: COCCNCc1ccc(-c2cc3nccc(Oc4ccc(NC(=O)CC(=O)N(C)c5ccc(F)cc5)cc4F)c3s2)nc1]
a a b
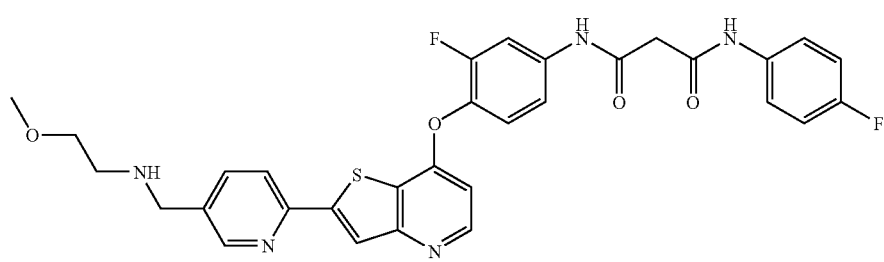 [SMILES: COCCNCc1ccc(-c2cc3nccc(Oc4ccc(NC(=O)CC(=O)Nc5ccc(F)cc5)cc4F)c3s2)nc1]
a a a
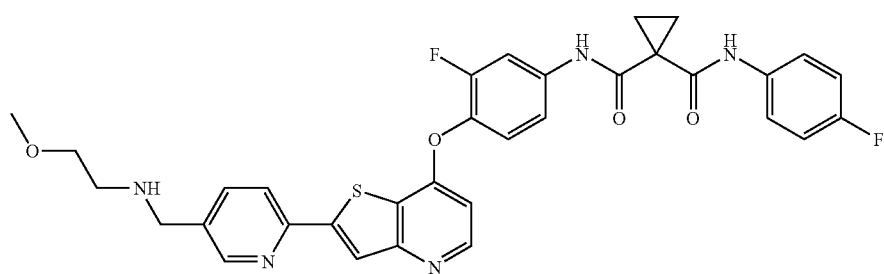 [SMILES: COCCNCc1ccc(-c2cc3nccc(Oc4ccc(NC(=O)C5(C(=O)Nc6ccc(F)cc6)CC5)cc4F)c3s2)nc1]
a a a
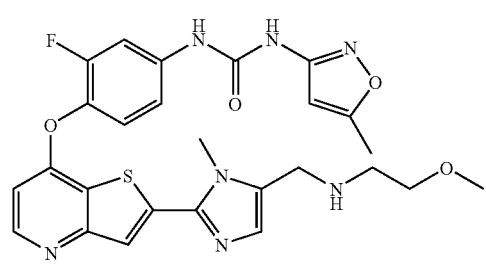 [SMILES: COCCNCc1cnc(-c2cc3nccc(Oc4ccc(NC(=O)Nc5cc(C)on5)cc4F)c3s2)n1C]
a TABLE 2-continued
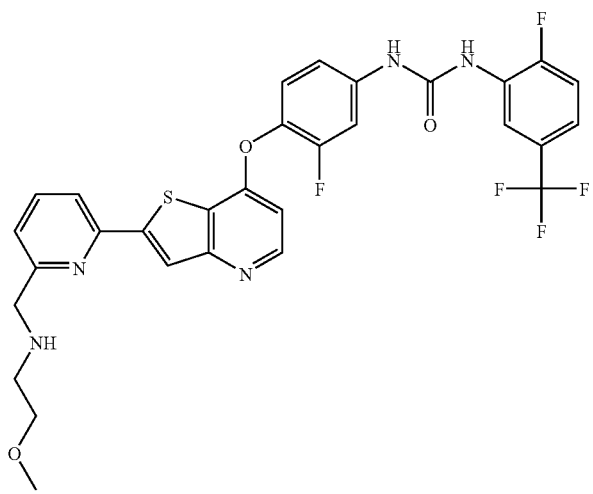 [SMILES: COCCNCc1cccc(-c2cc3nccc(Oc4ccc(NC(=O)Nc5cc(C(F)(F)F)ccc5F)cc4F)c3s2)n1]
a a
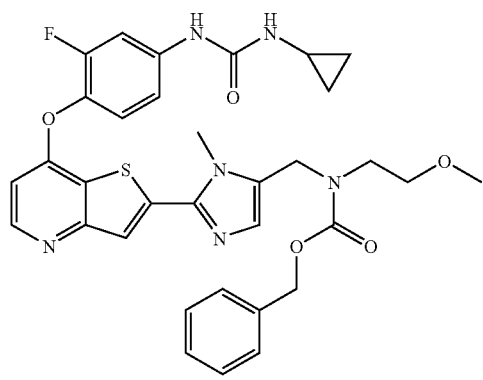 [SMILES: COCCN(Cc1cnc(-c2cc3nccc(Oc4ccc(NC(=O)NC5CC5)cc4F)c3s2)n1C)C(=O)OCc1ccccc1]
d B
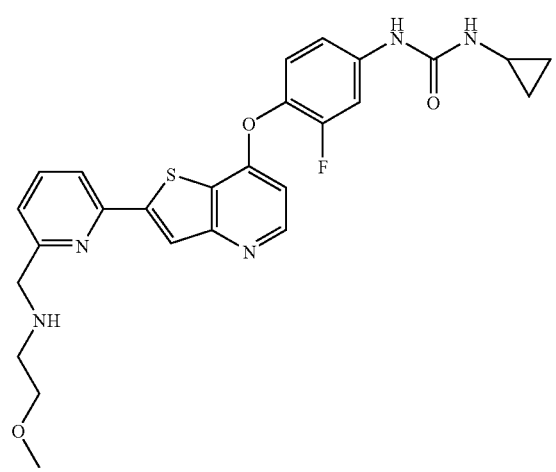 [SMILES: COCCNCc1cccc(-c2cc3nccc(Oc4ccc(NC(=O)NC5CC5)cc4F)c3s2)n1]
b b
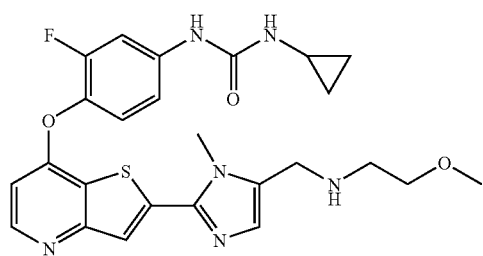 [SMILES: COCCNCc1cnc(-c2cc3nccc(Oc4ccc(NC(=O)NC5CC5)cc4F)c3s2)n1C]
b a TABLE 2-continued
| A Structure | E DU145 SCATT. INHIB IC50 (µM) | F CMET ELISA IN MKN45 IC50 (µM) |
|---|---|---|
| 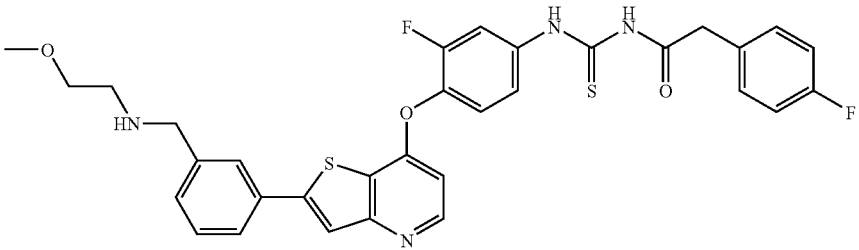 [SMILES: COCCNCc1cccc(-c2cc3nccc(Oc4ccc(NC(=S)NC(=O)Cc5ccc(F)cc5)cc4F)c3s2)c1] | b | a |
| 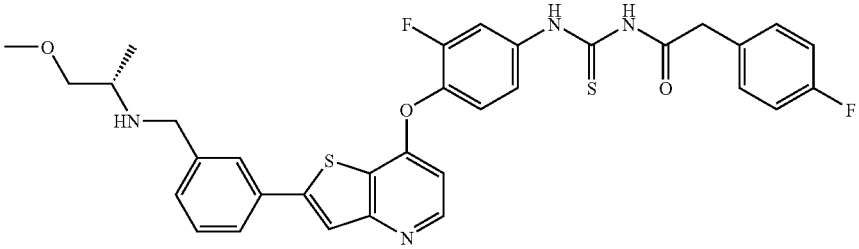 [SMILES: COC[C@H](C)NCc1cccc(-c2cc3nccc(Oc4ccc(NC(=S)NC(=O)Cc5ccc(F)cc5)cc4F)c3s2)c1] | a | a |
| 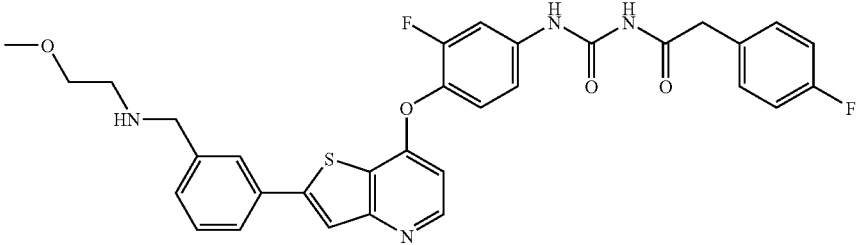 [SMILES: COCCNCc1cccc(-c2cc3nccc(Oc4ccc(NC(=O)NC(=O)Cc5ccc(F)cc5)cc4F)c3s2)c1] | b | b |
| 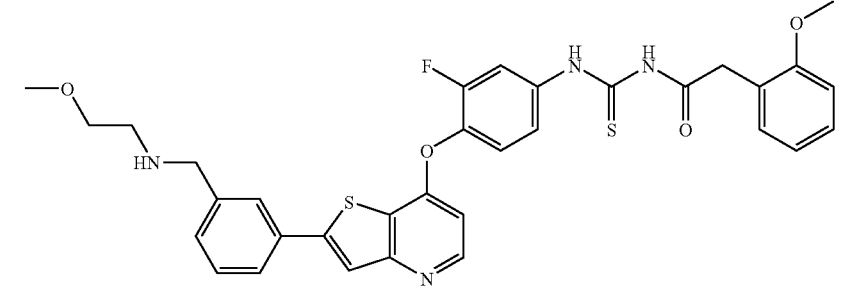 | b | a |
| 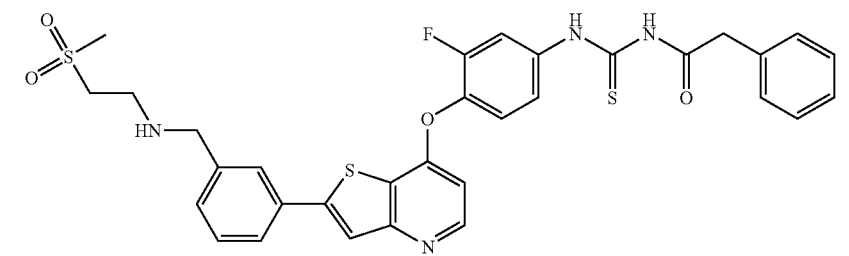 [SMILES: CS(=O)(=O)CCNCc1cccc(-c2cc3nccc(Oc4ccc(NC(=S)NC(=O)Cc5ccccc5)cc4F)c3s2)c1] | d | a |

TABLE 2-continued
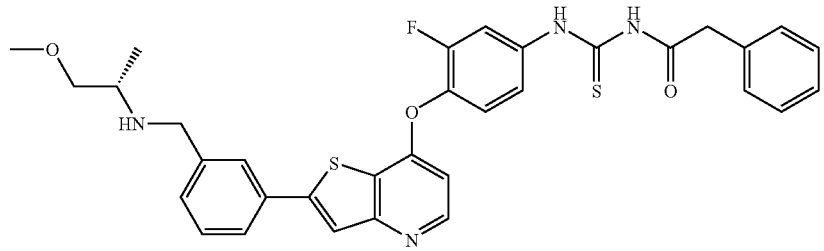 [SMILES: COC[C@H](C)NCc1cccc(-c2cc3nccc(Oc4ccc(NC(=S)NC(=O)Cc5ccccc5)cc4F)c3s2)c1] | b | a
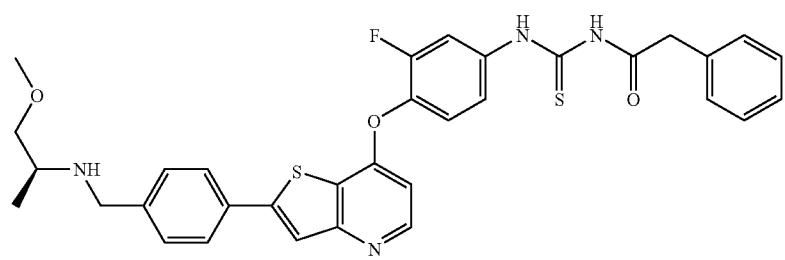 [SMILES: COC[C@H](C)NCc1ccc(-c2cc3nccc(Oc4ccc(NC(=S)NC(=O)Cc5ccccc5)cc4F)c3s2)cc1] | b | b
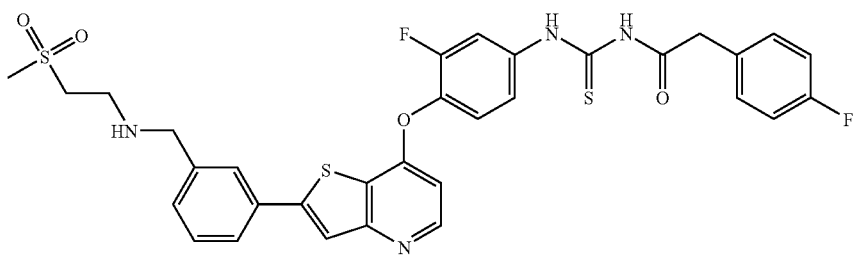 [SMILES: CS(=O)(=O)CCNCc1cccc(-c2cc3nccc(Oc4ccc(NC(=S)NC(=O)Cc5ccc(F)cc5)cc4F)c3s2)c1] | d | a
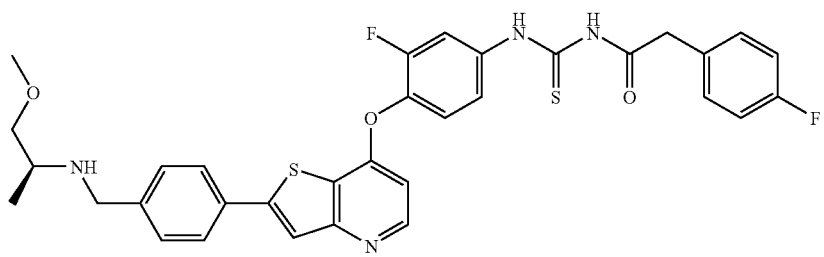 [SMILES: COC[C@H](C)NCc1ccc(-c2cc3nccc(Oc4ccc(NC(=S)NC(=O)Cc5ccc(F)cc5)cc4F)c3s2)cc1] | b | a
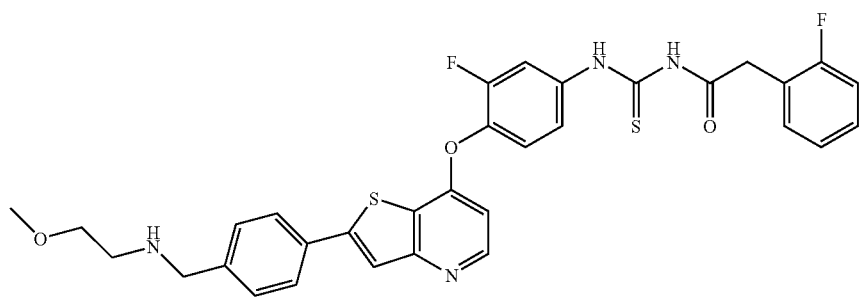 [SMILES: COCCNCc1ccc(-c2cc3nccc(Oc4ccc(NC(=S)NC(=O)Cc5ccccc5F)cc4F)c3s2)cc1] | b | a TABLE 2-continued
| | b | a |
|---|---|---|
| 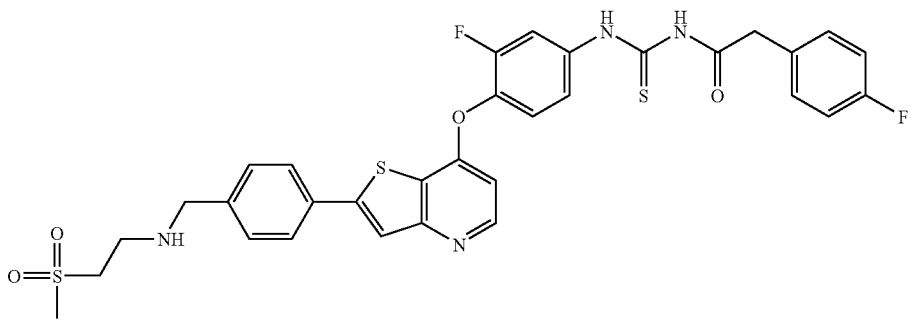 [SMILES: CS(=O)(=O)CCNCc1ccc(-c2cc3nccc(Oc4ccc(NC(=S)NC(=O)Cc5ccc(F)cc5)cc4F)c3s2)cc1] | b | a |
| 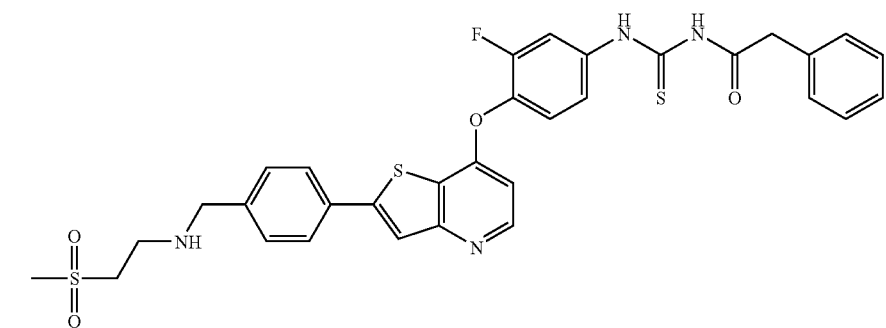 [SMILES: CS(=O)(=O)CCNCc1ccc(-c2cc3nccc(Oc4ccc(NC(=S)NC(=O)Cc5ccccc5)cc4F)c3s2)cc1] | b | a |
| 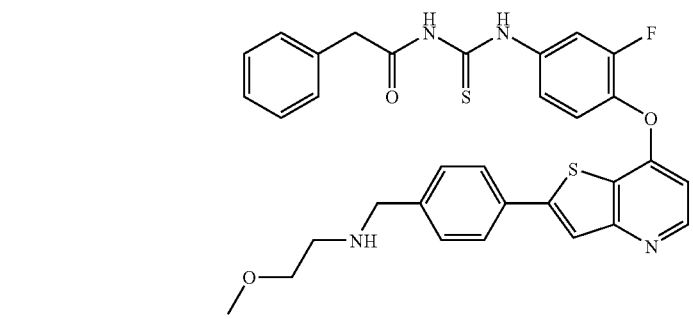 [SMILES: COCCNCc1ccc(-c2cc3nccc(Oc4ccc(NC(=S)NC(=O)Cc5ccccc5)cc4F)c3s2)cc1] | b | a |
| 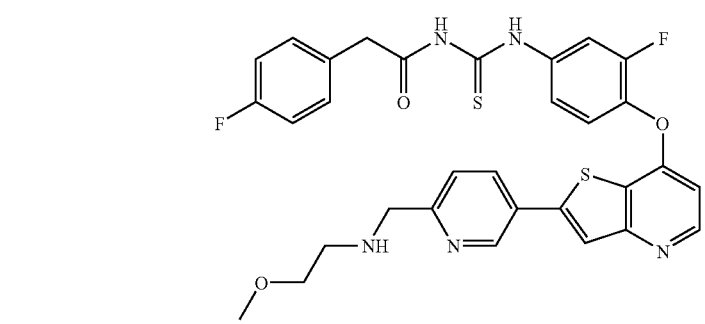 [SMILES: COCCNCc1ccc(-c2cc3nccc(Oc4ccc(NC(=S)NC(=O)Cc5ccc(F)cc5)cc4F)c3s2)cn1] | a | a |
| 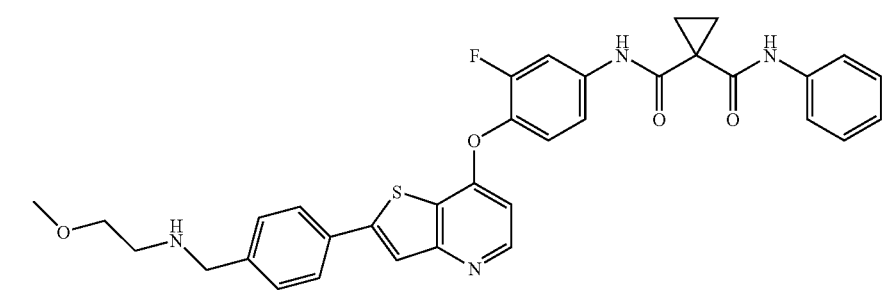 [SMILES: COCCNCc1ccc(-c2cc3nccc(Oc4ccc(NC(=O)C5(C(=O)Nc6ccccc6)CC5)cc4F)c3s2)cc1] | a | a |

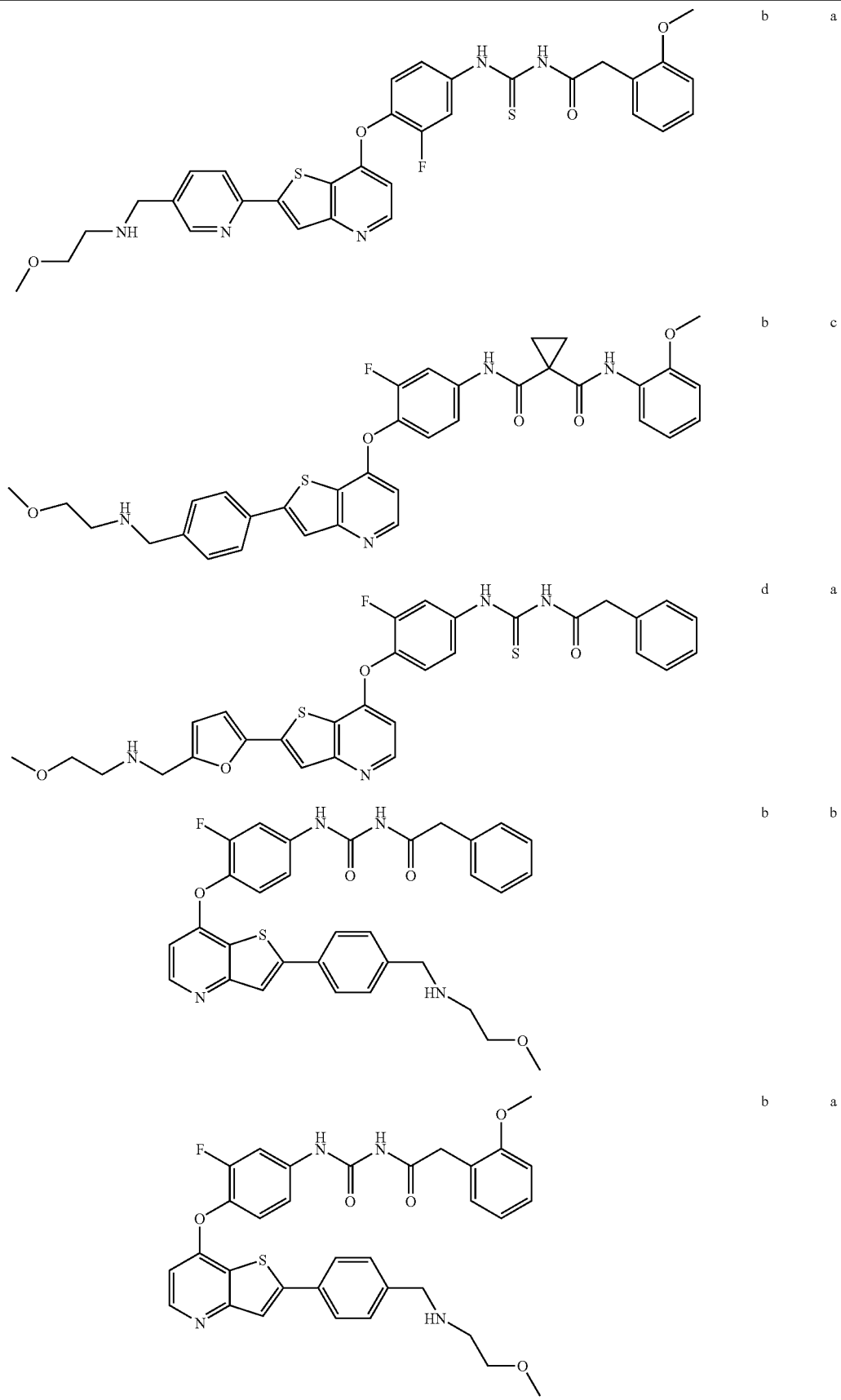

TABLE 2-continued
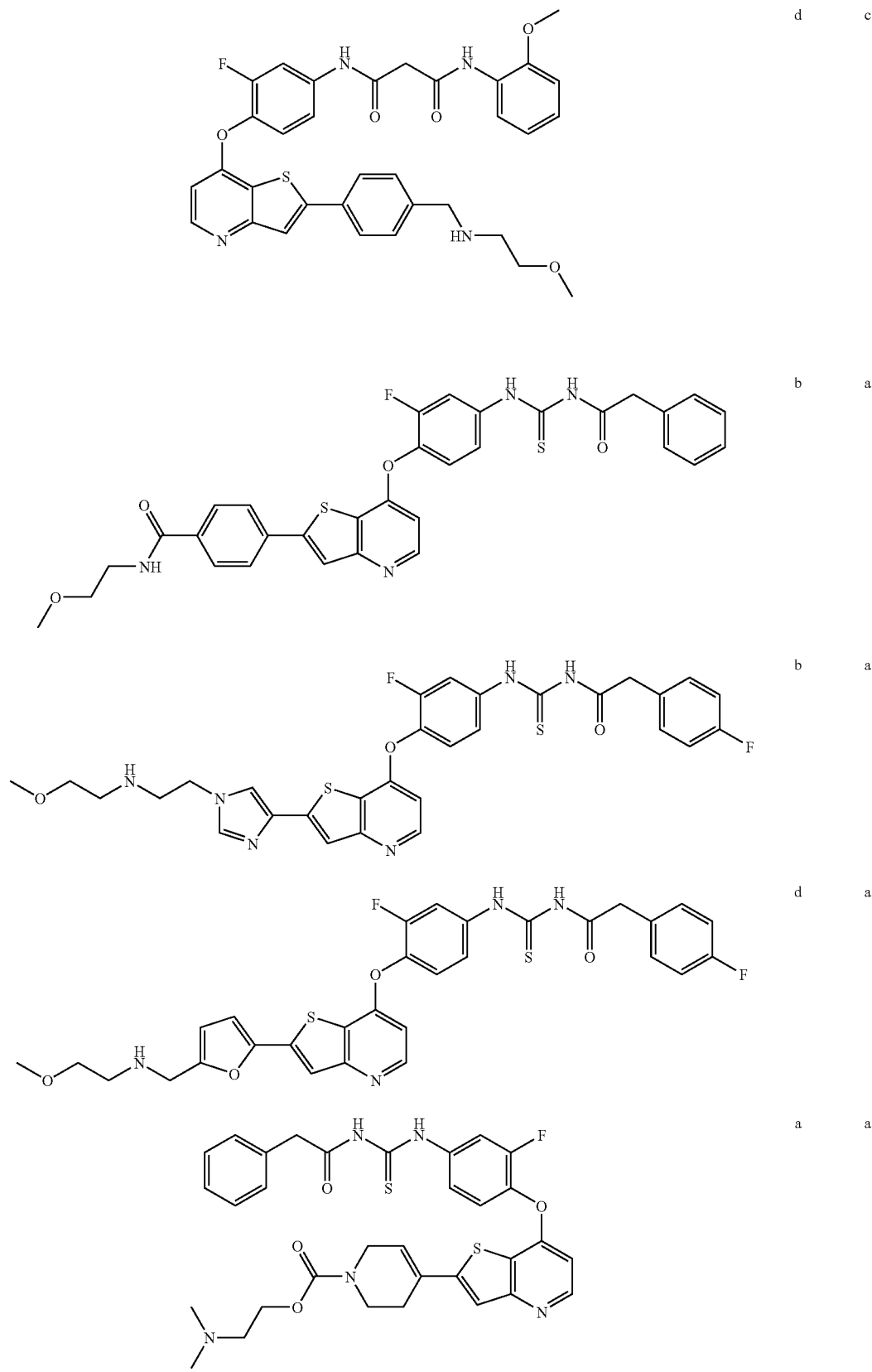

TABLE 2-continued
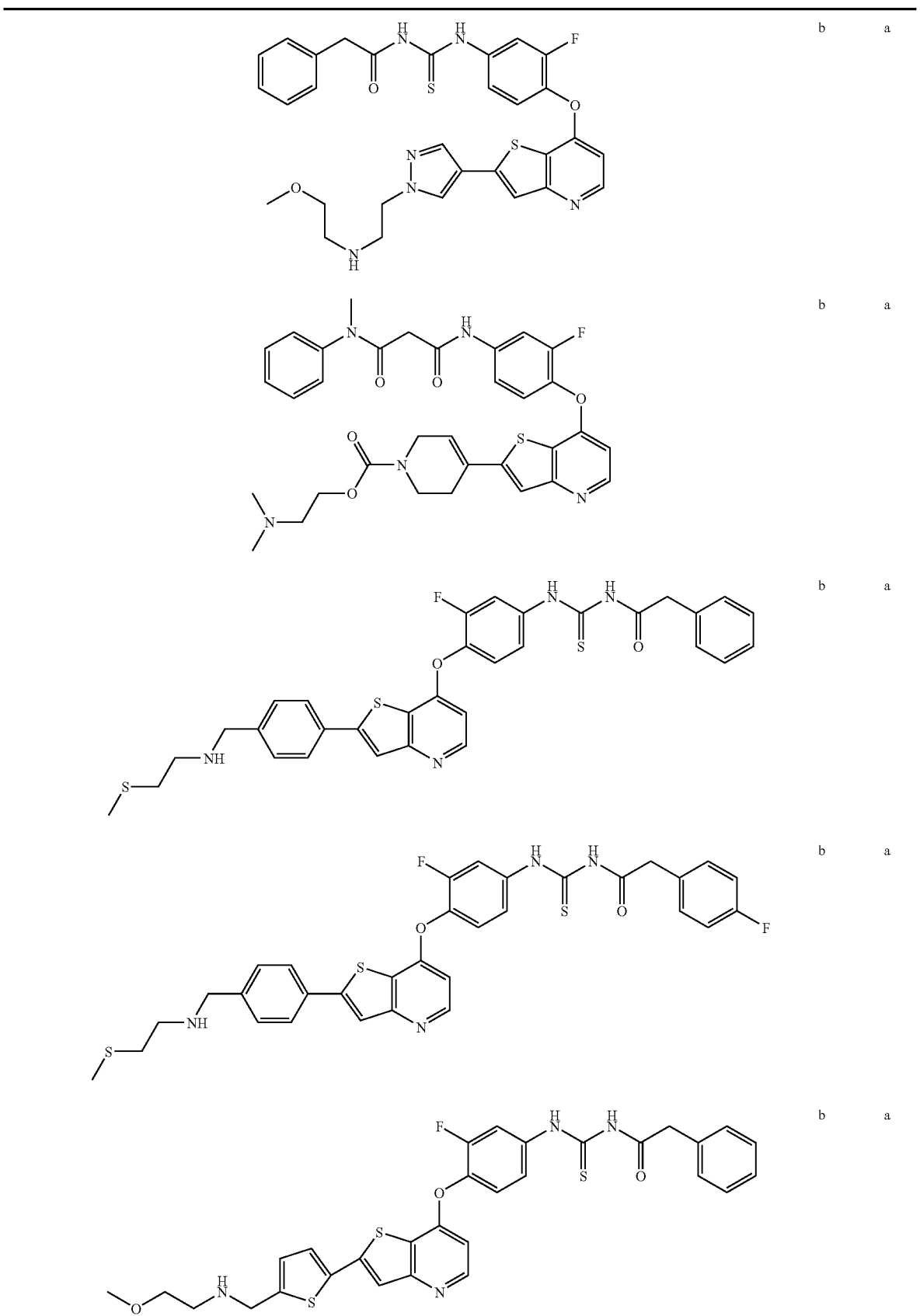
| | b | a |
|---|---|---|
| | b | a |
| | b | a |
| | b | a |
| | b | a |

TABLE 2-continued
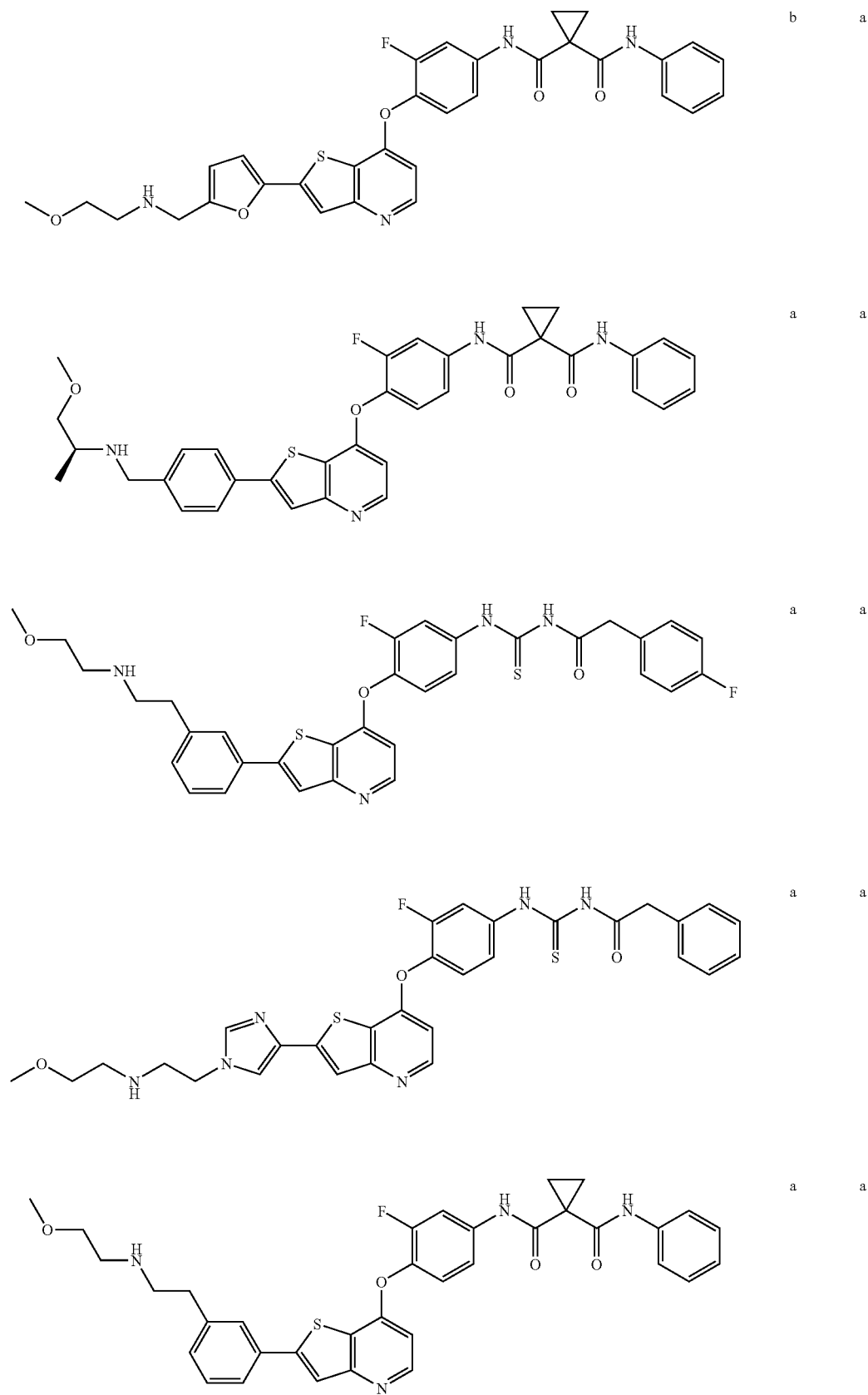

TABLE 2-continued
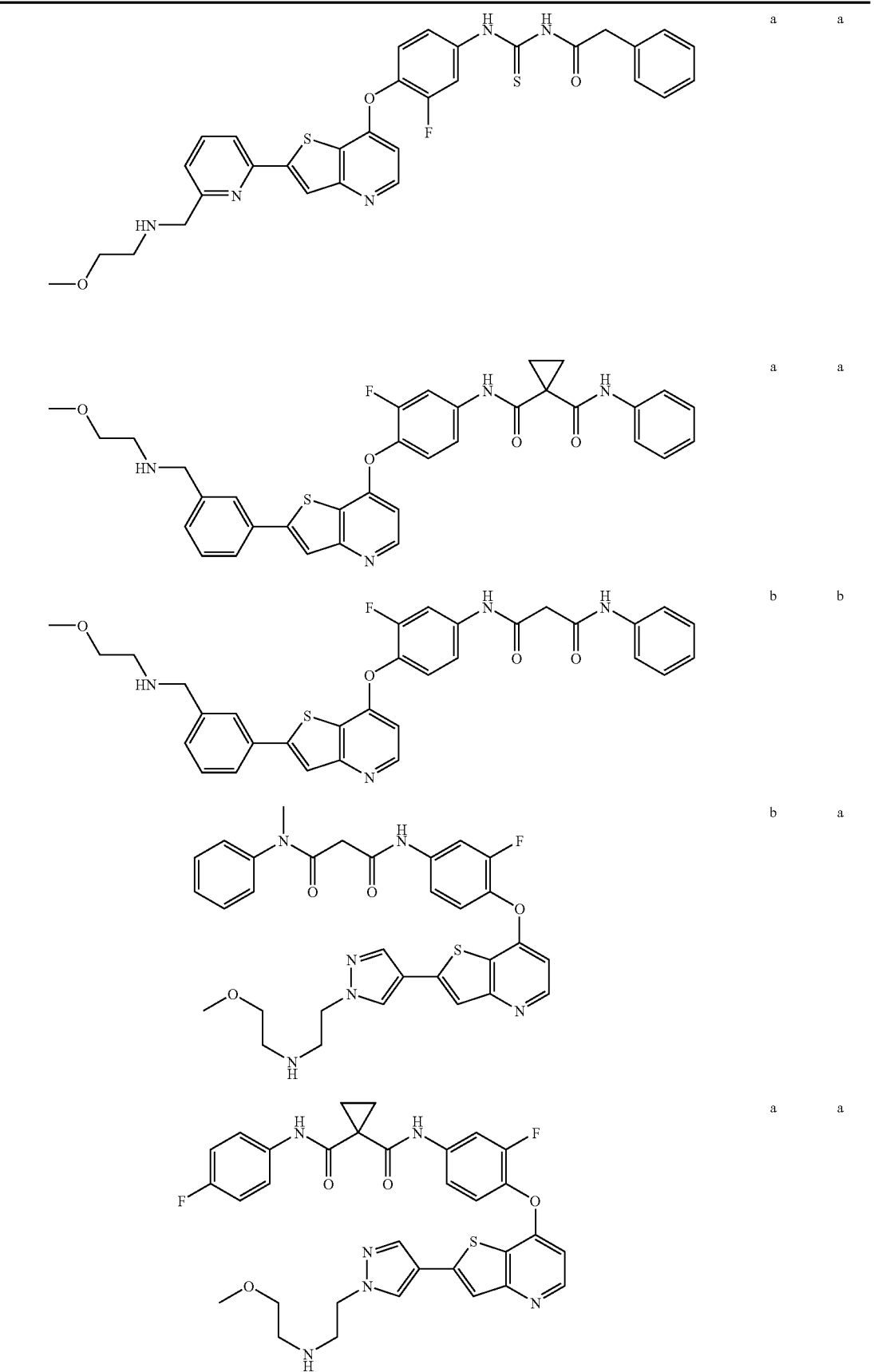
| | a | a |
| | a | a |
| | b | b |
| | b | a |
| | a | a |

TABLE 2-continued

| | b | a |
| | b | a |
| | a | a |
| | a | a |
| | a | a |

TABLE 2-continued
| | | |
|---|---|---|
| 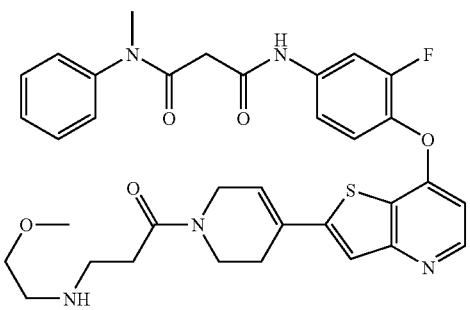 [SMILES: COCCNCCC(=O)N1CC=C(c2cc3nccc(Oc4ccc(NC(=O)CC(=O)N(C)c5ccccc5)cc4F)c3s2)CC1] | a | a |
| 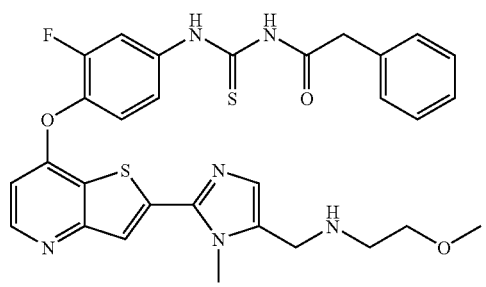 [SMILES: COCCNCc1cnc(-c2cc3nccc(Oc4ccc(NC(=S)NC(=O)Cc5ccccc5)cc4F)c3s2)n1C] | a | a |
| 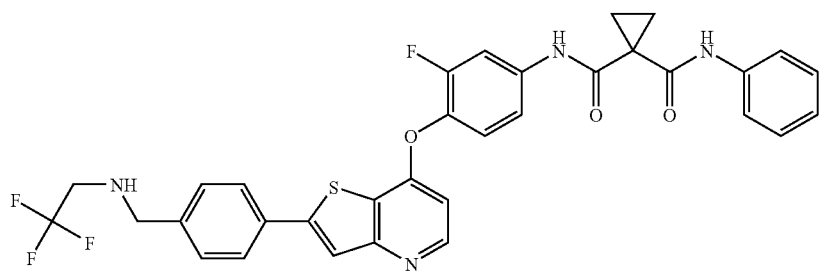 [SMILES: O=C(Nc1ccccc1)C1(C(=O)Nc2ccc(Oc3ccnc4cc(-c5ccc(CNCC(F)(F)F)cc5)sc34)c(F)c2)CC1] | a | a |
| 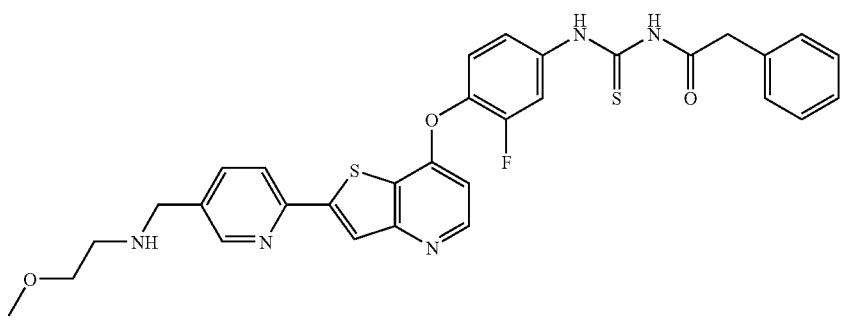 [SMILES: COCCNCc1ccc(-c2cc3nccc(Oc4ccc(NC(=S)NC(=O)Cc5ccccc5)cc4F)c3s2)nc1] | a | a |
| 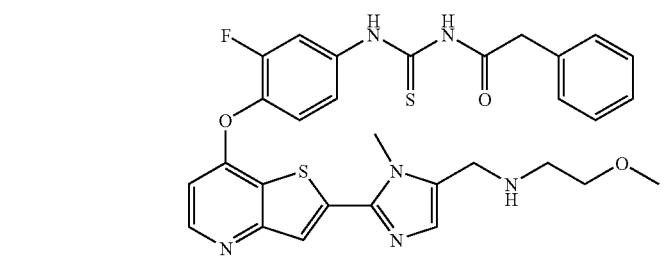 | b | a |

TABLE 2-continued
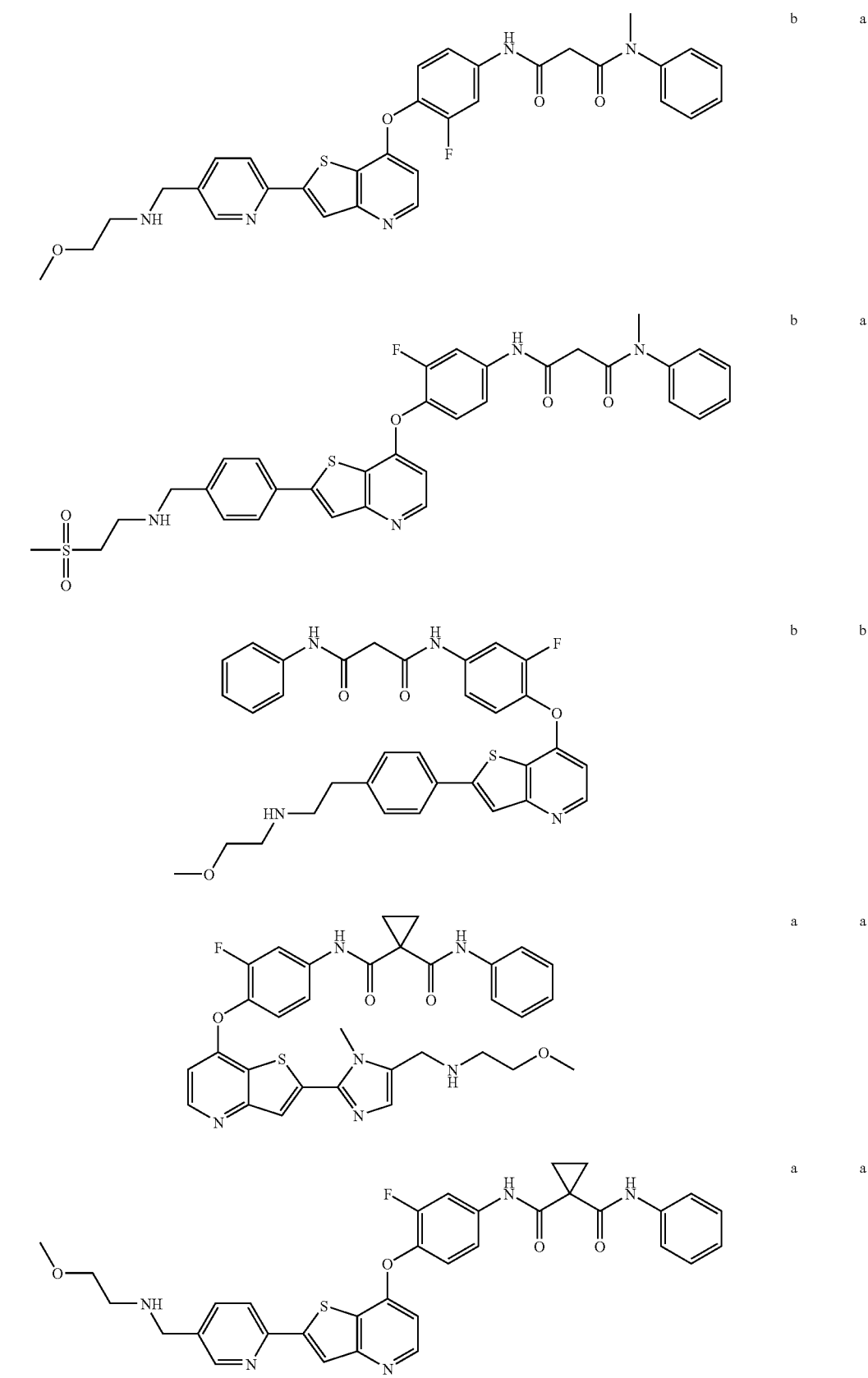
| | b | a |
| --- | --- | --- |
| | b | a |
| | b | b |
| | a | a |
| | a | a |

TABLE 2-continued
| | | |
|---|---|---|
| 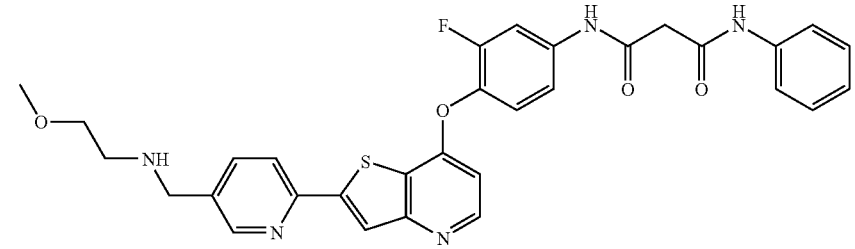 [SMILES: COCCNCc1ccc(-c2cc3nccc(Oc4ccc(NC(=O)CC(=O)Nc5ccccc5)cc4F)c3s2)nc1] | a | a |
| 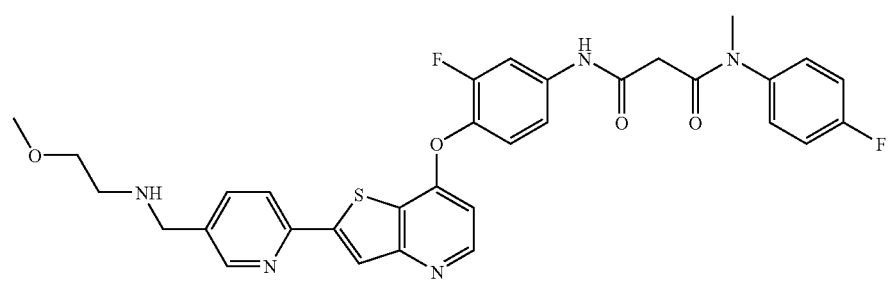 [SMILES: COCCNCc1ccc(-c2cc3nccc(Oc4ccc(NC(=O)CC(=O)N(C)c5ccc(F)cc5)cc4F)c3s2)nc1] | b | a |
| 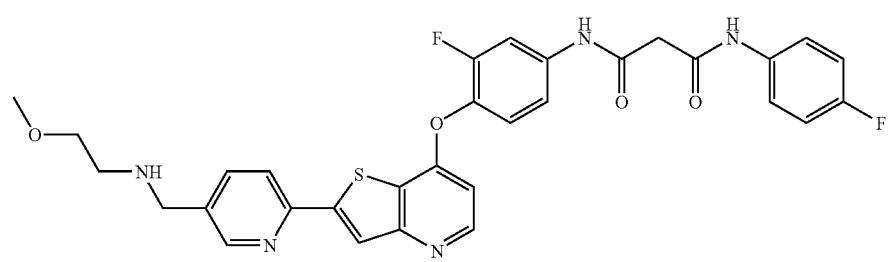 [SMILES: COCCNCc1ccc(-c2cc3nccc(Oc4ccc(NC(=O)CC(=O)Nc5ccc(F)cc5)cc4F)c3s2)nc1] | b | a |
| 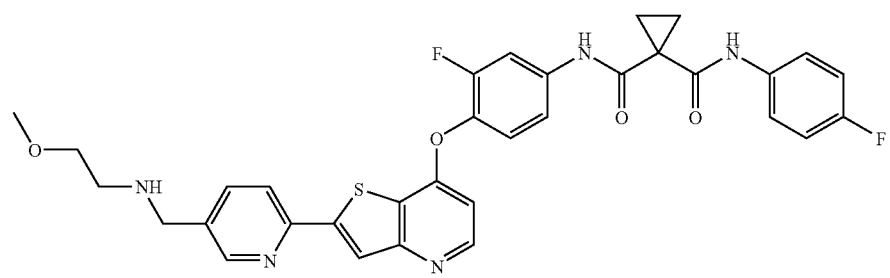 [SMILES: COCCNCc1ccc(-c2cc3nccc(Oc4ccc(NC(=O)C5(C(=O)Nc6ccc(F)cc6)CC5)cc4F)c3s2)nc1] | a | A |
| 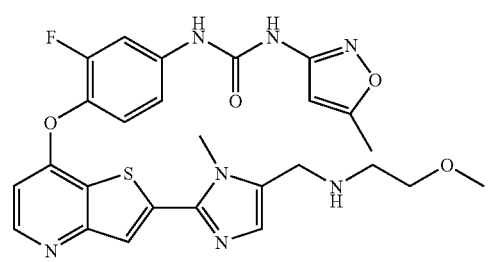 [SMILES: COCCNCc1cnc(-c2cc3nccc(Oc4ccc(NC(=O)Nc5cc(C)on5)cc4F)c3s2)n1C] | | |

TABLE 2-continued
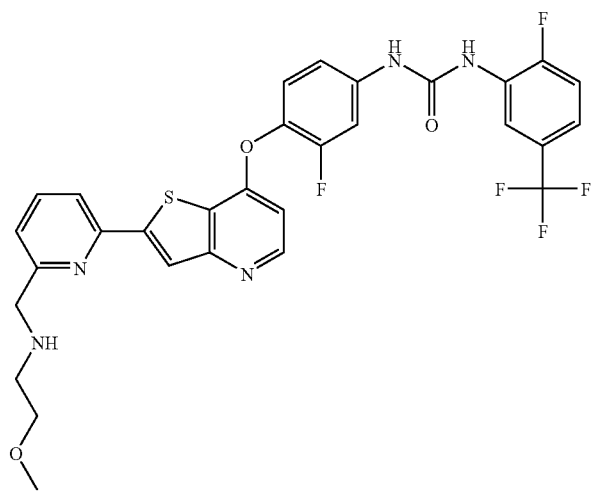 [SMILES: COCCNCc1cccc(-c2cc3nccc(Oc4ccc(NC(=O)Nc5cc(C(F)(F)F)ccc5F)cc4F)c3s2)n1]
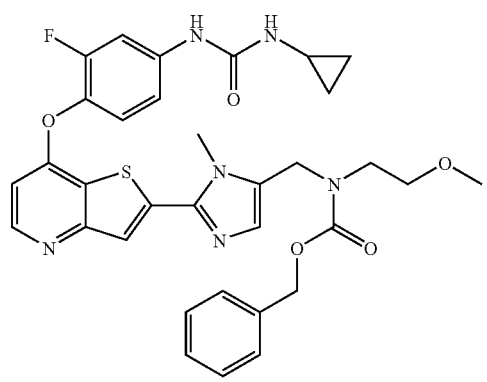 [SMILES: COCCN(Cc1cnc(-c2cc3nccc(Oc4ccc(NC(=O)NC5CC5)cc4F)c3s2)n1C)C(=O)OCc1ccccc1]
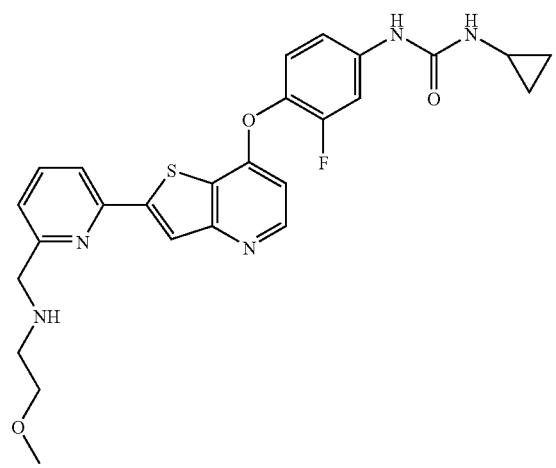 [SMILES: COCCNCc1cccc(-c2cc3nccc(Oc4ccc(NC(=O)NC5CC5)cc4F)c3s2)n1]
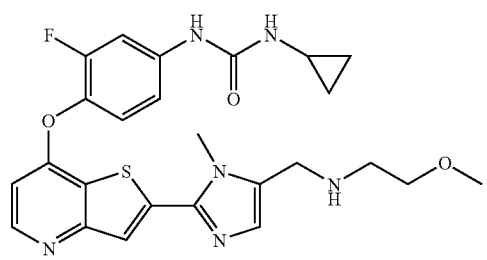 [SMILES: COCCNCc1cnc(-c2cc3nccc(Oc4ccc(NC(=O)NC5CC5)cc4F)c3s2)n1C]

Assay Example 4

In Vivo Solid Tumor Disease Model

This test measures the capacity of compounds to inhibit solid tumor growth.

Tumor xenografts are established in the flank of female athymic CD1 mice (Charles River Inc.), by subcutaneous injection of 1×106 U87, A431 or SKLMS cells/mouse. Once established, tumors are then serially passaged s.c. in nude mice hosts. Tumor fragments from these host animals are used in subsequent compound evaluation experiments. For compound evaluation experiments female nude mice weighing approximately 20 g are implanted s.c. by surgical implantation with tumor fragments of ~30 mg from donor tumors. When the tumors are approximately 100 mm3 in size (~7-10 days following implantation), the animals are randomized and separated into treatment and control groups. Each group contains 6-8 tumor-bearing mice, each of which is ear-tagged and followed individually throughout the experiment.

Mice are weighed and tumor measurements are taken by calipers three times weekly, starting on Day 1. These tumor measurements are converted to tumor volume by the well-known formula (L+W/4)3 4/3π. The experiment is terminated when the control tumors reach a size of approximately 1500 mm$^3$. In this model, the change in mean tumor volume for a compound treated group/the change in mean tumor volume of the control group (non-treated or vehicle treated)×100 (ΔT/ΔC) is subtracted from 100 to give the percent tumor growth inhibition (% TGI) for each test compound. In addition to tumor volumes, body weight of animals is monitored twice weekly for up to 3 weeks. The results are shown in Table 3. In the table, "A" indicates tumor growth inhibition of less than 25%; "B" indicates tumor growth inhibition of ≧25% but <50%; "C" indicates tumor growth inhibition of ≧50% but <75%; and "D" indicates tumor growth inhibition of ≧75%.

TABLE 3

In vivo efficacy of selected compounds dosed orally daily using PEG 400/0.1 N HCl in saline (40/60) as a vehicle

| Structure | Dosage (mg/kg) | Tumor type | Duration of experiment (days) | Tumor Growth Inhibition (%) |
|---|---|---|---|---|
| [Compound 1: MeO-CH2CH2-NH-CH2-phenyl-thieno[3,2-b]pyridine-O-fluorophenyl-NH-C(S)-NH-C(O)-CH2-(4-fluorophenyl)] | 20 | MNNG HOS<br>MKN45 | 6<br>7 | A<br>C |
| [Compound 2: (R)-MeO-CH2-CH(*)-NH-CH2-phenyl-thieno[3,2-b]pyridine-O-fluorophenyl-NH-C(S)-NH-C(O)-CH2-(4-fluorophenyl)] | 20 | MKN45 | 7 | B |
| [Compound 3: MeO-CH2CH2-NH-CH2-pyridyl-thieno[3,2-b]pyridine-O-fluorophenyl-NH-C(S)-NH-C(O)-CH2-phenyl] | 20 | MKN45 | 8 | A |

TABLE 3-continued
In vivo efficacy of selected compounds dosed orally daily using PEG 400/0.1 N HCl in saline (40/60) as a vehicle
| Structure | Dosage (mg/kg) | Tumor type | Duration of experiment (days) | Tumor Growth Inhibition (%) |
|---|---|---|---|---|
| 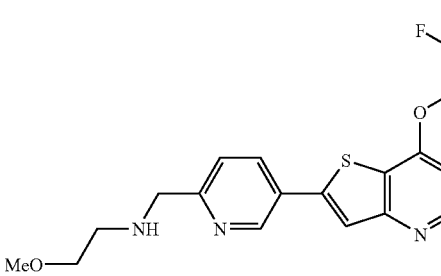 | 20 | MKN45 | 8 | B |
| 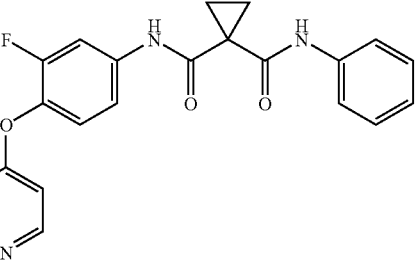 | 20 | MKN45 | 8 | D |
| 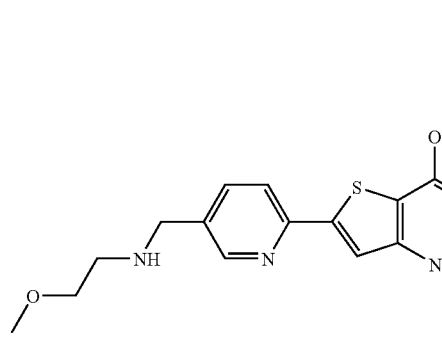 | 20 | MKN45 | 8 | B |
| 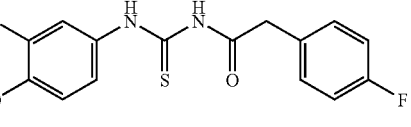 | 20 | U87MG | 12 | A |

TABLE 3-continued

In vivo efficacy of selected compounds dosed orally daily using PEG 400/0.1 N HCl in saline (40/60) as a vehicle

| Structure | Dosage (mg/kg) | Tumor type | Duration of experiment (days) | Tumor Growth Inhibition (%) |
|---|---|---|---|---|
| | 20 | U87MG | 10 | B |
| | 20 | SKLMS40 | 13 | C |
| | 20 | MKN45 | 14 | A |
| | 20 | U87MG | 10 | C |

TABLE 3-continued

In vivo efficacy of selected compounds dosed orally daily using PEG 400/0.1 N HCl in saline (40/60) as a vehicle

| Structure | Dosage (mg/kg) | Tumor type | Duration of experiment (days) | Tumor Growth Inhibition (%) |
|---|---|---|---|---|
| 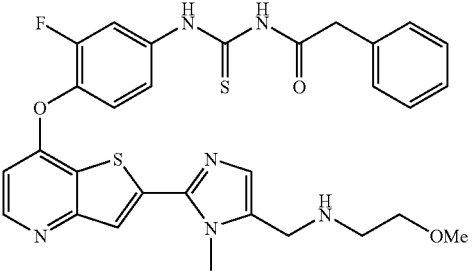 [SMILES: COCCNCc1cnc(-c2cc3nccc(Oc4ccc(NC(=S)NC(=O)Cc5ccccc5)cc4F)c3s2)n1C] | 20 | MKN45<br>A549<br>SKLMS40 | 13<br>12<br>13 | C<br>B<br>A |
| 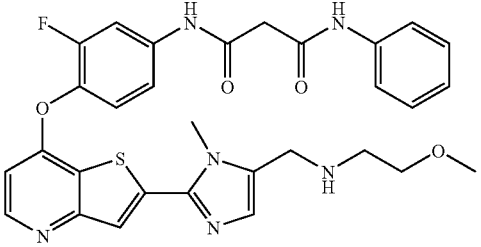 [SMILES: COCCNCc1cnc(-c2cc3nccc(Oc4ccc(NC(=O)CC(=O)Nc5ccccc5)cc4F)c3s2)n1C] | 40<br>20 | MKN45 | 14<br>13 | B<br>B |
| 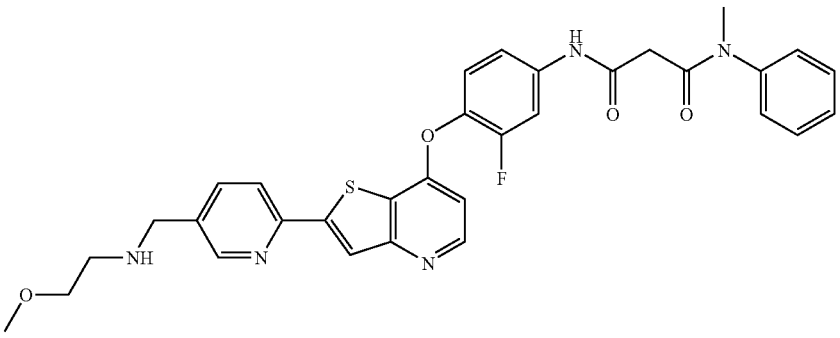 [SMILES: COCCNCc1ccc(-c2cc3nccc(Oc4ccc(NC(=O)CC(=O)N(C)c5ccccc5)cc4F)c3s2)nc1] | 20 | MKN45<br>A549<br>U87MG<br>SKLMS40 | 13<br>12<br>12<br>13 | C<br>C<br>B<br>A |
| 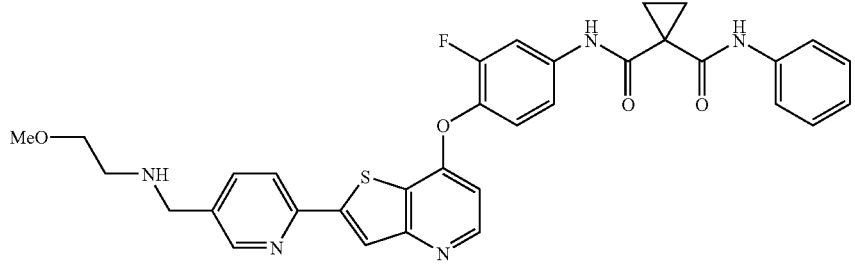 [SMILES: COCCNCc1ccc(-c2cc3nccc(Oc4ccc(NC(=O)C5(C(=O)Nc6ccccc6)CC5)cc4F)c3s2)nc1] | 20 | MKN45<br>A549<br>U87MG<br>SKLMS40 | 13<br>12<br>12<br>13 | D<br>C<br>D<br>C |

TABLE 3-continued

In vivo efficacy of selected compounds dosed orally daily using PEG 400/0.1 N HCl in saline (40/60) as a vehicle

| Structure | Dosage (mg/kg) | Tumor type | Duration of experiment (days) | Tumor Growth Inhibition (%) |
|---|---|---|---|---|
| | 20 | MKN45 | 13 | B |
| | | A549 | 12 | A |
| | 20 | U87MG | 12 | D |
| | | SKLMS40 | 13 | D |
| | | MDAMB231 | 13 | D |
| 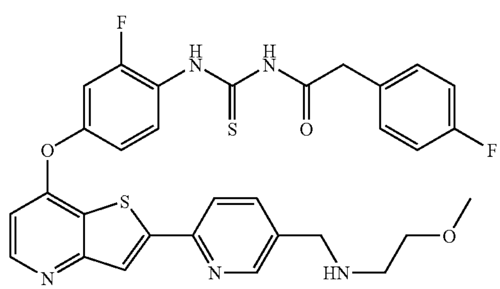 [SMILES: COCCNCc1ccc(-c2cc3nccc(Oc4ccc(NC(=S)NC(=O)Cc5ccc(F)cc5)c(F)c4)c3s2)nc1] | 15 | H1437 | 16 | A |
| | 20 | U87MG | 13 | D |
| | | SKLMS | 15 | D |
| | | Panc-1 | 13 | D |
| | 20 | HCT116 | 13 | C |

TABLE 3-continued

In vivo efficacy of selected compounds dosed orally daily using PEG 400/0.1 N HCl in saline (40/60) as a vehicle

| Structure | Dosage (mg/kg) | Tumor type | Duration of experiment (days) | Tumor Growth Inhibition (%) |
|---|---|---|---|---|
| | 20 | Panc-1 | 13 | D |
| | 20 | Panc-1 | 13 | A |
| | 20 | U87MG | 13 | D |
| | 20 | SKLMS40 | 15 | B |

TABLE 3-continued

In vivo efficacy of selected compounds dosed orally daily using PEG 400/0.1 N HCl in saline (40/60) as a vehicle

| Structure | Dosage (mg/kg) | Tumor type | Duration of experiment (days) | Tumor Growth Inhibition (%) |
|---|---|---|---|---|
| [structure] | 20 | SKLMS40 | 15 | D |
| [structure] | 20 | SKLMS40 | 15 | B |

Assay Example 5

In Vivo Colloidal Neovascularization (CNV) Model

This test measures the capacity of compounds to inhibit CNV progression. CNV is the main cause of severe vision loss in patients suffering from age-related macular degeneration (AMD).

Male Brown-Norway rats (Japan Clea Co., Ltd.) were used in these studies.

Rats were anesthetized by intraperitoneal injection of pentobarbital, and the right pupil was dilated with 0.5% tropicamide and 0.5% phenylephrine hydrochloride. The right eye received 6 laser burns between retinal vessels using a slit lamp delivery system of Green laser Photocoagulator (Nidex Inc., Japan), and microscope slide glass with Healon™ (AMO Inc) used as a contact lens. The laser power was 100 or 200 mW for 0.1 second and spot diameter was 100 μm. At the time of laser burn, bubble production was observed, which is an indication of rupture of Bruch's membrane which is important for CNV generation.

Rats were divided into the groups based on their body weight using SAS software (SAS institute Japan, R8.1) after laser irradiation (Day0). After animals were anesthetized, and the right pupil dilated (as above mentioned), the right eye of the animal received the compound or vehicle by intravitreal injection (5 or 10 μL/eye) at doses of 30 and/or 100 nmol/eyeon Day1 and/or Day3 and/or Day7. The compounds were dissolved or suspended in CBS, PBS, or other adequate vehicles before injection.

On Day 10, the animals were anesthetized with ether, and high molecular weight fluorescein isothiocyanate (FITC)-dextran (SIGMA, $2 \times 10^6$ MW) was injected via a tail vein (20 mg/rat). About 30 min after FITC-dextran injection, animals were euthanized by ether or carbon dioxide, and the eyes were removed and fixed with 10% formaline neutral buffer solution. After over 1 hour of fixation, RPE-choroid-sclera flat mounts were obtained by removing cornea, lens and retina from the eyeballs. The flat mounts were mounted in 50% glycerol on a microscope slide, and the portion burned by laser was photographed using a fluorescence microscope (Nikon Corporation, excitation filter: 465-495 nm, absorption filter: 515-555 nm). The CNV area was obtained by measurement of hyper-fluorescence area observed on the photograph using Scion image.

The average CNV area of 6 burns was used as an individual value of CNV area, and the average CNV area of compound treated group was compared with that of the vehicle-treated group. Results with some compounds of the present invention are shown in Table 4 and are indicated as % of inhibition of CNV progression ("A" indicates greater than or equal to 30% inhibition, and "B" indicates $\geq 10\%$ to <30% inhibition).

TABLE 4

| Cpd No. (Ex No.) | % Inhibition of CNV Progression |
|---|---|
| 13(49) | A |
| 116(223) | B |
| 80(187) | A |
| 14(50) | B |
| 146(253) | A |
| 145(252) | B |
| 148(255) | A |

TABLE 4-continued

| Cpd No. (Ex No.) | % Inhibition of CNV Progression |
|---|---|
| 161(268) | B |
| 162(269) | A |
| 163(270) | A |
| 167(274) | A |
| 170(277) | A |
| 173(280) | A |
| 177(284) | A |

What is claimed is:

1. A compound of Formula (I):

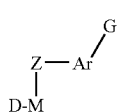

and pharmaceutically acceptable salts thereof, and racemic and scalemic mixtures, diastereomers and enantiomers thereof, wherein, D is selected from the group consisting of

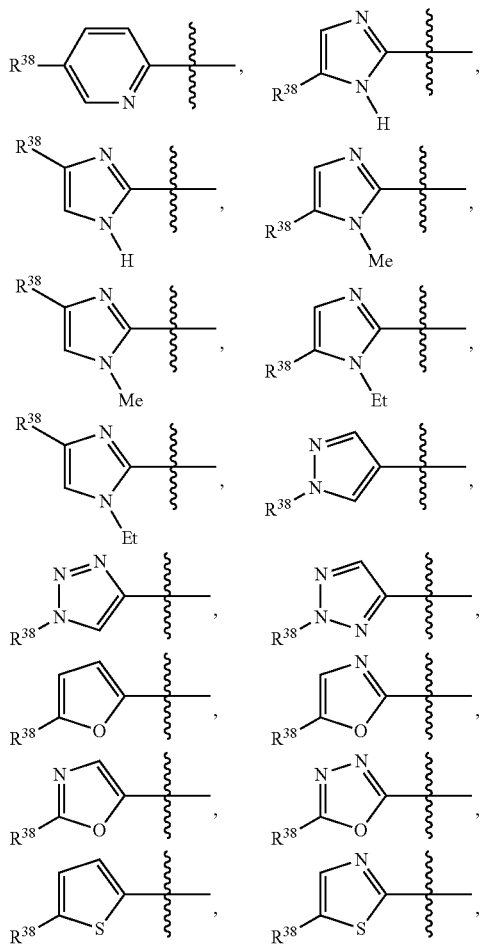

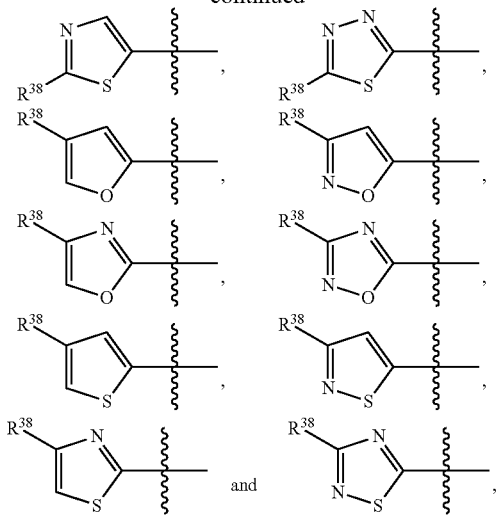

M is

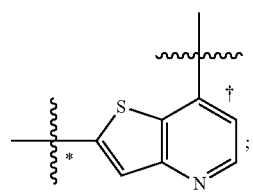 [SMILES: *c1cc2nccc(*)c2s1]

Z is selected from the group consisting of covalent bond, —O—;

Ar is phenyl substituted with 0 to 4 halogen, $C_1$—$C_6$ alkyl or $C_1$—$C_4$ alkoxy; and G is

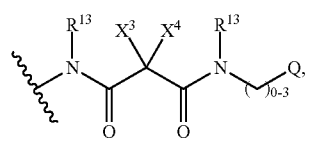

each $R^{38}$ is independently selected from the group consisting of halo, —C(O)O—$(CH_2)_n NR^{36}R^{39}$, —$(CH_2)_j NR^{39}$ $(CH_2)_i S(O)_j (C_1$-$C_6$ alkyl), —$(CH_2)_j NR^{39} (CH_2)_n R^{36}$, —C(O)$NR^{36}R^{39}$, —C(O)$(CH_2)_j NR^{39} (CH_2)_n R^{36}$, —$(CH_2)_n P(=O)(C_1$-$C_6$ alkyl$)_2$, —$(CH_2)_j NR^{39} CH_2$ $(CH_2)_n P(=O)(C_1$-$C_6$ alkyl$)_2$, —$NR^{13} C(X^1) NR^{13}$-aryl P(=O)$(C_1$-$C_6$ alkyl$)_2$ and —$NR^{13} C(X^1) NR^{13}$-heteroarylP(=O)$(C_1$-$C_6$ alkyl$)_2$, —$(CH_2)_j NR^{39} (CH_2)_i$[O $(CH_2)_i]_x (CH_2)_n R^{99}$, —$(CH_2)_j NR^{39} (CH_2)_i SO_{0-2} (CH_2)_i$ [O$(CH_2)_i]_j (CH_2)_n R^{99}$, —$(CH_2)_j NR^{39} (CH_2)_i R^{100}$ wherein each j is an integer independently ranging from 0 to 4, n is an integer ranging from 0 to 6, x is an integer ranging from 1-6, each i is an integer independently ranging from 1 to 3, and the —$(CH_2)_i$— and —$(CH_2)_n$— moieties of the foregoing $R^{38}$ groups are optionally substituted, and optionally include a carbon-carbon double or triple bond where n is an integer between 2 and 6;

$R^{36}$ is selected from the group consisting of H, —OH, $C_1$-$C_6$ alkyl, —O—$C_1$-$C_6$ alkyl, $C_3$-$C_{10}$ cycloalkyl, —$(CH_2)_n (C_6$-$C_{10}$ aryl), —$(CH_2)_n$(5-10 membered heterocyclyl) and —(CH$_2$)$_n$A$^4$R$^{37}$, wherein each n is an integer independently ranging from 0 to 6, A$^4$ is selected from the group consisting of a covalent bond, O, S, SO, SO$_2$, and the alkyl, cycloalkyl, aryl and heterocyclyl moieties of the foregoing R$^{36}$ groups are optionally substituted, with the proviso that when R$^{36}$ and R$^{39}$ are both attached to the same nitrogen, then R$^{36}$ and R$^{39}$ are not both bonded to the nitrogen directly through an oxygen;

each R$^{37}$ and R$^{41}$ is independently selected from H, —C$_1$-C$_6$ alkyl, —O—C$_1$-C$_6$ alkyl, —O—C$_3$-C$_{10}$ cycloalkyl, —O—(CH$_2$)$_n$(C$_6$-C$_{10}$ aryl), —O—(CH$_2$)$_n$(5-10 membered heterocyclyl), optionally substituted C$_1$-C$_6$ alkyl, optionally substituted C$_2$-C$_6$ alkenyl, optionally substituted C$_2$-C$_6$ alkynyl, optionally substituted C$_3$-C$_{10}$ cycloalkyl, optionally substituted —O—(CH$_2$)$_n$A$^4$-C$_1$-C$_6$ alkyl, optionally substituted —O—(CH$_2$)$_n$A$^4$-C$_2$-C$_6$ alkenyl, optionally substituted —O—(CH$_2$)$_n$A$^4$-C$_2$-C$_6$ alkynyl and optionally substituted —O—(CH$_2$)$_n$A$^4$-C$_3$-C$_{10}$cycloaoalkyl;

R$^{39}$ is selected from the group consisting of H, —OH, C$_1$-C$_6$ alkyl, —C(O)—C$_1$-C$_6$alkyl, —SO$_2$—C$_1$-C$_6$alkyl, —C(O)—O—C$_1$-C$_6$alkyl-aryl and a protecting group used to protect secondary amino groups, with the proviso that when R$^{36}$ and R$^{39}$ are both attached to the same nitrogen, then R$^{36}$ and R$^{39}$ are not both bonded to the nitrogen directly through an oxygen;

each R$^{40}$ is independently selected from H, C$_1$-C$_{10}$ alkyl, —(CH$_2$)$_n$(C$_6$-C$_{10}$ aryl), C$_3$-C$_{10}$ cycloalkyl, and —(CH$_2$)$_n$ (5-10 membered heterocyclyl), wherein n is an integer ranging from 0 to 6;

R$^{99}$ at each occurrence is independently selected from the group consisting of —H, halogen, trihalomethyl, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, P(=O)(OH)$_2$, —P(=O)(C$_1$-C$_6$alkyl)$_2$, —SO$_3$H—C(O)R$^3$, C$_1$-C$_4$ alkoxy, C$_1$-C$_4$ alkylthio, —O(CH$_2$)$_{0-6}$aryl, —O(CH$_2$)$_{0-6}$heteroaryl, —(CH$_2$)$_{0-5}$(aryl), —(CH$_2$)$_{0-5}$(heteroaryl), -, C$_1$-C$_6$ alkyl, C$_2$-C$_6$ alkenyl, C$_2$-C$_6$ alkynyl, —CH$_2$(CH$_2$)$_{0-4}$-T$^2$, wherein the aryl, heteroaryl, C$_1$-C$_6$ alkyl, C$_2$-C$_6$ alkenyl, and C$_2$-C$_6$ alkynyl are optionally substituted;

R$^{100}$ is a 12 to 24-membered optionally substituted heteroalicyclic macrocycle containing 4 to 8 oxygen atoms;

each R$^3$ is independently selected from the group consisting of —H and R$^4$;

R$^4$ is selected from the group consisting of a (C$_1$-C$_6$)alkyl, an aryl, a lower arylalkyl, a heterocyclyl and a lower heterocyclylalkyl, each of which is optionally substituted, or R$^3$ and R$^4$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

each R$^{13}$ is independently selected from the group consisting of —H, halogen, trihalomethyl, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, —C(O)SR$^3$, C$_1$-C$_4$ alkoxy, C$_1$-C$_4$ alkylthio, —O(CH$_2$)$_{0-6}$aryl, —O(CH$_2$)$_{0-6}$heteroaryl, —(CH$_2$)$_{0-5}$(aryl), —(CH$_2$)$_{0-5}$(heteroaryl), —(CH$_2$)$_{0-5}$(cycloalkyl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$ alkylcarbonyl, and a saturated or unsaturated three- to seven-membered carboxyclic or heterocyclic group, wherein the aryl, heteroaryl, C$_1$-C$_6$ alkyl, C$_2$-C$_6$ alkenyl, and C$_2$-C$_6$ alkynyl are optionally substituted;

two R$^{13}$, together with the atom or atoms to which they are attached, can combine to form a heteroalicyclic optionally substituted with between one and four of R$^{60}$, wherein the heteroalicyclic can have up to four annular heteroatoms, and the heteroalicyclic can have an aryl or heteroaryl fused thereto, in which case the aryl or heteroaryl is optionally substituted with an additional one to four of R$^{60}$;

R$^{60}$ is selected from the group consisting of —H, halogen, trihalomethyl, —CN, —NO$_2$, —NH$_2$, —OR$^3$, —NR$^3$R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, an optionally substituted (C$_1$-C$_6$)alkyl, an optionally substituted aryl, an optionally substituted heteroarylalkyl and an optionally substituted arylalkyl; or two R$^{60}$, when attached to a non-aromatic carbon, can be oxo;

Q is C$_1$-C$_6$alkyl or a three- to ten-membered ring system, optionally substituted with between zero and four of R$^{20}$;

each R$^{20}$ is independently selected from the group consisting of —H, halogen, trihalomethyl, —O-trihalomethyl, oxo, —CN, —NO$_2$, —NH$_2$, —OR$^3$, —OCF$_3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)C(O)OR$^3$, —C(O)R$^3$, —C(O)SR$^3$, C$_1$-C$_4$ alkoxy, C$_1$-C$_4$ alkylthio, —O(CH$_2$)$_{0-6}$aryl, —O(CH$_2$)$_{0-6}$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$ alkylcarbonyl, C$_{1-4}$ alkoxy, an amino optionally substituted by C$_{1-4}$ alkyl optionally substituted by C$_{1-4}$ alkoxy and a saturated or unsaturated three- to seven-membered carboxyclic or heterocyclic group and wherein the aryl, heteroaryl, C$_1$-C$_6$ alkyl, C$_2$-C$_6$ alkenyl, and C$_2$-C$_6$ alkynyl are optionally substituted;

T$^2$ is selected from the group consisting of —OH, —OMe, —OEt, —NH$_2$, —NHMe, —NMe$_2$, —NHEt and —NEt$_2$;

and

X$^1$ is selected from the group consisting of O, S, CH$_2$, N—CN, N—O-alkyl, NH and N(C$_1$-C$_6$alkyl)

X$^3$ and X$^4$ are each independently selected from the group consisting of —H, halogen, cyano, nitro, C$_1$-C$_6$ alkyl, or X$^3$ and X$^4$ together with the atom to which they are attached form a C$_3$-C$_4$ cycloalkyl.

2. The compound according to claim 1, wherein each R$^{38}$ is independently selected from the group consisting of —C(O)O—(CH$_2$)$_n$NR$^{36}$R$^{39}$, —(CH$_2$)$_j$NR$^{39}$(CH$_2$)$_i$S(O)$_x$(C$_1$-C$_6$ alkyl), —(CH$_2$)$_j$NR$^{39}$(CH$_2$)$_i$[O(CH$_2$)$_i$]$_x$(CH$_2$)$_j$R$^{99}$, and —(CH$_2$)$_j$NR$^{39}$(CH$_2$)$_n$R$^{36}$.

3. The compound according to claim 1, wherein each R$^{38}$ is independently selected from the group consisting of halo, —(CH$_2$)$_j$NR$^{39}$(CH$_2$)$_i$[O(CH$_2$)$_i$]$_x$(CH$_2$)$_j$R$^{99}$, and —(CH$_2$)$_j$NR$^{39}$(CH$_2$)$_j$R$^{36}$.

4. The compound according to claim 1, wherein each R$^{38}$ is independently selected from the group consisting of —(CH$_2$)$_n$ P(=O)(C$_1$-C$_6$alkyl)$_2$, —(CH$_2$)$_j$NR$^{39}$CH$_2$(CH$_2$)$_n$P(=O)(C$_1$-C$_6$alkyl)$_2$, —NR$^{13}$C(X$^1$)NR$^{13}$-arylP(=O)(C$_1$-C$_6$alkyl)$_2$ and —NR$^{13}$C(X$^1$)NR$^{13}$-heteroarylP(=O)(C$_1$-C$_6$alkyl)$_2$.

5. The compound according to claim 4, wherein X$^1$ is O or S.

6. The compound according to claim 1, wherein $R^{38}$ is $-(CH_2)_jNR^{39}(CH_2)_nR^{36}$, wherein the $-(CH_2)_n-$ group is optionally substituted with $C_1$-$C_6$alkyl, $R^{36}$ is $-(CH_2)_{n3}A^4R^{37}$, wherein each n3 is an integer independently ranging from 0 to 6, $R^{37}$ is optionally substituted $C_1$-$C_6$ alkyl, and $R^{39}$ is $-C(O)-C_1$-$C_3$alkyl.

7. The compound according to claim 1, wherein $R^{38}$ is independently selected from the group consisting of halo, $-C(O)O-(CH_2)_nNR^{36}R^{39}$, $-(CH_2)_jNR^{39}(CH_2)_iS(O)_i(C_1$-$C_6$ alkyl), and $-(CH_2)_jNR^{39}(CH_2)_nR^{36}$, wherein each j is an integer independently selected from 0 to 4, n is an integer from 0 to 6, $R^{39}$ is H or $C_1$-$C_6$alkyl, and $R^{36}$ is selected from the group consisting of H, $-OH$, $C_1$-$C_6$ alkyl, $C_3$-$C_{10}$ cycloalkyl, $-(CH_2)_{n3}(C_6$-$C_{10}$ aryl), $-(CH_2)_{n3}$(5-10 membered heterocyclyl) and $-(CH_2)_{n3}A^4R^{37}$, wherein each n3 is an independently selected integer ranging from 0 to 6, and $R^{37}$ is H or $C_1$-$C_6$alkyl.

8. The compound according to claim 7, wherein D is

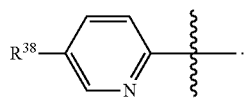

9. The compound according to claim 1, wherein $R^{38}$ is independently selected from the group consisting of halo, $-(CH_2)_nP(=O)(C_1$-$C_6$alkyl)$_2$, $-(CH_2)_jNR^{39}CH_2(CH_2)_nP(=O)(C_1$-$C_6$alkyl)$_2$, $-NR^{13}C(X^1)NR^{13}$-arylP$(=O)(C_1$-$C_6$alkyl)$_2$ and $-NR^{13}C(X^1)NR_{13}$-heteroarylP$(=O)(C_1$-$C_6$alkyl)$_2$, wherein $X^1$ is O or S, j is an integer from 0 to 4, n is an integer from 0 to 6, $R^{39}$ is H or $C_1$-$C_6$alkyl, and $R^{36}$ is selected from the group consisting of H, $-OH$, $C_1$-$C_6$ alkyl, $C_3$-$C_{10}$ cycloalkyl, $-(CH_2)_{n3}(C_6$-$C_{10}$ aryl), $-(CH_2)_{n3}$(5-10 membered heterocyclyl) and $-(CH_2)_{n3}A^4R^{37}$, wherein n3 is an integer ranging from 0 to 6, and $R^{37}$ is H or $C_1$-$C_6$alkyl.

10. The compound according to claim 9, wherein D is

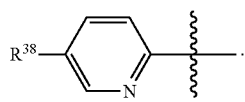

11. The compound according to claim 1, wherein G is selected from the group consisting of

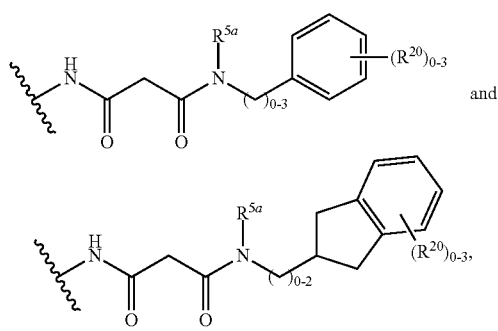

wherein each methylene in any of the above formulae, other than those in a depicted ring, is independently optionally substituted with $R^{25}$;

$R^{5a}$ is $-H$ or an optionally substituted $(C_1$-$C_6)$alkyl;

$R^{10}$ is an azolyl, wherein one or more hydrogen atoms are optionally substituted by a moiety selected from the group consisting of a halogen, $C_{1-4}$ alkyl, $C_{1-4}$ alkoxy, $C_{1-4}$ alkylthio, trihalomethyl, nitro, amino optionally independently substituted by one or two of $C_{1-4}$ alkyl, a $C_{1-4}$ alkoxycarbonyl $C_{1-4}$ alkyl, a $C_{1-4}$ alkylcarbonyl and a $C_{3-5}$ cyclic alkyl.

12. The compound according to claim 1, wherein G is selected from the group consisting of

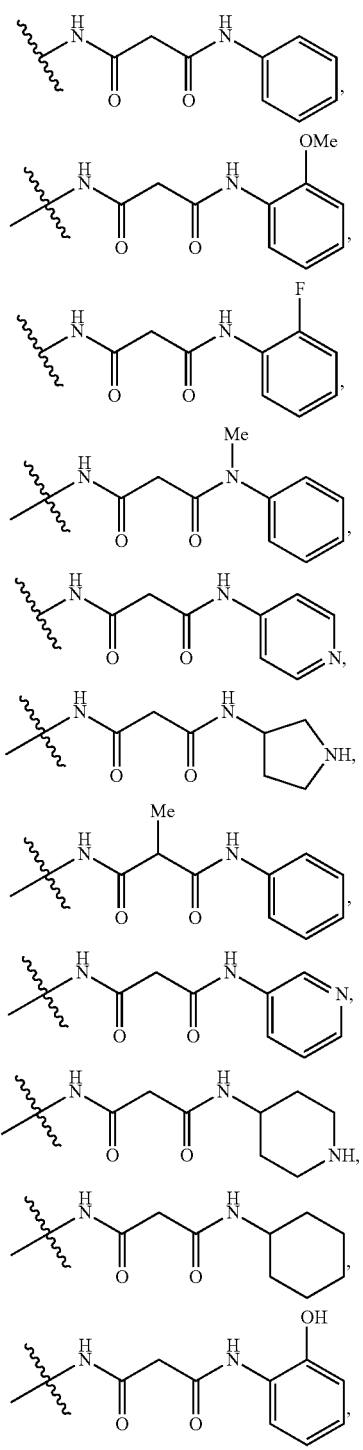

337
-continued
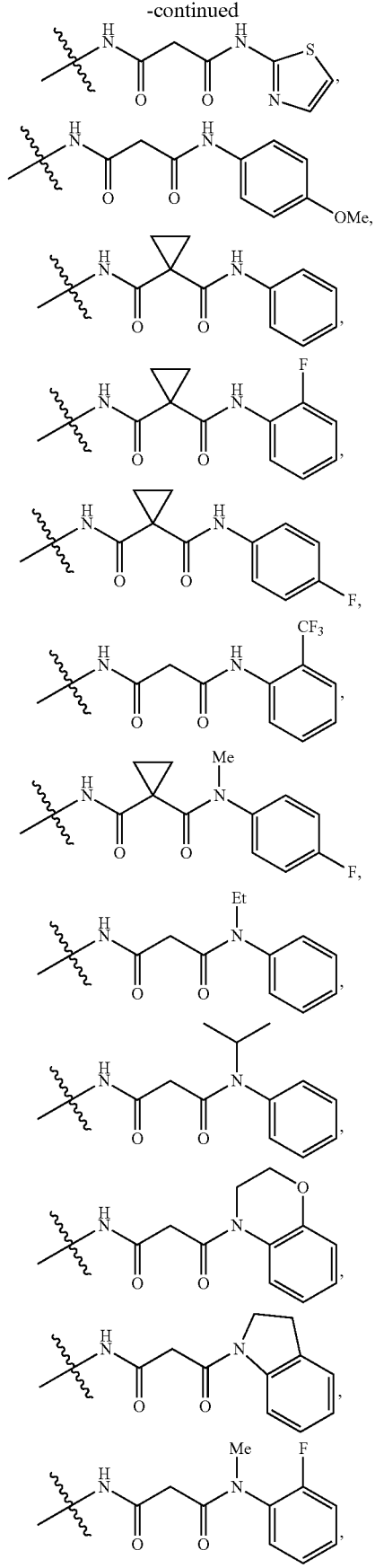
338
-continued
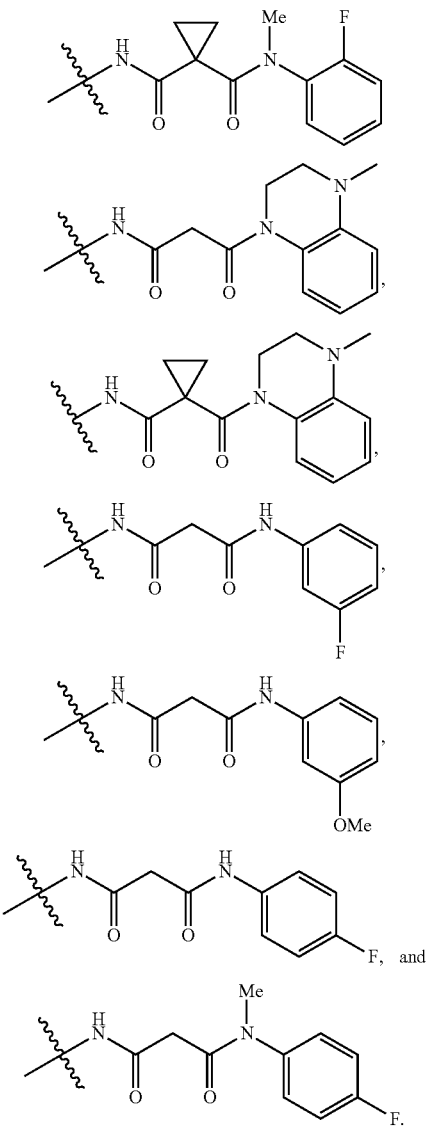
13. The compound according to claim 1, wherein G is selected from the group consisting of
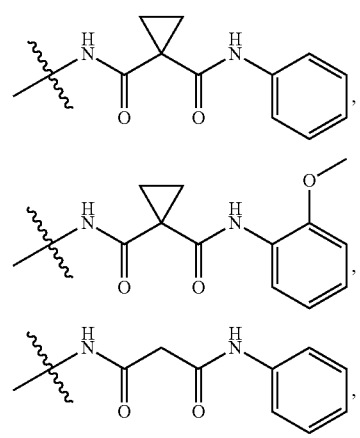

-continued

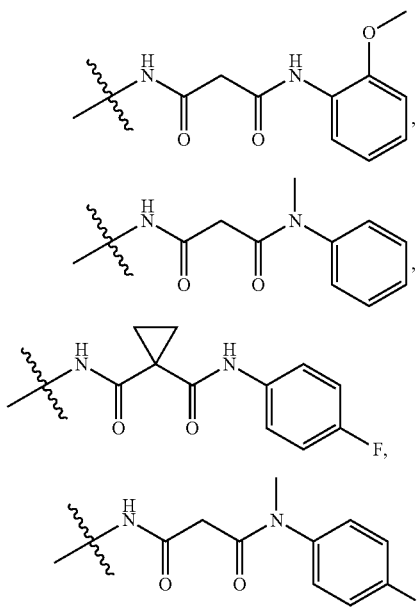

14. The compound according to claim 1, wherein
M is

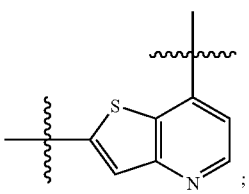 [SMILES: *c1cc2nccc(*)c2s1]

Z is —O—;

Ar is phenyl substituted with 0 to 4 halogen, $C_1$—$C_6$ alkyl or $C_1$—$C_4$ alkoxy; and G is

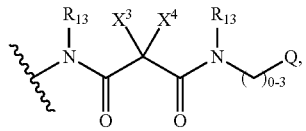

wherein Q is optionally substituted with from 0 to 4 independently selected $R^{20}$.

15. The compound according to claim 1, wherein $R^{38}$ is independently selected from the group consisting of halo, —C(O)O—$(CH_2)_n$$NR^{36}R^{39}$, —$(CH_2)_j$$NR^{39}$ $(CH_2)_i$S(O)$_j$($C_1$-$C_6$ alkyl), and —$(CH_2)_j$$NR^{39}$$(CH_2)_n$ $R^{36}$, wherein each j is an integer independently selected from 0 to 4, n is an integer from 0 to 6, i is 2 or 3, $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —$(CH_2)_{n3}$($C_6$-$C_{10}$ aryl), —$(CH_2)_{n3}$(5-10 membered heterocyclyl) and —$(CH_2)_{n3}A^4R^{37}$, wherein n3 is an integer ranging from 0 to 6, and $R^{37}$ is H or $C_1$-$C_6$alkyl;

M is

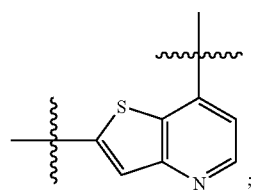 [SMILES: *c1cc2nccc(*)c2s1]

Z is —O—;

Ar is phenyl substituted with 0 to 4 halogen, $C_1$—$C_6$ alkyl or $C_1$—$C_4$ alkoxy; and G is

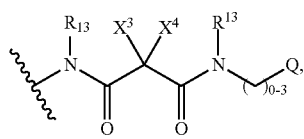

wherein Q is optionally substituted with from 0 to 4 independently selected $R^{20}$.

16. The compound according to claim 1, wherein
D is

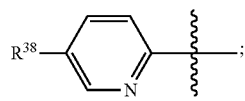

M is

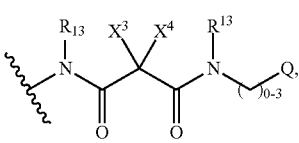

Z is —O—;

Ar is phenyl substituted with 0 to 4 halogen, $C_1$—$C_6$ alkyl or $C_1$—$C_4$ alkoxy; and G is wherein Q is optionally substituted with from 0 to 4 independently selected $R^{20}$.

17. The compound according to claim 1, wherein

D is

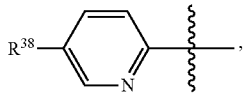

wherein

R$^{38}$ is selected from the group consisting of halo, —C(O)O—(CH$_2$)$_n$NR$^{36}$R$^{39}$, —(CH$_2$)$_j$NR$^{39}$(CH$_2$)$_i$S(O)$_j$C$_1$-C$_6$ alkyl), and —(CH$_2$)$_j$NR$^{39}$(CH$_2$)$_n$R$^{36}$, wherein each j is an integer independently selected from 0 to 4, n is an integer from 0 to 6, i is 2 or 3, R$^{39}$ is H or C$_1$-C$_6$alkyl, and R$^{36}$ is selected from the group consisting of H, —OH, C$_1$-C$_6$ alkyl, C$_3$-C$_{10}$ cycloalkyl, —(CH$_2$)$_{n3}$(C$_6$-C$_{10}$ aryl), —(CH$_2$)$_{n3}$(5-10 membered heterocyclyl) and —(CH$_2$)$_{n3}$A$^4$R$^{37}$, wherein n3 is an integer ranging from 0 to 6, and R$^{37}$ is H or C$_1$-C$_6$alkyl;

M is

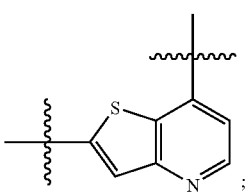 [SMILES: *c1cc2nccc(*)c2s1]

Z is —O—;

Ar is phenyl substituted with 0 to 4 halogen, C$_1$—C$_6$ alkyl or C$_1$—C$_4$ alkoxy; and G is

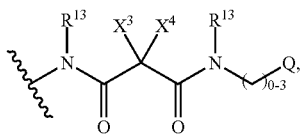

wherein Q is optionally substituted with from 0 to 4 independently selected R$^{20}$.

18. The compound according to claim 1, wherein

M is

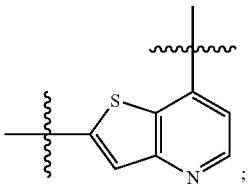 [SMILES: *c1cc2nccc(*)c2s1]

Z is —O—;

Ar is phenyl substituted with 0 to 4 halogen, C$_1$—C$_6$ alkyl or C$_1$—C$_4$ alkoxy; and G is

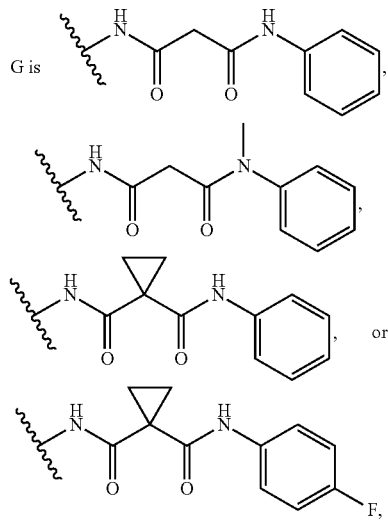

wherein phenyl groups of G are optionally substituted with from 0 to 4 independently selected R$^{20}$.

19. The compound according to claim 1, wherein

R$^{38}$ is independently selected from the group consisting of halo, —C(O)O—(CH$_2$)$_n$NR$^{36}$R$^{39}$, —(CH$_2$)$_j$NR$^{39}$(CH$_2$)$_i$S(O)$_j$(C$_1$-C$_6$alkyl), and —(CH$_2$)$_j$NR$^{39}$(CH$_2$)$_n$R$^{36}$, wherein each j is an integer independently selected from 0 to 4, n is an integer from 0 to 6, i is 2 or 3, R$^{39}$ is H or C$_1$-C$_6$alkyl, and R$^{36}$ is selected from the group consisting of H, —OH, C$_1$-C$_6$ alkyl, C$_3$-C$_{10}$ cycloalkyl, —(CH$_2$)$_{n3}$(C$_6$-C$_{10}$ aryl), —(CH$_2$)$_{n3}$(5-10 membered heterocyclyl) and —(CH$_2$)$_{n3}$A$^4$R$^{37}$, wherein n3 is an integer ranging from 0 to 6, and R$^{37}$ is H or C$_1$-C$_6$alkyl;

M is

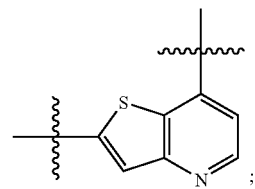 [SMILES: *c1cc2nccc(*)c2s1]

Z is —O—;

Ar is phenyl substituted with 0 to 4 halogen, C$_1$—C$_6$ alkyl or C$_1$—C$_4$ alkoxy; and G is

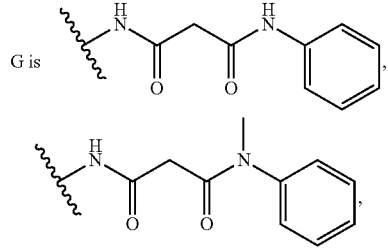

-continued

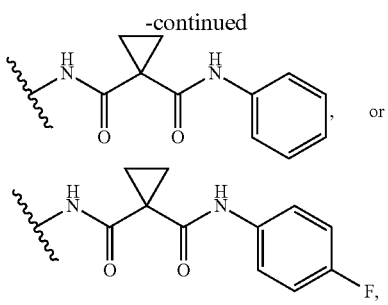
or wherein phenyl groups of G are optionally substituted with from 0 to 4 independently selected $R^{20}$.

20. The compound according to claim 1, wherein
D is

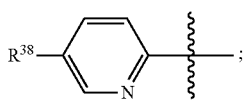

M is

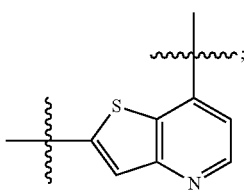 [SMILES: *c1cc2nccc(*)c2s1]

Z is —O—;
Ar is phenyl substituted with 0 to 4 halogen, $C_1$—alkyl or $C_1$—$C_4$ alkoxy; and
G is

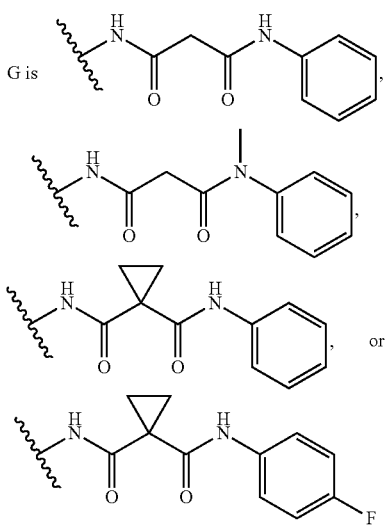

wherein phenyl groups of G are optionally substituted with from 0 to 4 independently selected $R^{20}$.

21. The compound according to claim 1, wherein
D is

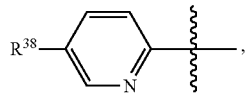

wherein $R^{38}$ is independently selected from the group consisting of halo, —C(O)O—$(CH_2)_n NR^{36}R^{39}$, —$(CH_2)_j NR^{39}(CH_2)_i S(O)_j(C_1$-$C_6$alkyl), and —$(CH_2)_j NR^{39}(CH_2)_n R^{36}$, wherein each j is an integer independently selected from 0 to 4, n is an integer from 0 to 6, i is 2 or 3, $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —$(CH_2)_{n3}(C_6$-$C_{10}$ aryl), —$(CH_2)_{n3}$(5-10 membered heterocyclyl) and —$(CH_2)_{n3} A^4 R^{37}$, wherein n3 is an integer ranging from 0 to 6, and $R^{37}$ is H or $C_1$-$C_6$alkyl;
M is

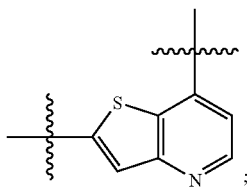 [SMILES: *c1cc2nccc(*)c2s1]

Z is —O—;
Ar is phenyl substituted with 0 to 4 halogen, $C_1$—$C_6$ alkyl or $C_1$—$C_4$ alkoxy; and
G is

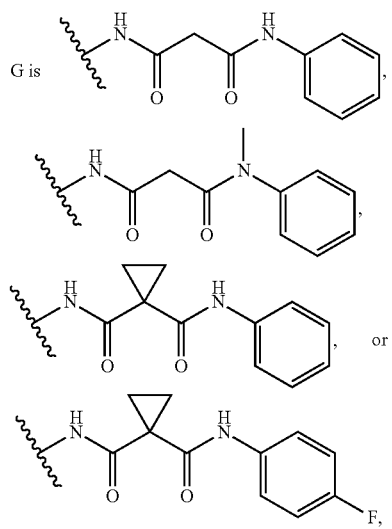

wherein phenyl groups of G are optionally substituted with from 0 to 4 independently selected $R^{20}$.

22. The compound according to claim 1,
wherein $R^{38}$ is independently selected from the group consisting of halo, —$(CH_2)_n P(=O)(C_1$-$C_6$alkyl)$_2$, —$(CH_2)_j NR^{39}CH_2(CH_2)_n P(=O)(C_1$-$C_6$alkyl)$_2$, —$NR^{13}C(X^1)NR^{13}$-arylP$(=O)(C_1$-$C_6$alkyl)$_2$ and —$NR^{13}C(X^1)NR^{13}$-heteroarylP$(=O)(C_1$-$C_6$alkyl)$_2$,
wherein j is an integer from 0 to 4, n is an integer from 0 to 6, $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —$(CH_2)_{n3}(C_6$-$C_{10}$ aryl), —$(CH_2)_{n3}$(5-10 membered heterocyclyl) and —$(CH_2)_{n3}A^4R^{37}$, wherein n3 is an integer ranging from 0 to 6, and $R^{37}$ is H or $C_1$-$C_6$alkyl;

M is

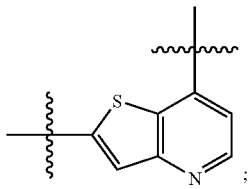 [SMILES: *c1cc2nccc(*)c2s1]

Z is —O—;
Ar is phenyl substituted with 0 to 4 halogen, $C_1$—$C_6$ alkyl or $C_1$—$C_4$ alkoxy; and
G is

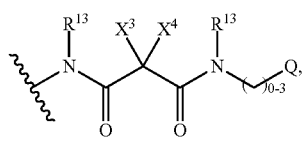

wherein Q is optionally substituted with from 0 to 4 independently selected $R^{20}$.

23. The compound according to claim 1, wherein D is

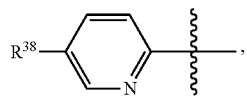

wherein $R^{38}$ is independently selected from the group consisting of halo, —$(CH_2)_nP(=O)(C_1$-$C_6$alkyl$)_2$, —$(CH_2)_j$NR$^{39}$CH$_2$(CH$_2$)$_n$(P=O)(C$_1$-C$_6$alkyl)$_2$, —NR$^{13}$C(X$^1$)NR$^{13}$-arylP(=O)(C$_1$-C$_6$alkyl)$_2$ and —NR$^{13}$C(X$^1$)NR$^{13}$-heteroarylP(=O)(C$_1$-C$_6$alkyl)$_2$, wherein j is an integer from 0 to 4, n is an integer from 0 to 6, $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —$(CH_2)_{n3}(C_6$-$C_{10}$ aryl), —$(CH_2)_{n3}$(5-10 membered heterocyclyl) and —$(CH_2)_{n3}A^4R^{37}$, wherein n3 is an integer ranging from 0 to 6, and $R^{37}$ is H or $C_1$-$C_6$alkyl;

M is

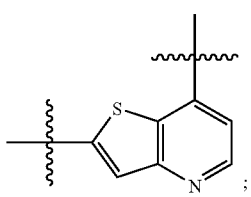

Z is —O—;
Ar is phenyl substituted with 0 to 4 halogen, $C_1$—$C_6$ alkyl or $C_1$—$C_4$ alkoxy; and G is

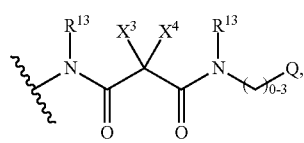

wherein Q is optionally substituted with from 0 to 4 independently selected $R^{20}$.

24. The compound according to claim 1, wherein $R^{38}$ is independently selected from the group consisting of halo, —$(CH_2)_nP(=O)(C_1$—$C_6$alkyl$)_2$, —$(CH_2)_j$NR$^{39}$CH$_2$(CH$_2$)$_n$P(=O)(C$_1$—$C_6$alkyl)$_2$, —NR$^{13}$C(X$^1$)NR$^{13}$—arylP(=O)(C$_1$—C$_6$ $_{alkyl)2}$ and —NR$^{13}$C(X$^1$)NR$^{13}$—heteroarylP(=O)(C$_1$—C$_6$alkyl)$_2$, wherein j is an integer from 0 to 4, n is an integer from 0 to 6, $R^{39}$ is H or $C_1$—$C_6$alkyl, and $R^{36}$ is selected from the group consisting of H, —OH, $C_1$—$C_6$ alyl, $C_3$—$C_{10}$ cycloalkyl, —$(CH_2)_{n3}(C_6$—$C_{10}$ aryl), —$(CH_2)_{n3}$(5-10 membered heterocyclyl) and —$(CH_2)_{n3}A^4R^{37}$, wherein n3 is an integer ranging from 0 to 6, and $R^{37}$ is H or $C_1$—$C_6$alkyl;

M is

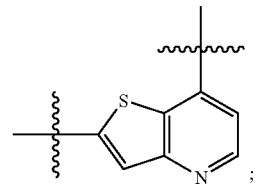 [SMILES: *c1cc2nccc(*)c2s1]

Z is —O—; Ar is phenyl substituted with 0 to 4 halogens, $C_1$—$C_6$ alkyl or $C_1$—$C_4$ alkoxy; and G is

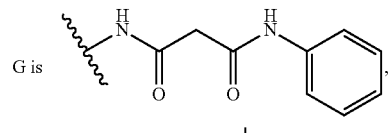

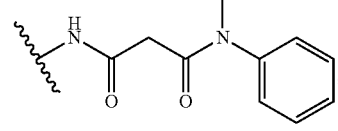

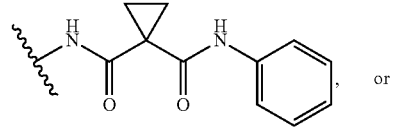
, or

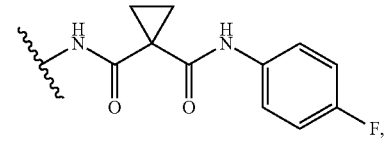

wherein phenyl groups of G are optionally substituted with from 0 to 4 independently selected $R^{20}$.

25. The compound according to claim 1, wherein

D is

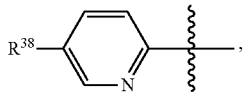, wherein $R^{38}$ is independently selected from the group consisting of halo, —$(CH_2)_nP(=O)(C_1-C_6alkyl)_2$, —$(CH_2)_j$NR$^{39}$CH$_2$(CH$_2$)$_n$P(=O)(C$_1$-C$_6$alkyl)$_2$, —NR$^{13}$C(X$^1$)NR$^{13}$-arylP(=O)(C$_1$-C$_6$alkyl)$_2$ and —NR$^{13}$C(X$^1$)NR$^{13}$-heteroarylP(=O)(C$_1$-C$_6$alkyl)$_2$, wherein j is an integer from 0 to 4, n is an integer from 0 to 6, $R^{39}$ is H or $C_1$-$C_6$alkyl, and $R^{36}$ is selected from the group consisting of H, —OH, $C_1$-$C_6$ alkyl, $C_3$-$C_{10}$ cycloalkyl, —(CH$_2$)$_{n3}$(C$_6$-C$_{10}$ aryl), —(CH$_2$)$_{n3}$ (5-10 membered heterocyclyl) and —(CH$_2$)$_{n3}$A$^4$R$^{37}$, wherein n3 is an integer ranging from 0 to 6, and $R^{37}$ is H or $C_1$-$C_6$alkyl;

M is

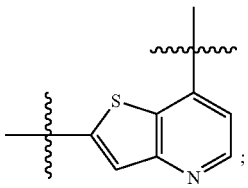 [SMILES: *c1cc2nccc(*)c2s1]

Z is —O—;

Ar is phenyl substituted with 0 to 4 halogen, $C_1$—$C_6$ alkyl or $C_1$—$C_4$ alkoxy; and G is,

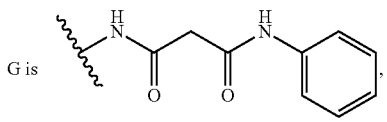

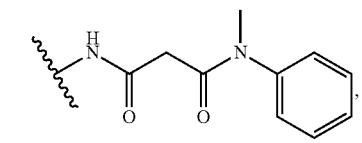

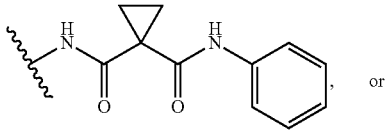

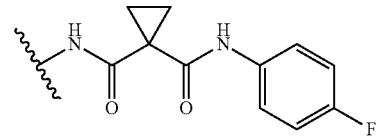

wherein phenyl groups of G are optionally substituted with from 0 to 4 independently selected $R^{20}$.

26. The compound according to claim 1, wherein

M is

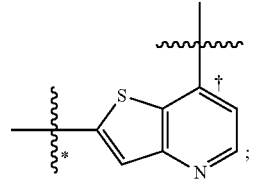 [SMILES: *c1cc2nccc(*)c2s1];

Z is —O—;

Ar is phenyl substituted with 0 to 4 halogen, $C_1$—$C_6$ alkyl or $C_1$—$C_4$ alkoxy; and G is

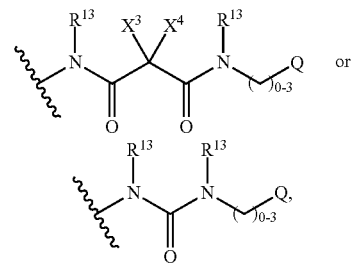

wherein Q is optionally substituted with from 0 to 4 independently selected $R^{20}$.

27. The compound according to claim 1, wherein $R^{38}$ is —(CH$_2$)$_j$NR$^{39}$(CH$_2$)$_n$R$^{36}$, wherein j is an integer from 0 to 4, n is an integer from 0 to 6, and the —(CH$_2$)$_n$— group is optionally substituted with $C_1$-$C_6$alkyl, $R^{36}$ is —(CH$_2$)$_{n3}$A$^4$R$^{37}$, wherein n3 is an integer ranging from 0 to 6, wherein the $R^{37}$ is optionally substituted $C_1$-$C_6$ alkyl, and $R^{39}$ is H or —C(O)—$C_1$-$C_3$alkyl;

M is

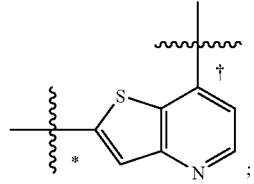 [SMILES: *c1cc2nccc(*)c2s1];

Z is —O—;

Ar is phenyl substituted with 0 to 4 halogen, $C_1$—$C_6$ alkyl or $C_1$—$C_4$ alkoxy; and G is

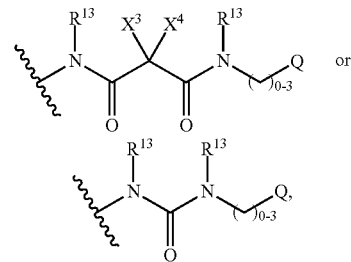

wherein Q is optionally substituted with from 0 to 4 independently selected $R^{20}$.

28. The compound according to claim 1, wherein,

D is

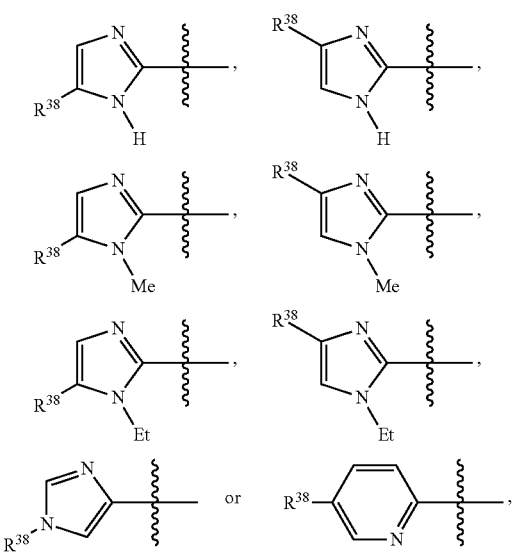

wherein $R^{38}$ is —$(CH_2)_j NR^{39}(CH_2)_n R^{36}$, wherein j is an integer from 0 to 4, n is an integer from 0 to 6, and the —$(CH_2)_n$— group is optionally substituted with $C_1$-$C_6$alkyl, $R^{36}$ is —$(CH_2)_{n3}A^4R^{37}$, wherein n3 is an integer ranging from 0 to 6, wherein the $R^{37}$ is optionally substituted $C_1$-$C_6$ alkyl, and $R^{39}$ is H or —C(O)—$C_1$-$C_3$alkyl;

M is

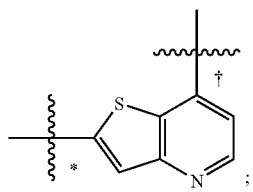 [SMILES: *c1cc2nccc(*)c2s1]

Z is —O—;
Ar is phenyl substituted with 0 to 4 halogen, $C_1$—$C_6$ alkyl or $C_1$—$C_4$ alkoxy; and
G is

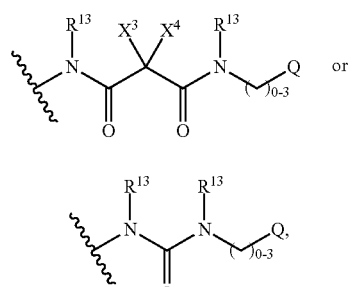

wherein Q is optionally substituted with from 0 to 4 independently selected $R^{20}$.

29. The compound according to claim 1, wherein

D is

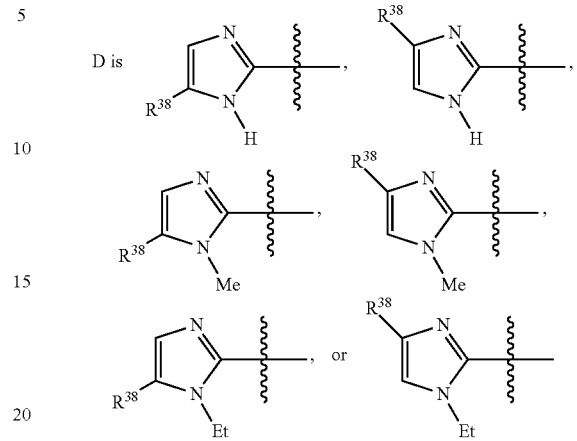

wherein $R^{38}$ is —$(CH_2)_j NR^{39}(CH_2)_n R^{36}$, wherein j is an integer from 0 to 4, n is an integer from 0 to 6, and $R^{36}$ is —$(CH_2)_{n3}OR^{37}$ wherein n3 is an integer ranging from 0 to 6, wherein the $R^{37}$ is optionally substituted $C_1$-$C_6$ alkyl, and $R^{39}$ is H;

M is

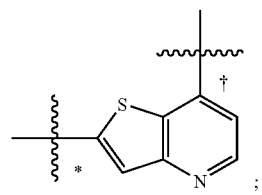 [SMILES: *c1cc2nccc(*)c2s1 ; ";"]

Z is —O—;
Ar is phenyl substituted with 0 to 4 halogen, $C_1$—$C_6$ alkyl or $C_1$—$C_4$ alkoxy; and
G is

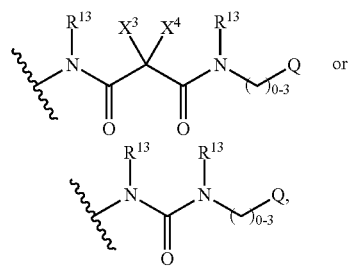

wherein Q is optionally substituted with from 0 to 4 independently selected $R^{20}$.

30. The compound according to claim 1, wherein

D is

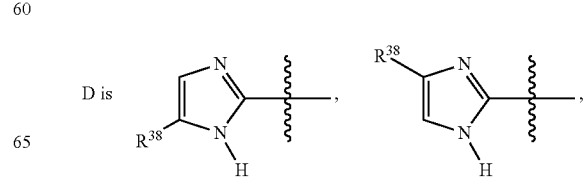

-continued

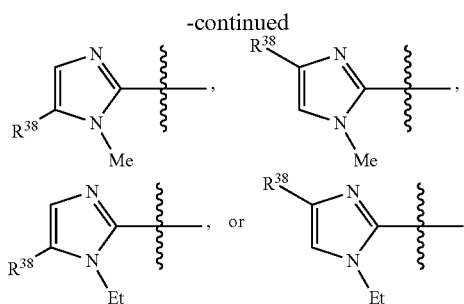

wherein $R^{38}$ is —$(CH_2)_jNR^{39}(CH_2)_nR^{36}$, wherein j is an integer from 0 to 4, n is an integer from 0 to 6, and $R^{36}$ is —$(CH_2)_{n3}OR^{37}$ wherein n3 is an integer ranging from 0 to 6, wherein the $R^{37}$ is optionally substituted $C_1$-$C_6$ alkyl, and $R^{39}$ is H;

M is

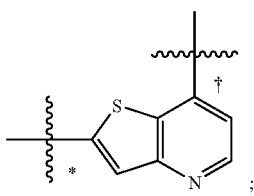

Z is —O—;

Ar is phenyl substituted with at least one halogen, $C_1$—$C_6$ alkyl or $C_1$—$C_4$ alkoxy; and G is

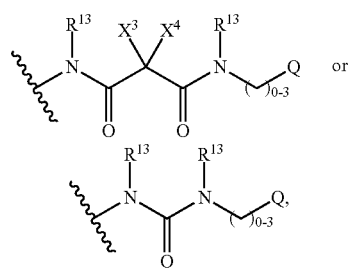

wherein Q is optionally substituted with from 0 to 4 independently selected $R^{20}$.

31. The compound according to claim 1, wherein
D is

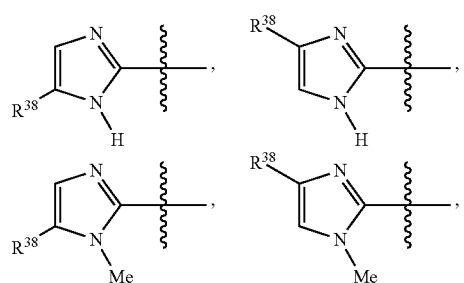

-continued

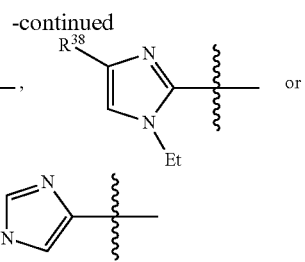

wherein $R^{38}$ is —$(CH_2)_jNR^{39}(CH_2)_nR^{36}$, wherein j is an integer from 0 to 4, n is an integer from 0 to 6, and $R^{36}$ is —$(CH_2)_{n3}OR^{37}$ wherein n3 is an integer ranging from 0 to 6, wherein the $R^{37}$ is optionally substituted $C_1$-$C_6$ alkyl, and $R^{39}$ is H;

M is

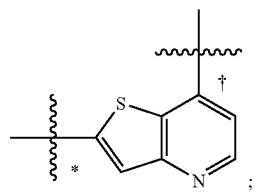

Z is —O—;

Ar is phenyl substituted with at least one halogen, $C_1$—$C_6$ alkyl or $C_1$—$C_4$ alkoxy;

G is

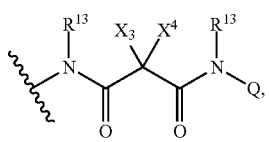

wherein
$R^{13}$ is H; and
Q is optionally substituted with from 0 to 4 independently selected $R^{20}$.

32. The compound according to claim 1, wherein
D is

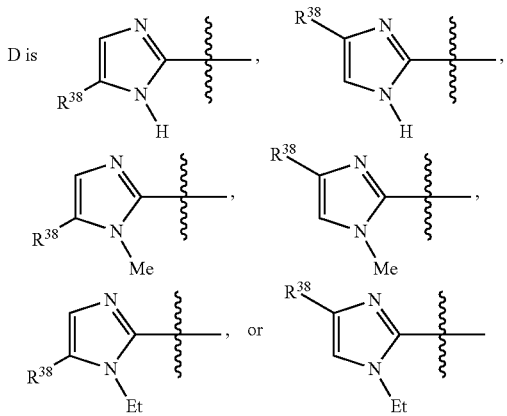

wherein $R^{38}$ is —$(CH_2)_jNR^{39}(CH_2)_nR^{36}$, wherein j is an integer from 0 to 4, n is an integer from 0 to 6, and $R^{36}$ is —(CH$_2$)$_{n3}$OR$^{37}$ wherein n3 is an integer ranging from 0 to 6, wherein the R$^{37}$ is optionally substituted C$_1$-C$_6$ alkyl, and R$^{39}$ is H;

M is

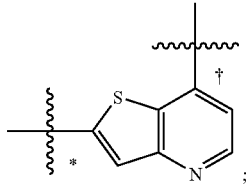 [SMILES: *c1cc2nccc(*)c2s1 ; ";"]

Z is —O—;
Ar is phenyl substituted with at least one halogen, C$_1$—C$_6$ alkyl or C$_1$—C$_4$ alkoxy;
G is

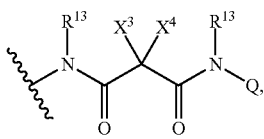

wherein
R$^{13}$ is H;
X$^3$ and X$^4$ are each H or taken together with the carbon to which they are attach are cyclopropyl; and
Q is cycloalkyl, heteroaryl or phenyl, optionally substituted with from 0 to 4 independently selected R$^{20}$.

33. The compound according to claim 1, wherein D is

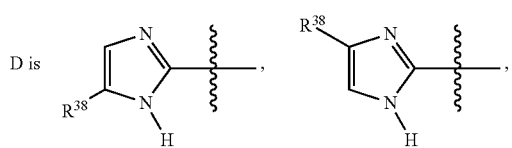

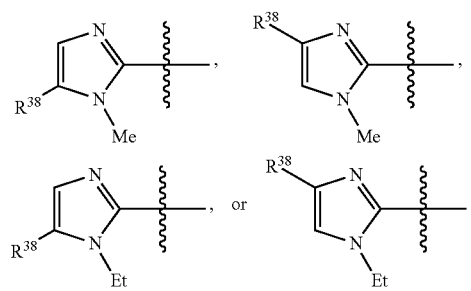

wherein R$^{38}$ is —(CH$_2$)$_j$NR$^{39}$(CH$_2$)$_n$R$^{36}$, wherein j is an integer from 0 to 4, n is an integer from 0 to 6, and R$^{36}$ is —(CH$_2$)$_{n3}$OR$^{37}$ wherein n3 is an integer ranging from 0 to 6, wherein the R$^{37}$ is optionally substituted C$_1$-C$_6$ alkyl, and R$^{39}$ is H;

M is

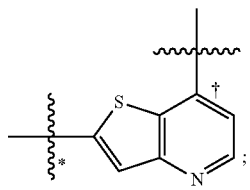 [SMILES: *c1cc2nccc(*)c2s1]

Z is —O—;
Ar is phenyl substituted with at least one halogen, C$_1$—C$_6$ alkyl or C$_1$—C$_4$ alkoxy;
G is

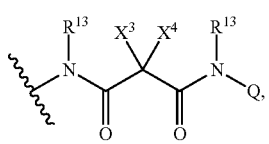

wherein
R$^{13}$ is H;
X$^3$ and X$^4$ are each H or taken together with the carbon to which they are attach are cyclopropyl; and
Q is cyclopropyl, isoxazole or phenyl, optionally substituted with from 0 to 2 independently selected halogen, C$_1$-C$_6$alkyl or —CF$_3$.

34. The compound according to claim 1, wherein, D is

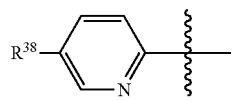

wherein R$^{38}$ is —(CH$_2$)$_j$NR$^{39}$(CH$_2$)$_n$R$^{36}$, wherein j is an integer from 0 to 4, n is an integer from 0 to 6, and R$^{36}$ is —(CH$_2$)$_{n3}$OR$^{37}$ wherein n3 is an integer ranging from 0 to 6, wherein the R$^{37}$ is optionally substituted C$_1$-C$_6$ alkyl, and R$^{39}$ is H;

M is

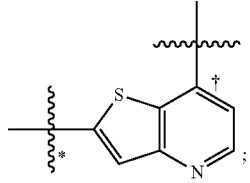 [SMILES: *c1cc2nccc(*)c2s1]

Z is —O—;
Ar is phenyl substituted with 0 to 4 halogen, C$_1$—C$_6$ alkyl or C$_1$—C$_4$ alkoxy; and
G is

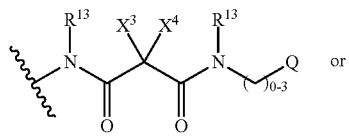 or

-continued

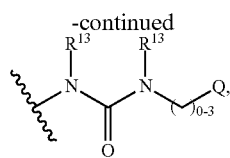

wherein Q is optionally substituted with from 0 to 4 independently selected $R^{20}$.

35. The compound according to claim 1, wherein

D is

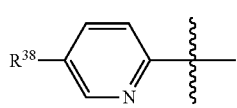

wherein $R^{38}$ is —$(CH_2)_jNR^{39}(CH_2)_nR^{36}$, wherein j is an integer from 0 to 4, n is an integer from 0 to 6, and $R^{36}$ is —$(CH_2)_{n3}OR^{37}$ wherein n3 is an integer ranging from 0 to 6, wherein the $R^{37}$ is optionally substituted $C_1$-$C_6$ alkyl, and $R^{39}$ is H;

M is

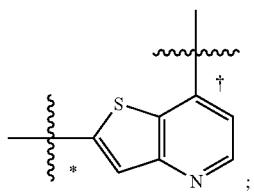

Z is —O—;

Ar is phenyl substituted with at least one halogen, $C_1$—$C_6$ alkyl or $C_1$—$C_4$ alkoxy; and G is

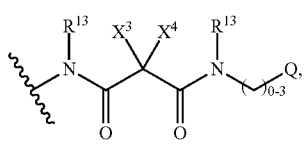

wherein Q is optionally substituted with from 0 to 4 independently selected $R^{20}$.

36. The compound according to claim 1, wherein

D is

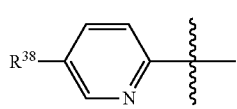

wherein $R^{38}$ is —$(CH_2)_jNR^{39}(CH_2)_nR^{36}$, wherein j is an integer from 0 to 4, n is an integer from 0 to 6, and $R^{36}$ is —$(CH_2)_{n3}OR^{37}$ wherein n3 is an integer ranging from 0 to 6, wherein the $R^{37}$ is optionally substituted $C_1$-$C_6$ alkyl, and $R^{39}$ is H;

M is

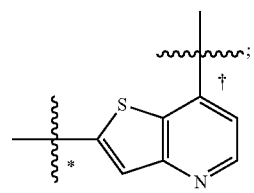 [SMILES: *c1cc2nccc(*)c2s1]

Z is —O—;

Ar is phenyl substituted with at least one halogen, $C_1$—$C_6$ alkyl or $C_1$—$C_4$ alkoxy;

G is

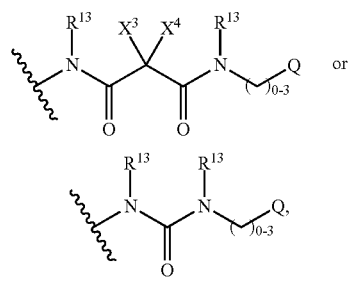

wherein $R^{13}$ is H; and

Q is optionally substituted with from 0 to 4 independently selected $R^{20}$.

37. The compound according to claim 1, wherein

D is

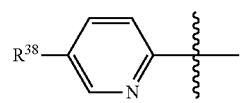

wherein $R^{38}$ is —$(CH_2)_jNR^{39}(CH_2)_nR^{36}$, wherein j is an integer from 0 to 4, n is an integer from 0 to 6, and $R^{36}$ is —$(CH_2)_{n3}OR^{37}$ wherein n3 is an integer ranging from 0 to 6, wherein the $R^{37}$ is optionally substituted $C_1$-$C_6$ alkyl, and $R^{39}$ is H;

M is

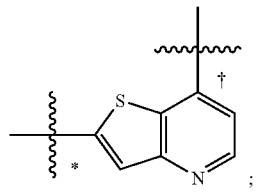 [SMILES: *c1cc2nccc(*)c2s1 ; ";"]

Z is —O—;

Ar is phenyl substituted with at least one halogen, $C_1$—$C_6$ alkyl or $C_1$—$C_4$ alkoxy;

G is

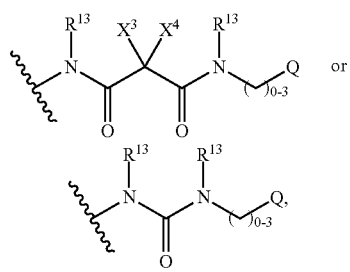

wherein
R$^{13}$ is H;
X$^3$ and X$^4$ are each H or taken together with the carbon to which they are attach are cyclopropyl; and
Q is cycloalkyl, heteroaryl or phenyl, optionally substituted with from 0 to 4 independently selected R$^{20}$.

38. The compound according to claim 1, wherein D is

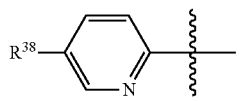

wherein R$^{38}$ is —(CH$_2$)$_j$NR$^{39}$(CH$_2$)$_n$R$^{36}$, wherein j is an integer from 0 to 4, n is an integer from 0 to 6, and R$^{36}$ is —(CH$_2$)$_{n3}$OR$^{37}$ wherein n3 is an integer ranging from 0 to 6, wherein the R$^{37}$ is optionally substituted C$_1$-C$_6$ alkyl, and R$^{39}$ is H;
M is

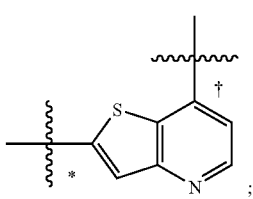 [SMILES: *c1cc2nccc(*)c2s1 ; ";"]

Z is —O—;
Ar is phenyl substituted with at least one halogen, C$_1$—C$_6$ alkyl or C$_1$—C$_4$ alkoxy;
G is

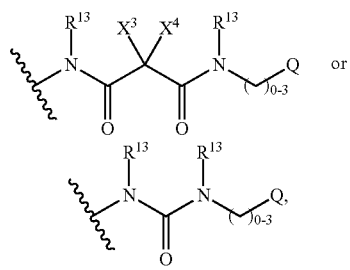

wherein
R$^{13}$ is H or C$_1$-C$_6$ alkyl;
X$^3$ and X$^4$ are each H or taken together with the carbon to which they are attach are cyclopropyl; and Q is cyclopropyl, cyclopentyl, cyclohexyl, pyridine or phenyl, optionally substituted with from 0 to 2 independently selected halogen, C$_1$-C$_6$alkyl, —S(O)$_2$(C$_1$-C$_6$) alkyl, —C(O)NH$_2$, —C(O)(C$_1$-C$_6$)alkyl or —CF$_3$.

39. A composistion comprising a compound according to claim 1 and a pharamaceutically acceptable carrier.

40. The compound according to claim 1, wherein,
D is

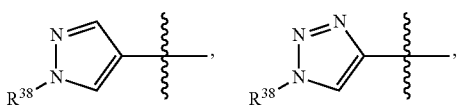

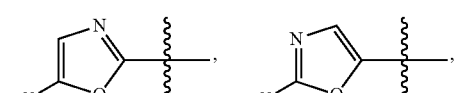

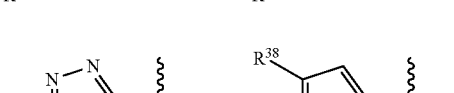

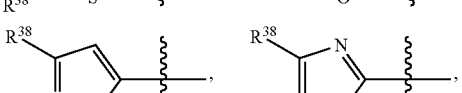

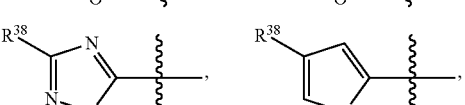

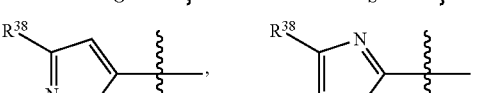

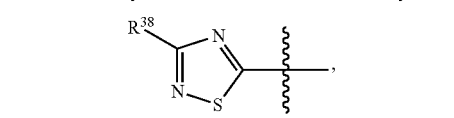

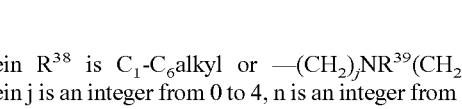

wherein R$^{38}$ is C$_1$-C$_6$alkyl or —(CH$_2$)$_j$NR$^{39}$(CH$_2$)$_n$R$^{36}$, wherein j is an integer from 0 to 4, n is an integer from 0 to 6, and the —(CH$_2$)$_n$— group is optionally substituted with C$_1$-C$_6$alkyl, R$^{36}$ is —(CH$_2$)$_{n3}$A$^4$R$^{37}$, wherein n3 is an integer ranging from 0 to 6, wherein the R$^{37}$ is optionally substituted C$_1$-C$_6$ alkyl, and R$^{39}$ is H or —C(O)—C$_1$-C$_3$alkyl;

M is

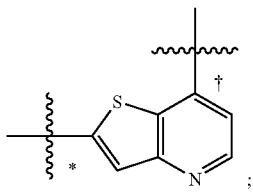 [SMILES: *c1cc2nccc(*)c2s1 ; ";"]

Z is —O—;
Ar is phenyl substituted with 0 to 4 halogen; and
G is

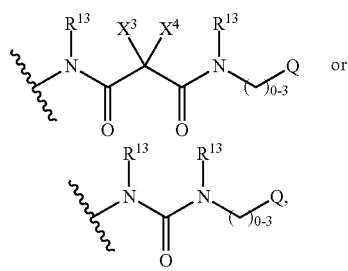

wherein Q is optionally substituted with from 0 to 4 independently selected $R^{20}$.

41. The compound according to claim 1, wherein D is

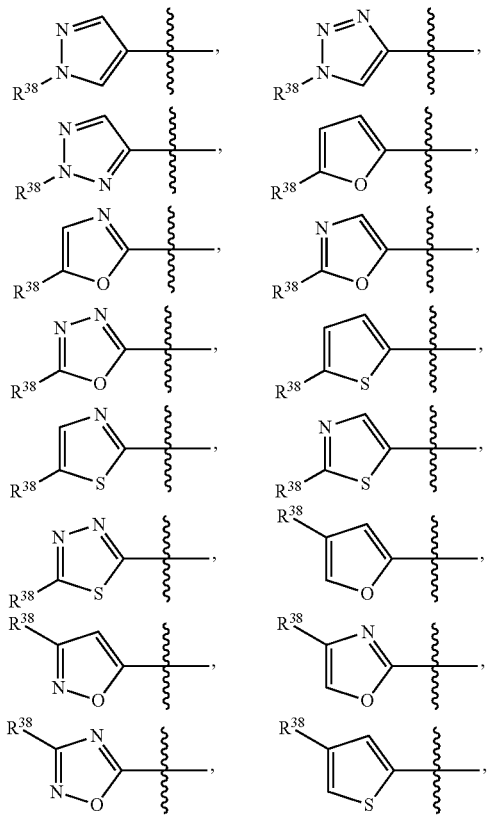

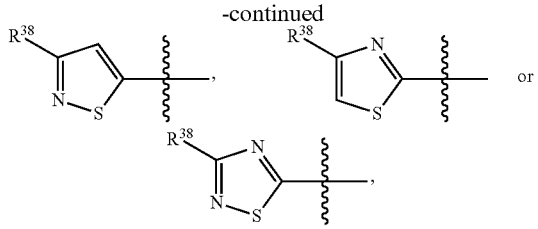

wherein $R^{38}$ is $-(CH_2)_j NR^{39}(CH_2)_n R^{36}$, wherein j is an integer from 0 to 4, n is an integer from 0 to 6, and $R^{36}$ is $-(CH_2)_{n3} OR^{37}$ wherein n3 is an integer ranging from 0 to 6, wherein the $R^{37}$ is optionally substituted $C_1$-$C_6$ alkyl, and $R^{39}$ is H;

M is

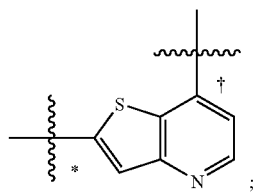

Z is —O—;
Ar is phenyl substituted with 0 to 4 halogen; and
G is

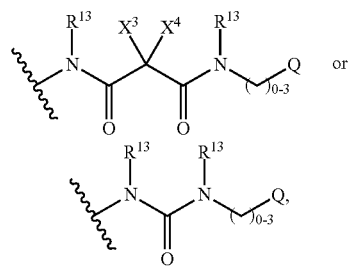

wherein Q is optionally substituted with from 0 to 4 independently selected $R^{20}$.

42. The compound according to claim 1, wherein D is

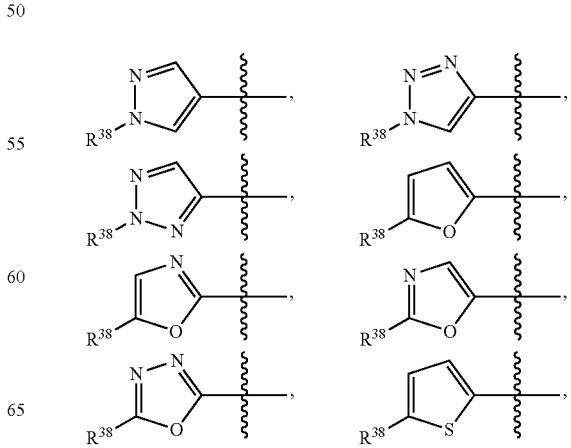

-continued

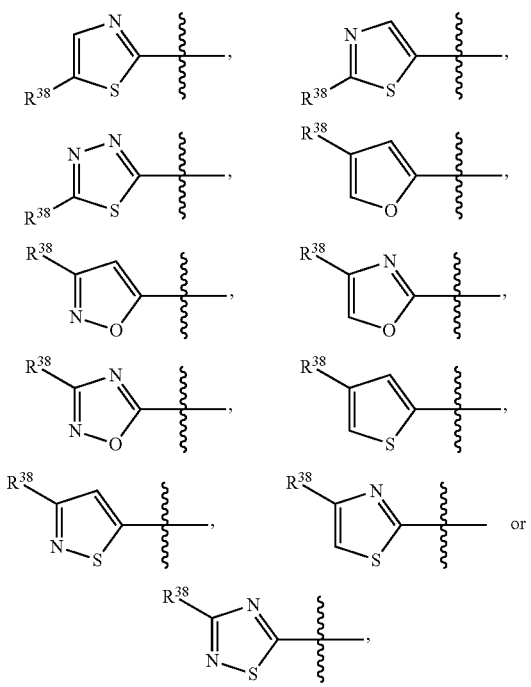

wherein R³⁸ is —(CH₂)ⱼNR³⁹(CH₂)ₙR³⁶, wherein j is an integer from 0 to 4, n is an integer from 0 to 6, and R³⁶ is —(CH₂)ₙ₃OR³⁷ wherein n3 is an integer ranging from 0 to 6, wherein the R³⁷ is optionally substituted $C_1$-$C_6$ alkyl, and R³⁹ is H;

M is

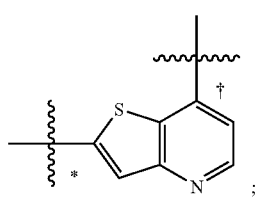 [SMILES: *c1cc2nccc(*)c2s1 ; ";"]

Z is —O—;
Ar is phenyl substituted with at least one halogen; and
G is

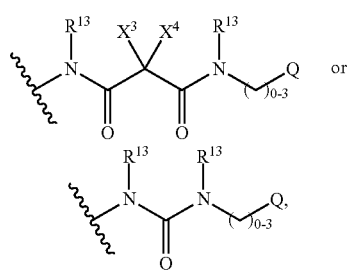

wherein Q is optionally substituted with from 0 to 4 independently selected R²⁰.

43. The compound according to claim 1, wherein D is

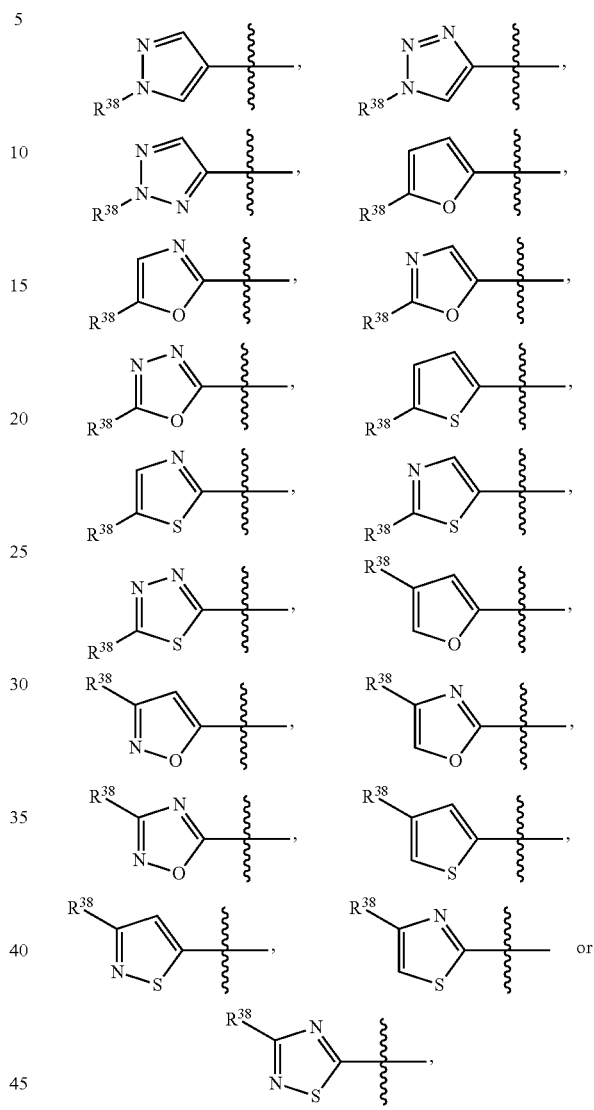

wherein R³⁸ is —(CH₂)ⱼNR³⁹(CH₂)ₙR³⁶, wherein j is an integer from 0 to 4, n is an integer from 0 to 6, and R³⁶ is —(CH₂)ₙ₃OR³⁷ wherein n3 is an integer ranging from 0 to 6, wherein the R³⁷ is optionally substituted $C_1$-$C_6$ alkyl, and R³⁹ is H;

M is

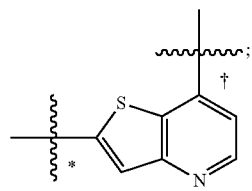 [SMILES: *c1cc2nccc(*)c2s1]

Z is —O—;
Ar is phenyl substituted with at least one halogen;

G is

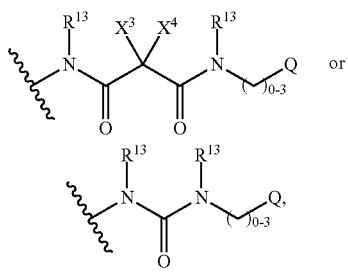

wherein
R$^{13}$ is H; and
Q is optionally substituted with from 0 to 4 independently selected R$^{20}$.

44. The compound according to claim 1, wherein D is

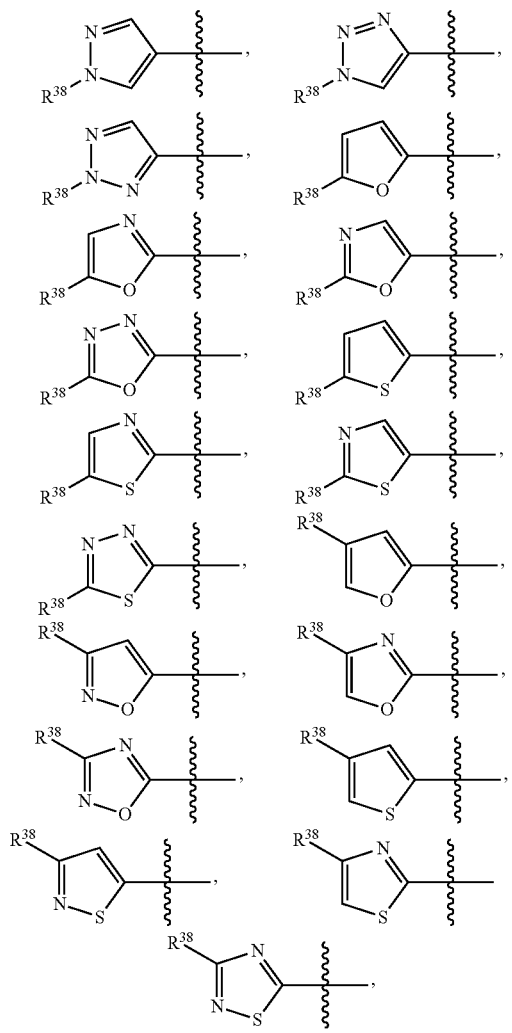

wherein R$^{38}$ is —(CH$_2$)$_j$NR$^{39}$(CH$_2$)$_n$R$^{36}$, wherein j is an integer from 0 to 4, n is an integer from 0 to 6, and R$^{36}$ is —(CH$_2$)$_{n3}$OR$^{37}$ wherein n3 is an integer ranging from 0 to 6, wherein the R$^{37}$ is optionally substituted C$_1$-C$_6$ alkyl, and R$^{39}$ is H;

M is

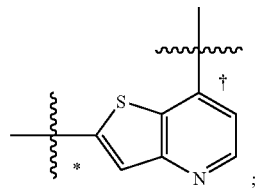 [SMILES: *c1cc2nccc(*)c2s1 ; ";"]

Z is —O—;
Ar is phenyl substituted with at least one halogen;
G is

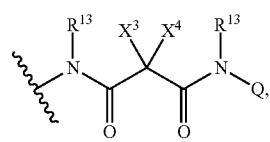

wherein
R$^{13}$ is H;
X$^3$ and X$^4$ are each H or taken together with the carbon to which they are attach are cyclopropyl; and
Q is cycloalkyl, heteroaryl or phenyl, optionally substituted with from 0 to 4 independently selected R$^{20}$.

45. The compound according to claim 1, wherein D is

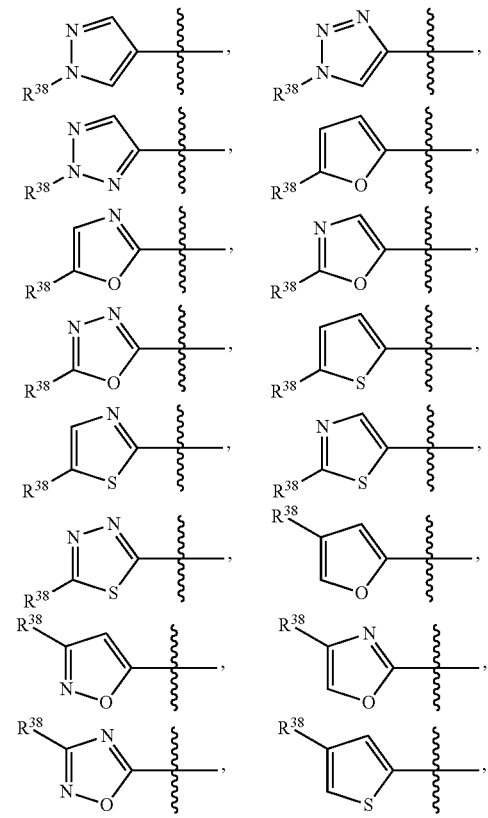

-continued

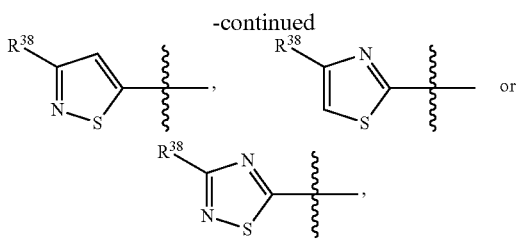

wherein R³⁸ is —(CH₂)ⱼNR³⁹(CH₂)ₙR³⁶, wherein j is an integer from 0 to 4, n is an integer from 0 to 6, and R³⁶ is —(CH₂)ₙ₃OR³⁷ wherein n3 is an integer ranging from 0 to 6, wherein the R³⁷ is optionally substituted C₁-C₆ alkyl, and R³⁹ is H;

M is

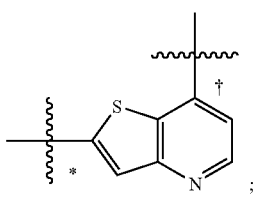 [SMILES: *c1cc2nccc(*)c2s1 ; ";"]

Z is —O—;

Ar is phenyl substituted with at least one halogen;

G is

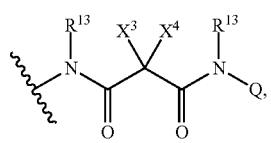

wherein

R¹³ is H;

X³ and X⁴ are each H or taken together with the carbon to which they are attach are cyclopropyl; and Q is cyclopropyl, isoxazole or phenyl, optionally substituted with from 0 to 2 independently selected halogen, C₁-C₆alkyl or —CF₃.

46. The compound according to claim 1, wherein the compound has the structure:

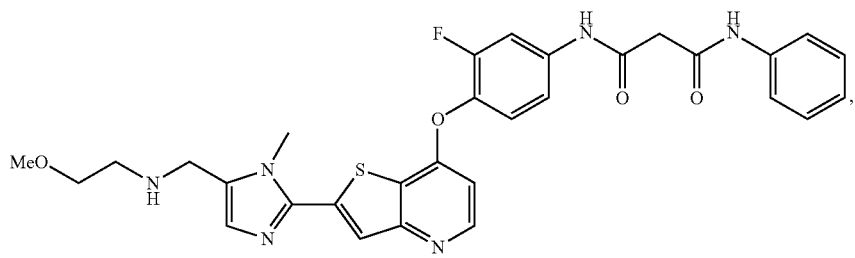

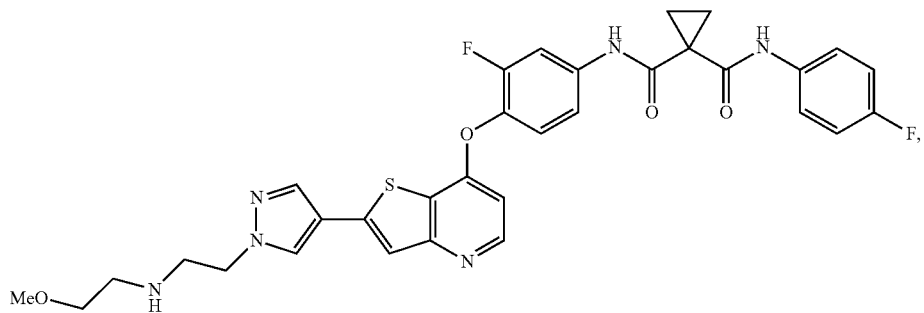

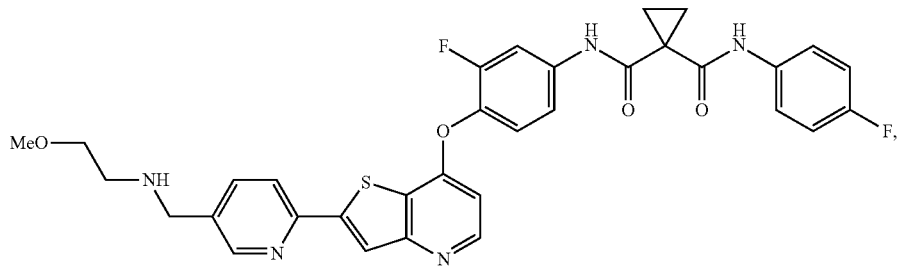 [SMILES: COCCNCc1ccc(-c2cc3nccc(Oc4ccc(NC(=O)C5(C(=O)Nc6ccc(F)cc6)CC5)cc4F)c3s2)nc1]

-continued
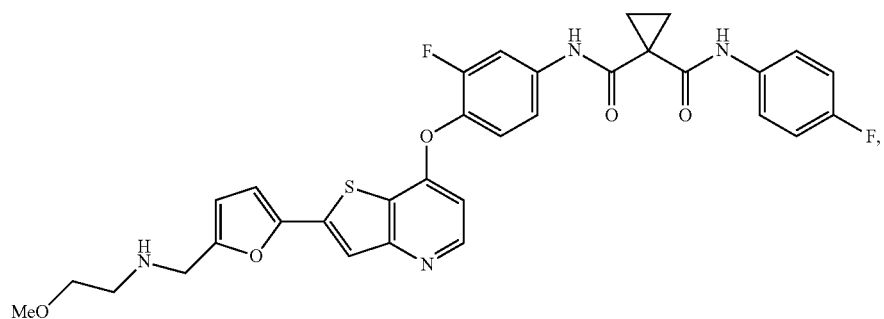
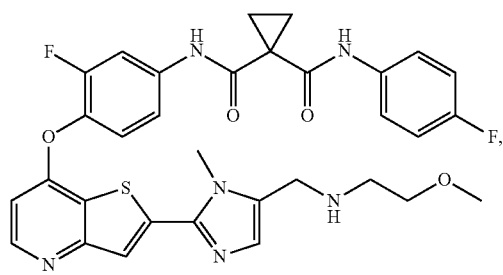
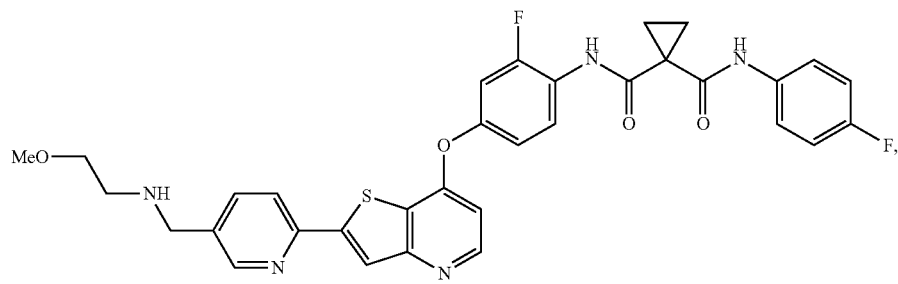
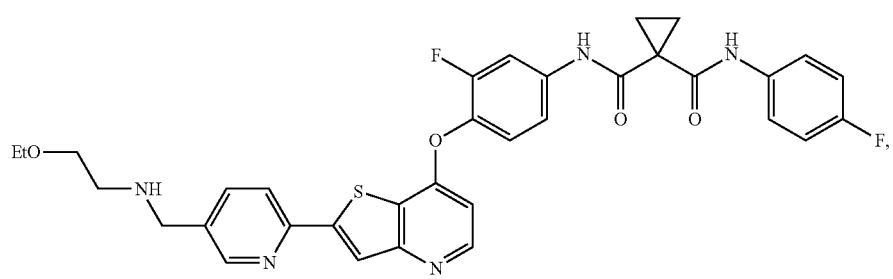
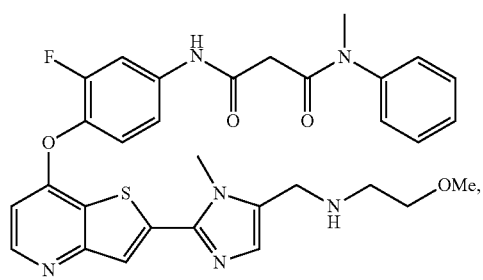
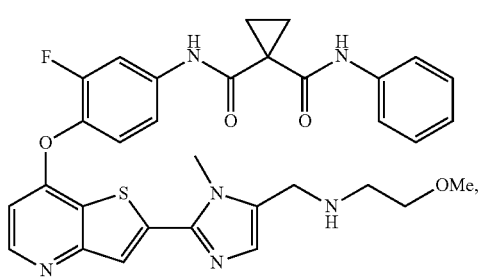

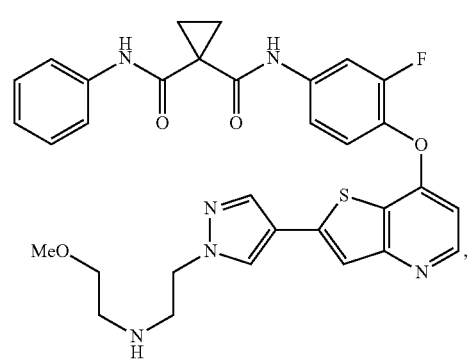
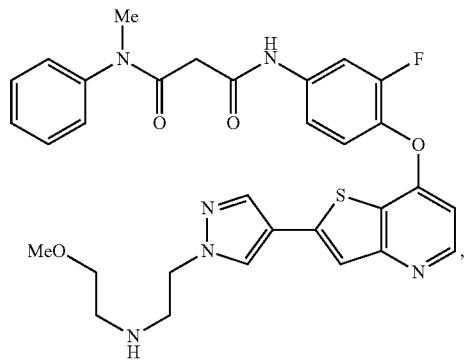
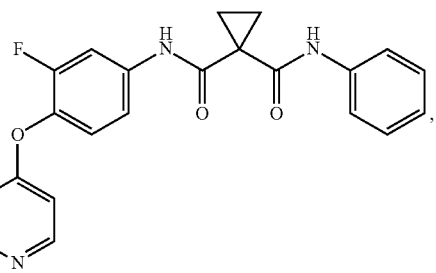
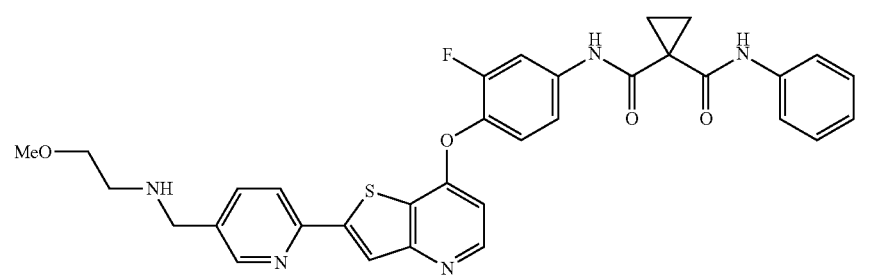
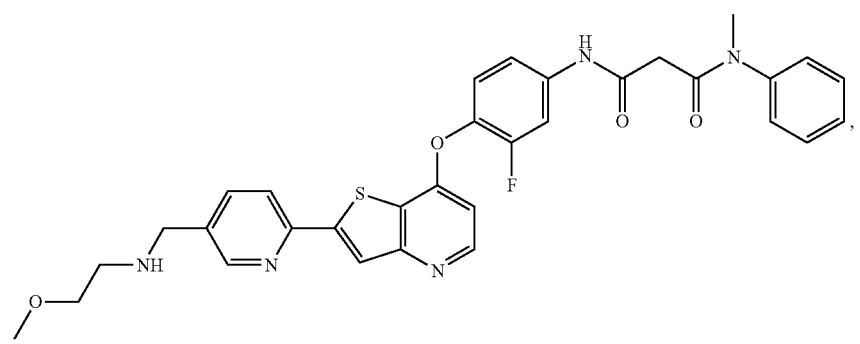
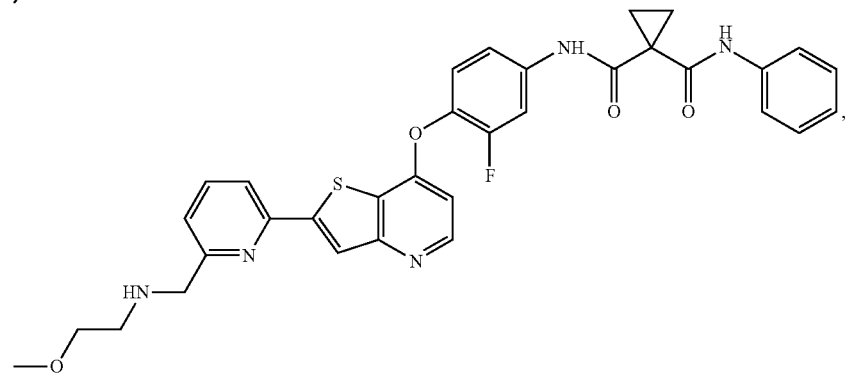

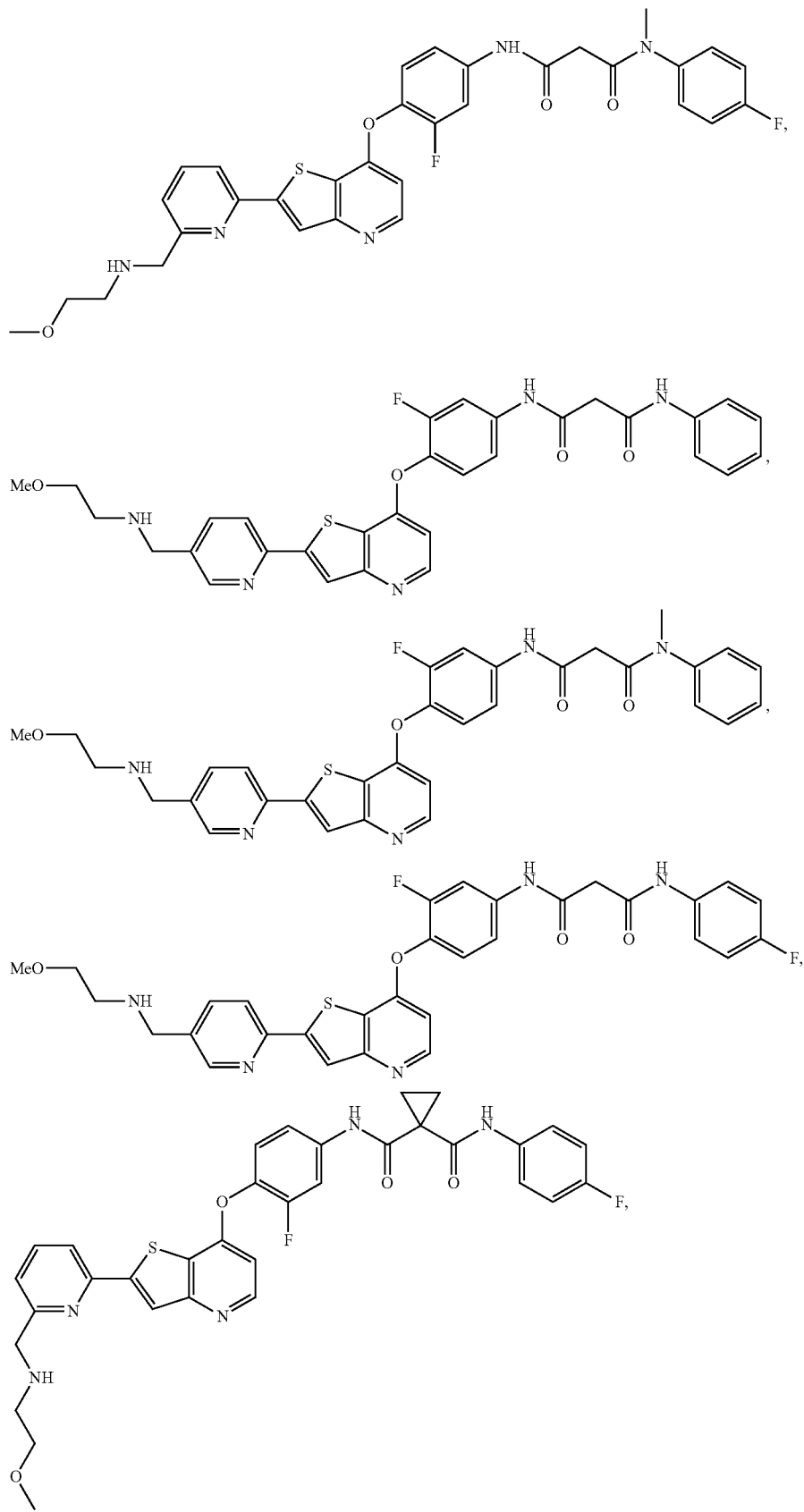

-continued
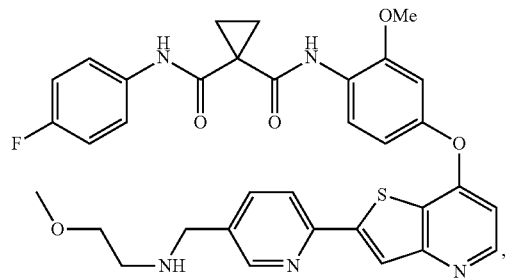
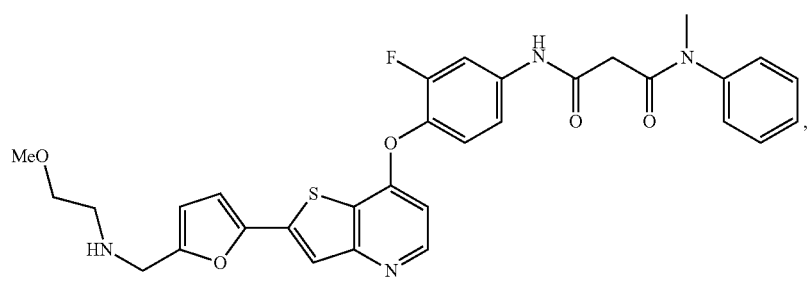
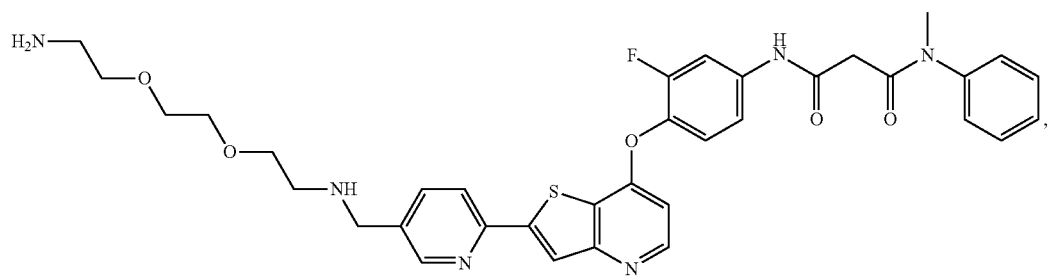
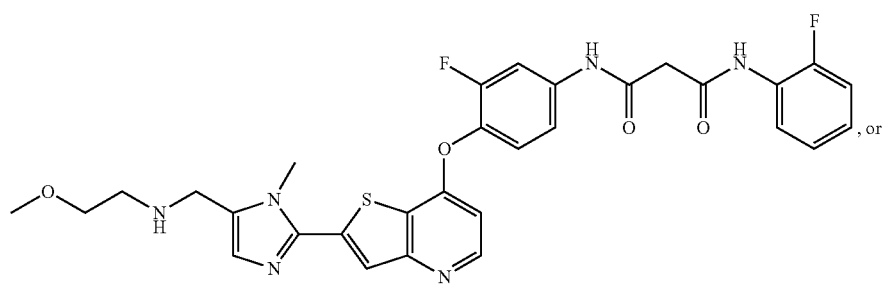
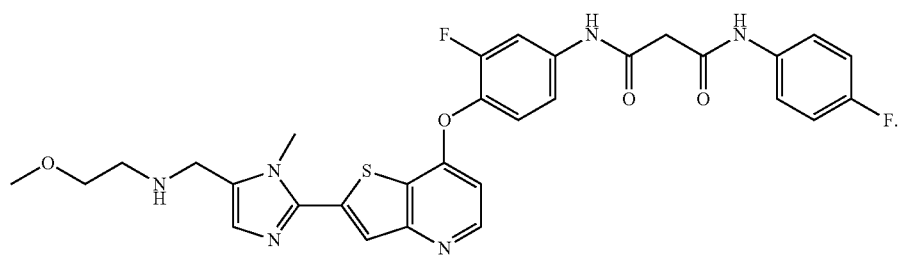

47. The compound according to claim 46, wherein the compound has the structure:
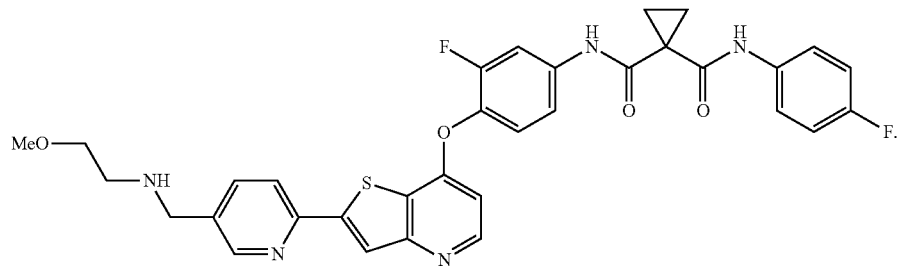
48. The compound according to claim 46, wherein the compound has the structure:
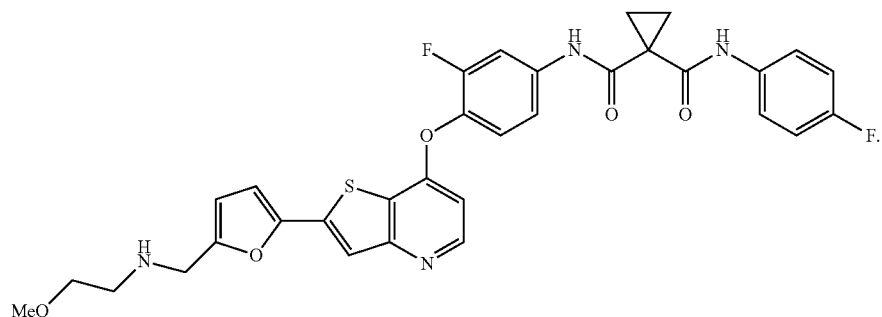 [SMILES: COCCNCc1ccc(-c2cc3nccc(Oc4ccc(NC(=O)C5(C(=O)Nc6ccc(F)cc6)CC5)cc4F)c3s2)o1]
49. The compound according to claim 46, wherein the compound has the structure:
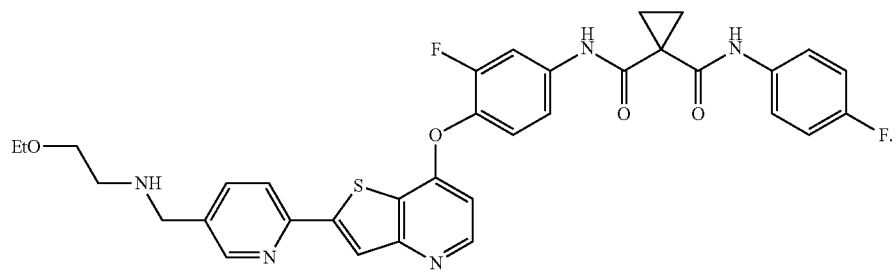 [SMILES: CCOCCNCc1ccc(-c2cc3nccc(Oc4ccc(NC(=O)C5(C(=O)Nc6ccc(F)cc6)CC5)cc4F)c3s2)nc1]
* * * * *